(12) United States Patent
Romano et al.

(10) Patent No.: US 10,981,901 B1
(45) Date of Patent: Apr. 20, 2021

(54) HETEROCYCLIC AMIDES USEFUL AS PROTEIN MODULATORS

(71) Applicant: GlaxoSmithKline Intellectual Property Development Limited, Middlesex (GB)

(72) Inventors: Joseph J. Romano, Collegeville, PA (US); Jianxing Kang, Collegeville, PA (US)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 334 days.

(21) Appl. No.: 16/091,189

(22) PCT Filed: Apr. 5, 2017

(86) PCT No.: PCT/IB2017/051945
§ 371 (c)(1),
(2) Date: Oct. 4, 2018

(87) PCT Pub. No.: WO2017/175147
PCT Pub. Date: Oct. 12, 2017

Related U.S. Application Data

(60) Provisional application No. 62/319,358, filed on Apr. 7, 2016, provisional application No. 62/461,301, filed on Feb. 21, 2017, provisional application No. 62/461,975, filed on Feb. 22, 2017.

(51) Int. Cl.
*C07D 413/14* (2006.01)
*C07D 403/14* (2006.01)

(52) U.S. Cl.
CPC ......... *C07D 413/14* (2013.01); *C07D 403/14* (2013.01)

(58) Field of Classification Search
CPC ............................ C07D 413/14; C07D 403/14
USPC ...................................................... 514/234.5
See application file for complete search history.

(56) References Cited

U.S. PATENT DOCUMENTS

| 2014/0364617 A1 | 12/2014 | Krueger et al. |
| 2018/0105514 A1 | 4/2018 | Mehlmann et al. |

FOREIGN PATENT DOCUMENTS

| CN | 103068824 A | 4/2013 |
| WO | WO 2011/091446 A1 | 7/2011 |
| WO | WO 2012/083053 A2 | 6/2012 |
| WO | WO 2015/185565 A1 | 12/2015 |
| WO | WO 2017/175147 A1 | 10/2017 |

*Primary Examiner* — Kristin A Vajda
(74) *Attorney, Agent, or Firm* — Robert H. Brink; Duke M. Fitch; Edward R. Gimmi

(57) ABSTRACT

Disclosed are compounds having the formula:

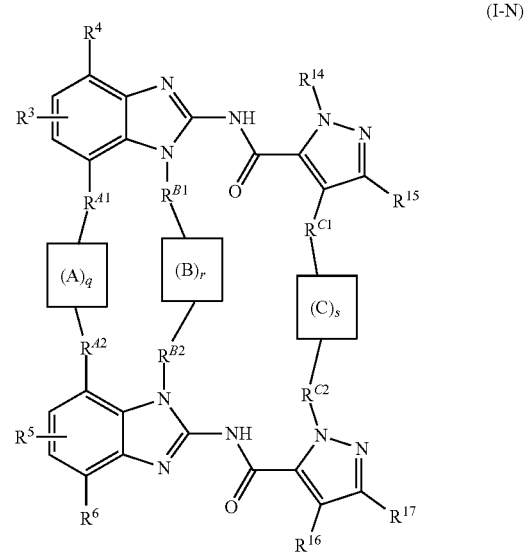

(I-N)

wherein q, r, s, A, B, C, $R^{A1}$, $R^{A2}$, $R^{B1}$, $R^{B2}$, $R^{C1}$, $R^{C2}$, $R^3$, $R^4$, $R^5$, $R^6$, $R^{14}$, $R^{15}$, $R^{16}$, and $R^{17}$, are as defined herein, or a tautomer thereof, or a salt, particularly a pharmaceutically acceptable salt, thereof.

10 Claims, No Drawings though its mechanism of action is currently not well understood. STING agonists may also have direct effects on cancer cells such as induction of apoptosis which contribute to efficacy in cancer immunotherapy. Activation of STING in the tumor microenvironment by CDN STING agonists has been shown to generate a strong CD8+ T cell mediated anti-tumor immunity (Corrales L. et al., Cell Reports 2015: 11, 1018-1030). Synthetic CDNs have greater stability and activity and have been combined with the GVAX cancer vaccine, consisting of GM-CSF expressing allogeneic tumor cells, in the STINGVAX approach (Fu J. et al., Science Translational Medicine 2015: 283ra52). STINGVAX demonstrated potent anti-tumor activity in multiple therapeutic models of established cancer, and tumors from STINGVAX treated animals demonstrated marked infiltration of CD8+ IFN-γ producing T cells in a STING dependent manner. Furthermore, when combined with PD-1 blockade, STINGVAX induced regression of PD-1 resistant tumors. Similarly, intra-tumoral injection of CDNs in mice has been shown to induce rapid and profound tumor regressions followed by long lasting systemic antigen specific T cell immunity able to reject distant metastases. (Corrales et al., Cell Reports 2015: 11, 1018-1030). Synthetic CDN STING agonists are now under investigation in clinical trials in cancer immunotherapy.

HETEROCYCLIC AMIDES USEFUL AS PROTEIN MODULATORS

RELATED APPLICATION

This application is a 371 of International Application No. PCT/IB2017/051945, filed 5 Apr. 2017, which claims priority to U.S. 62/319,358 filed 7 Apr. 2016, U.S. 62/461,301 filed 21 Feb. 2017 and U.S. 62/461,975 filed 22 Feb. 2017.

FIELD OF THE INVENTION

The present invention relates to heterocyclic amides that are useful as modulators of transmembrane protein 173 (TMEM173), which is also known as STING (Stimulator of Interferon Genes)) and methods of making and using the same.

BACKGROUND OF THE INVENTION

Vertebrates are constantly threatened by the invasion of microorganisms and have evolved mechanisms of immune defense to eliminate infective pathogens. In mammals, this immune system comprises two branches; innate immunity and adaptive immunity. The innate immune system is the first line of defense which is initiated by Pattern Recognition Receptors (PRRs) which detect ligands from the pathogens as well as damage associated molecular patterns (Takeuchi O. et al, Cell, 2010:140, 805-820). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signaling molecule in the innate immune response to cytosolic nucleic acids (Ishikawa Hand Barber G N, Nature, 2008: 455, 674-678; WO2013/1666000). Activation of STING results in up-regulation of IRF3 and NFκB pathways leading to induction of Interferon-β and other cytokines. STING is critical for responses to cytosolic DNA of pathogen or host origin, and of unusual nucleic acids called Cyclic Dinucleotides (CDNs)

CDNs were first identified as bacterial secondary messengers responsible for controlling numerous responses in the prokaryotic cell. Bacterial CDNs, such as c-di-GMP are symmetrical molecules characterized by two 3',5' phosphodiester linkages.

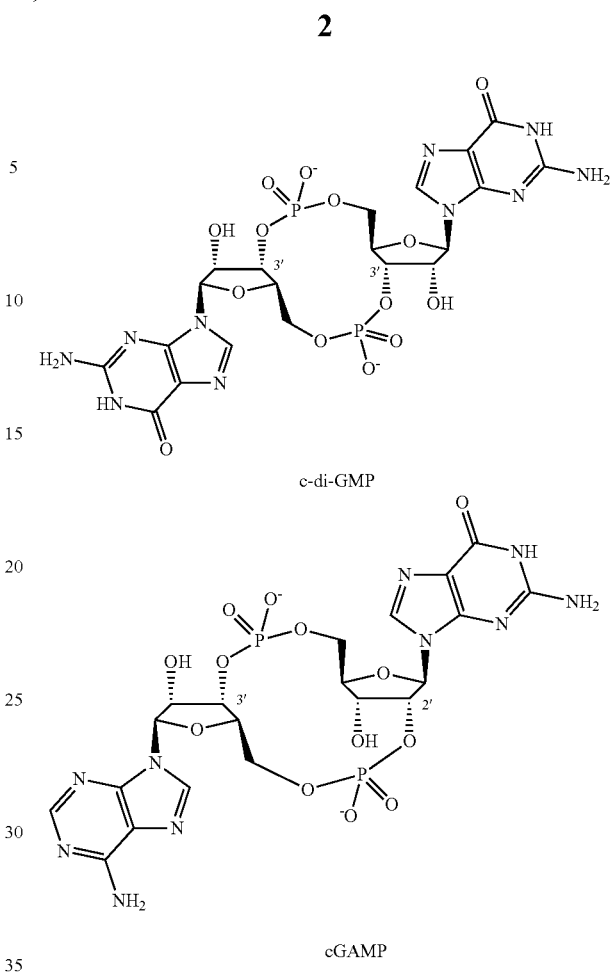

c-di-GMP cGAMP

Direct activation of STING by bacterial CDNs has recently been confirmed through X-ray crystallography (Burdette D L and Vance R E, Nature Immunology, 2013: 14, 19-26). Bacterial CDNs and their analogues have consequently attracted interest as potential vaccine adjuvants (Libanova R. et al, Microbial Biotechnology 2012: 5, 168-176; WO2007/054279, WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signaling molecule identified as cGAMP, which then activates STING. Unlike bacterial CDNs, cGAMP is an unsymmetrical molecule characterized by its mixed 2',5' and 3',5' phosphodiester linkages. (Gao P et al, Cell, 2013: 153, 1094-1107). Interaction of cGAMP (II) with STING has also been demonstrated by X-ray crystallography (Cai X et al, Molecular Cell, 2014: 54, 289-296).

Interferon was first described as a substance which could protect cells from viral infection (Isaacs & Lindemann, J. Virus Interference. Proc. R. Soc. Lon. Ser. B. Biol. Sci. 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could modulate the innate immune response, including the activation or inhibition of type I interferon production and other cytokines, could become an important strategy for the treatment or prevention of human diseases including viral infections and autoimmune disease. This type of immunomodulatory strategy has the potential to identify compounds which may be useful not only in infectious diseases innate immunity but also in cancer (Zitvogel, L., et al., *Nature Reviews Immunology,* 2015 15(7), p 405-414), allergic diseases (Moisan J. et al, *Am. J. Physiol. Lung Cell Mol. Physiol.,* 2006: 290, L987-995), neurodegenerative diseases such as amyotrophic lateral sclerosis and multiple sclerosis (Lemos, H. et al., *J. Immunol.,* 2014: 192(12), 5571-8; Cirulli, E et al., *Science,* 2015: 347(6229), 1436-41; Freischmidt, A., et a., *Nat. Neurosci.,* 18(5), 631-6), other inflammatory conditions such as irritable bowel disease (Rakoff-Nahoum S., *Cell.,* 2004, 23, 118(2): 229-41), and as vaccine adjuvants (Persing et al. *Trends Microbiol.* 2002: 10(10 Suppl), 532-7 and Dubensky et al., *Therapeutic Advances in Vaccines,* published on line Sep. 5, 2013).

STING is essential for antimicrobial host defense, including protection against a range of DNA and RNA viruses and bacteria (reviewed in Barber eta. *Nat. Rev. Immuno.* 2015: 15(2): 87-103, Ma and Damania, *Cell Host & Microbe,* 2016: 19(2)150-158). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm et al., *Nat Comm.* 2016: 7:10680; Ma et al, *PNAS* 2015: 112(31) E4306-E4315; Wu et al, *Cell Host Microbe* 2015: 18(3) 333-44; Liu et al, *J Virol* 2016: 90(20) 9406-19; Chen et al., *Protein Cell* 2014: 5(5) 369-81; Lau et al, *Science* 2013: 350(6260) 568-71; Ding et al, *J Hepato* 2013: 59(1) 52-8; Nitta et al, *Hepatology* 2013 57(1) 46-58; Sun et al, *PloS One* 2012: 7(2) e30802; Aguirre et al, *PoS Pathog* 2012: 8(10) e1002934; Ishikawa et al, *Nature* 2009: 461(7265) 788-92). Thus, small molecule activation of STING could be beneficial for treatment of these infectious diseases.

In contrast, increased and prolonged type I IFN production is associated with a variety of chronic infections, including Mycobacteria (Collins et al, *Cell Host Microbe* 2015: 17(6) 820-8); Wassermann et al., *Cell Host Microbe* 2015: 17(6) 799-810; Watson et al., *Cell Host Microbe* 2015: 17(6) 811-9), Franciscella (Storek et al., *J Immunol.* 2015: 194(7) 3236-45; Jin et al., *J Immunol.* 2011: 187(5) 2595-601), Chlamydia (Prantner et al., *J Immunol* 2010: 184(5) 2551-60; *Plasmodium* (Sharma et al., *Immunity* 2011: 35(2) 194-207 and HIV (Herzner et al., *Nat Immunol* 2015 16(10) 1025-33; Gao et al., *Science* 2013: 341(6148) 903-6. Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow Y J, et al., *Nat. Genet.* 2006; 38(8) 38917-920, Stetson D B, et al., *Cell* 2008; 134587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber J. P. et al *J Immunol* 2010: 185, 813-817).

Compounds that bind to STING and act as agonist have been shown to induce type 1 interferons and other cytokines on incubation with human PBMCs. Compounds which induce human interferons may be useful in the treatment of various disorders, for example the treatment of allergic diseases and other inflammatory conditions for example allergic rhinitis and asthma, the treatment of infectious diseases, neurodegenerative disease, pre-cancerous syndromes and cancer, and may also be useful as immugenic composition or vaccine adjuvants. Compounds that bind to STING may act as antagonists and could be useful in the treatment, for example of autoimmune diseases. It is envisaged that targeting STING with activation or inhibiting agents may be a promising approach for treating diseases and conditions in which modulation for the type 1 IFN pathway is beneficial, including inflammatory, allergic and autoimmune diseases, infectious diseases, cancer, pre-cancerous syndromes and as immugenic composition or vaccine adjuvants.

Skin cancers and various skin viral infections involve immune privileged environment and activation of local immune response to the lesions may be a topical therapeutic approach. STING agonists may be used for treating viral warts, superficial skin cancers and premalignant actinic keratoses. By a dual mechanism of action, STING activation (e.g., via microneedle patch delivery or topical formulation) may be used to control HPV directly via antiviral type I interferon production and indirectly by enhancing the adaptive immune response downstream of innate immune activation. STING agonist can activate the innate immune response in the lesion and drive the anti-HPV T-cell response.

Recent evidence has indicated that spontaneous activation of the STING pathway within tumor-resident dendritic cells leads to type I IFN production and adaptive immune responses against tumors. Furthermore, activation of this pathway in antigen presenting cells (APCs) within the tumor microenvironment drives the subsequent T-cell priming against tumor-associated antigens. Corrales and Gajewski, *Clin Cancer Res;* 21(21); 4774-9, 2015.

International Patent Applications WO2014/093936, WO2014/189805, WO2013/185052, U.S. 2014/0341976, WO 2015/077354, PCT/EP2015/062281 and GB 1501462.4 disclose certain cyclic di-nucleotides and their use in inducing an immune response via activation of STING.

The compounds of this invention modulate the activity of STING, and accordingly, may provide a beneficial therapeutic impact in treatment of diseases, disorders and/or conditions in which modulation of STING (Stimulator of Interferon Genes) is beneficial, for example for inflammation, allergic and autoimmune diseases, infectious diseases, cancer, pre-cancerous syndromes and as vaccine adjuvants.

SUMMARY OF THE INVENTION

The invention is directed to a compound according to Formula (I-N):

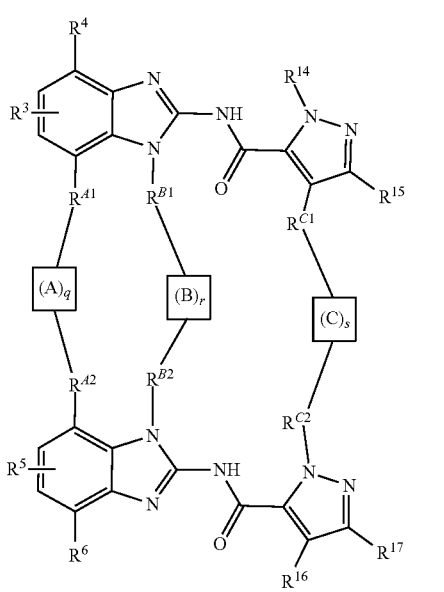

(I-N)

wherein:
q is 0 or 1;
r is 0 or 1;
s is 0 or 1;
wherein q+r+s=1 or 2;
when q is 0, $R^{A1}$ and $R^{A2}$ are each independently H, halogen, hydroxy, —O—P(O)(OH)$_2$, —O—P(O)(R$^I$R$^{II}$)$_2$, —N(R$^e$)(R$^f$), —CO$_2$R$^f$, —N(R$^f$)COR$^b$, —N(R$^g$)SO$_2$(C$_1$-C$_4$alkyl)-N(R$^e$)(R$^f$), —N(R$^g$)CO(C$_1$-C$_4$alkyl)-N(R$^h$)(R$^f$), optionally substituted (C1-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, —O—P(O)(OH)$_2$, —O—P(O)(R$^I$R$^{II}$)$_2$, C$_1$-C$_4$alkoxy-, —N(R$^e$)(R$^f$), —CO$_2$(R$^f$), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, —C$_1$-C$_4$alkyl-(C$_1$-C$_4$alkoxy) or C$_1$-C$_4$alkoxy-(C$_1$-C$_4$alkoxy)-;

when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(R$^I$R$^{II}$)$_2$, —OR$^c$, —NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;

when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_2$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-,
wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —O—P(O)(OH)$_2$, —O—P(O)(R$^I$R$^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$,
and
the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl- (5-6 membered heteroaryl)-$C_1$-$C_6$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, —($C_1$-$C_4$alkoxyl)-O—P(O)(OH)$_2$, —($C_1$-$C_4$alkoxyl)-O—P(O)($R^I R^{II}$)$_2$ and $C_1$-$C_4$alkoxy-($C_1$-$C_4$alkoxy)-;

when r is 1, $R^{B1}$ and $R^{B2}$ are each independently —CH$_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-,
wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —O—P(O)(OH)$_2$, —O—P(O)($R^I R^{II}$)$_2$, —OR$^c$, —NH$_2$, —NR$^c R^d$, —OCOR$^c$, —CO$_2$H, —CO$_2$R$^c$, —SOR$^c$, —SO$_2$R$^c$, —CONH$_2$, —CONR$^c R^d$, —SO$_2$NH$_2$, —SO$_2$NR$^c R^d$, —OCONH$_2$, —OCONR$^c R^d$, —NR$^d$COR$^c$, —NR$^d$SOR$^c$, —NR$^d$CO$_2$R$^c$, and —NR$^d$SO$_2$R$^c$, and
the $C_3$-$C_6$cycloalkyl, phenyl, 4-6 membered heterocloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)O—P(O)(OH)$_2$, —($C_2$-$C_4$alkoxy)-O—P(O)($R^I R^{II}$)$_2$, and $C_1$-$C_4$alkoxy-($C_1$-$C_4$alkoxy)-;

when s is 1, $R^{C1}$ and $R^{C2}$ are each independently —CH$_2$—, and C, taken together with $R^{C1}$ and $R^{C2}$, forms a linking group, wherein C is -halo($C_1$-$C_{12}$alkyl)-, optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-,
wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —O—P(O)(OH)$_2$, —O—P(O)($R^I R^{II}$)$_2$, —OR$^c$, —NH$_2$, —NR$^c R^d$, —OCOR$^c$, —CO$_2$H, —CO$_2$R$^c$, —SOR$^c$, —SO$_2$R$^c$, —CONH$_2$, —CONR$^c R^d$, —SO$_2$NH$_2$, —SO$_2$NR$^c R^d$, —OCONH$_2$, —OCONR$^c R^d$, —NR$^d$COR$^c$, —NR$^d$SOR$^c$, —NR$^d$CO$_2$R$^c$, and —NR$^d$SO$_2$R$^c$, and
the $C_3$-$C_6$cycloalkyl, phenyl, 4-6 membered heterocloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I R^{II}$)$_2$, and $C_1$-$C_4$alkoxy-($C_1$-$C_4$alkoxy)-;

$R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^I R^{II}$)$_2$, —NH$_2$, —NR$^c R^c$, —NR$^c R^d$, —COR$^c$, —CO$_2$R$^c$, —N($R^d$)COR$^c$, —N($R^d$)SO$_2$R$^c$, —N($R^g$)SO$_2$($C_1$-$C_2$alkyl)-N($R^h$)($R^f$), —N($R^g$)CO($C_1$-$C_2$alkyl)-N($R^h$)($R^f$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —O—P(O)(OH)$_2$, —O—P(O)($R^I R^{II}$)$_2$, —OR$^c$, —NH$_2$, —NR$^c R^c$, —NR$^c R^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$C$_2$R$^C$, —NR$^d$S$_2$R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_1$-C$_4$alkyl)amino-, (C$_1$-C$_4$alkyl)(C$_1$-C$_4$alkyl) amino-, C$_1$-C$_4$alkyl, halo(C$_1$-C$_4$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

R$^{14}$ is optionally substituted C$_1$-C$_4$alkyl, wherein said optionally substituted C$_1$-C$_4$alkyl is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

R$^{16}$ is H, halogen, or C$_1$-C$_4$alkyl;

R$^{15}$ and R$^{17}$ are each independently H, cyclopropyl, or C$_1$-C$_4$alkyl;

R$^a$ is H, —R$^c$, —COR$^c$, —C$_2$H, —CO$_2$R$^c$, —SOR$^c$, —S$_2$R$^c$, —CONH$_2$, —CONR$^c$R$^d$, —S$_2$NH$_2$, or —SO$_2$NR$^c$R$^d$;

each R$^b$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^I$R$^{II}$)$_2$, —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), or —(C$_1$-C$_4$alkyl)-CO—O—(C$_1$-C$_4$alkyl);

each R$^c$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^I$R$^{II}$)$_2$, —(C$_1$-C$_4$alkyl)-O—(C$_1$-C$_4$alkyl), —(C$_1$-C$_4$alkyl)-N(R$^e$)(R$^f$)—(C$_1$-C$_4$alkyl)-O—CO(C$_1$-C$_4$alkyl), —(C$_1$-C$_4$alkyl)-CO—O—(C$_1$-C$_4$alkyl), optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl, wherein the C$_3$-C$_6$cycloalkyl, phenyl, 4-6 membered heterocycloalkyl, 5-6 membered heteroaryl or 9-10 membered heteroaryl moiety of said optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl is optionally substituted by 1-4 substituents each independently selected from halogen, hydroxy, —O—P(O)(OH)$_2$, —O—P(O)(R$^I$R$^{II}$)$_2$, amino, —(C$_1$-C$_4$alkyl)NH$_2$, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

each R$^d$ is independently H or C$_1$-C$_4$alkyl;

each R$^e$ is independently H, (C$_1$-C$_4$alkyl), —CO(C$_1$-C$_4$alkyl), —OCO(C$_1$-C$_4$alkyl), —CO$_2$(C$_1$-C$_4$alkyl), —(C$_1$-C$_4$alkyl)NH$_2$, —(C$_1$-C$_4$alkyl) C$_1$-C$_4$alkoxy, —CO-(optionally substituted 5-6 membered heterocycloalkyl), —CO(C$_1$-C$_4$alkyl)-(optionally substituted 5-6 membered heterocycloalkyl), —CO(optionally substituted 5-6 membered heteroaryl), —CO(C$_1$-C$_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—P(O)(OH)$_2$, —O—P(O)(R$^I$R$^{II}$)$_2$, amino, (C$_1$-C$_4$alkyl) amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

each R$^f$ is independently H or (C$_1$-C$_4$alkyl);

R$^g$ and R$^h$ are each independently H or (C$_1$-C$_4$alkyl) or R$^g$ and R$^h$, taken together with the atom or atoms through which they are connected, form a 5-6 membered ring;

and each occurrence of R$^I$ and R$^{II}$ are independently (C$_1$-C$_6$alkyl)oxy-;

or a tautomer thereof;

or a salt thereof, particularly a pharmaceutically acceptable salt, thereof.

It is to be understood that the references herein to compounds of Formula (I-N), (I-P) or (I), and salts thereof covers the compounds of Formula (I-N), (I-P) or (I), as free bases, or as salts thereof, for example as pharmaceutically acceptable salts thereof. Thus, in one embodiment, the invention is directed to compounds of Formula (I-N), (I-P) or (I), as the free base. In another embodiment, the invention is directed to compounds of Formula (I-N), (I-P) or (I), and salts thereof. In a further embodiment, the invention is directed to compounds of Formula (I-N), (I-P) or (I), and pharmaceutically acceptable salts thereof.

The compounds according to Formula (I-N), (I-P) or (I), or salts, particularly pharmaceutically acceptable salts, thereof, are modulators of STING. Accordingly, this invention provides a compound of Formula (I-N), (I-P) or (I) or a salt thereof, particularly a pharmaceutically acceptable salt thereof, for use in therapy. This invention specifically provides for the use of a compound of Formula (I-N), (I-P) or (I), or a pharmaceutically acceptable salt thereof, as an active therapeutic substance in the treatment of a STING-mediated disease or disorder, specifically, for use in the treatment of a disease mediated by agonism or antagonism of STING. The invention also provides a compound of Formula (I-N), (I-P) or (I), or a salt thereof, particularly a pharmaceutically acceptable salt thereof, for use in the manufacture of a medicament for the treatment of a STING-mediated disease or disorder.

The invention is also directed to a method of modulating STING, which method comprises contacting a cell with a compound according to Formula (I-N), (I-P) or (I), or a salt, particularly a pharmaceutically acceptable salt, thereof. The invention is further directed to a method of treating a STING-mediated disease or disorder which comprises administering a therapeutically effective amount of a compound according to Formula (I-N), (I-P) or (I), or a salt, particularly a pharmaceutically acceptable salt thereof, to a patient (a human or other mammal, particularly, a human) in need thereof. Such STING-mediated diseases or disorders include inflammation, allergic and autoimmune diseases, infectious diseases, cancer, and pre-cancerous syndromes. In addition, modulators of STING may be useful as immugenic composition or vaccine adjuvants.

The present invention is further directed to a pharmaceutical composition comprising a compound according to Formula (I-N), (I-P) or (I), or a salt, particularly a pharmaceutically acceptable salt, thereof and a pharmaceutically acceptable excipient. Particularly, this invention is directed to a pharmaceutical composition for the treatment of a STING-mediated disease or disorder, where the composition comprises a compound according to Formula (I-N), (I-P) or (I), or a salt, particularly a pharmaceutically acceptable salt, thereof and a pharmaceutically acceptable excipient.

DETAILED DESCRIPTION OF THE APPLICATION

According to one aspect of the present invention, this invention relates to compounds of Formula (I-N)

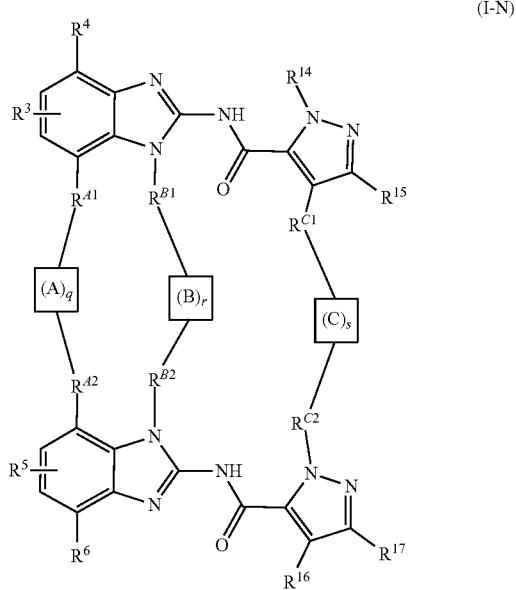

(I-N)

wherein:
q is 0 or 1;
r is 0 or 1;
s is 0 or 1;
wherein q+r+s=1 or 2;
when q is 0, $R^{A1}$ and $R^{A2}$ are each independently H, halogen, hydroxy, —O—P(O)(OH)$_2$, —O—P(O)(R$^I$R$^H$)$_2$, —N(R$^e$)(R$^f$), —CO$_2$R$^f$, —N(R$^f$)COR$^b$, —N(R$^g$)SO$_2$(C$_1$-C$_4$alkyl)-N(R$^e$)(R$^f$), —N(R$^g$)CO(C$_1$-C$_4$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, —O—P(O)(OH)$_2$, —O—P(O)(R$^I$R$^H$)$_2$, C$_1$-C$_4$alkoxy-, —N(R$^e$)(R$^f$), —CO$_2$(R$^f$), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$R$^H$)$_2$, amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$R$^H$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^H$)$_2$, —C$_1$-C$_4$alkyl-(C$_1$-C$_4$alkoxy) and C$_1$-C$_4$alkoxy-(C$_1$-C$_4$alkoxy)-;

when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(R$^I$R$^H$)$_2$, —OR$^c$, —NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;

when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_2$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, halo($C_1$-$C_4$alkyl), —OH, —O—P(O)(OH)$_2$, —O—P(O)($R^I R^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$C$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, —($C_1$-$C_4$alkoxyl)-O—P(O)(OH)$_2$, —($C_1$-$C_4$alkoxyl)-O—P(O)($R^I R^{II}$)$_2$ and $C_1$-$C_4$alkoxy-($C_1$-$C_4$alkoxy)-;

when r is 1, $R^{B1}$ and $R^{B2}$ are each independently —CH$_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —O—P(O)(OH)$_2$, —O—P(O)($R^I R^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)O—P(O)(OH)$_2$, —($C_2$-$C_4$alkoxy)-O—P(O)($R^I R^{II}$)$_2$, and $C_1$-$C_4$alkoxy-($C_1$-$C_4$alkoxy)-;

when s is 1, $R^{C1}$ and $R^{C2}$ are each independently —CH$_2$—, and C, taken together with $R^{C1}$ and $R^{C2}$, forms a linking group, wherein C is -halo($C_1$-$C_{12}$alkyl)-, optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —O—P(O)(OH)$_2$, —O—P(O)($R^I R^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^C$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$S OR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I R^{II}$)$_2$, and $C_1$-$C_4$alkoxy-($C_1$-$C_4$alkoxy)-;

$R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^IR^{II}$)$_2$, —NH$_2$, —NR$^c$R$^c$, —NR$^c$R$^d$, —COR$^c$, —CO$_2$R$^c$, —N(R$^d$)COR$^c$, —N(R$^d$)SO$_2$R$^c$, —N(R$^g$)SO$_2$(C$_1$-C$_2$alkyl)-N(R$^h$)(R$^f$), —N(R$^g$)CO(C$_1$-C$_2$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-, wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from —OH, —O—P(O)(OH)$_2$, —O—P(O)(R$^IR^{II}$)$_2$, —OR$^c$, —NH$_2$, —NR$^c$R$^c$, NR$^c$R$^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^IR^{II}$)$_2$, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^IR^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^IR^{II}$)$_2$, C$_1$-C$_4$alkoxy-(C$_1$-C$_4$alkoxy)-, —COR$^d$, —CON(R$^d$)(R$^f$), and —CO$_2$R$^d$;

$R^{14}$ is optionally substituted C$_1$-C$_4$alkyl, wherein said optionally substituted C$_1$-C$_4$alkyl is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

$R^{16}$ is H, halogen, or C$_1$-C$_4$alkyl;

$R^{15}$ and $R^{17}$ are each independently H, cyclopropyl, or C$_1$-C$_4$alkyl;

$R^a$ is H, —R$^c$, —COR$^c$, —CO$_2$H, —CO$_2$R$^c$, —SOR$^c$, —SO$_2$R$^c$, —CONH$_2$, —CONR$^c$R$^d$, —SO$_2$NH$_2$, or —SO$_2$NR$^c$R$^d$;

each $R^b$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^IR^{II}$)$_2$, —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), or —(C$_1$-C$_4$alkyl)-CO—O—(C$_1$-C$_4$alkyl);

each $R^c$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^IR^{II}$)$_2$, —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), —(C$_1$-C$_4$alkyl)-CO—O—(C$_1$-C$_4$alkyl), optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl, wherein the C$_3$-C$_6$cycloalkyl, phenyl, 4-6 membered heterocycloalkyl, 5-6 membered heteroaryl or 9-10 membered heteroaryl moiety of said optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl is optionally substituted by 1-4 substituents each independently selected from halogen, hydroxy, —O—P(O)(OH)$_2$, —O—P(O)(R$^IR^{II}$)$_2$, amino, —(C$_1$-C$_4$alkyl)NH$_2$, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^IR^{II}$)$_2$, C$_1$-C$_4$alkoxy-(C$_1$-C$_4$alkoxy)-, —COR$^d$, —CON(R$^d$)(R$^f$), and —CO$_2$R$^d$;

each $R^d$ is independently H or C$_1$-C$_4$alkyl;

each $R^e$ is independently H, (C$_1$-C$_4$alkyl), —CO(C$_1$-C$_4$alkyl), —OCO(C$_1$-C$_4$alkyl), —CO$_2$(C$_1$-C$_4$alkyl), —(C$_1$-C$_4$alkyl)NH$_2$, —(C$_1$-C$_4$alkyl) C$_1$-C$_4$alkoxy, —CO-(optionally substituted 5-6 membered heterocycloalkyl), —CO(C$_1$-C$_4$alkyl)-(optionally substituted 5-6 membered heterocycloalkyl), —CO(optionally substituted 5-6 membered heteroaryl), —CO(C$_1$-C$_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—P(O)(OH)$_2$, —O—P(O)(R$^IR^{II}$)$_2$, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)O—P(O)(OH)$_2$, —(C$_2$-C$_4$alkoxy)-O—P(O)(R$^IR^{II}$)$_2$, C$_1$-C$_4$alkoxy-(C$_1$-C$_4$alkoxy)-, —COR$^d$, —CON(R$^d$)(R$^f$), and —CO$_2$R$^d$;

each $R^f$ is independently H or (C$_1$-C$_4$alkyl);

$R^g$ and $R^h$ are each independently H or (C$_1$-C$_4$alkyl) or $R^g$ and $R^h$, taken together with the atom or atoms through which they are connected, form a 5-6 membered ring; and each occurrence of $R^I$ and $R^{II}$ are independently (C$_1$-C$_6$alkyl)oxy-;

or a tautomer thereof;

or a salt, particularly a pharmaceutically acceptable salt, thereof.

The invention is directed to a compound according to Formula (I-P):

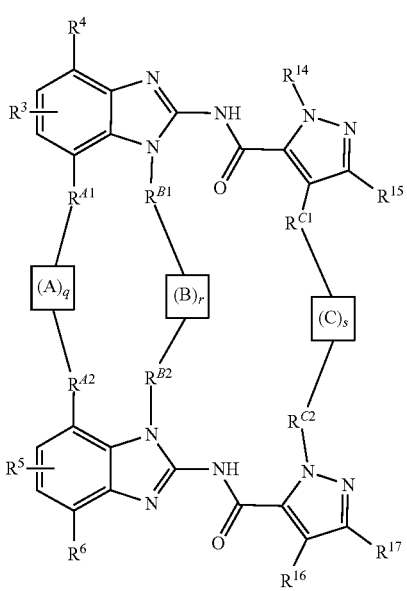

wherein:
q is 0 or 1;
r is 0 or 1;
s is 0 or 1;
wherein q+r+s=1 or 2;
when q is 0, $R^{A1}$ and $R^{A2}$ are each independently H, halogen, hydroxy, —O—P(O)(OH)$_2$, —O—P(O)($R^I R^{II}$)$_2$, —N($R^e$)($R^f$), —CO$_2 R^f$, —N($R^f$)COR$^b$, —N($R^g$)SO$_2$(C$_1$-C$_4$alkyl)-N($R^e$)($R^f$), —N($R^g$)CO(C$_1$-C$_4$alkyl)-N($R^h$)($R^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, —O—P(O)(OH)$_2$, —O—P(O)($R^I R^{II}$)$_2$, C$_1$-C$_4$alkoxy-, —N($R^e$)($R^f$), —CO$_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$,
—O—P(O)($R^I R^{II}$)$_2$, amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)($R^I R^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)($R^I R^{II}$)$_2$, or C$_1$-C$_4$alkoxy-(C$_1$-C$_4$alkoxy)-;
when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —O—P(O)(OH)$_2$, —O—P(O)($R^I R^{II}$)$_2$, —O$R^c$, —NH$_2$, —NR$^c R^c$, —NR$^c R^d$, —OCOR$^c$, —CO$_2$H, —CO$_2 R^c$, —SOR$^c$, —SO$_2 R^c$, —CONH$_2$, —CONR$^c R^d$, —SO$_2$NH$_2$, —SO$_2$NR$^c R^d$, —OCONH$_2$, —OCONR$^c R^d$, —NR$^d$COR$^c$, —NR$^d$SOR$^c$, —NR$^d$CO$_2 R^c$, and —NR$^d$SO$_2 R^c$;
when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^c R^d$, —CO$_2 R^c$, —CONR$^c R^d$, —SO$_2$NR$^c R^d$, and —OCONR$^c R^d$;
when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_2$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-,
wherein the alkyl moiety of said optionally substituted —C$_1$-C$_{12}$alkyl-, optionally substituted —C$_2$-C$_{12}$alkenyl-, optionally substituted —C$_2$-C$_2$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —O—P(O)(OH)$_2$, —O—P(O)($R^I R^{II}$)$_2$, —OR$^c$, —NH$_2$, —NR$^c R^d$, —OCOR$^c$, —CO$_2$H, —CO$_2 R^c$, —SOR$^c$, —SO$_2 R^c$, —CONH$_2$, —CONR$^c R^d$, —SO$_2$NH$_2$, —SO$_2$NR$^c R^d$, —OCONH$_2$, —OCONR$^c R^d$, —NR$^d$COR$^c$, —NR$^d$SOR$^c$, —NR$^d$CO$_2 R^c$, and —NR$^d$SO$_2 R^c$,
and
the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)($R^IR^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, —($C_1$-$C_4$alkoxyl)-O—P(O)(OH)$_2$, —($C_1$-$C_4$alkoxyl)-O—P(O)($R^IR^{II}$)$_2$ and $C_1$-$C_4$alkoxy-($C_1$-$C_4$alkoxy)-;

when r is 1, $R^{B1}$ and $R^{B2}$ are each independently —CH$_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —O—P(O)(OH)$_2$, —O—P(O)($R^IR^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^IR^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)O—P(O)(OH)$_2$, —($C_2$-$C_4$alkoxy)-O—P(O)($R^IR^{II}$)$_2$, and $C_1$-$C_4$alkoxy-($C_1$-$C_4$alkoxy)-;

when s is 1, $R^{C1}$ and $R^{C2}$ are each independently —CH$_2$—, and C, taken together with $R^{C1}$ and $R^{C2}$, forms a linking group, wherein C is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —O—P(O)(OH)$_2$, —O—P(O)($R^IR^{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^IR^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^IR^{II}$)$_2$, and $C_1$-$C_4$alkoxy-($C_1$-$C_4$alkoxy)-;

$R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^IR^{II}$)$_2$, —NH$_2$, —NR$^c$R$^c$, —NR$^c$R$^d$, —COR$^c$, —CO$_2$R$^c$, —N($R^d$)COR$^c$, —N($R^d$)SO$_2$R$^c$, —N($R^g$)SO$_2$($C_1$-$C_2$alkyl)-N($R^h$)($R^f$), —N($R^g$)CO($C_1$-$C_2$alkyl)-N($R^h$)($R^f$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —O—P(O)(OH)$_2$, —O—P(O)($R^IR^{II}$)$_2$, —OR$^c$, —NH$_2$, —NR$^c$R$^c$, —NR$^c$R$^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$R$^{II}$)$_2$, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

R$^{14}$ is optionally substituted C$_1$-C$_4$alkyl, wherein said optionally substituted C$_1$-C$_4$alkyl is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

R$^{16}$ is H, halogen, or C$_1$-C$_4$alkyl;

R$^{15}$ and R$^{17}$ are each independently H, cyclopropyl, or C$_1$-C$_4$alkyl;

R$^a$ is H, —R$^c$, —COR$^c$, —CO$_2$H, —CO$_2$R$^c$, —SOR$^c$, —SO$_2$R$^c$, —CONH$_2$, —CONR$^c$R$^d$, —SO$_2$NH$_2$, or —SO$_2$NR$^c$R$^d$;

each R$^b$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^I$R$^{II}$)$_2$, —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), or —(C$_1$-C$_4$alkyl)-CO—O—(C$_1$-C$_4$alkyl);

each R$^c$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkyl)-O—P(O)(R$^I$R$^{II}$)$_2$, —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), —(C$_1$-C$_4$alkyl)-CO—O—(C$_1$-C$_4$alkyl), optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl, wherein the C$_3$-C$_6$cycloalkyl, phenyl, 4-6 membered heterocycloalkyl, 5-6 membered heteroaryl or 9-10 membered heteroaryl moiety of said optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl is optionally substituted by 1-4 substituents each independently selected from halogen, hydroxy, —O—P(O)(OH)$_2$, —O—P(O)(R$^I$R$^{II}$)$_2$, amino, —(C$_1$-C$_4$alkyl)NH$_2$, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

each R$^d$ is independently H or C$_1$-C$_4$alkyl;

each R$^e$ is independently H, (C$_1$-C$_4$alkyl), —CO(C$_1$-C$_4$alkyl), —OCO(C$_1$-C$_4$alkyl), —CO$_2$(C$_1$-C$_4$alkyl), —(C$_1$-C$_4$alkyl)NH$_2$, —(C$_1$-C$_4$alkyl) C$_1$-C$_4$alkoxy, —CO-(optionally substituted 5-6 membered heterocycloalkyl), —CO(C$_1$-C$_4$alkyl)-(optionally substituted 5-6 membered heterocycloalkyl), —CO(optionally substituted 5-6 membered heteroaryl), —CO(C$_1$-C$_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—P(O)(OH)$_2$, —O—P(O)(R$^I$R$^{II}$)$_2$, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$;

each R$^f$ is independently H or (C$_1$-C$_4$alkyl);

R$^g$ and R$^h$ are each independently H or (C$_1$-C$_4$alkyl) or R$^g$ and R$^h$, taken together with the atom or atoms through which they are connected, form a 5-6 membered ring;

and each occurrence of R$^I$ and R$^{II}$ are independently (C$_1$-C$_6$alkyl)oxy-;

or a tautomer thereof;

or a salt thereof, particularly a pharmaceutically acceptable salt, thereof.

Another aspect of the present invention is directed to compounds of Formula (I)

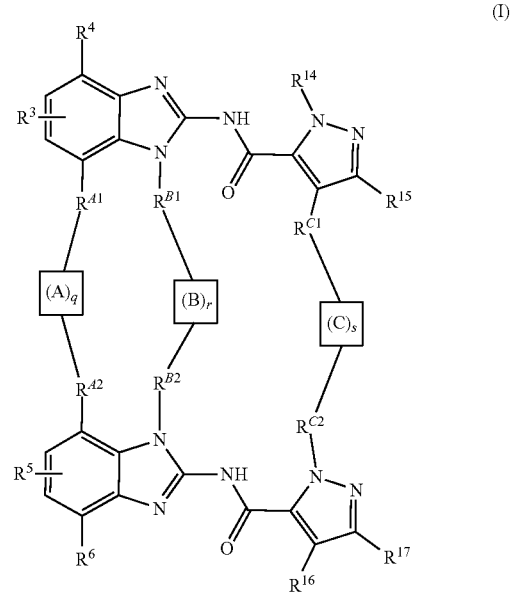

(I)

wherein:
q is 0 or 1;
r is 0 or 1;
s is 0 or 1;
wherein q+r+s=1 or 2;
when q is 0, R$^{41}$ and R$^{42}$ are each independently H, halogen, hydroxy, —N(R$^e$)(R$^f$), —CO$_2$R$^f$, —N(R)COR$^b$, —N(R$^g$)SO$_2$(C$_1$-C$_4$alkyl)-N(R$^e$)(R$^f$), —N(R$^g$)CO(C$_1$-C$_4$alkyl)-N ($R^h$)($R^f$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
  wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from hydroxy, $C_1$-$C_4$alkoxy-, —N($R^e$)($R^f$), —$CO_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;
when r is 0, $R^{B1}$ and $R^{B2}$ are each independently H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl,
  wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$;
when s is 0, $R^{C1}$ is H, halogen, or $C_1$-$C_4$alkyl and $R^{C2}$ is optionally substituted $C_1$-$C_4$alkyl, wherein said optionally substituted $C_1$-$C_4$alkyl group is optionally substituted by a substituent selected from —$OR^c$, —$NR^cR^d$, —$CO_2R^c$, —$CONR^cR^d$, —$SO_2NR^cR^d$, and —$OCONR^cR^d$;
when q is 1, $R^{A1}$ and $R^{A2}$ are each independently —$CH_2$—, —$NR^e$—, or —O—, and A, taken together with $R^{A1}$ and $R^{A2}$, forms a linking group, wherein A is -halo($C_1$-$C_{12}$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-,
  wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, halo($C_1$-$C_4$alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$,
  and
  the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;
when r is 1, $R^{B1}$ and $R^{B2}$ are each independently —$CH_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-,
  wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$,
  and
  the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;

when s is 1, $R^{C1}$ and $R^{C2}$ are each independently —$CH_2$—, and C, taken together with $R^{C1}$ and $R^{C2}$, forms a linking group, wherein C is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-,
  wherein the alkyl moiety of said optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and
  the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;

$R^3$ and $R^5$ are each independently —$CON(R^d)(R^f)$, or one of $R^3$ and $R^5$ is —$CON(R^d)(R^f)$, and the other of $R^3$ and $R^5$ is H or —$CO_2(R^c)$;

$R^4$ and $R^6$ are each independently selected from H, halogen, halo($C_1$-$C_6$alkyl), halo($C_1$-$C_6$alkoxy)-, hydroxy, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-$N(R^h)(R^f)$, —$N(R^g)CO(C_1$-$C_2$alkyl)-$N(R^h)(R^f)$, optionally substituted ($C_1$-$C_6$alkyl), optionally substituted ($C_1$-$C_6$alkyl) oxy-, optionally substituted ($C_1$-$C_6$alkyl)amino-, and optionally substituted ($C_1$-$C_6$alkyl)($C_1$-$C_4$alkyl)amino-,
  wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$;

$R^{14}$ is optionally substituted $C_1$-$C_4$alkyl, wherein said optionally substituted $C_1$-$C_4$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;

$R^{16}$ is H, halogen, or $C_1$-$C_4$alkyl;

$R^{15}$ and $R^{17}$ are each independently H, cyclopropyl, or $C_1$-$C_4$alkyl;

$R^a$ is H, —$R^c$, —$COR^c$, —$C_2H$, —$CO_2R^c$, —$SOR^c$, —$S_2R^c$, —$CONH_2$, —$CONR^cR^d$, —$S_2NH_2$, or —$SO_2NR^cR^d$;

each $R^b$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-$N(R^e)(R^f)$—($C_1$-$C_4$alkyl)-O—CO($C_1$-$C_4$alkyl), or —($C_1$-$C_4$alkyl)-CO—O—($C_1$-$C_4$alkyl);

each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-$N(R^e)(R^f)$, —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl,
  wherein the $C_3$-$C_6$cycloalkyl, phenyl, 4-6 membered heterocycloalkyl, 5-6 membered heteroaryl or 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, $(C_1-C_4alkyl)$amino-, $(C_1-C_4alkyl)(C_1-C_4alkyl)$amino-, $C_1-C_4alkyl$, halo$(C_1-C_4alkyl)$, halo$(C_1-C_4alkoxy)$-, $C_1-C_4alkoxy$-, hydroxy-$(C_2-C_4alkoxy)$-, $C_1-C_4alkoxy$-$(C_1-C_4alkoxy)$-, —$COR^d$, —$CON(R^d)(R^f)$, and —$CO_2R^d$;

each $R^d$ is independently H or $C_1-C_4alkyl$;

each $R^e$ is independently H, $(C_1-C_4alkyl)$, —$CO(C_1-C_4alkyl)$, —$OCO(C_1-C_4alkyl)$, —$CO_2(C_1-C_4alkyl)$, —CO-(optionally substituted 5-6 membered heterocycloalkyl), —$CO(C_1-C_4alkyl)$-(optionally substituted 5-6 membered heterocycloalkyl), —CO(optionally substituted 5-6 membered heteroaryl), —$CO(C_1-C_4alkyl)$-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, amino, $(C_1-C_4alkyl)$amino-, $(C_1-C_4alkyl)(C_1-C_4alkyl)$amino-, $C_1-C_4alkyl$, halo$(C_1-C_4alkyl)$, halo$(C_1-C_4alkoxy)$-, $C_1-C_4alkoxy$-, hydroxy-$(C_2-C_4alkoxy)$-, $C_1-C_4alkoxy$-$(C_1-C_4alkoxy)$-, —$COR^d$, —$CON(R^d)(R^f)$, and —$CO_2R^d$;

each $R^f$ is independently H or $(C_1-C_4alkyl)$;

$R^g$ and $R^h$ are each independently H or $(C_1-C_4alkyl)$ or $R^g$ and $R^h$, taken together with the atom or atoms through which they are connected, form a 5-6 membered ring;

or a tautomer thereof;

or a salt, particularly a pharmaceutically acceptable salt, thereof.

The alternative definitions for the various groups and substituent groups of Formula (I-N), (I) or Formula (I-P) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will be appreciated by those skilled in the art that the compounds of this invention may exist in other tautomeric forms including zwitterionic forms, or isomeric forms. All tautomeric (including zwitterionic forms) and isomeric forms of the formulas and compounds described herein are intended to be encompassed within the scope of the present invention.

It will also be appreciated by those skilled in the art that the compounds of this invention may exist in tautomeric forms including, but not limited to, Formula (A), Formula (B) and/or Formula (C) or zwitterionic forms including, but not limited to, Formula (D) or Formula (E).

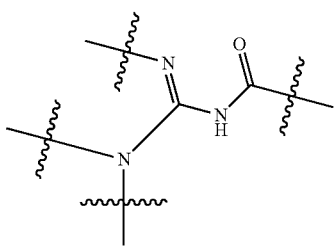

Formula (A)

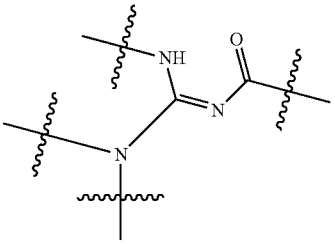

Formula (B)

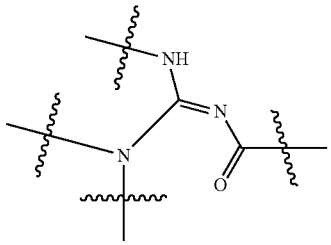

Formula (C)

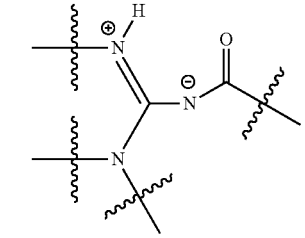

Formula (D)

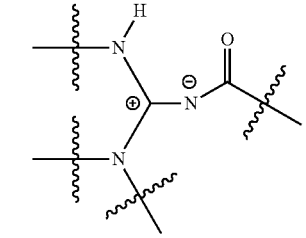

Formula (E)

The chemical names provided for the intermediate compounds and/or the compounds of this invention described herein may refer to any one of the tautomeric representations of such compounds (in some instances, such alternate names are provided with the experimental). It is to be understood that any reference to a named compound (an intermediate compound or a compound of the invention) or a structurally depicted compound (an intermediate compound or a compound of the invention) is intended to encompass all tautomeric forms including zwitterionic forms of such compounds and any mixture thereof.

As used herein, the term "alkyl" represents a saturated, straight or branched hydrocarbon group having the specified number of carbon atoms. The term "$C_1-C_4alkyl$" refers to a straight or branched alkyl moiety containing from 1 to 4 carbon atoms. Exemplary alkyls include, but are not limited to methyl, ethyl, n-propyl, isopropyl, n-butyl, isobutyl, s-butyl, t-butyl, pentyl and hexyl.

When a substituent term such as "alkyl" is used in combination with another substituent term, for example as in "hydroxy$(C_1-C_4alkyl)$", the linking substituent term (e.g., alkyl) is intended to encompass a divalent moiety, wherein the point of attachment is through that linking substituent. Examples of "hydroxy$(C_1-C_4alkyl)$" groups include, but are not limited to, hydroxymethyl, hydroxyethyl, and hydroxyisopropyl.

As used herein, the term "halo(alkyl)" represents a saturated, straight or branched hydrocarbon group having the specified number (n) of carbon atoms and one or more (up to 2n+1) halogen atoms. For example, the term "halo($C_1$-$C_4$alkyl)" represents a group having one or more halogen atoms, which may be the same or different, at one or more carbon atoms of an alkyl moiety containing from 1 to 4 carbon atoms. Examples of "halo($C_1$-$C_4$alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having the specified number of carbon atoms and at least 1 and up to 3 carbon-carbon double bonds. Examples include ethenyl and propenyl.

"Alkynyl" refers to straight or branched hydrocarbon group having the specified number of carbon atoms and at least 1 and up to 3 carbon-carbon triple bonds. Examples include ethynyl and propynyl.

"Alkoxy-" or "(alkyl)oxy-" refers to an "alkyl-oxy-" group, containing an alkyl moiety, having the specified number of carbon atoms, attached through an oxygen linking atom. For example, the term "$C_1$-$C_4$alkoxy-" represents a saturated, straight or branched hydrocarbon moiety having at least 1 and up to 4 carbon atoms attached through an oxygen linking atom. Exemplary "$C_1$-$C_4$alkoxy-" or "($C_1$-$C_4$alkyl)oxy-" groups include, but are not limited to, methoxy, ethoxy, n-propoxy, isopropoxy, n-butoxy, s-butoxy, and t-butoxy.

As used herein, the term "halo(alkoxy)-" represents a saturated, straight or branched hydrocarbon group having the specified number (n) of carbon atoms and one or more (up to 2n+1) halogen atoms, attached through an oxygen linking atom. For example, the term "halo($C_1$-$C_4$alkoxy)-" refers to a "haloalkyl-oxy-" group, containing a "halo($C_1$-$C_4$alkyl)" moiety attached through an oxygen linking atom. Exemplary "halo($C_1$-$C_4$alkoxy)-" groups include, but are not limited to, —$OCHF_2$ (difluoromethoxy), —$OCF_3$ (trifluoromethoxy), —$OCH_2CF_3$ (trifluoroethoxy), and —OCH$(CF_3)_2$ (hexafluoroisopropoxy).

A carbocyclic group or moiety is a cyclic group or moiety in which the ring members are carbon atoms, which may be saturated, partially unsaturated (non-aromatic) or fully unsaturated (aromatic).

"Cycloalkyl" refers to a non-aromatic, saturated, hydrocarbon ring group containing the specified number of carbon atoms in the ring. For example, the term "$C_3$-$C_6$cycloalkyl" refers to a cyclic group having from three to six ring carbon atoms. Exemplary "$C_3$-$C_6$cycloalkyl" groups include cyclopropyl, cyclobutyl, cyclopentyl, and cyclohexyl.

A heterocyclic group or moiety is a cyclic group or moiety having, as ring members, atoms of at least two different elements, which cyclic group or moiety may be saturated, partially unsaturated (non-aromatic) or fully unsaturated (aromatic).

"Heteroatom" refers to a nitrogen, sulfur, or oxygen atom, for example a nitrogen atom or an oxygen atom.

"Heterocycloalkyl" refers to a non-aromatic, monocyclic or bicyclic group containing 3-10 ring atoms and containing one or more (generally one or two) heteroatom ring members independently selected from oxygen, sulfur, and nitrogen. The point of attachment of a heterocycloalkyl group may be by any suitable carbon or nitrogen atom.

Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, and hexahydro-1H1,4-diazepinyl.

Examples of "4-membered heterocycloalkyl" groups include oxetanyl, thietanyl and azetidinyl.

The term "5-6 membered heterocycloalkyl" represents a saturated, monocyclic group, containing 5 or 6 ring atoms, which includes one or two heteroatoms selected independently from oxygen, sulfur, and nitrogen. Illustrative examples of 5-6 membered heterocycloalkyl groups include, but are not limited to pyrrolidinyl, tetrahydrofuranyl, tetrahydrothienyl, tetrahydropyranyl, tetrahydrothiopyranyl, piperidinyl, piperazinyl, morpholinyl, and thiomorpholinyl.

"Heteroaryl" refers to an aromatic monocyclic or bicyclic group containing 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups containing either a phenyl ring fused to a heterocyclic moiety or a heteroaryl ring moiety fused to a carbocyclic moiety. The point of attachment of a heteroaryl group may be by any suitable carbon or nitrogen atom.

The term "5-6 membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, and oxadiazolyl. Selected 6-membered heteroaryl groups include pyridinyl (pyridyl), pyrazinyl, pyrimidinyl, pyridazinyl and triazinyl.

The term "9-10 membered heteroaryl" refers to an aromatic bicyclic group containing 9 or 10 ring atoms, including 1 to 4 heteroatoms independently selected from nitrogen, oxygen and sulfur. Examples of 9-membered heteroaryl (6,5-fused heteroaryl) groups include benzothienyl, benzofuranyl, indolyl, indolinyl (dihydroindolyl), isoindolyl, isoindolinyl, indazolyl, isobenzofuryl, 2,3-dihydrobenzofuryl, benzoxazolyl, benzoisoxazolyl, benzothiazolyl, benzoisothiazolyl, benzimidazolyl, benzoxadiazolyl, benzothiadiazolyl, benzotriazolyl, purinyl, imidazopyridinyl, pyrazolopyridinyl, triazolopyridinyl and 1,3-benzodioxolyl.

Examples of 10-membered heteroaryl (6,6-fused heteroaryl) groups include quinolinyl (quinolyl), isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, 1,2,3,4-tetrahydroquinolinyl (tetrahydroquinolinyl), 1,2,3,4-tetrahydroisoquinolinyl (tetrahydroisoquinolinyl), cinnolinyl, pteridinyl, and 2,3-dihydrobenzo[b][1,4]dioxinyl.

The terms "halogen" and "halo" refers to a halogen radical, for example, a fluoro, chloro, bromo, or iodo substituent.

"Oxo" represents a double-bonded oxygen moiety; for example, if attached directly to a carbon atom forms a carbonyl moiety (C=O).

"Hydroxy" or "hydroxyl" is intended to mean the radical —OH.

As used herein, the term "cyano" refers to a nitrile group, —C≡N.

As used herein, the term "optionally substituted" indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s) as defined in the substituent definitions (A, $R^3$, etc,) provided herein. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the terms "compound(s) of the invention" or "compound(s) of this invention" mean a compound of Formula (I-N), Formula (I) or Formula (I-P), as defined herein, in any form, i.e., any tautomeric form, any isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi- hydrates)), and mixtures of various forms.

Accordingly, included within the present invention are the compounds of Formula (I-N), (I-P) or (I), as defined herein, in any salt or non-salt form and any physical form thereof, and mixtures of various forms. While such are included within the present invention, it will be understood that the compounds of Formula (I-N), (I-P) or (I), as defined herein, in any salt or non-salt form, and in any physical form thereof, may have varying levels of activity, different bioavailabilities and different handling properties for formulation purposes.

In one embodiment of the compounds of this invention, $R^3$ and $R^5$ are each independently —CON($R^d$)($R^f$), or one of $R^3$ and $R^5$ is —CON($R^d$)($R^f$), and the other of $R^3$ and $R^5$ is H or —CO$_2$($R^c$). In one embodiment, $R^3$ and $R^5$ are each independently —CON($R^d$)($R^f$). In another embodiment, one of $R^3$ and $R^5$ is —CON($R^d$)($R^f$) and the other of $R^3$ and $R^5$ is H. In a specific embodiment, $R^3$ and $R^5$ are each —CONH$_2$.

It is to be understood that when q is 0, A is absent and $R^{A1}$ and $R^{A2}$ are not connected. Similarly, it is to be understood that when r is 0, B is absent and $R^{B1}$ and $R^{B2}$ are not connected. Similarly, it is to be understood that when s is 0, C is absent and $R^{C1}$ and $R^{C2}$ are not connected.

In one embodiment of the compounds of this invention, q is 1, r is 0 and s is 0 (q+r+s=1) and the compound has Formula (I-A) or (I-a):

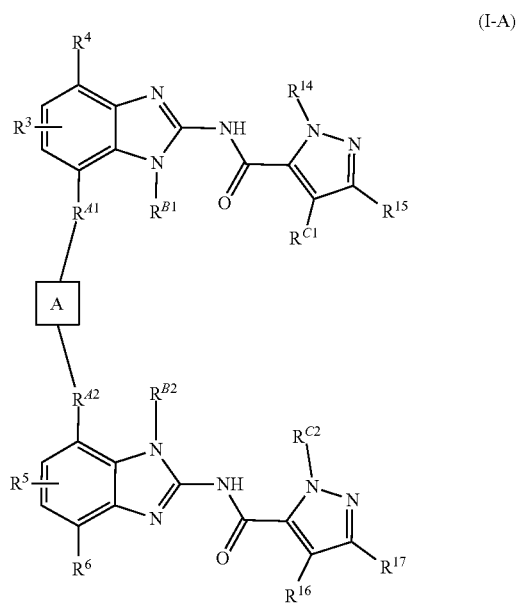

(I-A)

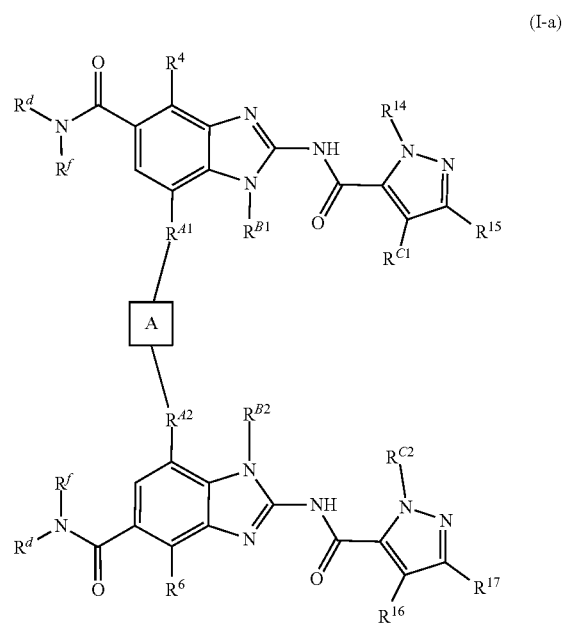

(I-a)

In one embodiment of the compounds of this invention, q is 0, r is 1 and s is 0 (q+r+s=1) and the compound has Formula (I-B) or (I-b):
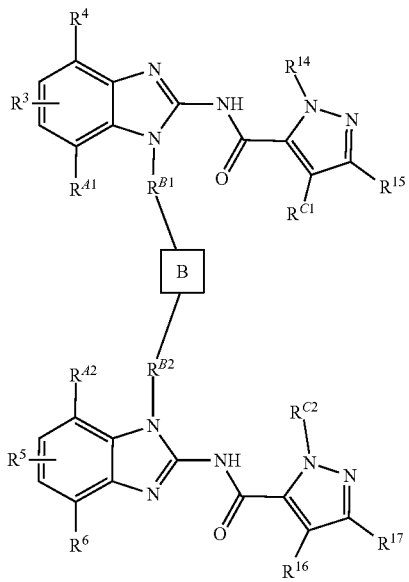
(I-B)
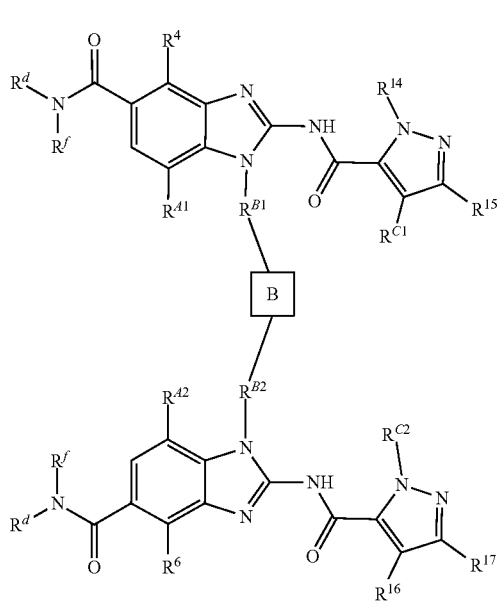
(I-b)
In one embodiment of the compounds of this invention, q is 0, r is 0 and s is 1 (q+r+s=1) and the compound has Formula (I-C) or (I-c):
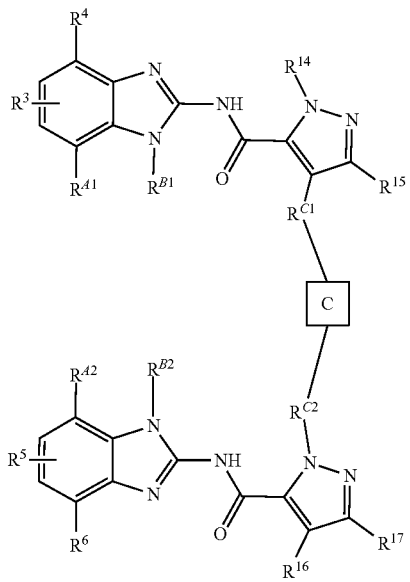
(I-C)
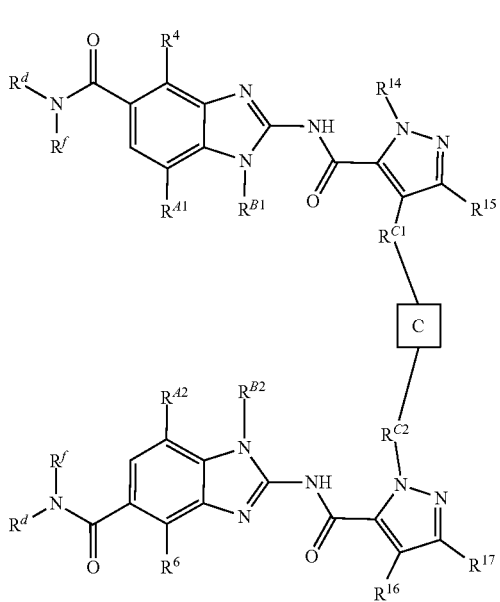
(I-c)

In one embodiment of the compounds of this invention, q is 1, r is 1 and s is 0 (q+r+s=2) and the compound has Formula (I-AB) or (I-ab):
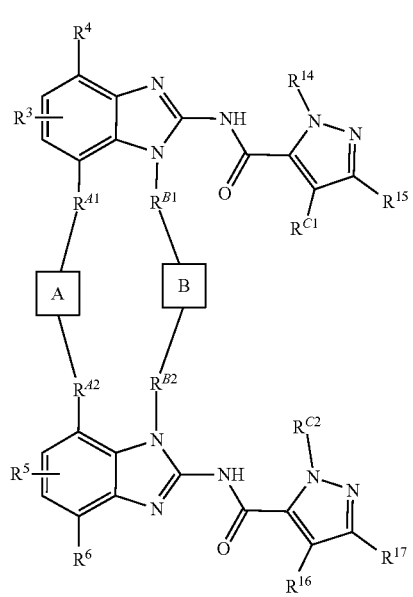
(I-AB)
In one embodiment of the compounds of this invention, q is 1, r is 0 and s is 1 (q+r+s=2) and the compound has Formula (I-AC) or (I-ac):
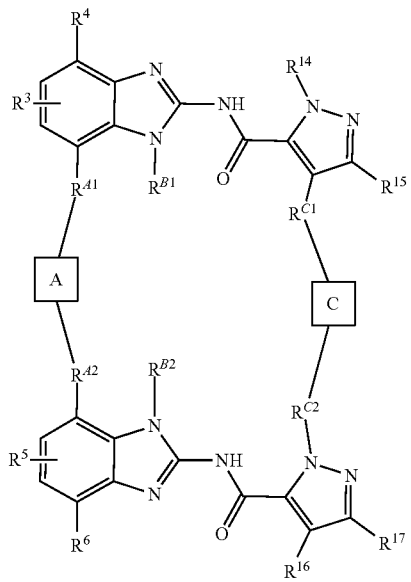
(I-AC)
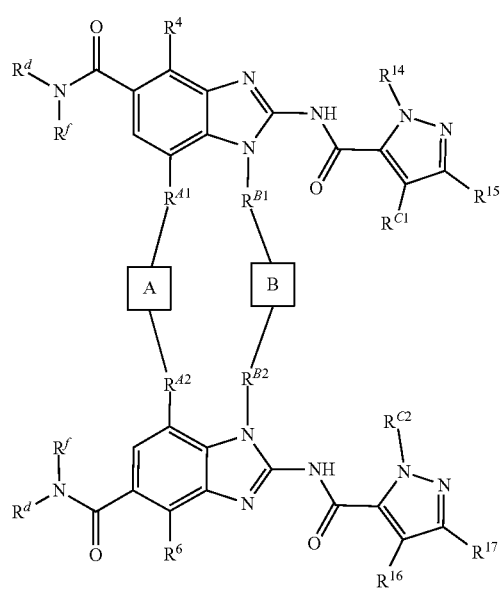
(I-ab)
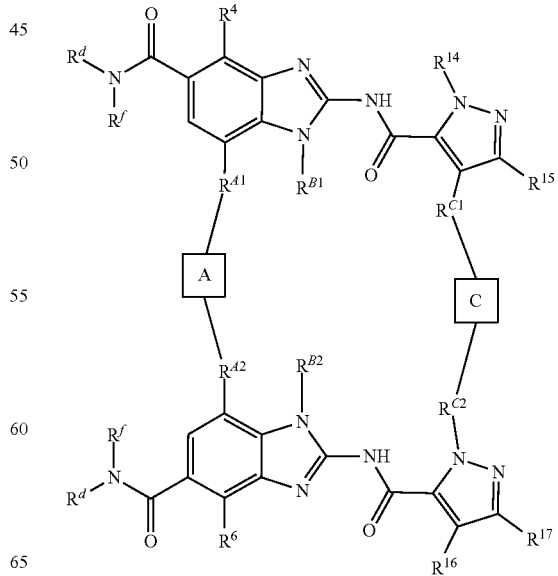
(I-ac)

In one embodiment of the compounds of this invention, q is 0, r is 1 and s is 1 (q+r+s=2) and the compound has Formula (I-BC) or (I-bc):

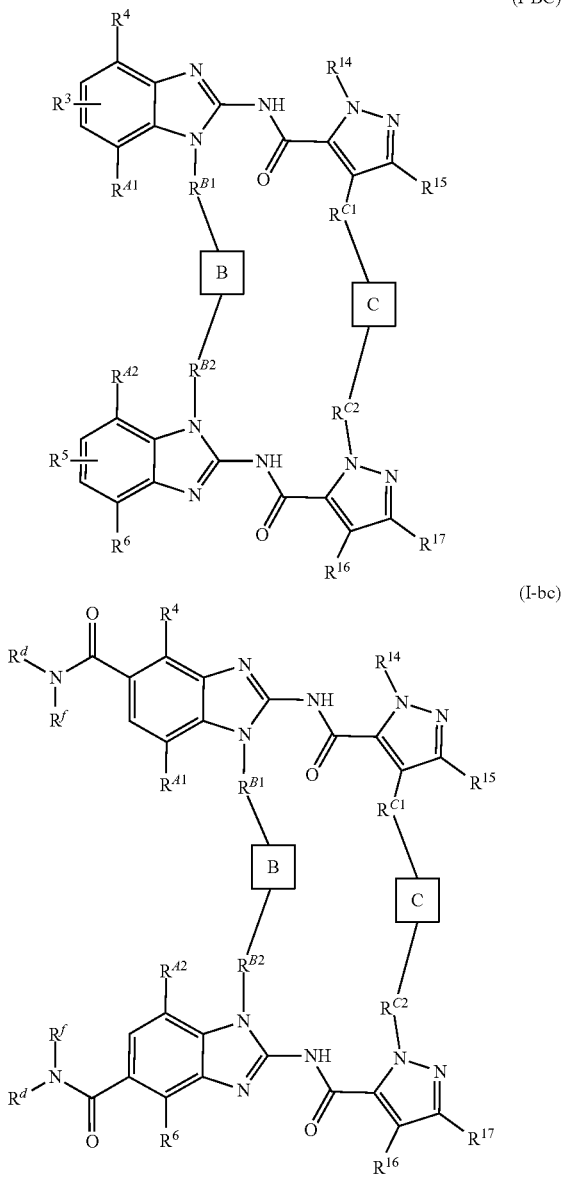

In one embodiment of the compounds of this invention, q is 0 and $R^{A1}$ and $R^{A2}$ are each independently H, halogen, hydroxy, —N($R^e$)($R^f$), —CO$_2R^f$, —N($R^f$)COR$^b$, —N($R^g$)SO$_2$(C$_1$-C$_4$alkyl)-N($R^e$)($R^f$), —N($R^g$)CO(C$_1$-C$_4$alkyl)-N($R^h$)($R^f$) optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxyl, C$_1$-C$_4$alkoxy-, —N($R^e$)($R^f$), —CO$_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, halo(C$_1$-C$_4$alkoxy)-, C$_1$-C$_4$alkoxy-, hydroxy-(C$_2$-C$_4$alkoxy)-, and C$_1$-C$_4$alkoxy-(C$_1$-C$_4$alkoxy)-.

In one embodiment of the compounds of this invention, q is 0 and $R^A$ and $R^{A2}$ are each independently H, halogen, hydroxy, —O—P(O)(OH)$_2$, —O—P(O)($R^IR^{II}$)$_2$, —N($R^e$)($R^f$), —CO$_2R^f$, —N($R^f$)COR$^b$, —N($R^g$)SO$_2$(C$_1$-C$_4$alkyl)-N($R^e$)($R^f$), —N($R^g$)CO(C$_1$-C$_4$alkyl)-N($R^h$)($R^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxyl, —O—P(O)(OH)$_2$, —O—P(O)($R^IR^{II}$)$_2$, C$_1$-C$_4$alkoxy-, —N($R^e$)($R^f$), —CO$_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)($R^IR^{II}$)$_2$, amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)($R^IR^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)($R^IR^{II}$)$_2$, and C$_1$-C$_4$alkoxy-(C$_1$-C$_4$alkoxy)-.

In one embodiment of the compounds of this invention, q is 0 and $R^A$ and $R^{A2}$ are each independently H, hydroxy, amino, (C$_1$-C$_4$alkyl)amino-, (C$_1$-C$_4$alkyl)(C$_1$-C$_4$alkyl)amino-, (C$_1$-C$_4$alkyl), hydroxy(C$_1$-C$_4$alkyl)-, amino(C$_1$-C$_4$alkyl)-, (C$_1$-C$_4$alkyl)amino(C$_1$-C$_4$alkyl)-, (C$_1$-C$_4$alkyl)(C$_1$-C$_4$alkyl)amino(C$_1$-C$_4$alkyl)-, C$_1$-C$_4$alkoxy-, hydroxy(C$_2$-C$_4$alkoxy)-, amino(C$_2$-C$_4$alkoxy)-, (C$_1$-C$_4$alkyl)amino(C$_2$-C$_4$alkoxy)-, (C$_1$-C$_4$alkyl)(C$_1$-C$_4$alkyl)amino(C$_2$-C$_4$alkoxy)-, 6-membered heterocycloalkyl-(C$_1$-C$_4$alkyl)-, phenyl(C$_1$-C$_4$alkoxy)-, (C$_1$-C$_4$alkyl)OCONH(C$_1$-C$_4$alkyl)-, hydroxy(C$_1$-C$_4$alkyl)amino-, (C$_1$-C$_4$alkyl)CONH—, (C$_1$-C$_4$alkyl)CON(C$_1$-C$_4$alkyl)-, —CO$_2$H, —CO$_2$(C$_1$-C$_4$alkyl), amino(C$_1$-C$_4$alkyl)CONH—, (C$_1$-C$_4$alkyl)amino(C$_1$-C$_4$alkyl)CONH—, (C$_1$-C$_4$alkyl)(C$_1$-C$_4$alkyl)amino(C$_1$-C$_4$alkyl)CONH—, amino(C$_1$-C$_4$alkyl)CON(C$_1$-C$_4$alkyl)-, (C$_1$-C$_4$alkyl)amino(C$_1$-C$_4$alkyl)CON(C$_1$-C$_4$alkyl)-, hydroxy(C$_1$-C$_4$alkyl)CONH—, (C$_1$-C$_4$alkyl)(C$_1$-C$_4$alkyl)amino(C$_1$-C$_4$alkyl)CON(C$_1$-C$_4$alkyl)-, hydroxy(C$_1$-C$_4$alkyl)CON(C$_1$-C$_4$alkyl)-, HO$_2$C(C$_1$-C$_4$alkoxy)-, (C$_1$-C$_4$alkyl)OCO(C$_1$-C$_4$alkoxy)-, H$_2$NCO(C$_1$-C$_4$alkoxy)-, (C$_1$-C$_4$alkyl)HNCO(C$_1$-C$_4$alkoxy)-, (C$_1$-C$_4$alkyl)(C$_1$-C$_4$alkyl)NCO(C$_1$-C$_4$alkoxy)-, and —NHSO$_2$(C$_1$-C$_4$alkyl).

In one embodiment of the compounds of this invention, q is 0 and $R^A$ and $R^{A2}$ are each independently H, hydroxy, —O—P(O)(OH)$_2$, —O—P(O)($R^IR^{II}$)$_2$, amino, (C$_1$-C$_4$alkyl)amino-, (C$_1$-C$_4$alkyl)(C$_1$-C$_4$alkyl)amino-, (C$_1$-C$_4$alkyl), hydroxy($C_1$-$C_4$alkyl)-, amino($C_1$-$C_4$alkyl)-, ($C_1$-$C_4$alkyl)amino($C_1$-$C_4$alkyl)-, ($C_1$-$C_4$alkyl)($C_1$-$C_4$alkyl)amino($C_1$-$C_4$alkyl)-, $C_1$-$C_4$alkoxy-, hydroxy($C_2$-$C_4$alkoxy)-, —($C_2$-$C_4$alkoxy)-O—P(O)(OH)$_2$, —($C_2$-$C_4$alkoxy)-O—P(O)($R^I R^{II}$)$_2$, amino($C_2$-$C_4$alkoxy)-, ($C_1$-$C_4$alkyl)amino($C_2$-$C_4$alkoxy)-, ($C_1$-$C_4$alkyl)($C_1$-$C_4$alkyl)amino($C_2$-$C_4$alkoxy)-, 6-membered heterocycloalkyl-($C_1$-$C_4$alkyl)-, phenyl($C_1$-$C_4$alkoxy)-, ($C_1$-$C_4$alkyl)OCONH($C_1$-$C_4$alkyl)-, hydroxy($C_1$-$C_4$alkyl)amino-, -amino($C_1$-$C_4$alkyl)-O—P(O)(OH)$_2$, -amino($C_1$-$C_4$alkyl)-O—P(O)($R^I R^{II}$)$_2$, ($C_1$-$C_4$alkyl)CONH—, ($C_1$-$C_4$alkyl)CON($C_1$-$C_4$alkyl)-, —CO$_2$H, —CO$_2$($C_1$-$C_4$alkyl), amino($C_1$-$C_4$alkyl)CONH—, ($C_1$-$C_4$alkyl)amino($C_1$-$C_4$alkyl)CONH—, ($C_1$-$C_4$alkyl)($C_1$-$C_4$alkyl)amino($C_1$-$C_4$alkyl)CONH—, amino($C_1$-$C_4$alkyl)CON($C_1$-$C_4$alkyl)-, ($C_1$-$C_4$alkyl)amino($C_1$-$C_4$alkyl)CON($C_1$-$C_4$alkyl)-, hydroxy($C_1$-$C_4$alkyl)CONH—, —NHCO($C_1$-$C_4$alkyl)-O—P(O)(OH)$_2$, —NHCO($C_1$-$C_4$alkyl)-O—P(O)($R^I R^{II}$)$_2$, ($C_1$-$C_4$alkyl)($C_1$-$C_4$alkyl)amino($C_1$-$C_4$alkyl)CON($C_1$-$C_4$alkyl)-, hydroxy($C_1$-$C_4$alkyl)CON($C_1$-$C_4$alkyl)-, —($C_1$-$C_4$alkyl)NCO($C_1$-$C_4$alkyl)-O—P(O)(OH)$_2$, —($C_1$-$C_4$alkyl)NCO($C_1$-$C_4$alkyl)-O—P(O)($R^I R^{II}$)$_2$, HO$_2$C($C_1$-$C_4$alkoxy)-, ($C_1$-$C_4$alkyl)OCO($C_1$-$C_4$alkoxy)-, H$_2$NCO($C_1$-$C_4$alkoxy)-, ($C_1$-$C_4$alkyl)HNCO($C_1$-$C_4$alkoxy)-, ($C_1$-$C_4$alkyl)($C_1$-$C_4$alkyl)NCO($C_1$-$C_4$alkoxy)-, and —NHSO$_2$($C_1$-$C_4$alkyl).

In one embodiment, q is 0 and $R^A$ and $R^{A2}$ are each independently H, ($C_1$-$C_6$alkyl)oxy- or hydroxy($C_2$-$C_6$alkyl)oxy-. In one embodiment, q is 0 and $R^{A1}$ and $R^{A2}$ are each independently H, ($C_1$-$C_6$alkyl)oxy-, hydroxy($C_2$-$C_6$alkyl)oxy-, —($C_2$-$C_4$alkoxy)-O—P(O)(OH)$_2$, —($C_2$-$C_4$alkoxy)-O—P(O)($R^I R^{II}$)$_2$. In one embodiment, q is 0 and $R^{A1}$ and $R^{A2}$ are each H. In selected embodiments, q is 0 and $R^A$ and $R^{A2}$ are independently selected from H, —OCH$_2$CH$_2$CH$_2$OH and —OCH$_3$.

In one embodiment, q is 0 and $R^{A2}$ and $R^{A1}$ are each independently H, optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, —O—P(O)(OH)$_2$, —O—P(O)($R^I R^{II}$)$_2$, $C_1$-$C_4$alkoxyl, —N($R^e$)($R^f$), —COOH, optionally substituted phenyl, and optionally substituted 5-6 membered heterocycloalkyl, and each $R^e$ is independently selected from H, $C_1$-$C_4$alkyl, —CO($C_1$-$C_4$alkyl), —OCO($C_1$-$C_4$alkyl), —($C_1$-$C_4$alkyl)NH$_2$, —($C_1$-$C_4$alkyl)$C_1$-$C_4$alkoxy, or —CO$_2$($C_1$-$C_4$alkyl).

In one embodiment, q is 0 and $R^{A2}$ and $R^{A1}$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —O—P(O)(OH)$_2$, —O—P(O)($R^I R^{II}$)$_2$, —N($R^e$)($R^f$), $C_1$-$C_4$alkoxyl, phenyl, and optionally substituted 5-6 membered heterocycloalkyl containing at least one nitrogen or oxygen as a member of the ring, and each $R^e$ is each independently selected from H, $C_1$-$C_4$alkyl, —($C_1$-$C_4$alkyl)NH$_2$, or —($C_1$-$C_4$alkyl)$C_1$-$C_4$alkoxy.

In one embodiment, q is 0 and at least one of $R^{A2}$ or $R^A$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl and morpholinyl and each $R^e$ is each independently selected from H, $C_1$-$C_4$alkyl, —($C_1$-$C_4$alkyl)NH$_2$, or —($C_1$-$C_4$alkyl)$C_1$-$C_4$alkoxy.

In one embodiment, q is 0 and at least one of $R^{A2}$ or $R^{A1}$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from tetrahydropyran, pyrrolidinyl, piperazinyl, piperidyl and morpholinyl, and each $R^e$ is each independently selected from H or $C_1$-$C_4$alkyl.

In one embodiment of the compounds of this invention, r is 0 and $R^{B1}$ and $R^{B2}$ are each independently H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —$OR^c$, —NH$_2$, —$NR^c R^c$, —$NR^c R^d$, —$OCOR^c$, —CO$_2$H, —CO$_2R^c$, —$SOR^c$, —SO$_2R^c$, —CONH$_2$, —$CONR^c R^d$, —SO$_2$NH$_2$, —SO$_2NR^c R^d$, —OCONH$_2$, —$OCONR^c R^d$, —$NR^d COR^c$, —$NR^d SOR^c$, —$NR^d CO_2R^c$, and —$NR^d SO_2R^c$.

In one embodiment, r is 0 and $R^{B1}$ and $R^{B2}$ are each H.

In another embodiment, r is 0 and $R^{B1}$ and $R^{B2}$ are each independently H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted 5-6 membered heteroaryl or optionally substituted 9 membered heteroaryl.

In one embodiment of the compounds of this invention, s is 0 and $R^{C1}$ is H, halogen, or $C_1$-$C_4$alkyl and $R^{C2}$ is optionally substituted $C_1$-$C_4$alkyl, wherein said optionally substituted $C_1$-$C_4$alkyl group is optionally substituted by a substituent selected from —$OR^c$, —$NR^c R^d$, —CO$_2R^c$, —$CONR^c R^d$, —SO$_2NR^c R^d$, and —$OCONR^c R^d$.

In one embodiment of the compounds of this invention, when s is 0, $R^{C1}$ and $R^{C2}$ are each independently H or $C_1$-$C_4$alkyl. In another embodiment, when s is 0, $R^{C1}$ is $C_1$-$C_3$alkyl, specifically methyl. In another embodiment, when s is 0, $R^{C2}$ is $C_1$-$C_3$alkyl, specifically methyl or ethyl. In a selected embodiment, when s is 0, $R^{C2}$ is ethyl.

In one embodiment of the compounds of this invention, q is 1 and $R^A$ and $R^{A2}$ are each independently —CH$_2$—, —$NR^e$—, or —O—, and A, taken together with $R^{A1}$ and $R^{A2}$, forms a linking group, wherein A is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, halo($C_1$-$C_4$alkyl), —OH, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In one embodiment of the compounds of this invention, q is 1 and R$^A$ and R$^{A2}$ are each independently —CH$_2$—, —NR$^e$—, or —O—, and A, taken together with R$^{A1}$ and R$^{A2}$, forms a inking group, wherein A is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_2$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, halo($C_1$-$C_4$alkyl), —OH, —O—P(O)(OH)$_2$, —O—P(O)(R$_I$R$_{II}$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)(R$^I$R$^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)(R$^I$R$^{II}$)$_2$, and $C_1$-$C_4$alkoxy-($C_1$-$C_4$alkoxy)-.

In one embodiment, q is 1 and A, taken together with R$^{A1}$ and R$^{A2}$, forms a 4-8 membered linking group. In a further embodiment, q is 1 and A, taken together with R$^A$ and R$^{A2}$, forms a 4-6 membered linking group. In a still further embodiment, q is 1 and A, taken together with R$^{A1}$ and R$^{A2}$, forms a 5 membered linking group.

In another embodiment, q is 1, R$^A$ and R$^{A2}$ are each independently —CH$_2$—, —NR$^e$—, or —O—, and A is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-NR$^a$—$C_1$-$C_4$alkyl- group, said substituted —$C_2$-$C_{10}$alkyl- group is substituted by 1-4 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, R$^A$ and R$^{A2}$ are each independently —CH$_2$—, —NR$^e$—, or —O—, and A is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-NR$^a$—$C_1$-$C_4$alkyl- group, said substituted —$C_2$-$C_{10}$alkyl- group is substituted by 1-4 substituents each independently selected from halogen, hydroxy, —O—P(O)(OH)$_2$, —O—P(O)(R$^I$R$^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, R$^A$ and R$^{A2}$ are each independently —CH$_2$—, —NR$^e$—, or —O—, and A is a substituted —$C_2$-$C_8$alkyl- group or is an unsubstituted —$C_2$-$C_8$alkyl-, —$C_2$-$C_8$alkenyl-, —$C_2$-$C_8$alkynyl-, —$C_1$-$C_2$alkyl-O—$C_1$-$C_2$alkyl-, or —$C_1$-$C_2$alkyl-NR$^a$—$C_1$-$C_2$alkyl- group, said substituted —$C_2$-$C_8$alkyl- group is substituted by 1-2 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, R$^A$ and R$^{A2}$ are each independently —CH$_2$—, —NR$^e$—, or —O—, and A is a substituted —$C_2$-$C_6$alkyl- group or is an unsubstituted —$C_2$-$C_8$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-NR$^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)(R$^I$R$^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, R$^A$ and R$^{A2}$ are each independently —CH$_2$—, —NR$^e$—, or —O—, and A is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-NR$^a$—$C_1$-$C_2$alkyl- group, said substituted —$C_2$-$C_6$alkyl- group is substituted by 1-2 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, $R^A$ and $R^{A2}$ are each independently —$CH_2$—, —NR$^e$—, or —O—, and A is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-NR$^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)(R$^I$R$^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, q is 1, $R^{A1}$ and $R^{A2}$ are each independently —$CH_2$— or —O—, and A is a —$C_2$-$C_4$alkyl-, —$C_2$-$C_4$alkenyl-, or —$C_2$-$C_4$alkynyl- group.

In selected embodiments, q is 1, $R^A$ and $R^{A2}$ are each —O—, and A is —$CH_2CH_2CH_2$—, wherein A, taken together with $R^A$ and $R^{A2}$, form a —$OCH_2CH_2CH_2O$— group.

In another embodiment, q is 1, $R^A$ and $R^{A2}$ are each —O—, and A is —$CH_2$-phenyl-$CH_2$—, wherein A, taken together with $R^{A1}$ and $R^{A2}$, form a —$OCH_2$-phenyl-$CH_2$— group. In a specific embodiment, q is 1, A, taken together with $R^{A1}$ and $R^{A2}$, form a —$OCH_2$-phenyl-$CH_2O$— group, wherein the —$OCH_2$— groups are located 1,4 on the phenyl ring moiety.

The length of the linking groups defined herein represents the lowest number of atoms in a direct chain composed of —$R^{A1}$-A-$R^{A2}$— and/or —$R^{B1}$—B—$R^{B2}$— and/or —$R^{C1}$—C—$R^{C2}$—. For example, when B is an optionally substituted phenyl, the linking group —$R^{B1}$—B—$R^{B2}$— may be represented as —($CH_2$)-phenyl-($CH_2$)—. This linking group is characterized as a 4-membered linking group when the 2-($CH_2$)— moieties are located on adjacent carbon atoms of the phenyl ring (1,2 substituted phenyl). In another embodiment, this linking group is characterized as a 6-membered linking group when the 2-($CH_2$)— moieties are substituted at para positions on the phenyl ring (1,4 substituted phenyl). It will be understood that any alkyl, alkenyl, or alkynyl group or moiety of A, B or C is a straight or branched-alkyl, alkenyl, or alkynyl group or moiety. For example, a —$R^{B1}$—B—$R^{B2}$— linking group, wherein B is —$C_1$-$C_{10}$alkyl- may contain an 8-membered linking group having a ($C_1$-$C_4$alkyl) branching group or 2-4 ($C_1$-$C_3$alkyl) branching groups, for example, 4 branching methyl groups (2 gem-dimethyl groups) or 2 branching methyl groups.

In one embodiment of the compounds of this invention, r is 1 and $R^{B1}$ and $R^{B2}$ are each independently —$CH_2$—, and B, taken together with $R^{B1}$ and $R^{B2}$, forms a linking group, wherein B is a bond or B is -halo(C-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_{10}$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In one embodiment of the compounds of this invention, r is 1 and $R^{B1}$ and $R^{B2}$ are each independently —$CH_2$—, and B, taken together with $R^{B1}$ and $R^{B2}$, forms a linking group, wherein B is a bond or B is -halo(C-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —O—P(O)(OH)$_2$, —O—P(O)($R^I R^{II}$)$_2$, —O$R^c$, —NH$_2$, —N$R^c R^d$, —OCO$R^c$, —CO$_2$H, —CO$_2 R^c$, —SO$R^c$, —SO$_2 R^c$, —CONH$_2$, —CON$R^c R^d$, —SO$_2$NH$_2$, —SO$_2$N$R^c R^d$, —OCONH$_2$, —OCON$R^c R^d$, —N$R^d$CO$R^c$, —N$R^d$SO$R^c$, —N$R^d$CO$_2 R^c$, and —N$R^d$SO$_2 R^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In one embodiment of the compounds of this invention, r is 1, $R^{B1}$ and $R^{B2}$ are each independently —CH$_2$—, and B, taken together with $R^{B1}$ and $R^{B2}$, forms a 2-6 membered linking group. In a further embodiment, r is 1, $R^{B1}$ and $R^{B2}$ are each independently —CH$_2$—, and B, taken together with $R^{B1}$ and $R^{B2}$, forms a 3-6 membered linking group. In a still further embodiment, r is 1, $R^{B1}$ and $R^{B2}$ are each independently —CH$_2$—, and B, taken together with $R^{B1}$ and $R^{B2}$, forms a 4-5 membered linking group.

In one embodiment, B is a bond.

In another embodiment, r is 1, $R^{B1}$ and $R^{B2}$ are each independently —CH$_2$—, and B is a substituted —$C_1$-$C_{10}$alkyl- group or is an unsubstituted —$C_1$-$C_{10}$alkyl-, —$C_2$-$C_{10}$alkenyl-, —$C_2$-$C_{10}$alkynyl-, —$C_1$-$C_6$alkyl-O—$C_1$-$C_6$alkyl-, or —$C_1$-$C_{10}$alkyl-N$R^a$—$C_1$-$C_6$alkyl- group, said substituted —$C_1$-$C_{10}$alkyl- group is substituted by 1-4 substituents each independently selected from halogen, hydroxy, amino, ($C_1$-$C_6$alkyl)amino-, ($C_1$-$C_6$alkyl)($C_1$-$C_6$alkyl)amino-, halo($C_1$-$C_6$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —NHCO($C_1$-$C_4$alkyl), optionally substituted phenyl, optionally substituted 5-6 membered heterocycloalkyl and optionally substituted 5-6 membered heteroaryl, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_6$alkyl)amino-, ($C_1$-$C_6$alkyl)($C_1$-$C_6$alkyl)amino-, halo($C_1$-$C_6$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In another embodiment, r is 1, $R^{B1}$ and $R^{B2}$ are each independently —CH$_2$—, and B is a substituted —$C_1$-$C_{10}$alkyl- group or is an unsubstituted —$C_1$-$C_{10}$alkyl-, —$C_2$-$C_{10}$alkenyl-, —$C_2$-$C_{10}$alkynyl-, —$C_1$-$C_6$alkyl-O—$C_1$-$C_6$alkyl-, or —$C_1$-$C_{10}$alkyl-N$R^a$—$C_1$-$C_6$alkyl- group, said substituted —$C_1$-$C_{10}$alkyl- group is substituted by 1-4 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —CH$_2$—, and B is a substituted —$C_1$-$C_{10}$alkyl- group or is an unsubstituted —$C_1$-$C_{10}$alkyl-, —$C_2$-$C_{10}$alkenyl-, —$C_2$-$C_{10}$alkynyl-, —$C_1$-$C_6$alkyl-O—$C_1$-$C_6$alkyl-, or —$C_1$-$C_{10}$alkyl-N$R^a$—$C_1$-$C_6$alkyl- group, said substituted —$C_1$-$C_{10}$alkyl- group is substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —CH$_2$—, and B is a substituted —$C_1$-$C_8$alkyl- group or is an unsubstituted —$C_1$-$C_8$alkyl-, —$C_2$-$C_8$alkenyl-, —$C_2$-$C_8$alkynyl-, —$C_1$-$C_4$alkyl-O—$C_1$-$C_4$alkyl-, or —$C_1$-$C_4$alkyl-N$R^a$—$C_1$-$C_4$alkyl- group, said substituted —$C_1$-$C_8$alkyl- group is substituted by 1-4 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —CH$_2$—, and B is a substituted —$C_1$-$C_8$alkyl- group or is an unsubstituted —$C_1$-$C_8$alkyl-, —$C_2$-$C_8$alkenyl-, —$C_2$-$C_8$alkynyl-, —$C_1$-$C_4$alkyl-O—$C_1$-$C_4$alkyl-, or —$C_1$-$C_4$alkyl-N$R^a$—$C_1$-$C_4$alkyl- group, said substituted —$C_1$-$C_8$alkyl- group is substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —CH$_2$—, and B is a substituted —$C_1$-$C_6$alkyl- group or is an unsubstituted —$C_1$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-N$R^a$—$C_1$-$C_2$alkyl- group, said substituted —$C_1$-$C_6$alkyl- group is substituted by 1-2 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —CH$_2$—, and B is a substituted —$C_1$-$C_6$alkyl- group or is an unsubstituted —$C_1$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-N$R^a$—$C_1$-$C_2$alkyl- group, said substituted —$C_1$-$C_6$alkyl- group is substituted by 1-2 substituents each independently selected from halogen, hydroxy, —O—P(O)(OH)$_2$, —O—P(O)(R$^I$R$^H$)$_2$, amino, (C$_1$-C$_4$alkyl)amino-, (C$_1$-C$_4$alkyl)(C$_1$-C$_4$alkyl)amino-, halo(C$_1$-C$_4$alkyl), halo(C$_1$-C$_4$alkoxy)-, and C$_1$-C$_4$alkoxy-.

In another embodiment, r is 1, R$^{B1}$ and R$^{B2}$ are each independently —CH$_2$—, and B is a substituted —C$_2$-C$_4$alkyl- group or is an unsubstituted —C$_2$-C$_4$alkyl-, —C$_2$-C$_4$alkenyl-, —C$_2$-C$_4$alkynyl-, —C$_1$alkyl-O—C$_1$alkyl-, or —C$_1$alkyl-NR$^a$—C$_1$alkyl- group, said substituted —C$_2$-C$_4$alkyl- group is substituted by 1-2 substituents each independently selected from halogen, hydroxy, amino, (C$_1$-C$_4$alkyl)amino-, (C$_1$-C$_4$alkyl)(C$_1$-C$_4$alkyl)amino-, halo(C$_1$-C$_4$alkyl), halo(C$_1$-C$_4$alkoxy)-, and C$_1$-C$_4$alkoxy-.

In another embodiment, r is 1, R$^{B1}$ and R$^{B2}$ are each independently —CH$_2$—, and B is a substituted —C$_2$-C$_4$alkyl- group or is an unsubstituted —C$_2$-C$_4$alkyl-, —C$_2$-C$_4$alkenyl-, —C$_2$-C$_4$alkynyl-, —C$_1$alkyl-O—C$_1$alkyl-, or —C$_1$alkyl-NR$^a$—C$_1$alkyl- group, said substituted —C$_2$-C$_4$alkyl- group is substituted by 1-2 substituents each independently selected from halogen, hydroxy, —O—P(O)(OH)$_2$, —O—P(O)(R$^I$R$^H$)$_2$, amino, (C$_1$-C$_4$alkyl)amino-, (C$_1$-C$_4$alkyl)(C$_1$-C$_4$alkyl)amino-, halo(C$_1$-C$_4$alkyl), halo(C$_1$-C$_4$alkoxy)-, and C$_1$-C$_4$alkoxy-.

In selected embodiments, r is 1, R$^{B1}$ and R$^{B2}$ are each independently —CH$_2$—, and B is —CH=CH—, —CH$_2$CH$_2$—, —CH(OH)CH(OH)—, or —CH$_2$N(CH$_3$)CH$_2$—. In these embodiments, r is 1, B, taken together with R$^{B1}$ and R$^{B2}$, form a —CH=CHCH$_2$—, —CH$_2$CH$_2$CH$_2$CH$_2$—, —CH$_2$CH(OH)CH(OH)CH$_2$—, or —CH$_2$CH$_2$N(CH$_3$)CH$_2$CH$_2$— group. In these embodiments, r is 1, B, taken together with R$^{B1}$ and R$^{B2}$, form a —CH$_2$CH=CHCH$_2$—.

In one embodiment of the compounds of this invention, s is 1 and R$^{C1}$ and R$^{C2}$ are each independently —CH$_2$—, and C, taken together with R$^{C1}$ and R$^{C2}$, forms a linking group, wherein C is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_2$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1 or 2 substituents each independently selected from halogen, halo(C$_1$-C$_4$alkyl), —OH, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, and C$_1$-C$_4$alkoxy-(C$_1$-C$_4$alkoxy)-.

In one embodiment of the compounds of this invention, s is 1 and R$^{C1}$ and R$^{C2}$ are each independently —CH$_2$—, and C, taken together with R$^{C1}$ and R$^{C2}$, forms a linking group, wherein C is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_2$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1 or 2 substituents each independently selected from halogen, halo(C$_1$-C$_4$alkyl), —OH, —O—P(O)(OH)$_2$, —O—P(O)(R$^I$R$^H$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$R$^H$)$_2$, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^H$)$_2$, and C$_1$-C$_4$alkoxy-(C$_1$-C$_4$alkoxy)-.

In one embodiment of the compounds of this invention, s is 1, R$^{C1}$ and R$^{C2}$ are each independently —CH$_2$—, and C, taken together with R$^{C1}$ and R$^{C2}$, forms a 4-8 membered linking group. In a further embodiment, s is 1 and C, taken together with R$^{C1}$ and R$^{C2}$, forms a 4-6 membered linking group. In a still further embodiment, s is 1 and C, taken together with R$^{C1}$ and R$^{C2}$, forms a 5 membered linking group.

In another embodiment, s is 1, $R^{C1}$ and $R^{C2}$ are each independently —$CH_2$—, and C is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-$NR^a$—$C_1$-$C_4$alkyl- group, said substituted —$C_2$-$C_{10}$alkyl- group is substituted by 1-4 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-$NR^a$—$C_1$-$C_4$alkyl- group, said substituted —$C_2$-$C_{10}$alkyl- group is substituted by 1-4 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_8$alkyl- group or is an unsubstituted —$C_2$-$C_8$alkyl-, —$C_2$-$C_8$alkenyl-, —$C_2$-$C_8$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_8$alkyl- group is substituted by 1-2 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_8$alkyl- group or is an unsubstituted —$C_2$-$C_8$alkyl-, —$C_2$-$C_8$alkenyl-, —$C_2$-$C_8$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_8$alkyl- group is substituted by 1-2 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_6$alkyl- group or is an unsubstituted —$C_2$-$C_6$alkyl-, —$C_2$-$C_6$alkenyl-, —$C_2$-$C_8$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)($R^I R^{II}$)$_2$, amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a —$C_2$-$C_4$alkyl-, —$C_2$-$C_4$alkenyl-, or —$C_2$-$C_4$alkynyl- group.

In selected embodiments, s is 1, $R^{C1}$ and $R^{C2}$ are each independently —$CH_2$—, and C is —$CH_2CH_2CH_2$—, wherein C, taken together with $R^{C1}$ and $R^{C2}$, form a —$CH_2CH_2CH_2CH_2CH_2$— group.

In one embodiment of the compounds of this invention, $R^4$ and $R^6$ are each independently selected from H, halogen, halo($C_1$-$C_6$alkyl), halo($C_1$-$C_6$alkoxy)-, hydroxy, —$NH_2$, —$NR^c R^c$, —$NR^c R^d$, —$COR^c$, —$CO_2 R^c$, —$N(R^d)COR^c$, —$N(R^d)S_2 R^c$, —$N(R^g)S_2(C_1$-$C_2$alkyl)-$N(R^h)(R^g)CO(C_1$-$C_2$alkyl)-$N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^c R^c$, —$NR^c R^d$, —$CO_2 H$, —$CO_2 R^c$, —$OCOR^c$, —$CO_2 H$, —$CO_2 R^c$, —$SOR^c$, —$SO_2 R^c$, —$CONH_2$, —$CONR^c R^d$, —$SO_2 NH2$, —$SO_2 NR^c R^d$, —$OCONH_2$, —$OCONR^c R^d$, —$NR^d COR^c$, —$NR^d SOR^c$, —$NR^d CO_2 R^c$, —$NR^d SO_2 R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2 R^d$.

In one embodiment of the compounds of this invention, $R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^I R^{II}$)$_2$, —$NH_2$, —$NR^c R^c$, —$NR^c R^d$, —$COR^c$, —$CO_2 R^c$, —$N(R^d)COR^c$, —$N(R^d)S_2 R^c$, —$N(R^g)SO_2(C_1$-$C_2$alkyl)-$N(R^h)(R^f)$, —$N(R^g)CO(C_1$-$C_2$alkyl)-$N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —O—P(O)(OH)$_2$, —O—P(O)($R^I R^{II}$)$_2$, —$OR^c$, —$NH_2$, —$NR^c R^c$, —$NR^c R^d$, —$CO_2 H$, —$CO_2 R^c$, $OCOR^c$, —$CO_2 H$, —$CO_2 R^c$, —$SOR^c$, —$SO_2 R^c$, —$CONH_2$, —$CONR^c R^d$, —$SO_2 NH_2$, —$SO_2 NR^c R^d$, —$OCONH_2$, —$OCONR^c R^d$, —$NR^d COR^c$, —$NR^d SOR^c$, —$NR^d C_2 R^c$, —$NR^d S_2 R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, —($C_1$-$C_4$alkyl)-O—P(O)

(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, C$_1$-C$_4$alkoxy-(C$_1$-C$_4$alkoxy)-, —COR$^d$, —CON(R$^d$)(R$^f$), and —CO$_2$R$^d$.

In one embodiment, R$^4$ and R$^6$ are each H.

In one embodiment of the compounds of this invention, R$^{14}$ is optionally substituted C$_1$-C$_4$alkyl, wherein said optionally substituted C$_1$-C$_4$alkyl is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$.

In one embodiment of the compounds of this invention, R$^6$ is H, halogen, or C$_1$-C$_4$alkyl.

In one embodiment of the compounds of this invention, R$^{15}$ and R$^{17}$ are each independently H, cyclopropyl, or C$_1$-C$_4$alkyl.

In one embodiment of the compounds of this invention, R$^{14}$, R$^{15}$, R$^{16}$, and R$^{17}$ are each independently H or C$_1$-C$_4$alkyl.

In one embodiment of this invention, R$^6$ is H.

In another embodiment, R$^{14}$, R$^{15}$, and R$^{17}$ are each independently C$_1$-C$_4$alkyl.

In another embodiment, R$^{14}$, R$^{15}$, and R$^{17}$ are each independently C$_1$-C$_3$alkyl, specifically, methyl or ethyl. In a selected embodiment, R$^{14}$ is ethyl.

In another embodiment, R$^{15}$ and R$^{17}$ are each methyl.

In one embodiment of the compounds of this invention, R$^a$ is H, —R$^c$, —COR$^c$, —CO$_2$H, —CO$_2$R$^c$, —SOR$^c$, —SO$_2$R$^c$, —CONH$_2$, —CONR$^c$R$^d$, —SO$_2$NH$_2$, or —SO$_2$NR$^c$R$^d$.

In another embodiment, R$^a$ is H, C-C$_4$alkyl, —CO(C$_1$-C$_4$alkyl), —CO(C$_1$-C$_4$alkyl)-OH, —CO(C$_1$-C$_4$alkyl)-O—(C$_1$-C$_4$alkyl), —CO(C$_1$-C$_4$alkyl)-NH$_2$, —CO(C$_1$-C$_4$alkyl)-NH(C$_1$-C$_4$alkyl), or —CO(C$_1$-C$_4$alkyl)-N(C$_1$-C$_4$alkyl)(C$_1$-C$_4$alkyl).

One embodiment of this invention is directed to a compound Formula (I-N), Formula (I) or Formula (I-P) wherein:

q+r+s=1 or 2;

q is 0 and R$^{A1}$ and R$^{A2}$ are independently selected from H, —OCH$_2$CH$_2$CH$_2$OH and —OCH$_3$; or q is 1, R$^{A1}$ and R$^{A2}$ are each —O—, and A is —CHCH$_2$CH$_2$—;

r is 0 and R$^{B1}$ and R$^{B2}$ are each H; or r is 1, R$^{B1}$ and R$^{B2}$ are each independently —CH$_2$—, and B is —CH═CH—, —CH$_2$CH$_2$—, —CH(OH)CH(OH)—, or —CH$_2$N(CH$_3$)CH$_2$—;

s is 0, R$^{C1}$ is methyl and R$^{C2}$ is ethyl; or s is 1, R$^{C1}$ and R$^{C2}$ are each independently —CH$_2$—, and C is —CHCH$_2$CH$_2$—;

R$^3$ and R$^5$ are each —CONH$_2$;

R$^4$ and R$^6$ are each H;

R$^{14}$ is ethyl;

R$^{15}$ is methyl;

R$^{16}$ is H;

R$^{17}$ is methyl;

or a salt, particularly a pharmaceutically acceptable salt, thereof.

In one embodiment of this invention, the compound of invention has Formula (I-N-B')

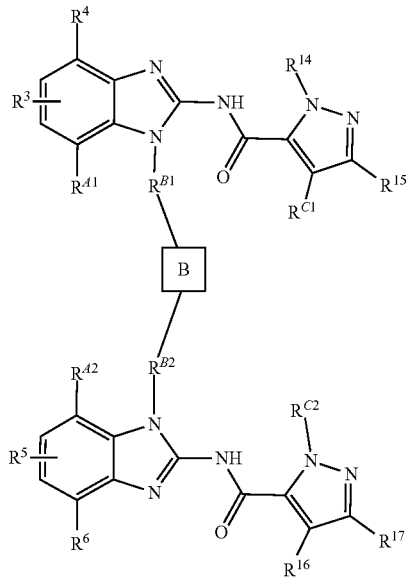

wherein
R$^3$ and R$^5$ are each independently —CON(R$^d$)(R$^f$), or one of R$^3$ and R$^5$ is —CON(R$^d$)(R$^f$), and the other of R$^3$ and R$^5$ is H, COOH or —CO$_2$(R$^c$);

R$^c$ is C$_1$-C$_4$alkyl;

R$^{B1}$ and R$^{B2}$ are each independently —CH$_2$—;

B is -halo(C$_1$-C$_5$alkyl), unsubstituted —C$_1$-C$_5$alkyl, or unsubstituted —C$_2$-C$_5$alkenyl-;

R$^{A2}$ and R$^{A1}$ are each independently H, halogen, hydroxyl, —O—P(O)(OH)$_2$, —O—P(O)(R$^I$R$^{II}$)$_2$, optionally substituted (C$_1$-C$_6$alkyl), or optionally substituted (C$_1$-C$_6$alkyl)oxy-, wherein C$_1$-C$_6$alkyl of said optionally substituted (C$_1$-C$_6$alkyl), or optionally substituted (C$_1$-C$_6$alkyl)oxy- is optionally substituted with 1-4 substituents each independently selected from the group consisting of hydroxyl, —O—P(O)(OH)$_2$, —O—P(O)(R$^I$R$^{II}$)$_2$, C$_1$-C$_4$alkoxyl, —N(R$^e$)(R$^f$), —CO$_2$(R$^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, —(C$_1$-C$_6$alkyl)-NH$_2$, —C$_1$-C$_4$alkyl-(C$_1$-C$_4$alkoxy) and C$_1$-C$_4$alkoxy-(C$_1$-C$_4$alkoxy)-;

each R$^d$ is independently H or C$_1$-C$_4$alkyl;

R$^e$ is selected from H, (C$_1$-C$_4$alkyl), —CO(C$_1$-C$_4$alkyl), —OCO(C$_1$-C$_4$alkyl), —(C$_1$-C$_4$alkyl)-NH$_2$, —(C$_1$-C$_4$alkyl) C$_1$-C$_4$alkoxy, or —CO$_2$(C$_1$-C$_4$alkyl), each occurrence of R$^f$ is H or (C$_1$-C$_4$alkyl);

R$^4$ and R$^6$ are H;

R$^{14}$ is C$_1$-C$_4$alkyl;

R$^{C1}$ is H or C$_1$-C$_4$alkyl;

R$^{C2}$ is C$_1$-C$_4$alkyl;

R$^{15}$ is H or C$_1$-C$_4$alkyl;

$R^{16}$ is H or $C_1$-$C_4$alkyl;

$R^{17}$ is H or $C_1$-$C_4$alkyl; and each occurrence of $R^I$ and $R^{II}$ are independently ($C_1$-$C_6$alkyl)oxy-, or a tautomer thereof, or a salt thereof, particularly a pharmaceutically acceptable salt thereof.

In one embodiment of this invention, the compound of invention has Formula (I-P-B')

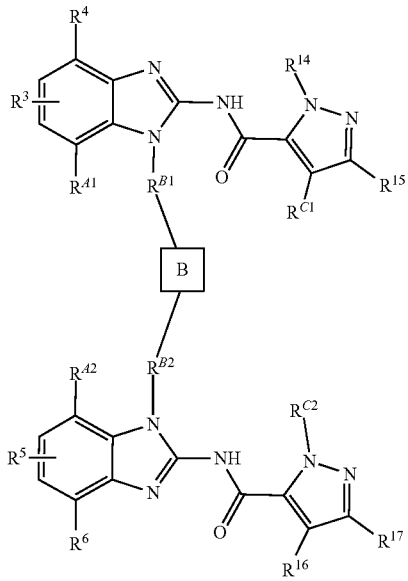

wherein $R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^c$ is $C_1$-$C_4$alkyl;

$R^{B1}$ and $R^{B2}$ are each independently —CH$_2$—;

B is -halo($C_1$-$C_5$alkyl), unsubstituted —$C_1$-$C_5$alkyl, or unsubstituted —$C_2$-$C_5$alkenyl-;

$R^{A2}$ and $R^{A1}$ are each independently H, halogen, hydroxyl, —O—P(O)(OH)$_2$, —O—P(O)($R^I R^{II}$)$_2$, optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, —O—P(O)(OH)$_2$, —O—P(O)($R^I R^{II}$)$_2$, $C_1$-$C_4$alkoxyl, —N($R^e$)($R^f$), —CO$_2$($R^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)($R^I R^{II}$)$_2$, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, —($C_1$-$C_4$alkyl)-O—P(O)(OH)$_2$, —($C_1$-$C_4$alkyl)-O—P(O)($R^I R^{II}$)$_2$, halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I R^{II}$)$_2$, —($C_1$-$C_6$alkyl)-NH$_2$, and $C_1$-$C_4$alkoxy-($C_1$-$C_4$alkoxy)-;

each $R^d$ is independently H or $C_1$-$C_4$alkyl;

$R^e$ is selected from H, ($C_1$-$C_4$alkyl), —CO($C_1$-$C_4$alkyl), —OCO($C_1$-$C_4$alkyl), —($C_1$-$C_4$alkyl)-NH$_2$, —($C_1$-$C_4$alkyl) $C_1$-$C_4$alkoxy, or —CO$_2$($C_1$-$C_4$alkyl), each occurrence of $R^f$ is H or ($C_1$-$C_4$alkyl);

$R^4$ and $R^6$ are H;

$R^{14}$ is $C_1$-$C_4$alkyl;

$R^{C1}$ is H or $C_1$-$C_4$alkyl;

$R^{C2}$ is $C_1$-$C_4$alkyl;

$R^{15}$ is H or $C_1$-$C_4$alkyl;

$R^{16}$ is H or $C_1$-$C_4$alkyl;

$R^{17}$ is H or $C_1$-$C_4$alkyl; and each occurrence of $R^I$ and $R^{II}$ are independently ($C_1$-$C_6$alkyl)oxy-, or a tautomer thereof, or a salt thereof, particularly a pharmaceutically acceptable salt thereof.

In one embodiment of this invention, the compound of invention is Formula (I-B')

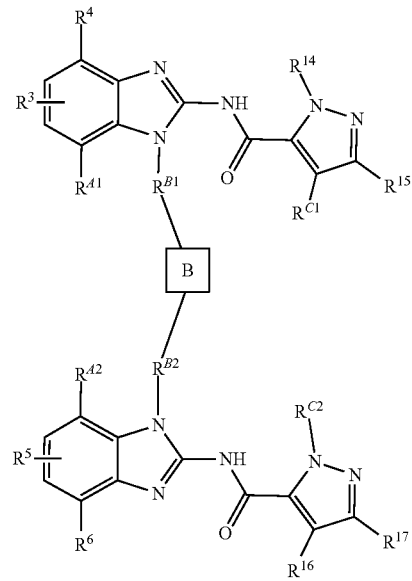

wherein $R^3$ and $R^5$ are each independently —CON($R^d$)($R^f$), or one of $R^3$ and $R^5$ is —CON($R^d$)($R^f$), and the other of $R^3$ and $R^5$ is H or —CO$_2$($R^c$);

$R^c$ is $C_1$-$C_4$alkyl;

$R^{B1}$ and $R^{B2}$ are each independently —CH$_2$—;

B is -halo($C_1$-$C_5$alkyl), unsubstituted —$C_1$-$C_5$alkyl, or unsubstituted —$C_2$-$C_5$alkenyl-;

$R^{A2}$ and $R^{A1}$ are each independently H, halogen, hydroxyl, optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, $C_1$-$C_4$alkoxyl, —N($R^e$)($R^f$), —CO$_2$(R), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, halo(C$_1$-C$_4$alkoxy)-, C-C$_4$alkoxy-, hydroxy-(C$_2$-C$_4$alkoxy)-, and C$_1$-C$_4$alkoxy-(C$_1$-C$_4$alkoxy)-;

each R$^d$ is independently H or C$_1$-C$_4$alkyl;
R$^e$ is selected from H, (C$_1$-C$_4$alkyl), —CO(C$_1$-C$_4$alkyl), —OCO(C$_1$-C$_4$alkyl), or —CO$_2$(C$_1$-C$_4$alkyl);
each R$^f$ is H or (C$_1$-C$_4$alkyl);
R$^4$ and R$^6$ are H;
R$^{14}$ is C$_1$-C$_4$alkyl;
R$^{C1}$ is H or C$_1$-C$_4$alkyl;
R$^{C2}$ is C$_1$-C$_4$alkyl;
R$^{15}$ is H or C$_1$-C$_4$alkyl;
R$^{16}$ is H or C$_1$-C$_4$alkyl;
R$^{17}$ is H or C$_1$-C$_4$alkyl; and each occurrence of R$^I$ and R$^{II}$ are independently (C$_1$-C$_6$alkyl)oxy-, a tautomer, a salt, or a prodrug thereof.

In one embodiment of this invention, the compound of invention is Formula (I-N-b'),

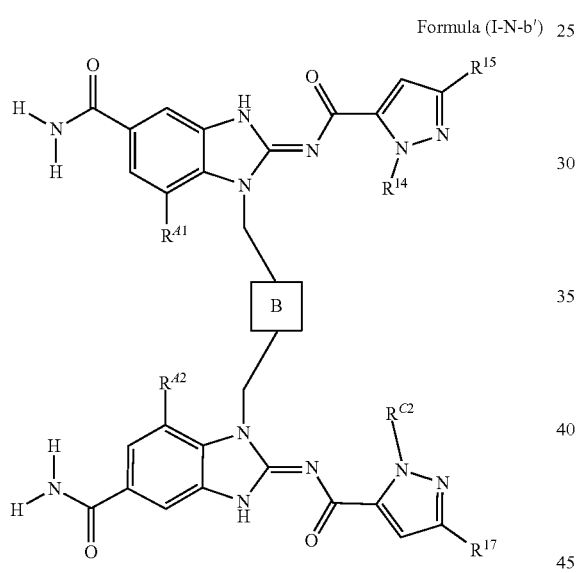

Formula (I-N-b')

wherein

B is -halo(C$_1$-C$_5$alkyl), unsubstituted —C$_1$-C$_5$alkyl, or unsubstituted —C$_2$-C$_5$alkenyl-;

R$^{A2}$ and R$^{A1}$ are each independently H, halogen, hydroxyl, —O—P(O)(OH)$_2$, —O—P(O)(R$^I$R$^{II}$)$_2$, optionally substituted (C$_1$-C$_6$alkyl), or optionally substituted (C$_1$-C$_6$alkyl)oxy-, wherein C$_1$-C$_6$alkyl of said optionally substituted (C$_1$-C$_6$alkyl) or optionally substituted (C$_1$-C$_6$alkyl)oxy- is optionally substituted with 1-4 substituents each independently selected from the group consisting of hydroxyl, C$_1$-C$_4$alkoxyl, —N(R$^e$)(R$^f$), —CO$_2$(R$^f$), optionally substituted phenyl, and optionally substituted 5-6 membered heterocycloalkyl, and wherein said optionally substituted phenyl, or 5-6 membered heterocycloalkyl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$_I$R$_{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, —(C$_1$-C$_6$alkyl)-NH$_2$, —C$_1$-C$_4$alkyl-(C$_1$-C$_4$alkoxy) and C$_1$-C$_4$alkoxy-(C$_1$-C$_4$alkoxy)-;

R$^e$ is selected from H, (C$_1$-C$_4$alkyl), —CO(C$_1$-C$_4$alkyl), —OCO(C$_1$-C$_4$alkyl), —(C$_1$-C$_4$alkyl)-NH$_2$, —(C$_1$-C$_4$alkyl) C$_1$-C$_4$alkoxy, or —CO$_2$(C$_1$-C$_4$alkyl),
each R$^f$ is H or (C$_1$-C$_4$alkyl);
R$^{14}$ is C$_1$-C$_4$alkyl;
R$^{C2}$ is C$_1$-C$_4$alkyl;
R$^{15}$ is C$_1$-C$_4$alkyl; and
R$^1$ is C$_1$-C$_4$alkyl;
each occurrence of R$^I$ and R$^{II}$ are independently (C$_1$-C$_6$alkyl)oxy-,
a tautomer, a salt, or a prodrug thereof.

In one embodiment of this invention, the compound of invention has Formula (I-P-b'),

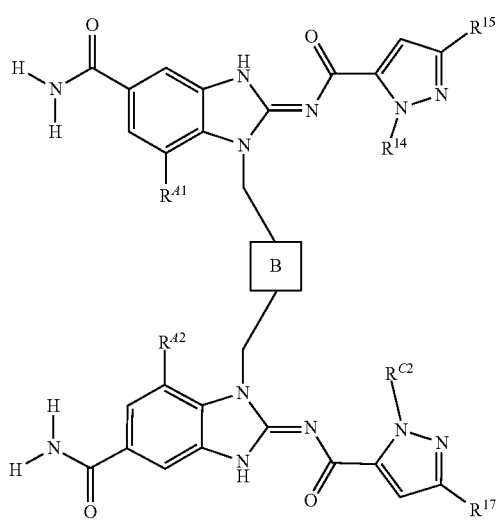

Formula (I-P-b')
wherein

B is -halo(C$_1$-C$_5$alkyl), unsubstituted —C$_1$-C$_5$alkyl, or unsubstituted —C$_2$-C$_5$alkenyl-; R$^{A2}$ and R$^{A1}$ are each independently H, halogen, hydroxyl, —O—P(O)(OH)$_2$, —O—P(O)(R$^I$R$^{II}$)$_2$, optionally substituted (C$_1$-C$_6$alkyl), or optionally substituted (C$_1$-C$_6$alkyl)oxy-, wherein C$_1$-C$_6$alkyl of said optionally substituted (C$_1$-C$_6$alkyl), or optionally substituted (C$_1$-C$_6$alkyl)oxy- is optionally substituted with 1-4 substituents each independently selected from the group consisting of hydroxyl, C$_1$-C$_4$alkoxyl, —N(R$^e$)(R$^f$), —CO$_2$(R$^f$), optionally substituted phenyl, and optionally substituted 5-6 membered heterocycloalkyl, and wherein said optionally substituted phenyl, or 5-6 membered heterocycloalkyl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$_I$R$_{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$R$^{II}$)$_2$, —(C$_1$-C$_6$alkyl)-NH$_2$, and C$_1$-C$_4$alkoxy-(C$_1$-C$_4$alkoxy)-;

$R^e$ is selected from H, ($C_1$-$C_4$alkyl), —CO($C_1$-$C_4$alkyl), —OCO($C_1$-$C_4$alkyl), —($C_1$-$C_4$alkyl)-$NH_2$, —($C_1$-$C_4$alkyl) $C_1$-$C_4$alkoxy, or —$CO_2$($C_1$-$C_4$alkyl),
each $R^f$ is H or ($C_1$-$C_4$alkyl);
$R^{14}$ is $C_1$-$C_4$alkyl;
$R^{C2}$ is $C_1$-$C_4$alkyl;
$R^{15}$ is $C_1$-$C_4$alkyl; and
$R^1$ is $C_1$-$C_4$alkyl;
each occurrence of $R^I$ and R are independently ($C_1$-$C_6$alkyl)oxy-,
a tautomer, a salt, or a prodrug thereof.

In one embodiment of this invention, the compound of invention has Formula (I-b'),

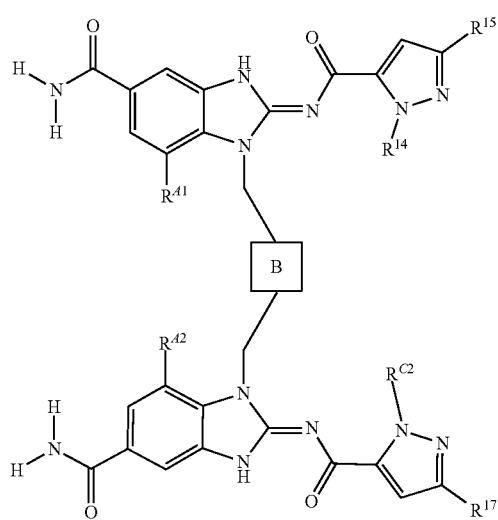

wherein
B is -halo($C_1$-$C_5$alkyl), unsubstituted —$C_1$-$C_5$alkyl, or unsubstituted —$C_2$-$C_5$alkenyl-; $R^{42}$ and $R^{41}$ are each independently H, halogen, optionally substituted ($C_1$-$C_6$alkyl), or optionally substituted ($C_1$-$C_6$alkyl)oxy-,
wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, $C_1$-$C_4$alkoxyl, —N($R^e$)($R^f$), —$CO_2$($R^f$), optionally substituted phenyl, and optionally substituted 5-6 membered heterocycloalkyl, and wherein said optionally substituted phenyl, or 5-6 membered heterocycloalkyl is optionally substituted by 1-4 substituents each independently selected from halogen, hydroxy, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;
$R^e$ is H, ($C_1$-$C_4$alkyl), —CO($C_1$-$C_4$alkyl), —OCO($C_1$-$C_4$alkyl), or —$CO_2$($C_1$-$C_4$alkyl), each occurrence of $R^f$ is H or ($C_1$-$C_4$alkyl);
$R^{14}$ is $C_1$-$C_4$alkyl;
$R^{C2}$ is $C_1$-$C_4$alkyl;
$R^{15}$ is $C_1$-$C_4$alkyl; and
$R^{17}$ is $C_1$-$C_4$alkyl;
each occurrence of $R^I$ and $R^{II}$ are independently ($C_1$-$C_6$alkyl)oxy-,
a tautomer, a salt, or a prodrug thereof.

In one embodiment of the compound of Formula (I-N-B'), (I-P-B'), (I-N-b'), or (I-P-b'), wherein $R^{42}$ and $R^{41}$ are each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —O—P(O)(OH)$_2$, —O—P(O)($R^I R^{II}$)$_2$, —N($R^e$)($R^f$), $C_1$-$C_4$alkoxyl, phenyl, optionally substituted 5-6 membered heterocycloalkyl containing at least one nitrogen or oxygen as a member of the ring, each $R^e$ is independently selected from H, ($C_1$-$C_4$alkyl), —($C_1$-$C_4$alkyl)-$NH_2$, or —($C_1$-$C_4$alkyl) $C_1$-$C_4$alkoxy and each $R^f$ is independently H or ($C_1$-$C_4$alkyl).

In one embodiment of the compound of Formula (I-N-B'), (I-P-B'), (I-B'), (I-N-b'), (I-P-b') or (I-b'), wherein $R^{42}$ and $R^{41}$ are each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —N($R^e$)($R^f$), $C_1$-$C_4$alkoxyl, phenyl, optionally substituted 5-6 membered heterocycloalkyl containing at least one nitrogen or oxygen as a member of the ring, and $R^e$ and $R^f$ are each independently H or ($C_1$-$C_4$alkyl).

In one embodiment of the compound of Formula (I-N-B'), (I-P-B'), (I-N-b'), or (I-P-b'), wherein at least one of $R^{42}$ or $R^{41}$ is independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl and morpholinyl, each $R^e$ is independently selected from H, ($C_1$-$C_4$alkyl), —($C_1$-$C_4$alkyl)-$NH_2$, or —($C_1$-$C_4$alkyl) $C_1$-$C_4$alkoxy and each $R^f$ is independently H or ($C_1$-$C_4$alkyl).

In one embodiment of the compound of Formula (I-N-B'), (I-P-B'), (I-B'), (I-N-b'), (I-P-b') or (I-b'), wherein at least one of $R^{42}$ or $R^{41}$ is each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl or morpholinyl, and $R^e$ and $R^f$ are each independently H or ($C_1$-$C_4$alkyl).

In one embodiment of the compound of Formula (I-N-B'), (I-P-B'), (I-B'), (I-N-b'), (I-P-b') or (I-b'), wherein
B is unsubstituted —$C_1$-$C_5$alkyl, or unsubstituted —$C_2$-$C_5$alkenyl-;
$R^{42}$ and $R^{41}$ are each independently H, halogen, optionally substituted ($C_1$-$C_6$alkyl), or optionally substituted ($C_1$-$C_6$alkyl)oxy-,
wherein $C_1$-$C_6$alkyl of said optionally substituted ($C_1$-$C_6$alkyl), or optionally substituted ($C_1$-$C_6$alkyl)oxy- is optionally substituted with 1-2 substituents each independently selected from the group consisting of hydroxyl, $C_1$-$C_4$alkoxyl, —N($R^e$)($R^f$), —$CO_2$($R^f$), unsubstituted phenyl and unsubstituted 5-6 membered heterocycloalkyl,
$R^e$ is H, ($C_1$-$C_4$alkyl), —CO($C_1$-$C_4$alkyl), —OCO($C_1$-$C_4$alkyl), or —$C_2$($C_1$-$C_4$alkyl), each occurrence of $R^f$ is H or ($C_1$-$C_4$alkyl);
$R^{14}$ is $C_1$-$C_4$alkyl;
$R^{C2}$ is $C_1$-$C_4$alkyl;
$R^{15}$ is $C_1$-$C_4$alkyl; and
$R^{17}$ is $C_1$-$C_4$alkyl;

each occurrence of $R^I$ and $R^{II}$ are independently $(C_1-C_6\text{alkyl})\text{oxy-}$,
or a tautomer thereof,
or a salt thereof,
or a prodrug thereof.

In one embodiment, the compound of Formula (I-b'), wherein

B is unsubstituted —$C_2$-$C_5$alkenyl-;

$R^{A2}$ and $R^{A1}$ are each independently H, optionally substituted $(C_1-C_6\text{alkyl})$, or optionally substituted $(C_1-C_6\text{alkyl})\text{oxy-}$,
  wherein $C_1$-$C_6$alkyl of said optionally substituted $(C_1-C_6\text{alkyl})$, or optionally substituted $(C_1-C_6\text{alkyl})\text{oxy-}$ is optionally substituted with 1 substituents each independently selected from the group consisting of hydroxyl, $C_1$-$C_4$alkoxyl, unsubstituted 5-6 membered heterocycloalkyl, $R^{14}$ is $C_1$-$C_4$alkyl;
$R^{C2}$ is $C_1$-$C_4$alkyl;
$R^{15}$ is $C_1$-$C_4$alkyl; and
$R^{17}$ is $C_1$-$C_4$alkyl;
or a tautomer thereof,
or a salt thereof,
or a prodrug thereof.

In one embodiment, the compound of Formula (I-b'), wherein

B is unsubstituted ethenyl;

$R^{A2}$ and $R^{A1}$ are each independently H or optionally substituted $(C_1-C_6\text{alkyl})\text{oxy-}$, wherein $C_1$-$C_6$alkyl of said optionally substituted $(C_1-C_6\text{alkyl})\text{oxy-}$ is optionally substituted with one substituent selected from hydroxyl or unsubstituted morpholinyl;

$R^{14}$ is methyl or ethyl;
$R^{C2}$ is methyl or ethyl;
$R^{15}$ is methyl or ethyl; and
$R^{17}$ is methyl or ethyl;
or a tautomer thereof,
or a salt thereof,
or a prodrug thereof.

In one embodiment, the compound of Formula A,

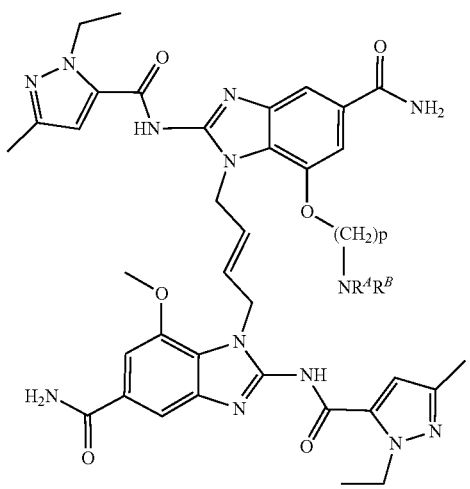

wherein
P is an integer among 1 to 6,
$R^A$ and $R^B$ are independently H, $(C_1-C_4\text{alkyl})$ or N, $R^A$ and $R^B$ form an optionally substituted 5 or 6 membered heterocyclic ring, wherein the heterocyclic ring is selected from the group consisting of morpholinyl, piperidinyl, piperazinyl and pyrrolidinyl, and
the heterocyclic ring is optionally substituted by one or two substituents independently selected from the group consisting of hydroxyl and $C_1$-$C_3$ alkyl optionally substituted with one or two substituent of hydroxyl or $C_1$-$C_3$ alkoxyl,
or a tautomer thereof,
or a salt thereof,
or a prodrug thereof.

In one embodiment, the compound of the invention has Formula (I-P-bc)

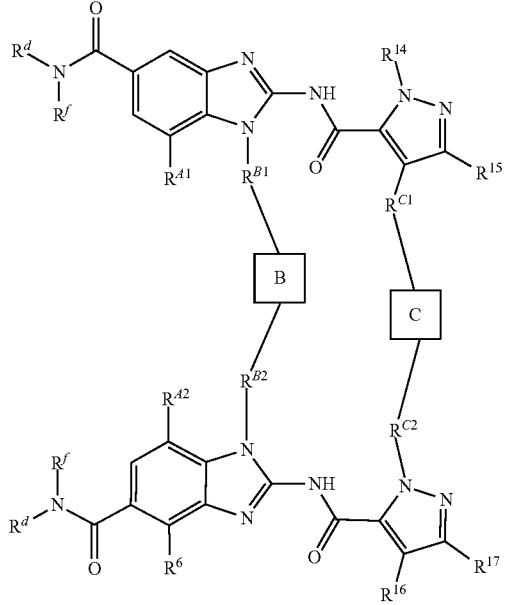

wherein
$R^{C1}$ and $R^{C2}$ are each independently —$CH_2$—;
C is -halo($C_1$-$C_5$alkyl), unsubstituted —$C_1$-$C_5$alkyl, or unsubstituted —$C_2$-$C_5$alkenyl-;

$R^{B1}$ and $R^{B2}$ are each independently —$CH_2$—;

B is -halo($C_1$-$C_5$alkyl), unsubstituted —$C_1$-$C_5$alkyl, or unsubstituted —$C_2$-$C_5$alkenyl-;

$R^{A2}$ and $R^{A1}$ are each independently H, halogen, hydroxyl, —O—P(O)(OH)$_2$, —O—P(O)($R^I R^{II}$)$_2$, optionally substituted ($C_1$-$C_6$alkyl), or optionally substituted $(C_1-C_6\text{alkyl})\text{oxy-}$,
  wherein $C_1$-$C_6$alkyl of said optionally substituted $(C_1-C_6\text{alkyl})$, or optionally substituted $(C_1-C_6\text{alkyl})\text{oxy-}$ is optionally substituted with 1-4 substituents each independently selected from the group consisting of hydroxyl, —O—P(O)(OH)$_2$, —O—P(O)($R^I R^{II}$)$_2$, $C_1$-$C_4$alkoxyl, —N($R^e$)($R^f$), —CO$_2$($R^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)($R^I R^{II}$)$_2$, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, —($C_1$-$C_4$alkyl)-O—P(O)(OH)$_2$, —($C_1$-$C_4$alkyl)-O—P(O)($R^I R^{II}$)$_2$, halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I R^{II}$)$_2$, —($C_1$-$C_6$alkyl)-NH$_2$, and $C_1$-$C_4$alkoxy-($C_1$-$C_4$alkoxy)-;

each $R^d$ is independently H or $C_1$-$C_4$alkyl;

$R^e$ is selected from H, ($C_1$-$C_4$alkyl), —CO($C_1$-$C_4$alkyl), —OCO($C_1$-$C_4$alkyl), —($C_1$-$C_4$alkyl)-NH$_2$, —($C_1$-$C_4$alkyl) $C_1$-$C_4$alkoxy, or —CO$_2$($C_1$-$C_4$alkyl), each $R^f$ is H or ($C_1$-$C_4$alkyl);

$R^6$ is H;

$R^{14}$ is $C_1$-$C_4$alkyl;

$R^{15}$ is $C_1$-$C_4$alkyl;

$R^{16}$ is $C_1$-$C_4$alkyl;

$R^{17}$ is $C_1$-$C_4$alkyl; and each occurrence of $R^I$ and $R^{II}$ are independently ($C_1$-$C_6$alkyl)oxy-, or a tautomer thereof;

or a salt thereof, particularly a pharmaceutically acceptable salt thereof.

In one embodiment, the compound of the invention has Formula (I-bc)

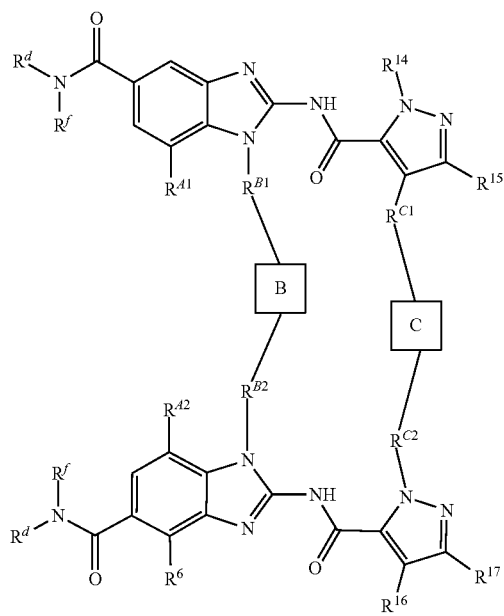

Wherein $R^{C1}$ and $R^{C2}$ are each independently —CH$_2$—,

C is -halo($C_1$-$C_5$alkyl), unsubstituted —$C_1$-$C_5$alkyl, or unsubstituted —$C_2$-$C_5$alkenyl-;

$R^{B1}$ and $R^{B2}$ are each independently —CH$_2$—;

B is -halo($C_1$-$C_5$alkyl), unsubstituted —$C_1$-$C_5$alkyl, or unsubstituted —$C_2$-$C_5$alkenyl-;

$R^{A2}$ and $R^{A1}$ are each independently H, halogen, hydroxyl, optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, $C_1$-$C_4$alkoxyl, —N($R^e$)($R^f$), —CO$_2$($R^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy) and $C_1$-$C_4$alkoxy-($C_1$-$C_4$alkoxy)-;

each $R^d$ is independently H or $C_1$-$C_4$alkyl;

$R^e$ is selected from H, ($C_1$-$C_4$alkyl), —CO($C_1$-$C_4$alkyl), —OCO($C_1$-$C_4$alkyl), or —CO$_2$($C_1$-$C_4$alkyl), each $R^f$ is H or ($C_1$-$C_4$alkyl);

$R^6$ is H;

$R^{14}$ is optionally substituted $C_1$-$C_4$alkyl;

$R^{15}$ is $C_1$-$C_4$alkyl;

$R^{16}$ is $C_1$-$C_4$alkyl;

$R^1$ is $C_1$-$C_4$alkyl; and each occurrence of $R^I$ and $R^{II}$ are independently ($C_1$-$C_6$alkyl)oxy-, or a tautomer thereof, or a salt thereof, particularly a pharmaceutically acceptable salt thereof.

In one embodiment, the compound of Formula (I-P-bc), wherein $R^{A2}$ and $R^{A1}$ are each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —O—P(O)(OH)$_2$, —O—P(O)($R^I R^{II}$)$_2$, —N($R^e$)($R^f$), $C_1$-$C_4$alkoxyl, phenyl, optionally substituted 5-6 membered heterocycloalkyl containing at least one nitrogen or oxygen as a member of the ring, each $R^e$ is independently selected from H, ($C_1$-$C_4$alkyl), —($C_1$-$C_4$alkyl)-NH$_2$, or —($C_1$-$C_4$alkyl) $C_1$-$C_4$alkoxy and each $R^f$ is independently H or ($C_1$-$C_4$alkyl).

In one embodiment, the compound of Formula (I-P-bc) or (I-bc), wherein $R^{A2}$ and $R^{A1}$ are each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —N($R^e$)($R^f$), $C_1$-$C_4$alkoxyl, phenyl, optionally substituted 5-6 membered heterocycloalkyl containing at least one nitrogen or oxygen as a member of the ring, and $R^e$ and $R^f$ are each independently H or ($C_1$-$C_4$alkyl).

In one embodiment, the compound of Formula (I-P-bc), wherein at least one of $R^{A2}$ or $R^{A1}$ is independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl and morpholinyl, each $R^e$ is independently selected from H, ($C_1$-$C_4$alkyl), —($C_1$-$C_4$alkyl)-NH$_2$, or —($C_1$-$C_4$alkyl) $C_1$-$C_4$alkoxy and each $R^f$ is independently H or ($C_1$-$C_4$alkyl).

In one embodiment, the compound of Formula (I-P-bc) or (I-bc), wherein at least one of $R^{A2}$ or $R^{A1}$ is each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl or morpholinyl, and $R^e$ and $R^f$ are each independently H or ($C_1$-$C_4$alkyl).

Representative compounds of this invention include the compounds of the Examples. It will be appreciated that the present invention encompasses compounds of Formula (I-N), Formula (I) and Formula (I-P) as the free base and as salts thereof, for example as a pharmaceutically acceptable salt thereof. In one embodiment the invention relates to compounds of Formula (I-N), Formula (I) and Formula (I-P) in the form of a free base. In another embodiment the invention relates to compounds of Formula (I-N), Formula (I) and Formula (I-P) in the form of a salt, particularly, a pharmaceutically acceptable salt. It will be further appreciated that, in one embodiment, the invention relates to compounds of the Examples in the form of a free base. In another embodiment the invention relates to compounds of the Examples in the form of a salt, particularly, a pharmaceutically acceptable salt.

Specific embodiments of the compounds of this invention include:

1,1'-((2R,3R)-2,3-dihydroxybutane-1,4-diyl)bis(2-(1-ethyl-3-methyl-1H-pyrazole-5-carboxamido)-1H-benzo[d]imidazole-5-carboxamide);

(E)-1,1'-(but-2-ene-1,4-diyl)bis(2-(1-ethyl-3-methyl-1H-pyrazole-5-carboxamido)-1H-benzo[d]imidazole-5-carboxamide);

1,1'-((methylazanediyl)bis(ethane-2,1-diyl))bis(2-(1-ethyl-3-methyl-1H-pyrazole-5-carboxamido)-1H-benzo[d]imidazole-5-carboxamide);

methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate;

1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide;

(E)-1,1'-(but-2-ene-1,4-diyl)bis(2-(1-ethyl-3-methyl-1H-pyrazole-5-carboxamido)-7-(3-hydroxypropoxy)-1H-benzo[d]imidazole-5-carboxamide);

8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide;

8-ethyl-10,18,30-trimethyl-7,20-dioxo-7,8,11,12,13,14,15,20,21,28,29,30,31,32-tetradecahydro-1H-benzo[4,5]imidazo[2,1-b]benzo[4,5]imidazo[1,2-i]dipyrazolo[5,1-m:4',3'-f][1,3,6,9,11,14]hexaazacyclodocosine-3,24-dicarboxamide; and 1,15-bis(1-ethyl-3-methyl-1H-pyrazole-5-carboxamido)-8,9,16,17,18,19-hexahydro-7H-6,10-dioxa-2,14,15a,19a-tetraazacyclopentadeca[1,2,3-cd:11,10,9-c'd']diindene-4,12-dicarboxamide;

as a free base,
or a tautomer thereof;
or a salt thereof, particularly a pharmaceutically acceptable salt, thereof.

Further embodiments of the compounds of this invention include:

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1,1'-(but-2-ene-1,4-diyl)bis(2-(1-ethyl-3-methyl-1H-pyrazole-5-carboxamido)-7-(3-morpholinopropoxy)-1H-benzo[d]imidazole-5-carboxamide);

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide;

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-hydroxy-1H-benzo[d]imidazole-5-carboxamide;

1,1'-(2,2,3,3-tetrafluorobutane-1,4-diyl)bis(2-(1-ethyl-3-methyl-1H-pyrazole-5-carboxamido)-1H-benzo[d]imidazole-5-carboxamide);

di-tert-butyl(3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl) phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate;

(E)-7-bromo-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazole-5-carboxamide;

ethyl(E)-3-(5-carbamoyl-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate;

ethyl(E)-3-(5-Carbamoyl-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazol-7-yl)propanoic acid;

methyl-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate;

methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate;

1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic acid;

(E)-1,1'-(but-2-ene-1,4-diyl)bis(2-(1-ethyl-3-methyl-1H-pyrazole-5-carboxamido)-7-methoxy-1H-benzo[d]imidazole-5-carboxamide);

1,1'-(butane-1,4-diyl)bis(2-(1-ethyl-3-methyl-1H-pyrazole-5-carboxamido)-7-(3-hydroxypropoxy)-1H-benzo[d]imidazole-5-carboxamide);

(E)-8-ethyl-4,26-bis(3-hydroxypropoxy)-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-l][1,3,6,15,17]pentaazacyclohenicosine-2,24-dicarboxamide;

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-(3-methoxypropoxy)-1H-benzo[d]imidazole-5-carboxamide;

(E)-1-(4-(5-carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-(2-methoxyethoxy)-1H-benzo[d]imidazole-5-carboxamide;

(E)-1,1'-(but-2-ene-1,4-diyl)bis(2-(1-ethyl-3-methyl-1H-pyrazole-5-carboxamido)-7-isopropoxy-1H-benzo[d]imidazole-5-carboxamide);

(E)-7-(benzyloxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide;

(E)-1-(4-(5-carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-methyl-1Hbenzo[d]imidazole-5-carboxamide;

(E)-1,1'-(but-2-ene-1,4-diyl)bis(7-butoxy-2-(1-ethyl-3-methyl-1H-pyrazole-5-carboxamido)-1H-benzo[d]imidazole-5-carboxamide);

(E)-1-(4-(5-carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-isopropoxy-1H-benzo[d]imidazole-5-carboxamide;

(E)-1,1'-(but-2-ene-1,4-diyl)bis(2-(1-ethyl-3-methyl-1H-pyrazole-5-carboxamido)-7-(3-isopropoxypropoxy)-1H-benzo[d]imidazole-5-carboxamide);

(E)-2-(1-ethyl-3-methyl-1H-pyrazole-5-carboxamido)-1-(4-(2-(1-ethyl-3-methyl-1H-pyrazole-5-carboxamido)-7-(morpholinomethyl)-1H-benzo[d]imidazol-1-yl)but-2-en-1-yl)-1H-benzo[d]imidazole-5-carboxamide;

as a free base,
or a tautomer thereof;
or a salt thereof, particularly a pharmaceutically acceptable salt, thereof.

One embodiment of the compounds of this invention include:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyldihydrogen phosphate;

(E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate;

or a tautomer thereof;
or a salt thereof, particularly a pharmaceutically acceptable salt, thereof.

In one embodiment, the compounds of Formula (I-N), Formula (I) or Formula (I-P) are not the following compounds:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]

imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy) propyldihydrogen phosphate;

(E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy) propyl dihydrogen phosphate;

or a tautomer thereof;

or a salt thereof, particularly a pharmaceutically acceptable salt, thereof.

In one embodiment, the compounds of Formula (I-N), Formula (I) or Formula (I-P) are not the following compounds:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

or a tautomer thereof;

or a salt thereof, particularly a pharmaceutically acceptable salt, thereof.

In one embodiment, the compounds of Formula (I-N), Formula (I) or Formula (I-P) are not the following compounds:

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

or a tautomer thereof;

or a salt thereof, particularly a pharmaceutically acceptable salt, thereof.

In one embodiment, the compounds of Formula (I-N), Formula (I) or Formula (I-P) are not the following compounds:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

or a tautomer thereof;

or a salt thereof, particularly a pharmaceutically acceptable salt, thereof.

In one embodiment, the compounds of Formula (I-N), Formula (I) or Formula (I-P) are not the following compounds:

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

or a tautomer thereof;

or a salt thereof, particularly a pharmaceutically acceptable salt, thereof.

In one embodiment, the compounds of Formula (I-N), Formula (I) or Formula (I-P) are not the following compounds:

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyldihydrogen phosphate;

(E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate;

or a tautomer thereof;

or a salt thereof, particularly a pharmaceutically acceptable salt, thereof.

In one embodiment, the compound of Formula (I-N), Formula (I) or Formula (I-P) is (E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide

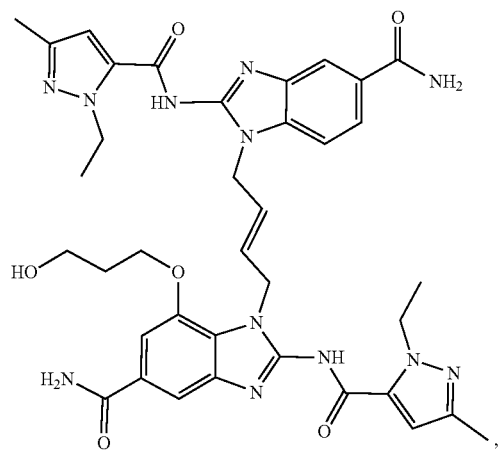

or a tautomer thereof;

or a salt thereof, particularly a pharmaceutically acceptable salt, thereof.

In one embodiment, the compound of Formula (I-N), Formula (I) or Formula (I-P) is (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

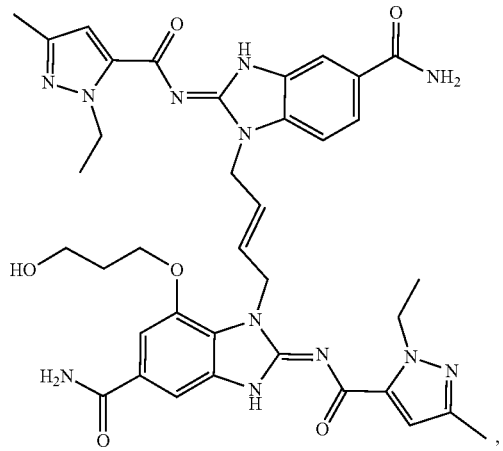

or a tautomer thereof;

or a salt thereof, particularly a pharmaceutically acceptable salt, thereof.

In one embodiment, the compound of Formula (I-N), Formula (I) or Formula (I-P) is (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

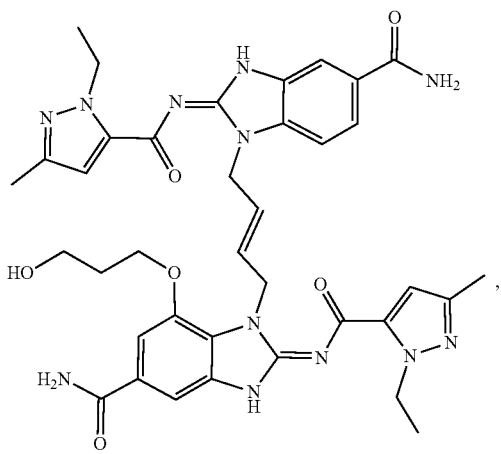

or a tautomer thereof;

or a salt thereof, particularly a pharmaceutically acceptable salt, thereof.

In one embodiment, the compound of Formula (I-N), Formula (I) or Formula (I-P) is (E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

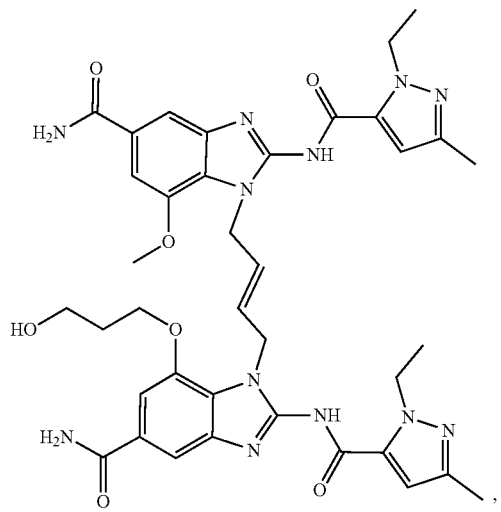 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCO)c21]

or a tautomer thereof;

or a salt thereof, particularly a pharmaceutically acceptable salt, thereof.

In one embodiment, the compound of Formula (I-N), Formula (I) or Formula (I-P) is (E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

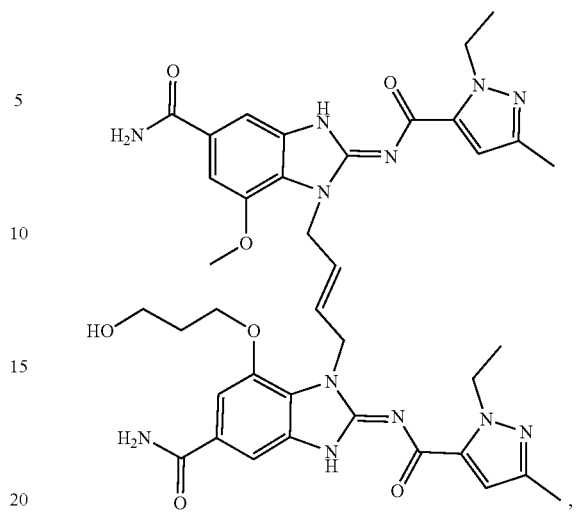

or a tautomer thereof;

or a salt thereof, particularly a pharmaceutically acceptable salt, thereof.

In one embodiment, the compound of Formula (I-N), Formula (I) or Formula (I-P) is (Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

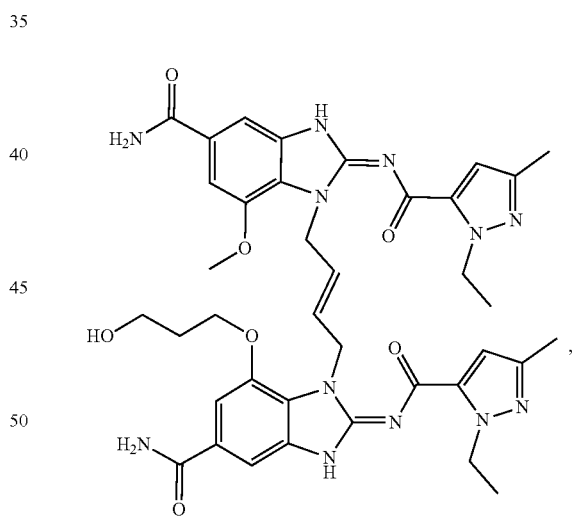

or a tautomer thereof;

or a salt thereof, particularly a pharmaceutically acceptable salt, thereof.

In one embodiment, the compound of Formula (I-N), Formula (I) or Formula (I-P) is (E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide

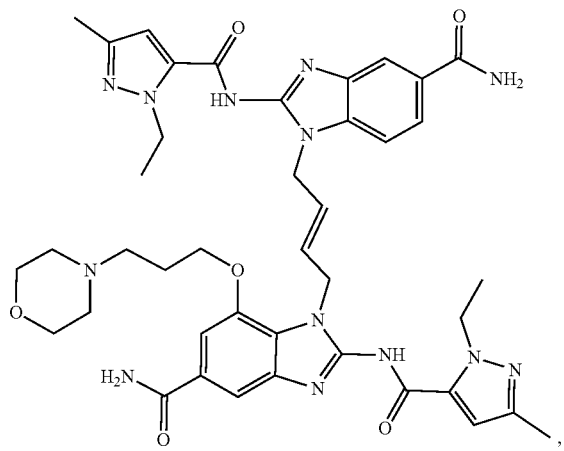 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCN3CCOCC3)c21]

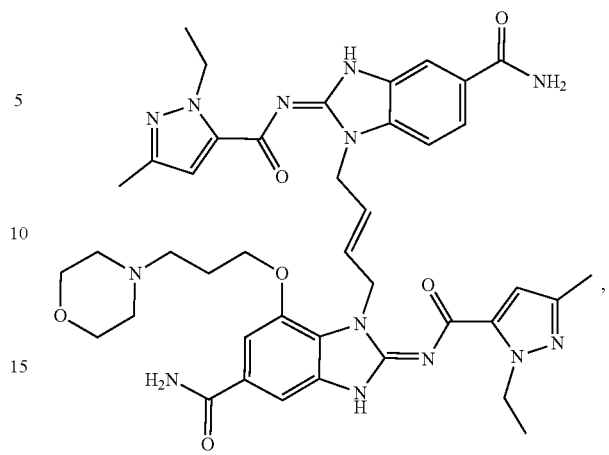

or a tautomer thereof;

or a salt thereof, particularly a pharmaceutically acceptable salt, thereof.

In one embodiment, the compound of Formula (I-N), Formula (I) or Formula (I-P) is (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide or a tautomer thereof;

or a salt thereof, particularly a pharmaceutically acceptable salt, thereof.

In one embodiment, the compound of Formula (I-N), Formula (I) or Formula (I-P) is (E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

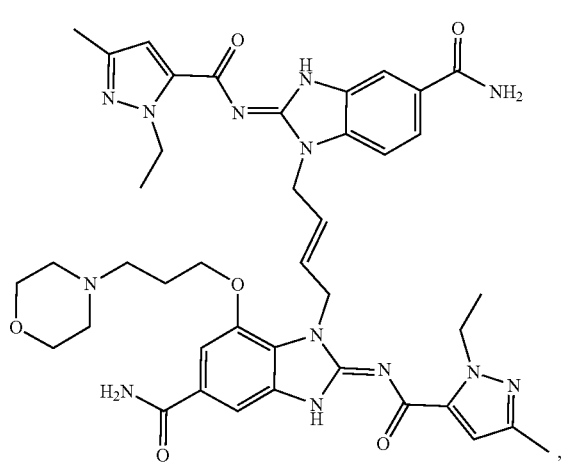 [SMILES: CCn1nc(C)cc1C(=O)/N=c1\[nH]c2cc(C(N)=O)ccc2n1C/C=C/Cn1/c(=N/C(=O)c2cc(C)nn2CC)[nH]c2cc(C(N)=O)cc(OCCCN3CCOCC3)c21]

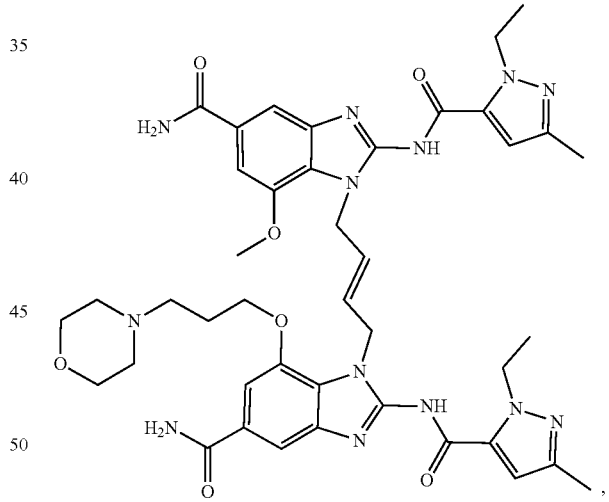

or a tautomer thereof;

or a salt thereof, particularly a pharmaceutically acceptable salt, thereof.

In one embodiment, the compound of Formula (I-N), Formula (I) or Formula (I-P) is (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide or a tautomer thereof;

or a salt thereof, particularly a pharmaceutically acceptable salt, thereof.

In one embodiment, the compound of Formula (I-N), Formula (I) or Formula (I-P) is (E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

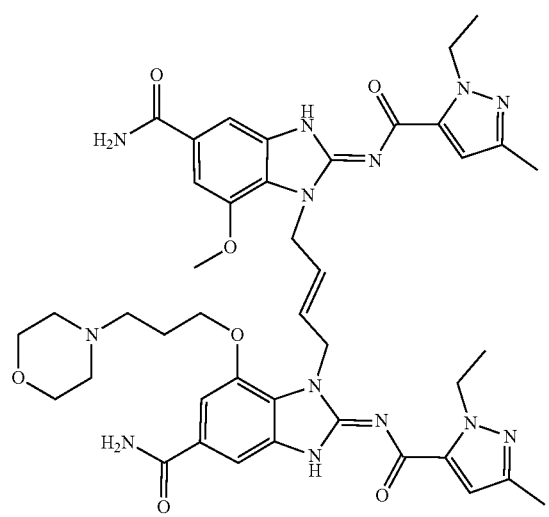

or a tautomer thereof;

or a salt thereof, particularly a pharmaceutically acceptable salt, thereof.

In one embodiment, the compound of Formula (I-N), Formula (I) or Formula (I-P) is (Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

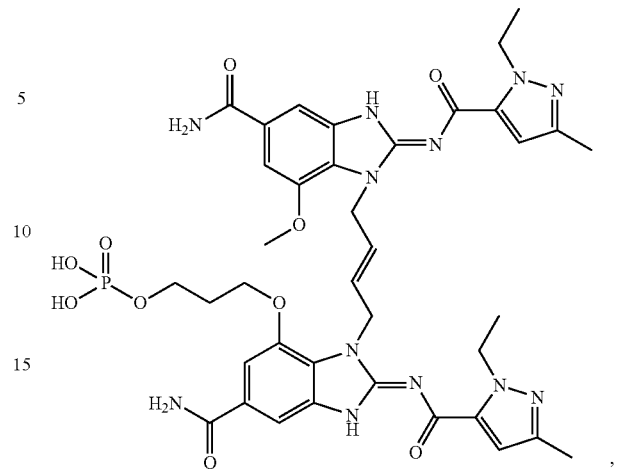

or a tautomer thereof;

or a salt thereof, particularly a pharmaceutically acceptable salt, thereof.

In one embodiment, the compound of Formula (I-N), Formula (I) or Formula (I-P) is (E)-3-((5-carbamoyl-1-(4-(5-carbamoyl-2-((1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate

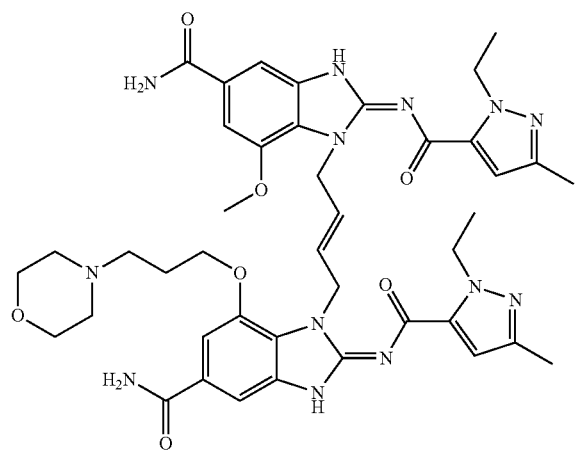

or a tautomer thereof;

or a salt thereof, particularly a pharmaceutically acceptable salt, thereof.

In one embodiment, the compound of Formula (I-N), Formula (I) or Formula (I-P) is 3-(((Z)-6-Carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate

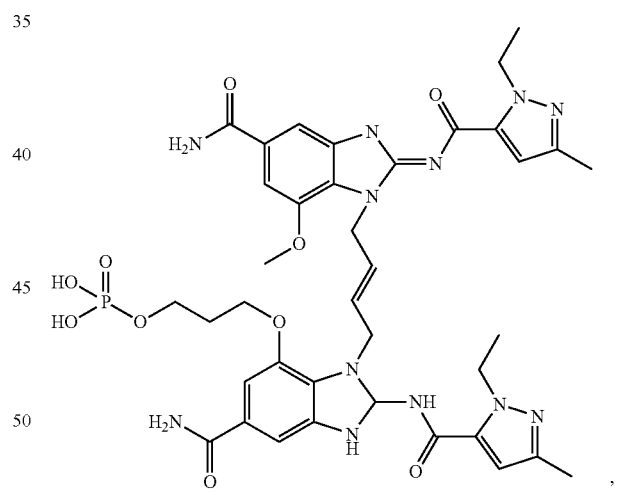

or a tautomer thereof;

or a salt thereof, particularly a pharmaceutically acceptable salt, thereof.

In one embodiment, the compound of Formula (I-N), Formula (I) or Formula (I-P) is or 3-(((Z)-6-Carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate

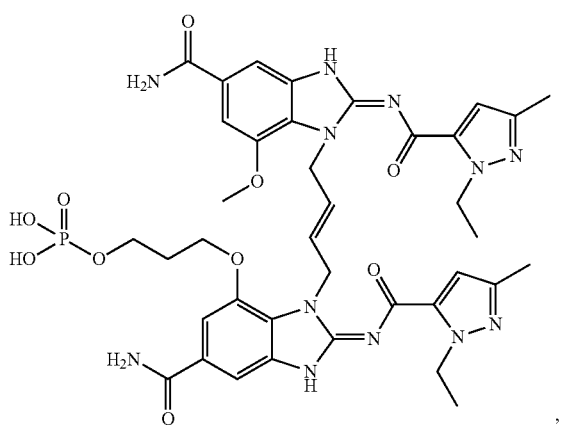 [SMILES: CCn1nc(C)cc1C(=O)/N=c1/[nH]c2cc(C(N)=O)cc(OC)c2n1C/C=C/Cn1/c(=N\C(=O)c2cc(C)nn2CC)[nH]c2cc(C(N)=O)cc(OCCCOP(=O)(O)O)c21]

or a tautomer thereof;
or a salt thereof, particularly a pharmaceutically acceptable salt, thereof.

The compounds of this invention may contain one or more asymmetric centers (also referred to as a chiral center), such as a chiral carbon, or a chiral —SO— moiety. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

The stereochemistry of the chiral center present in compounds of this invention is generally represented in the compound names and/or in the chemical structures illustrated herein. Where the stereochemistry of a chiral center present in a compound of this invention, or in any chemical structure illustrated herein, is not specified, the structure is intended to encompass any stereoisomer and all mixtures thereof. Accordingly, the present invention encompasses all isomers of the compounds of Formula (I-N), (I-P) or (I), and salts thereof, whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Individual stereoisomers of a compound of this invention may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The invention also includes various deuterated forms of the compounds of this invention. Each available hydrogen atom attached to a carbon atom may be independently replaced with a deuterium atom. A person of ordinary skill in the art will know how to synthesize deuterated forms of the compounds of this invention. For example, α-deuterated α-amino acids are commercially available or may be prepared by conventional techniques (see for example: Elemes, Y and Ragnarsson, U. J. Chem. Soc., Perkin Trans. 1, 1996, 6, 537-40). Employing such compounds may allow for the preparation of compounds in which the hydrogen atom at a chiral center is replaced with a deuterium atom. Other commercially available deuterated starting materials may be employed in the preparation of deuterated analogs of the compounds of this invention (see for example: methyl-d-amine available from Aldrich Chemical Co., Milwaukee, Wis.), or they may be synthesized using conventional techniques employing deuterated reagents (e.g. by reduction using lithium aluminum deuteride or sodium borodeuteride or by metal-halogen exchange followed by quenching with $D_2O$ or methanol-$d_3$).

Suitable pharmaceutically acceptable salts of the compounds of Formula (I-N), (I-P) or (I) can include acid addition salts or base addition salts. For reviews of suitable pharmaceutically acceptable salts see Berge et al., J. Pharm. Sci., 66:1-19, (1977) and P. H. Stahl and C. G. Wermuth, Eds., Handbook of Pharmaceutical Salts: Properties, Selection and Use, Weinheim/Zürich:Wiley-VCH/VHCA (2002).

Salts of the compounds of Formula (I-N), (I-P) or (I) containing a basic amine or other basic functional group may be prepared by any suitable method known in the art, such as treatment of the free base with a suitable inorganic or organic acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate (hemi-fumarate, etc.), galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride (dihydrochloride, etc.), hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate (diphosphate, etc.), proprionate, pyroglutamate, salicylate, sebacate, stearate, succinate, sulfate, tartrate, thiocyanate, p-toluenesulfonate (tosylate), undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N-bisdehydroabietylamine, glucamine, N-methylglucamine, collidine, choline, quinine, quinoline, and basic amino acids such as lysine and arginine.

The invention includes within its scope all possible stoichiometric and non-stoichiometric forms of the salts (e.g., hydrobromide, dihydrobromide, fumarte, hemi-fumarate, etc) of the compounds of Formula (I-N), (I-P) or (I).

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that the invention includes all polymorphs of any compound of this invention, e.g., all polymorphic forms of any compound named or depicted by structure herein, including any salts and/or solvates (particularly, hydrates) thereof.

Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the conditions used in crystallizing/recrystallizing the compound. Polymorphic forms may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The skilled artisan will appreciate that pharmaceutically acceptable solvates (particularly, hydrates) of a compound of Formula (I-N), (I-P) or (I), including pharmaceutically acceptable solvates of a pharmaceutically acceptable salt of a compound of Formula (I-N), (I-P) or (I), may be formed when solvent molecules are incorporated into the crystalline lattice during crystallization. Solvates may involve non-aqueous solvents such as ethanol, or they may involve water as the solvent that is incorporated into the crystalline lattice. Solvates wherein water is the solvent that is incorporated into the crystalline lattice are typically referred to as "hydrates."

The present invention includes within its scope all possible stoichiometric and non-stoichiometric salt and/or hydrate forms.

Salts and solvates (e.g. hydrates and hydrates of salts) of the compounds of the invention which are suitable for use in medicine are those wherein the counterion or associated solvent is pharmaceutically acceptable. Salts having non-pharmaceutically acceptable counterions are within the scope of the present invention, for example, for use as intermediates in the preparation of other compounds of the invention.

Typically, a pharmaceutically acceptable salt may be readily prepared by using a desired acid or base as appropriate. The resultant salt may crystallize or precipitate from solution, or form by trituration, and may be recovered by filtration, or by evaporation of the solvent.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The invention encompasses all prodrugs of the compounds of this invention, which upon administration to the recipient are capable of providing (directly or indirectly) a compound of this invention, or an active metabolite or residue thereof. Such derivatives are recognisable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

It is to be further understood that the present invention includes within its scope all tautomeric or isomer forms of any free base form of the compounds of this invention as well as all possible stoichiometric and non-stoichiometric salt forms. The compounds of the invention are useful in the treatment or prevention of diseases and disorders in which modulation of STING is beneficial. Such STING mediated diseases and disorders include inflammation, allergic and autoimmune diseases, infectious diseases, cancer and precancerous syndromes. The compounds of the invention are also useful as an immugenic composition or vaccine adjuvant. Accordingly, this invention is directed to a method of modulating STING comprising contacting a cell with a compound of the invention.

One aspect of the invention provides methods of treatment or prevention of STING mediated diseases and disorders, in which agonizing STING is beneficial. Exemplary diseases/disorders includes, but are not limited to, cancer, infectious disease (e.g., HIV, HBV, HCV, HPV, and influenza), vaccine adjuvant.

In one embodiment, this invention provides a compound of the invention for use in therapy. This invention also provides a compound of Formula (I-N), (I-P) or (I), or a pharmaceutically acceptable salt thereof, for use in therapy. This invention particularly provides a compound of Formula (I-N), (I-P) or (I), or a pharmaceutically acceptable salt thereof, for use in the treatment of a STING-mediated disease or disorder.

This invention also provides a compound of Formula (I-N), (I-P) or (I), or a pharmaceutically acceptable salt thereof, for use as a vaccine adjuvant. There is also therefore provided an immugenic composition or vaccine adjuvant comprising a compound of Formula (I-N), (I-P) or (I), or a pharmaceutically acceptable salt thereof.

In a further embodiment of the invention, there is provided a composition comprising a compound of Formula (I-N), (I-P) or (I), or a pharmaceutically acceptable salt thereof, and one or more immunostimulatory agents.

In another embodiment, this invention provides a compound of the invention for use in the treatment of a STING-mediated disease or disorder and/or for use as an immugenic composition or a vaccine adjuvant. In another embodiment, this invention provides a compound of Formula (I-N), (I-P) or (I), or a pharmaceutically acceptable salt thereof, for use in the amelioration of organ injury or damage sustained as a result of a STING-mediated disease or disorder.

The invention further provides for the use of a compound of the invention in the manufacture of a medicament for treatment of a STING-mediated disease or disorder. The invention further provides for the use of a compound of Formula (I-N), (I-P) or (I), or a salt thereof, particularly a pharmaceutically acceptable salt thereof, in the manufacture of a medicament for treatment of a STING-mediated disease or disorder, for example the diseases and disorders recited herein.

The invention further provides for the use of a compound of Formula (I-N), (I-P) or (I), or a salt thereof, particularly a pharmaceutically acceptable salt thereof, in the manufacture of a vaccine. There is further provided the use of a compound of Formula (I-N), (I-P) or (I), or a pharmaceutically acceptable salt thereof, for the manufacture of an immunogenic composition comprising an antigen or antigenic composition, for the treatment or prevention of disease. There is further provided the use of a compound of Formula (I-N), (I-P) or (I), or a pharmaceutically acceptable salt thereof, for the manufacture of a vaccine composition comprising an antigen or antigenic composition, for the treatment or prevention of disease.

In another embodiment, the invention is directed to a method of treating a STING-mediated disease or disorder comprising administering a therapeutically effective amount of a compound of this invention to a human in need thereof. In another embodiment, the invention is directed to a method of treating a STING-mediated disease or disorder comprising administering a therapeutically effective amount of a compound of Formula (I-N), (I) or (I-P) or a salt, particularly a pharmaceutically acceptable salt thereof, to a human in need thereof.

In another embodiment, the invention is directed to a method of treating or preventing disease comprising the administration to a human subject suffering from or susceptible to disease, an immunogenic composition comprising an antigen or antigenic composition and a compound of Formula (I-N), (I-P) or (I), or a pharmaceutically acceptable salt thereof. In another embodiment, the invention is directed to a method of treating or preventing disease comprising the administration to a patient human subject suffering from or susceptible to disease, a vaccine composition comprising an antigen or antigenic composition and a compound of Formula (I-N), (I-P) or (I), or a pharmaceutically acceptable salt thereof.

In one embodiment, this invention is directed to a compound of Formula (I-N), (I-P) or (I), or a pharmaceutically acceptable salt thereof for use in the treatment of inflammation. In a further aspect there is provided a method of treating inflammation comprising administering to a human in need thereof a therapeutically effective amount of a compound of Formula (I-N), (I-P) or (I), or a pharmaceutically acceptable salt thereof. In a further aspect there is provided a compound of Formula (I-N), (I-P) or (I) or a pharmaceutically acceptable salt thereof for use in the manufacture of a medicament for the treatment of inflammation.

In one embodiment, this invention is directed to a compound of Formula (I-N), (I-P) or (I) or a pharmaceutically acceptable salt thereof for use in the treatment of an allergic disease. In a further aspect there is provided a method of treating an allergic disease comprising administering to a human in need thereof a therapeutically effective amount of a compound of Formula (I-N), (I-P) or (I) or a pharmaceutically acceptable salt thereof. In a further aspect there is provided a compound of Formula (I-N), (I-P) or (I) or a pharmaceutically acceptable salt thereof for use in the manufacture of a medicament for the treatment of an allergic disease.

In one embodiment, this invention is directed to a compound of Formula (I-N), (I-P) or (I) or a pharmaceutically acceptable salt thereof for use in the treatment of an autoimmune disease. In a further aspect there is provided a method of treating an autoimmune disease comprising administering to a human in need thereof a therapeutically effective amount of a compound of Formula (I-N), (I-P) or (I) or a pharmaceutically acceptable salt thereof. In a further aspect there is provided a compound of Formula (I-N), (I-P) or (I) or a pharmaceutically acceptable salt thereof for use in the manufacture of a medicament for the treatment of an autoimmune disease.

In one embodiment, this invention is directed to a compound of Formula (I-N), (I-P) or (I) or a pharmaceutically acceptable salt thereof for use in the treatment of an infectious disease. In a further aspect there is provided a method of treating an infectious disease comprising administering to a human in need thereof a therapeutically effective amount of a compound of Formula (I-N), (I-P) or (I) or a pharmaceutically acceptable salt thereof. In a further aspect there is provided a compound of Formula (I-N), (I-P) or (I) or a pharmaceutically acceptable salt thereof for use in the manufacture of a medicament for the treatment of an infectious disease.

In one embodiment, this invention is directed to a method of treating an HIV infection in a human by administering to the human a therapeutically effective amount of a compound of Formula (I-N), (I-P) or (I), or a pharmaceutically acceptable salt thereof. In one embodiment, this invention is directed to a method of treating an HIV infection, in a human having or at risk of having the infection by administering to the human a therapeutically effective amount of a compound of Formula (I-N), (I-P) or (I), or a pharmaceutically acceptable salt thereof. In another embodiment, this invention is directed to a method of treating an AIDS infection, in a human having the infection by administering to the human a therapeutically effective amount of a compound of Formula (I-N), (I-P) or (I), or a pharmaceutically acceptable salt thereof.

In one embodiment, this invention is directed to a method of treating an HBV infection in a human by administering to the human a therapeutically effective amount of a compound of Formula (I-N), (I-P) or (I), or a pharmaceutically acceptable salt thereof. In one embodiment, this invention is directed to a method of treating an HBV infection, in a human having or at risk of having the infection by administering to the human a therapeutically effective amount of a compound of Formula (I-N), (I-P) or (I), or a pharmaceutically acceptable salt thereof. In one embodiment, this invention is directed to a method of treating an HCV infection in a human by administering to the human a therapeutically effective amount of a compound of Formula (I-N), (I-P) or (I), or a pharmaceutically acceptable salt thereof. In one embodiment, this invention is directed to a method of treating an HCV infection, in a human having or at risk of having the infection by administering to the human a therapeutically effective amount of a compound of Formula (I-N), (I-P) or (I), or a pharmaceutically acceptable salt thereof.

In one embodiment, this invention is directed to a method of treating influenza in a human by administering to the human a therapeutically effective amount of a compound of Formula (I-N), (I-P) or (I), or a pharmaceutically acceptable salt thereof. In one embodiment, this invention is directed to a method of treating influenza, in a human having or at risk of having the infection by administering to the human a therapeutically effective amount of a compound of Formula (I-N), (I-P) or (I), or a pharmaceutically acceptable salt thereof.

In one embodiment, this invention is directed to a method of treating human papilomavirus (HPV) infection in a human by administering to the human a therapeutically effective amount of a compound of Formula (I-N), (I-P) or (I), or a pharmaceutically acceptable salt thereof. In one embodiment, this invention is directed to a method of treating HPV infection, in a human having or at risk of having the infection by administering to the human a therapeutically effective amount of a compound of Formula (I-N), (I-P) or (I), or a pharmaceutically acceptable salt thereof.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In one embodiment, this invention is directed to a compound of Formula (I-N), (I-P) or (I) or a pharmaceutically acceptable salt thereof for use in the treatment of cancer and pre-cancerous syndromes. In a further aspect there is provided a method of treating cancer and pre-cancerous syndromes comprising administering to a human in need thereof a therapeutically effective amount of a compound of Formula (I-N), (I-P) or (I) or a pharmaceutically acceptable salt thereof. In a further aspect there is provided a compound of Formula (I-N), (I-P) or (I) or a pharmaceutically acceptable salt thereof for use in the manufacture of a medicament for the treatment of cancer and pre-cancerous syndromes.

Autoimmune diseases associated include, but are not limited to STING associated vasculitis with onset at infancy (SAVI), Aicardi Goutieres syndrome (AGS), chilblain lupus, ataxia telanogiectasia (also referred to as Louis-Bar Syndrome), retinal vasculopathy with cerebral leukodystrophy (RCVL), systemic lupus erythematosus (SLE), cutaneous lupus, lupus nephritis, psoriasis, diabetes mellitus including insulin-dependent diabetes mellitus (IDDM), dermatomyositis, human immunodeficiency virus (HIV), AIDS, polymyositis, systemic sclerosis (scleroderma), and Sjögren's syndrome (SS), rheumatoid arthritis, psoriatic arthritis, polyarthritis, myasthenia gravis, polyarteritis nodosa, vasculitis, cutaneous vasculitis, anti-neutrophil cytoplasmic antibody (ANCA)-associated vasculitis, Henoch-Schönlein purpura, autoimmune hepatitis, primary sclerosing cholangitis, Wegener's granulomatosis, microscopi polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Inflammation represents a group of vascular, cellular and neurological responses to trauma. Inflammation can be characterized as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present, and to allow for the physiological process or healing and tissue repair to progress.

The compounds of this invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis, CNS vasculitis, and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compounds of this invention may be used to treat autoimmune conditions having an inflammatory component. Such conditions include acute disseminated alopecia universalise, Behcet's disease, Chagas' disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-associated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compounds of this invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the compounds of this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome, Sezary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic pulmonary disease, and inflammation accompanying infectious conditions (e.g., sepsis). In one embodiment, the compounds of this invention may be used to treat asthma.

Examples of cancer diseases and conditions in which a compounds of this invention may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer. In some embodiments, the compounds of the present invention may be used to treat solid or liquid tumors. In some embodiments, the compounds of the present invention may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and/or Non Hodgkin lymphoma (NHL). Suitably the present invention relates to a method for treating or lessening the severity of pre-cancerous syndromes in a mammal, including a human, wherein the pre-cancerous syndrome is selected from: cervical intraepithelial neoplasia, monoclonal gammopathy of unknown significance (MGUS), myelodysplastic syndrome, aplastic anemia, cervical lesions, skin nevi (pre-melanoma), prostatic intraepithelial (intraductal) neoplasia (PIN), Ductal Carcinoma in situ (DCIS), colon polyps and severe hepatitis or cirrhosis.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lymphoblastic leukemia (CLL), follicular lymphoma, acute myeloid leukemia and chronic myelogenous leukemia.

In one embodiment, the compounds of the present invention may be useful for treatment of skin cancers (e.g., non-melanoma skin cancer, squamous cell carcinoma, basal cell carcinoma) or actinic keratosis. In addition to a field effect for clearing superficial skin cancers, the compounds of the present invention may prevent the development of subsequent skin cancers and pre-malignant actinic keratosis in treated patients.

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

The compounds of this invention may be used to treat neurodegenerative diseases. Exemplary neurodegenerative diseases includes, but are not limited to, multiple sclerosis, Huntington's disease, Alzheimer's disease, Parkinson's disease, amyotrophic lateral sclerosis (ALS).

The compounds of this invention may be used to treat an infectious disease, which is any disease instigated by or coincident with an infection from a pathogen. Pathogens are broadly defined as any species of organism that is foreign to a human tissue environment. Common disease causing pathogens include bacteria (many like TB), viruses (many like HBV, HIV, flu) and parasitic protozoans (like *P falciparum* that causes malaria). The compounds of this invention may be used to treat infectious diseases derived from bacteria, such as TB infection (*Mycobacterium tuberculosis*), *Chlamydia*, Tularemia infection (*Francisella tularensis*), *plasmodium* infection or infections from DNA or RNA virus. The compounds of this invention may be used to treat infectious diseases derived from the DNA virus families: Herpesviridae (herpes simplex virus-1, Kaposi's sarcoma-associated virus and Epstein-Barr virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Hepatitis C virus), Orthomyxoviridae (influenza), and Coronaviridae (human coronavirus and SARS coronzvirus).

The compounds of this invention may be employed alone or in combination with other therapeutic agents. As modulators of the immune response, the compounds of this invention may also be used in monotherapy or used in combination with another therapeutic agent in the treatment of diseases and conditions in which modulation of STING is beneficial. Combination therapies according to the present invention thus comprise the administration of a compound of Formula (I-N), (I-P) or (I) or a pharmaceutically acceptable salt thereof, and at least one other therapeutically active agent. In one embodiment, combination therapies according to the present invention comprise the administration of at least one compound of Formula (I-N), (I-P) or (I) or a pharmaceutically acceptable salt thereof, and at least one other therapeutic agent. The compound(s) of Formula (I-N), (I-P) or (I) and pharmaceutically acceptable salts thereof, and the other therapeutic agent(s) may be administered together in a single pharmaceutical composition or separately and, when administered separately this may occur simultaneously or sequentially in any order. The amounts of the compound(s) of Formula (I-N), (I-P) or (I) and pharmaceutically acceptable salts thereof, and the other therapeutic agent(s) and the relative timings of administration will be selected in order to achieve the desired combined therapeutic effect. Thus, in a further aspect, there is provided a combination comprising a compound of Formula (I-N), (I-P) or (I), or a pharmaceutically acceptable salt thereof, together with one or more other therapeutic agents.

The compounds of Formula (I-N), (I-P) or (I) and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The compounds of Formula (I-N), (I-P) or (I) and pharmaceutically acceptable salts thereof may be used in combination with radiotherapy and/or surgery and/or at least one other therapeutic agent which may be useful in the treatment of cancer and pre-cancerous syndromes. Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; cell cycle signaling inhibitors; immuno-oncology agents and immunostimulatory agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevfolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q. v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosuppression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated for use as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diamine [1,1-cyclobutane-dicarboxylate(2-)—O,O'], is commercially available as PARAPLATIN® as an injectable solution. Carboplatin is primarily indicated in the first and second line treatment of advanced ovarian carcinoma.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated for use as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and for use in combination with other agents for the second line treatment of Hodgkin's Disease.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthracyclines such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-Fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-Fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine (EHNA), fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl]methylamino] benzoyl]-L-glutamic acid, is commercially available as methotrexate sodium. Methotrexate exhibits cell phase effects specifically at S-phase by inhibiting DNA synthesis, repair and/or replication through the inhibition of dihydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irinotecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents relegation of single strand breaks caused by Topoisomerase I in response to torsional strain of the DNA molecule. Topotecan is indicated for second line treatment of metastatic carcinoma of the ovary and small cell lung cancer.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrozole, vorozole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, and anti-estrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signaling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic therapeutic agents including non-receptor MEK angiogenesis inhibitors may also be useful. Anti-angiogenic agents such as those which inhibit the effects of vascular endothelial growth factor, (for example the anti-vascular endothelial cell growth factor antibody bevacizumab [Avastin™], and compounds that work by other mechanisms (for example linomide, inhibitors of integrin $\alpha v\beta 3$ function, endostatin and angiostatin).

Agents used in immunotherapeutic regimens may also be useful in combination with the compounds of Formula (I-N), (I-P) or (I). Immunotherapy approaches, including for example ex-vivo and in-vivo approaches to increase the immunogenecity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

Therapeutic agents used in proapoptotic regimens (e.g., bcl-2 antisense oligonucleotides) may also be used in the combination of the present invention.

Cell cycle signaling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of Formula (I-N), (I-P) or (I), or a salt thereof, particularly a pharmaceutically acceptable salt thereof, and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In one embodiment, the combination of the present invention comprises a compound of Formula (I-N), (I-P) or (I), or a salt thereof, particularly a pharmaceutically acceptable salt thereof, and at least one anti-neoplastic agent which is an anti-microtubule agent selected from diterpenoids and vinca alkaloids.

In a further embodiment, at least one anti-neoplastic agent is a diterpenoid. In a further embodiment, at least one anti-neoplastic agent is a vinca alkaloid.

In one embodiment, the combination of the present invention comprises a compound of Formula (I-N), (I-P) or (I), or a salt thereof, particularly a pharmaceutically acceptable salt thereof, and at least one anti-neoplastic agent, which is a platinum coordination complex.

In a further embodiment, at least one anti-neoplastic agent is paclitaxel, carboplatin, or vinorelbine. In a further embodiment, at least one anti-neoplastic agent is carboplatin. In a further embodiment, at least one anti-neoplastic agent is vinorelbine. In a further embodiment, at least one anti-neoplastic agent is paclitaxel. In one embodiment, the combination of the present invention comprises a compound of Formula (I-N), (I-P) or (I), or a salt, particularly a pharmaceutically acceptable salt thereof, and at least one anti-neoplastic agent which is a signal transduction pathway inhibitor.

In a further embodiment, the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms. In a further embodiment, the signal transduction pathway inhibitor is an inhibitor of a serine/threonine kinase rafk, akt, or PKC-zeta. In a further embodiment, the signal transduction pathway inhibitor is an inhibitor of a non-receptor tyrosine kinase selected from the src family of kinases. In a further embodiment, the signal transduction pathway inhibitor is an inhibitor of c-src. In a further embodiment, the signal transduction pathway inhibitor is an inhibitor of Ras oncogene selected from inhibitors of farnesyl transferase and geranylgeranyl transferase. In a further embodiment, the signal transduction pathway inhibitor is an inhibitor of a serine/threonine kinase selected from the group consisting of PI3K.

In a further embodiment, the signal transduction pathway inhibitor is a dual EGFr/erbB2 inhibitor, for example N-{3-chloro-4-[(3-fluorobenzyl) oxy]phenyl}-6-[5-({[2-(methanesulphonyl) ethyl]amino}methyl)-2-furyl]-4-quinazolin-amine.

In one embodiment, the combination of the present invention comprises a compound of Formula (I-N), (I-P) or (I), or a salt, particularly a pharmaceutically acceptable salt thereof, and at least one anti-neoplastic agent which is a cell cycle signaling inhibitor. In further embodiment, cell cycle signaling inhibitor is an inhibitor of CDK2, CDK4 or CDK6.

Additional examples of other therapeutic agents (e.g., anti-neoplastic agent) for use in combination or co-administered with a compound of Formula (I-N), (I-P) or (I) are immuno-modulators.

As used herein "immuno-modulators" refer to any substance including monoclonal antibodies that affects the immune system. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, ICOS antibodies, OX-40 antibodies, PD-L1 antibodies, LAG3 antibodies, TIM-3 antibodies, 41BB antibodies and GITR antibodies.

Additional examples of other therapeutic agents (anti-neoplastic agent) for use in combination or co-administered with a compound of this invention are anti-PD-L1 agents. Anti-PD-L1 antibodies and methods of making the same are known in the art. Such antibodies to PD-L1 may be polyclonal or monoclonal, and/or recombinant, and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 20110280877, 2014/0341902 and 20130045201. Additional exemplary antibodies to PD-L1 (also referred to as CD274 or B7-H1) and methods for use are disclosed in U.S. Pat. Nos. 7,943,743; 8,168,179; and 7,595,048 WO2014055897, WO2016007235 and US Patent Appln. Pub. Nos. 20130034559, 20130034559 and 20150274835. PD-L1 antibodies are in development as immuno-modulatory agents or immuno-modulator for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149. In another embodiment, the antibody to PD-L1 is an antibody disclosed in U.S. Pat. No. 8,779,108. In another embodiment, the anti-PD-L1 antibody comprises the CDRs of an antibody disclosed in U.S. Pat. No. 8,779,108. In another embodiment, the antibody to PD-L1 is an antibody disclosed in US Patent Appln. Pub. No. 20130045201. In another embodiment, the anti-PD-L1 antibody comprises the CDRs of an antibody disclosed in US Patent Appln. Pub. No. 20130045201. In one embodiment, the anti-PD-L1 antibody is BMS-936559 (MDX-1105), which was described in WO 2007/005874. In another embodiment, the anti-PD-L1 antibody is MPDL3280A (RG7446). In another embodiment, the anti-PD-L1 antibody is MEDI4736, which is an anti-PD-L1 monoclonal antibody described in WO 2011/066389 and US 2013/034559. In another embodiment, the anti-PD-L1 antibody is TECENTRIQ™ (atezolizumab), which is an anti-PDL1 cancer immunotherapy which was approved in the US in May 2016 for specific types of bladder cancer. In another embodiment, anti-PD-L1 antibody is YW243.55.S70 which is an anti-PD-L1 described in WO 2010/077634 and U.S. Pat. No. 8,217,149. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C.

Additional examples of other therapeutic agents (anti-neoplastic agent) for use in combination or co-administered with a compound of this invention are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCDIL2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6; nivolumab, a human IgG4 mAb with the structure described in WHO Drug Information, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-1 and PD-L2, resulting in the activation of T-cells and cell-mediated immune responses against tumor cells or pathogens. Activated PD-1 negatively regulates T-cell activation and effector function through the suppression of PI3K/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of other therapeutic agents (antineoplastic agent) for use in combination or co-administered with a compound of Formula (I-N), (I-P) or (I) are antibodies to ICOS.

ICOS is a co-stimulatory T cell receptor with structural and functional relation to the CD28/CTLA-4-Ig superfamily (Hutloff, et al., "ICOS is an inducible T-cell co-stimulator structurally and functionally related to CD28", Nature, 397: 263-266 (1999)). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao S et al., "B7-H2 is a costimulatory ligand for CD28 in human", Immunity, 34(5); 729-40 (2011)). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naïve $T_H1$ and $T_H2$ effector T cell populations (Paulos C M et al., "The inducible costimulator (ICOS) is critical for the development of human Th17 cells", Sci Transl Med, 2(55); 55ra78 (2010)). ICOS expression is highly induced on CD4+ and CD8+ effector T cells following activation through TCR engagement (Wakamatsu E, et al., "Convergent and divergent effects of costimulatory molecules in conventional and regulatory CD4+ T cells", Proc Natal Acad Sci USA, 110(3); 1023-8 (2013)).

CDRs for murine antibodies to human ICOS having agonist activity are shown in PCT/EP2012/055735 (WO 2012/131004). Antibodies to ICOS are also disclosed in WO 2008/137915, WO 2010/056804, EP 1374902, EP1374901, and EP1125585.

Agonist antibodies to ICOS or ICOS binding proteins are disclosed in WO2012/13004, WO 2014/033327, WO2016/120789, US20160215059, and US20160304610. In one embodiment, agonist antibodies to ICOS include ICOS binding proteins or antigen binding portions thereof comprising one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR as disclosed in WO2016/120789, which is incorporated by reference in its entirety herein. In one embodiment, the ICOS binding protein or antigen binding portion thereof is an agonist antibody to ICOS comprising a $V_H$ domain comprising an amino acid sequence at least 90% identical to the amino acid sequence set forth in SEQ ID NO:7 and/or a $V_L$ domain comprising an amino acid sequence at least 90% identical to the amino acid sequence as set forth in SEQ ID NO:8 as set forth in WO2016/120789 wherein said ICOS binding protein specifically binds to human ICOS. In one embodiment, the ICOS binding protein is an agonist antibody to ICOS comprising a $V_H$ domain comprising the amino acid sequence set forth in SEQ ID NO:7 and a $V_L$ domain comprising the amino acid sequence set forth in SEQ ID NO:8 as set forth in WO2016/120789.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in US Patent Nos: U.S. Pat. Nos. 7,504,101; 7,758,852; 7,858,765; 7,550,140; 7,960,515; WO2012027328; WO2013028231.

In one embodiment, the OX40 antigen binding protein is one disclosed in WO2012/027328 (PCT/US2011/048752), international filing date 23 Aug. 2011. In another embodiment, the antigen binding protein comprises the CDRs of an antibody disclosed in WO2012/027328 (PCT/US2011/048752), international filing date 23 Aug. 2011, or CDRS with 90% identity to the disclosed CDR sequences. In a further embodiment the antigen binding protein comprises a VH, a VL, or both of an antibody disclosed in WO2012/027328 (PCT/US2011/048752), international filing date 23 Aug. 2011, or a VH or a VL with 90% identity to the disclosed VH or VL sequences.

In another embodiment, the OX40 antigen binding protein is disclosed in WO2013/028231 (PCT/US2012/024570), international filing date 9 Feb. 2012, which is incorporated by reference in its entirety herein. In another embodiment, the antigen binding protein comprises the CDRs of an antibody disclosed in WO2013/028231 (PCT/US2012/024570), international filing date 9 Feb. 2012, or CDRs with 90% identity to the disclosed CDR sequences. In a further embodiment, the antigen binding protein comprises a VH, a VL, or both of an antibody disclosed in WO2013/028231 (PCT/US2012/024570), international filing date 9 Feb. 2012, or a VH or a VL with 90% identity to the disclosed VH or VL sequences. In one embodiment, the OX40 antigen binding protein is an isolated agonist antibody to OX40 comprising a light chain variable region having a sequence at least 90% identical to the amino acid sequence of SEQ ID NO:10 as set forth in WO2013/028231 and a heavy chain variable region having a sequence at least 90% identical to the amino acid sequence of SEQ ID NO:4 as set forth in WO2013/028231. In one embodiment, the OX40 antigen binding protein is an isolated antibody comprising a light chain variable comprising the amino acid sequence of SEQ ID NO:10 as set forth in WO2013/028231 and a heavy chain variable region comprising the amino acid sequence of SEQ ID NO:4 as set forth in WO2013/028231.

Thus, in one embodiment methods of treating a human in need thereof are provided comprising administering a compound of Formula (I-N), (I-P) or (I) or a salt thereof and at least one immuno-modulator. In one embodiment, the immuno-modulator is selected from an ICOS agonist antibody, an OX-40 antibody or a PD-1 antibody. In one embodiment, the human has cancer. Also provided herein is the use of a compound of Formula (I-N), (I-P) or (I), or a salt thereof in combination with at least one immuno-modulator for the treatment of a human in need thereof.

Additional examples of other therapeutic agents for use in combination or co-administered with a compound of Formula (I-N), (I-P) or (I), or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity. In humans, ten TLR have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidylic acid (Poly I:C), a TLR3 agonist; polyadenosine-polyuridylic acid (poly AU), a TLR3 agonist; Polyinosinic-Polycytidylic acid stabilized with poly-L-lysine and carboxymethylcellulose (Hiltonol), a TLR3 agonist; bacterial flagellin a TLR5 agonist; imiquimod, a TLR7 agonist; resiquimod, a TLR7/8 agonist; loxoribine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial LPS. An example of a semisynthetic TLR4 agonist is monophosphoryl lipid A (MPL). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonist.

In one embodiment the immunostimulatory agent for use in combination with the compounds of the present invention is a TLR4 agonist. In one embodiment, the TLR4 agonist are referred to as CRX-601 and CRX-527. Their structures are set forth as follows:

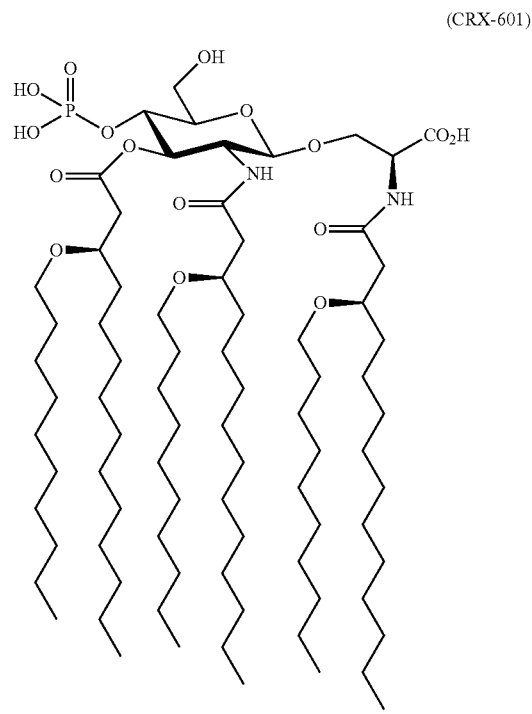

(CRX-601)

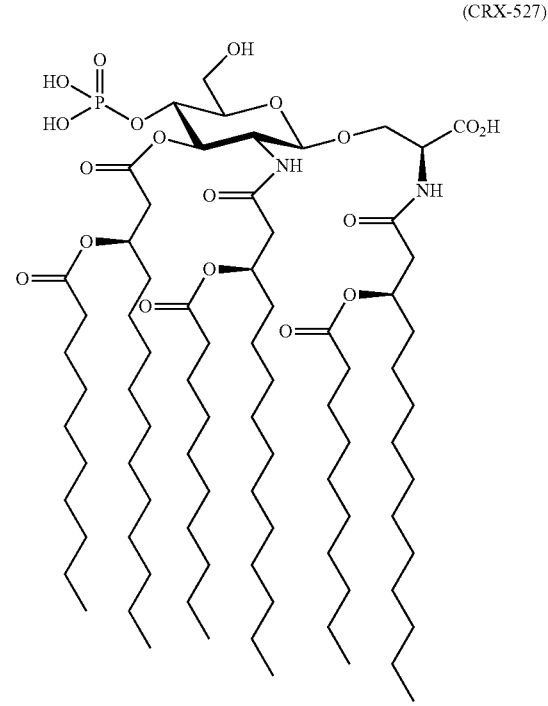

(CRX-527)

Additionally, another preferred embodiment employs the TLR4 agonist CRX 547 having the structure shown.

CRX 547

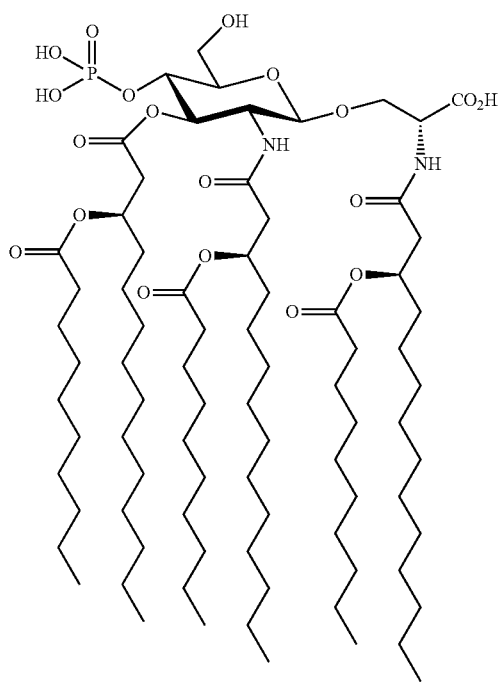

Still other embodiments include AGPs such as CRX 602 or CRX 526 providing increased stability to AGPs having shorter secondary acyl or alkyl chains.

CRX 602

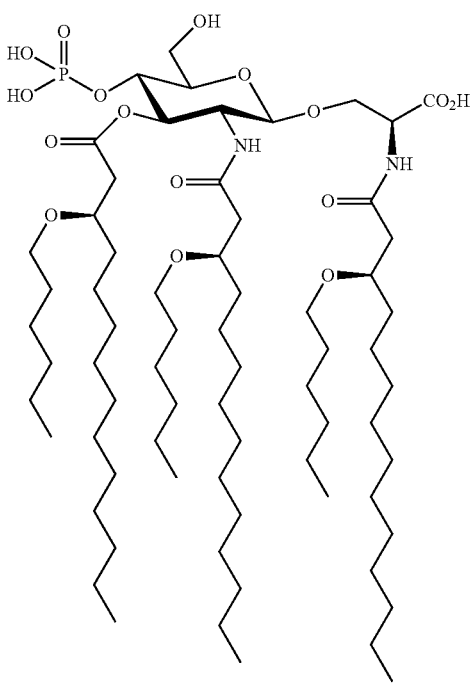

CRX-526

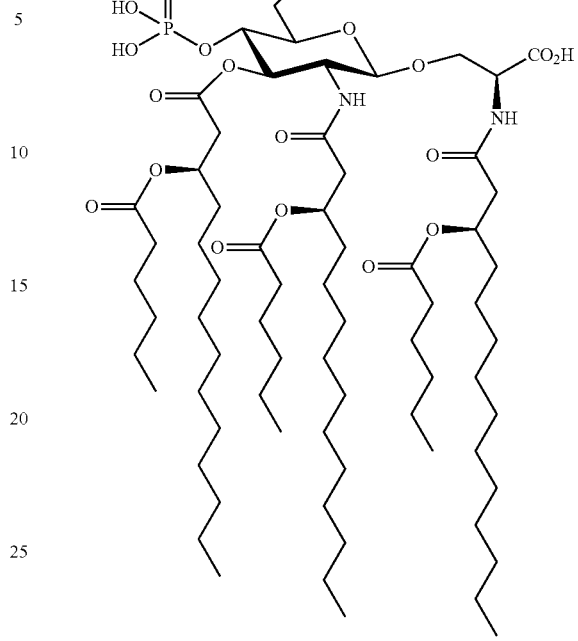

Thus, in one embodiment, methods of treating a human in need thereof are provided comprising administering a compound of Formula (I-N), (I-P) or (I) or a salt thereof and at least one immunostimulatory agent. In one embodiment, the immunostimulatory agent is a TLR4 agonist. In one embodiment, the immunostimulatory agent is an AGP. In yet another embodiment, the TLR4 agonist is selected from a compound having the formula CRX-601, CRX-527, CRX-547, CRX-602 or CRX-526. In one embodiment, the human has cancer. Also provided herein is the use a compound of Formula (I-N), (I-P) or (I), or a salt thereof in combination with at least one immunestimulatory agent for the treatment of a human in need thereof.

In addition to the immunostimulatory agents described above, the compositions of the present invention may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacteria. rt.-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula (I-N), (I-P) or (I) that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance. (Lemos H, et al., Cancer Res. 2016 Apr. 15; 76(8):2076-81), (Munn D H, et at., Trends Immunol. 2016 March; 37(3):193-207). Further active ingredients (antineoplastic agents) for use in combination or co-administered with the presently invented compounds of Formula (I-N), (I-P) or (I) are IDO inhibitors. Epacadostat, ((Z)—N-(3-bromo-4-fluorophenyl)-N'-hydroxy-4-[2-(sulfamoylamino) ethylamino]-1,2,5-oxadiazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of other therapeutic agents (antineoplastic agent) for use in combination or co-administered with a compound of Formula (I-N), (I-P) or (I) are CD73 inhibitors and A2a and A2b adenosine antagonists.

In one embodiment, the compound of the invention may be employed with other therapeutic methods of treating infectious disease. In particular, antiviral and antibacterial agents are envisaged.

The compounds of Formula (I-N), (I-P) or (I) and pharmaceutically acceptable salts thereof may be used in combination with at least one other therapeutic agent useful in the prevention or treatment of bacterial and viral infections. Examples of such agents include, without limitation: polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, rilpivirine and similar agents; entry inhibitors such as enfuvirtide (T-20), T-1249, PRO-542, PRO-140, TNX-355, BMS-806, 5-Helix and similar agents; integrase inhibitors such as dolutegravir, elvitegravir, raltegravir L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; pharmacokinetic enhancers such as cobicistat; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents.

The compounds of Formula (I-N), (I-P) or (I) and pharmaceutically acceptable salts thereof may also be used in combination with other therapeutic agents which may be useful in the treatment of Kaposi's sarcoma-associated herpesvirus infections (KSHV and KSHV-related) include, without limitation chemotherapeutic agents such as bleomycin, vinblastine, vincristine, cyclophosphamide, prednisone, alitretinoin and liposomal anthracyclines such as doxorubicin, daunorubicin, immunotherapeutics such as Rituximab, Tocilizumab, Siltuximab and others such as Paclitaxel and Rapamycin.

In one embodiment of this invention, the at least one other therapeutic agent is an antimycobacterial agent or a bactericidal antibiotic. The compounds of Formula (I-N), (I-P) or (I) and pharmaceutically acceptable salts thereof may also be used in combination with at least one other therapeutic agent which may be useful in the treatment of TB infection (*Mycobacterium tuberculosis*) and Tularemia (*Francisella tularensis*) include without limitation to first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amoxicillin/clavulanate thioacetazone imipenem/cilastatin high dose isoniazid clarithromycin, ciprofloxacin. The compounds of Formula (I-N), (I-P) or (I) and pharmaceutically acceptable salts thereof may also be used in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluoroquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex©), streptomycin, viomycin, capreomycin (Capastat®)), bedaquiline fumarate (Sirturo®), oxazolidinone (Sutezolid®), PNU-100480, or delamanid (OPC-67683).

The compounds of Formula (I-N), (I-P) or (I) and pharmaceutically acceptable salts thereof may also be used in combination with at least one other therapeutic agent which may be useful in the treatment of *Chlamydia* include, without limitations Azithromycin, Doxycycline, Erythromycin, Levofloxacin, Ofloxacin.

The compounds of this invention may also be used in combination with at least one other therapeutic agent which may be useful in the treatment of *plasmodium* infection include, without limitations to chloroquine, atovaquone-proguanil, artemether-lumefantrine, mefloquine, quinine, quinidine, doxocycline, cindamycin, artesunate, primaquine.

In the treatment of amyotrophic lateral sclerosis (ALS), a compound of Formula (I-N), (I-P) or (I) or a pharmaceutically acceptable salts thereof may be used in combination with a glutamate blocker (Riluzole (Rilutek®)), quinidine (Nuedexta®), anticholinergics (Amitriptyline®, Artane®, scopolamine patch (Transderm Scop®)), sympathomimetics (pseudoephedrine), mucolytics (guaifenesin), or analgesics (tramadol (Ultram®); ketorolac (Toradol®); morphine; fentanyl patch (Duragesic®)).

In the treatment of multiple sclerosis, a compound of Formula (I-N), (I-P) or (I) or pharmaceutically acceptable salts thereof may be used in combination with corticosteroids (prednisone, methylprednisolone), Interferon Beta-1A (Avonex®, Extavia®, Rebif®, Betaseron®), peginterferon beta-1A (Plegridy®), Glatiramer acetate (Copaxone®); glatiramer acetate (Glatopa®-generic equivalent of Copaxone); Dimethyl fumarate (Tecfidera®); Fingolimod (Gilenya®)); teriflunomide (Aubagio®); dalfampridine (Ampyra®); daclizumab (Zinbryta); alemtuzumab (Lemtrada); natalizumab (Tysabri®); or mitoxantrone hydrochloride (Novantrone®).

The compounds of this invention may also be used as adjuvants to improve the immune response raised to any given antigen and/or reduce reactogenicity/toxicity in a patient, particularly a human, in need thereof. As such, a compound of this invention may be used in combination with vaccine compositions to modify, especially to enhance, the immune response for example by increasing the level or duration of protection and/or allowing a reduction in the antigenic dose.

The compounds of Formula (I-N), (I-P) or (I) and pharmaceutically acceptable salts thereof may be used in combination with one or more vaccines or immunogenic antigens useful in the prevention or treatment of viral infections. Such vaccines or immunogenic antigens include, without limitation to pathogen derived proteins or particles such as attenuated viruses, virus particles, and viral proteins typically used as immunogenic substances. Examples of viruses and viral antigens include, without limitations to Polioviruses, Cioronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herepesviruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), H1N1 influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

Accordingly, this invention provides an immunogenic composition comprising an antigen or antigenic composition and a compound of Formula (I-N), (I-P) or (I), or a pharmaceutically acceptable salt thereof. There is further provided a vaccine composition comprising an antigen or antigenic composition and a compound of Formula (I-N), (I-P) or (I), or a pharmaceutically acceptable salt thereof.

The compounds of Formula (I-N), (I-P) or (I) and pharmaceutically acceptable salts thereof may also be used in combination with at least one other therapeutic agent which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, anti-fibrotic agents, anti-inflammatory agents such as corticosteroids or NSAIDs (non-steroidal anti-inflammatory agents) and similar agents.

A compound that modulate STING, particularly a compound of Formula (I-N), (I-P) or (I) or a pharmaceutically acceptable salt thereof, may be administered in combination with other anti-inflammatory agents, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL17 biologics, anti-CD22, anti-integrin agents, anti-IFNa, anti-CD20 or CD4 biologics and other cytokine inhibitors or biologics to T-cell or B-cell receptors or interleukins.

For example, in the treatment of systemic lupus erythematosus and related lupus disorders, a compound that modulates STING, particularly a compound of Formula (I-N), (I-P) or (I), or a pharmaceutically acceptable salt thereof, may be administered in combination with at least one other therapeutic agent, including, a corticosteroid (such as prednisolone (Delatsone®, Orapred, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Cellcept®), Tacrolimus®, Sirolimus®), B-cell therapy (belimumab (Benlysta®), B-cell inhibitor (Atacicept®), Apratuzumab® (anti-CD22), SBI-087 (anti-CD20), an anti-BAFF antibody (LY2127399, A623), Velcade®), azathioprine (Azasan®, Imuran®), triamcinolone (Clinacort®, Kenalog-10®), hydroxychloroquine (Plaquenil®), thalidomide (Immunoprin®, Contergan®), immunoglobulin therapy (HyQiva®, Flebogamma®, Gamunex®, Privigen®, Gammagard®), anti-interferon-alpha therapy (Rontalizumab®, Sifalimumab®, AGS-009®, IFN Kinoid), TLR7 and TLR9 blockers (IMO-3100), anti-cytokine therapies (anti-IL6 (CNTO-136), anti-interferon-gamma (AMG811), immunomodulatory therapy (Lupuzor™, Abatacept, Orencia®, AMG557, Laquinimod, Paquinimod, Leflunomide, anti-ICOS (Medi-570), anti-CD40 ligand antibody (CDP7657)), and/or a platelet aggregation inhibitor (aspirin).

In treatment of vasculitis and disease with inflammation of small or medium size blood vessels, a compound that modulates STING, particularly a compound of Formula (I-N), (I-P) or (I), or a pharmaceutically acceptable salt thereof, may be administered in combination with alkylating agents (cyclophosphamide, Cytoxan®), anti-rheumatic anti-CD20 antibody (Rituxan®, Rituximab®), and anti-TNFα inhibitors (Etanrcept®).

In the treatment of psoriasis, a compound that modulates STING, particularly a compound of Formula (I-N), (I-P) or (I), or a pharmaceutically acceptable salt thereof, may be administered in combination with ixekizumab, tildrakizumab (MK-3222), or secukinumab (AIN457).

In one embodiment of this invention, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, a compound that inhibits STING, particularly a compound of Formula (I-N), (I-P) or (I) or a pharmaceutically acceptable salt thereof, may be administered in combination with an inhaled corticosteroid ((ICS) such as fluticasone proprionate (Flovent®), beclomethasone dipropionate (QVAR®), budesonide (Pulmicort), trimcinolone acetonide (QVAR®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-Dur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta® Neohaler®), an epinephrine inhalation aerosol (E004), fluticasone furoate/fluticasone proprionate, vinanterol inhalation/fluticasone furoate powder (Relovair™), fluticasone propionate/eformoterol fumarate dehydrate (Flutiform®), reslizumab, salbutamol dry-powder inhalation, tiotropium bromide (Spiriva® HandiHaler®), formoterol/budesonide (Symbicort® SMART®), fluticasone furoate (Veramyst®), Vectura's VR506, lebrikizumab (RG3637), a combination phosphodiesterase (PDE)-3 and (PDE)-4 inhibitor (RPL554).

In one embodiment of this invention, the at least one other therapeutic agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. For example, in the treatment of COPD, a compound that modulates STING, particularly a compound of Formula (I-N), (I-P) or (I) or a pharmaceutically acceptable salt thereof, may be administered in combination with a LABA (such as salmeterol xinafoate (Serevent), umeclidinium/vilanterol (Anuro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate (ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In one embodiment of this invention, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of Formula (I-N), (I-P) or (I) or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In the treatment of Sjögren's syndrome, a compound that modulates STING, particularly a compound of Formula (I-N), (I-P) or (I) or a pharmaceutically acceptable salt thereof, may be administered in combination with anti-rheumatic agents (hydroxychloroquine and Plaquenil®, Ridaura®, Kineret®), cholinergic agonists (Salagen®, Evoxac®), a JAK inhibitor (Xelijanz®, and anti-TNFα treatments (Remicade®, Humira®, Enbrel®, Cimzia®, Simponi®).

In one embodiment of this invention, the at least one other therapeutic agent is a ciliary neurtotrophic growth factor or a gene transfer agent. For example, in the treatment of retinitis pigmentosa, a compound that modulates STING, particularly a compound of Formula (I-N), (I-P) or (I) or a pharmaceutically acceptable salt thereof, may be administered in combination with a ciliary neurtotrophic growth factor (NT-501-CNTF) or gene transfer agent, UshStat®.

In one embodiment of this invention, the at least one other therapeutic agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. For example, in the treatment of influenza, a compound that modulates STING, particularly a compound of Formula (I-N), (I-P) or (I) or a pharmaceutically acceptable salt thereof, may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®.

In the treatment of a *staphylococcus* infection, a compound that modulates STING, particularly a compound of Formula (I-N), (I-P) or (I) or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In one embodiment of this invention, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, a compound that modulates STING, particularly a compound of Formula (I-N), (I-P) or (I), or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), anon-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

The compounds of the invention may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminum salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of Formula (I-N), (I-P) or (I), or a pharmaceutically acceptable salt thereof. There is further provided a vaccine composition comprising a compound of Formula (I-N), (I-P) or (I), or a pharmaceutically acceptable salt thereof, and an antigen or antigen composition.

A therapeutically "effective amount" is intended to mean that amount of a compound that, when administered to a patient in need of such treatment, is sufficient to effective treat or prevent, as defined herein. Thus, e.g., a therapeutically effective amount of a compound of Formula (I-N), (I-P) or (I), or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for retardation, therapy or cure of a STING-mediated disease or disorder, as described hereinabove. In one embodiment, "treat" "treating" or "treatment" in reference to cancer refers to alleviating the cancer, eliminating or reducing one or more symptoms of the cancer, slowing or eliminating the progression of the cancer, and delaying the reoccurrence of the condition in a previously afflicted or diagnosed patient or subject.

"Prevent", "preventing" or "prevention" refers to the prophylactic administration of a drug to diminish the likelihood of the onset of or to delay the onset of a disease or biological manifestation thereof. Prophylactic therapy is appropriate, for example, when a subject is considered at high risk for developing cancer, such as when a subject has a strong family history of cancer or when a subject has been exposed to a carcinogen.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

In addition to the above described routes of administration suitable for treatment of oncology, the pharmaceutical compositions may be adapted for administration by intratumoral or peritumoral injection. The intratumoral or peritumoral injection of a compound of the present invention directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities, (van derJeught, et al., *Oncotarget*, 2015, 6(3), 1359-1381). A further advantage of local or intratumoral or peritumoral administration is the ability to achieve equivalent efficacy at much lower doses, thus minimizing or eliminating adverse events that may be observed at much higher systemic doses (Marabelle, A., et al., Clinical Cancer Research, 2014, 20(7), p1747-1756).

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg, preferably, total daily dosages range from 1 mg to 250 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and at least one pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I-N), (I-P) or (I), or a salt, particularly a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a STING-mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional therapeutic agents, (e.g., pharmaceutically active compounds).

As used herein, "pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc. For example, tablets may be prepared using conventional methods and are formulated as follows: Compound, 5 mg; Microcrystalline cellulose, 100 mg; Lactose, 100 mg; Sodium starch glycollate, 30 mg; Magnesium stearate, 2 mg; Total wt. 237 mg. Capsules may be prepared using conventional methods and are formulated as follows: Compound, 15 mg; dried starch, 178 mg; Magnesium stearate, 2 mg; Total wt. 195 mg.

It will be understood that the compounds of this invention may also be formulated with vaccines as adjuvants to modulate their activity. Such compositions may contain antibody (antibodies) or antibody fragment(s) or an antigenic component including but not limited to protein, DNA, live or dead bacteria and/or whole, inactivated or split viruses or virus-like particles, recombinant proteins or antigenic fragments thereof, optionally together with one or more other components with adjuvant activity including but not limited to aluminum salts, oil and water emulsions, heat shock proteins, saponins, lipid A preparations and derivatives, glycolipids, liposomes, TLR agonists such as CpG DNA or similar agents, cytokines such as GM-CSF or IL-12, or similar agents.

Certain compounds of the invention may be potent immunomodulators and accordingly, care should be exercised in their handling.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

It will be understood that certain compounds of the invention may be potent immunomodulators and accordingly, care should be exercised in their handling.

The reactions described herein are applicable for producing compounds of the invention having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. Suitable protecting groups and the methods for protecting and de-protecting different substituents using such suitable protecting groups are well known to those skilled in the art; examples of which may be found in T. W. Greene 'Protective Groups in Organic Synthesis' (4th edition, J. Wiley and Sons, 2006). Unless otherwise noted, all starting materials were obtained from commercial suppliers and used without further purification.

Certain intermediate compounds described herein form a yet further aspect of the invention.

General Synthetic Methods

The compounds of this invention may be prepared using synthetic procedures illustrated in the reaction schemes below, which can be readily adapted to prepare other compounds of the invention by drawing on the knowledge of a skilled organic chemist. The syntheses provided in these schemes are applicable for producing compounds of the invention having a variety of different R groups employing appropriate precursors, which are suitably protected if needed, to achieve compatibility with the reactions outlined herein. Subsequent deprotection, where needed, affords compounds of the nature generally disclosed. While the schemes are shown with compounds only of Formula (I-N), (I-P) or (I), they are illustrative of processes that may be used to make the compounds of the invention. Intermediates (compounds used in the preparation of the compounds of the invention) may also be present as salts.

Method 1: An appropriate nitro-halo benzamide (1A) may be treated with an amine (allylamine used as an example) under base or metal-mediated coupling conditions to afford the aniline (1B). Subsequent reduction of the nitro group via appropriate conditions will provide dianiline (1C). Reaction with cyanogen bromide provides the aminobenzimidazole (1D). Peptide coupling between the aminobenzimiazole and pyrazole acid (1E) generates the amidobenzimidazole monomer (1F). Cross metathesis reaction between two molecules of (1F) affords the unsaturated dimer (1G), which can be hydrogenated to afford saturated dimer 1H.

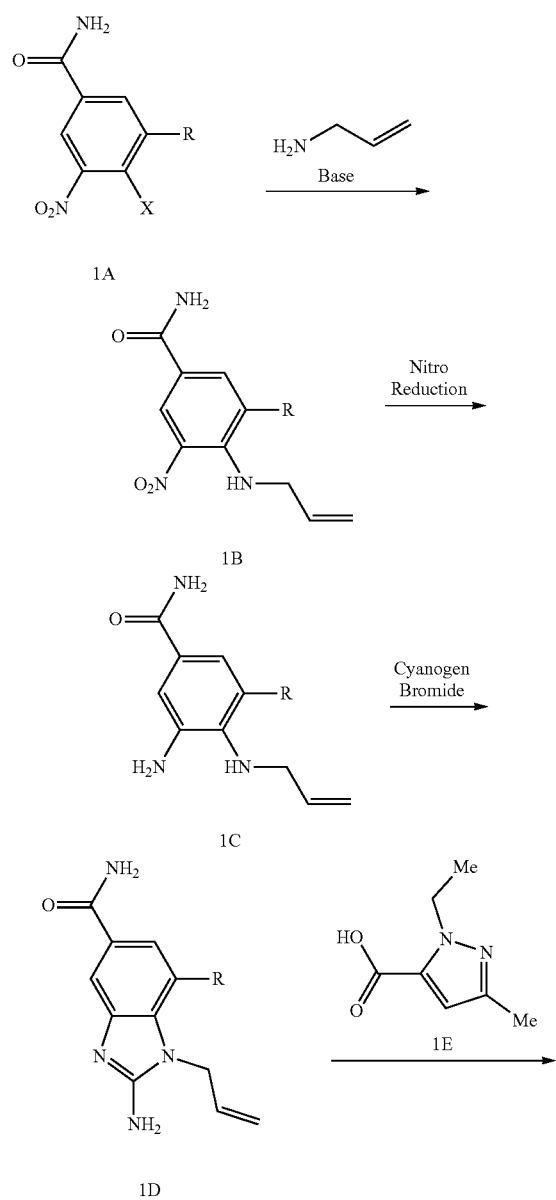

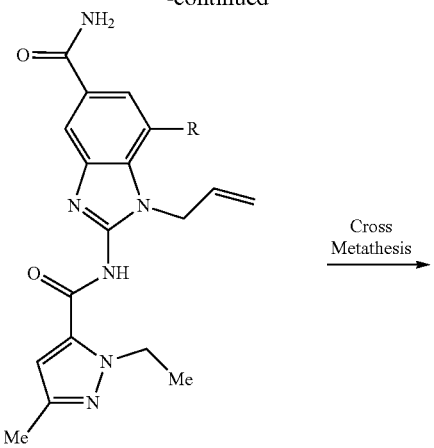

Method 2: Two molecules of an appropriate nitro-halo benzamide (2A) may be treated with a diamine under base or metal-mediated coupling conditions to afford the bis-coupled aniline (2B). Subsequent bis-reduction of the nitro groups via appropriate conditions can provide the dianiline (2C). Reaction with cyanogen bromide provides the amino-benzimidazole dimer (2D). Peptide coupling between bis amine (2D) and two molecules of pyrazole acid (2E) generates the amidobenzimidazole dimer (2F).

Method 2:

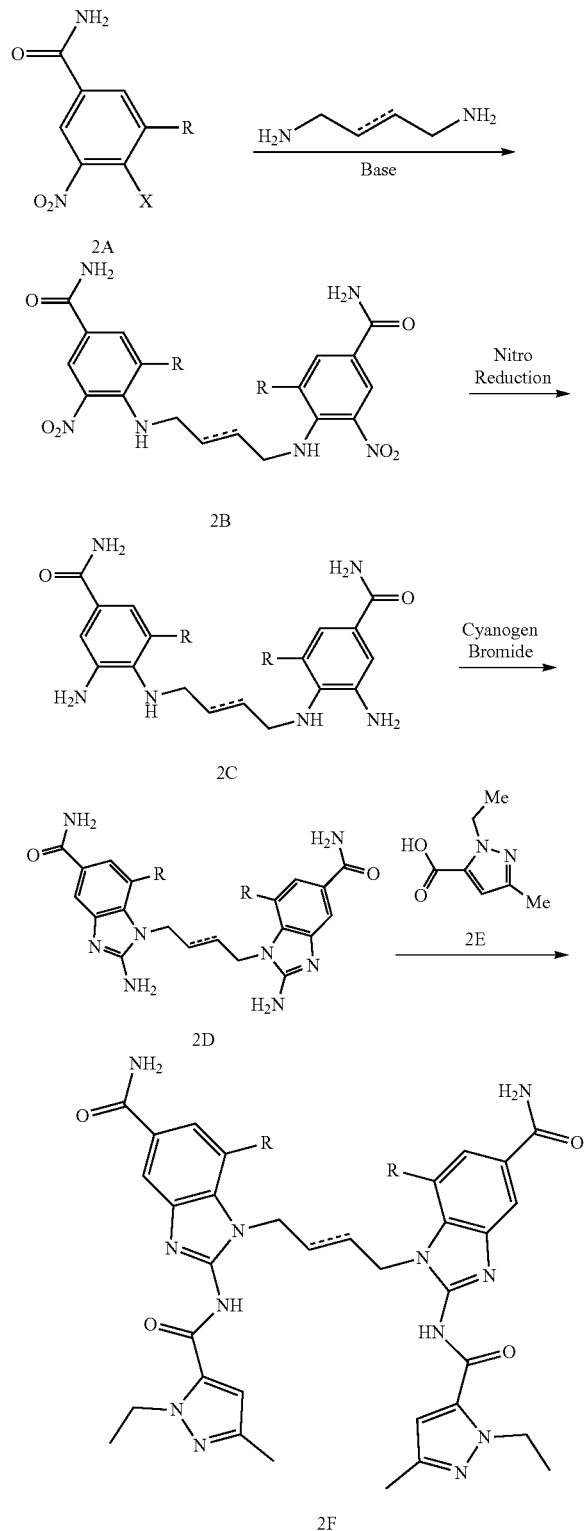

Method 3: Fluoronitrobenzamide (3A) is treated with a monoprotected diamine under base or metal-mediated coupling conditions to afford the aniline (3B). Subsequent reduction of the nitro group via appropriate conditions can provide the dianiline (3C). Reaction with cyanogen bromide provides the aminobenzimidazole (3D). Peptide coupling between amine (3D) and pyrazole acid (3E) generates the amidobenzimidazole (3I), which can be deprotected under appropriate conditions for the amine protecting group to afford amine (3G). Amine (3G) can be coupled with an appropriate halonitrobenzamide (3H) to provide (3I); reduction of the nitro group can provides dianiline (3J). Treatment of (3J) with cyanogen bromide generates aminobenzimidazole (3K), which can be treated with pyrazole acid (3E) under amide coupling conditions to afford the unsymmetrical dimer (3L).

Method 3:

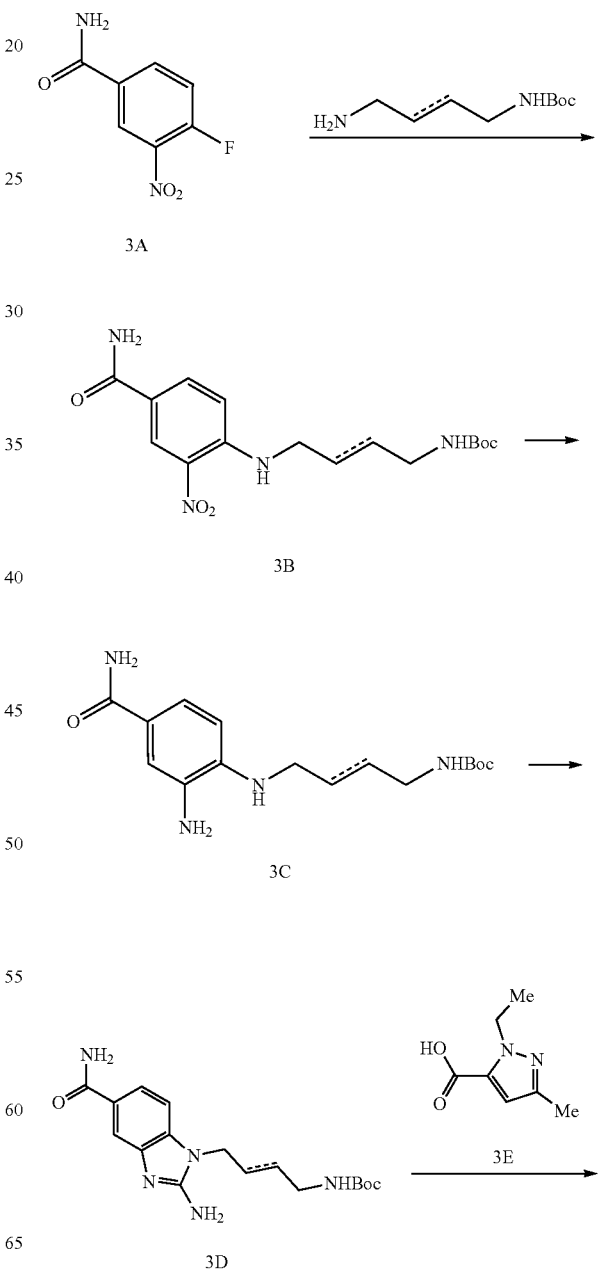

123
-continued

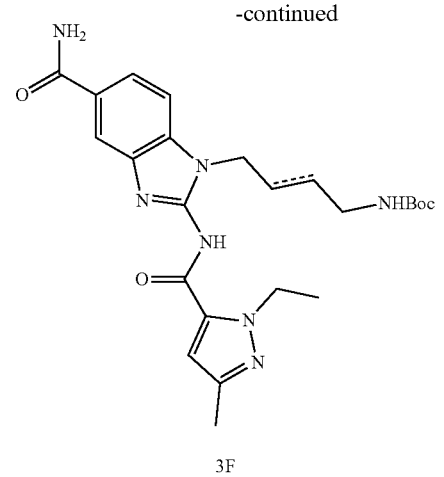

3F

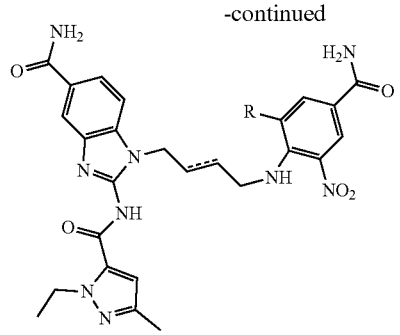

3I

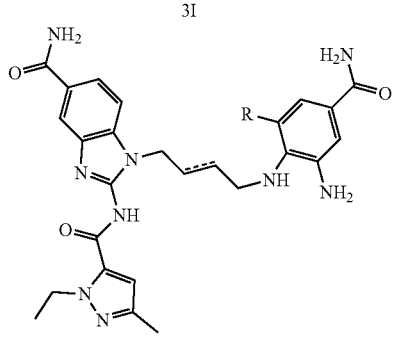

3J

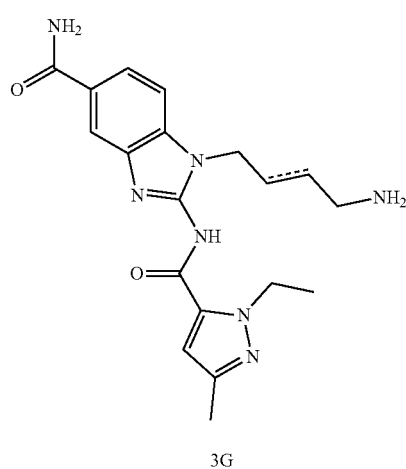

3G

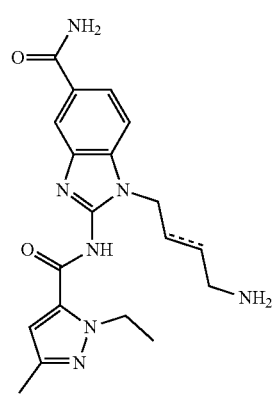

3G

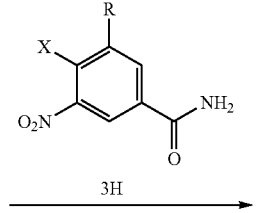

3H

124
-continued

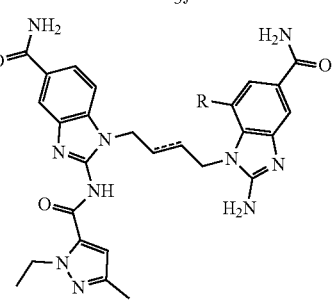

3K

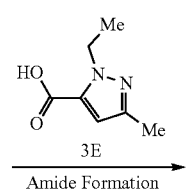

3E
Amide Formation

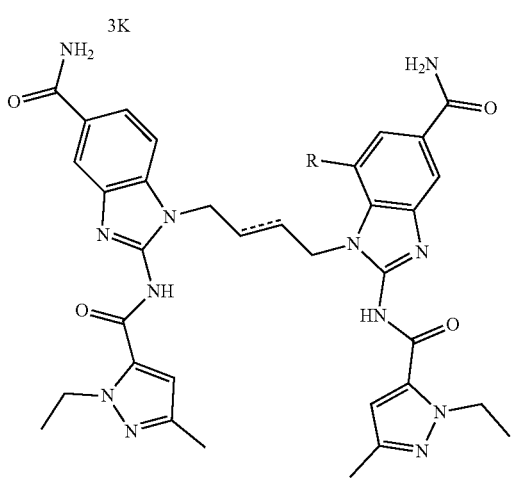

3L

Method 4: An appropriate nitro-halo benzamide (4A) is treated with a monoprotected diamine under base or metal-mediated coupling conditions to afford the allylaniline (4B). Subsequent reduction of the nitro group via appropriate conditions will provide the dianiline (4C). Reaction with cyanogen bromide provides the aminobenzimidazole (4D).

125

Peptide coupling between amine (4D) and pyrazole acid (4E) generates the amidobenzimidazole (4F), which can be deprotected under appropriate conditions for the amine protecting group to afford amine (4G). Amine (4G) can be coupled with fluoronitrobenzamide (4H) to provide (4I), and then reduction of the nitro group will provide dianiline (4J). Treatment of (4J) with cyanogen bromide generates aminobenzimidazole (4K), which can be treated with pyrazole acid (4E) under amide coupling conditions to afford the unsymmetrical dimer (4L).

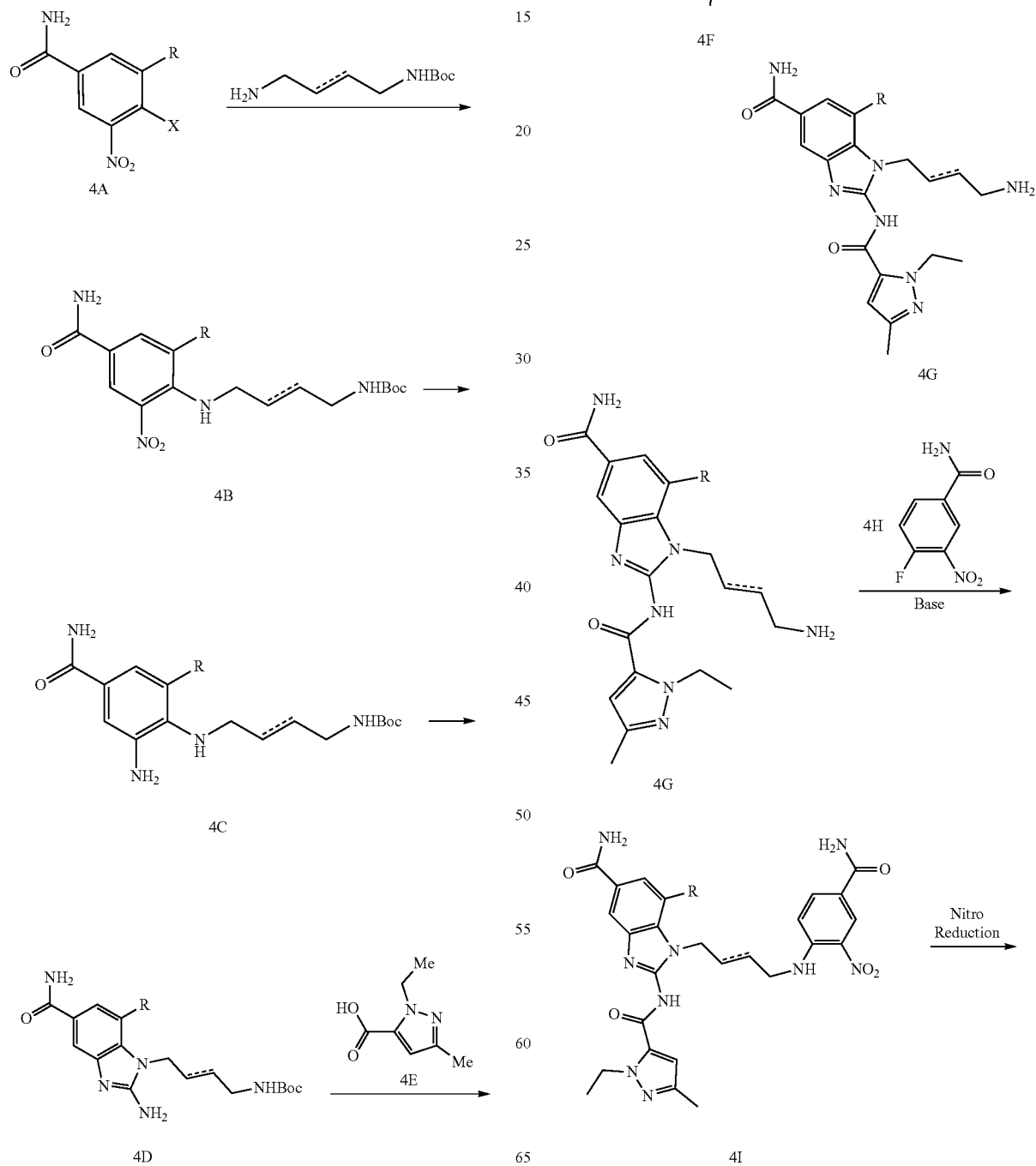

127
-continued

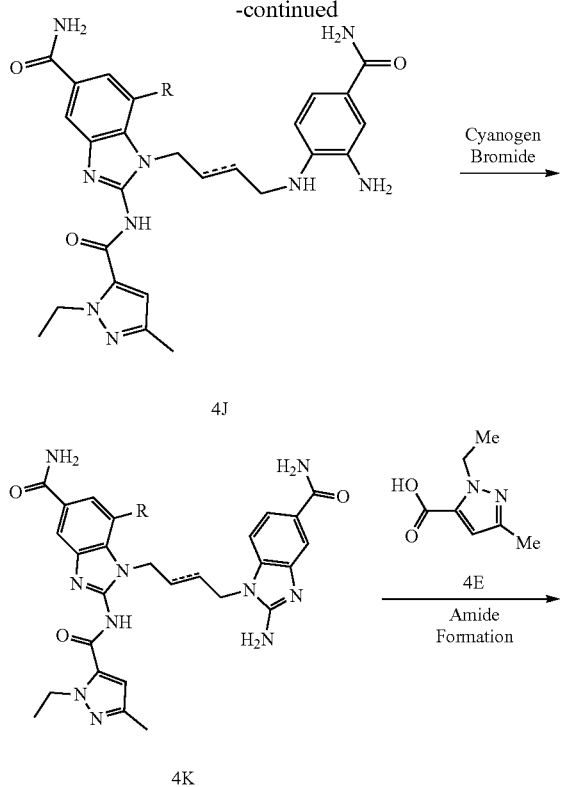

4J

4K

128
-continued

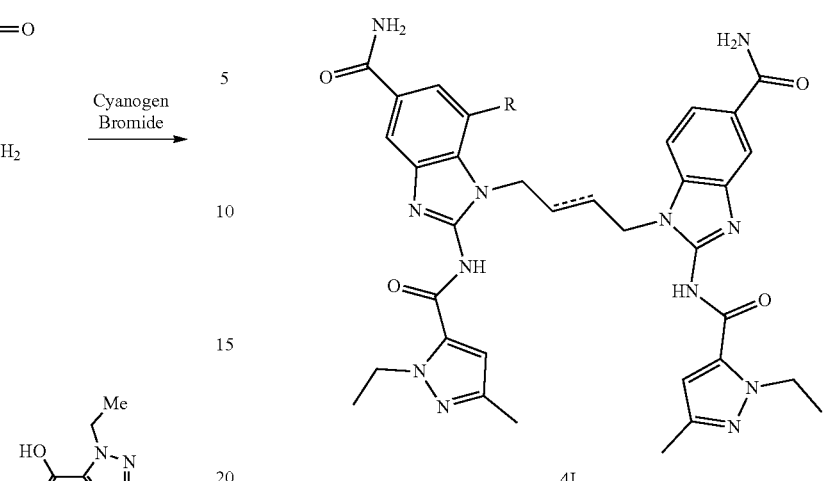

4L

Method 5 Two molecules of an appropriate phenol (5A) are reacted with a bis-electrophile such as dibromopropane to provide ether linked dimer (5B). Dimer (5B) is then reacted with a suitable diamine to afford macrocycle (5C). Reduction of the nitro groups, followed by treatment with cyanogen bromide affords bisaminobenzimidazole (5D). Amide coupling with an appropriate acid (5E) affords bisamidobenzimidazole macrocycle (5F).

Method 5:

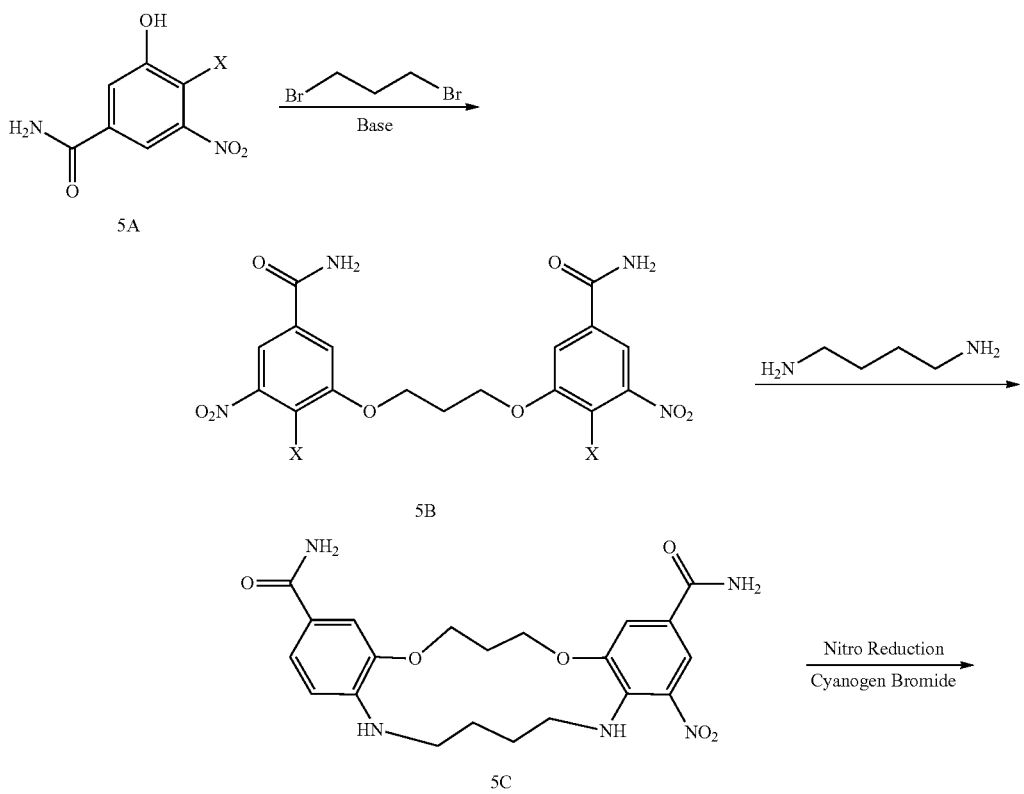

129 130
-continued
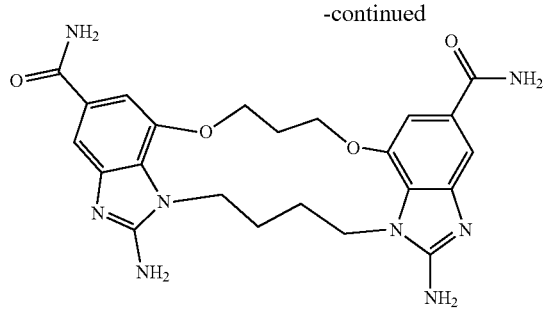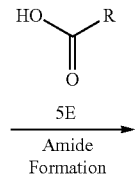
5D
5E
Amide Formation
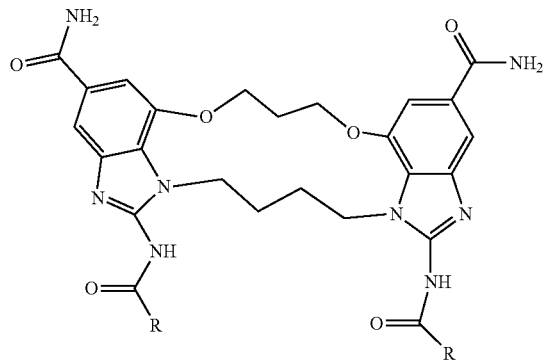
5F
Method 6: Bispyrazole acid 6A (Method 8) is reacted with Aminobenzimidazole dimer (6B) under amide coupling conditions to afford amidobenzimidazole macrocycle (6C), wherein each R may be the same or different.
Method 6:
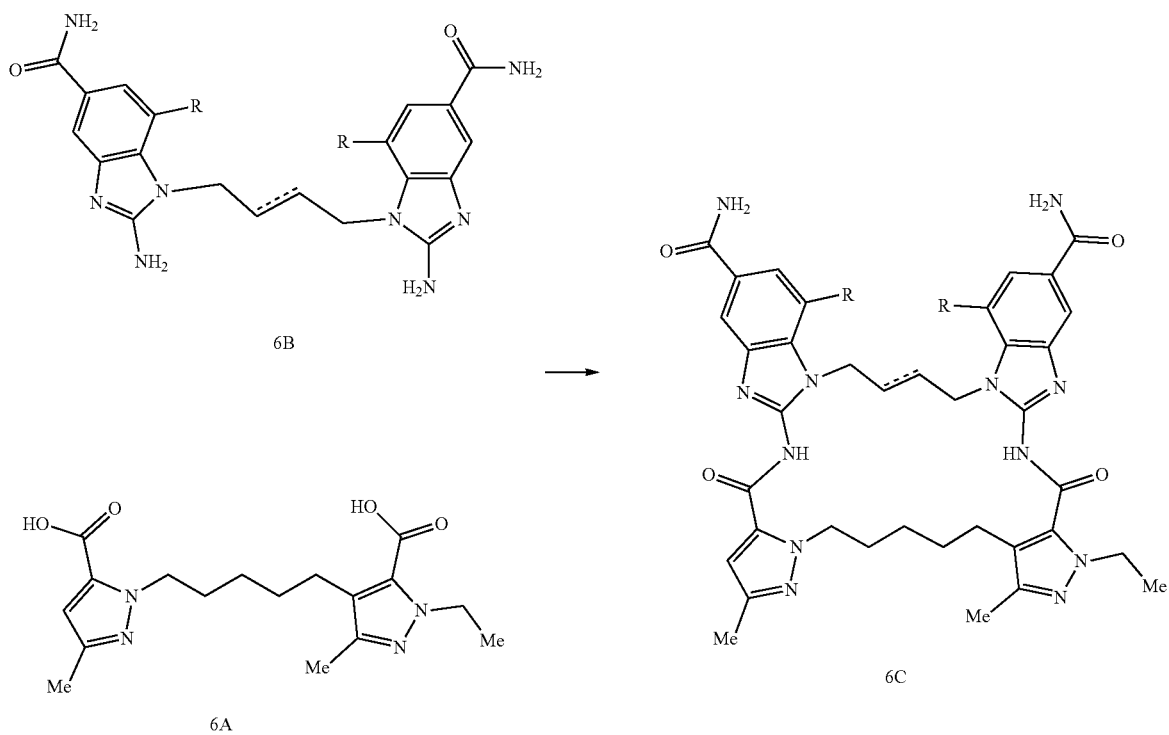

Method 7: Bispyrazole acid 7A (Method 8) is reacted with two molecules of aminobenzimidazole (7B) under amide coupling conditions to afford pyrazole-linked dimer (7C).
Ring closing metathesis reaction will afford the unsaturated macrocycle (7D), which can be hydrogenated to provide the saturated amidobenzimidazole macrocycle (7E).
Method 7:
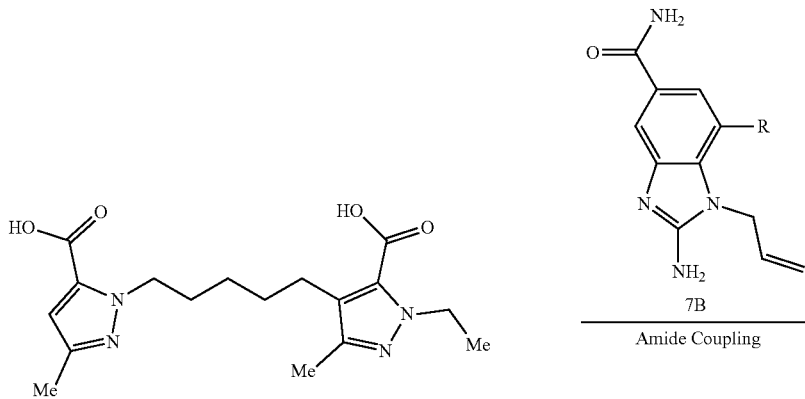
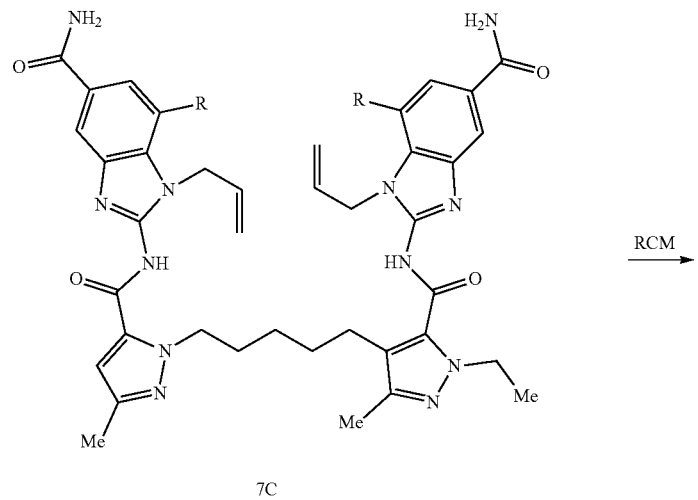
7C
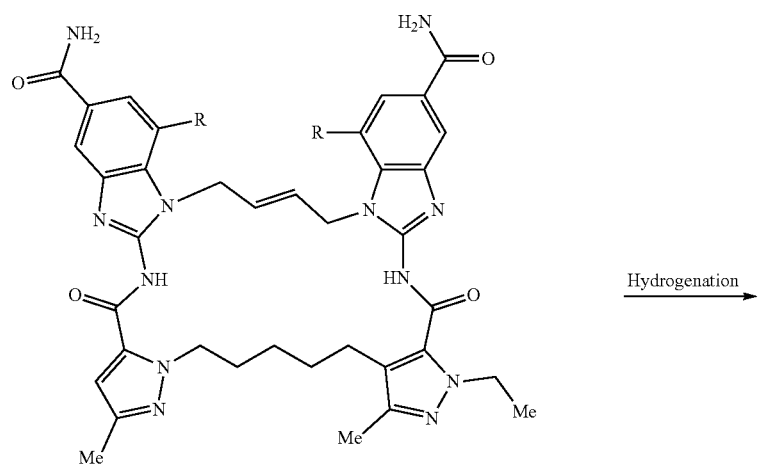
7D

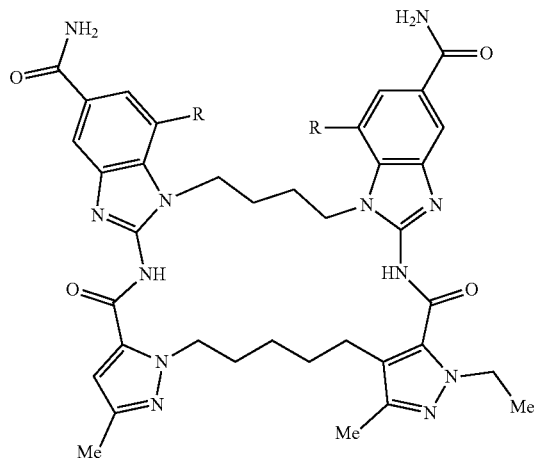

7E

Method 8: A substituted (pent-4-yn-1-yl)-1H-pyrazole-carboxylate (8C) may be formed by N-alkylation of a substituted 1H-pyrazole-carboxylate (8A) with (5-chloro-pent-1-yn-1-yl)trimethylsilane followed by de-silylation. A 4-iodo-1H-pyrazole-carboxylate (8F) may be formed by esterification of the corresponding 1H-pyrazole-carboxylic acid (8D), followed by iodination using 1-iodopyrrolidine-2,5-dione. Palladium catalyzed coupling of the substituted (pent-4-yn-1-yl)-1H-pyrazole-carboxylate (8C) with the 4-iodo-1H-pyrazole-carboxylate (8F) forms an alkynyl-linked bispyrazole (8G). Hydrogenation of the alkynyl-linked bispyrazole, followed by hydrolysis provided the bispyrazole acid used in Methods 6 and 7 (6A/7A), above.

Method 8:

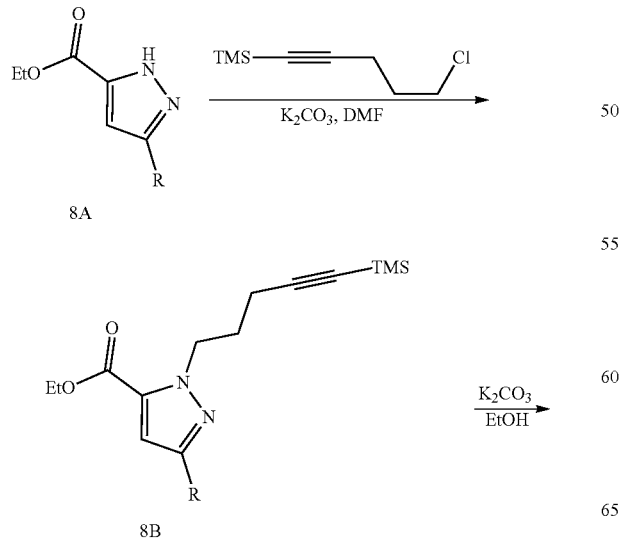

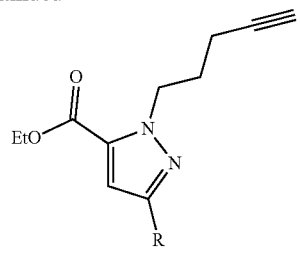

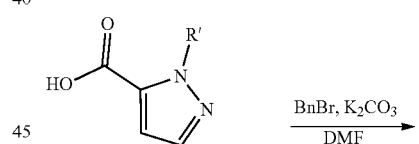

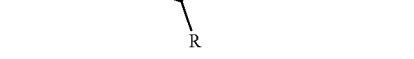

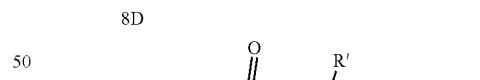

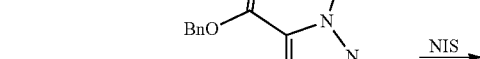

-continued

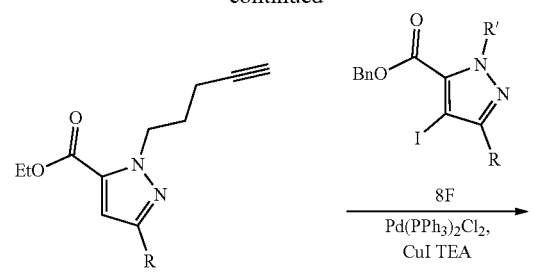

8C

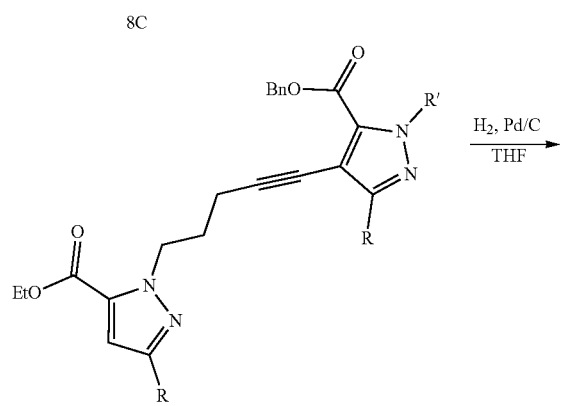

8G

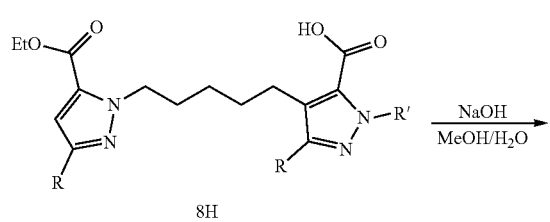

8H

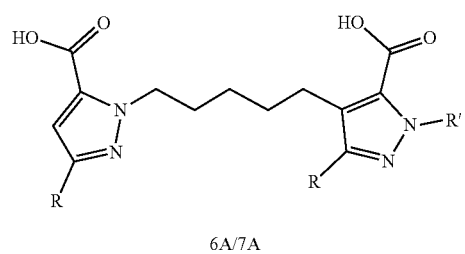

6A/7A

Method 9

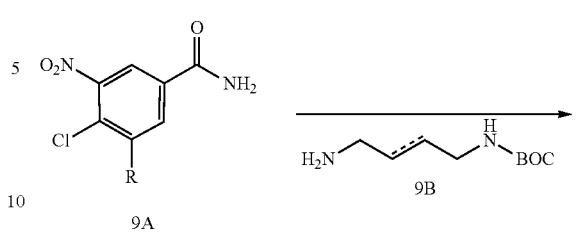

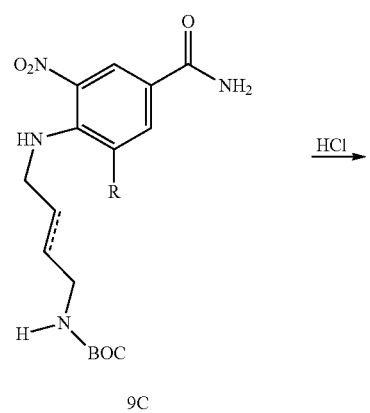

9C

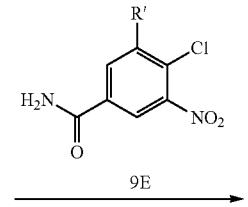

9D

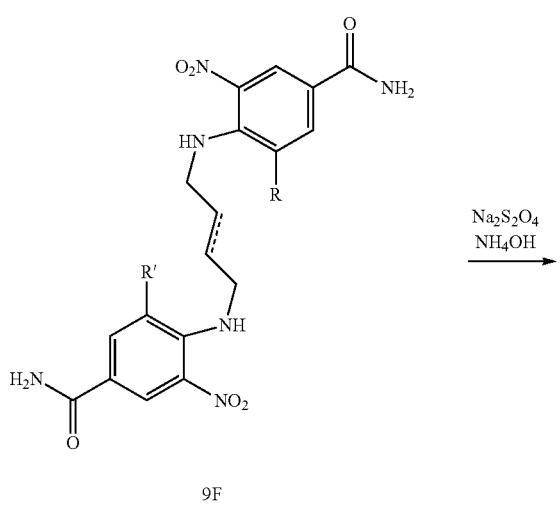

9F

Method 9: An appropriate nitro-halo benzamide (9A) may be treated with a monoprotected diamine (such as 9B) under base or metal-mediated coupling conditions to afford the coupled aniline (9C). Subsequent deprotection of the primary amine will provide amine 9D. A second nitro-halo benzamide (9E) may be reacted with amine 9D under base or metal-mediated coupling conditions to afford a bis-nitro dimeric benzamide (9F). Double reduction of the nitro groups via appropriate conditions can provide the dianiline (9G). Reaction with cyanogen bromide provides the aminobenzimidazole dimer (9H). Peptide coupling between bis amine 9H and two molecules of pyrazole acid (9I) generates the amidobenzimidazole dimer (9J).

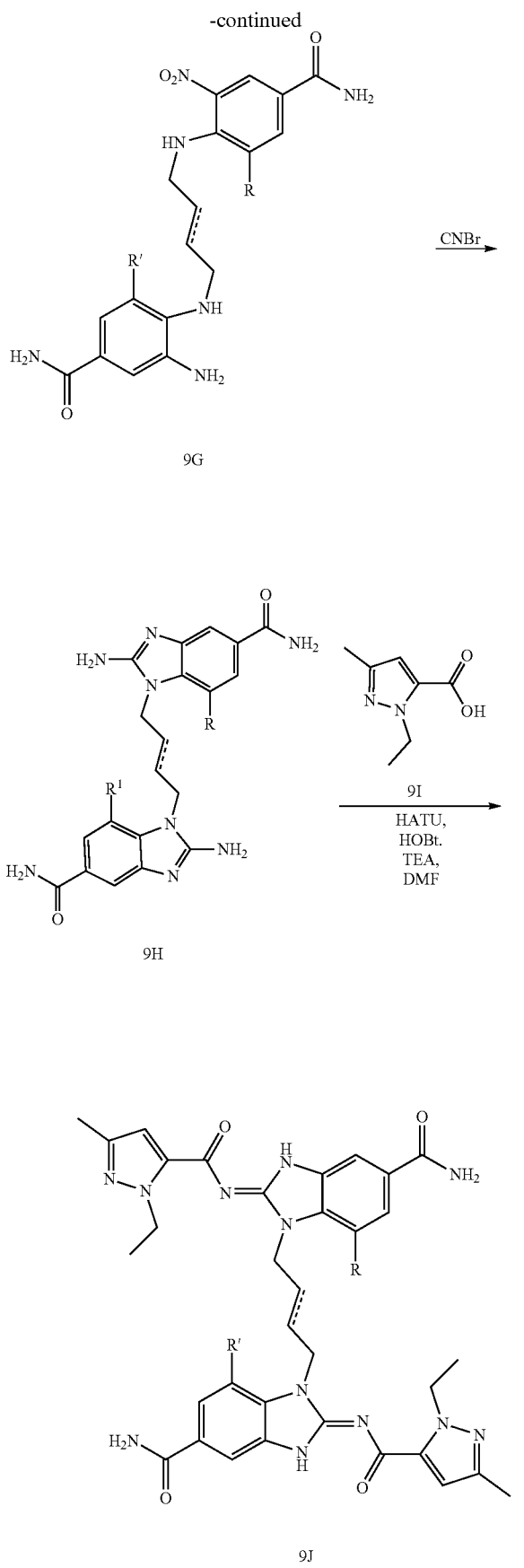

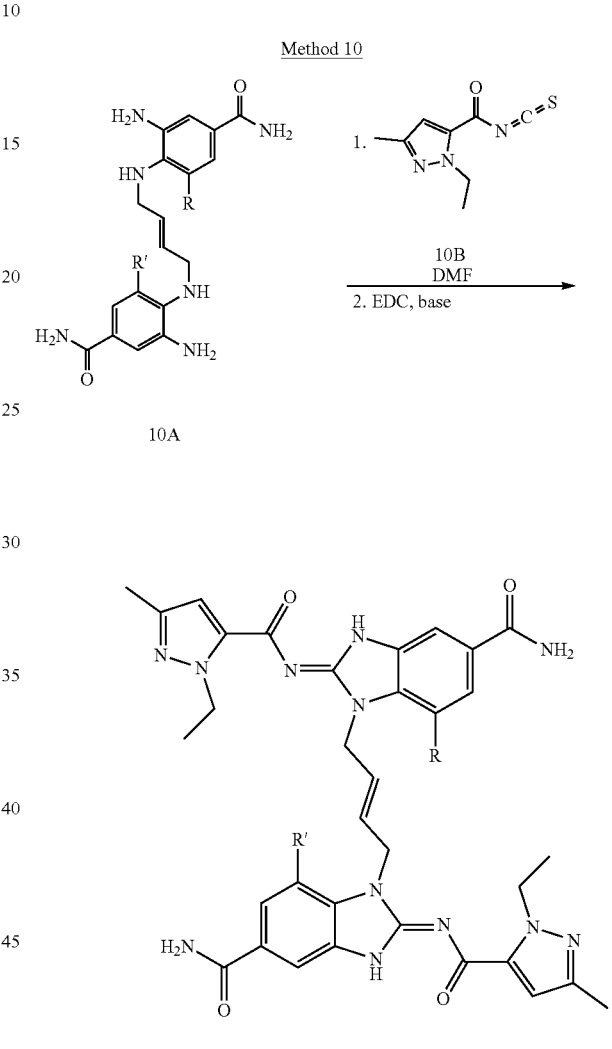

Method 10: A tetraaniline (10A, prepared by method 9 or another general method) may be treated with isothiocyanate (10B) until completion of the reaction. Upon completion of step 1, EDC (or other suitable coupling reagent) and triethylamine (or other suitable base) are added and the reaction stirred until completion to afford amidobenzimidazole dimer (10C).

Method 11: All variables are as defined in Formula (I-N), (I-P) or Formula (I). A suitably substituted halonitrobenzamide (11A) is reacted with a monoprotected diamine such as 11B to provide nitroaniline 11C. Deprotection of the amine protecting group affords amine 11D, which can be reacted with a halo-nitrophenyl compound 11E to afford bis-nitro 11F. Reduction of both nitro groups will provide a bis-aniline 11G which is treated with cyanogen bromide to afford bisaminobenzimidazole 11H. Amide coupling with a pyrazole acid such as 11I will afford a substituted amidobenzimidazole dimer 11J. When suitable functional groups are present on 11J, further functionalization of these groups will be possible to afford additional compounds such as 11K.

Method 11:
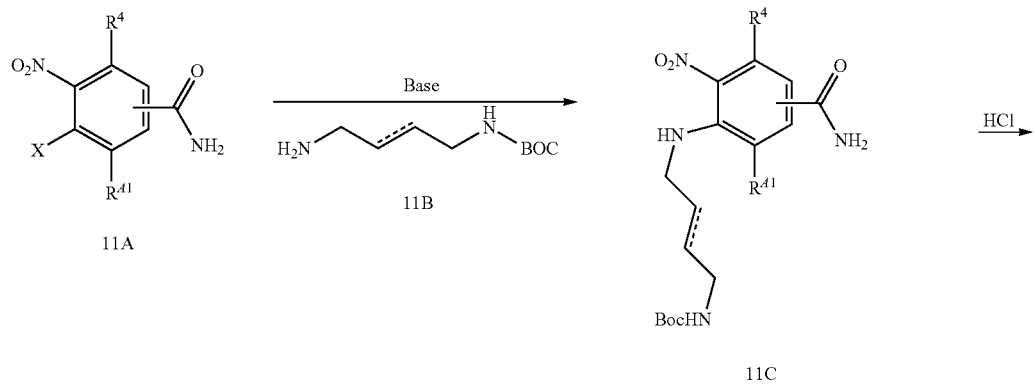
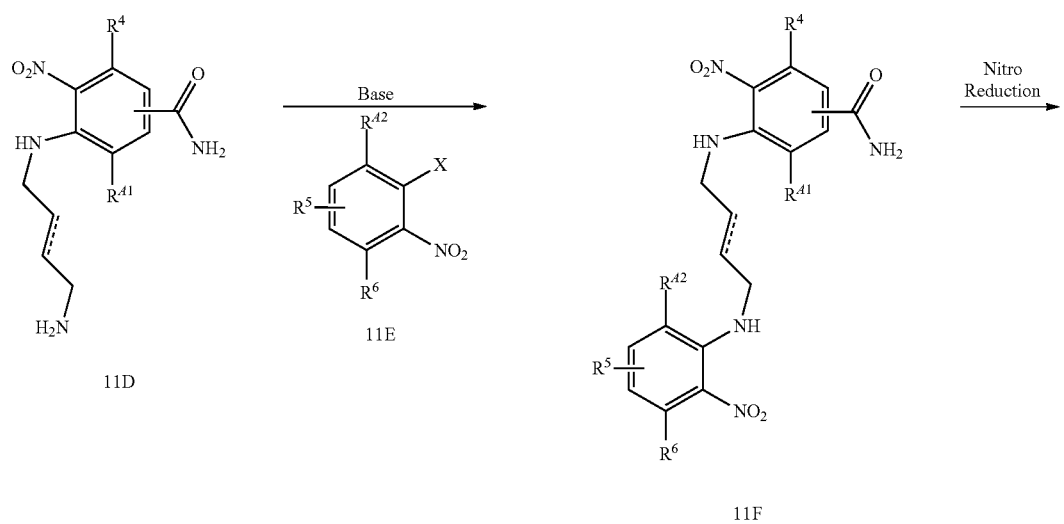
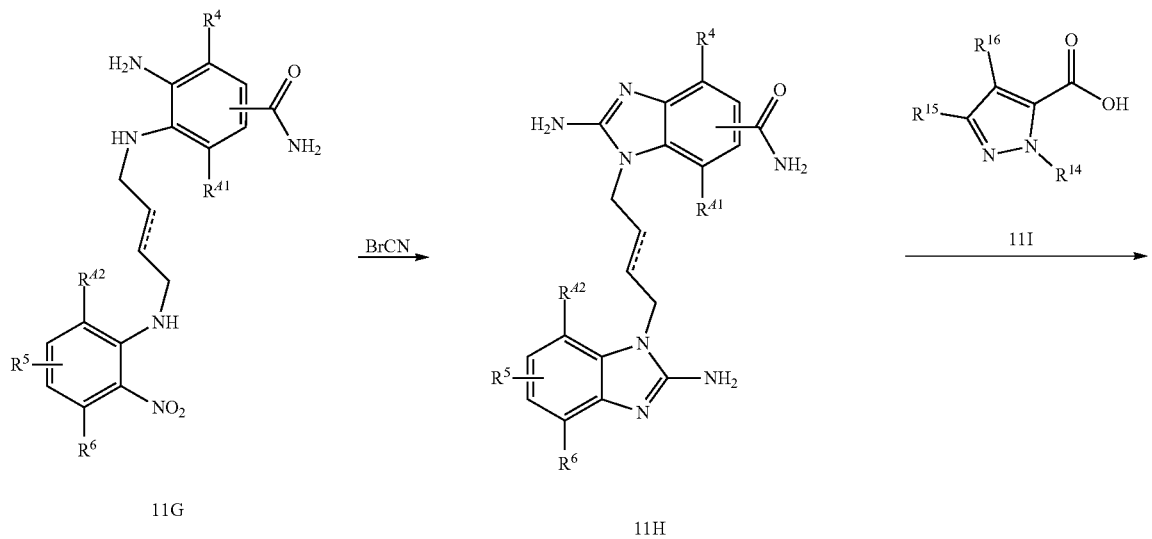

-continued

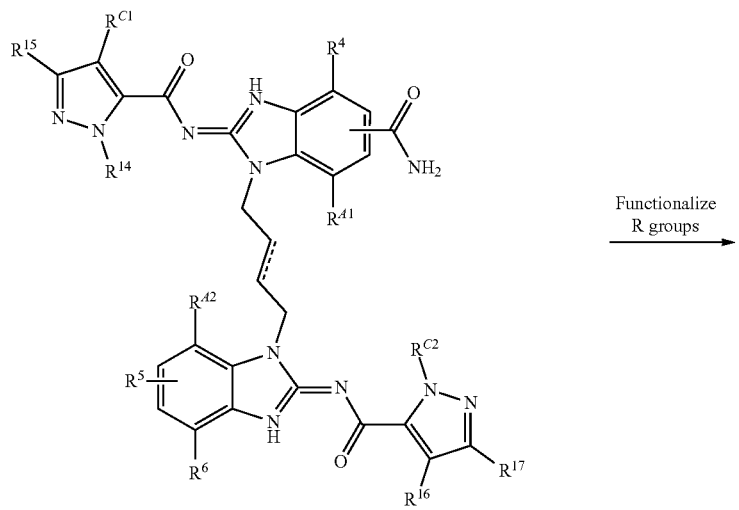

11J

Functionalize R groups →

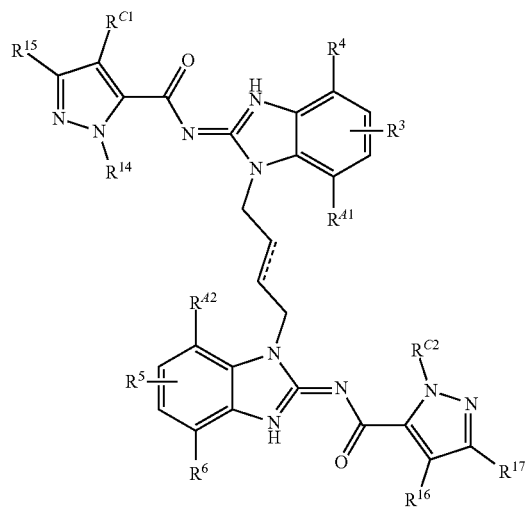

11J

Method 12: In method 12, $R^{C2}=R^{14}$, $R^{17}=R^{15}$ and $R^{16}=R^{C1}$, all other variables are as defined in Formula (I-N), Formula (I-P) or Formula (I). A tetraaniline (12A, prepared by method 11, 16 or another general method) may be treated with an isothiocyanate such as 12B until completion of the reaction. Upon completion of step 1, EDC (or other suitable coupling reagent) and triethylamine (or other suitable base) are added and the reaction stirred until completion to afford amidobenzimidazole dimer (12C).

Method 12

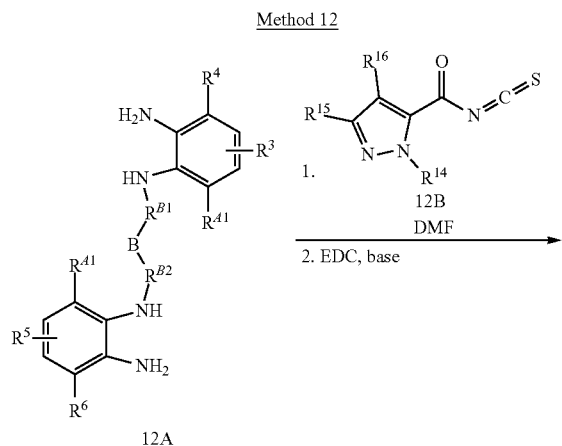

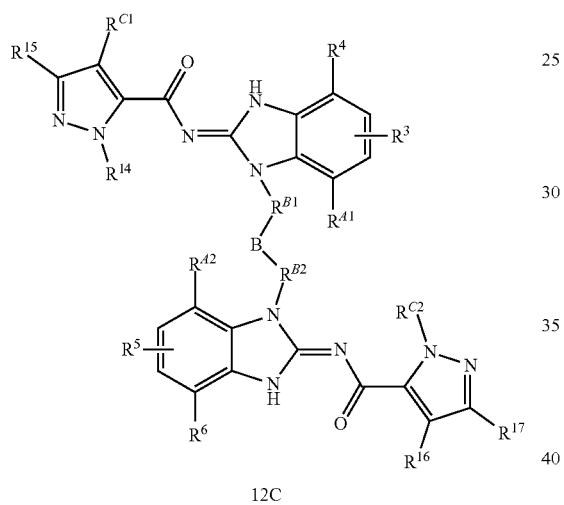

Method 13

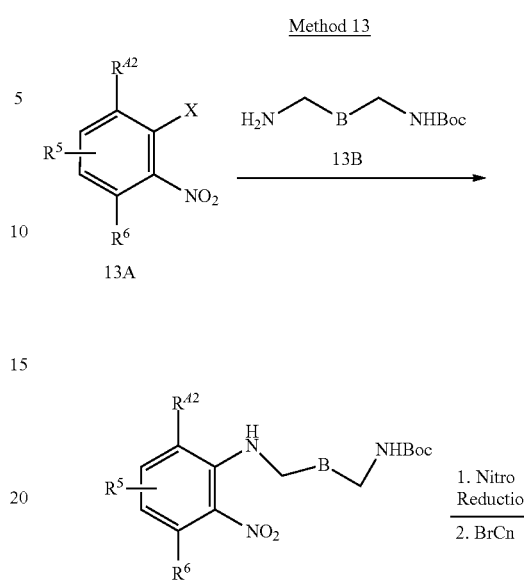

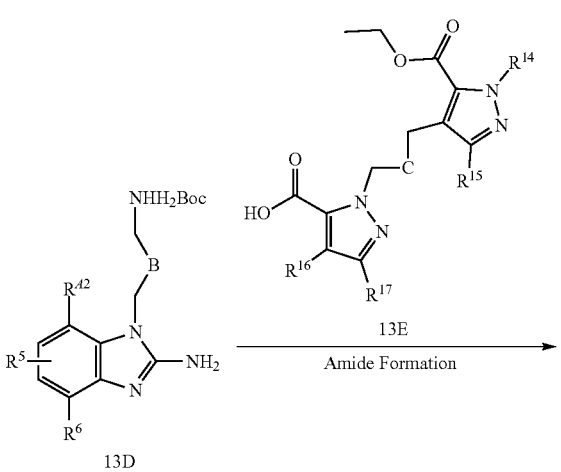

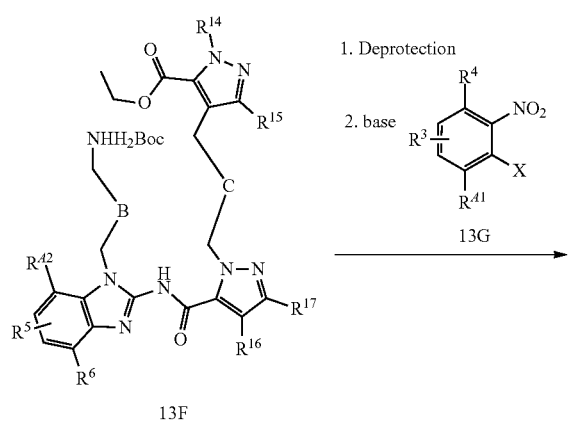

Method 13: In method 13, all variables are as defined in Formula (I-N), Formula (I-P) or Formula (I). Macrocyclic compounds with substitutions can be prepared via this method. A substituted halonitrophenyl compound (13A) is treated with a suitable diamine (13B) containing a linker group (B) between the two amine groups to afford amine 13C. Reduction of the nitro group followed by treatment with cyanogen bromide can afford aminobenzimidazole 13D. Amide coupling between 13D and a mono-carboxylic acid bis-pyrazole (such as 13E) containing a linker group (C) between the two pyrazoles will afford an amidobenzimidazole (13F). Deprotection of the amine group enables addition to a second substituted halo-nitro-phenyl (13G) to provide nitro-ester 13H. Reduction of the nitro group of 13H followed by treatment with cyanogen bromide will provide aminobenzimidazole 13I. Hydrolysis of the pyrazole ester then enables a macrocyclic amide formation to provide the macrocyclic amidobenzimidazole 13J. When suitable functional groups are present on 13J, further functionalization of these groups will be possible to afford additional compounds such as 13K.

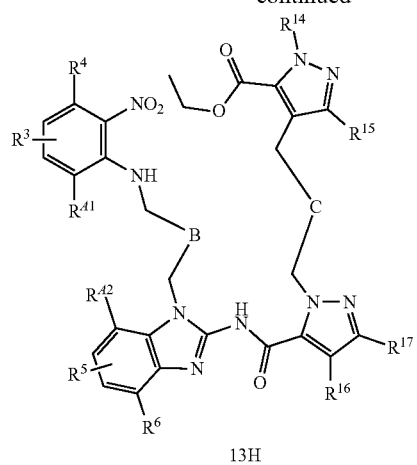

13H

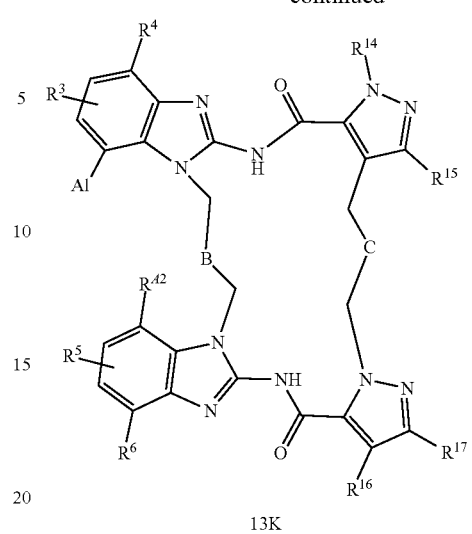

13K

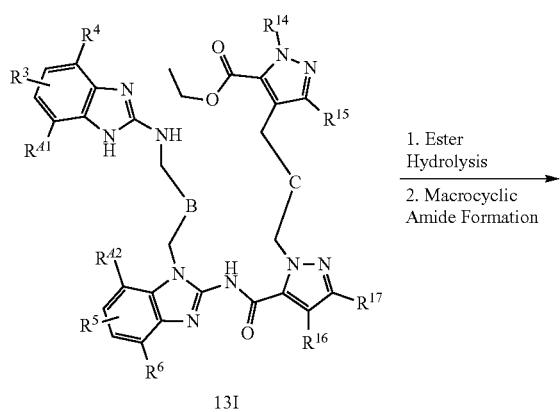

13I

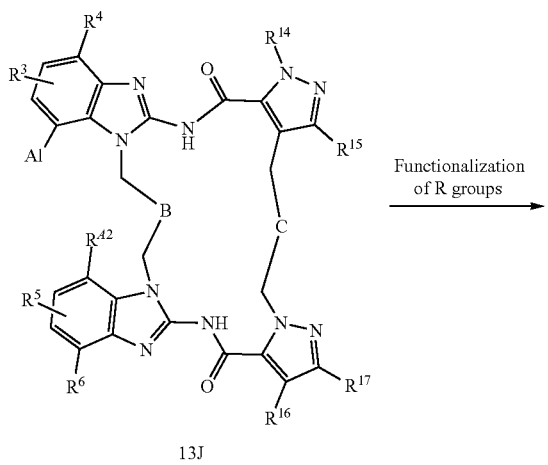

13J

Method 14: —O-M¹ is defined as optionally substituted $(C_1\text{-}C_6\text{alkyl})\text{oxy}$ as defined for $R^{41}$ when q is 0 in Formula (I) Formula (I-N), or Formula (I-P). All other variables are as defined in Formula (I-N), Formula (I-P) or Formula (I). A dimeric amidobenzimidazole containing a phenol, such as 14A, prepared via one of the general synthetic methods described here, can be alkylated on the phenol through the use of a suitable alkylating agent such as an alkyl bromide and base such as potassium carbonate. When suitable functional groups are present on 14B, further functionalization of these groups will be possible to afford additional compounds.

Method 14

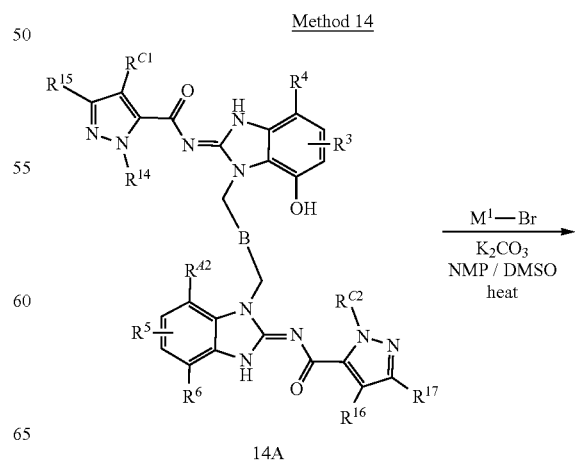

14A

-continued

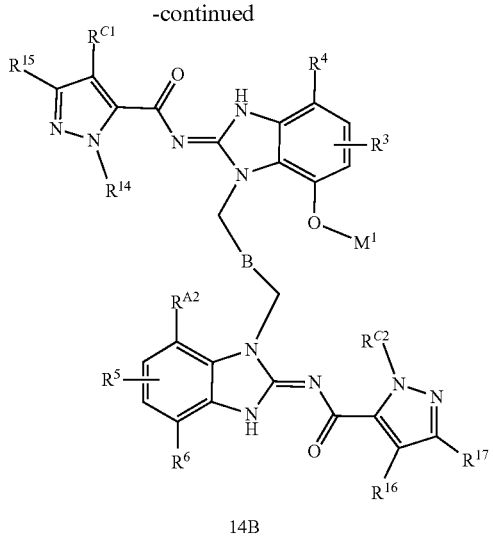

14B

Method 15: All variables are as defined in Formula (I-N), Formula (I-P) or Formula (I). A suitably substituted halo-nitrophenyl compound (15A) is reacted with a diamine containing a linker group (B) such as 15B to provide bis-nitro dimer 15C. Reduction of both nitro groups will provide a tetraaniline 15D which can be converted to an amidobenzimidazole dimer (15E) via one of two methods: 1) Treatment with cyanogen bromide to afford a bisaminobenzimidazole followed by amide coupling with a pyrazole acid such as 15F; or 2) Treatment with isothiocyanate (15G) until completion of the reaction, then addition of EDC (or other suitable coupling reagent) and triethylamine (or other suitable base) and the reaction is stirred until completion. When suitable functional groups are present on 15E, further functionalization of these groups will be possible to afford additional compounds.

Method 15

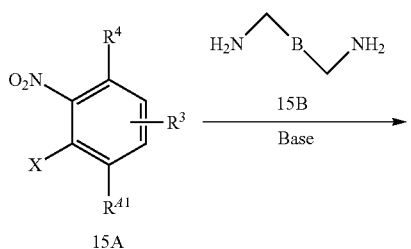

15A

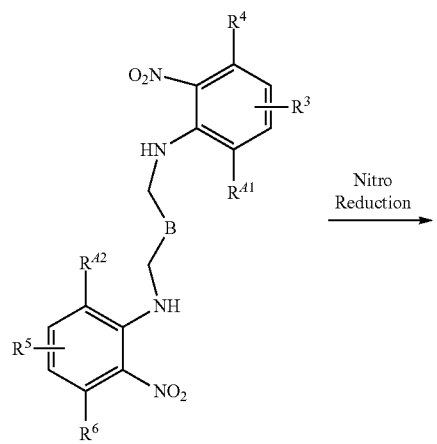

15C

-continued

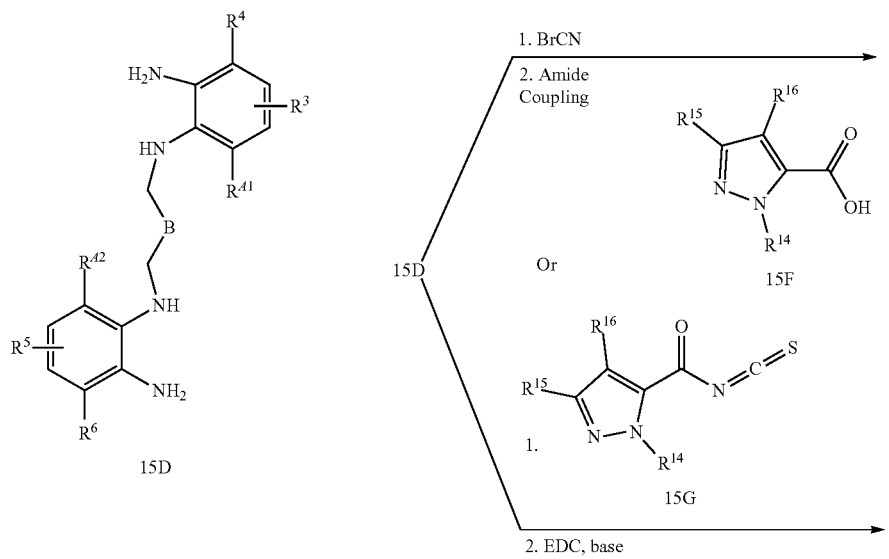

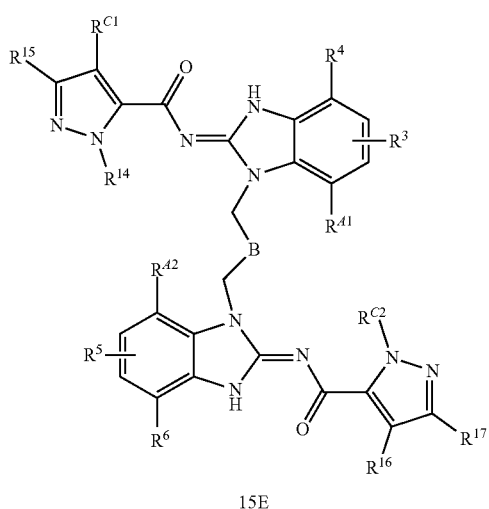

15E

Method 16: All variables are as defined in Formula (I-N), Formula (I-P) or Formula (I). A suitably substituted halo-nitrophenyl compound (16A) is reacted with a monoprotected diamine containing a linker group (B) such as 16B to provide nitro-aniline 16C. Deprotection of the amine protecting group affords amine 16D, which can be reacted with a halo-nitrophenyl compound 16E to afford bis-nitro dimer 16F. Reduction of both nitro groups will provide a tetraaniline 16G which can be converted to an amidobenzimidazole dimer (16H) via one of two methods: 1) Treatment with cyanogen bromide to afford a bisaminobenzimidazole followed by amide coupling with a pyrazole acid such as 16I; or 2) Treatment with isothiocyanate (16J) until completion of the reaction, then addition of EDC (or other suitable coupling reagent) and triethylamine (or other suitable base) and the reaction is stirred until completion. When suitable functional groups are present on 16H, further functionalization of these groups will be possible to afford additional compounds.

Method 16
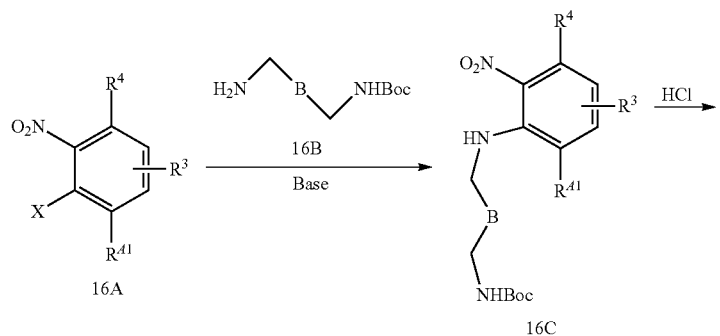
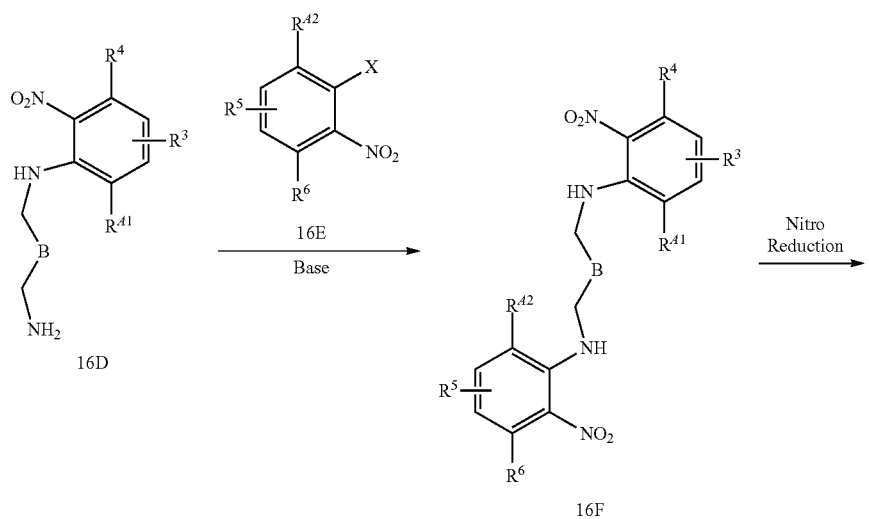
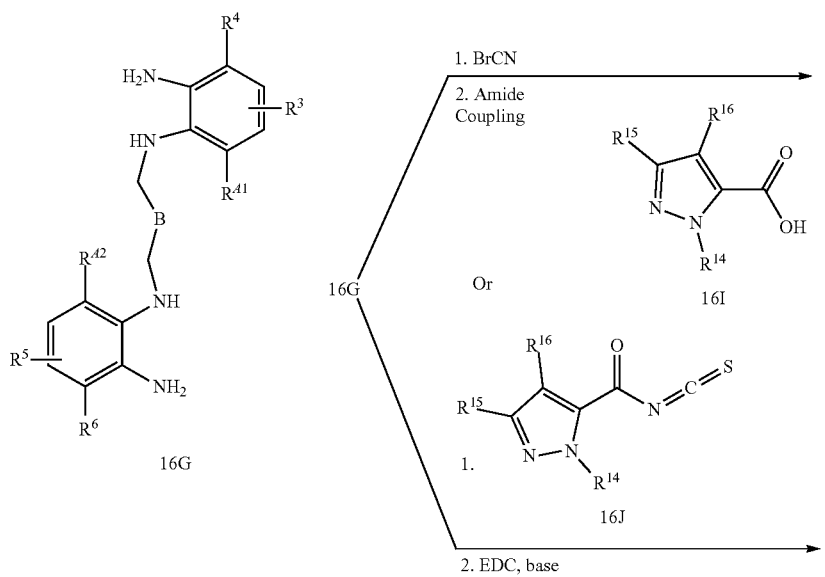

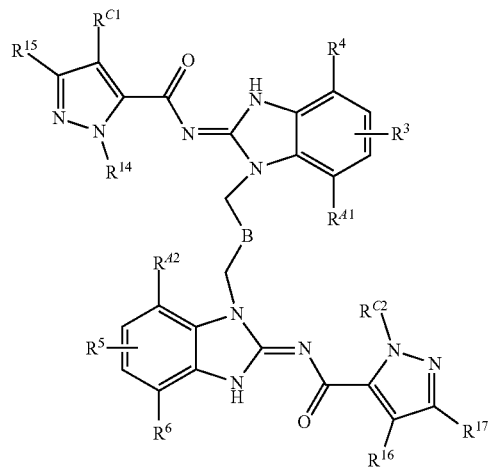

16H

Method 17: $M^2$ is $C_1$-$C_6$alkyl or $COOM^2$ can be any ester that is inactive to hydrogenolysis of benzyl ester. All other variables are as defined in Formula (I-N), Formula (I-P) or Formula (I). A substituted pyrazole ester such as (pent-4-yn-1-yl)-1H-pyrazole-carboxylate (17D) may be formed by esterification of a substituted 1H-pyrazole-carboxylate (17A) to afford ester 17B followed by N-alkylation under mitsunobu conditions. A 4-iodo-pyrazole ester (17G) may be formed by esterification of the corresponding pyrazole-carboxylic acid (17E), followed by iodination using 1-iodopyrrolidine-2,5-dione (NIS). Palladium-catalyzed coupling of an alkylated pyrazole such as 17D with the 4-iodo-pyrazole-ester (17G) forms a linked bispyrazole (17H). Reduction and hydrogenolysis of the linked bispyrazole will provide a bispyrazole monoacid (17I).

Method 17

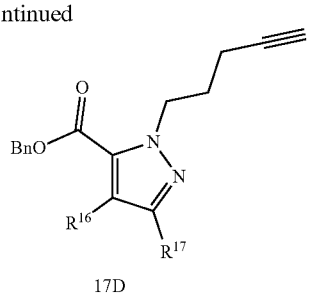

155

-continued

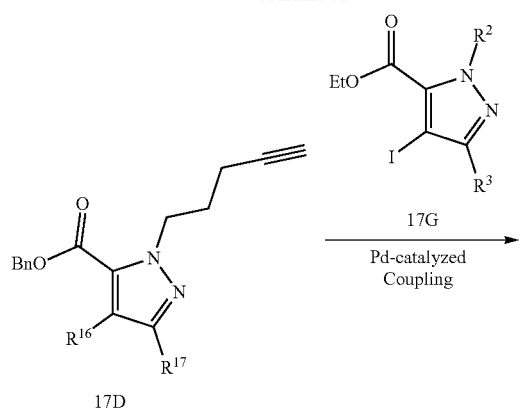

17D

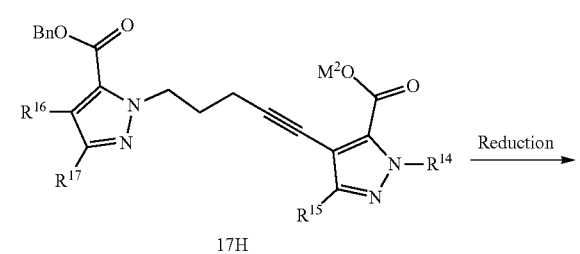

17H

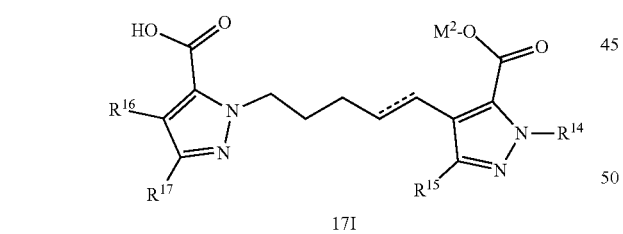

17I

156

Method 18

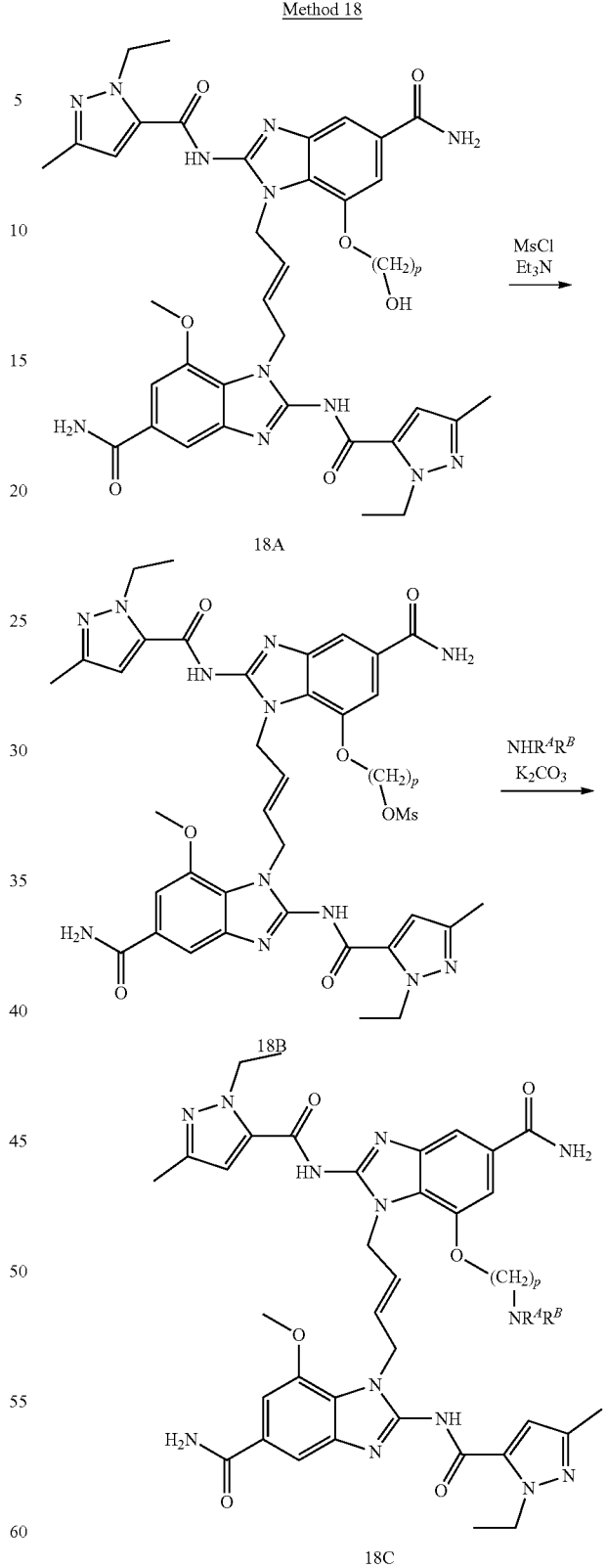

Method 18: all variables are as defined in Formula (A). (E)-1-(4-(5-carbamoyl-2-(1-ethyl-3-methyl-1H-pyrazole-5-carboxamido)-7-(3-hydroxy-propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (18A) may be treated with methanesulfonyl chloride and triethylamine. Upon completion of step 1, the resulting mesylate (18B) is treated with an amine (NHR$^A$R$^B$) and K$_2$CO$_3$ and the reaction heated at 50-80° C. until completion to afford the desired compounds (18C).

Method 19: All variables are as defined in Formula (I-N), Formula (I-P) or Formula (I). A suitably substituted bis-aminobenzimidazole (19B) containing a linker group (B), prepared via one of the methods described here, is reacted with a bispyrazole (19A) incorporating a linker group (C)

and amide coupling reagents to afford a macrocylic bisamidobenzimidazole.

Method 19

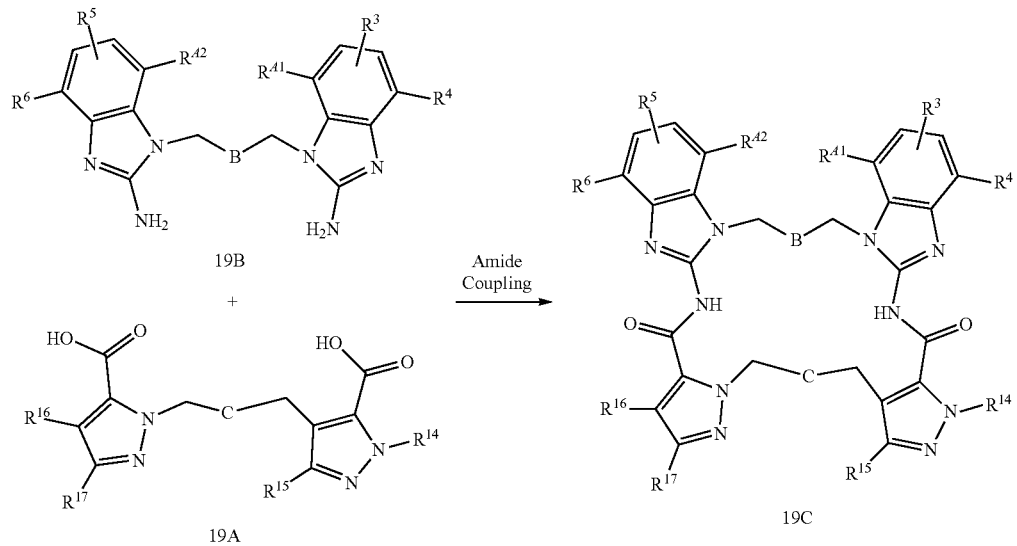

Method 20: All variables are as defined in Formula (I-N), Formula (I-P) or Formula (I). A suitably substituted halo-nitrophenyl compound (20A) is reacted with a monoprotected diamine containing a linker group (B) such as 20B to provide nitro-aniline 20C. Reduction of the nitro group under appropriate conditions will afford dianiline 20D, which can be converted to an amidobenzimidazole 20F via one of two methods: 1) treatment with cyanogen bromide followed by amide coupling with a pyrazole acid such as 20E; or 2) treatment with isothiocyanate (20L) until completion of the reaction, then addition of EDC (or other suitable coupling reagent) and triethylamine (or other suitable base) and the reaction is stirred until completion. Deprotection of the amine protecting group affords amine 20G, which can be reacted with a halo-nitrophenyl compound 20H to afford dimeric nitro aniline 20I. Reduction of the nitro group will provide bis-aniline 20J which can be converted to an amidobenzimidazole dimer (20K) via one of two methods: 1) Treatment with cyanogen bromide to afford a bisaminobenzimidazole followed by amide coupling with a pyrazole acid such as 20M; or 2) Treatment with isothiocyanate (20N) until completion of the reaction, then addition of EDC (or other suitable coupling reagent) and triethylamine (or other suitable base) and the reaction is stirred until completion. When suitable functional groups are present on 20K, further functionalization of these groups will be possible to afford additional compounds.

Method 20:

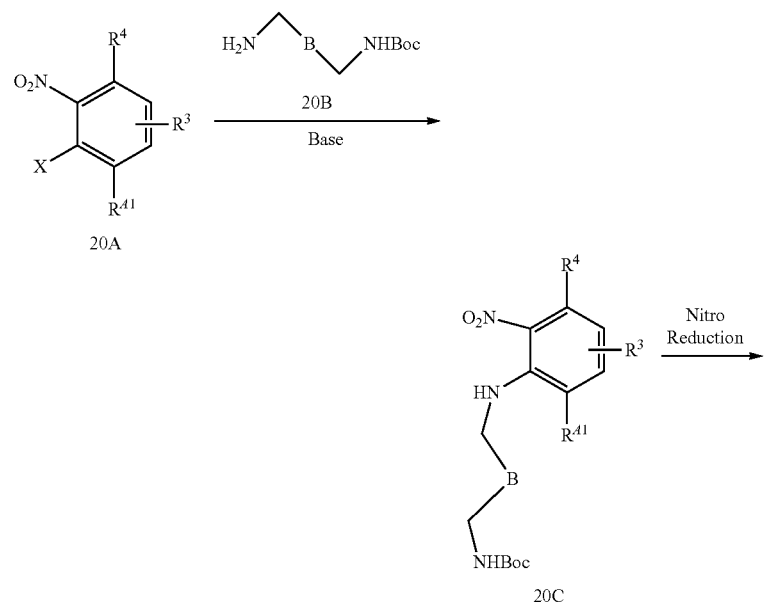

-continued
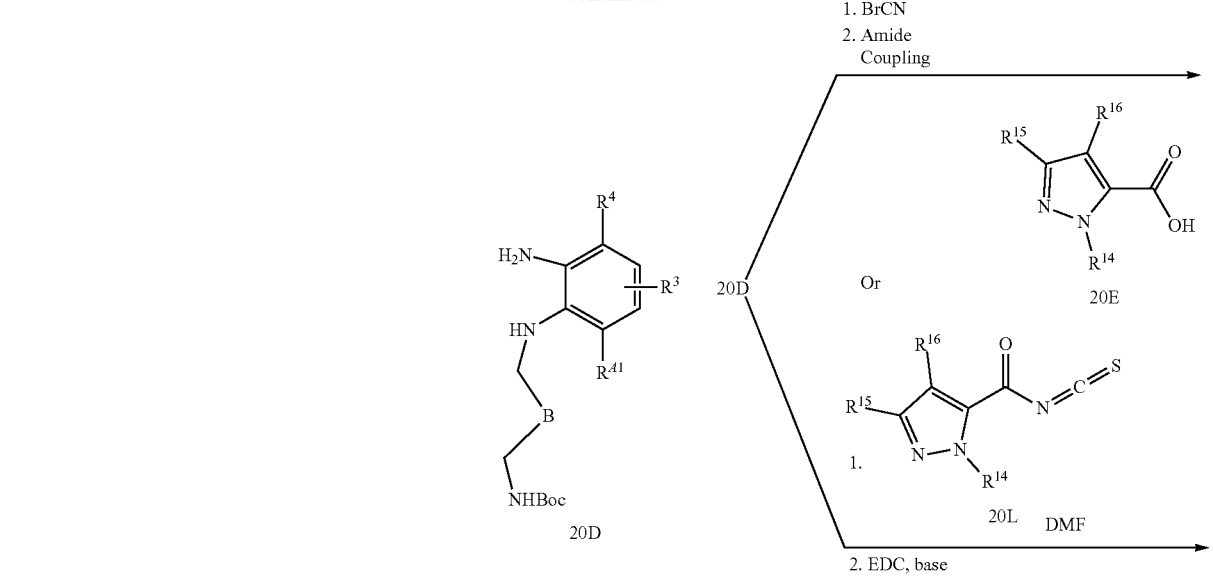
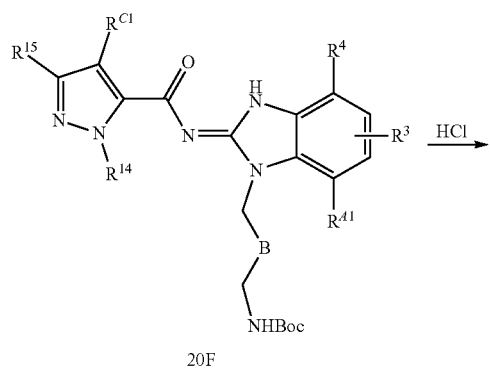
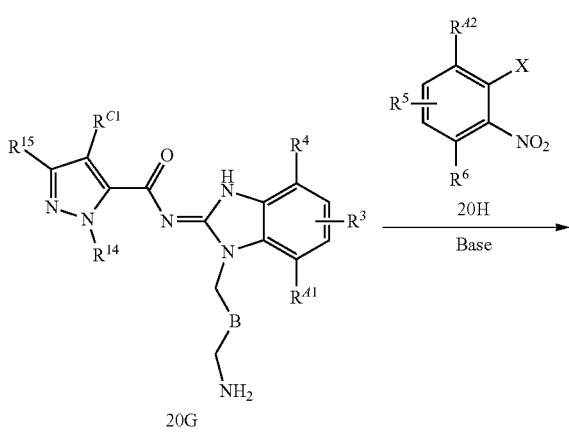

-continued
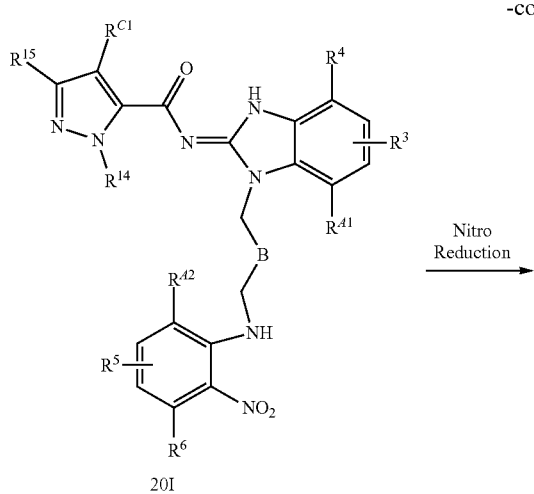
20I
Nitro Reduction →
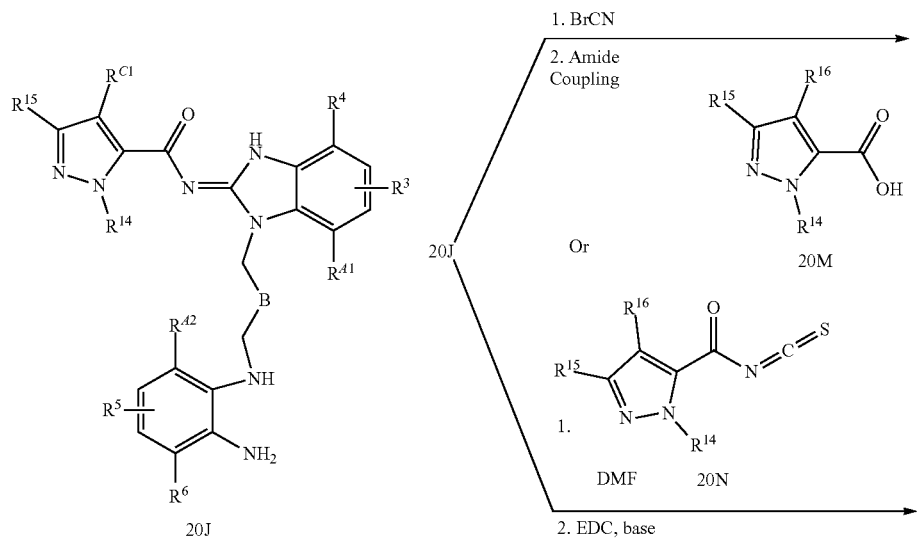
20J
1. BrCN
2. Amide Coupling
Or
1. DMF
2. EDC, base
20M
20N
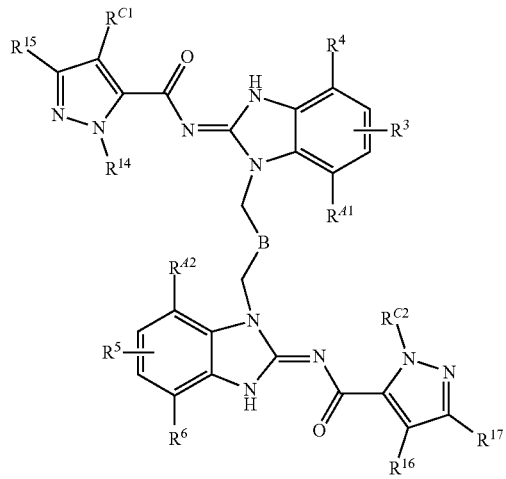
20K Method 21: All variables are as defined in Formula (I-N), Formula (I-P) or Formula (I). Two molecules of an appropriate functionalized nitro-halo-phenyl (21A) are dimerized to provide bis-nitro dimer 21B containing a linker group (A). 21B is then reacted with an amine or diamine to afford dianiline 21C. Reduction of the nitro groups, provides tetraaniline 21C which can be converted to an amidobenzimidazole dimer (21G) via one of two methods: 1) Treatment with cyanogen bromide to afford a bisaminobenzimidazole followed by amide coupling with a pyrazole acid such as 21E; or 2) Treatment with isothiocyanate (21F) until completion of the reaction, then addition of EDC (or other suitable coupling reagent) and triethylamine (or other suitable base) and the reaction is stirred until completion. When suitable functional groups are present on 21G, further functionalization of these groups will be possible to afford additional compounds. A general example of a dimerization would be the reaction of a suitable nitro-phenol (21H) with a bis-halide and a base to afford the bis-phenol dimer 21J.

Method 21

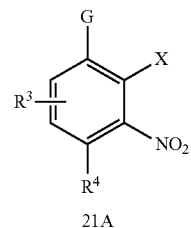

21A

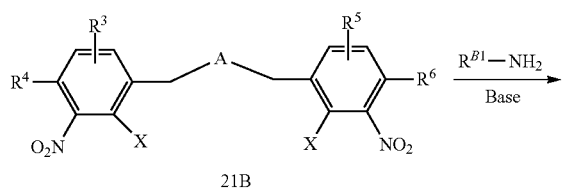

21B

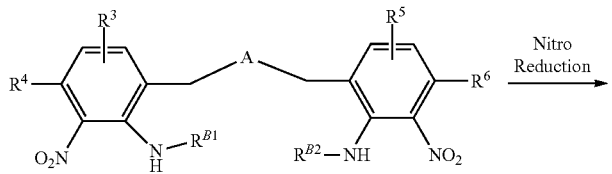

21C

1. BrCN
2. Amide Coupling

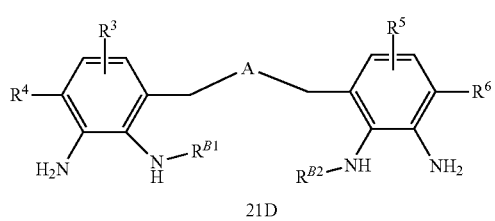

21D

Or

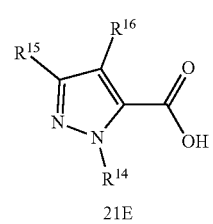

21E

1.

21F
DMF

2. EDC, base

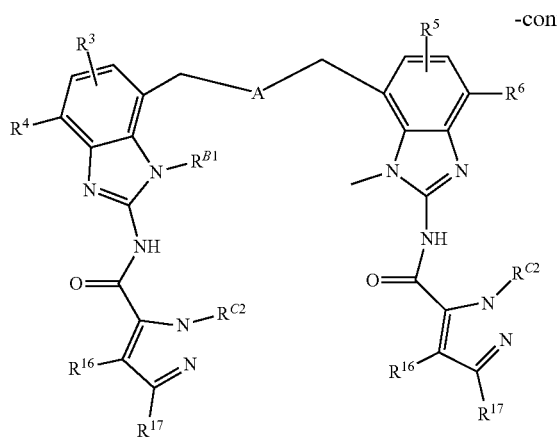

21G

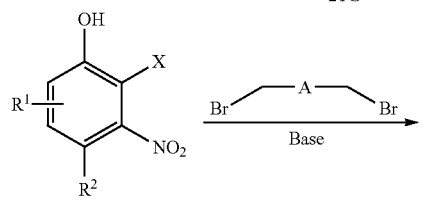

21H

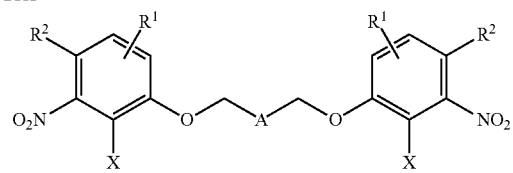

21J

Method 22: All variables are as defined in Formula (I-N), Formula (I-P) or Formula (I). A suitably substituted aminobenzimidazole (22A), prepared via one of the methods described here, is reacted with a bispyrazole (22B) incorporating a linker group (C) and amide coupling reagents to afford a dimeric bisamidobenzimidazole. When suitable functional groups are present on 22C, further functionalization of these groups will be possible to afford additional compounds.

Method 22

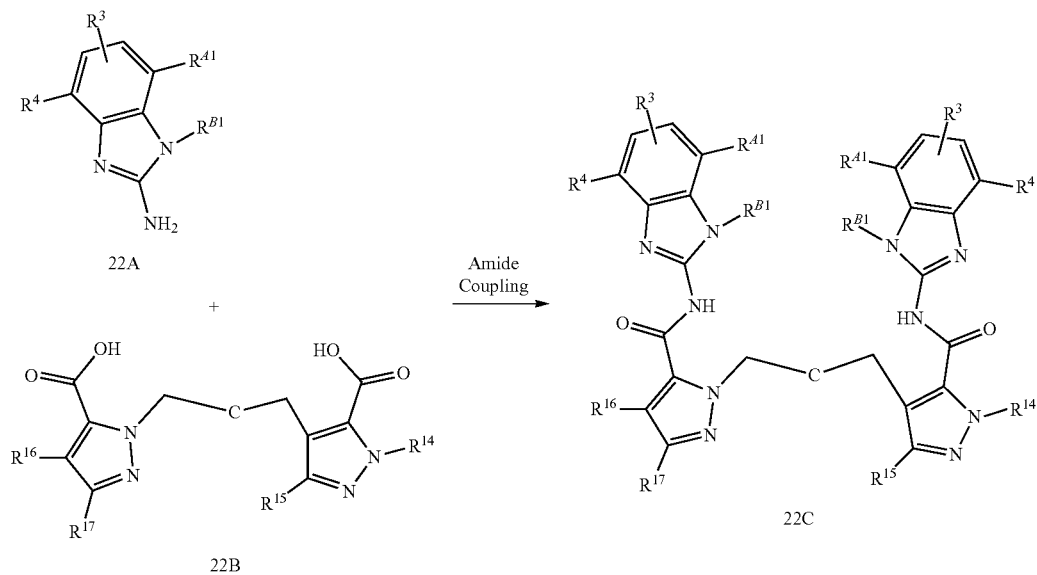

Method 23: All variables are as defined in Formula (I-N), Formula (I-P) or Formula (I). A suitably substituted aminobenzimidazole (23A), prepared via one of the methods described here, is reacted with a mono-carboxylic acid bispyrazole (23B) incorporating a linker group (C), and amide coupling reagents to afford an amidobenzimidazole ester such as 23C. Hydrolysis of the pyrazole ester will provide acid 23D, which can be coupled with a second aminobenzimidazole (23E) to provide a dimeric bisamidobenzimidazole (23F). When suitable functional groups are present on 23F, further functionalization of these groups will be possible to afford additional compounds.

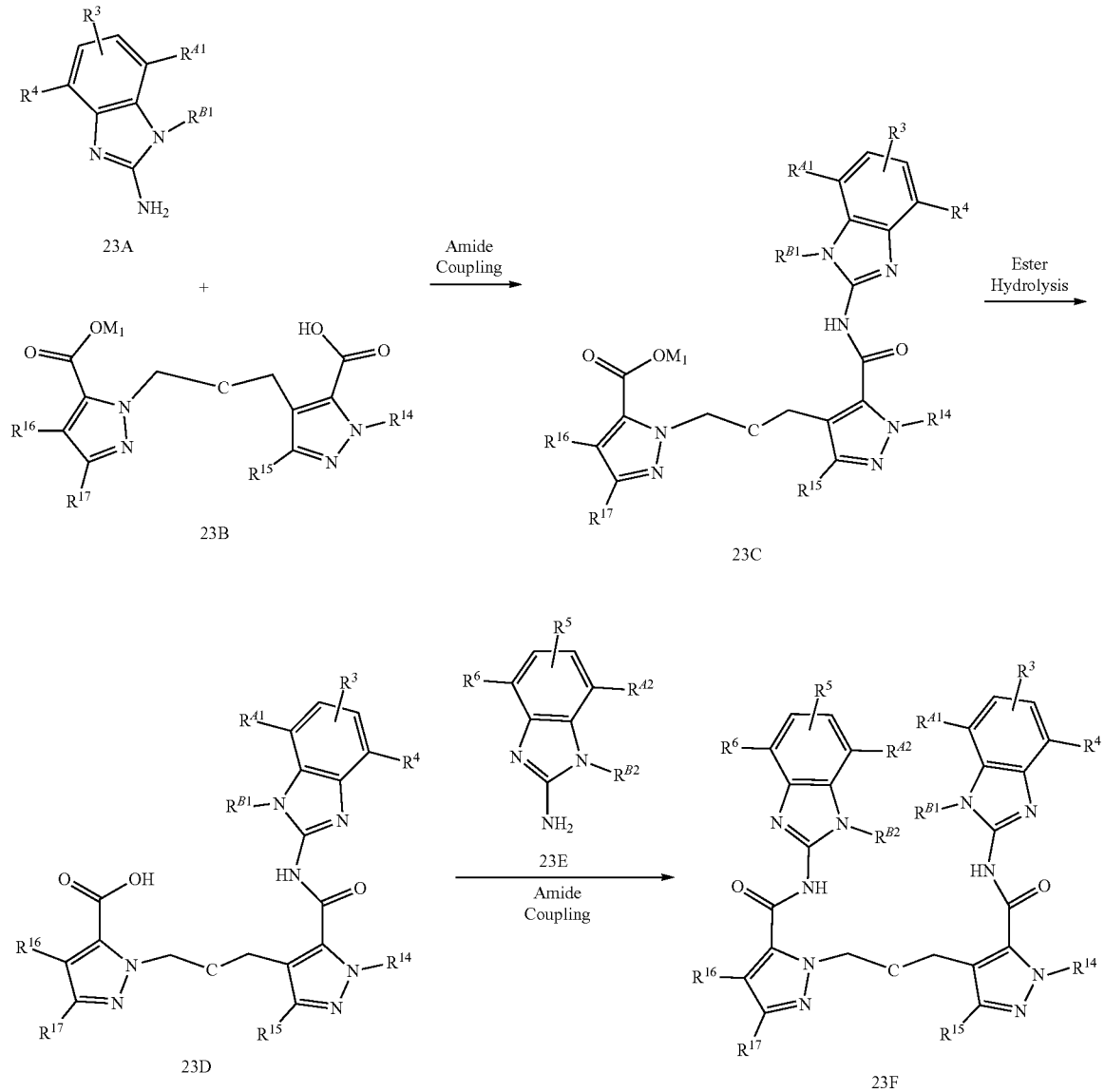

Method 23

Method 24: $M^2$ is $C_1$-$C_6$alkyl or $COOM^2$ can be any ester that is inactive to hydrogenolysis of benzyl ester. All other variables are as defined in Formula (I-N), Formula (I-P) or Formula (I). A substituted pyrazole ester such as (pent-4-yn-1-yl)-1H-pyrazole-carboxylate (24D) may be formed by esterification of a substituted 1/pyrazole-carboxylate (24A) to afford ester 24B followed by N-alkylation under suitable conditions such as an alkyl halide and base. In the case of using with (5-chloropent-1-yn-1-yl)trimethylsilane, a subsequent desilation will afford pyrazole ester 24D. A 4-iodo-pyrazole ester (24G) may be formed by esterification of the corresponding pyrazole-carboxylic acid (24E), followed by iodination using 1-iodopyrrolidine-2,5-dione (NIS). Palladium-catalyzed coupling of an alkylated pyrazole such as 24D with the 4-iodo-pyrazole-ester (24G) forms a linked bispyrazole (24H). Reduction and hydrogenolysis of the linked bispyrazole will provide a bispyrazole monoacid (24I), which can be further hydrolyzed to afford a bispyrazole di acid 24J.

Method 24:

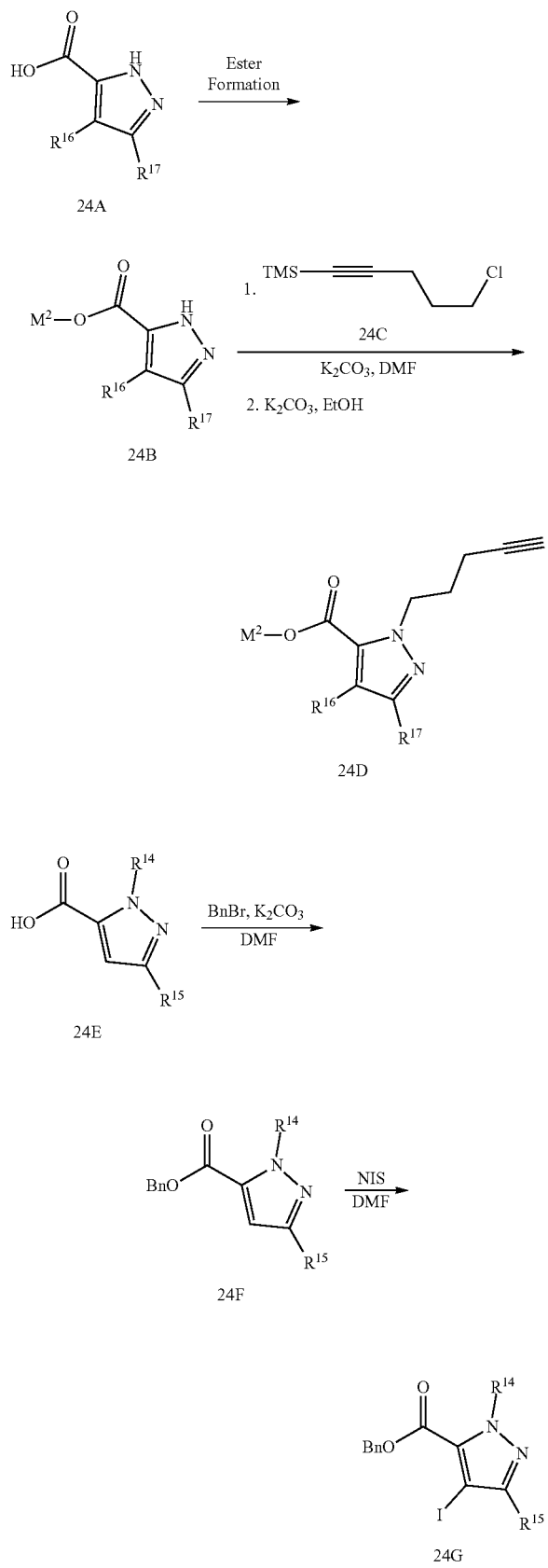

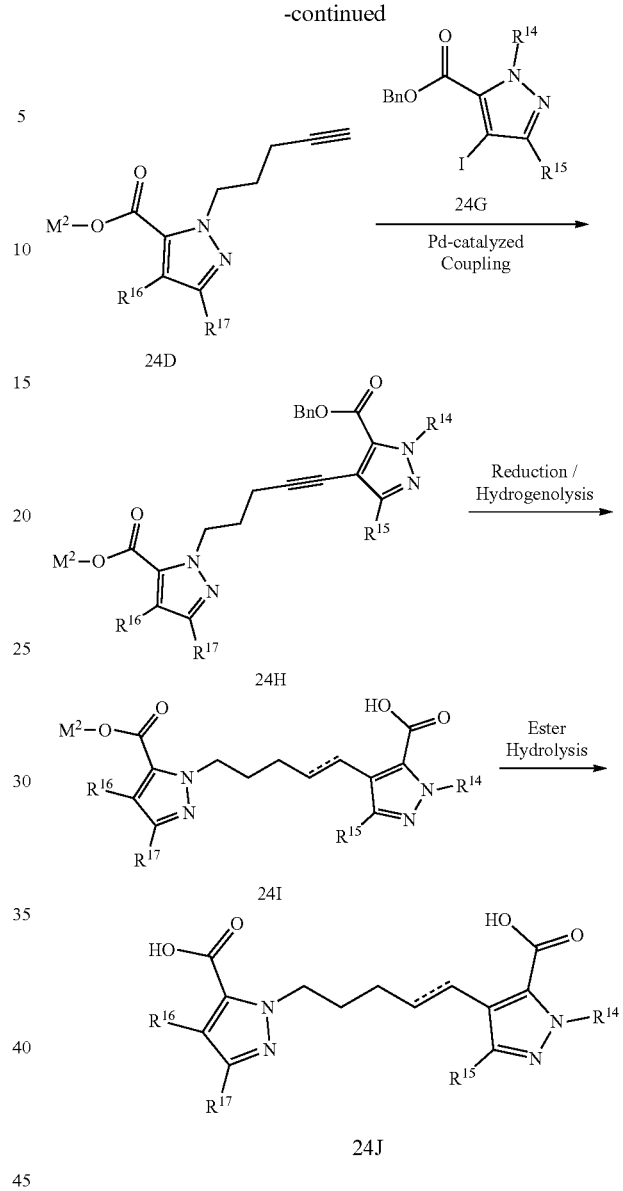

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Names for the intermediate and final compounds described herein were generated using the software naming programs ChemDraw Pro 12.0.2.1076 Plug-In inside of Perkin Elmer E-Notebook or MarvinSketch 5.11.4_b82 (Chemaxon).

It will be appreciated by those skilled in the art that in certain instances these programs may name a structurally depicted compound as a tautomer or isomer of that compound. It is to be understood that any reference to a named compound or a structurally depicted compound is intended to encompass all tautomers or isomers of such compounds and any mixtures of tautomers and/or isomers thereof.

The definitions for LCMS analysis conditions listed below and apply to all compounds.

| LCMS Method | LCMS Method A |
| --- | --- |
| Wavelength | 214 nm and 254 nm |
| Instrument | Agilent 1200-6110 |
| Column | Halo C18 4.6 × 50 um |
| Flow Rate | 1.8 mL/min |

Gradient Method

| Time (min) | ACN (0.05% FA) | H₂O (0.05% FA) |
| --- | --- | --- |
| 0 | 5 | 95 |
| 1 | 95 | 5 |
| 2 | 95 | 5 |
| 2.5 | 5 | 95 |

| LCMS Method | LCMS Method B |
| --- | --- |
| Wavelength | 214 nm and 254 nm |
| Instrument | Shimadzu 2020 |
| Column | Halo C18 4.6 × 50 um |
| Flow Rate | 1.5 mL/min |

Gradient Method

| Time (min) | ACN (0.05% FA) | H₂O (0.05% FA) |
| --- | --- | --- |
| 0 | 5 | 95 |
| 1 | 95 | 5 |
| 4 | 95 | 5 |
| 4.5 | 5 | 95 |
| 5 | 5 | 95 |

LCMS Method: LCMS Method C

| Instrumentation | |
| --- | --- |
| LC: | Shimadzu 10Avp (controller, pumps, and UV detector) |
| UV: | Shimadzu 10AVp (214 nm) |
| ELS: | Sedere Sedex 75 C (45 C) |
| MS: | PE Sciex Single Quadrupole 150 EX |
| | Polarity (positive); Mode (profile); Scan Time (0.33 s); Step (0.2 m/z) |
| | Capillary V (5500); Cone V (25-45) or |
| | Waters ZQ Single Quadrupole |
| | Polarity (positive); Mode (continuum); |
| | Scan Time (0.25 s) |
| | Capillary V (3500); Cone V (25-35) |
| Autosampler: | CTC Leap; 3 uL loop; default injection volume = 2 uL (default) |
| Column: | Thermo Hypersil Gold (C18, 20 × 2.1 mm, 1.9 u particle diam.) |
| Heater: | Phenomenex 50-55° C. |
| Solvent A: | H₂O, 0.02% TFA |
| Solvent B: | MeCN, 0.02% TFA |

| Gradient: | Time (min) | Flow (mL/min) | Sol. B |
| --- | --- | --- | --- |
| | 0.02 | 1.4 | 4.0 |
| | 1.90 | | 95.0 |
| | 1.91 | | 4.0 |
| | 2.00 | Stop | |

LCMS Method: LCMS Method D

| Instrumentation | |
| --- | --- |
| LC: | Waters Acquity Binary Solvent Manager, Column Manager 55C |
| Autosampler: | CTC Leap PAL Autosampler |
| UV: | Waters Acquity PDA (210-360 nm) |
| ELS: | Waters Acquity ELSD (50C) or Sedere Sedex 75C (45C) |
| MS: | Waters Acquity SQD |
| | Polarity (positive or negative); Mode (continuum); |
| | Scan Time (0.15 s) |
| | Capillary V (3500); Cone V (25-35); |
| Column: | Thermo Hypersil Gold (C18, 20 × 2.1 mm, 1.9 u particle diam.) |
| Solvent A: | H₂O, 0.02% TFA |
| Solvent B: | MeCN, 0.02% TFA |

| Gradient: | Time (min) | Flow (mL/min) | Sol. B |
| --- | --- | --- | --- |
| | 0.02 | 1.6 | 2.0 |
| | 1.90 | | 95.0 |
| | 1.91 | stop | 4.0 |

LCMS Method: LCMS Method E

| Instrumentation | |
| --- | --- |
| LC: | Waters Acquity I-Class Binary Solvent Manager, Column Manager 55C |
| Autosampler: | CTC Leap PAL 3 Autosampler |
| UV: | Waters Acquity PDA (210-360 nm) |
| ELS: | Waters Acquity ELSD (50C) or Sedere Sedex 85C (45C) |
| MS: | Waters Acquity QDa Mass Detector |
| | Polarity (positive or negative); Mode (continuum); |
| | Scan Time (10 Hz) |
| | Capillary kV (0.8); Cone V (12); |
| Column: | Thermo Hypersil Gold (C18, 20 × 2.1 mm, 1.9 u particle diam.) |
| Solvent A: | H₂O, 0.02% TFA |
| Solvent B: | MeCN, 0.02% TFA |

| Gradient: | Time (min) | Flow (mL/min) | Sol. B % |
| --- | --- | --- | --- |
| | 0.02 | 1.6 | 0.5 |
| | 1.90 | | 90 to 95 |
| | 1.91 | stop | 0.5 |

LCMS Method: LCMS Method F

| Instrumentation | |
| --- | --- |
| LC: | Waters Acquity Binary Solvent Manager, Column Manager 55C |
| Autosampler: | CTC Leap PAL Autosampler |
| UV: | Waters Acquity PDA (210-360 nm) |
| ELS: | Waters Acquity ELSD (50C) or Sedere Sedex 75C (45C) |
| MS: | Waters Acquity SQD |
| | Polarity (positive or negative); Mode (continuum); |
| | Scan Time (0.15 s) |
| | Capillary V (3500); Cone V (25-35); |
| Column: | Waters BEH (C18, 30 × 2.1 mm, 1.7 u particle diam.) |
| Solvent A: | H₂O, 0.02% TFA |
| Solvent B: | MeCN, 0.02% TFA |

| Gradient: | Time (min) | Flow (mL/min) | Sol. B |
| --- | --- | --- | --- |
| | 0.02 | 1.5 | 1.0 |
| | 4.90 | | 85.0 |
| | 4.91 | | 1.0 |
| | 5.00 | stop | 1.0 |

LCMS Method: LCMS Method G

The UPLC analysis was conducted on an Acquity UPLC CSH C18 column (50 mm × 2.1 mm i.d. 1.7 μm packing diameter) at 40 degrees centigrade.
The solvents employed were:
A = 0.1% v/v solution of Formic Acid in Water.
B = 0.1% v/v solution of Formic Acid in Acetonitrile.

The gradient employed was:

| Time (min) | Flow Rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 ul
MS Conditions MS: Waters ZQ
Ionisation mode: Alternate-scan Positive and Negative Electrospray Scan

LCMS Method: LCMS Method H

The UPLC analysis was conducted on an Acquity UPLC CSH C18 column (50 mm × 2.1 mm i.d. 1.7 μm packing diameter) at 40 degrees centigrade.
The solvents employed were:
A = 10 mM Ammonium Bicarbonate in water adjusted to pH 10 with ammonia solution.
B = Acetonitrile.

The gradient employed was:

| Time (min) | Flow Rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.3 ul
MS Conditions MS: Waters ZQ
Ionisation mode: Alternate-scan Positive and Negative Electrospray

LCMS Method: LCMS Method I

The UPLC analysis was conducted on an Acquity UPLC CSH C18 column (50 mm × 2.1 mm i.d. 1.7 μm packing diameter) at 40 degrees centigrade.
The solvents employed were:
A = 10 mM Ammonium Bicarbonate in water adjusted to pH 10 with 25% ammonium hydroxide solution.
B = Acetonitrile The gradient employed was:

| Time (min) | Flow Rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 uL
MS Conditions
MS: Waters Acquity SQD or QDa mass detector
Ionisation mode: Alternate-scan Positive and Negative

LCMS Method: LCMS Method J

The UPLC analysis was conducted on an Acquity UPLC CSH C18 column (50 mm × 2.1 mm i.d. 1.7 μm packing diameter) at 40 degrees centigrade.
The solvents employed were:
A = 0.1% v/v solution of Formic Acid in Water.
B = 0.1% v/v solution of Formic Acid in Acetonitrile.

The gradient employed was:

| Time (min) | Flow Rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 uL
MS Conditions
MS: Waters Acquity SQD or QDa mass detector
Ionisation mode: Alternate-scan Positive and Negative

LCMS Method: LCMS Method K

The UPLC analysis was conducted on an Acquity UPLC CSH C18 column (50 mm × 2.1 mm i.d. 1.7 μm packing diameter) at 40 degrees centigrade.
The solvents employed were:
A = 0.1% v/v solution of TFA in Water.
B = 0.1% v/v solution of TFA in Acetonitrile.

The gradient employed was:

| Time (min) | Flow Rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 uL
MS Conditions
MS: Waters Acquity SQD or QDa mass detector
Ionisation mode: Alternate-scan Positive and Negative Electrospray

| LCMS Method: LCMS Method L | |
|---|---|
| Instrumentation | |
| LC: | Waters Acquity I-Class Binary Solvent Manager, I-Class Column Manager 55C |
| Autosampler | CTC PAL 3 Autosampler |
| UV: | Waters Acquity PDA (210-360 nm) |
| ELS: | Sedere Sedex 85C (45C) |
| MS: | Waters Acquity QDa Mass Detector Polarity (positive or negative); Mode (continuum); Scan Time (10Hz) Capillary kV (0.8); Cone V (12); |
| Column: | Thermo Hypersil Gold (C18, 20 × 2.1 mm, 1.9 u particle diam.) |
| Solvent A: | H$_2$O, 0.02% TFA |
| Solvent B: | MeCN, 0.02% TFA |

| Gradient: | Time (min) | Flow (mL/min) | Sol. B % |
|---|---|---|---|
| | 0.02 | 1.6 | 0.5 |
| | 1.90 | | 95 |
| | 1.91 | | 0.5 |
| | 2.00 | stop | |

LCMS Method: LCMS Method M

The LCMS analysis was conducted on a Waters Sunfire C18 column (50 mm×3.0 mm i.d. 5 μm packing diameter) at Ambient temperature on an Agilent 1200 HPLC with a Model 6140 Quad MS The solvents employed were: A=0.1% v/v solution of TFA in Water. B=0.1% v/v solution of TFA in Acetonitrile.

The gradient employed was:

| Time | Flow | % A | % B |
|---|---|---|---|
| 0 | 1 mL | 90 | 10 |
| 2.5 | 1 mL | 0 | 100 |
| 4.2 | 1 mL | 0 | 100 |

The UV detection wavelength (Bandwidth 8): 220 nm and 254 nm. Injection volume: 1 ul MS Conditions MS: Agilent 6140 Quad MS Ionisation mode: Positive LCMS Method: LCMS Method N The LCMS analysis was conducted on an Agilent Zorbax Eclipse XDB-C18 (150 mm×4.6 mm, i.d. 5 μm packing diameter) at Ambient temperature on an Agilent 1200 HPLC with a Model 6140 Quad MS The solvents employed were: A=0.1% v/v solution of TFA in Water. B=0.1% v/v solution of TFA in Acetonitrile.

The gradient employed was:

| Time | Flow | % A | % B |
|---|---|---|---|
| 0 | 1 mL | 90 | 10 |
| 12 | 1 mL | 0 | 100 |
| 13 | 1 mL | 0 | 100 |

The UV detection wavelength (Bandwidth 8): 220 nm and 254 nm.

Injection volume: 1 ul

MS Conditions

MS: Agilent 6140 Quad MS

Ionisation mode: Positive

The following abbreviations may be used in this specification:

| Abbreviation | Meaning |
|---|---|
| AcOH | acetic acid |
| aq. | aqueous |
| BBr$_3$ | boron tribromide |
| BOC, tBOC | tert-butoxycarbonyl |
| brine | saturated aqueous sodium chloride |
| BuOH | butanol |
| CDCl$_3$ | deuterated chloroform |
| CDI | 1,1'-carbonyldiimidazole |
| CH$_2$Cl$_2$ or DCM | methylene chloride or dichloromethane |
| CH$_3$CN or MeCN | acetonitrile |
| CH$_3$NH$_2$ | methylamine |
| d | day |
| DAST | diethylaminosulfur trifluoride |
| DCE | 1,2-dichloroethane |
| DIEA or DIPEA | diisopropyl ethylamine |
| DMA | dimethylacetamide |
| DMAP | 4-dimethylaminopyridine |
| DMF | N,N-dimethylformamide |
| DMSO | dimethylsulfoxide |
| EDC | 1-ethyl-3-(3-dimethylaminopropyl)carbodiimide |
| equiv | equivalents |
| Et | ethyl |
| Et$_3$N or TEA | triethylamine |
| Et$_2$O | diethyl ether |
| EtOAc | ethyl acetate |
| EtOH | ethanol |
| FCC | flash column chromatography |
| h, hr | hour(s) |
| HATU | O-(7-azabenzotriazol-1yl)-N,N,N',N'-tetramethylyronium hexafluorophosphate |
| HCl | hydrochloric acid |
| HOAt | 1-hydroxy-7-azabenzotriazole |
| HOBt | hydroxybenzotriazole |
| HPLC | high-performance liquid chromatography |
| ICl | iodine monochloride |
| IPA | isopropyl alcohol |
| i-Pr$_2$NEt | N',N'-diisopropylethylamine |
| K$_2$CO$_3$ | potassium carbonate |
| KHMDS | potassium bis(trimethylsilyl)amide |
| KOt-Bu | potassium tert-butoxide |
| KOH | potassium hydroxide |
| LCMS | liquid chromatography-mass spectroscopy |
| LiAlH$_4$ | lithium aluminum hydride |
| LiHDMS | lithium hexamethyldisilazide |
| LiOH | lithium hydroxide |
| Me | methyl |
| MeOH or CH$_3$OH | methanol |
| MgSO$_4$ | magnesium sulfate |
| min | minute(s) |
| MS | mass spectrum |
| μw | microwave |
| NaBH$_4$ | sodium borohydride |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| NBS | N-bromosuccinimide |
| N$_2$H$_2$ | hydrazine |
| NH$_4$Cl | ammonium chloride |
| NH$_4$OH | ammonium hydroxide |
| NiCl$_2$ • 6H$_2$O | nickel (II) chloride hexahydrate |
| NMP | N-methyl-2-pyrrolidone |
| NMR | nuclear magnetic resonance |
| Pd/C | palladium on carbon |
| Ph | phenyl |
| POCl$_3$ | phosphoryl chloride |
| PSI | pound-force per square inch |
| RB | round bottom |
| rm or rxn mixture | reaction mixture |
| rt/RT | room temperature |
| satd. | saturated |
| sm | starting material |
| TBAF | tetra-n-butylammonium fluoride |
| TFA | trifluoroacetic acid |
| THF | tetrahydrofuran |

| Abbreviation | Meaning |
|---|---|
| TMEDA | tetramethylethylenediamine |
| TMSI | trimethylsilyl iodide |
| TMSN$_3$ | trimethylsilyl azide |
| T3P | 2,4,6-tripropyl-1,3,5,2,4,6-trioxatriphosphorinane-2,4,6-trioxide |
| t$_R$ or Rf or Rt | retention time |
| TsOH | p-toluenesulfonic acid |

Intermediate 1

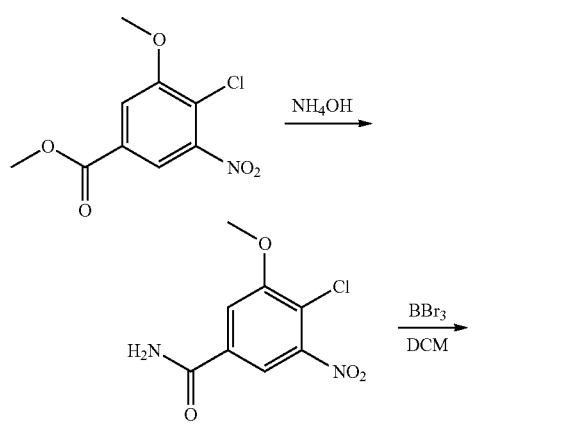

Step 1: 4-chloro-3-methoxy-5-nitrobenzamide

Methyl 4-chloro-3-methoxy-5-nitrobenzoate (1000 mg, 4.07 mmol) was stirred in NH$_4$OH (10 mL, 77 mmol) at RT for 24 h. The reaction temperature was then increased to 50° C. for 2 h. An additional 2 mL (3.7 eq) of NH$_4$OH was added to the vessel. After an additional 2 h stirring at 50° C. (4 h total) the reaction was cooled to RT. The solid was filtered and rinsed with cold water. The solid was dried under house vacuum and lyophilized to give 4-chloro-3-methoxy-5-nitrobenzamide (710 mg, 2.99 mmol, 73% yield) as a tan solid. $^1$H NMR (400 MHz, DMSO-d$_6$) δ ppm 8.31 (br. s., 1H), 8.06 (d, J=1.77 Hz, 1H), 7.88 (d, J=1.77 Hz, 1H), 7.81 (br. s., 1H), 4.02 (s, 3H). LCMS (LCMS Method D): Rt=0.71 min, [M+H]$^+$=230.9.

Step 2: 4-chloro-3-hydroxy-5-nitrobenzamide

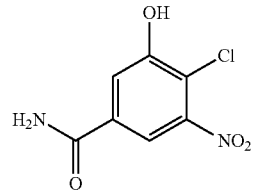 [SMILES: NC(=O)c1cc(O)c(Cl)c([N+](=O)[O-])c1]

4-chloro-3-methoxy-5-nitrobenzamide (1 g, 4.34 mmol) was suspended in dry DCM (15 mL) and stirred at rt. To the reaction was added BBr$_3$ (17.4 mL, 1M in DCM) dropwise. A slurry rapidly formed which was stirred overnight at rt under nitrogen. The reaction was poured into ice water (300 mL) and stirred vigorously for 30 min. The resulting suspension was filtered and the solids dried to afford the title compound (610 mg, 2.82 mmol, 65% yield). $^1$H NMR (400 MHz, DMSO-d$_6$) δ ppm 11.53 (br. s., 1H), 8.17 (br. s., 1H), 7.92 (s, 1H), 7.72 (s, 1H), 7.66 (br. s., 1H). LC-MS (LCMS Method D) Rt=0.60 min, [M+H]$^+$=217.

Intermediate 2

4-(5-(5-Carboxy-3-methyl-1H-pyrazol-1-yl)pentyl)-1-ethyl-3-methyl-1H-pyrazole-5-carboxylic Acid

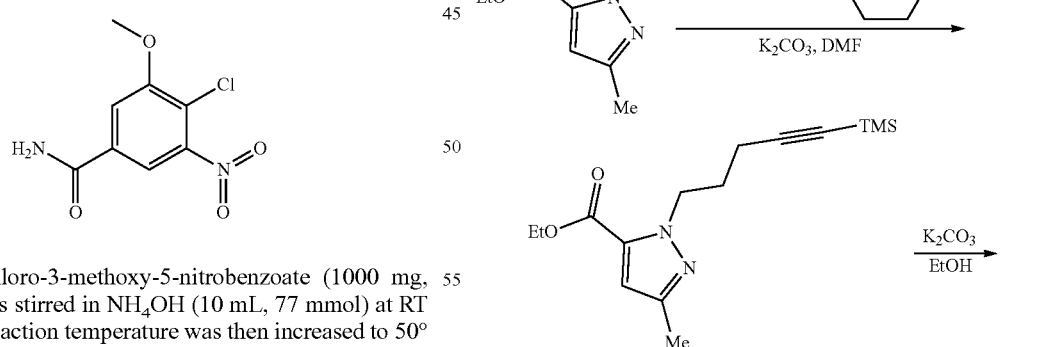

-continued

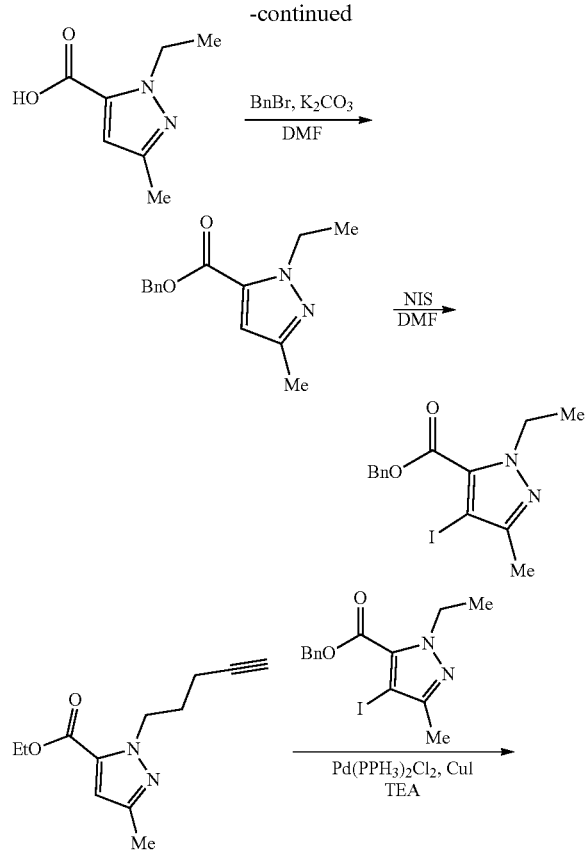

Step 1: Ethyl 3-methyl-1-(5-(trimethylsilyl)pent-4-yn-1-yl)-1H-pyrazole-5-carboxylate

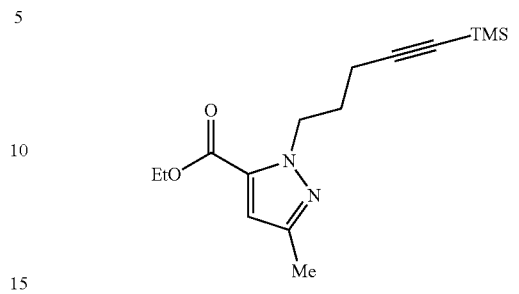

A mixture of ethyl 3-methyl-1H-pyrazole-5-carboxylate (22 g, 143 mmol), (5-chloropent-1-yn-1-yl)trimethylsilane (24.94 g, 143 mmol), $K_2CO_3$ (39.4 g, 285 mmol), and DMF (4 mL) was stirred at 60° C. overnight under a nitrogen gas atmosphere. The mixture was then dissolved in DCM and washed with water. The organic phase was dried over anhydrous $Na_2SO_4$, filtered, concentrated under reduced pressure, and purified by column chromatography on silica gel (petroleum ether/EtOAc=10:1) to afford ethyl 3-methyl-1-(5-(trimethylsilyl)pent-4-yn-1-yl)-1H-pyrazole-5-carboxylate (12.5 g, 42.7 mmol, 30% yield) as a colorless oil. LCMS (LCMS Method A): Rt=2.43 min, [M+H]$^+$=293.

Step 2: Ethyl 3-methyl-1-(pent-4-yn-1-yl)-1H-pyrazole-5-carboxylate

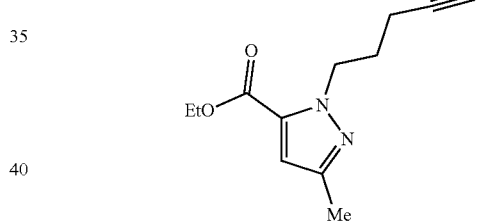

A mixture of ethyl 3-methyl-1-(5-(trimethylsilyl)pent-4-yn-1-yl)-1H-pyrazole-5-carboxylate (37.7 g, 129 mmol), $K_2CO_3$ (44.5 g, 322 mmol), and EtOH (800 mL) was stirred at rt overnight. The mixture was then filtered and the filtrate was concentrated under reduced pressure. The residue was dissolved in DCM, washed with water, dried over anhydrous $Na_2SO_4$, filtered, and concentrated under reduced pressure to afford ethyl 3-methyl-1-(pent-4-yn-1-yl)-1H-pyrazole-5-carboxylate (20 g, 91 mmol, 70.4% yield) as a colorless oil. LCMS (LCMS Method A): Rt=2.08 min, [M+H]$^+$=221.

Step 3: Benzyl 1-ethyl-3-methyl-1H-pyrazole-5-carboxylate

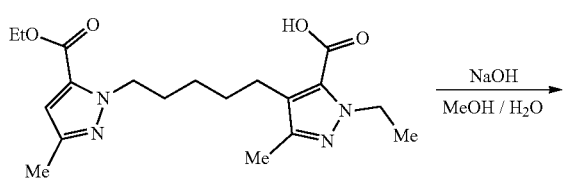

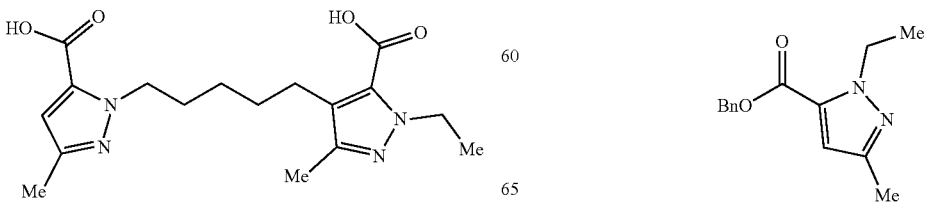

A mixture of 1-ethyl-3-methyl-1H-pyrazole-5-carboxylic acid (20 g, 130 mmol), (bromomethyl)benzene (22.2 g, 130 mmol), $K_2CO_3$ (26.9 g, 195 mmol), and DMF (200 mL) was stirred at 60° C. overnight. The mixture was then dissolved in DCM, washed with water, dried over anhydrous $Na_2SO_4$, filtered, concentrated under reduced pressure, and purified by column chromatography on silica gel (petroleum ether/EtOAc=10:1) to afford benzyl 1-ethyl-3-methyl-pyrazole-5-carboxylate (31.4 g, 129 mmol, 99% yield) as a colorless oil. LCMS (LCMS Method A): Rt=2.09 min, [M+H]$^+$=245.

Step 4: Benzyl 1-ethyl-4-iodo-3-methyl-1H-pyrazole-5-carboxylate

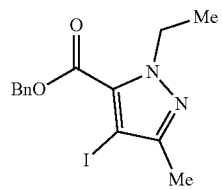

A mixture of benzyl 1-ethyl-3-methyl-1H-pyrazole-5-carboxylate (31.6 g, 129 mmol), 1-iodopyrrolidine-2,5-dione (34.9 g, 155 mmol) and DMF (400 mL) was stirred at 90° C. for 2 days. The mixture was then allowed to cool to rt, dissolved in DCM, and washed with a saturated aqueous sodium thiosulfate solution. The organic layer was dried over anhydrous $Na_2SO_4$, filtered, concentrated under reduced pressure, and purified by column chromatography (petroleum ether/EtOAc=10:1) to afford benzyl 1-ethyl-4-iodo-3-methyl-1H-pyrazole-5-carboxylate (42.6 g, 115 mmol, 89% yield). LCMS (LCMS Method A): Rt=2.31 min, [M+H]$^+$=371.

Step 5: Benzyl 4-(5-(5-(ethoxycarbonyl)-3-methyl-1H-pyrazol-1-yl)pent-1-yn-1-yl)-1-ethyl-3-methyl-1-pyrazole-5-carboxylate

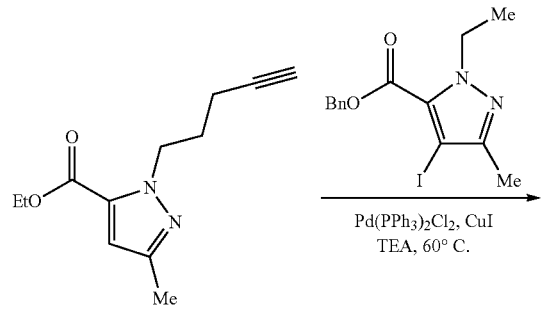

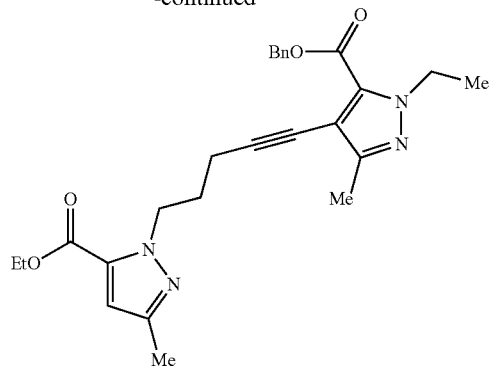

A mixture of ethyl 3-methyl-1-(pent-4-yn-1-yl)-1H-pyrazole-5-carboxylate (10.0 g, 45.4 mmol), benzyl 1-ethyl-4-iodo-3-methyl-1H-pyrazole-5-carboxylate (16.8 g, 45.4 mmol), copper(I) iodide (0.864 g, 4.54 mmol), bis(triphenylphosphine)palladium(II) chloride (0.319 g, 0.454 mmol), and $Et_3N$ (200 mL) was stirred at 60° C. overnight under a nitrogen gas atmosphere. The mixture was then dissolved in DCM and washed with water. The organic phase was dried over anhydrous $Na_2SO_4$, filtered, concentrated under reduced pressure, and purified by column chromatography on silica gel (petroleum ether/EtOAc=5:1) to afford benzyl 4-(5-(5-(ethoxycarbonyl)-3-methyl-1H-pyrazol-1-yl)pent-1-yn-1-yl)-1-ethyl-3-methyl-1H-pyrazole-5-carboxylate (9.5 g, 20.5 mmol, 45.3% yield) as a yellow solid. LCMS (LCMS Method B): Rt=2.66 min, [M+H]$^+$=463.

Step 6: 4-(5-(5-(Ethoxycarbonyl)-3-methyl-1H-pyrazol-1-yl)pentyl)-1-ethyl-3-methyl-1H-pyrazole-5-carboxylic Acid

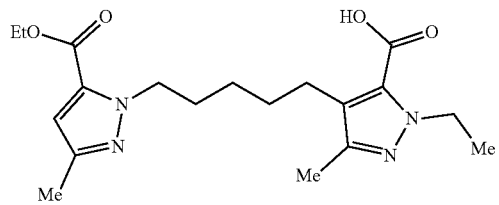 [SMILES: CCn1nc(C)c(CCCCCn2nc(C)cc2C(=O)O)c1C(=O)O]

A mixture of benzyl 4-(5-(5-(ethoxycarbonyl)-3-methyl-1H-pyrazol-1-yl)pent-1-yn-1-yl)-1-ethyl-3-methyl-1H-pyrazole-5-carboxylate (19.0 g, 41.10 mmol), 10% Pd/C (0.22 g, 2.05 mmol), and THF (500 mL) was stirred at rt under a hydrogen gas atmosphere (4 atm) for 2 days. The reaction mixture was then filtered and concentrated under reduced pressure. The residue obtained was recrystallized from EtOAc/petroleum ether (1:5, v/v) to afford 4-(5-(5-(ethoxycarbonyl)-3-methyl-pyrazol-1-yl)pentyl)-1-ethyl-3-methyl-pyrazole-5-carboxylic acid (10.5 g, 27.90 mmol, 67.9% yield). 1H-NMR (400 MHz, $CDCl_3$) δ NMR (400 MHz, CDCl, v/v) to afford 4-(5-(5-(ethoxycarbonyl)-3-methyl-pyrazol-1-yl)pentyl)-1-ethyl-3-methyl-pyrazole-5-carboxylic acid (10.5 g, 27.90 mmol, 67.9% yield). 1H-NMR (400 MHz, $CDCl_3$) δ ppm 6.63 (s, 1H), 4.57-4.48 (m, 4H), 4.38-4.32 (m, 2H), 2.74-2.62 (m, 2H), 2.32 (s, 3H), 2.23 (s, 3H), 1.91-1.86 (m, 2H), 1.59-1.54 (m, 2H), 1.45-1.37 (m, 8H). LCMS (LCMS Method A): Rt=1.59 min, [M+H]$^+$=377.

Step 7: 4-4-(7-(5-Carboxy-3-methyl-1-pyrazol-1-yl)heptyl)-1-ethyl-3-methyl-1H-pyrazole-5-carboxylic Acid

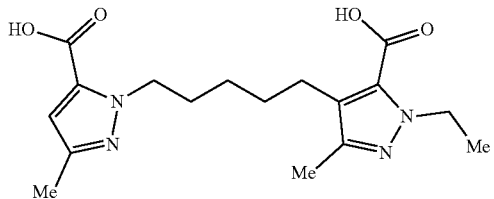

To a suspension of 4-(5-(5-(ethoxycarbonyl)-3-methyl-1H-pyrazol-1-yl)pentyl)-1-ethyl-3-methyl-pyrazole-5-carboxylic acid (9.0 g, 23.9 mmol) in MeOH (120 mL) and water (120 mL) stirred at rt was added a 2 M aq. NaOH solution (60 mL, 119.5 mmol). The reaction mixture was stirred at rt for 30 min. The mixture was then acidified to pH 4 with the addition of a 6 M HCl solution upon which a solid precipitated from the reaction mixture. The solid was collected by filtration and dried under reduced pressure to afford 4-(5-(5-carboxy-3-methyl-1H-pyrazol-1-yl)pentyl)-1-ethyl-3-methyl-1H-pyrazole-5-carboxylic acid (6.5 g, 18.7 mmol, 78.1% yield) as a white solid. 1H-NMR (400 MHz, DMSO-$d_6$) δ ppm 6.57 (s, 1H), 4.40-4.34 (m, 4H), 2.53 (t, J=7.6 Hz, 2H), 2.16 (s, 3H), 2.09 (s, 3H), 1.74-1.67 (m, 2H), 1.44-1.37 (m, 2H), 1.27-1.16 (m, 5H). LCMS (LCMS Method A): Rt=1.40 min, [M+H]$^+$=349.

Intermediate 3

(3-Bromopropoxy)(tert-butyl)dimethylsilane

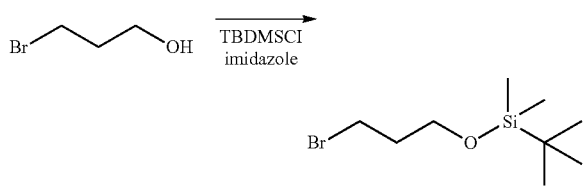

To 1H-imidazole (13.4 g, 197 mmol) in DCM (100 mL) was added 3-bromopropan-1-ol (13.7 g, 99 mmol) followed slowly by tert-butylchlorodimethylsilane (17.8 g, 118 mmol) in DCM (20 ml). After 3 hr at RT, the reaction was concentrated to 100 mL and poured in EtOAc (800 mL), washed with 5% aq citric acid (2×200 mL) and brine. The organic layer was dried over MgSO$_4$, filtered and concentrated to yield the title compound (10.0 g, 39.5 mmol, 40% yield). $^1$H NMR (400 MHz, chloroform-d) δ ppm 3.78 (t, J=5.70 Hz, 2H), 3.56 (t, J=6.46 Hz, 2H), 2.07 (t, J=5.83 Hz, 2H), 0.94 (s, 9H), 0.11 (s, 6H).

Intermediate 4

2,2,3,3-Tetrafluorobutane-1,4-diamine

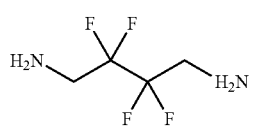

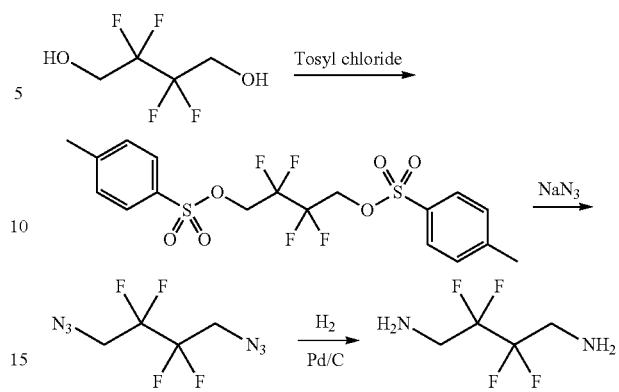

Step 1: 2,2,3,3-Tetrafluorobutane-1,4-diyl bis(4-methylbenzenesulfonate)

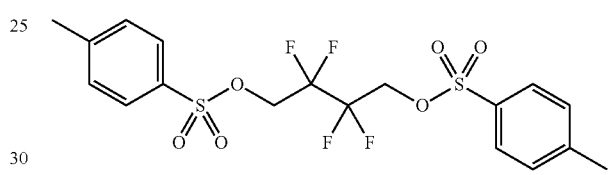

To 2,2,3,3-tetrafluorobutane-1,4-diol (10.0 g, 61.7 mmol) in pyridine (150 mL) at 0° C. was added 4-methylbenzene-1-sulfonyl chloride (29.4 g, 154 mmol) over 5 min, and then the reaction was heated to 55° C. After 1 day, the reaction was quenched with ice water, and the resulting solid was collected by filtration, dissolved in DCM (200 mL) and washed with 5% aq H2SO$_4$ (100 mL×3). The organic layer was dried over Na$_2$SO$_4$ and concentrated to yield the title compound (27.3 g, 58.0 mmol, 94% yield) as a white solid. LCMS (LCMS Method A): Rt=1.750 min, [M+H]$^+$=470.9

Step 2: 1,4-Diazido-2,2,3,3-tetrafluorobutane

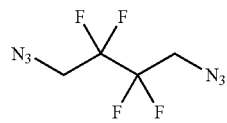 [SMILES: [N-]=[N+]=NCC(F)(F)C(F)(F)CN=[N+]=[N-]]

2,2,3,3-Tetrafluorobutane-1,4-diyl bis(4-methylbenzenesulfonate) (10.0 g, 21.3 mmol) and sodium azide (5.53 g, 85.0 mmol) in DMF (40 mL) was stirred at 110° C. overnight. The reaction was quenched with NaClO(aq) and extracted with DCM (5 mL×3). The combined organic layers were washed with water (10 mL), dried over Na$_2$SO$_4$ and concentrated to yield the title compound (3.5 g, 16.5 mmol, 78% yield). LCMS (LCMS Method A): Rt=1.520 min, [M+H]$^+$=213.1

Step 3: 2,2,3,3-Tetrafluorobutane-1,4-diamine

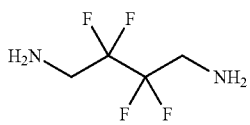

To a solution of 1,4-diazido-2,2,3,3-tetrafluorobutane (36.0 g, 170 mmol) in MeOH (350 mL) was added 10% Pd on carbon (18.1 g, 17.0 mmol). The reaction mixture was stirred at 40° C. under hydrogen (4 atm) for 16 hrs. The mixture was filtered through a pad of Celite, washed with MeOH and the filtrate was concentrated in vacuo to yield the title compound (22.0 g, 124 mmol, 73% yield). $^{1}$H NMR (400 MHz, chloroform-d) δ ppm 3.12-3.37 (m, 4H), 1.43 (br. s., 4H).

Intermediate 5

1-ethyl-3-methyl-1H-pyrazole-5-carbonyl isothiocyanate

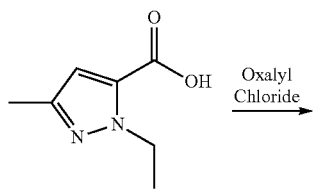

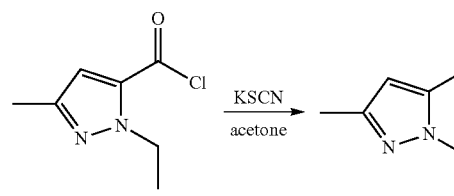

To a 1 L round bottom flask was added 1-ethyl-3-methyl-1H-pyrazole-5-carboxylic acid (25 g, 162 mmol) and DCM (500 mL). To this heterogeneous solution was added DMF (0.1 mL, 1.291 mmol) followed by the slow addition of oxalyl chloride (15.61 mL, 178 mmol). During the addition, bubbling was noticed. After stirring for 1 hr at room temperature, the volatiles were removed under vacuum and the crude was co-evaporated twice with dichloromethane (100 mL each). It was assumed 100% yield and the crude (1-ethyl-3-methyl-1H-pyrazole-5-carbonyl chloride (28.0 g, 162 mmol, 100% yield)) was used directly as it is in the next reaction.

To a dry 1 L round bottom flask was added KSCN (18.92 g, 195 mmol) and acetone (463 ml). This clear homogenous solution was cooled to 0° C. After 5 min. stirring at 0° C., 1-ethyl-3-methyl-1H-pyrazole-5-carbonyl chloride (28 g, 162 mmol) was added as a solution in acetone (25 mL). Once the addition was complete, the reaction was allowed to stir at 0° C. After 1 min. Additional KSCN was added (~2 g) and the reaction was stirred for an additional 20 min. At this time, hexanes (200 mL) was added to the reaction mixture and the crude heterogeneous solution was concentrated in vacuo to one third of the volume. The process of hexanes addition and concentration was repeated twice (300 mL of Hexanes each). After the last concentration, hexanes (200 mL) were added and the solid was removed by filtration, rinsing with hexanes (100 mL). The resulting clear light yellow filtrate concentrated and purified by chromatography (330 g Gold silica column; eluting with 0-20% EtOAc/hexanes). The desired product elutes at ~7% EtOAc/hexanes. The desired fractions were combined and concentrated yielding 1-ethyl-3-methyl-1H-pyrazole-5-carbonyl isothiocyanate (27.5 g, 139 mmol, 86% yield) as a clear colorless liquid. 1H NMR (400 MHz, chloroform-d) δ ppm 6.77 (s, 1H), 4.54 (q, J=7.10 Hz, 2H), 2.34 (s, 3H), 1.44 (t, J=7.22 Hz, 3H); LCMS (LCMS Method D): Rt=1.16 min, [M+H]$^{+}$=196.1. The acylisothiocyanate product degrades over time, and so a ~0.4 M 1,4-dioxane solution was prepared and frozen to avoid/slow decomposition. This solution was thawed and used directly in subsequent reactions.

Intermediate 6

(E)-1-(4-Aminobut-2-en-1-yl)-2-(1-ethyl-3-methyl-1H-pyrazole-5-carboxamido)-1H-benzo[d]imidazole-5-carboxamide Hydrochloride

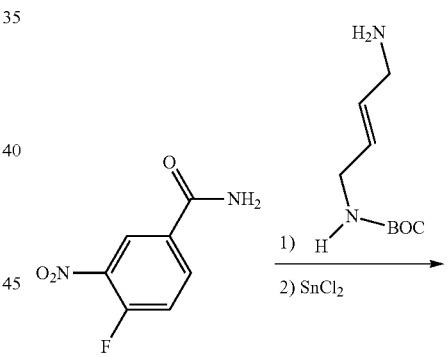

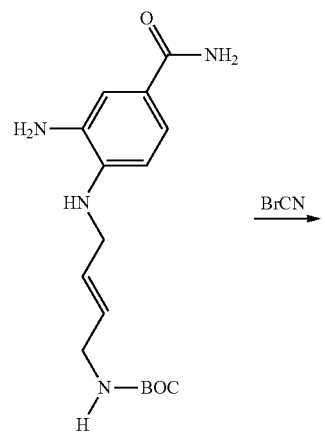

187

-continued

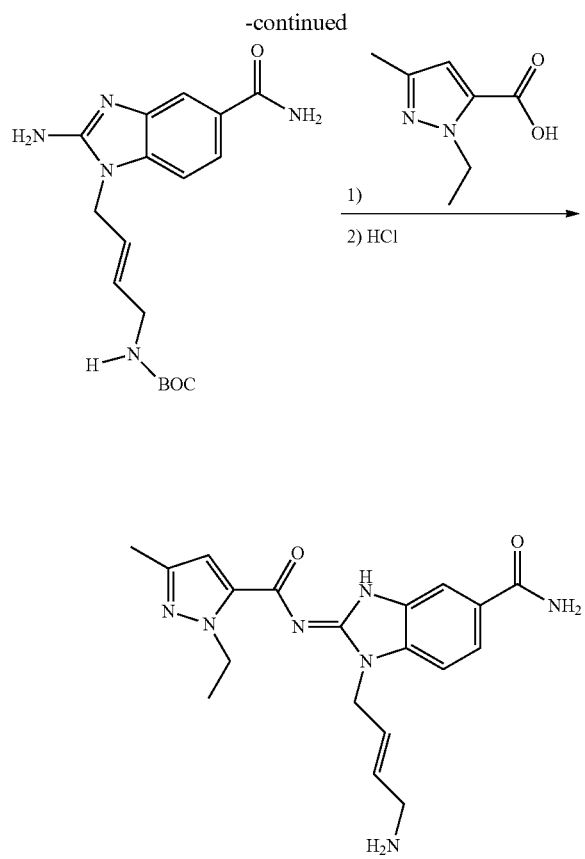

Step 1: (E)-tert-Butyl (4-((4-carbamoyl-2-nitrophenyl)amino)but-2-en-1-yl)carbamate A mixture of 4-fluoro-3-nitrobenzamide (10.0 g, 54.3 mmol), (E)-tert-butyl (4-aminobut-2-en-1-yl)carbamate (10.62 g, 57.0 mmol) and $K_2CO_3$ (15.01 g, 109 mmol) in DMSO (200 mL) was stirred at RT overnight. The reaction was poured into water (2000 mL) and stirred for 30 min. The resulting solid was collected by filtration to yield the title compound (18.3 g, 52.2 mmol, 96% yield). LCMS (LCMS Method A): Rt=1.38 min, [2M+H]⁺=700.5

188

Step 2: (E)-tert-Butyl (4-((2-amino-4-carbamoylphenyl)amino)but-2-en-1-yl)carbamate

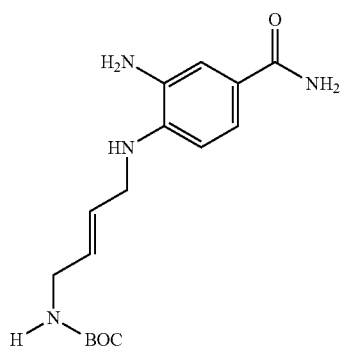 [SMILES: CC(C)(C)OC(=O)NC/C=C/CNc1ccc(C(N)=O)cc1[N+](=O)[O-]]

To (E)-tert-butyl (4-((4-carbamoyl-2-nitrophenyl)amino)but-2-en-1-yl)carbamate (18.3 g, 52.2 mmol) in DMF (300 mL) was added stannous chloride dihydrate (58.9 g, 261 mmol). After stirring at RT overnight, the reaction was added to sat aq $NaHCO_3$ (2000 mL), dropwise, and extracted with EtOAc (5×500 mL). The combined organic layers were washed with brine (200 mL), dried over $Na_2SO_4$, filtered and concentrated to yield the title compound (16.5 g, 51.5 mmol, 99% yield) as a yellow oil. LCMS (LCMS Method A): Rt=1.275 min, [M-BOC+H]⁺=221.1

Step 3: (E)-tert-Butyl (4-(2-amino-5-carbamoyl-1Hbenzo[d]imidazol-1-yl)but-2-en-1-yl)carbamate

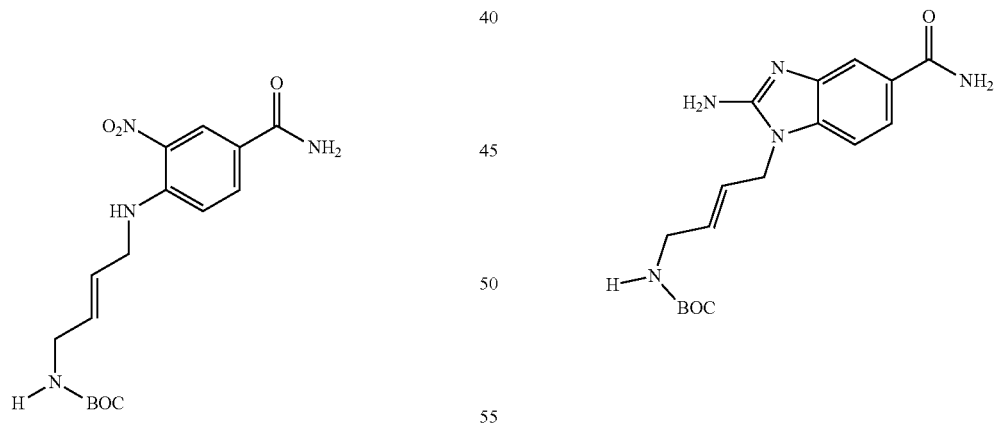

A mixture of (E)-tert-butyl (4-((2-amino-4-carbamoylphenyl)amino)but-2-en-1-yl)carbamate (16.5 g, 51.5 mmol) and cyanogen bromide (8.18 g, 77 mmol) in THF (200 mL) was heated to reflux overnight. The reaction was cooled to room temperature, diluted with sat aq $NaHCO_3$ (500 mL), and extracted with EtOAc (5×300 mL). The combined organic layers were washed with brine, dried over $Na_2SO_4$, filtered and concentrated. The residue was purified over silica gel, eluting with 50:1 to 20:1 DCM in MeOH (+3% $NH_4OH$) to yield the title compound (13.7 g, 39.7 mmol, 77% yield) as an off-white solid. LCMS (LCMS Method A): Rt=1.150 min, [M+H]⁺=346.1

Step 4: (E)-tert-Butyl (4-(5-carbamoyl-2-(1-ethyl-3-methyl-1H-pyrazole-5-carboxamido)-1H-benzo[d]imidazol-1-yl)but-2-en-1-yl)carbamate

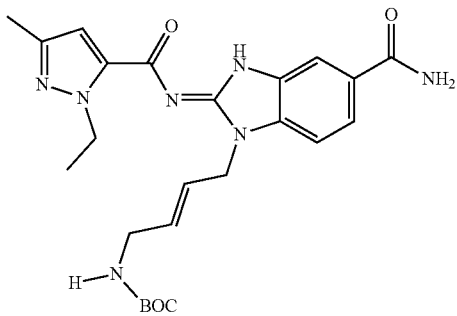 [SMILES: CCn1nc(C)cc1C(=O)/N=c1\[nH]c2cc(C(N)=O)ccc2n1C/C=C/CNC(=O)OC(C)(C)C]

To 1-ethyl-3-methyl-1H-pyrazole-5-carboxylic acid (9.17 g, 59.5 mmol) in DCM (500 mL) at 0° C. was added EDC (20.53 g, 107 mmol) and HOBT (18.22 g, 119 mmol). After 15 min, a mixture of (E)-tert-butyl (4-(2-amino-5-carbamoyl-1H-benzo[d]imidazol-1-yl)but-2-en-1-yl)carbamate (13.7 g, 39.7 mmol) in DMF (50 mL) was added, followed by TEA (27.6 mL, 198 mmol). The reaction was warmed to RT, stirred overnight and concentrated. The residue was diluted with water (500 mL) and extracted with ethyl acetate (3×300 mL), and the combined organic phases were washed with brine, dried over $Na_2SO_4$, filtered and concentrated. The residue was purified over silica gel, eluting with 50:1 to 20:1 DCM: MeOH to give the crude product, which was washed with DCM (300 mL) and collected by filtration to yield the title compound (14.0 g, 29.1 mmol, 73% yield) as an off-white solid. $^1$H NMR (400 MHz, DMSO-$d_6$) δ ppm 12.84 (s, 1H), 8.00-7.97 (m, 2H), 7.80-7.78 (m, 1H), 7.49 (d, J=8.4 Hz, 1H), 7.34 (s, 1H), 6.95 (t, J=5.5 Hz, 1H), 6.66 (s, 1H), 5.73-5.65 (m, 2H), 4.83 (d, J=4.3 Hz, 2H), 4.62 (q, J=7.0 Hz, 2H), 3.52 (s, 2H), 2.18 (s, 3H), 1.38-1.33 (m, 12H); LCMS (LCMS Method A): Rt=1.409 min, [M+H]$^+$=482.0

Step 5: (E)-1-(4-Aminobut-2-en-1-yl)-2-(1-ethyl-3-methyl-1H-pyrazole-5-carboxamido)-1H-benzo[d]imidazole-5-carboxamide Hydrochloride

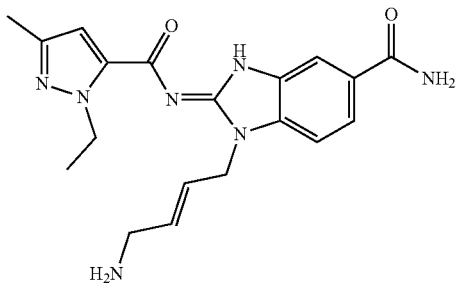 [SMILES: CCn1nc(C)cc1C(=O)/N=c1\[nH]c2cc(C(N)=O)ccc2n1C/C=C/CN]

To a suspension of (E)-tert-butyl (4-(5-carbamoyl-2-(1-ethyl-3-methyl-1H-pyrazole-5-carboxamido)-1H-benzo[d]imidazol-1-yl)but-2-en-1-yl)carbamate (3.00 g, 6.23 mmol) in dioxane (60 mL) was added 4N HCl in dioxane (15.6 mL, 62.3 mmol), followed by MeOH (15 mL) to dissolve some remaining solid. After 30 min at RT, the reaction mixture became cloudy and was allowed to stir for approximately 3 days. The resulting solid was collected by filtration and washed with DCM to yield the title compound (2.0 g, 4.8 mmol, 77% yield) as a white solid. $^1$H NMR (400 MHz, DMSO-$d_6$) δ ppm 7.97-8.09 (br. s., 1H), 7.82 (d, J=8.11 Hz, 1H), 7.50 (d, J=8.11 Hz, 1H), 7.38 (br. s., 1H), 6.70 (s, 1H), 5.97-6.08 (m, 1H), 5.68-5.80 (m, 1H), 4.91 (d, J=4.31 Hz, 2H), 4.60 (q, J=6.67 Hz, 2H), 3.42 (br. s., 2H), 2.18 (s, 3H), 1.36 (t, J=6.97 Hz, 3H); LCMS (LCMS Method D): Rt=0.53 min, [M+H]$^+$=382.2

Intermediate 7

1-(5-(5-(ethoxycarbonyl)-1-ethyl-3-methyl-1H-pyrazol-4-yl)pentyl)-3-methyl-1H-pyrazole-5-carboxylic Acid

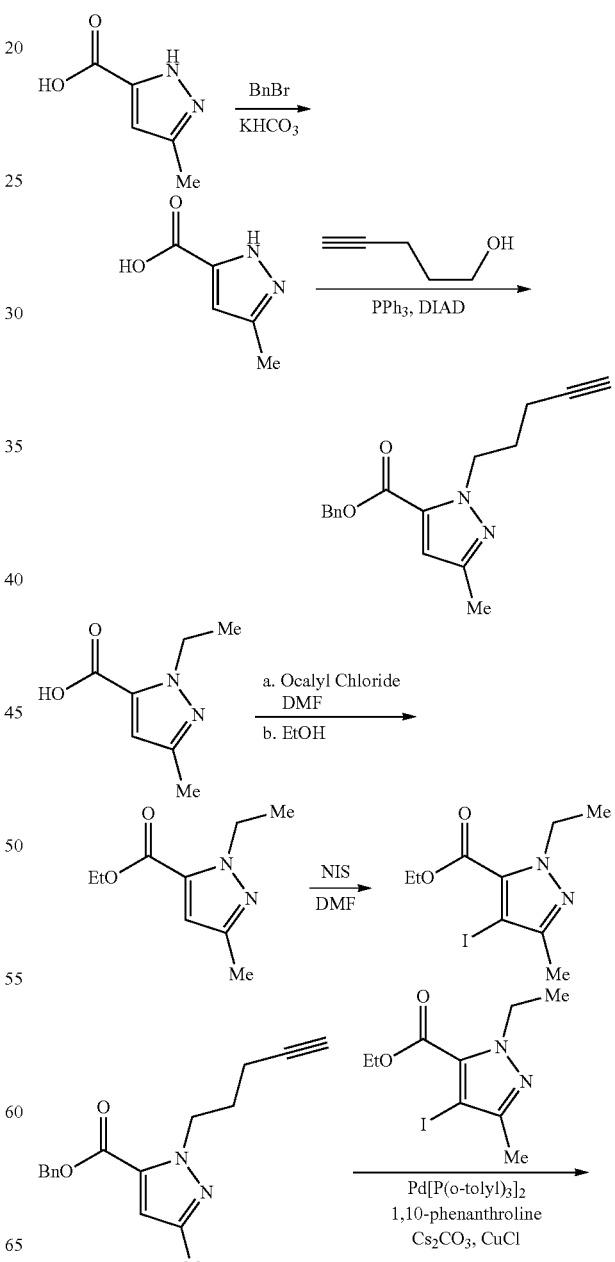

-continued

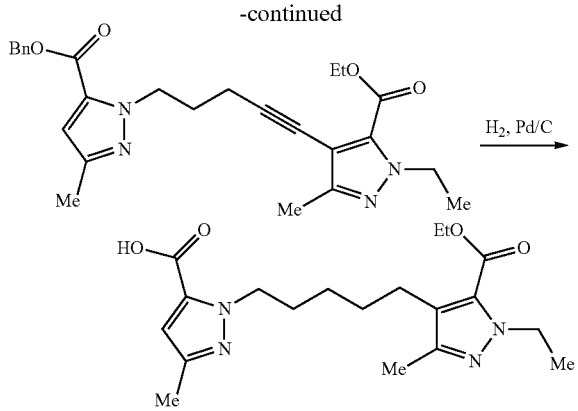

Step 1: benzyl 3-methyl-1H-pyrazole-5-carboxylate

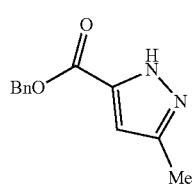 [SMILES: Cc1cc(C(=O)OCc2ccccc2)[nH]n1]

A mixture of 3-methyl-1H-pyrazole-5-carboxylic acid (50 mg, 0.396 mmol) and $KHCO_3$ (47.6 mg, 0.476 mmol) in DMSO (2 mL) was stirred for 30 min, and (bromomethyl)benzene (0.045 mL, 0.377 mmol) was added. The mixture was stirred for 4 h at RT, diluted with EtOAc (20 mL), washed with water and brine, and dried over $Na_2SO_4$. The mixture was filtered and concentrated, and the residue was purified by column chromatography (Combiflash, 0-50% EtOAc in hexane) to afford the title compound (66 mg, 0.305 mmol, 77% yield) as a white solid. $^1$H NMR (400 MHz, DMSO-$d_6$) δ ppm 13.19 (br. s., 1H) 7.34-7.48 (m, 5H) 6.52 (s, 1H) 5.29 (s, 2H) 2.27 (s, 3H). LCMS (LCMS Method D): Rt=0.86 min, [M+H]$^+$=216.9.

Step 2: benzyl 3-methyl-1-(pent-4-yn-1-yl)-1H-pyrazole-5-carboxylate

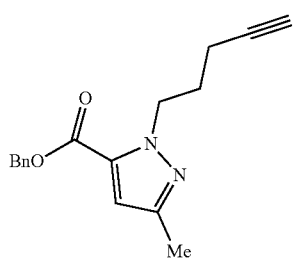 [SMILES: C#CCCCn1nc(C)cc1C(=O)OCc1ccccc1]

A mixture of DIAD (25.9 mL, 133 mmol) and triphenylphosphine (34.9 g, 133 mmol) in tetrahydrofuran (THF) (600 mL) was stirred for 30 min at 0° C., and pent-4-yn-1-ol (11.36 mL, 122 mmol) was then added. The mixture was stirred for 30 min, and benzyl 3-methyl-1H-pyrazole-5-carboxylate (24 g, 111 mmol) was added. It was allowed to warm to RT and stirred overnight. The reaction was diluted with EtOAc (1000 mL), washed with saturated $NaHCO_3$, and brine, dried over $Na_2SO_4$, filtered and concentrated. The oily residue was treated with 10% EtOAc in hexane (500 mL), and a white precipitate formed. The precipitate was filtered off and washed with 10% EtOAc in hexane. The combined filtrates were concentrated, and the residue was purified by column chromatography (Combiflash, 0-15% EtOAc in hexane) to afford the title compound (27.5 g, 97 mmol, 88% yield) as a white solid. $^1$H NMR (400 MHz, CHLOROFORM-o) δ ppm 7.34-7.47 (m, 5H) 6.68 (s, 1H) 5.33 (s, 2H) 4.63 (t, J=7.03 Hz, 2H) 2.30 (s, 3H) 2.19-2.26 (m, 2H) 2.09 (quin, J=7.09 Hz, 2H) 1.97 (br. s., 1H); LCMS (LCMS Method D): Rt=1.21 min, [M+H]$^+$=283.0.

Step 3: ethyl 1-ethyl-3-methyl-1H-pyrazole-5-carboxylate

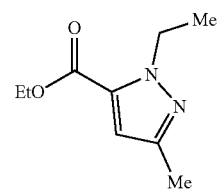 [SMILES: CCOC(=O)c1cc(C)nn1CC]

Oxalyl chloride (5.68 ml, 64.9 mmol) was added to a suspension of 1-ethyl-3-methyl-1H-pyrazole-5-carboxylic acid (5 g, 32.4 mmol) in DCM (40 mL) at RT under $N_2$ and two drops of DMF were added. The mixture was stirred for 2 hours at RT, concentrated and dried in vacuo. Ethanol (50 ml, 856 mmol) was added, and the mixture was stirred for 1 hour at RT. The reaction was concentrated and dried in vacuo to give a light-yellow oil which was taken into EtOAc (100 mL), washed with saturated $NaHCO_3$ and brine, dried over $Na_2SO_4$, filtered, concentrated and the resulting residue was dried in vacuo to give the title compound (5.5 g, 30.2 mmol, 93% yield) as a light-yellow oil. $^1$H NMR (400 MHz, CHLOROFORM-0) δ ppm 6.63 (s, 1H) 4.56 (q, J=7.11 Hz, 2H) 4.35 (q, J=7.11 Hz, 2H) 2.30 (s, 3H) 1.44 (t, J=7.28 Hz, 3H) 1.39 (t, J=7.28 Hz, 3H). LCMS (LCMS Method E): Rt=0.81 min, [M+H]$^+$=183.1.

Step 4: ethyl 1-ethyl-4-iodo-3-methyl-1H-pyrazole-5-carboxylate

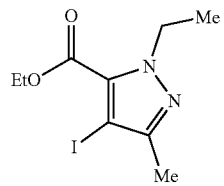 [SMILES: CCOC(=O)c1c(I)c(C)nn1CC]

A mixture of ethyl 1-ethyl-3-methyl-1H-pyrazole-5-carboxylate (5.5 g, 30.2 mmol) and NIS (8.15 g, 36.2 mmol) in DMF (100 mL) was heated to 90° C. and stirred for 3 days under $N_2$. The reaction was cooled to RT, diluted with EtOAc (200 mL), washed with saturated $Na_2S_2O_3$, 5% LiCl, and brine, dried over $Na_2SO_4$, filtered, concentrated, and the resulting residue was purified by column chromatography (Combiflash, 0-7% EtOAc in hexane) to afford the title compound (9.1 g, 29.5 mmol, 98% yield) as a colorless oil.

¹H NMR (400 MHz, CHLOROFORM-d) δ ppm 4.57 (q, J=7.03 Hz, 2H) 4.43 (q, J=7.03 Hz, 2H) 2.32 (s, 3H) 1.45-1.50 (m, 3H) 1.39-1.45 (m, 3H). LCMS (LCMS Method D): Rt=1.12 min, [M+H]⁺=308.9.

Step 5: 1 ethyl 4-(5-(5-((benzyloxy)carbonyl)-3-methyl-1H-pyrazol-1-yl)pent-1-yn-1-yl)-1-ethyl-3-methyl-H-pyrazole-5-carboxylate

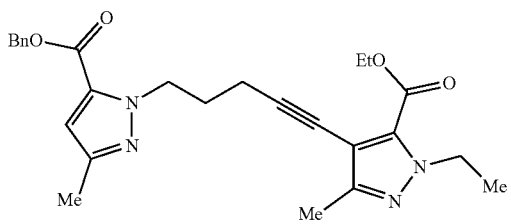 [SMILES: CCOC(=O)c1c(C#CCCCn2nc(C)cc2C(=O)OCc2ccccc2)c(C)nn1CC]

A flask which was previously purged with nitrogen was charged with Cs₂CO₃ (23.08 g, 70.8 mmol), 1,10-phenanthroline (1.915 g, 10.63 mmol), copper(I) chloride (0.175 g, 1.771 mmol), benzyl 3-methyl-1-(pent-4-yn-1-yl)-1H-pyrazole-5-carboxylate (10 g, 35.4 mmol), ethyl 1-ethyl-4-iodo-3-methyl-1H-pyrazole-5-carboxylate (13.10 g, 42.5 mmol), Pd[P(o-tollyl)₃]₂ (0.760 g, 1.063 mmol), and degassed Toluene (100 mL). The mixture was degassed for 15 min, heated to 100° C. and stirred overnight (18 hr) under N₂. The reaction was cooled to RT and diluted with EtOAc. The inorganic solids were filtered off and washed with EtOAc. The combined organics were concentrated and the residue was purified via silica gel chromatography (EtOAc/Hexanes 0-25%) to afford the title compound (11.38 g, 24.60 mmol, 69.5% yield) as a colorless oil. ¹H NMR (400 MHz, CHLOROFORM-d) δ ppm 7.34-7.47 (m, 5H) 6.68 (s, 1H) 5.31 (s, 2H) 4.67 (t, J=7.03 Hz, 2H) 4.51 (q, J=7.19 Hz, 2H) 4.39 (q, J=7.03 Hz, 2H) 2.51 (t, J=7.28 Hz, 2H) 2.31 (s, 3H) 2.29 (s, 3H) 2.17 (t, J=7.15 Hz, 2H) 1.40 (t, J=7.03 Hz, 6H). LCMS (LCMS Method D): Rt=1.43 min, [M+H]⁺=463.3.

Step 6: 1-(5-(5-(ethoxycarbonyl)-1-ethyl-3-methyl-1H-pyrazol-4-yl)pentyl)-3-methyl-1H-pyrazole-5-carboxylic Acid

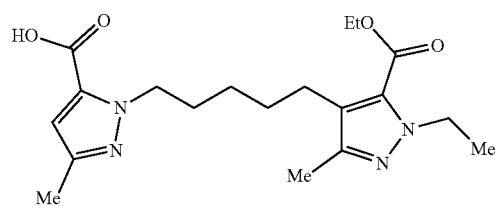 [SMILES: CCOC(=O)c1c(CCCCCn2nc(C)cc2C(=O)O)c(C)nn1CC]

To a flask charged with ethyl 4-(5-(5-((benzyloxy)carbonyl)-3-methyl-1H-pyrazol-1-yl)pent-1-yn-1-yl)-1-ethyl-3-methyl-1H-pyrazole-5-carboxylate (11.3 g, 24.43 mmol) and Pd/C (2.60 g, 2.443 mmol) was added ethanol (200 mL). The flask was purged with N₂, then hydrogen (via balloon) and the mixture was stirred under a H2 atmosphere overnight (18 hr). The catalyst was filtered off and the filtrate was concentrated in vacuo to afford the title compound (8.89 g, 23.62 mmol, 97% yield) as a white solid. ¹H NMR (400 MHz, DMSO-d₆) δ ppm 13.14 (br. s., 1H) 6.57 (s, 1H) 4.33-4.43 (m, 4H) 4.28 (m, J=7.09 Hz, 2H) 2.51-2.56 (m, 2H) 2.16 (s, 3H) 2.10 (s, 3H) 1.72 (m, J=7.34 Hz, 2H) 1.41 (m, J=7.58 Hz, 2H) 1.25-1.31 (m, 6H) 1.16-1.24 (m, 2H). LCMS (LCMS Method D): Rt=1.07 min, [M+H]⁺=377.2.

Example 1

1,1'-((2R,3R)-2,3-dihydroxybutane-1,4-diyl)bis(2-(1-ethyl-3-methyl-1H-pyrazole-5-carboxamido)-1H-benzo[d]imidazole-5-carboxamide), 2 Trifluoroacetic Acid Salt

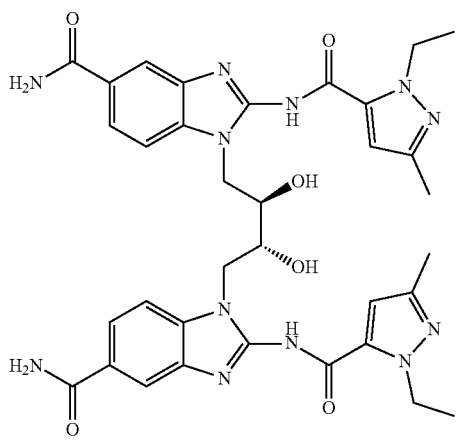 [SMILES: CCn1nc(C)cc1C(=O)Nc1nc2cc(C(N)=O)ccc2n1C[C@@H](O)[C@H](O)Cn1c(NC(=O)c2cc(C)nn2CC)nc2cc(C(N)=O)ccc21]

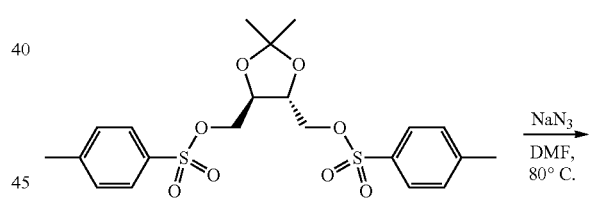

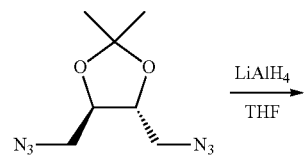

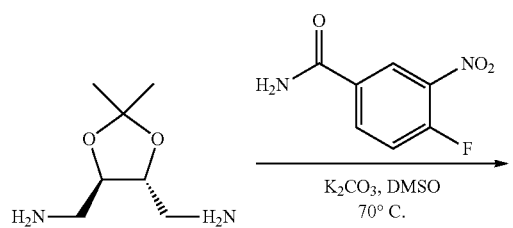

195
-continued

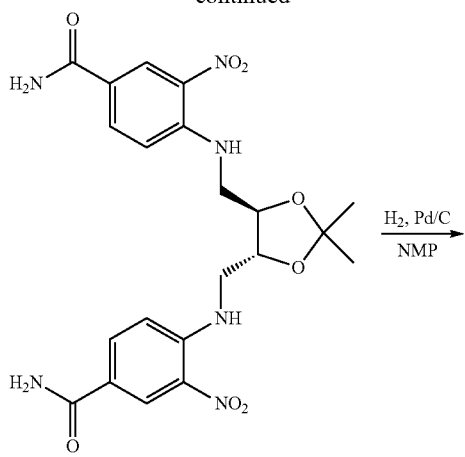

196
-continued

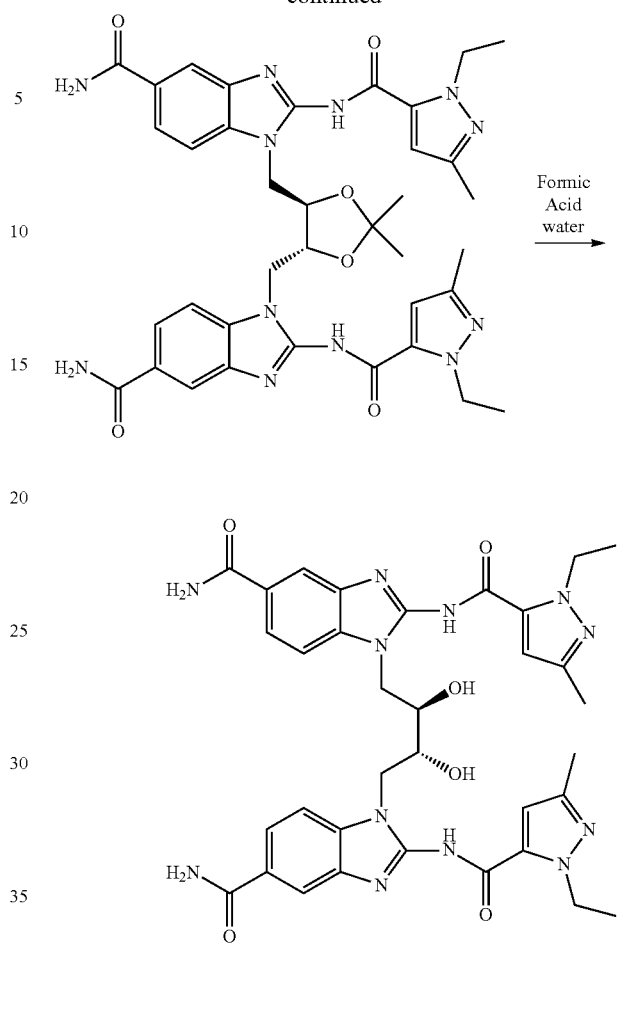

Step 1: (4R,5R)-4,5-bis(azidomethyl)-2,2-dimethyl-1,3-dioxolane

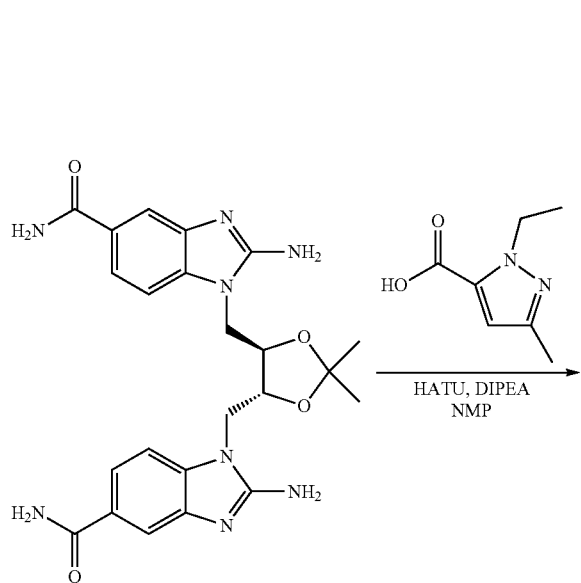

A mixture of ((4R,5R)-2,2-dimethyl-1,3-dioxolane-4,5-diyl)bis(methylene) bis(4-methylbenzenesulfonate) (3.874 g, 8.23 mmol) and sodium azide (1.338 g, 20.58 mmol) in DMF (20 mL) was heated at 80° C. for 15 h. The reaction was concentrated in vacuo to remove DMF and the residue was dissolved in DCM/water. The biphasic solution was transferred to a separatory funnel and the layers were separated. The DCM layer was washed twice with water and once with brine, dried over $Na_2SO_4$, filtered, and concentrated in vacuo to give the title compound a pale yellow liquid (1.564 g; 7.37 mmol, 90% yield). $^1$H NMR (400 MHz, CHLOROFORM-o) δ ppm 4.10 (dd, J=2.78, 1.26 Hz, 2H) 3.55-3.66 (m, 2H) 3.32-3.44 (m, 2H) 1.51 (s, 6H). LCMS (LCMS Method C): Rt.=0.89 min, [M+H]$^+$=214.0

Step 2: ((4R,5R)-2,2-dimethyl-1,3-dioxolane-4,5-diyl)dimethanamine

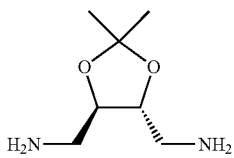

To a solution of (4R,5R)-4,5-bis(azidomethyl)-2,2-dimethyl-1,3-dioxolane (1.561 g, 7.36 mmol) in dry THF (30 mL) at rt in an open 250 mL RB flask was added 2M LAlH$_4$ in THF (3.68 mL, 7.36 mmol) dropwise over 10 min. The reaction was then diluted with THF (30 mL) and the mixture was stirred for 30 min. The reaction was quenched by added 1.24 mL of a saturated aqueous Na$_2$SO$_4$ solution dropwise to the reaction. The quenched yellow reaction was stirred for 10 min and then allowed to settle. The resulting solid was removed by filtration and the filtrate was dried over Na$_2$SO$_4$, filtered, and concentrated to give the title compound as a pale yellow oil (977 mg, 6.1 mmol, 83% yield). $^1$H NMR (400 MHz, CHLOROFORM-d) δ ppm 3.72-3.91 (m, 2H) 2.71-3.11 (m, 4H) 1.18-1.65 (m, 6H). LCMS (LCMS Method C): Rt.=0.11 min, [M+H]$^+$=161.0

Step 3: 4,4'-((((4R,5R)-2,2-dimethyl-1,3-dioxolane-4,5-diyl)bis(methylene))bis(azanediyl))bis(3-nitrobenzamide)

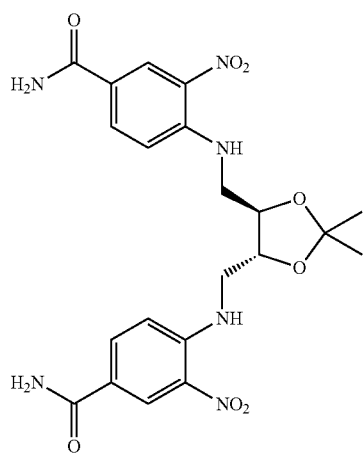

A mixture of 4-fluoro-3-nitrobenzamide (2.233 g, 12.13 mmol), ((4R,5R)-2,2-dimethyl-1,3-dioxolane-4,5-diyl)dimethanamine (0.9713 g, 6.06 mmol), and K$_2$CO$_3$ (1.843 g, 13.34 mmol) in DMSO (20 mL) was stirred at 70° C. for 90 min. The reaction was cooled slightly and diluted with 200 mL of water. The resulting orange suspension was stirred vigorously for 60 min, isolated by filtration, the filtered solid was dried in the Buchner funnel for 20 min. The slightly wet solid was transferred to a beaker containing Et$_2$O and the solid was further crushed with a spatula in order to remove excess water from the solid. The resulting solid was isolated by filtration, transferred to a 250 mL RB flask, and dried for 3 days at 56° C. in a vacuum oven to give the title product (2.31 g, 4.73 mmol, 78% yield) as a yellow powder. $^1$H NMR (400 MHz, DMSO-d$_6$) δ ppm 8.66 (d, J=2.27 Hz, 2H) 8.50 (t, J=5.56 Hz, 2H) 7.98-8.10 (m, 4H) 7.34 (br. s., 2H) 7.19 (d, J=9.09 Hz, 2H) 4.22 (br. s., 2H) 3.64-3.86 (m, 4H) 1.38 (s, 6H). LCMS (LCMS Method C): Rt=0.78 min, [M+H]$^+$=489.2

Step 4: 4,4'-((((4R,5R)-2,2-dimethyl-1,3-dioxolane-4,5-diyl)bis(methylene))bis(azanediyl))bis(3-aminobenzamide)

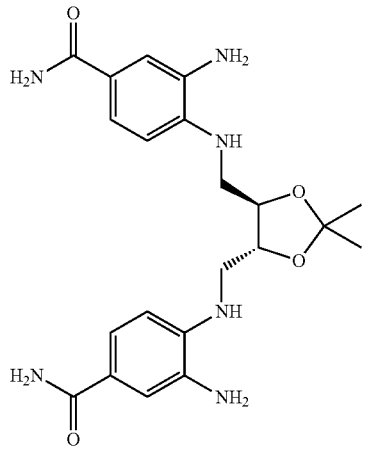 [SMILES: CC1(C)O[C@H](CNc2ccc(C(N)=O)cc2[N+](=O)[O-])[C@@H](CNc2ccc(C(N)=O)cc2[N+](=O)[O-])O1]

A mixture of 4,4'-((((4R,5R)-2,2-dimethyl-1,3-dioxolane-4,5-diyl)bis(methylene)) bis(azanediyl))bis(3-nitrobenzamide) (2.293 g, 4.69 mmol) and 10% wet Pd/C (230 mg) in NMP (25 mL) in a 250 mL RB flask was evacuated and placed under a balloon of hydrogen for 18 h at rt followed by heating at 80° C. for 20 h. The reaction was then cooled and filtered through Celite® while washing with 4 mL of NMP. The filtrate containing the product was used directly in the next reaction as a solution in NMP. LCMS (LCMS Method C): Rt.=0.50 min, [M+H]$^+$=429.2

Step 5: 1,1'-(((4R,5R)-2,2-dimethyl-1,3-dioxolane-4,5-diyl)bis(methylene))bis(2-amino-1H-benzo[d]imidazole-5-carboxamide), 2Hydrobromide

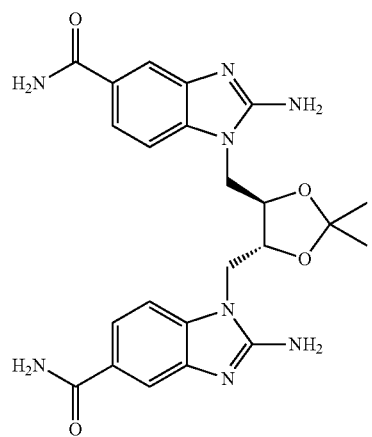 [SMILES: CC1(C)O[C@H](Cn2c(N)nc3cc(C(N)=O)ccc32)[C@@H](Cn2c(N)nc3cc(C(N)=O)ccc32)O1]

A solution of 4,4'-((((4R,5R)-2,2-dimethyl-1,3-dioxolane-4,5-diyl)bis(methylene))-bis(azanediyl))bis(3-aminobenzamide) (1.0 g, 2.334 mmol) in NMP (16 mL) was treated with cyanogen bromide (0.618 g, 5.83 mmol) and the homogeneous reaction was stirred at rt for 3 hrs. Additional cyanogen bromide (0.618 g) was added and the reaction was stirred for 18 hrs at rt. Additional cyanogen bromide (1.236 gm, 5.0 eq.) was then added and the reaction was stirred at rt. After 5.5 hrs, the reaction was heated at 72° C. for 55 min, cooled, and diluted with 160 mL EtOAc. The resulting suspension was stirred for 20 min and the solid was isolated by filtration washing with EtOAc. The resulting dark green, hygroscopic solid was transferred to a vial and dried in a vacuum oven at 40° C. for 3 days to afford the title product (1.35 g, 2.11 mmol, 90% yield) as a dark brown solid. $^1$H NMR (400 MHz, DMSO-$d_6$) δ ppm 12.99 (br. s., 1H) 8.87 (br. s., 3H) 8.10 (br. s., 2H) 7.85-7.91 (m, 4H) 7.68 (d, J=9.09 Hz, 2H) 7.49 (br. s., 2H) 4.69-4.76 (m, 2H) 4.55-4.63 (m, 2H) 4.36 (br. s., 2H) 1.25 (s, 6H). LCMS (LCMS Method C): Rt.=0.40 min, [M+H]$^+$=479.2

Step 6: 1,1'-(((4R,5R)-2,2-dimethyl-1,3-dioxolane-4,5-diyl)bis(methylene))bis(2-(1-ethyl-3-methyl-1H-pyrazole-5-carboxamido)-1H-benzo[d]imidazole-5-carboxamide), 2 trifluoroacetic acid salt

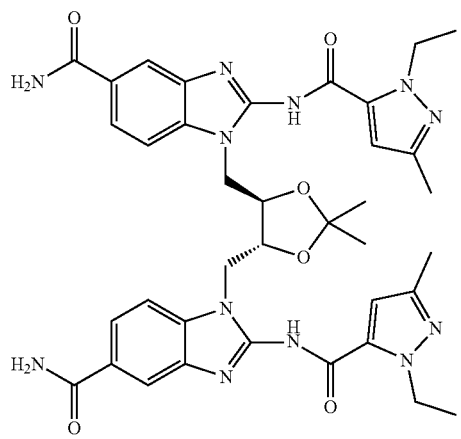 [SMILES: CCn1nc(C)cc1C(=O)Nc1nc2cc(C(N)=O)ccc2n1C[C@H]1OC(C)(C)O[C@@H]1Cn1c(NC(=O)c2cc(C)nn2CC)nc2cc(C(N)=O)ccc21]

A mixture of 1,1'-(((4R,5R)-2,2-dimethyl-1,3-dioxolane-4,5-diyl)bis(methylene))bis(2-amino-1H-benzo[d]imidazole-5-carboxamide), 2 hydrobromide (0.6647 g, 1.038 mmol), 1-ethyl-3-methyl-1H-pyrazole-5-carboxylic acid (0.32 g, 2.076 mmol), HATU (0.868 g, 2.284 mmol), and DIPEA (1.088 mL, 6.23 mmol) in NMP (4 mL) was heated at 140° C. for 30 min in a microwave reactor. The reaction was purified directly via reverse phase HPLC (Gilson®, 13-43% MeCN/0.1% TFA water, 15 min gradient, Luna column). The desired fractions were combined, concentrated in vacuo, and placed under high vacuum for 15 h to afford the title product (140.0 mg, 0.143 mmol, 13.7% yield) as a dark green solid. $^1$H NMR (400 MHz, DMSO-$d_6$) δ ppm 12.94 (br. s., 2H) 7.98 (s, 4H) 7.66-7.76 (m, 2H) 7.47 (d, J=8.59 Hz, 2H) 7.38 (br. s., 2H) 6.86 (s, 2H) 4.75 (d, J=10.11 Hz, 2H) 4.55-4.69 (m, 6H) 4.40 (br. s., 2H) 2.05 (s, 6H) 1.37 (t, J=7.20 Hz, 6H) 1.14 (s, 6H). LCMS (LCMS Method C): Rt.=0.84 min, [M+H]$^+$=751.6

Step 7: 1,1'-((2R,3R)-2,3-dihydroxybutane-1,4-diyl)bis(2-(1-ethyl-3-methyl-H-pyrazole-5-carboxamido)-1H-benzo[d]imidazole-5-carboxamide), 2 Trifluoroacetic Acid Salt

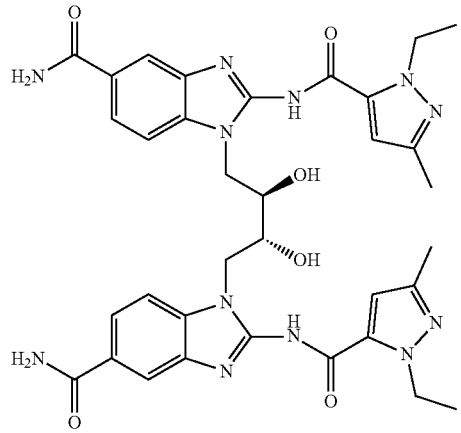 [SMILES: CCn1nc(C)cc1C(=O)Nc1nc2cc(C(N)=O)ccc2n1C[C@@H](O)[C@H](O)Cn1c(NC(=O)c2cc(C)nn2CC)nc2cc(C(N)=O)ccc21]

1,1'-(((4R,5R)-2,2-dimethyl-1,3-dioxolane-4,5-diyl)bis(methylene))bis(2-(1-ethyl-3-methyl-1H-pyrazole-5-carboxamido)-1H-benzo[d]imidazole-5-carboxamide), 2trifluoroacetic acid salt (113.8 mg, 0.116 mmol) was dissolved in formic acid (3.0 mL) and water (0.3 mL) and stirred at rt for 4 days. The reaction was concentrated in vacuo at rt to give a green solid. The crude solid was diluted with 1.4 mL of DMSO and purified by HPLC (Gilson® Autoprep, acidic Luna column, 5-35% MeCN: 0.1% TFA water, 7 min gradient). The desired fractions were concentrated in vacuo and placed under high vacuum for 3 days to yield 1,1'-((2R,3R)-2,3-dihydroxybutane-1,4-diyl)bis(2-(1-ethyl-3-methyl-1H-pyrazole-5-carboxamido)-1H-benzo[d]imidazole-5-carboxamide), 2 trifluoroacetic acid salt (27 mg, 0.029 mmol, 24.7% yield) as an off white solid. $^1$H NMR (400 MHz, DMSO-$d_6$) δ ppm 12.89 (br. s., 2H) 8.00 (s, 4H) 7.79 (d, J=8.34 Hz, 2H) 7.55 (d, J=8.34 Hz, 2H) 7.35 (br. s., 2H) 6.59 (s, 2H) 5.50 (br. s, 2H), 4.51-4.67 (m, 4H) 4.27-4.47 (m, 4H) 4.09 (br. s., 2H) 2.09 (s, 6H) 1.32 (t, J=7.07 Hz, 6H). LCMS (LCMS Method C): rt=0.67 min, [M+H]$^+$=711.6.

Example 2

(E)-1,1'-(but-2-ene-1,4-diyl)bis(2-(1-ethyl-3-methyl-1H-pyrazole-5-carboxamido)-1H-benzo[d]imidazole-5-carboxamide)

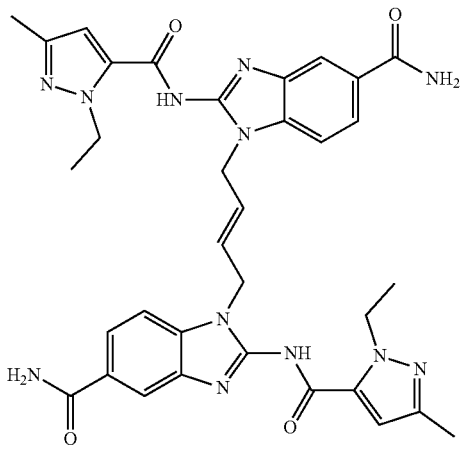

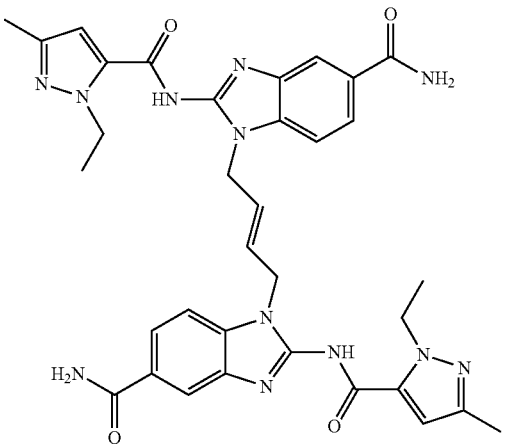

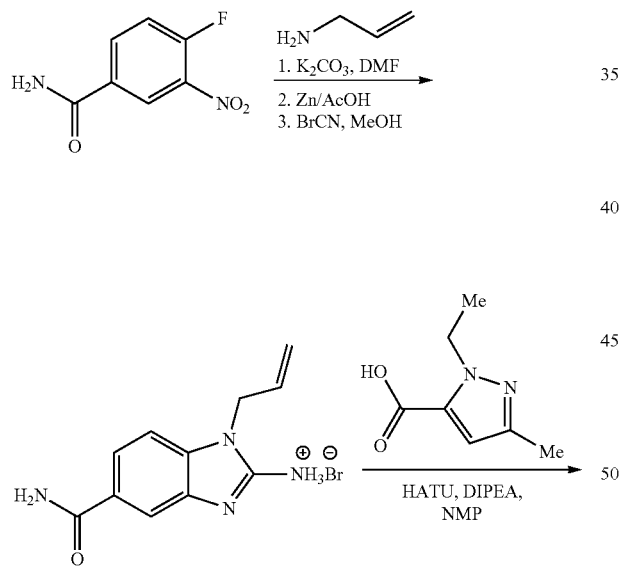

Step 1: 1-allyl-2-amino-1H-benzo[d]imidazole-5-carboxamide, Hydrobromide

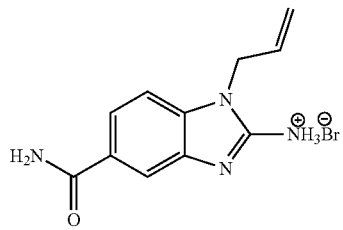

To a solution of 4-fluoro-3-nitrobenzamide (10.0 g, 54.3 mmol) in DMF (60 mL) was added allylamine (36.6 mL, 489 mmol) dropwise at rt and the mixture was stirred for 5 min. After this period, $K_2CO_3$ (15.01 g, 109 mmol) was added in one portion and the mixture was stirred at rt for 30 min. DMF was then removed in vacuo, the residue was suspended in 500 mL of water, the resulting orange precipitate was filtered off, washed with water, and dried in vacuo.

The above precipitate was dissolved in AcOH (600.0 mL), the flask was placed into a 20° C. water bath, and zinc (10.65 g, 163 mmol) was added carefully in small portions. The reaction was monitored by LCMS and additional zinc (ap

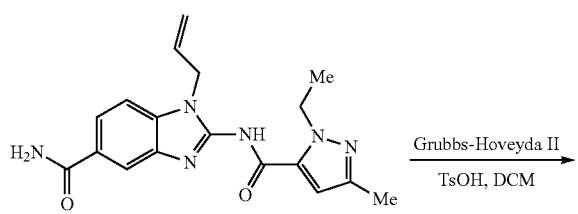

proximately 3 eq) was added in small portions as needed until the reduction was complete. Upon reaction completion by LCMS, the solids were filtered off and the filtrate concentrated in vacuo. The evaporation residue was taken up in DCM (500 mL) and EtOH (150 mL) and washed with 15% aq. $K_2CO_3$ (100 mL). The organic layer was separated, dried over $Na_2SO_4$, filtered, and concentrated in vacuo.

The above evaporation residue was dissolved in MeOH (200.0 mL), 5.0 M cyanogen bromide in $CH_3CN$ (11.95 mL, 59.7 mmol) was added rapidly in one portion, and the mixture was stirred at rt for 18 hr. After this period, the reaction mixture was concentrated in vacuo, then dissolved again in MeOH (200.0 mL). A mixture of toluene (100 mL) and $CH_3CN$ (100 mL) was added and the resulting mixture was concentrated to dryness at 40° C. (0-1 mbar) and dried in vacuo for 16 hr. to afford 1-allyl-2-amino-1H-benzo[d]imidazole-5-carboxamide, hydrobromide (11.3 g, 38.0 mmol, 70.0% yield) as a dark purple powder. $^1$H NMR (400 MHz, DMSO-$d_6$) δ ppm 8.83 (s, 2H), 8.07 (br. s., 1H), 7.88 (d, J=1.00 Hz, 1H), 7.82 (dd, J=8.41, 1.38 Hz, 1H), 7.52 (d, J=8.53 Hz, 1H), 7.43 (br. s., 1H), 5.87-6.02 (m, 1H), 5.25 (dd, J=10.42, 0.88 Hz, 1H), 5.17 (dd, J=17.32, 1.00 Hz, 1H), 4.84 (d, J=5.02 Hz, 2H); LCMS (LCMS Method C): Rt=0.38 min, [M+H]$^+$=216.9.

Step 2: 1-allyl-2-(1-ethyl-3-methyl-1H-pyrazole-5-carboxamido)-1H-benzo[d]imidazole-5-carboxamide was then poured into 500 mL of ice-cold water and stirred vigorously for 1 h. The dark purple solid was filtered off, brine (100 mL) was added, and the next crop of somewhat lighter precipitate was filtered off. The resulting clear pink filtrate was allowed to stand at rt for 4 day whereupon the lightest pink precipitate crashed out of the solution. This final precipitate was filtered off, washed with water, and air-dried to afford 1-allyl-2-(1-ethyl-3-methyl-1H-pyrazole-5-carboxamido)-1H-benzo[d]imidazole-5-carboxamide (1.88 g, 5.33 mmol, 63.4% yield) as a pale pink powder. $^1$H NMR (400 MHz, DMSO-$d_6$) δ ppm 12.84 (br. s., 1H), 8.01 (s, 1H), 7.96 (br. s., 1H), 7.78 (dd, J=8.44, 1.59 Hz, 1H), 7.46 (d, J=8.31 Hz, 1H), 7.32 (br. s., 1H), 6.66 (s, 1H), 5.94-6.05 (m, 1H), 5.21 (dd, J=10.27, 1.22 Hz, 1H), 5.15 (dd, J=17.12, 1.22 Hz, 1H), 4.86 (d, J=5.14 Hz, 2H), 4.61 (q, J=6.93 Hz, 2H), 2.17 (s, 3H), 1.35 (t, J=7.09 Hz, 3H) LCMS (LCMS Method E): Rt=0.75 min, [M+H]$^+$=353.2.

Step 3: (E)-1,1'-(but-2-ene-1,4-diyl)bis(2-(1-ethyl-3-methyl-1H-pyrazole-5-carboxamido)-1H-benzo[d]imidazole-5-carboxamide)

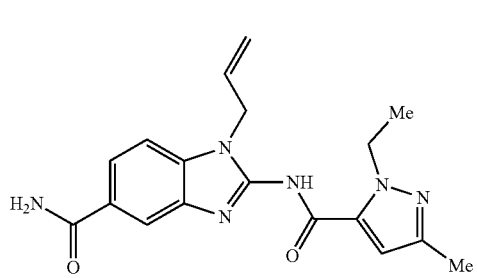 [SMILES: C=CCn1c(NC(=O)c2cc(C)nn2CC)nc2cc(C(N)=O)ccc21]

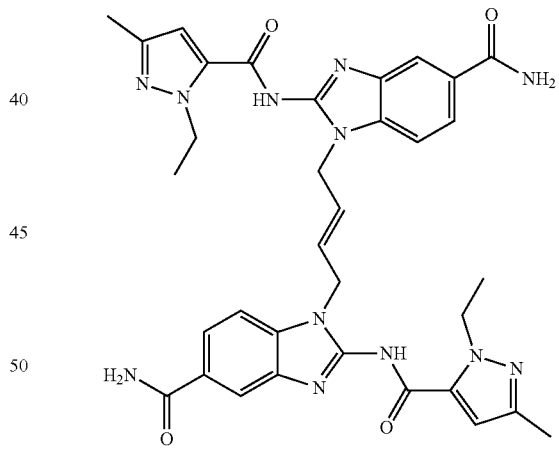

A 100 mL RB flask was charged with 1-allyl-2-amino-1H-benzo[d]imidazole-5-carboxamide, hydrobromide (2.5 g, 8.41 mmol), HATU (3.52 g, 9.25 mmol), 1-ethyl-3-methyl-1H-pyrazole-5-carboxylic acid (1.427 g, 9.25 mmol), and NMP (25 mL). After 1 minute of stirring at rt, DIPEA (7.33 mL, 42.1 mmol) was added and the mixture was stirred at rt for 40 hr. After this period, 2.0 mL of water were added and the mixture was stirred for 30 min at rt. It To a solution of 1-allyl-2-(1-ethyl-3-methyl-1H-pyrazole-5-carboxamido)-1H-benzo[d]imidazole-5-carboxamide (70 mg, 0.199 mmol) in DCM (1.0 mL) and MeOH (1.0 mL)

was added dropwise a solution of p-toluenesulfonic acid monohydrate (37.8 mg, 0.199 mmol) in MeOH (1.0 mL) and the resulting clear solution was concentrated in vacuo. The glassy evaporation residue was stirred with DCM (4.0 mL) until a milky suspension was obtained. Hoveyda-Grubbs 2nd gen. catalyst (18.67 mg, 0.030 mmol) was added into a 5 mL Biotage® sealed tube under $N_2$ atm. The above milky suspension was then added and the mixture was heated to 80° C. for 4 h in a microwave reactor. After this period, 5.0 mL of MeOH was added, followed by a solution of 1.0 M KHMDS in THF (0.25 mL) in MeOH (1.0 mL). The mixture was stirred for 5 min at rt, concentrated in vacuo, and subjected to normal phase silica gel chromatography (Biotage® Ultra SNAP 25 g silica gel cartridge; 0-40% gradient MeOH/DCM) to afford a greenish-white solid. The solid was then washed with 0.2 mL of MeOH to remove the dark green ruthenium residue to afford (E)-1,1'-(but-2-ene-1,4-diyl)bis(2-(1-ethyl-3-methyl-1H-pyrazole-5-carboxamido)-1H-benzo[d]imidazole-5-carboxamide) (14 mg, 0.02 mmol, 19.8% yield). $^1$H NMR (400 MHz, DMSO-$d_6$) δ ppm 12.82 (br. s., 2H), 7.97 (s, 2H), 7.94 (br. s, 2H), 7.71 (dd, J=8.34, 1.26 Hz, 2H), 7.44 (d, J=8.34 Hz, 2H), 7.34 (br. s., 2H), 6.55 (s, 2H), 5.93 (br. s., 2H), 4.83 (br. s., 4H), 4.53 (q, J=6.82 Hz, 4H), 2.12 (s, 6H), 1.27 (t, J=7.07 Hz, 6H); LCMS (LCMS Method C): Rt=0.79 min, [M+H]$^+$=677.5.

The compound prepared by the above process may exist in a tautomeric or an isomeric form, e.g., as (2E,2'E)-1,1'-((E)-but-2-ene-1,4-diyl)bis(2-((1-ethyl-3-methyl-1H-pyrazole-5-carbonyl)imino)-2,3-dihydro-1H-benzo[d]imidazole-5-carboxamide)

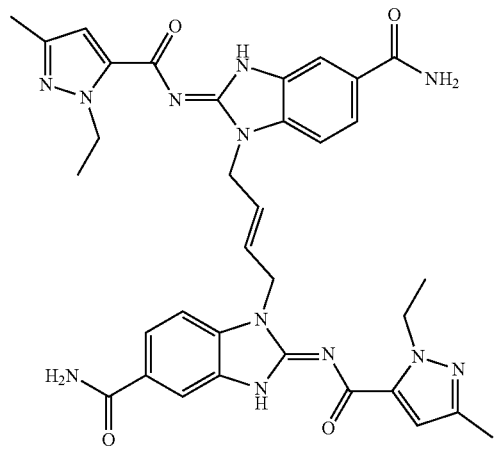

Example 3

1,1'-((Methylazanediyl)bis(ethane-2,1-diyl))bis(2-(1-ethyl-3-methyl-1H-pyrazole-5-carboxamido)-1H-benzo[d]imidazole-5-carboxamide), Trifluoroacetic Acid Salt

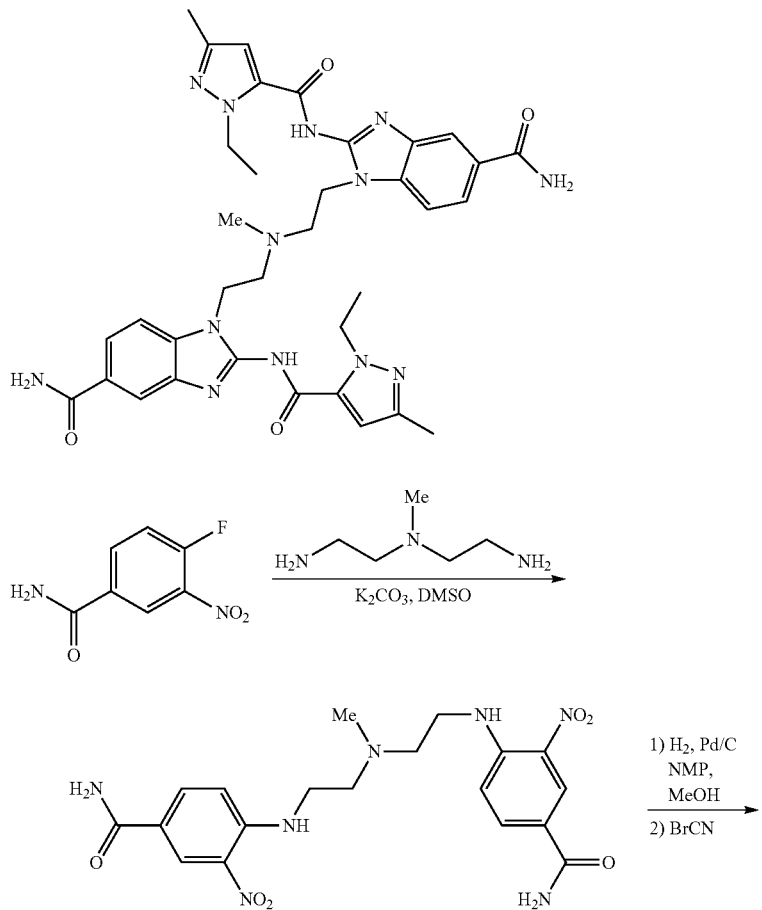

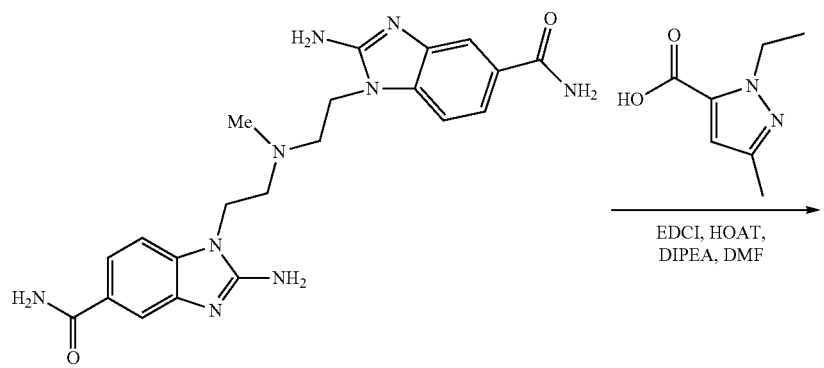

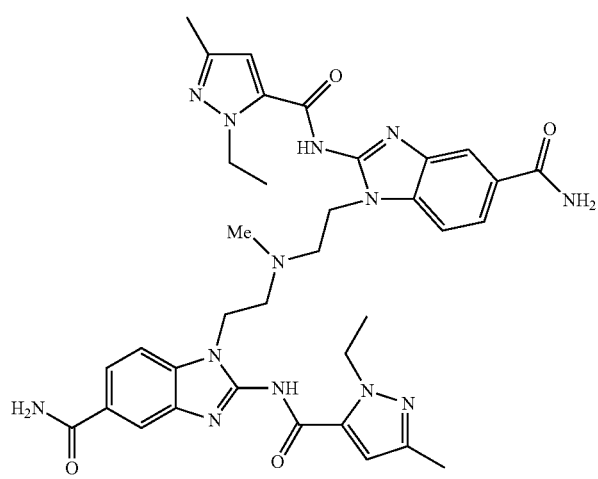

Step 1: 4,4'-(((Methylazanediyl)bis(ethane-2,1-diyl))bis(azanediyl))bis(3-nitrobenzamide)

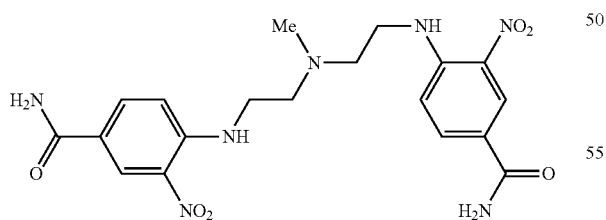

A mixture of N'-(2-aminoethyl)-M-methylethane-1,2-diamine (0.318 g, 2.72 mmol), K$_2$CO$_3$ (1.501 g, 10.86 mmol) and 4-fluoro-3-nitrobenzamide (1 g, 5.43 mmol) in DMSO (20 mL) was stirred at rt overnight. Water was added and the resulting precipitate was collected by filtration and was dried under reduced pressure to afford 4,4'-(((methylazanediyl)bis(ethane-2,1-diyl))bis(azanediyl))bis(3-nitrobenzamide) (800 mg, 1.62 mmol, 59.6% yield) as a yellow solid. LCMS (LCMS Method A): Rt=1.01 min, [M+H]$^+$=446.

Step 2: 1,1'-((Methylazanediyl)bis(ethane-2,1-diyl))bis(2-amino-1H-benzo[d]imidazole-5-carboxamide)

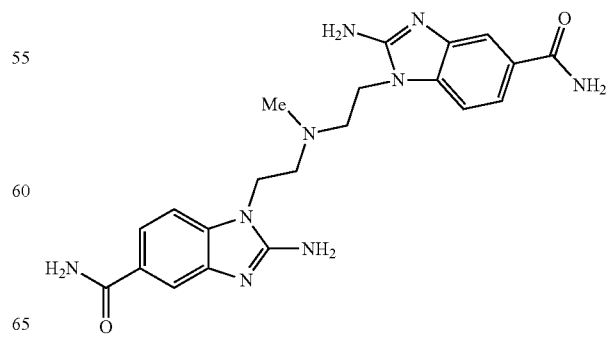

4,4'-(((Methylazanediyl)bis(ethane-2,1-diyl))bis(azanediyl))bis(3-nitrobenzamide) (700 mg, 1.572 mmol) and 10% Pd/C (84 mg, 0.079 mmol) in NMP (20 mL) and MeOH (30 mL) was stirred under a hydrogen gas atmosphere at rt overnight. The catalyst was removed by filtration and the MeOH was removed under reduced pressure. Cyanogen bromide (416 mg, 3.93 mmol) was then added and the reaction mixture was stirred at 60° C. for 4 hr. Et$_2$O was added and the resulting precipitate was collected by filtration and dried under reduced pressure to afford 1,1'-((methylazanediyl)bis(ethane-2,1-diyl))bis(2-amino-benzo-1H-[d]imidazole-5-carboxamide) (500 mg, 1.03 mmol, 65.8% yield) as a red solid. LCMS (LCMS Method A): Rt=0.94 min, [M+H]$^+$=435.8.

Step 3: 1,1'-((Methylazanediyl)bis(ethane-2,1-diyl))bis(2-(1-ethyl-3-methyl-1H-pyrazole-5-carboxamido)-1H-benzo[d]imidazole-5-carboxamide) Trifluoroacetic Acid Salt

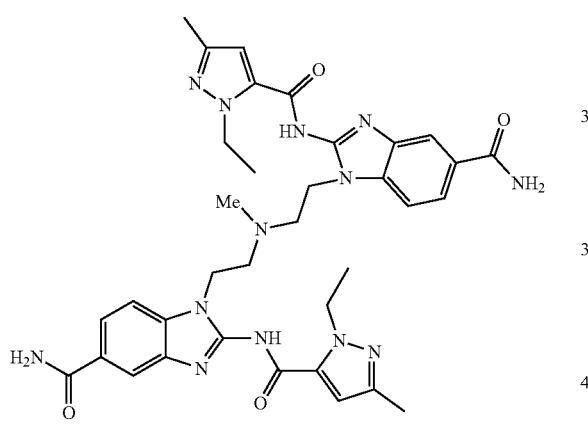

To a mixture of 1,1'-((methylazanediyl)bis(ethane-2,1-diyl))bis(2-amino-1H benzo[d]imidazole-5-carboxamide) (300 mg, 0.689 mmol), 1-ethyl-3-methyl-1H-pyrazole-5-carboxylic acid (212 mg, 1.378 mmol), HOAt (281 mg, 2.067 mmol) and EDC hydrochloride (396 mg, 2.067 mmol) in DMF (25 mL) was added DIPEA (267 mg, 2.067 mmol). The reaction mixture was stirred at rt overnight. The reaction was quenched with water (30 mL) and extracted with DCM (3×50 mL). The organic layer was dried over anhydrous Na$_2$SO$_4$, filtered and concentrated under reduced pressure. The residue was purified by prep-HPLC (Gilson®, Gemini® C18 column, gradient 35-95% MeCN:H$_2$O 0.1% TFA) to afford 1,1'-((methylazanediyl)bis(ethane-2,1-diyl))bis(2-(1-ethyl-3-methyl-1H-pyrazole-5-carboxamido)-1H-benzo[d]imidazole-5-carboxamide) trifluoroacetic acid salt (130 mg, 0.18 mmol, 26% yield) as a gray solid. $^1$H NMR (400 MHz, DMSO-d$_6$) δ ppm 12.82 (s, 1H), 7.98 (s, 4H), 7.74 (d, J=8.0 Hz, 2H), 7.47 (s, 2H), 7.37 (s, 2H), 6.59 (s, 2H), 4.56 (d, J=6.7 Hz, 4H), 4.18 (s, 4H), 3.35 (s, 8H), 2.09 (s, 6H), 1.32-1.25 (m, 6H). LCMS (LCMS Method A): Rt=1.14 min, [M+H]$^+$=708.

Example 4

Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate

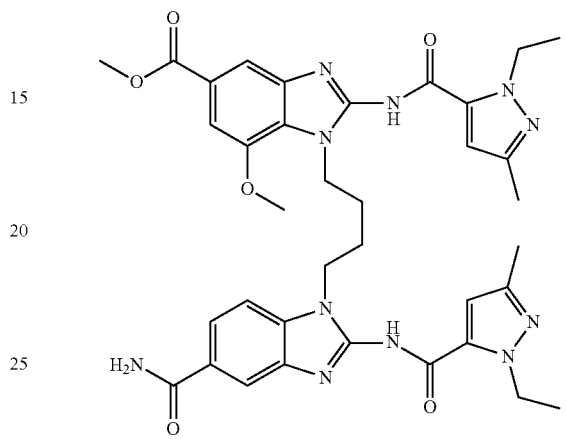

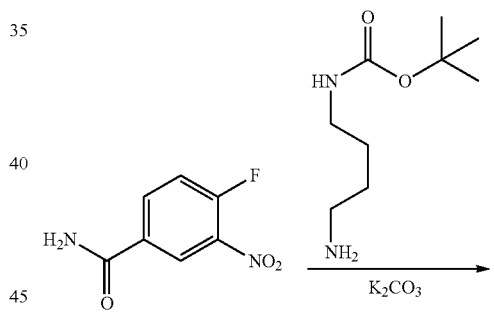

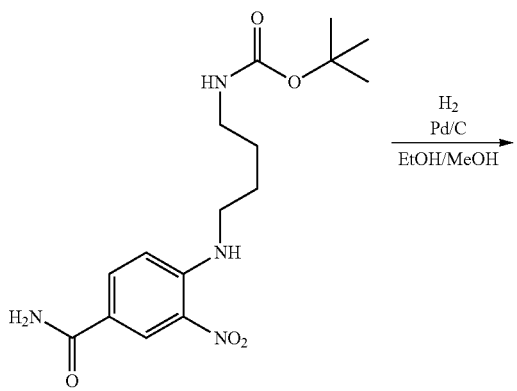

211
-continued
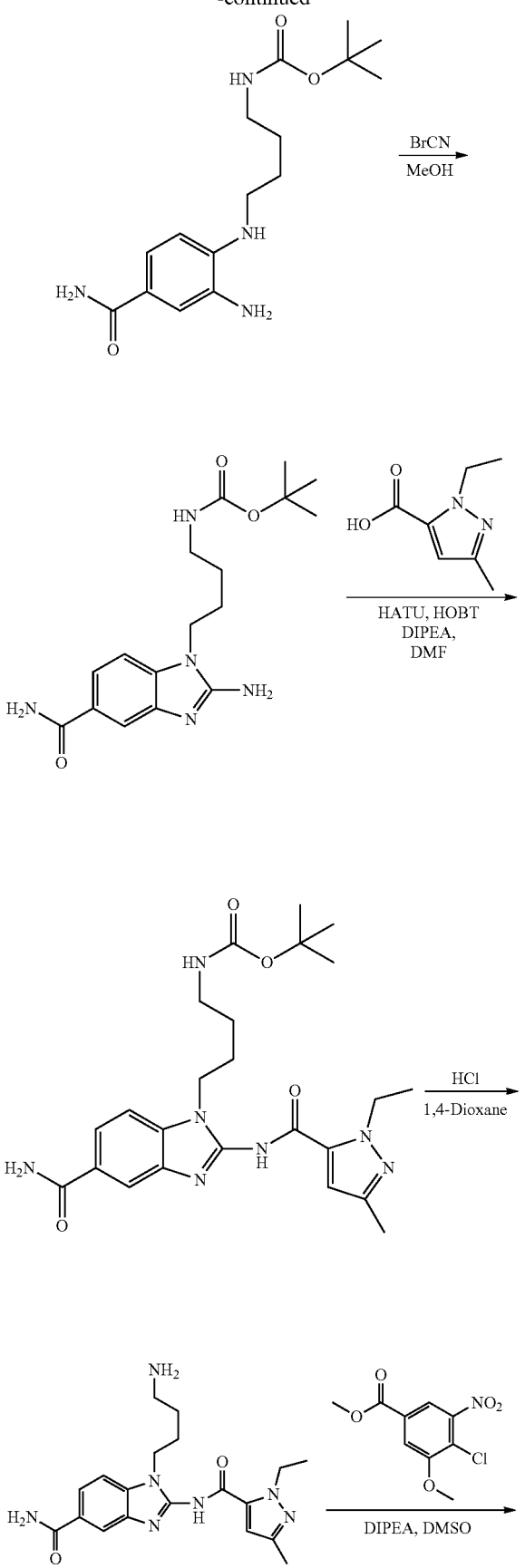
212
-continued
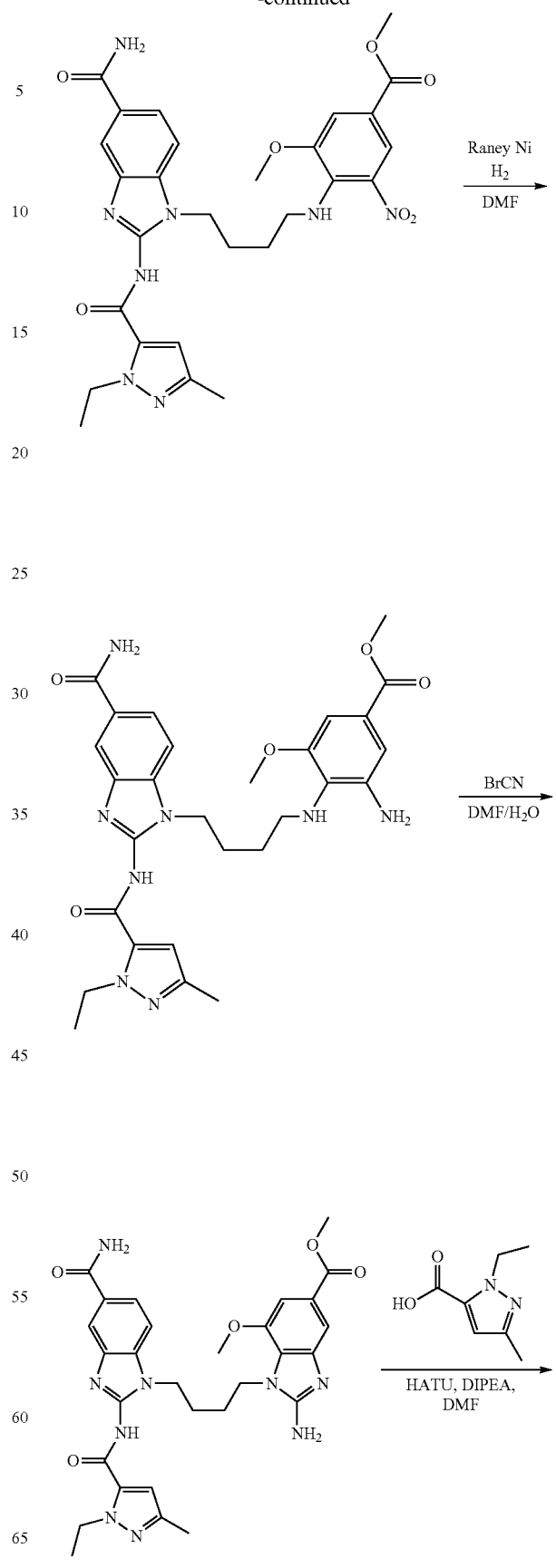

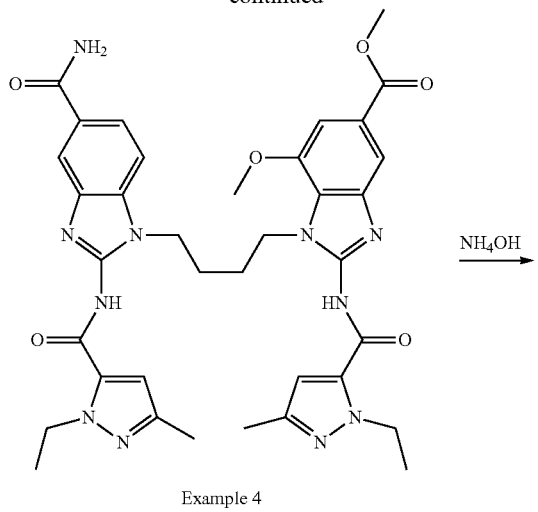

Example 4

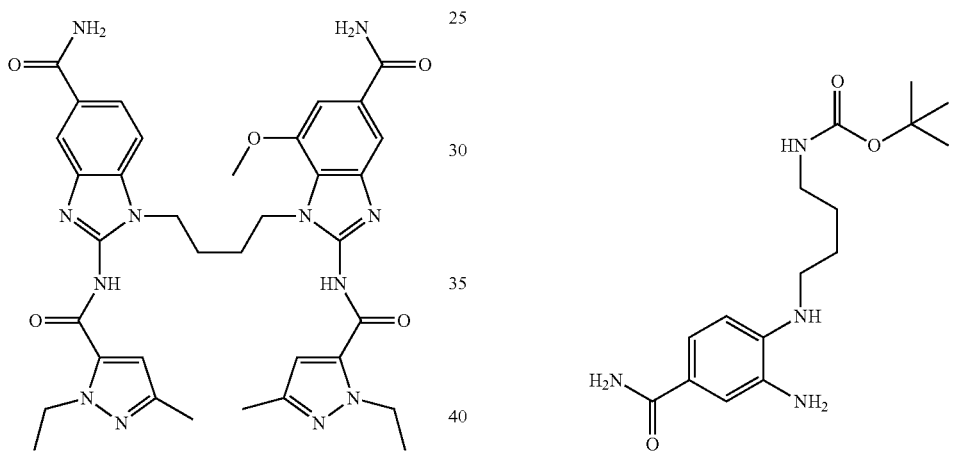

Example 5

Step 1: tert-butyl (4-((4-carbamoyl-2-nitrophenyl)amino)butyl)carbamate

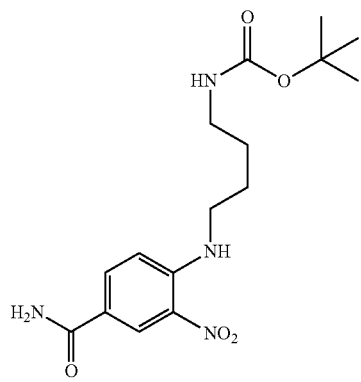 [SMILES: CC(C)(C)OC(=O)NCCCCNc1ccc(C(N)=O)cc1[N+](=O)[O-]]

A mixture of tert-butyl (4-aminobutyl)carbamate (5.00 g, 26.6 mmol), 4-fluoro-3-nitrobenzamide (4.89 g, 26.6 mmol), and $K_2CO_3$ (4.04 g, 29.2 mmol) in DMSO (25 mL) was stirred at 70° C. for 2 h. The reaction was cooled to rt and slowly diluted with 125 mL of water via addition funnel. The resulting solid was isolated by filtration, dried in a Buchner funnel, and placed in a vacuum oven at 56° C. for 3 days to give the title compound (9.2 g, 26.1 mmol, 98% yield) as a yellow solid. $^1$H NMR (400 MHz, DMSO-$d_6$) δ ppm 8.67 (d, J=2.02 Hz, 1H) 8.40 (t, J=5.43 Hz, 1H) 8.01 (d, J=6.82 Hz, 2H) 7.30 (br. s., 1H) 7.12 (d, J=9.09 Hz, 1H) 6.87 (br. s., 1H) 3.42 (q, J=6.57 Hz, 2H) 2.91-3.01 (m, 2H) 1.60 (d, J=6.57 Hz, 2H) 1.43-1.54 (m, 2H) 1.38 (s, 9H). LCMS (LCMS Method C): Rt.=0.86 min, [M+H]$^+$=353.

Step 2: tert-butyl (4-((2-amino-4-carbamoylphenyl)amino)butyl)carbamate

A 500 mL RB flask was charged with tert-butyl (4-((4-carbamoyl-2-nitrophenyl)amino)butyl)carbamate (9.2 g, 26.1 mmol), 10% Pd/C (0.920 g, 8.64 mmol) (Degussa wet type), EtOH (100 mL) and MeOH (100 mL). The flask was evacuated and placed under a balloon of hydrogen with stirring. A condenser was placed on top of the flask and the hydrogen balloon was placed atop the condenser. The mixture was stirred at rt for 20 h, then the flask was evacuated and the suspension was filtered through a bed of Celite® using EtOH to aid in rinsing. The filtrate was concentrated in vacuo and placed under high vacuum to give the title compound (8.4 g, 26.1 mmol, 100% yield) as a black solid. $^1$H NMR (400 MHz, DMSO-$d_6$) δ ppm 7.44 (br. s., 1H) 7.04-7.15 (m, 2H) 6.85 (t, J=5.43 Hz, 1H) 6.74 (br. s., 1H) 6.37 (d, J=8.08 Hz, 1H) 4.89 (t, J=5.18 Hz, 1H) 4.60 (br. s., 2H) 3.07 (q, J=6.48 Hz, 2H) 2.97 (q, J=6.40 Hz, 2H) 1.45-1.64 (m, 4H) 1.39 (s, 9H). LCMS (LCMS Method C): Rt.=0.68 min, [M+H]$^+$=323.1

Step 3: tert-butyl (4-(2-amino-5-carbamoyl-1H-benzo[d]imidazol-1-yl)butyl)carbamate, Hydrobromide

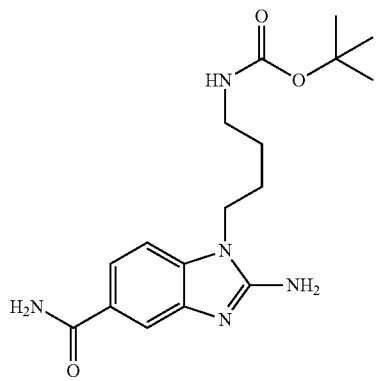 [SMILES: CC(C)(C)OC(=O)NCCCCn1c(N)nc2cc(C(N)=O)ccc21]

tert-Butyl (4-((2-amino-4-carbamoylphenyl)amino)butyl) carbamate (8.40 g, 26.1 mmol) was dissolved in MeOH (110 mL) and a solution of 5M cyanogen bromide in CH$_3$CN (5.73 mL, 28.7 mmol) was added via syringe. The dark reaction was capped and stirred for 15 h at rt. The reaction was concentrated in vacuo and placed under high vacuum to give the title compound (11.17 g, 26.1 mmol, 100% yield) as a dark solid. $^1$H NMR (400 MHz, DMSO-4) δ ppm 12.85 (br. s., 1H) 8.74 (br. s., 2H) 8.08 (br. s., 1H) 7.80-7.90 (m, 2H) 7.64 (d, J=8.34 Hz, 1H) 7.44 (br. s., 1H) 6.89 (t, J=5.56 Hz, 1H) 4.15 (t, J=7.20 Hz, 2H) 2.96 (q, J=6.32 Hz, 2H) 1.66 (d, J=7.07 Hz, 2H) 1.42-1.50 (m, 2H) 1.38 (s, 9H). LCMS (LCMS Method C): Rt.=0.62 min, [M+H]$^+$=348.1

Step 4: tert-butyl (4-(5-carbamoyl-2-(1-ethyl-3-methyl-1H-pyrazole-5-carboxamido)-1H-benzo[d]imidazol-1-yl)butyl)carbamate

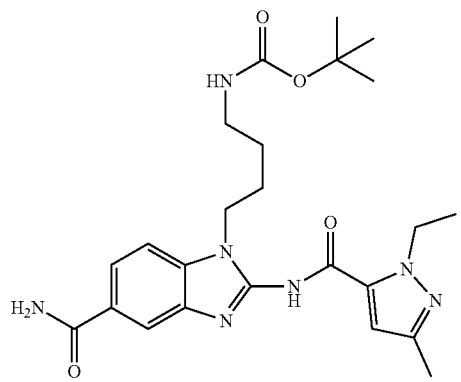 [SMILES: CCn1nc(C)cc1C(=O)Nc1nc2cc(C(N)=O)ccc2n1CCCCNC(=O)OC(C)(C)C]

A mixture of tert-butyl (4-(2-amino-5-carbamoyl-1H-benzo[d]imidazol-1-yl)butyl)carbamate, hydrobromide (11.17 g, 26.1 mmol), 1-ethyl-3-methyl-1H-pyrazole-5-carboxylic acid (4.82 g, 31.3 mmol), HATU (11.90 g, 31.3 mmol), DIPEA (18.22 mL, 104 mmol), and HOBt (1.997 g, 13.04 mmol) in DMF (100 mL) was stirred at rt for 21 h. The reaction was diluted with 300 mL of water and 300 mL of EtOAc, transferred to a separatory funnel, and the layers were separated and the aqueous layer was extracted with EtOAc (2×150 mL). The combined EtOAc layers were washed with saturated NH$_4$Cl (2×200 mL), water (1×200 mL), and brine (2×200 mL). The organic layer was dried over Na$_2$SO$_4$, filtered, concentrated in vacuo, and placed under high vacuum. The solid was purified via chromatography on silica gel (Isco® Combiflash, 0-20% MeOH:DCM, 330 gm column, loaded in 50 mL of DCM). The desired fractions were combined, concentrated in vacuo, and placed under high vacuum to give the title compound as a purple solid, (9.53 g, 19.71 mmol, 76% yield). $^1$H NMR (400 MHz, DMSO-d$_6$) δ ppm 12.85 (s, 1H) 8.01 (br. s., 2H) 7.81 (d, J=8.34 Hz, 1H) 7.59 (d, J=8.34 Hz, 1H) 7.36 (br. s., 1H) 6.80-6.86 (m, 1H) 6.68 (s, 1H) 4.64 (q, J=6.82 Hz, 2H) 4.23 (t, J=6.44 Hz, 2H) 2.98 (d, J=5.81 Hz, 2H) 2.19 (s, 3H) 1.76 (d, J=6.57 Hz, 2H) 1.40-1.48 (m, 2H) 1.30-1.40 (m, 13H). LCMS (LCMS Method C): Rt.=0.89 min, [M+H]$^+$=484.3

Step 5: 1-(4-aminobutyl)-2-(1-ethyl-3-methyl-1H-pyrazole-5-carboxamido)-1H-benzo[d]imidazole-5-carboxamide, 2 hydrochloride

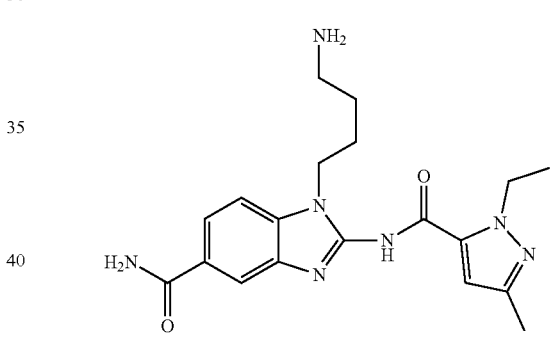

An ice-cooled 500 mL RB flask containing tert-butyl (4-(5-carbamoyl-2-(1-ethyl-3-methyl-1H-pyrazole-5-carboxamido)-1H-benzo[d]imidazol-1-yl)butyl)carbamate (9.53 g, 19.71 mmol) was treated with 4M HCl in 1,4-dioxane (42.0 mL, 168 mmol). The ice bath was removed and the purple slurry was stirred at rt for 2.5 h. The reaction was then concentrated in vacuo, placed under high vacuum, and the resulting solid was placed in a vacuum oven at 50° C. for 15 hrs and cooled under high vacuum to afford impure title compound as a grey solid which also contained 1,4-dioxane (11.89 grams, assumed 19.7 mmol, 100% yield). Material was used as is without further purification. $^1$H NMR (400 MHz, DMSO-d$_6$) δ ppm 12.91 (br. s, 1H) 8.03 (d, J=1.26 Hz, 2H) 7.77-7.87 (m, 4H) 7.62 (d, J=8.34 Hz, 1H) 7.38 (br. s., 1H) 6.70 (s, 1H) 6-5 ppm (br. s, 1H), 4.63 (q, J=7.07 Hz, 2H) 4.28 (t, J=6.57 Hz, 2H) 2.77-2.87 (m, 2H) 2.20 (s, 3H) 1.81-1.91 (m, 2H) 1.52-1.60 (m, 2H) 1.38 (t, J=7.07 Hz, 3H). LCMS (LCMS Method C): Rt.=0.60 min, [M+H]$^+$=384.2

217

Step 6: Methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate

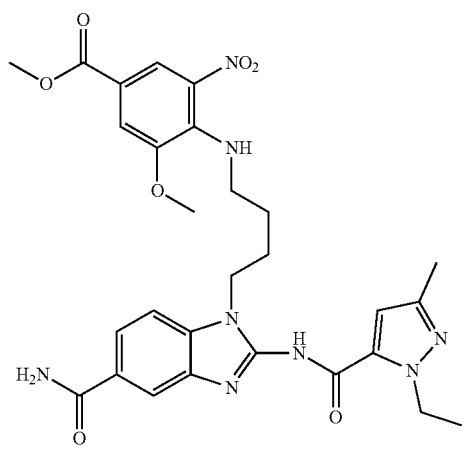 [SMILES: CCn1nc(C)cc1C(=O)Nc1nc2cc(C(N)=O)ccc2n1CCCCNc1c(N)cc(C(=O)OC)cc1OC]

A 250 mL 3-neck RB flask equipped with a condenser, a large stir bar, and an internal thermometer was charged with 1-(4-aminobutyl)-2-(1-ethyl-3-methyl-1H-pyrazole-5-carboxamido)-1H-benzo[d]imidazole-5-carboxamide, 2 hydrochloride (9.38 g, 20.55 mmol) and methyl 4-chloro-3-methoxy-5-nitrobenzoate (5.048 g, 20.55 mmol). DMSO (50 mL) was added followed by DIPEA (17.95 mL, 103 mmol) and the dark suspension was heated at 100° C. for approximately 24 h, cooled, and added dropwise to 500 mL of stirred water. After the addition was complete, the resulting orange suspension was stirred for 20 min and filtered. The isolated orange-red paste was washed with water and hexanes, dried in the Buchner funnel, and then in a vacuum oven at 56° C. for 20 hrs. The reddish solid was then triturated with Et$_2$O (60 mL) and isolated by filtration. The trituration and filtration was repeated. The resulting solid was placed in a vacuum oven at 56° C. for 3 days to give afford the title compound (11.17 g, 18.85 mmol, 92% yield) as a reddish solid. $^1$H NMR (400 MHz, DMSO-d$_6$) δ ppm 12.78 (br. s., 1H) 8.12 (s, 1H) 7.99 (s, 1H) 7.93 (d, J=7.53 Hz, 2H) 7.79 (d, J=8.28 Hz, 1H) 7.53 (d, 7.78 Hz, 1H) 7.36 (s, 1H) 7.31 (br. s., 1H) 6.60 (s, 1H) 4.60 (d, J=7.03 Hz, 2H) 4.23 (br. s., 2H) 3.84 (s, 3H) 3.80 (s, 3H) 3.53 (d, J=5.77 Hz, 2H) 2.15 (s, 3H) 1.82 (br. s., 2H) 1.62 (br. s., 2H) 1.35 (t, J=7.03 Hz, 3H). LCMS (LCMS Method D): Rt.=0.67 min, [M+H]$^+$=711.6

218

Step 7: Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate

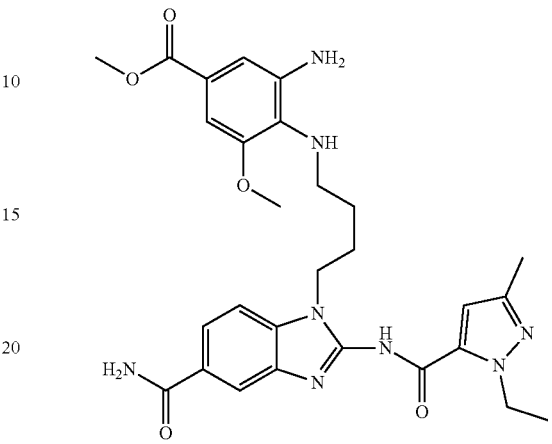

Methyl 4-((4-(5-carbamoyl-2-(1-ethyl-3-methyl-1H-pyrazole-5-carboxamido)-1H-benzo[d] imidazol-1-yl)butyl)amino)-3-methoxy-5-nitrobenzoate (5.0 g, 8.44 mmol) was mostly dissolved in DMF (50 mL) with stirring at rt in a 250 mL RB flask. Raney nickel (Raney 2800 nickel in water, ca. 10 mL of slurry, Aldrich) was added and a condenser was added atop the flask. A 3-way stopcock adapter with an attached hydrogen balloon was placed on top of the condenser and the setup was evacuated, filled with hydrogen, evacuated, and finally filled with hydrogen. The reaction was heated at 70° C. for 7 h. An additional 8 mL of Raney nickel slurry were added and the reaction was heated at 70° C. for 14 h. The reaction was cooled and filtered through Celite® while washing with DMF. The filtrate, a solution of ca. 100 mL DMF and 20 mL water from the Raney nickel slurry, containing the desired product was used as a solution directly in the next reaction. Assumed quantitative yield. LCMS (LCMS Method D): Rt.=0.73 min, [M+H]$^+$=563.4

Step 8: Methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, Hydrobromide

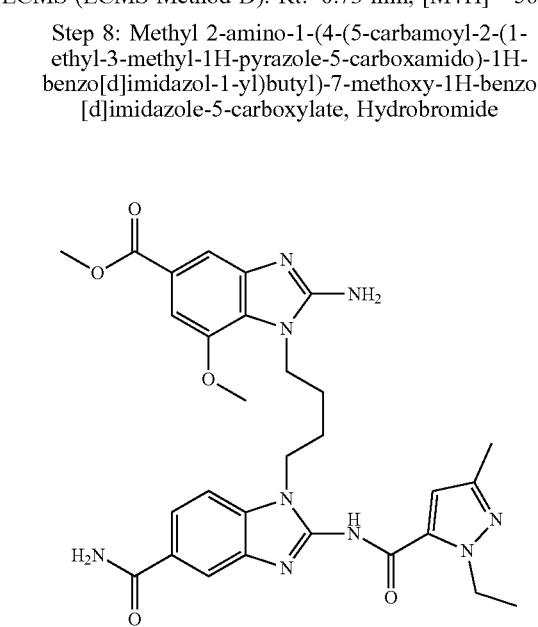

Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate (solution in DMF/water from previous step) was treated with 5M cyanogen bromide in CH$_3$CN (1.875 mL, 9.37 mmol) and the resulting solution was stirred at rt for 22 hrs. The reaction was concentrated in vacuo and placed under high vacuum to give a brown semi-solid. The semi-solid was triturated with EtOAc, stirred vigorously for 30 min, and the resulting solid was isolated by filtration and dried in a Buchner funnel to provide impure title product as a tan solid (5.08 g). This impure material was used without purification. LCMS (LCMS Method D): Rt.=0.72 min, [M+H]$^+$=588.5.

Example 4

Step 9: Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate

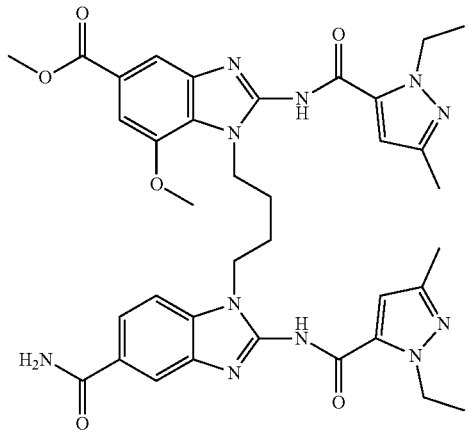 [SMILES: CCn1nc(C)cc1C(=O)Nc1nc2cc(C(N)=O)ccc2n1CCCCn1c(NC(=O)c2cc(C)nn2CC)nc2cc(C(=O)OC)cc(OC)c21]

A mixture of methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, hydrobromide (5.073 g, 7.59 mmol), 1-ethyl-3-methyl-H-pyrazole-5-carboxylic acid (1.287 g, 8.35 mmol), HATU (3.46 g, 9.11 mmol), and DIPEA (3.98 mL, 22.76 mmol) in DMF (30 mL) was stirred at rt for 17 hrs. The reaction was concentrated in vacuo then the resulting residue was triturated with water (100 mL) and stirred for 30 min. The resulting suspension was filtered and partially dried in a Buchner funnel to give a dark tan solid. The solid was mostly dissolved in 150 mL of 10% IPA: chloroform, diluted with water and filtered. The filtrate layers were then separated and the organic layer was dried over Na$_2$SO$_4$, filtered, concentrated, and placed under high vacuum to give a tan solid. The solid was triturated with warm 10% IPA: chloroform (100 mL) and filtered. The filtrate layers were separated, the organic layer was dried over Na$_2$SO$_4$, filtered, added to the original tan solid, concentrated in vacuo and placed under high vacuum. The solid was purified via chromatography on silica gel (Biotage® Isolera, 120 gm Gold column, 0-10% MeOH: DCM over 30 min, loaded as a solution in DCM/MeOH). The desired product fractions were combined, concentrated, and placed under high vacuum to give a light tan solid. The solid was triturated with DCM (50 mL) and isolated by filtration, and placed in a vacuum oven at 56° C. for 30 h to provide methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate as a white solid (1.0 g, 1.4 mmol, 18% yield). $^1$H NMR (400 MHz, DMSO-d$_6$) δ ppm 12.89 (s, 1H) 12.82 (s, 1H) 7.90-8.01 (m, 2H) 7.70-7.81 (m, 2H) 7.53 (d, J=8.28 Hz, 1H) 7.30-7.40 (m, 2H) 6.59 (d, J=5.02 Hz, 2H) 4.50-4.64 (m, 4H) 4.38 (br. s., 2H) 4.27 (br. s., 2H) 3.87 (d, J=3.76 Hz, 6H) 2.10 (s, 6H) 1.86 (br. s., 4H) 1.23-1.39 (m, 6H). LCMS (LCMS Method D): Rt.=1.00 min, [M+H]$^+$=724.5.

Example 5

1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide, 2 Trifluoroacetic Acid Salt

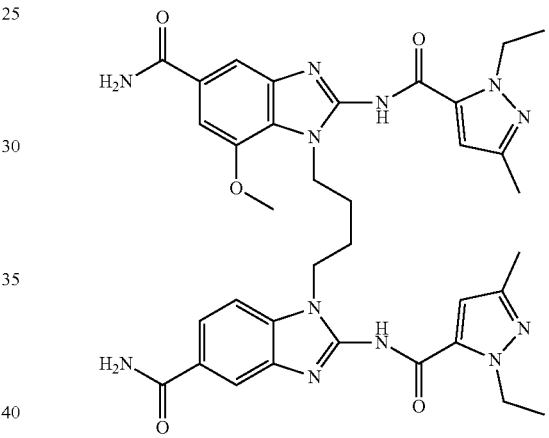

Methyl 1-(4-(5-carbamoyl-2-(1-ethyl-3-methyl-1H-pyrazole-5-carboxamido)-1H-benzo[d] imidazol-1-yl)butyl)-2-(1-ethyl-3-methyl-1H-pyrazole-5-carboxamido)-7-methoxy-1H-benzo[d]imidazole-5-carboxylate (0.1624 g, 0.224 mmol) was suspended in NH$_4$OH (50 mL, 725 mmol) and the reaction was stirred for 6 days at rt. The reaction was concentrated in vacuo and the residue was purified via HPLC (Gilson® Autoprep, acidic Luna column, loaded as a solution in DMSO, 20%-50% MeCN:water w/0.1% TFA). The desired fractions were combined and concentrated to give a white solid. The solid was purified again (Gilson® Autoprep, acidic Luna column, loaded as a solution in DMSO, 20-50% MeCN:water w/0.1% TFA) and the desired fractions were combined, concentrated, placed under high vacuum, and then dried in the vacuum oven for 15 h at 56° C. to afford 1-(4-(5-carbamoyl-2-(1-ethyl-3-methyl-1H-pyrazole-5-carboxamido)-1H-benzo[d]imidazol-1-yl) butyl)-2-(1-ethyl-3-methyl-1H-pyrazole-5-carboxamido)-7-methoxy-1H-benzo[d]imidazole-5-carboxamide, 2 trifluoroacetic acid salt as a white solid (76 mg, 0.081 mmol, 36% yield). $^1$H NMR (400 MHz, DMSO-d$_6$) δ ppm 12.79 (br. s., 1H) 7.97 (d, J=1.47 Hz, 3H) 7.76 (dd, J=8.56, 1.47 Hz, 1H) 7.64 (d, J=1.22 Hz, 1H) 7.53 (d, J=8.31 Hz, 1H) 7.27-7.39 (m, 3H) 6.60 (d, J=8.31 Hz, 2H) 4.57 (quin, J=7.09 Hz, 4H) 4.37 (br. s., 2H) 4.28 (br. s., 2H) 3.82 (s, 3H)

2.11 (d, J=4.16 Hz, 6H) 1.86 (br. s., 4H) 1.31 (td, J=7.03, 4.52 Hz, 6H). LCMS (LCMS Method E): Rt.=0.85 min, [M+H]⁺=709.5

Example 6

(E)-1,1'-(but-2-ene-1,4-diyl)bis(2-(1-ethyl-3-methyl-1H-pyrazole-5-carboxamido)-7-(3-hydroxy-propoxy)-1H-benzo[d]imidazole-5-carboxamide), 2 Trifluoroacetic Acid Salt

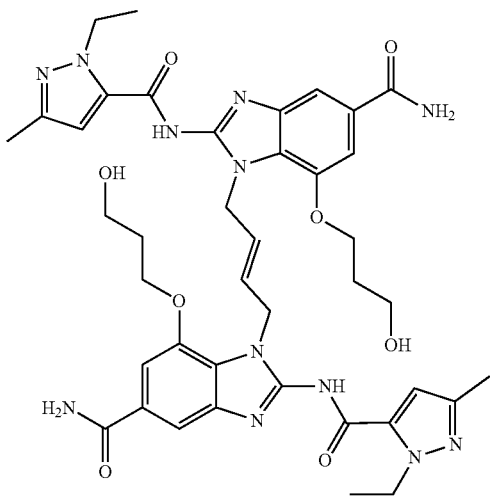

Step 1: 3-(3-((tert-butyldimethylsilyl)oxy)propoxy)-4-chloro-5-nitrobenzamide

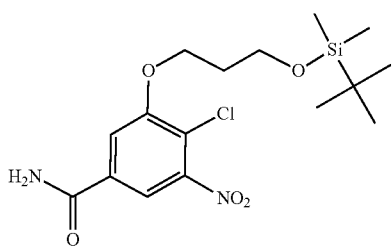 [SMILES: CC(C)(C)[Si](C)(C)OCCCOc1cc(C(N)=O)cc([N+](=O)[O-])c1Cl]

(3-bromopropoxy)(tert-butyl)dimethylsilane (7.3 g, 28.8 mmol) was dissolved in dry DMF (75 mL), 4-chloro-3-hydroxy-5-nitrobenzamide (4.8 g, 22.16 mmol) was added followed by K₂CO₃ (6.13 g, 44.3 mmol) and stirred for 2 hr at 100° C. under nitrogen. The reaction was cooled to rt, poured into EtOAc (600 mL), washed with water (600 mL), brine, dried with MgSO₄, filtered, and concentrated in vacuo. The residue was purified by silica gel chromatography eluting with 20-80% hexanes/EtOAc to afford the title compound (7.43 g, 19.1 mmol, 86% yield). ¹H NMR (400 MHz, DMSO-d₆) δ ppm 8.29 (br. s., 1H), 8.05 (d, J=1.71 Hz, 1H), 7.89 (d, J=1.71 Hz, 1H), 7.77 (br. s., 1H), 4.30 (t, J=5.99 Hz, 2H), 3.80 (t, J=5.99 Hz, 2H), 1.98 (quin, J=5.99 Hz, 2H), 0.80-0.90 (m, 9H), 0.02 (s, 6H). LCMS (LCMS Method E): Rt.=1.40 min, [M+H]⁺=389.

Step 2: 4-(allylamino)-3-(3-((tert-butyldimethylsilyl)oxy)propoxy)-5-nitrobenzamide

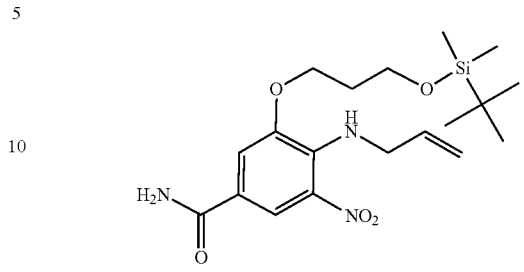

3-(3-((tert-butyldimethylsilyl)oxy)propoxy)-4-chloro-5-nitrobenzamide (2.05 g, 5.27 mmol) was dissolved in dry NMP (12 mL), allylamine (1.204 g, 21.08 mmol) was added and the reaction heated to 120° C. in a microwave reactor for 30 min. To the reaction was added additional allylamine (900 mg, 15.8 mmol) and heated at 120° C. for an additional 20 min. The reaction was poured into EtOAc (150 mL), washed with water (150 mL), brine, dried with MgSO₄, filtered, and concentrated in vacuo. The residue was purified by silica gel chromatography eluting with 20-80% hexanes/EtOAc to afford the title compound (1.99 g, 4.86 mmol, 92% yield). ¹H NMR (400 MHz, DMSO-d₆) δ ppm 8.19 (s, 1H), 8.02 (br. s., 1H), 7.74 (t, J=6.02 Hz, 1H), 7.57 (s, 1H), 7.31 (br. s., 1H), 5.89 (ddt, J=16.53, 10.89, 5.36, 5.36 Hz, 1H), 5.05-5.19 (m, 2H), 4.09-4.22 (m, 4H), 3.79 (t, J=5.90 Hz, 2H), 1.99 (t, 5.77 Hz, 2H), 0.87 (s, 9H), 0.04 (s, 6H). LC-MS (LCMS Method D): Rt=1.41 min, [M+H]⁺=410.

Step 3: 4-(allylamino)-3-amino-5-(3-((tert-butyldimethylsilyl)oxy)propoxy)benzamide

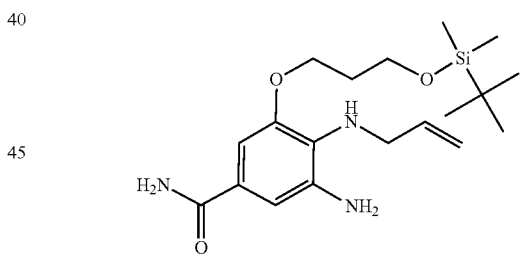

4-(allylamino)-3-(3-((tert-butyldimethylsilyl)oxy)propoxy)-5-nitrobenzamide (1.91 g, 4.66 mmol) was dissolved in AcOH (13.3 mL), zinc powder (1.220 g, 18.65 mmol) was added (in one portion) and the reaction stirred at rt under nitrogen. After 45 min an additional portion of zinc was added (610 mg, 9.32 mmol) and stirred an additional 2 hr at rt. The reaction was filtered, the filtrate poured into EtOAc (125 mL), washed with 10% aq Na₂CO₃ (125 mL), brine, dried with MgSO₄, filtered, and concentrated in vacuo to afford the title compound. ¹H NMR (400 MHz, DMSO-d₆) δ ppm 7.60 (br. s., 1H), 6.93 (d, J=8.80 Hz, 1H), 6.85 (d, J=1.71 Hz, 1H), 6.78 (d, J=1.96 Hz, 1H), 5.82-5.95 (m, 1H), 5.14 (dd, J=17.12, 1.96 Hz, 1H), 4.95-5.08 (m, 1H), 4.68 (br. s., 1H), 3.97-4.07 (m, 2H), 3.71-3.86 (m, 2H), 3.60 (d, J=5.87 Hz, 1H), 1.84-1.96 (m, 4H), 0.75-0.92 (m, 9H), −0.02-0.08 (m, 6H). LC-MS (LCMS Method D): Rt=1.04 min, [M+H]⁺=380.

Step 4: 1-allyl-2-amino-7-(3-((tert-butyldimethylsilyl)oxy)propoxy)-1H-benzo[d]imidazole-5-carboxamide, Hydrobromide

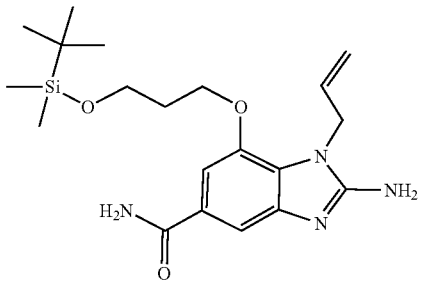 [SMILES: C=CCn1c(N)nc2cc(C(N)=O)cc(OCCCO[Si](C)(C)C(C)(C)C)c21]

4-(allylamino)-3-amino-5-(3-((tert-butyldimethylsilyl)oxy)propoxy)benzamide (1.769 g, 4.66 mmol) was dissolved in dry MeOH (25 mL), cyanogen bromide (0.543 g, 5.13 mmol) was added and the reaction stirred overnight at rt under nitrogen. The reaction was concentrated in vacuo and the residue stirred with EtOAc (20 mL) at rt for 30 min. The solids were isolated by filtration and dried to afford the title compound (1.56 g, 3.21 mmol, 69% yield). $^1$H NMR (400 MHz, DMSO-$d_6$) δ ppm 12.94 (br. s., 1H), 8.60 (br. s., 2H), 8.08 (br. s., 1H), 7.51 (d, J=0.98 Hz, 1H), 7.43 (d, J=0.98 Hz, 2H), 5.92-6.08 (m, 1H), 5.21 (dd, J=10.51, 0.98 Hz, 1H), 4.98-5.08 (m, 1H), 4.92 (d, J=4.65 Hz, 1H), 4.16-4.29 (m, 2H), 3.74-3.81 (m, 2H), 1.93-2.07 (m, 2H), 0.81-0.91 (m, 9H), −0.04-0.07 (m, 6H). LC-MS (LCMS Method D): Rt=1.02 min, [M+H]$^+$=405.

Step 5: 1-allyl-7-(3-(((tert-butyldimethylsilyl)oxy)propoxy)-2-(1-ethyl-3-methyl-1H-pyrazole-5-carboxamido)-1H-benzo[d]imidazole-5-carboxamide

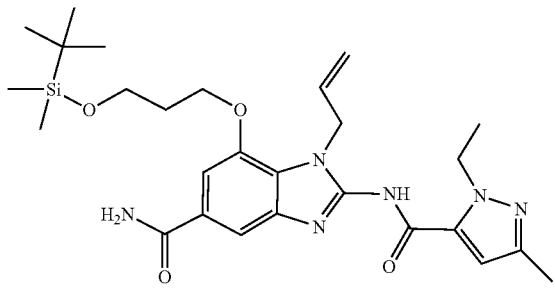

1-ethyl-3-methyl-1H-pyrazole-5-carboxylic acid (0.579 g, 3.76 mmol), HATU (1.429 g, 3.76 mmol) and HOBt (0.240 g, 1.565 mmol) were combined with dry DMF (12 mL). Et$_3$N (1.7 mL, 12.52 mmol) was added and the reaction stirred at rt for 5 min. To the reaction was added 1-allyl-2-amino-7-(3-(((tert-butyldimethylsilyl)oxy)propoxy)-1H-benzo[d]imidazole-5-carboxamide, hydrobromide (1.52 g, 3.13 mmol) and stirred at rt overnight under nitrogen. The reaction was poured into EtOAc (120 mL), washed with water (120 mL), brine, dried (MgSO$_4$), filtered, and concentrated in vacuo. The residue was purified by silica gel chromatography eluting with 80-100% EtOAc/hexanes to afford the title compound (1.07 g, 1.98 mmol, 63% yield). $^1$H NMR (400 MHz, DMSO-$d_6$) δ ppm 12.85 (br. s., 1H), 7.91-8.05 (m, 1H), 7.67 (s, 1H), 7.37 (s, 1H), 7.32 (br. s., 1H), 6.63 (s, 1H), 5.96-6.13 (m, 1H), 5.14 (d, J=9.29 Hz, 1H), 4.91-5.03 (m, 3H), 4.61 (q, J=7.01 Hz, 2H), 4.24 (t, J=5.87 Hz, 2H), 3.81 (t, J=6.11 Hz, 2H), 2.18 (s, 3H), 1.93-2.07 (m, 2H), 1.34 (t, J=7.09 Hz, 3H), 0.80-0.92 (m, 9H), 0.04 (s, 6H). LC-MS (LCMS Method D): Rt=1.40 min, [M+H]$^+$=541.

Step 6: 1-allyl-2-(1-ethyl-3-methyl-1H-pyrazole-5-carboxamido)-7-(3-hydroxypropoxy)-1H-benzo[d]imidazole-5-carboxamide

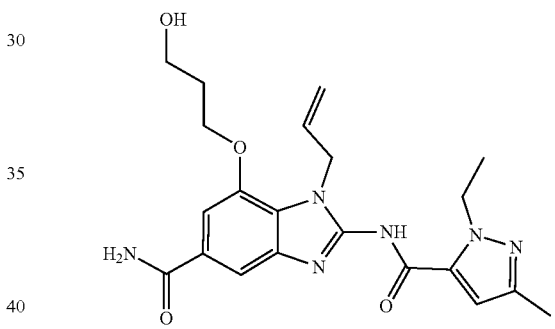

1-allyl-7-(3-(((tert-butyldimethylsilyl)oxy)propoxy)-2-(1-ethyl-3-methyl-1H-pyrazole-5-carboxamido)-1H-benzo[d]imidazole-5-carboxamide (700 mg, 1.30 mmol) was dissolved in dry THF (6 mL), AcOH (0.15 mL, 2.60 mmol) was added followed by TBAF (2.6 mL, 1M in THF). The reaction was stirred overnight at rt under nitrogen and poured into EtOAc and water (40 mL each) and shaken vigorously. Insoluble material was filtered and dried to afford the 1-allyl-2-(1-ethyl-3-methyl-1H-pyrazole-5-carboxamido)-7-(3-hydroxypropoxy)-1H-benzo[d]imidazole-5-carboxamide (460 mg, 1.08 mmol, 83%). $^1$H NMR (400 MHz, DMSO-$d_6$) δ ppm 12.84 (br. s., 1H), 7.99 (br. s., 1H), 7.67 (s, 1H), 7.38 (s, 1H), 7.32 (br. s., 1H), 6.62 (s, 1H), 5.98-6.12 (m, 1H), 5.15 (d, J=9.05 Hz, 1H), 4.92-5.04 (m, 3H), 4.54-4.68 (m, 3H), 4.24 (t, J=6.24 Hz, 2H), 3.63 (q, J=6.11 Hz, 2H), 2.18 (s, 3H), 1.97 (quin, J=6.17 Hz, 2H), 1.35 (t, J=7.09 Hz, 3H). LC-MS (LCMS Method D): Rt=0.79 min, [M+H]$^+$=427.

Example 6

Step 7: (E)-1,1'-(but-2-ene-1,4-diyl)bis(2-(1-ethyl-3-methyl-1H-pyrazole-5-carboxamido)-7-(3-hydroxypropoxy)-1H-benzo[d]imidazole-5-carboxamide), 2 Trifluoroacetic Acid Salt

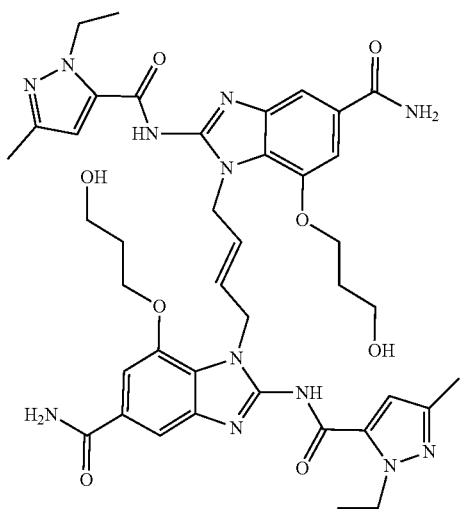

1-allyl-2-(1-ethyl-3-methyl-1H-pyrazole-5-carboxamido)-7-(3-hydroxypropoxy)-1H-benzo[d]imidazole-5-carboxamide (100 mg, 0.23 mmol) was dissolved in 1:1 DCM:MeOH (5 mL). To the solution was added TsOH·H$_2$O (45 mg, 0.23 mmol) as a solution in MeOH (1.5 mL) and the reaction was concentrated in vacuo. To the residue was added DCM (5 mL) and the fine suspension transferred to a microwave vial containing (1,3-dimesitylimidazolidin-2-ylidene)(2-isopropoxy benzylidene)ruthenium(VI) chloride (22 mg, 0.035 mmol). The flask was degassed and heated at 80° C. in a microwave reactor for 3 h. The reaction was treated with MeOH (3 mL) and evaporated under nitrogen. The residue was purified by HPLC (Gilson®, eluting with 10-60% ACN/water/0.1% TFA) and the product-containing fractions were collected and lyophilized to afford (E)-1,1'-(but-2-ene-1,4-diyl)bis(2-(1-ethyl-3-methyl-1H-pyrazole-5-carboxamido)-7-(3-hydroxypropoxy)-1H-benzo[d]imidazole-5-carboxamide), 2 trifluoroacetic acid salt (57 mg, 23% yield). $^1$H NMR (400 MHz, DMSO-d$_6$) δ ppm 12.84 (br. s., 2H) 7.99 (br. s., 2H) 7.64 (s, 2H) 7.35 (br. s., 2H) 7.31 (s, 2H) 6.52 (s, 2H) 5.81 (br. s., 2H) 4.91 (br. s., 4H) 4.52 (q, J=6.93 Hz, 5H) 4.02 (t, J=6.36 Hz, 5H) 3.41 (t, J=5.99 Hz, 4H) 2.06-2.15 (m, 6H) 1.59-1.70 (m, 4H) 1.27 (t, J=7.09 Hz, 6H). LC-MS (LCMS Method D): Rt=0.81 min, [M+H]$^+$=825.

The compound prepared by the above process may exist in a tautomeric or an isomeric form, e.g., as (2E,2'E)-1,1'-((E)-but-2-ene-1,4-diyl)bis(2-((1-ethyl-3-methyl-1H-pyrazole-5-carbonyl)imino)-7-(3-hydroxypropoxy)-2,3-dihydro-1H-benzo[d]imidazole-5-carboxamide), 2 trifluoroacetic acid salt

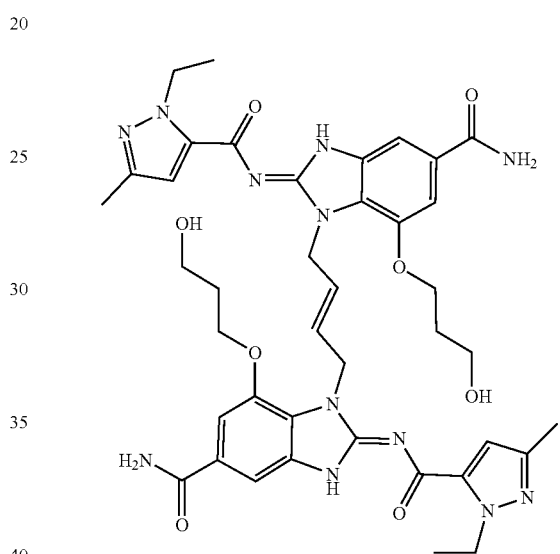

Example 7

8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

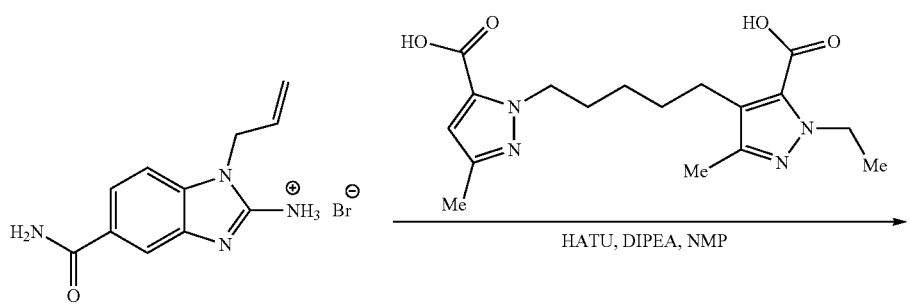

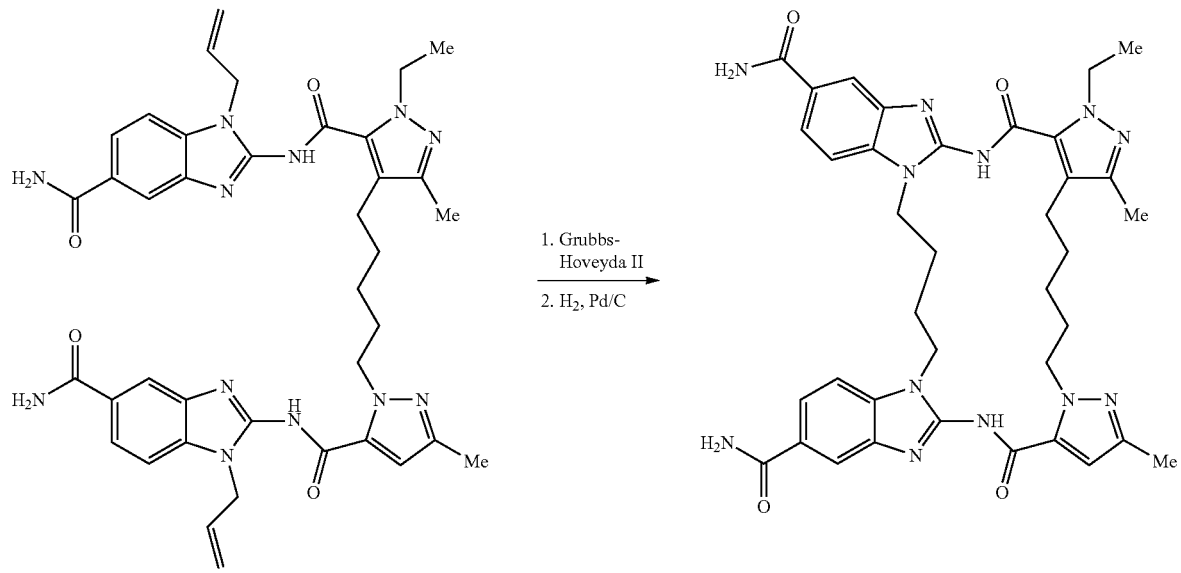

1. Grubbs-Hoveyda II
2. H₂, Pd/C

Step 1: 1-allyl-2-(1-(5-(5-((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide

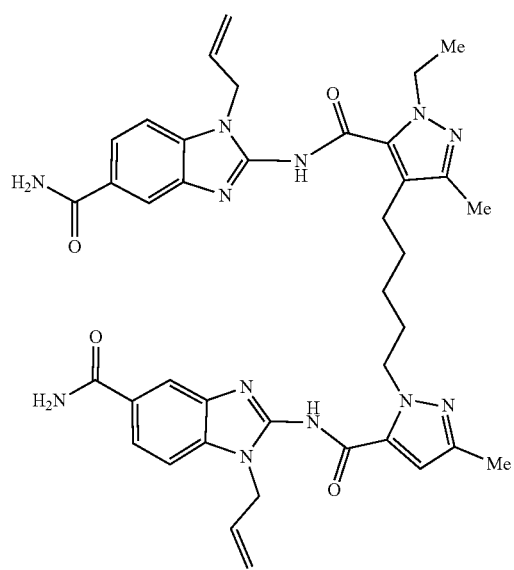 [SMILES: C=CCn1c(NC(=O)c2cc(C)nn2CCCCCc2c(C)nn(CC)c2C(=O)Nc2nc3cc(C(N)=O)ccc3n2CC=C)nc2cc(C(N)=O)ccc21]

A 5.0 mL Biotage® sealed tube was charged with 4-(5-(5-carboxy-3-methyl-1H-pyrazol-1-yl)pentyl)-1-ethyl-3-methyl-1H-pyrazole-5-carboxylic acid (634 mg, 1.820 mmol), 1-allyl-2-amino-1H-benzo[d]imidazole-5-carboxamide, hydrobromide (1352 mg, 4.55 mmol), HATU (1730 mg, 4.55 mmol), and NMP (13 mL). After 1 minute of stirring at rt, DIPEA (3.17 mL, 18.20 mmol) was added and the mixture was stirred at rt for 5 min, then heated in a microwave reactor at 140° C. for 1 hr. After this period, 5.0 mL of water was added and the mixture was stirred at rt for 5 min. It was then poured into 250 mL of ice-cold water and stirred vigorously for 1 hr. The resulting solid was filtered off, washed with water, dissolved from the filter using MeOH/DCM, concentrated in vacuo, and subjected to silica gel chromatography (Biotage® Ultra SNAP 100 g SiO₂ column: 0-40% MeOH/EtOAc) to yield 1-allyl-2-(1-(5-(5-((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide (840 mg, 1.128 mmol, 62% yield) as a pink solid. $^1$H NMR (400 MHz, DMSO-$d_6$) δ ppm 12.88 (s, 1H), 12.81 (s, 1H), 7.99-8.02 (m, 2H), 7.97 (br. s., 2H), 7.77 (ddd, J=8.34, 3.66, 1.39 Hz, 2H), 7.41 (dd, J=16.93, 8.34 Hz, 2H), 7.34 (br. s., 2H), 6.65 (s, 1H), 5.87-6.02 (m, 2H), 4.99-5.22 (m, 4H), 4.82 (dd, J=11.62, 4.80 Hz, 4H), 4.50-4.61 (m, 4H), 2.73 (t, J=7.45 Hz, 2H), 2.15 (s, 3H), 2.08 (s, 3H), 1.71-1.85 (m, 2H), 1.45-1.55 (m, 2H), 1.27-1.34 (m, 5H); LCMS (LCMS Method C): Rt=0.93 min, [M+H]⁺=745.7.

229

Step 2: 8-ethyl-10,18-dimethyl-7,20-dioxo-6,7,8,11,
12,13,14,15,20,21,28,31-dodecahydrobenzo[4,5]
imidazo[1,2-a]benzo[4,5]imidazo[2,1-p]dipyrazolo
[5,1-e:4',3'-l][1,3,6,15,17]pentaazacyclohenicosine-
3,24-dicarboxamide

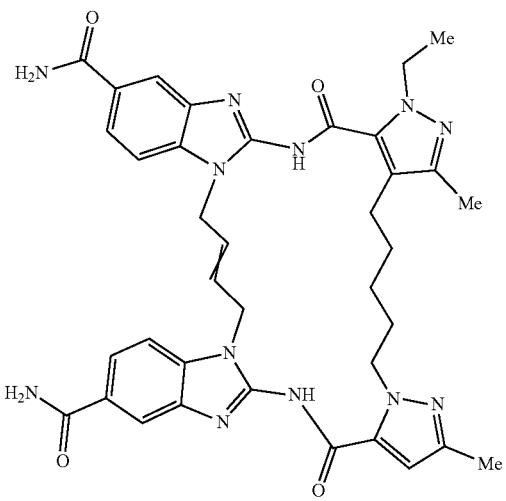 [SMILES: CCn1nc(C)c2c1C(=O)Nc1nc3cc(C(N)=O)ccc3n1CC=CCn1c(nc3cc(C(N)=O)ccc31)NC(=O)c1cc(C)nn1CCCCC2]

Four 20 mL Biotage® microwave sealed tubes were charged with a total of 1-allyl-2-(1-(5-(5-(((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide (160 mg, 0.215 mmol), Hoveyda-Grubbs II catalyst (26.9 mg, 0.043 mmol), and freshly degassed 1,2-dichloroethane (DCE) (80 mL). The sealed tubes were heated in a microwave reactor for 4 hr at 100° C. After the mixture cooled to rt, MeOH (1.0 mL) was added to each tube and the resulting clear solution was stirred at rt for 5 min. A solution of potassium 2-isocyanoacetate (15 mg in 1.5 mL of MeOH) was added to each tube and the resulting mixture was stirred at rt for 5 min. The tubes were combined, concentrated in vacuo, then the evaporation residue was taken up in a minimal volume of DCM/MeOH, and purified by silica gel chromatography (Biotage® Ultra SNAP 100 g SiO$_2$ column; 0-40% MeOH/EtOAc) to afford the desired product (61 mg) as a pale green solid with a mixture of alkene isomers. The product was further purified (Biotage® Ultra SNAP 25 g SiO$_2$ column; 0-20% MeOH/DCM gradient) to yield 8-ethyl-10,18-dimethyl-7,20-dioxo-6,7,8,11,12,13,14,15, 20,21,28,31-dodecahydrobenzo[4,5]imidazo[1,2-a]benzo[4, 5]imidazo[2,1-p]dipyrazolo[5,1-e:4',3'-l][1,3,6,15,17]pentaazacyclohenicosine-3,24-dicarboxamide as a 7:1 trans:cs mixture (54 mg, 0.075 mmol, 35% yield). Characterization of the trans isomer: $^1$H NMR (400 MHz, DMSO-d$_6$) δ ppm 12.87 (s, 1H), 12.84 (s, 1H), 7.98 (br. s., 4H), 7.77 (dd, J=7.71, 3.16 Hz, 2H), 7.33-7.48 (m, 4H), 6.55 (s, 1H), 5.89-5.98 (m, 1H), 5.66-5.75 (m, 1H), 4.90 (d, J=7.83 Hz, 4H), 4.73 (t, J=6.95 Hz, 2H), 4.47 (q, J=6.99 Hz, 2H), 2.72-2.80 (m, 2H), 2.17 (s, 3H), 2.10 (s, 3H), 1.72 (br. s., 2H), 1.44 (br. s., 2H), 1.30 (t, J=7.07 Hz, 5H); LCMS (LCMS Method C): Rt=0.82 min, [M+H]$^+$=717.6.

230

Example 7

Step 3: 8-ethyl-10,18-dimethyl-7,20-dioxo-6,7,8,11,
12,13,14,15,20,21,28,29,30,31-tetradecahydrobenzo
[4,5]imidazo[1,2-a]benzo[4,5]imidazo[2,1-p]dipyra-
zolo[5,1-e:4',3'-l][1,3,6,15,17]
pentaazacyclohenicosine-3,24-dicarboxamide

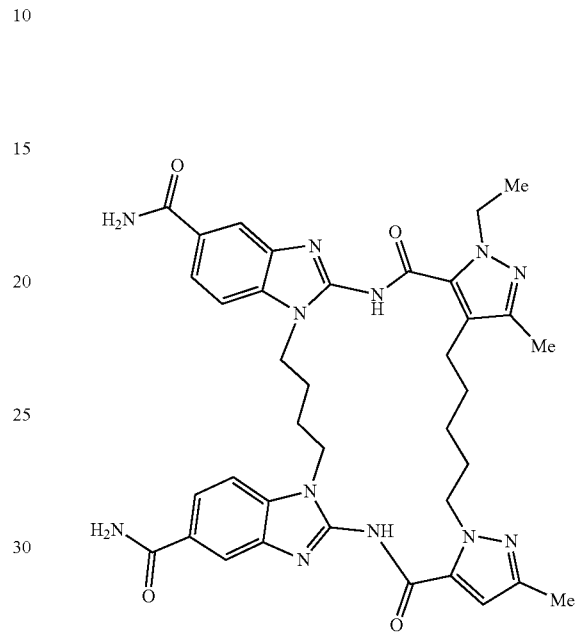

A RB flask was charged with 10% Pd/C (200 mg, 0.188 mmol) and purged with nitrogen. A solution of 8-ethyl-10, 18-dimethyl-7,20-dioxo-6,7,8,11,12,13,14,15,20,21,28,31-dodecahydrobenzo[4,5]imidazo[1,2-a]benzo[4,5]imidazo[2, 1-p]dipyrazolo[5,1-e:4,3-l][1,3,6,15,17] pentaazacyclohenicosine-3,24-dicarboxamide (100 mg, 0.140 mmol, 7:1 trans:cismixture) in a mixture of MeOH (20.0 mL) and THF (20.0 mL) was added, the flask was purged with hydrogen, and the reaction mixture was stirred under hydrogen atmosphere (1 atm) for 23 hr. The flask was then opened to air, stirred vigorously for 15 min and filtered, the Pd/C washed with MeOH/THF, the filtrate concentrated in vacuo, and subjected to silica gel chromatography (Biotage® Ultra SNAP 25 g SiO$_2$ column; 0-20% MeOH/ DCM) to yield 8-ethyl-10,18-dimethyl-7,20-dioxo-6,7,8,11, 12,13,14,15,20,21,28,29,30,31-tetradecahydrobenzo[4,5] imidazo[1,2-a]benzo[4,5]imidazo[2,1-p]dipyrazolo[5,1-e: 4',3'-l][1,3,6,15,17]pentaazacyclohenicosine-3,24-dicarboxamide (56 mg, 0.078 mmol, 55.8% yield) as a pale pink solid. $^1$H NMR (400 MHz, DMSO-d$_6$) δ ppm 12.88 (br. s., 2H), 8.02 (s, 4H), 7.79-7.87 (m, 2H), 7.67 (d, J=8.34 Hz, 1H), 7.63 (d, J=8.34 Hz, 1H), 7.37 (br. s., 2H), 6.57 (s, 1H), 4.74 (t, J=6.57 Hz, 2H), 4.48 (q, J=6.99 Hz, 2H), 4.19-4.31 (m, 4H), 2.78-2.86 (m, 2H), 2.16 (s, 3H), 2.08 (s, 3H), 1.91 (br. s., 4H), 1.77-1.86 (m, 2H), 1.44-1.54 (m, 2H), 1.35-1.42 (m, 2H), 1.29 (t, J=7.07 Hz, 3H); LCMS (LCMS Method C): Rt=0.81 min, [M+H]$^+$=719.7.

Example 8
8-Ethyl-10,18,30-trimethyl-7,20-dioxo-7,8,11,12,13,
14,15,20,21,28,29,30,31,32-tetradecahydro-1H-
benzo[4,5]imidazo[2,1-b]benzo[4,5]imidazo[1,2-i]
dipyrazolo[5,1-m:4',3'-t][1,3,6,9,11,14]
hexaazacyclodocosine-3,24-dicarboxamide
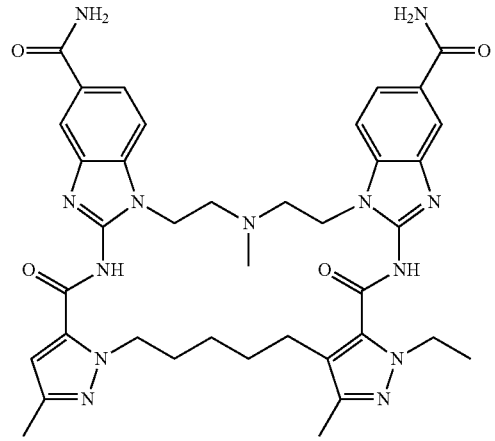
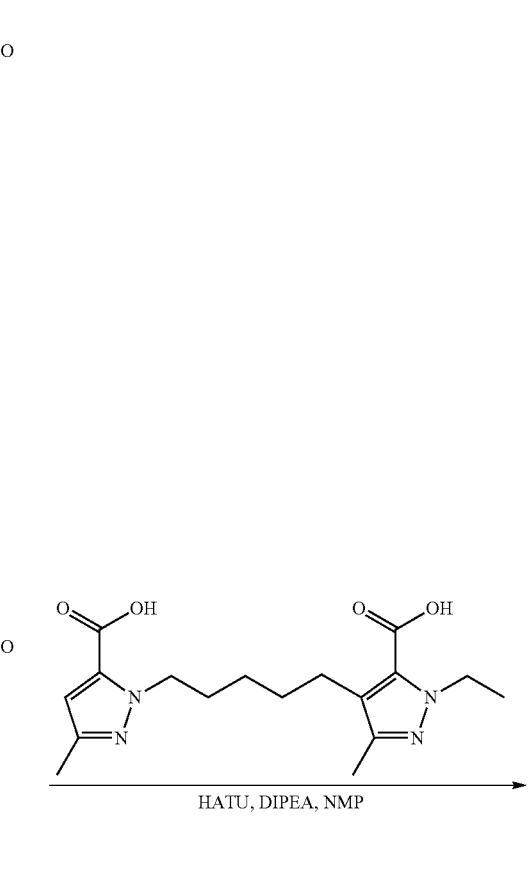
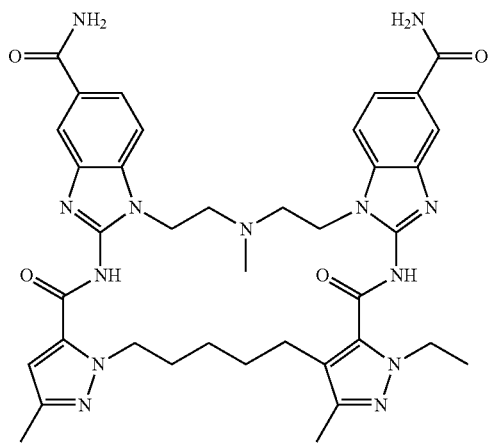

Example 8

8-Ethyl-10,18,30-trimethyl-7,20-dioxo-7,8,11,12,13,14,15,20,21,28,29,30,31,32-tetradecahydro-1H-benzo[4,5]imidazo[2,1-b]benzo[4,5]imidazo[1,2-i]dipyrazolo[5,1-m:4',3'-t][1,3,6,9,11,14]hexaazacyclodocosine-3,24-dicarboxamide

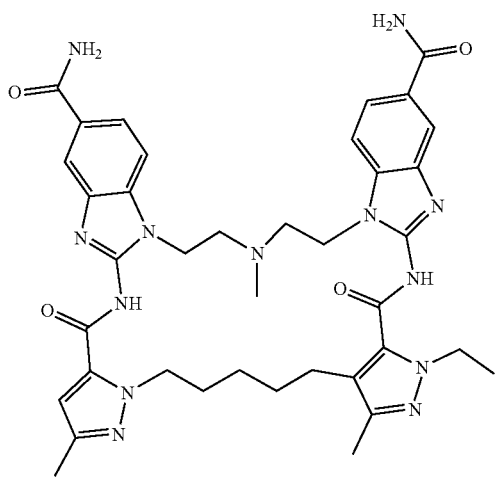 [SMILES: CCn1nc(C)c2c1C(=O)Nc1nc3cc(C(N)=O)ccc3n1CCN(C)CCn1c(nc3cc(C(N)=O)ccc31)NC(=O)c1cc(C)nn1CCCCC2]

To a solution of 2-(7-aza-1H-benzotriazole-1-yl)-1,1,3,3-tetramethyluronium hexafluorophosphate (576 mg, 1.516 mmol), 1,1'-((methylazanediyl)bis(ethane-2,1-diyl))bis(2-amino-1H-benzo[d]imidazole-5-carboxamide) (300 mg, 0.689 mmol, from Example 3) and 4-(5-(5-carboxy-3-methyl-1H-pyrazol-1-yl)pentyl)-1-ethyl-3-methyl-1H-pyrazole-5-carboxylic acid (240 mg, 0.689 mmol) in NMP (10 mL) was added DIPEA (267 mg, 2.067 mmol). The reaction mixture was stirred at rt for 0.5 h and then the reaction was heated in a microwave reactor at 140° C. for 1 h (150 W). The reaction mixture was allowed to cool to rt, water was added and the mixture was extracted with DCM. The organic phase was washed with water (2×20 mL), dried over anhydrous $Na_2SO_4$, filtered, and concentrated under reduced pressure. The residue was purified by prep-HPLC (Gilson®, Gemini® C18 column, gradient 2-95% $MeCN:H_2O$ 0.1% TFA) to afford 8-ethyl-10,18,30-trimethyl-7,20-dioxo-7,8,11,12,13,14,15,20,21,28,29,30,31,32-tetradecahydro-benzo[4,5]imidazo[2,1-b]benzo[4,5]imidazo[1,2-i]dipyrazolo[5,1-m:4',3'-f][1,3,6,9,11,14]hexaazacyclodocosine-3,24-dicarboxamide (25 mg, 0.03 mmol, 4.56% yield) as a brown solid. 1H-NMR (400 MHz, $CD_3OD$) δ ppm 8.00 (d, J=12.0 Hz, 2H), 7.92-7.87 (m, 2H), 7.57 (d, J=8.0 Hz, 2H), 6.76 (s, 1H), 4.79-4.77 (m, 2H), 4.70-4.67 (m, 2H), 4.57-4.51 (m, 4H), 3.98 (s, 2H), 3.78 (s, 2H), 3.15 (s, 3H), 2.78 (t, J=8.0 Hz, 2H), 2.18-2.15 (m, 6H), 1.81-1.74 (m, 2H), 1.39-1.33 (m, 6H), 1.17-1.07 (s, 2H). LCMS (LCMS Method A): Rt=1.26 min, $[M+H]^+$=748.

Example 9

1,15-bis(1-ethyl-3-methyl-1H-pyrazole-5-carboxamido)-8,9,16,17,18,19-hexahydro-7H-6,10-dioxa-2,14,15a,19a-tetraazacyclopentadeca[1,2,3-cd:11,10,9-c'd']diindene-4,12-dicarboxamide

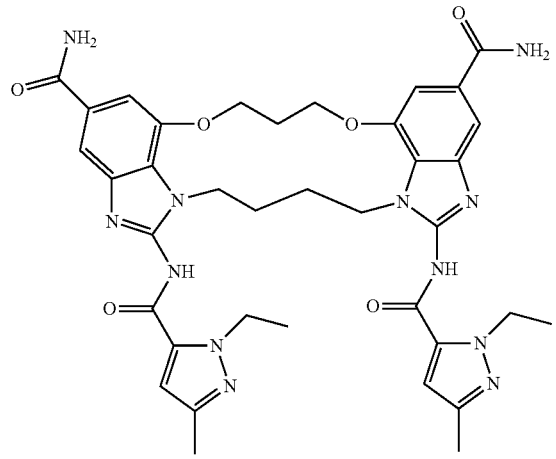

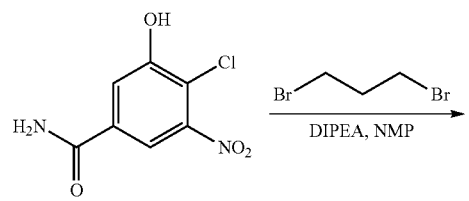

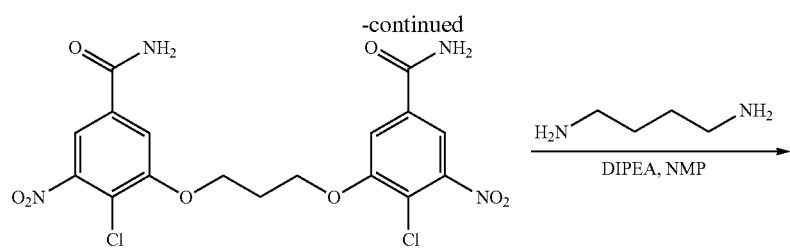
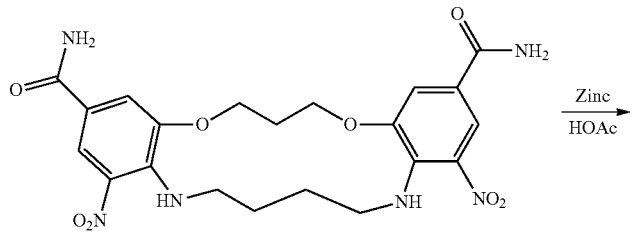
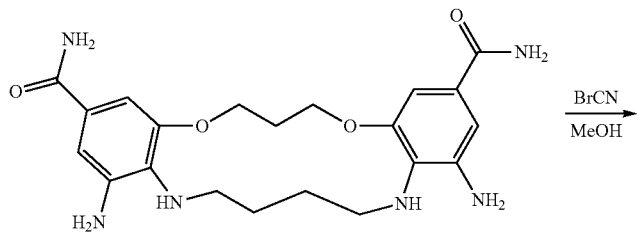
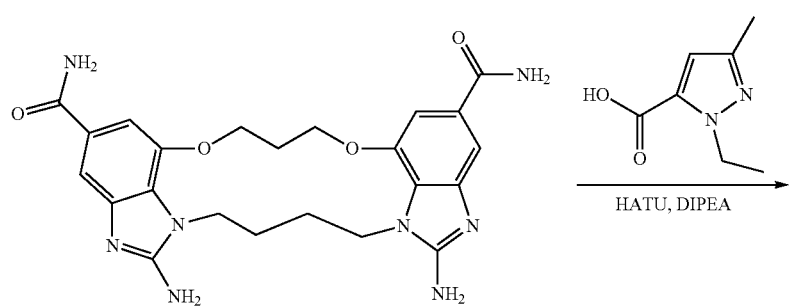
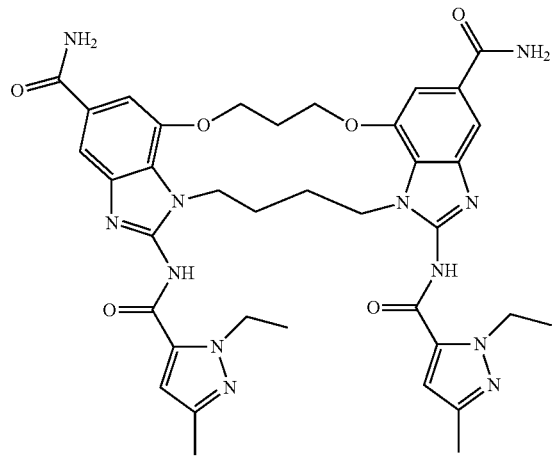

237

Step 1: 5,5'-(propane-1,3-diylbis(oxy))bis(4-chloro-3-nitrobenzamide)

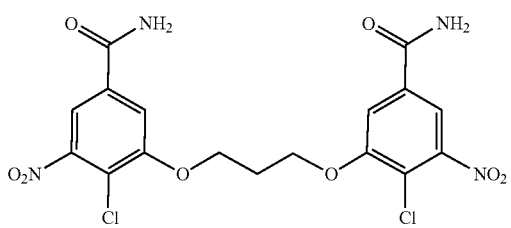 [SMILES: NC(=O)c1cc(OCCCOc2cc(C(N)=O)cc([N+](=O)[O-])c2Cl)c(Cl)c([N+](=O)[O-])c1]

4-chloro-3-hydroxy-5-nitrobenzamide (2 g, 9.23 mmol), 1,3-dibromopropane (932 mg, 4.62 mmol), DIPEA (3.23 mL, 18.47 mmol) were stirred in NMP (5 mL) in a 20 mL microwave vial. The reaction was then heated in microwave reactor at 100° C. for 15 min. Water (30 mL) was added to the reaction and the precipitate was isolated by filtration and washed with water. The solid was then dried in vacuo at 55° C. overnight to afford the title compound (3 g, 5.71 mmol, 61.8% yield). LCMS (LCMS Method D) Rt=0.99 mins, [M+H]$^+$=473.1.

Step 2: 1,13-dinitro-7,8,14,15,16,17,18,19-octahydro-6H-dibenzo[b,j][1,12,4,9]dioxadiazacyclopentadecine-3,11-dicarboxamide

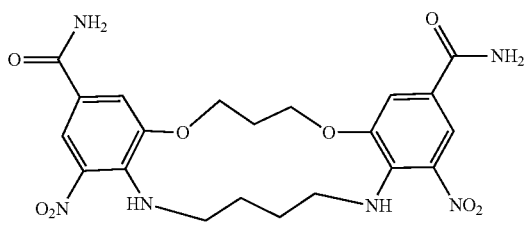 [SMILES: NC(=O)c1cc2c(c([N+](=O)[O-])c1)NCCCCNc1c(cc(C(N)=O)cc1[N+](=O)[O-])OCCCO2]

5,5'-(propane-1,3-diylbis(oxy))bis(4-chloro-3-nitrobenzamide) (2700 mg, 5.71 mmol), butane-1,4-diamine (503 mg, 5.71 mmol), DIPEA (2.491 mL, 14.26 mmol), were stirred in DMSO (8 mL) in a 20 mL microwave vial. It was then heated in microwave at 120° C. for 15 min. The reaction was diluted with water and filtered to afford the desired product as orange solid. The solid was then dried in vacuo at 55° C. overnight to give the orange solid (approximately 2.5 g, 5.12 mmol, 90% yield). $^1$H NMR (400 MHz, DMSO-a) δ ppm 8.20-8.16 (m, 2H), 8.05-7.95 (m, 4H), 7.62 (d, J=1.71 Hz, 2H), 4.32 (t, J=5.26 Hz, 4H), 3.56-3.42 (m, 4H), 2.47-2.38 (m, 2H), 1.65 (br. s., 4H). LCMS (LCMS Method D) Rt=0.93 min, [M+H]$^+$=489.2.

238

Step 3: 1,13-diamino-7,8,14,15,16,17,18,19-octahydro-6H-dibenzo[b,j][1,12,4,9]dioxadiazacyclopentadecine-3,11-dicarboxamide

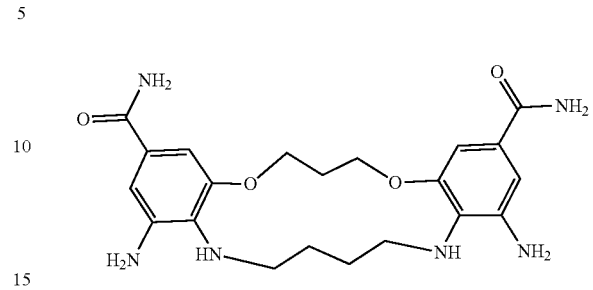

In a 50 mL RB flask, 1,13-dinitro-7,8,14,15,16,17,18,19-octahydro-6H-dibenzo[b,j][1,12,4,9] dioxadiazacyclopentadecine-3,11-dicarboxamide (2.5 g, 5.12 mmol) was stirred in AcOH (14.7 mL, 256 mmol). Zinc (1.67 g, 25.6 mmol) was then added in portions and the reaction was stirred at rt for 1 hr. The reaction mixture was then filtered and the filtrate was concentrated in vacuo. The material was purified by HPLC (Gilson®, Gemini® column: CH$_3$CN, 0.1% NH$_4$OH/water gradient 2-20%) to afford the title compound (90 mg, 0.2 mmol, 3.9% yield). LCMS (LCMS Method D) Rt=0.39 mins, [M+H]$^+$=429.3.

Step 4: 1,15-diamino-8,9,16,17,18,19-hexahydro-7H-6,10-dioxa-2,14,15a,19a-tetraazacyclopentadeca[1,2,3-cd:11,10,9-c'd']diindene-4,12-dicarboxamide

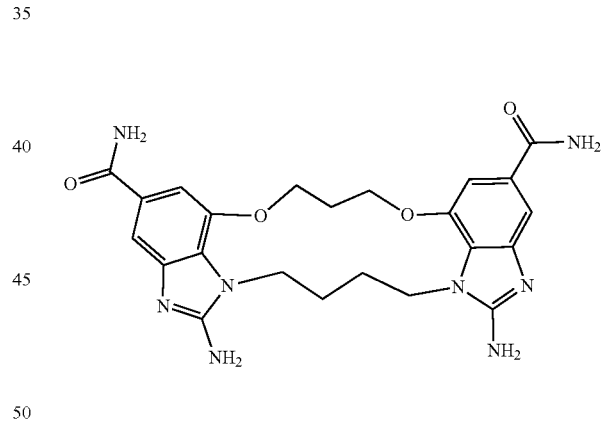

In a 20 mL reaction vial, 1,13-diamino-7,8,14,15,16,17,18,19-octahydro-6H-dibenzo[b,j] [1,12,4,9]dioxadiazacyclopentadecine-3,11-dicarboxamide (140 mg, 0.327 mmol) was stirred in MeOH (5 mL) and treated with cyanogen bromide (69.2 mg, 0.653 mmol). The reaction mixture was stirred at rt overnight. Water (10 mL) was then added to the reaction mixture, the solid was isolated by filtration and was dried in vacuo overnight to afford the title compound (100 mg, 0.188 mmol, 57.6% yield). $^1$H NMR (400 MHz, METHANOL-d$_4$) δ ppm 7.04 (d, J=2.01 Hz, 2H), 6.97 (d, J=1.76 Hz, 2H), 4.30 (s, 4H), 3.04 (br. s., 4H), 2.46-2.33 (m, 2H), 1.45 (br. s., 4H). LCMS (LCMS Method D) Rt=0.47 mins, [M+H]$^+$=479.3.

Example 9

Step 5: 1,15-bis(1-ethyl-3-methyl-1H-pyrazole-5-carboxamido)-8,9,16,17,18,19-hexahydro-7H-6,10-dioxa-2,14,15a,19a-tetraazacyclopentadeca[1,2,3-cd:11,10,9-c'd']diindene-4,12-dicarboxamide

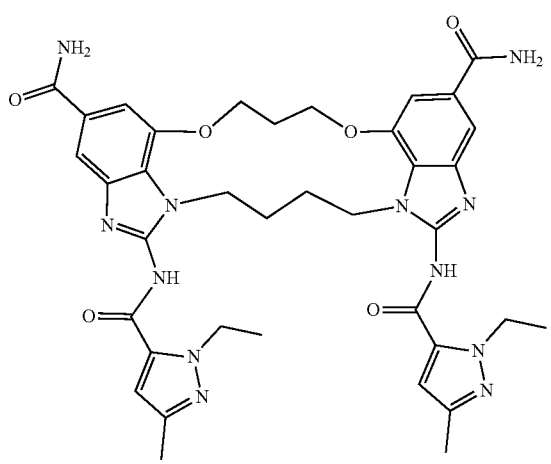 [SMILES: CCn1nc(C)cc1C(=O)Nc1nc2cc(C(N)=O)cc3c2n1CCCCn1c(NC(=O)c2cc(C)nn2CC)nc2cc(C(N)=O)cc(c21)OCCCO3]

To a 20 mL reaction vial was added 1-ethyl-3-methyl-1H-pyrazole-5-carboxylic acid (90 mg, 0.581 mmol), 2-(3H-[1,2,3]triazolo[4,5-b]pyridin-3-yl)-1,1,3,3-tetramethylisouronium hexafluoro-phosphate(V) (221 mg, 0.581 mmol), DIPEA (0.135 mL, 0.775 mmol), DMF (5 mL), followed by the addition of 1,15-diamino-8,9,16,17,18,19-hexahydro-7H-6,10-dioxa-2,14,15a,19a-tetraazacyclopentadeca[1,2,3-cd:11,10,9-c'd']diindene-4,12-dicarboxamide (90 mg, 0.194 mmol). The reaction vial was sealed and heated to 140° C. for 30 min. Water (20 mL) was added to the solution and the resulting solid was isolated by filtration and dried in air to give a brown solid. The crude product was then dissolved in DMSO (6 mL) and water was added (20 mL). The resulting solid was isolated by filtration and dried in vacuo to afford 1,15-bis(1-ethyl-3-methyl-1H-pyrazole-5-carboxamido)-8,9,16,17,18,19-hexahydro-7H-6,10-dioxa-2,14,15a,19a-tetraazacyclopentadeca[1,2,3-cd:11,10,9-c'd']diindene-4,12-dicarboxamide (50 mg, 0.063 mmol, 32.7% yield) as a light brown solid. $^1$H NMR (400 MHz, DMSO-$d_6$) δ ppm 12.84 (br. s., 2H), 8.00 (br. s., 2H), 7.67 (s, 2H), 7.46 (s, 2H), 7.37 (br. s., 2H), 6.59 (s, 2H), 4.60 (d, J=6.78 Hz, 4H), 4.48 (d, J=4.52 Hz, 4H), 4.38 (br. s., 4H), 2.55 (s, 6H), 2.12 (s, 4H), 2.06 (d, J=6.02 Hz, 2H), 1.33 (t, J=7.03 Hz, 6H) LCMS (LCMS Method D) Rt=0.92 mins, [M+H]$^+$=751.5.

Example 10

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide

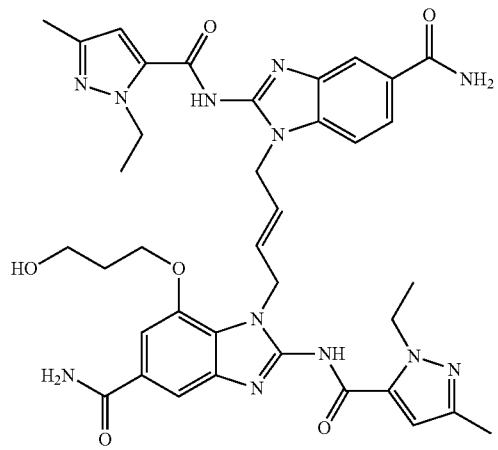 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCO)c21]

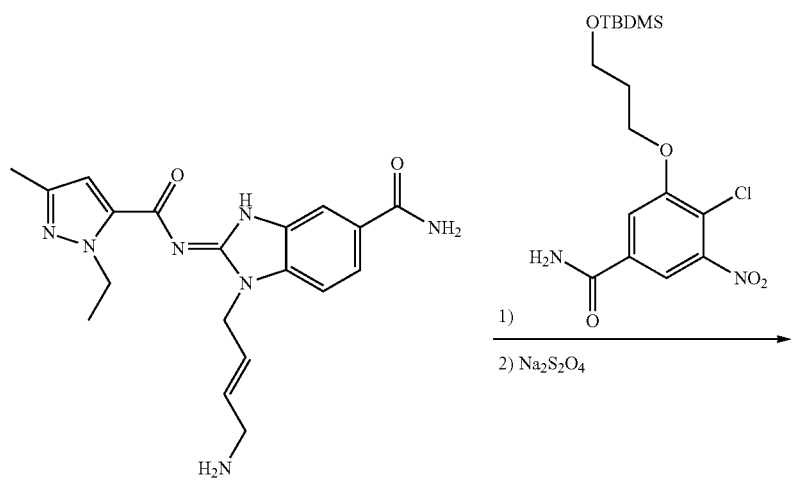

-continued
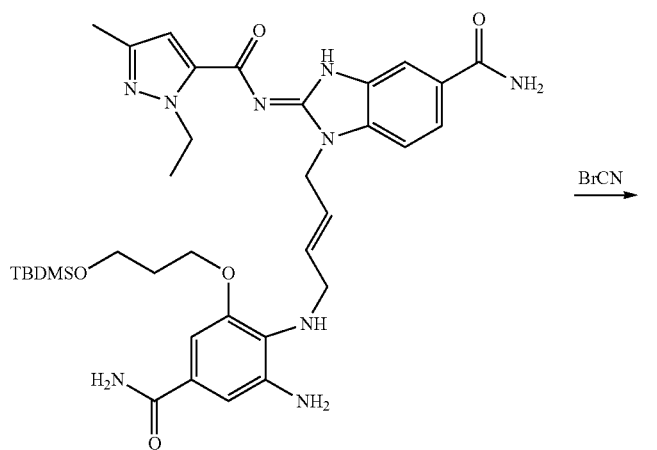
BrCN →
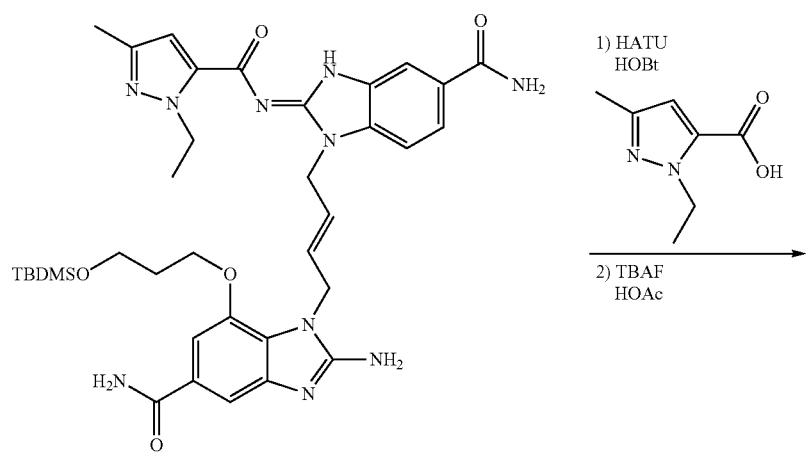
1) HATU
HOBt
[pyrazole carboxylic acid structure]
2) TBAF
HOAc
→
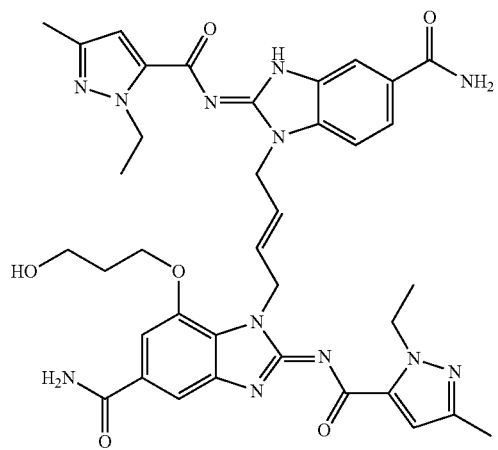

243

Step 1: (E)-1-(4-((2-(3-((tert-Butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide

244

Step 2: (E)-1-(4-((2-Amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzo[d]imidazole-5-carboxamide

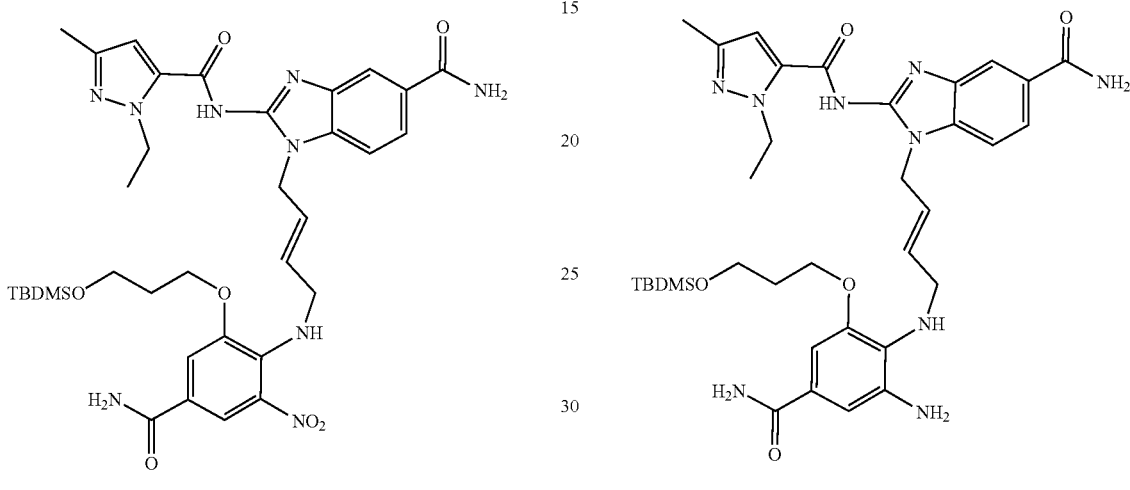

A microwave tube containing (E)-1-(4-aminobut-2-en-1-yl)-2-(1-ethyl-3-methyl-1H-pyrazole-5-carboxamido)-1H-benzo[d]imidazole-5-carboxamide hydrochloride (517 mg, 1.24 mmol, in DMSO (10 mL) was treated with TEA (0.28 mL, 2.0 mmol), followed by K$_2$CO$_3$ (274 mg, 1.98 mmol) and 3-(3-((tert-butyldimethylsilyl)oxy)propoxy)-4-chloro-5-nitrobenzamide (385 mg, 0.990 mmol). The reaction was heated to 75° C. After 7 hr, the mixture was concentrated, and the residue was purified over silica gel, eluting with 10-90% EtOAc to remove impurities, followed by 0-10% MeOH in DCM to yield the title compound (200 mg, 0.273 mmol, 28% yield) as an orange solid. $^1$H NMR (400 MHz, DMSO-d$_6$) δ ppm 8.16 (d, J=1.52 Hz, 1H), 7.94-8.08 (m, 3H), 7.74 (d, J=8.11 Hz, 2H), 7.50 (s, 1H), 7.31-7.43 (m, 3H), 6.62 (s, 1H), 5.74-5.81 (m, 2H), 4.80 (br. s., 2H), 4.59 (d, J=6.84 Hz, 2H), 4.13 (br. s., 2H), 4.01 (t, J=6.08 Hz, 2H), 3.63 (t, J=5.96 Hz, 2H), 2.16 (s, 3H), 1.76-1.88 (m, 2H), 1.33 (t, J=7.10 Hz, 3H), 0.74-0.82 (m, 9H), −0.06 (s, 6H); LCMS (LCMS Method D): Rt=1.23 min, [M+H]$^+$=734.6

(E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide (1 g, 1.363 mmol) was suspended in MeOH (20 mL) and ammonium hydroxide (4.62 mL, 34.1 mmol) was added and stirred for 5 mins at RT. Sodium hydrosulfite (1.675 g, 8.18 mmol) in Water (5 mL) was then added. After 60 mins, EtOAc (300 ml) was added and the mixture was extracted with water (50 ml×3). The organic phase was separated, dried with Na$_2$SO$_4$, and concentrated in vacuo to afford title compound (710 mg, 1.009 mmol, 74.0% yield) as light yellow solid which was used without further purification. $^1$H NMR (400 MHz, DMSO-d$_6$) δ ppm 12.80 (br. s., 1H), 8.00 (s, 1H), 7.97 (br. s., 1H), 7.75 (dd, J=8.49, 1.14 Hz, 1H), 7.63 (br. s., 1H), 7.28-7.41 (m, 2H), 7.00 (br. s., 1H), 6.84 (d, J=1.52 Hz, 1H), 6.74 (d, J=1.52 Hz, 1H), 6.65 (s, 1H), 5.79-5.96 (m, 1H), 5.64-5.78 (m, 1H), 4.81 (d, J=4.82 Hz, 2H), 4.68 (br. s., 2H), 4.61 (d, J=7.10 Hz, 2H), 3.92 (t, J=5.83 Hz, 2H), 3.84 (br. s., 1H), 3.63 (t, J=6.08 Hz, 2H), 3.57 (br. s., 2H), 2.17 (s, 3H), 1.70-1.82 (m, 2H), 1.34 (t, J=7.10 Hz, 3H), 0.68-0.83 (m, 9H), −0.06 (s, 6H); LCMS (LCMS Method J): Rt=1.05 min, [M+H]$^+$=704.3

Step 3: (E)-2-Amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide

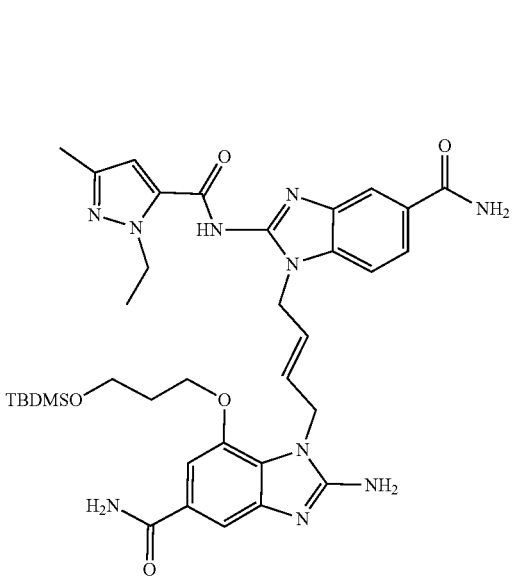 [SMILES: CCn1nc(C)cc1C(=O)Nc1nc2cc(C(N)=O)ccc2n1C/C=C/Cn1c(N)nc2cc(C(N)=O)cc(OCCCO[Si](C)(C)C(C)(C)C)c21]

To a solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzo[d]imidazole-5-carboxamide (120 mg, 0.170 mmol) in MeOH (5 mL) was added cyanogen bromide (36 mg, 0.34 mmol) at RT. After 2 hr, the reaction was concentrated, and EtOAc was added (10 mL). After stirring 30 min, the solid was isolated by filtration, and washed with EtOAc to yield the title compound (120 mg, 0.165 mmol, 97% yield) as a light brown solid, which was used without further purification. $^1$H NMR (400 MHz, MeOH-d$_4$) δ ppm 8.00 (d, J=1.27 Hz, 1H), 7.81 (dd, J=8.36, 1.77 Hz, 1H), 7.49 (d, J=1.27 Hz, 1H), 7.39-7.45 (m, 1H), 7.36 (d, J=1.27 Hz, 1H), 6.61 (s, 1H), 5.82-5.99 (m, 2H), 4.96-5.01 (m, 2H), 4.56-4.65 (m, 2H), 4.12 (t, J=6.21 Hz, 2H), 3.62-3.75 (m, 2H), 2.18-2.29 (m, 3H), 1.79 (t, J=6.21 Hz, 2H), 1.24-1.54 (m, 5H), 0.84-0.98 (m, 9H), −0.01-0.11 (m, 6H); LCMS (LCMS Method D): Rt=0.97 min, [M+H]$^+$=729.5

Step 4: (E)-7-(3-((tert-Butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

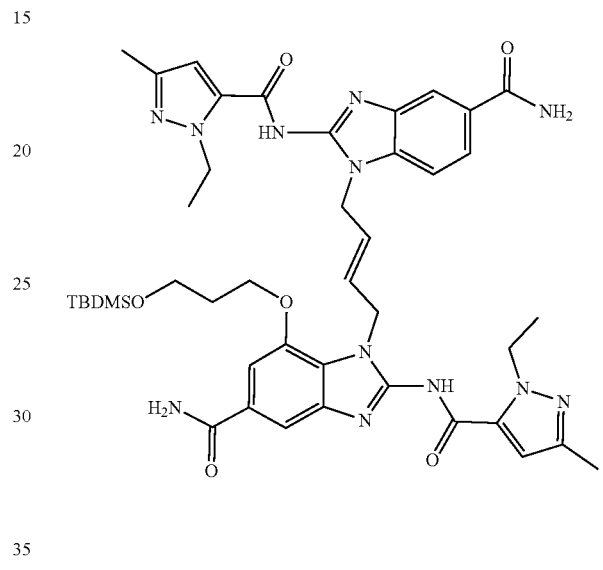

To a solution of 1-ethyl-3-methyl-1H-pyrazole-5-carboxylic acid (33 mg, 0.21 mmol) in DMF (3 mL) was added HATU (75 mg, 0.20 mmol) and HOBt (12.6 mg, 0.082 mmol). After stirring at RT 10 min, triethylamine (0.09 mL, 0.66 mmol) was added, followed by (E)-2-amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide (120 mg, 0.165 mmol) and the reaction was continued at RT. After 3 days, a solid was precipitated out of the reaction by the dropwise addition of water. The solid was isolated by filtration and washed with water. The solid was then purified over silica gel (12 g HP Gold column), eluting with 0-20% MeOH in DCM. The desired fractions were combined and concentrated to yield the title compound (29 mg, 0.034 mmol, 20% yield) as an off-white solid. $^1$H NMR (400 MHz, THF-d$_4$) δ ppm 12.53 (br. s., 2H), 8.00 (d, J=1.01 Hz, 1H), 7.61 (d, J=1.01 Hz, 1H), 7.53 (dd, J=8.36, 1.52 Hz, 1H), 7.36 (d, J=6.84 Hz, 2H), 7.29 (d, J=1.01 Hz, 1H), 7.12 (d, J=8.36 Hz, 1H), 6.83 (br. s., 2H), 6.66 (d, J=2.28 Hz, 2H), 6.06 (dt, J=15.46, 5.58 Hz, 1H), 5.87 (dt, J=15.46, 5.83 Hz, 1H), 5.09 (d, J=5.32 Hz, 2H), 4.89 (d, J=5.58 Hz, 2H), 4.59-4.72 (m, 4H), 3.97 (t, J=6.21 Hz, 2H), 3.69 (t, J=5.96 Hz, 2H), 2.20 (s, 6H), 1.73-1.78 (m, 2H), 1.40 (td, J=7.03, 1.14 Hz, 6H), 0.82-0.94 (m, 9H), −0.03-0.09 (m, 6H); LCMS (LCMS Method D): Rt=1.21 min, [M/2+H]$^+$=433.6

247

Step 5: (E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide

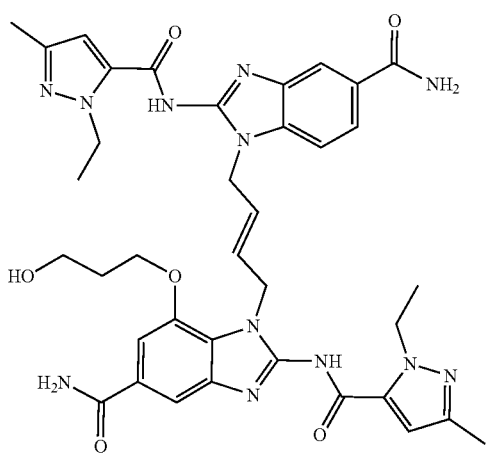

To a solution of (E)-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (25 mg, 0.029 mmol) and 1M TBAF in THF (0.058 mL, 0.058 mmol) in THF (2 mL) at RT was added acetic acid (3.3 μL, 0.058 mmol). After 12 hr the reaction was concentrated, triturated with diethyl ether and EtOAc, and further purified over silica gel (12 g Gold column) eluting with 0-25% methanol in DCM. The desired fractions were concentrated to yield the title compound (7 mg, 9 μmole, 32% yield) as an off-white solid. $^1$H NMR (400 MHz, THF-$d_4$) δ ppm 12.51 (br. s., 2H), 8.01 (d, J=1.01 Hz, 2H), 7.55-7.65 (m, 3H), 7.33 (d, J=1.01 Hz, 2H), 7.14-7.20 (m, 2H), 6.00-6.15 (m, 2H), 5.82-5.96 (m, 2H), 5.05-5.13 (m, 4H), 4.04 (t, J=6.59 Hz, 4H), 3.78-3.90 (m, 5H), 2.19 (d, J=2.03 Hz, 6H), 1.87-2.00 (m, 2H), 1.36-1.44 (m, 6H); LCMS (LCMS Method D): Rt=0.79 min, [M+H]$^+$=751.4.

248

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

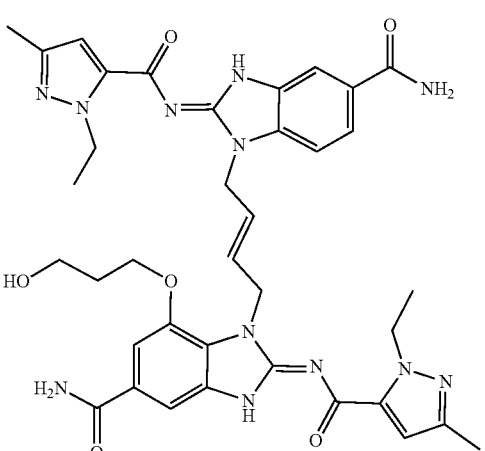

or (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

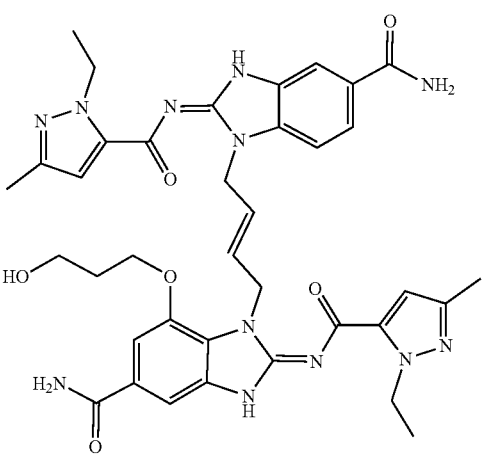

Example 11
(E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide
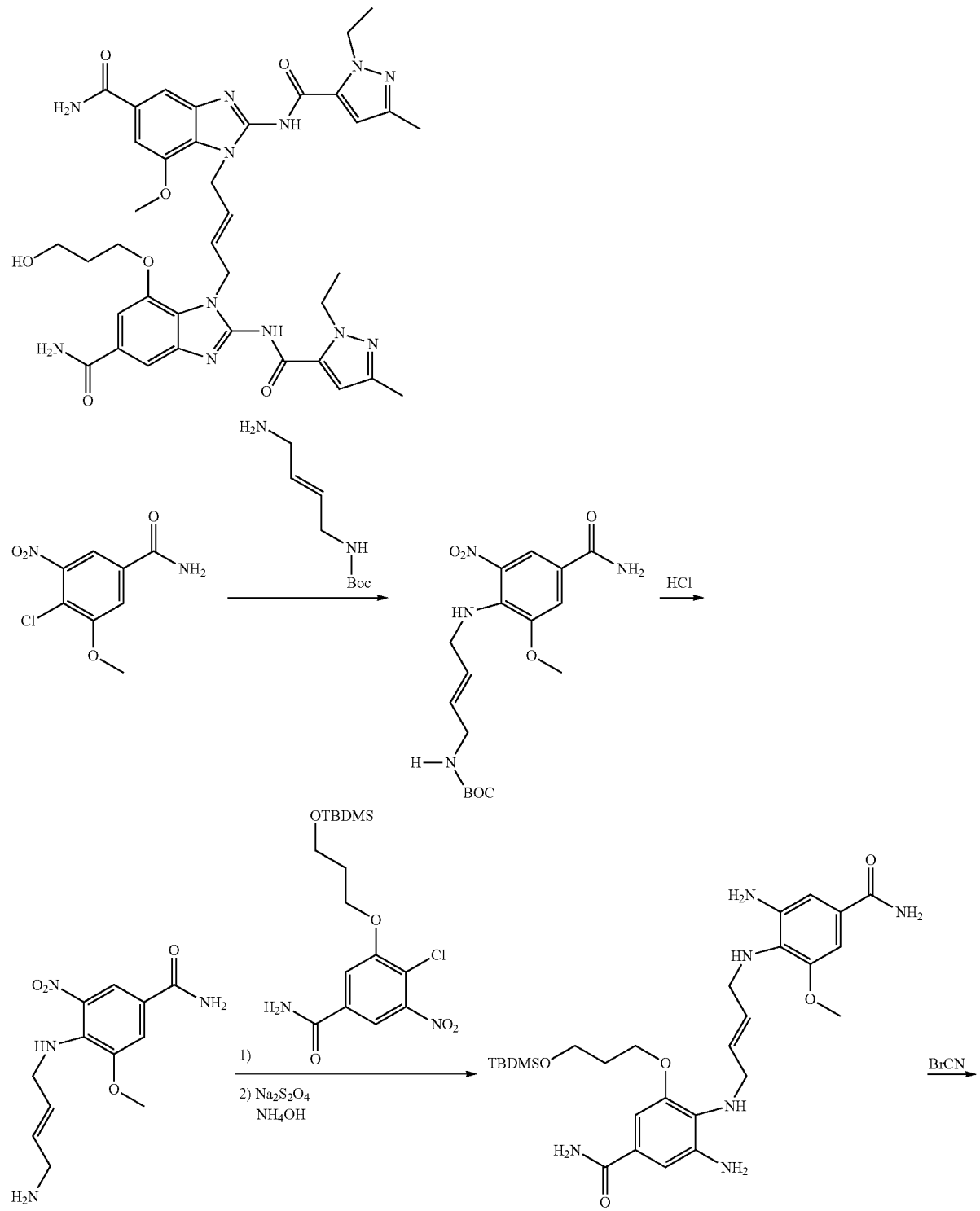

-continued

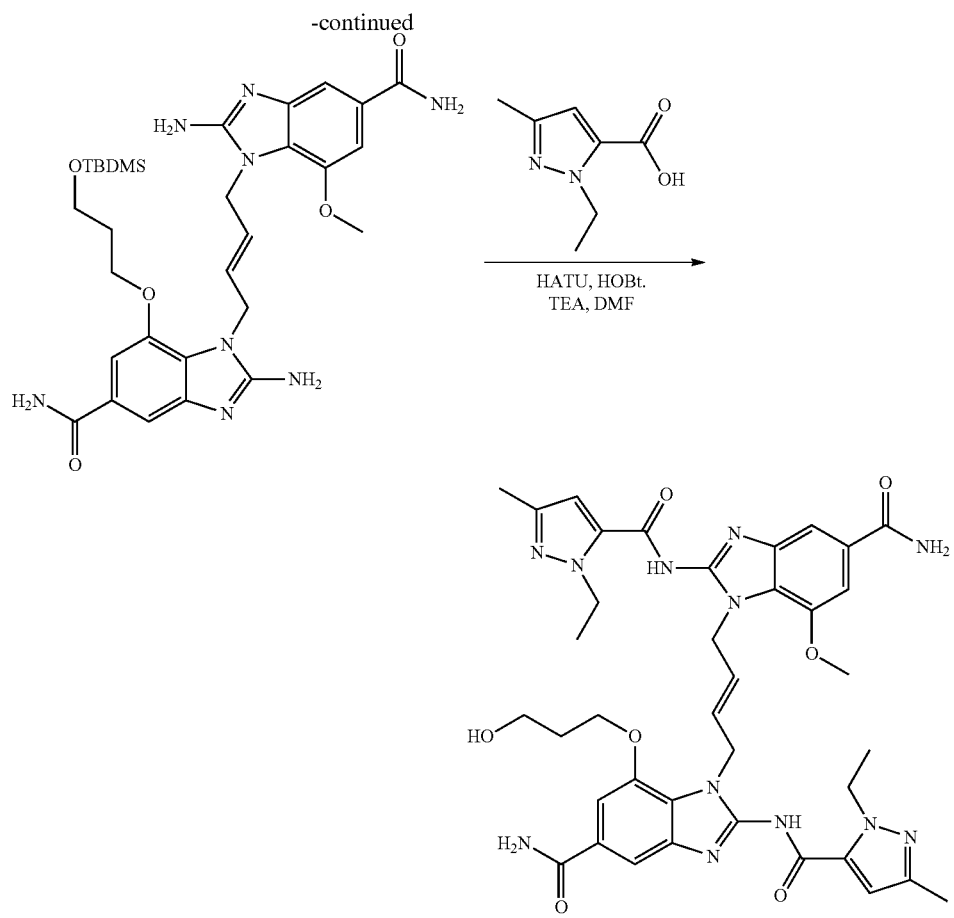

Step 1: (E)-tert-Butyl (4-((4-carbamoyl-2-methoxy-6-nitrophenyl)amino)but-2-en-1-yl)carbamate To a suspension of 4-chloro-3-methoxy-5-nitrobenzamide (1.50 g, 6.50 mmol) in EtOH (25 mL) was added (E)-tert-butyl (4-aminobut-2-en-1-yl)carbamate (1.454 g, 7.81 mmol) and DIEA (3.4 mL, 20 mmol). The reaction was stirred at 120° C. in a sealed tube overnight and allowed to cool to RT. The resulting orange solid was collected by filtration and washed with EtOH to afford the title compound (2.10 g, 5.52 mmol, 85% yield). $^1$H NMR (400 MHz, DMSO-d$_6$) δ ppm 8.19 (d, J=1.77 Hz, 1H) 8.03 (br. s., 1H) 7.76 (t, J=6.08 Hz, 1H) 7.55 (d, J=1.52 Hz, 1H) 7.34 (br. s., 1H) 6.95 (t, J=5.45 Hz, 1H) 5.53 (br. s., 2H) 4.09 (br. s., 2H) 3.88 (s, 3H) 3.48 (br. s., 2H) 1.35 (s, 9H); LCMS (LCMS Method D): Rt=0.89 min, [M-t-Bu+H]$^+$=325.1

Step 2: (E)-4-((4-Aminobut-2-en-1-yl)amino)-3-methoxy-5-nitrobenzamide, Hydrochloride

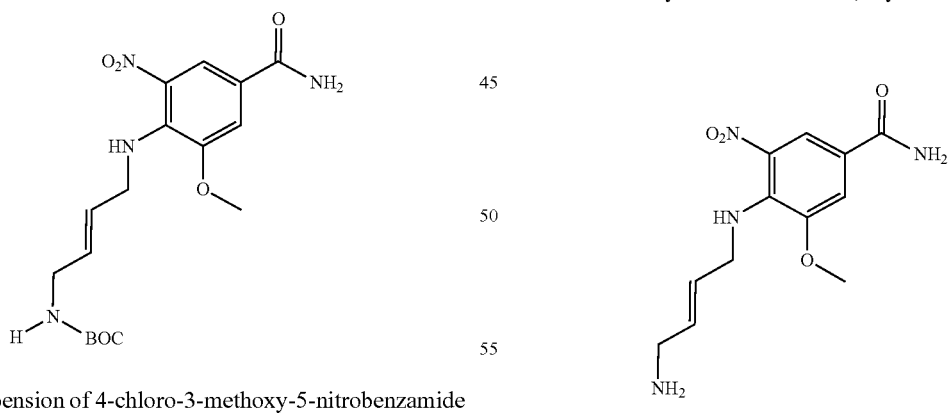

To a suspension of tert-butyl (E)-(4-((4-carbamoyl-2-methoxy-6-nitrophenyl)amino)but-2-en-1-yl)carbamate (20 g, 47.3 mmol) in methanol (50 mL) was added slowly 4M HCl in dioxane (100 mL, 400 mmol). The reaction mixture was stirred at RT for 1 hr, then the resulting solid was isolated by filtration, washed with Et$_2$O 3 times (100 ml×3), and dried under high vacuum column to provide the title compound (13.90 g, 43.9 mmol, 93% yield). $^1$H NMR (400 MHz, DMSO-d$_6$) δ ppm 8.22 (d, J=2.03 Hz, 1H), 7.76-8.16

(br. m., 5H), 7.60 (d, J=2.03 Hz, 1H), 7.37 (br. s., 1H), 5.87 (dt, J=15.52, 5.80 Hz, 1H), 5.62 (dt, J=15.65, 6.37 Hz, 1H), 4.18 (d, J=5.32 Hz, 2H), 3.90 (s, 3H), 3.40 (t, J=5.70 Hz, 2H); LCMS (LCMS Method K): Rt=0.41 min, [M+H]$^+$=281.1

Step 3: (E)-3-(3-((tert-Butyldimethylsilyl)oxy) propoxy)-4-((4-((4-carbamoyl-2-methoxy-6-nitrophenyl)amino)but-2-en-1-yl)amino)-5-nitrobenzamide Step 4: (E)-3-Amino-4-((4-((2-amino-4-carbamoyl-6-methoxyphenyl)amino)but-2-en-1-yl)amino)-5-(3-((tert-butyldimethylsilyl)oxy)propoxy)benzamide

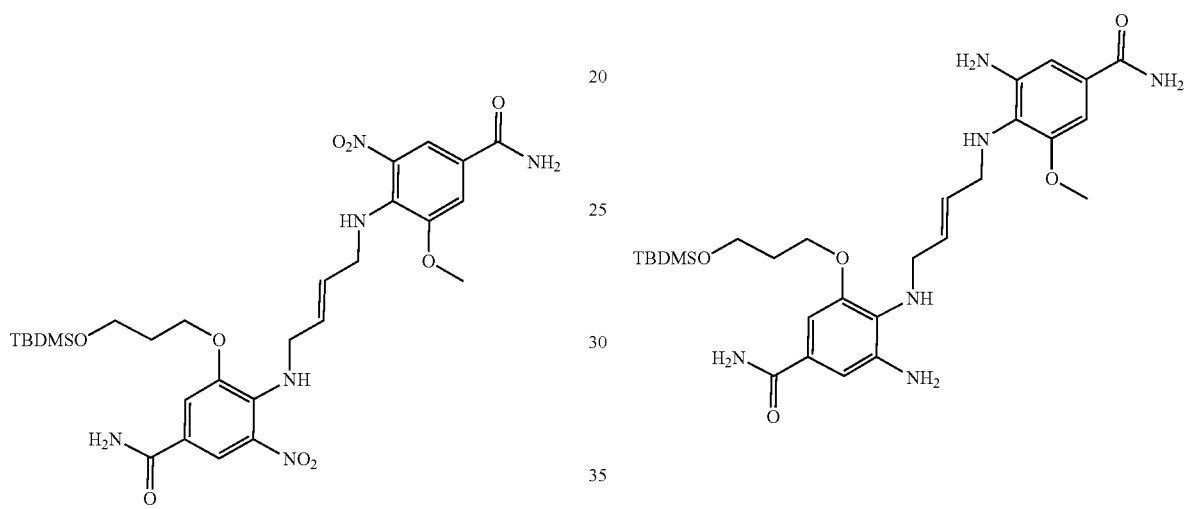

To a suspension of (E)-4-((4-aminobut-2-en-1-yl)amino)-3-methoxy-5-nitrobenzamide, hydrochloride (9.77 g, 30.9 mmol) in 1-Butanol (90 mL) was added sodium bicarbonate (5.18 g, 61.7 mmol) and DIEA (22.45 mL, 129 mmol). The mixture was stirred at RT for 10 min, then 3-(3-((tert-butyldimethylsilyl)oxy)propoxy)-4-chloro-5-nitrobenzamide (10 g, 25.7 mmol) was added and the reaction mixture was stirred at 120° C. overnight. The solution was allowed to cool to RT and the resulting dark orange solid was isolated by filtration and washed EtOH (15 ml). The crude material was then stirred in water (100 mL) for 10 min., filtered and washed again with water (100 mL), EtOAc (50 mL) and EtOH (20 mL). The material was dried in vacuum oven to provide the title compound (10 g, 14.54 mmol, 56.5% yield). $^1$H NMR (400 MHz, DMSO-d$_6$) δ ppm 8.16 (t, J=1.77 Hz, 2H), 8.04 (br. s., 2H), 7.72 (d, J=5.83 Hz, 2H), 7.53 (s, 2H), 7.35 (br. s., 2H), 5.53-5.68 (m, 2H), 3.99-4.16 (m, 6H), 3.74 (t, J=6.08 Hz, 2H), 3.43 (br. s., 3H), 1.92 (t, J=6.08 Hz, 2H), 0.74-0.88 (m, 9H), 0.00 (s, 6H); LCMS (LCMS Method K): Rt=1.32 min, [M+H]$^+$=633.4

To a solution of (E)-3-(3-((tert-butyldimethylsilyl)oxy) propoxy)-4-((4-((4-carbamoyl-2-methoxy-6-nitrophenyl) amino)but-2-en-1-yl)amino)-5-nitrobenzamide (5 g, 7.90 mmol) in methanol (120 mL) at 0° C., was added sodium hydrosulfite (16.19 g, 79 mmol) in water (50 mL) and ammonium hydroxide (25.6 mL, 198 mmol). The reaction mixture was allowed to warm to RT. After 10 min. at RT, the mixture was extracted with EtOAc (100×3), dried over Na$_2$SO$_4$, and concentrated in vacuo. The crude material was purified by silica gel chromatography (Isco column) eluting with hexane: (EtOH: EtOAc 3:1) with 2% NH$_4$OH additive (0-100% gradient) to yield the title compound (2.1 g, 3.34 mmol, 42.2% yield). $^1$H NMR (400 MHz, DMSO-d$_6$) δ ppm 7.63 (br. s., 2H), 6.99 (d, J=5.58 Hz, 2H), 6.72-6.91 (m, 6H), 5.62-5.73 (m, 2H), 4.66 (d, J=8.36 Hz, 4H), 4.00 (t, J=5.96 Hz, 2H), 3.69-3.84 (m, 4H), 3.40-3.49 (m, 2H), 3.35 (s, 3H), 1.90 (t, J=6.08 Hz, 2H), 0.79-0.91 (m, 9H), −0.03-0.07 (m, 6H); LCMS (LCMS Method K): Rt=0.46 min, [M+H]$^+$=573.3

Step 5: (E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

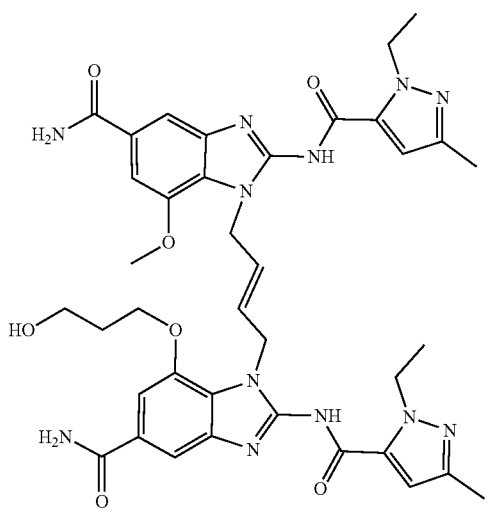 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCO)c21]

To a solution of (E)-3-amino-4-((4-((2-amino-4-carbamoyl-6-methoxyphenyl)amino)but-2-en-1-yl)amino)-5-(3-((tert-butyldimethylsilyl)oxy)propoxy)benzamide (1.02 g, 1.78 mmol) in MeOH (15 mL) was added cyanogen bromide (943 mg, 8.90 mmol). After stirring at room temperature for 20 min, a light yellow solid precipitated, which was collected by filtration, washed with EtOAc and determined by LCMS to be a mixture of ⅔ of the TBDMS-protected compound (E)-2-amino-1-(4-(2-amino-5-carbamoyl-7-methoxy-1H-benzo[d]imidazol-1-yl)but-2-en-1-yl)-7-(3-((tert-butyldimethylsilyl)oxy)propoxy)-1H-benzo[d]imidazole-5-carboxamide and ⅓ deprotected alcohol (E)-2-amino-1-(4-(2-amino-5-carbamoyl-7-(3-hydroxypropoxy)-1H-benzo[d]imidazol-1-yl)but-2-en-1-yl)-7-methoxy-1H-benzo[d]imidazole-5-carboxamide. This mixture (ca. 900 mg) was added, after TEA (1.07 mL, 7.7 mmol), to a solution of 1-ethyl-3-methyl-1H-pyrazole-5-carboxylic acid (0.89 g, 5.78 mmol), HATU (2.2 g, 5.78 mmol) and HOBt (443 mg, 2.89 mmol) in DMF (10 mL) which had been stirred for 15 min at RT. After 20 hr, 5N aq NaOH (3 mL) was added. After 30 min at RT, water (30 mL) was added, and the resulting white precipitate was collected by filtration and purified over silica gel (40 g Isco column), eluting with 0-30% MeOH in DCM to yield the title compound (545 mg, 0.684 mmol, 38% yield for 2 steps). $^1$H NMR (400 MHz, DMSO-d$_6$) δ ppm 12.83 (br. s., 2H), 7.99 (br. s., 2H), 7.64 (d, J=3.04 Hz, 2H), 7.28-7.42 (m, 4H), 6.52 (s, 2H), 5.84 (br. s., 2H), 4.91 (br. s., 4H), 4.53 (d, J=6.34 Hz, 4H), 4.06 (t, J=6.34 Hz, 2H), 3.75 (s, 3H), 3.45 (t, J=5.96 Hz, 2H), 2.10 (d, J=2.53 Hz, 6H), 1.71 (t, J=6.08 Hz, 2H), 1.27 (td, J=7.03, 1.90 Hz, 6H); LCMS (LCMS Method D): Rt=0.85 min, [M/2+H]$^+$=391.3833

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

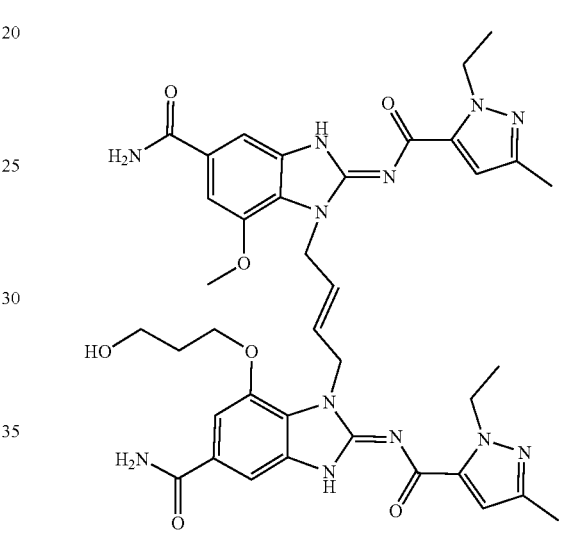

or (Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

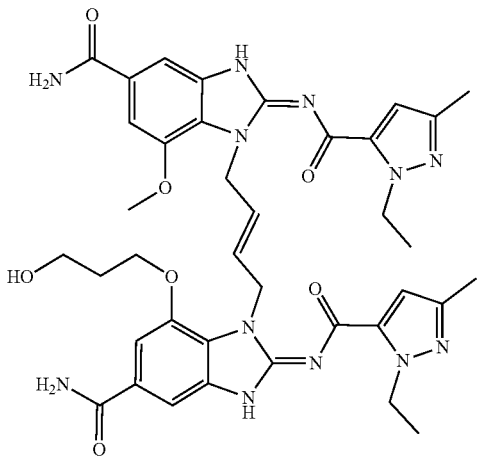 [SMILES: CCn1nc(C)cc1C(=O)/N=c1/[nH]c2cc(C(N)=O)cc(OC)c2n1C/C=C/Cn1/c(=N\C(=O)c2cc(C)nn2CC)[nH]c2cc(C(N)=O)cc(OCCCO)c21]

Example 12
(E)-1,1'-(But-2-ene-1,4-diyl)bis(2-(1-ethyl-3-methyl-1H-pyrazole-5-carboxamido)-7-(3-morpholino-propoxy)-1H-benzo[d]imidazole-5-carboxamide)
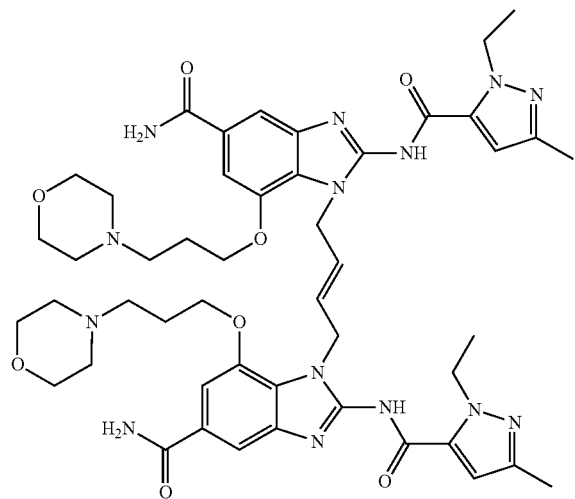 [SMILES: CCn1nc(C)cc1C(=O)Nc1nc2cc(C(N)=O)cc(OCCCN3CCOCC3)c2n1C/C=C/Cn1c(NC(=O)c2cc(C)nn2CC)nc2cc(C(N)=O)cc(OCCCN3CCOCC3)c21]
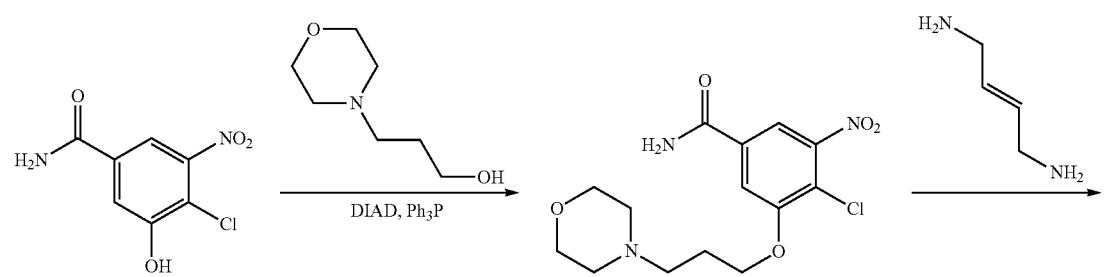
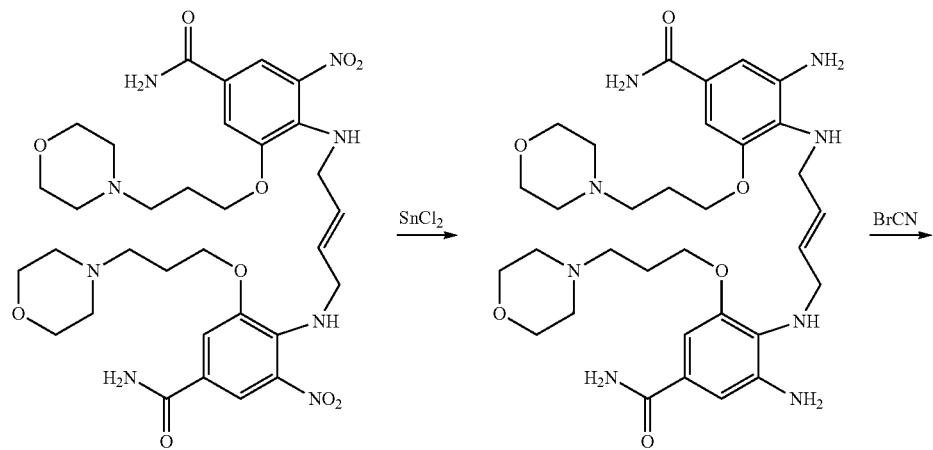

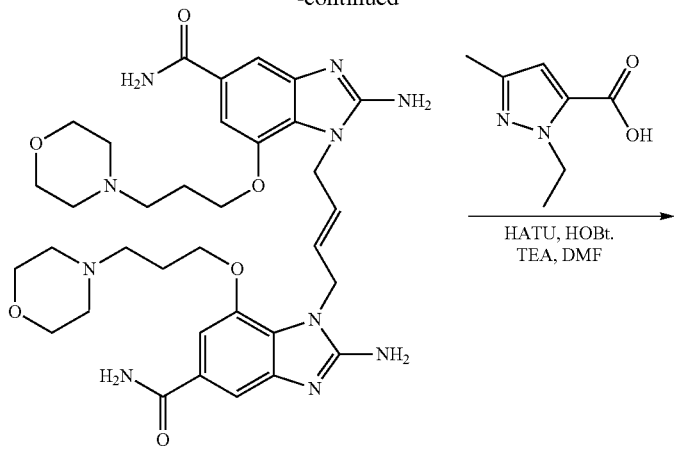

Step 1: 4-Chloro-3-(3-morpholinopropoxy)-5-nitrobenzamide

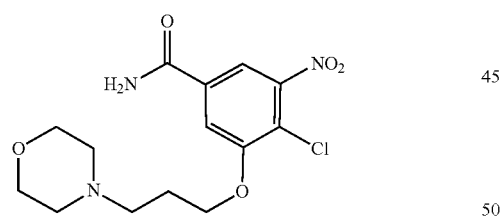

To a suspension of 4-chloro-3-hydroxy-5-nitrobenzamide (1.00 g, 4.62 mmol), 3-morpholinopropan-1-ol (1.00 g, 6.89 mmol) and triphenylphosphine (1.82 g, 6.93 mmol) in DCM (46 mL) was added DIAD (1.35 mL, 6.93 mmol). After stirring 1 hr, additional triphenylphosphine (480 mg, 1.83 mmol) was added, and after an additional 30 min, DIAD (0.40 mL, 2.1 mmol) was added. After 1 hr, the reaction was partitioned between saturated aq. ammonium chloride and DCM. The organic layer was dry-loaded and purified on silica gel (ISCO-R$^f$ 4 g column), eluting with 0-100% (3:1 EtOAc: EtOH) in hexane to afford the title compound (630 mg, 1.83 mmol, 40% yield). $^1$H NMR (400 MHz, DMSO-d$_6$) δ ppm 8.30 (s, 1 H), 8.05 (d, J=1.77 Hz, 1H), 7.88 (d, J=1.77 Hz, 1H), 7.80 (s, 1H), 4.28 (t, J=6.21 Hz, 2H), 3.57 (t, J=4.56 Hz, 4H), 2.41-2.47 (m, 2H), 2.37 (br. s., 4H), 1.97 (dd, 13.94, 7.35 Hz, 2H); LCMS (LCMS Method D): Rt=0.51 min, [M+H]$^+$=344.1

Step 2: (E)-4,4'-(But-2-ene-1,4-diylbis(azanediyl))bis(3-(3-morpholinopropoxy)-5-nitrobenzamide)

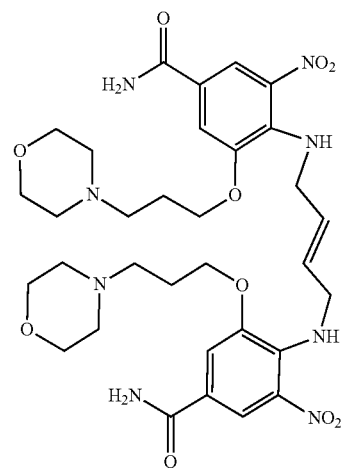 [SMILES: NC(=O)c1cc(OCCCN2CCOCC2)c(NC/C=C/CNc2c(OCCCN3CCOCC3)cc(C(N)=O)cc2[N+](=O)[O-])c([N+](=O)[O-])c1]

To a suspension of (E)-but-2-ene-1,4-diamine dihydrochloride (171 mg, 1.07 mmol) and 4-chloro-3-(3-morpholinopropoxy)-5-nitrobenzamide (630 mg, 1.65 mmol) in EtOH (4 mL) was added DIEA (1.0 mL, 5.8 mmol). The reaction was heated at 120° C. in a heating block, and after 47 hr, additional (E)-but-2-ene-1,4-diamine dihydrochloride (30 mg, 0.19 mmol) was added. Heating was continued at 120° C. for approximately 3 days, then the reaction was dry-loaded and purified on silica gel (ISCO-Rf 120 g column), eluting with 0-40% MeOH in DCM to afford the title compound (130 mg, 0.186 mmol, 11% yield) as a bright orange solid. $^1$H NMR (400 MHz, DMSO-$d_6$) δ ppm 8.18 (d, J=1.77 Hz, 2H), 8.04 (br. s., 2H), 7.76-7.85 (m, 2H), 7.51 (d, J=1.52 Hz, 2H), 7.35 (br. s., 2H), 5.63 (br. s., 2H), 4.13 (br. s., 4H), 4.01 (t, J=6.34 Hz, 4H), 3.55 (t, J=4.56 Hz, 8H), 2.27-2.42 (m, 12H), 1.86 (t, J=6.72 Hz, 4H); LCMS (LCMS Method D): Rt=0.53 min, [M+H]$^+$=701.4623

Step 3: (E)-4,4'-(But-2-ene-1,4-diylbis(azanediyl)) bis(3-amino-5-(3-morpholinopropoxy)benzamide) dihydrochloride

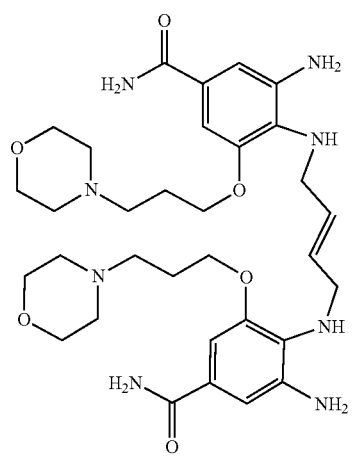 [SMILES: NC(=O)c1cc(N)c(NC/C=C/CNc2c(N)cc(C(N)=O)cc2OCCCN2CCOCC2)c(OCCCN2CCOCC2)c1]

To tin (II) chloride (40.6 mg, 0.214 mmol) in conc. aq HCl (892 μL, 10.7 mmol) was added (E)-4,4'-(but-2-ene-1,4-diylbis(azanediyl))bis(3-(3-morpholinopropoxy)-5-nitrobenzamide) (15 mg, 0.021 mmol). After 20 min, the reaction was allowed to cool in a refrigerator and after 15 min the resulting solid was collected by filtration to afford the title compound (12 mg, 0.017 mmol, 79% yield) as a white solid. $^1$H NMR (400 MHz, DMSO-$d_6$) δ ppm 11.07 (br. s., 2H), 7.99 (br. s., 2H), 7.41 (br. s., 2H), 7.05 (s, 2H), 6.91 (br. s., 2H), 5.94 (br. s., 2H), 3.97-4.08 (m, 8H), 3.78-3.88 (m, 8H), 3.48 (d, J=12.17 Hz, 4H), 3.35-3.43 (m, 4H), 3.05-3.19 (m, 4H), 2.21 (br. s., 4H); LCMS (LCMS Method D): Rt=0.34 min, [M/2+H]$^+$=321.3990

Step 4: (E)-1,1'-(But-2-ene-1,4-diyl)bis(2-amino-7-(3-morpholinopropoxy)-1H-benzo[d]imidazole-5-carboxamide) dihydrobromide

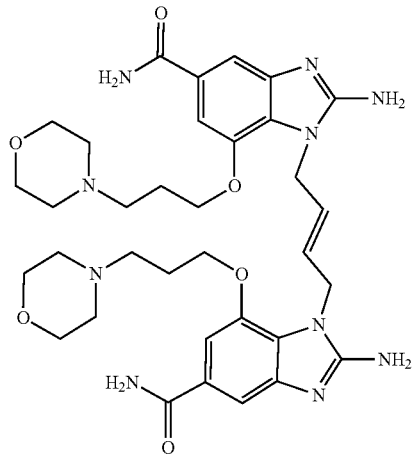 [SMILES: NC(=O)c1cc(OCCCN2CCOCC2)c2c(c1)nc(N)n2C/C=C/Cn1c(N)nc2cc(C(N)=O)cc(OCCCN3CCOCC3)c21]

To a solution of (E)-4,4'-(but-2-ene-1,4-diylbis (azanediyl))bis(3-amino-5-(3-morpholinopropoxy)benzamide) dihydrochloride (102 mg, 0.143 mmol) in water (1.4 mL) was added cyanogen bromide (136 mg, 1.29 mmol). After 2 days at RT the reaction was added dropwise to acetonitrile (100 mL), and the resulting white solid was collected by filtration to afford the title compound (76 mg, 0.09 mmol, 62% yield). $^1$H NMR (400 MHz, DMSO-$d_6$) δ ppm 13.21 (br. s., 2H), 11.16 (br. s., 2H), 8.88 (br. s., 2H), 8.13 (br. s., 2H), 7.55 (s, 2H), 7.50 (br. s., 2H), 7.42 (s, 2H), 5.71 (br. s., 2H), 4.91 (br. s., 4H), 4.13 (br. s., 4H), 3.97 (br. s., 4H), 3.82 (br. s., 4H), 3.29-3.40 (m, 4H), 3.17 (br. s., 4H), 2.99-3.09 (m, 4H) 2.08 (br. s., 4H); LCMS (LCMS Method D): Rt=0.28 min, [M+H]$^+$=691.6058

Step 5: (E)-1,1'-(but-2-ene-1,4-diyl)bis(2-(1-ethyl-3-methyl-1H-pyrazole-5-carboxamido)-7-(3-morpholinopropoxy)-1H-benzo[d]imid-azole-5-carboxamide)

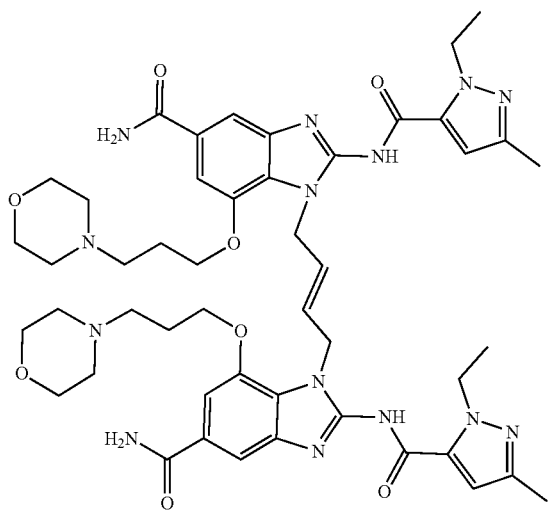 [SMILES: CCn1nc(C)cc1C(=O)Nc1nc2cc(C(N)=O)cc(OCCCN3CCOCC3)c2n1C/C=C/Cn1c(NC(=O)c2cc(C)nn2CC)nc2cc(C(N)=O)cc(OCCCN3CCOCC3)c21]

To a solution of 1-ethyl-3-methyl-1H-pyrazole-5-carboxylic acid (133 mg, 0.862 mmol), HATU (328 mg, 0.862 mmol) and HOBt (66.0 mg, 0.431 mmol) in N,N-dimethylformamide (DMF) (1150 µL) was added a suspension of (E)-1,1'-(but-2-ene-1,4-diyl)bis(2-amino-7-(3-morpholinopropoxy)-1H-benzo[d]imidazole-5-carboxamide), dihydrobromide (209 mg, 0.245 mmol) and TEA (240 µL, 1.724 mmol) in N,N-dimethylformamide (DMF) (4598 µL). The reaction was stirred at rt overnight. The reaction was concentrated to dryness under a stream of nitrogen. The resulting residue was dissolved in methanol and dry-loaded onto silica gel for purification via ISCO-Rf, 40 g, 0%-50% methanol, DCM. Desired fractions were concentrated to dryness to afford (E)-1,1'-(but-2-ene-1,4-diyl)bis(2-(1-ethyl-3-methyl-1H-pyrazole-5-carboxamido)-7-(3-morpholinopropoxy)-1H-benzo[d]imid-azole-5-carboxamide) (112 mg, 0.115 mmol, 47% yield) as an off-white solid. $^1$H NMR (400 MHz, DMSO-d$_6$) δ ppm 12.84 (br. s., 2H), 7.98 (br. s., 2H), 7.66 (d, J=1.01 Hz, 2H), 7.36 (br. s., 2H), 7.25 (s, 2H), 6.58 (s, 2H), 5.82 (br. s., 2H), 4.92 (br. s., 4H), 4.57 (q, J=7.10 Hz, 4H), 3.85 (t, J=5.96 Hz, 4H), 3.45 (t, J=4.18 Hz, 8H), 2.09-2.24 (m, 18H), 1.54 (t, J=6.72 Hz, 4H), 1.32 (t, J=7.10 Hz, 6H); LCMS (LCMS Method D): Rt=0.65 min, [M+H]$^+$=963.938

Example 13

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide

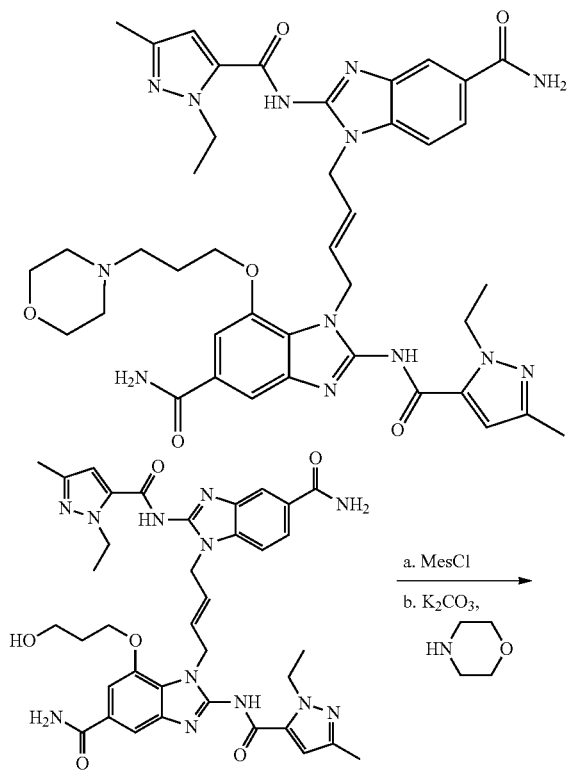

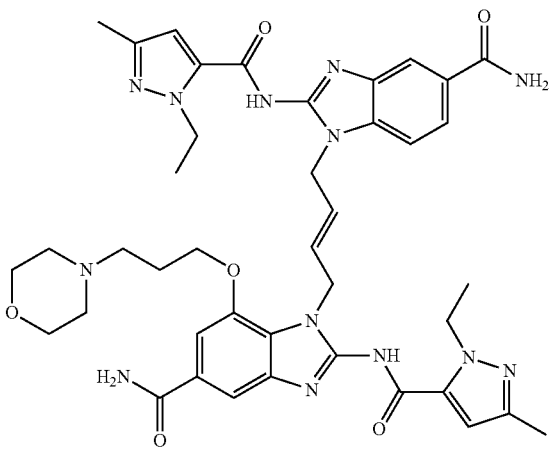

Step 1: To (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxy-propoxy)-1H-benzo[d]imidazole-5-carboxamide (17 mg, 0.023 mmol) in THF (3 mL) was added triethylamine (9.5 µL, 0.068 mmol). After 10 min at RT, methanesulfonyl chloride (2.1 µL, 0.027 mmol) was added. After 2 hr, LCMS indicated presence of (E)-3-((5-Carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl methanesulfonate, and the reaction mixture was used directly in the next reaction. LCMS (LCMS Method D): Rt=0.80 min, [M+H]$^+$=751.6010.

Step 2: To a solution of (E)-3-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl methanesulfonate (18 mg, 0.022 mmol) in THF (5 mL) was added morpholine (9.5 µL, 0.11 mmol) and K$_2$CO$_3$ (9.0 mg, 0.065 mmol). After 5 hr at RT, the reaction was heated to 45° C. for 2 hr and then concentrated. The residue was purified over silica gel eluting with 0-20% MeOH in DCM to yield the title compound (7 mg, 9 µmole, 39% yield). $^1$H NMR (400 MHz, MeOH-d$_4$) δ ppm 7.99 (d, J=1.27 Hz, 1H), 7.73 (dd, J=8.36, 1.52 Hz, 1H), 7.59 (d, J=1.27 Hz, 1H), 7.36 (d, J=8.62 Hz, 1H), 7.28 (d, J=1.27 Hz, 1H), 6.64 (s, 1H), 6.57 (s, 1H), 5.92-6.05 (m, 1H), 5.73-5.88 (m, 1H), 4.51-4.71 (m, 4H), 4.00 (t, J=6.21 Hz, 2H), 3.56-3.67 (m, 8H), 2.27-2.46 (m, 6H), 2.22 (d, J=10.39 Hz, 6H), 1.83 (dt, J=14.19, 6.84 Hz, 2H), 1.26-1.44 (m, 6H); LCMS (LCMS Method D): Rt=0.73 min, [M/2+H]$^+$=410.9876

265

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide

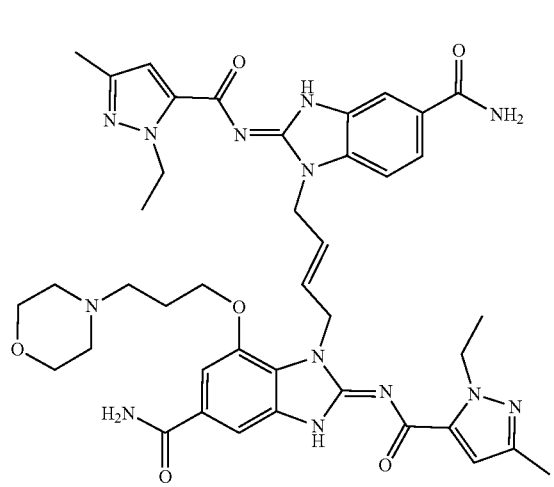 [SMILES: CCn1nc(C)cc1C(=O)/N=c1\[nH]c2cc(C(N)=O)ccc2n1C/C=C/Cn1/c(=N/C(=O)c2cc(C)nn2CC)[nH]c2cc(C(N)=O)cc(OCCCN3CCOCC3)c21]

or (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide

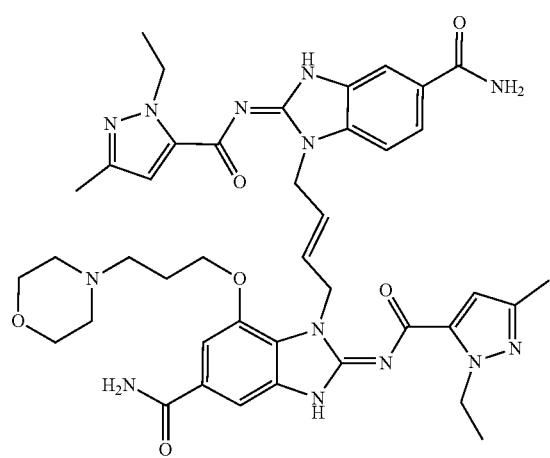 [SMILES: CCn1nc(C)cc1C(=O)/N=c1/[nH]c2cc(C(N)=O)ccc2n1C/C=C/Cn1/c(=N\C(=O)c2cc(C)nn2CC)[nH]c2cc(C(N)=O)cc(OCCCN3CCOCC3)c21]

266

Example 14

(E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide Tris Hydrochloride

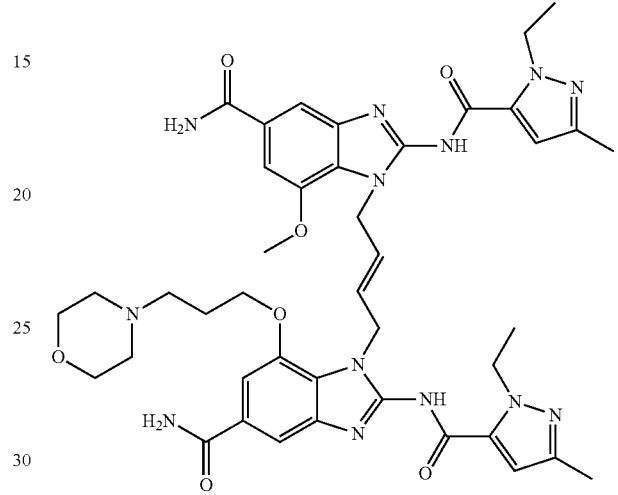

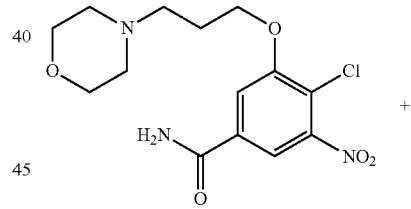

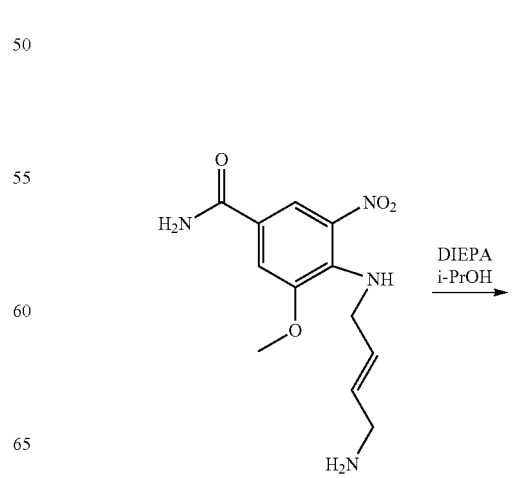

267

-continued

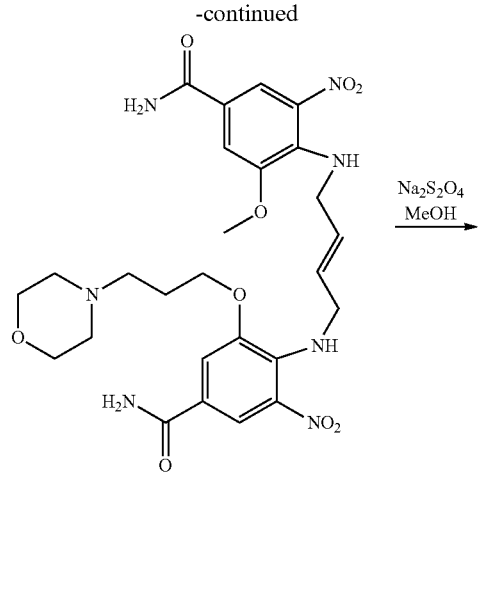

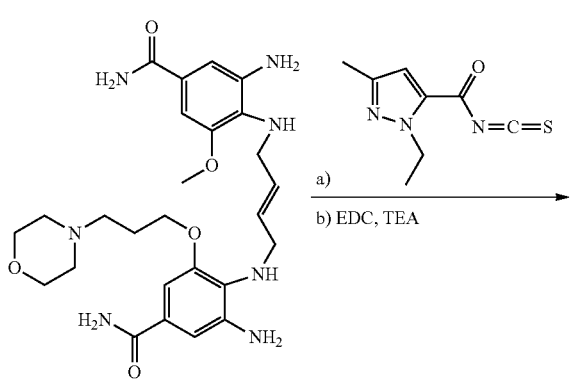

268

Step 1: (E)-4-((4-((4-Carbamoyl-2-(3-morpholino-propoxy)-6-nitrophenyl)amino)but-2-en-1-yl)amino)-3-methoxy-5-nitrobenzamide

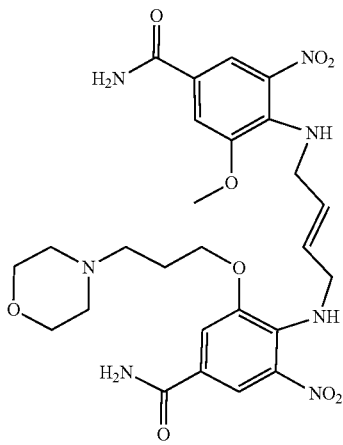 [SMILES: COc1cc(C(N)=O)cc([N+](=O)[O-])c1NC/C=C/CNc1c(OCCCN2CCOCC2)cc(C(N)=O)cc1[N+](=O)[O-]]

(E)-4-((4-aminobut-2-en-1-yl)amino)-3-methoxy-5-nitrobenzamide, hydrochloride (1.7 g, 5.37 mmol), 4-chloro-3-(3-morpholinopropoxy)-5-nitrobenzamide (1.655 g, 4.81 mmol) i-PrOH (15 ml) and DIPEA (2.94 ml, 16.85 mmol) were divided into two 24 mL vials, then the vials were capped heated to 120° C. for 42 hrs. The solid was isolated by filtration, rinsed with i-PrOH (2×3 mL) to afford (E)-4-((4-((4-carbamoyl-2-(3-morpholinopropoxy)-6-nitrophenyl)amino)but-2-en-1-yl)amino)-3-methoxy-5-nitrobenzamide (1.95 g, 2.79 mmol, 51.9% yield) as a brick red solid. LCMS (LCMS Method K): Rt=0.60 min, [M+H]$^+$=588.2

Step 2: (E)-3-Amino-4-((4-((2-amino-4-carbamoyl-6-(3-morpholinopropoxy)phenyl)amino)but-2-en-1-yl)amino)-5-methoxybenzamide

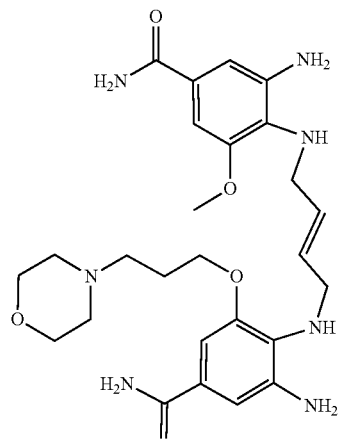

To (E)-4-((4-((4-carbamoyl-2-(3-morpholinopropoxy)-6-nitrophenyl)amino)but-2-en-1-yl)amino)-3-methoxy-5-nitrobenzamide (4.6 g, 6.65 mmol) in MeOH (83.0 mL) at RT was added sodium hydrosulfite (19.08 g, 93.0 mmol) in water (70 mL). After 15 min, solid sodium bicarbonate (24 grams) was added. After 10 min., the reaction was filtered,

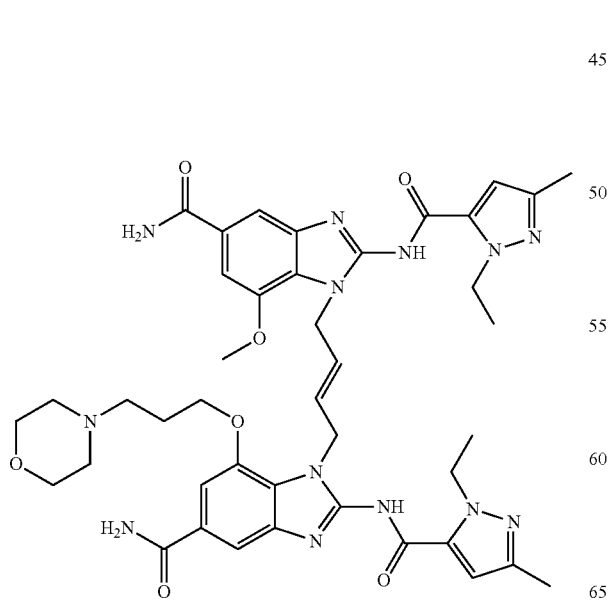

and the solid was rinsed with MeOH (4×20 mL). The combined filtrates were concentrated onto Celite, and the was purified by dry-loading onto silica gel (80 g Gold column), eluting with 2-40% (10:1 MeOH: aq NH$_4$OH) in DCM to afford the title compound (1.81 g, 3.26 mmol, 49% yield) as a dark yellow film. $^1$H NMR (400 MHz, DMSO-d$_6$) δ ppm 7.64 (br. s., 2H), 6.99 (br. s., 2H), 6.85 (dd, J=5.07, 1.77 Hz, 2H), 6.78 (dd, J=4.31, 1.77 Hz, 2H), 5.63-5.72 (m, 2H), 4.66 (d, J=8.11 Hz, 4H), 3.96 (t, J=6.21 Hz, 2H), 3.74 (s, 3H), 3.51-3.60 (m, 6H), 3.17 (br. s., 4H), 2.43 (t, J=7.10 Hz, 2H), 2.35 (br. s., 4H), 1.87 (t, J=6.72 Hz, 2H); LCMS (LCMS Method K): Rt=0.37 min, [M+H]$^+$=528.4

Step 3: (E)-1-(4-(5-Carbamoyl-2-(1-ethyl-3-methyl-1H-pyrazole-5-carboxamido)-7-(3-morpholino-propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide Tris Hydrochloride

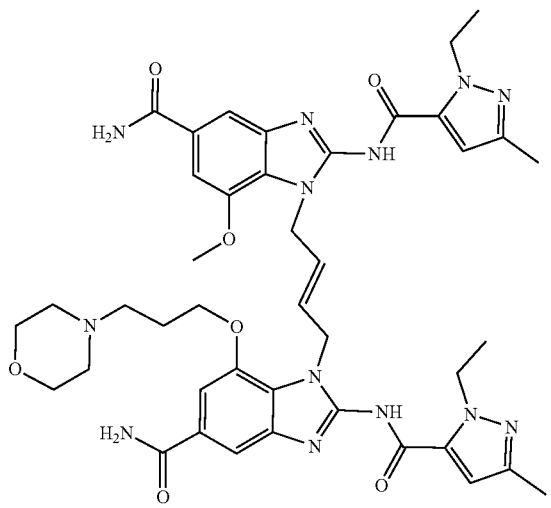 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCN3CCOCC3)c21]

To (E)-3-amino-4-((4-((2-amino-4-carbamoyl-6-(3-morpholinopropoxy)phenyl)amino)-but-2-en-1-yl)amino)-5-methoxybenzamide (368 mg, 0.697 mmol) in DMF (6.97 mL) at 0° C. was added 0.4 M 1-ethyl-3-methyl-1H-pyrazole-5-carbonyl isothiocyanate in dioxane (2.0 mL, 0.80 mmol). After ~10 min, another portion of 0.4 M 1-ethyl-3-methyl-1H-pyrazole-5-carbonyl isothiocyanate in dioxane (0.5 mL, 0.20 mmol) was added, followed ~15 min later by a final portion (0.5 mL, 0.20 mmol). After 35 min total reaction time, EDC (334 mg, 1.74 mmol) was added followed by triethylamine (0.486 mL, 3.49 mmol). The mixture was allowed to warm to RT and stirred overnight (~14 hours). The reaction was quenched with 3:1 water: saturated aqueous NH$_4$Cl solution (40 mL) and extracted with 3:1 chloroform: ethanol (2×40 mL). The combined organic phases were washed with water (20 mL), dried over MgSO$_4$ and concentrated. The resulting residue was purified over silica gel (40 g Gold column), eluting with 2-40% (10:1 MeOH: aq NH$_4$OH) in DCM to give pure material as the free base. This product was partially dissolved in MeOH and treated with 4M HCl in dioxane (0.35 mL, 1.40 mmol), then concentrated. The residue was taken up in MeCN-water and lyophilized to yield the title compound (403.6 mg, 0.421 mmol, 60% yield) as an off-white solid. $^1$H NMR (400 MHz, methanol-d$_4$) δ 7.70 (dd, J=2.66, 1.14 Hz, 2H), 7.42 (d, J=1.27 Hz, 2H), 6.72 (d, J=3.04 Hz, 2H), 5.79-6.12 (m, 2H), 5.19 (dd, J=11.03, 5.45 Hz, 4H), 4.61-4.81 (m, 4H), 4.00-4.25 (m, 4H), 3.79-3.96 (m, 5H), 3.45 (d, J=12.42 Hz, 2H), 3.28-3.36 (m, 2H), 3.14 (td, J=12.23, 3.68 Hz, 2H), 2.28 (s, 6H), 2.07-2.25 (m, 2H), 1.46 (td, J=7.10, 3.80 Hz, 6H); LCMS (LCMS Method K): Rt=0.68 min, [M+H]$^+$=850.6. The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide tris hydrochloride

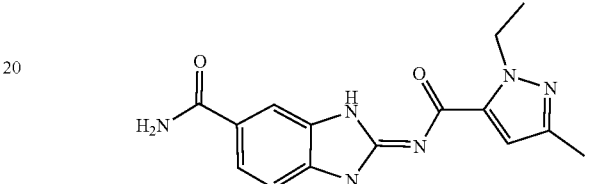
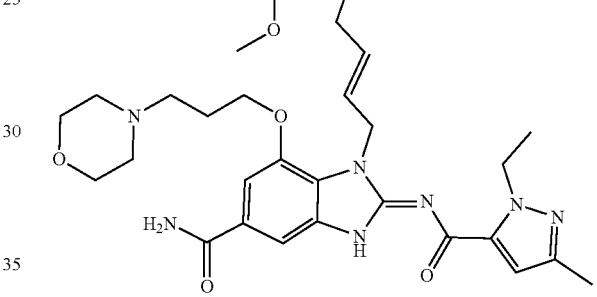

or (Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide tris hydrochloride

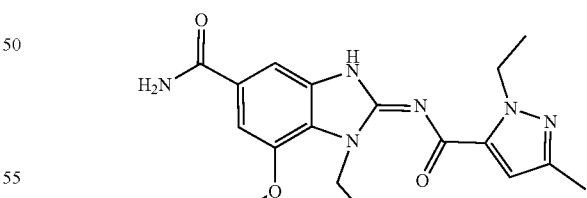
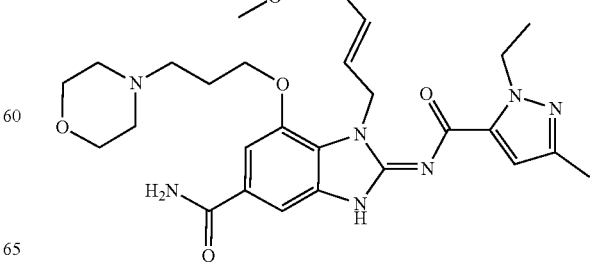

Example 15
(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide
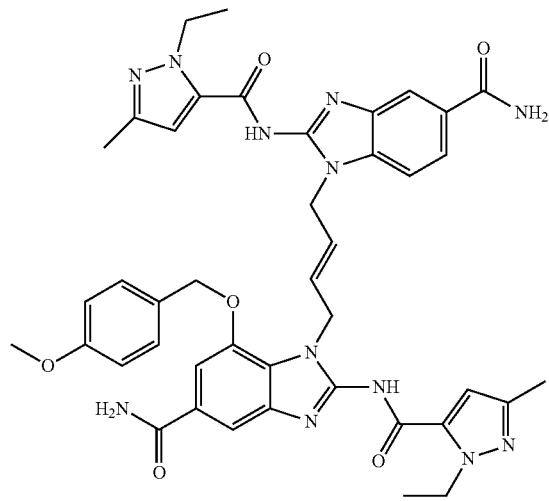
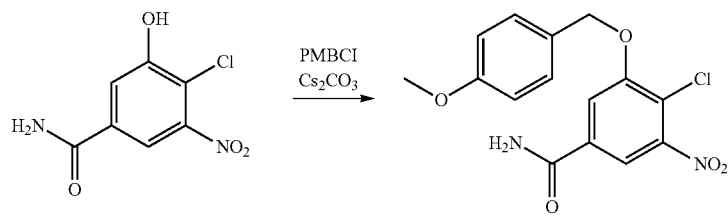
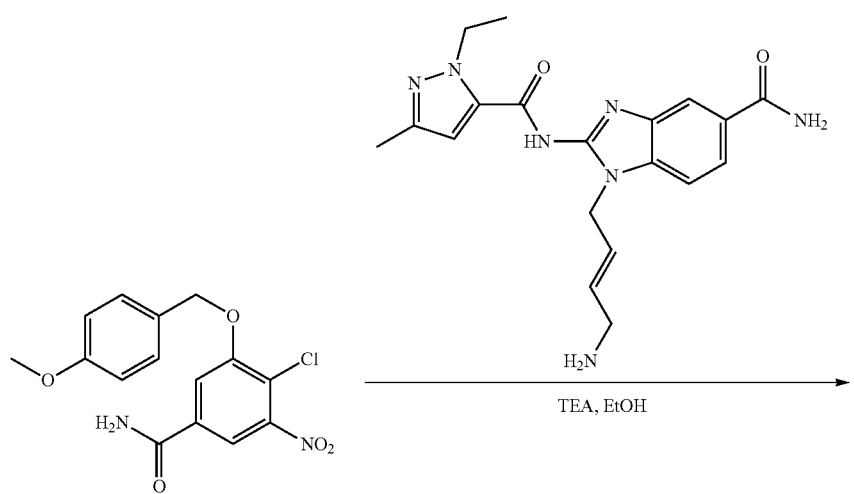

-continued
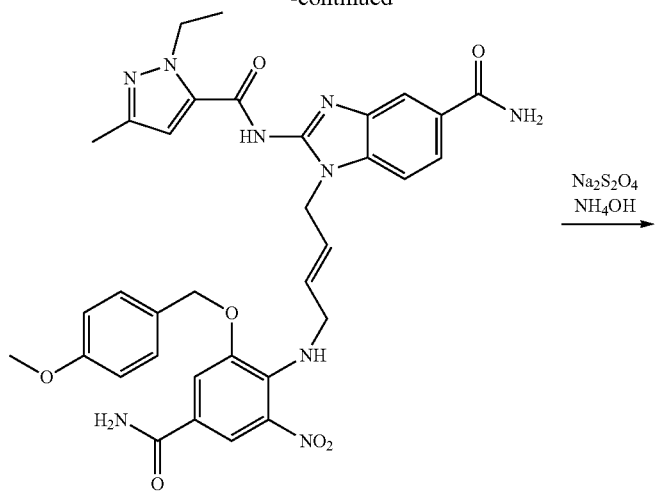
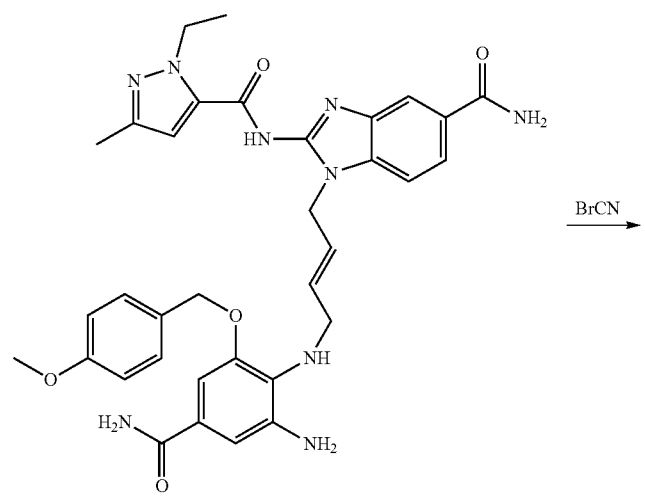
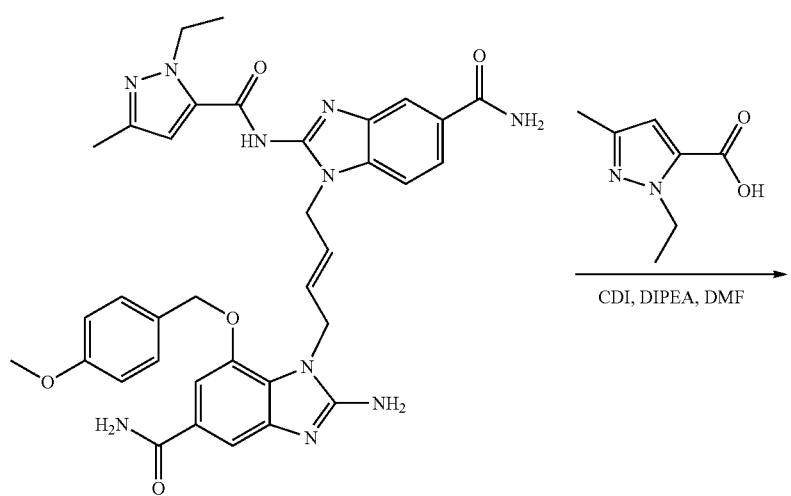

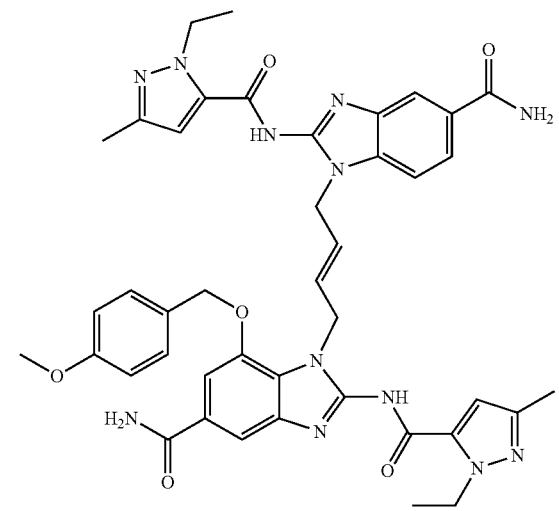

Step 1: 4-choro-3-((4-methoxybenzyl)oxy)-5-nitrobenzamide

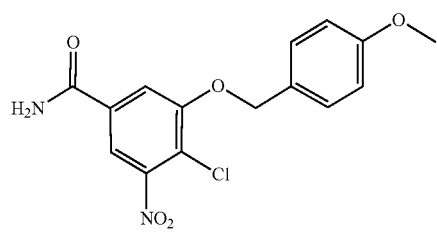 [SMILES: COc1ccc(COc2cc(C(N)=O)cc([N+](=O)[O-])c2Cl)cc1]

4-chloro-3-hydroxy-5-nitrobenzamide (942 mg, 4.35 mmol) was dissolved in DMF (7 mL), $Cs_2CO_3$ (1.559 g, 4.78 mmol) was added followed by 4-methoxybenzyl chloride (0.622 mL, 4.57 mmol) and the reaction mixture was stirred for 24 hours at RT. With vigorous stirring, water (15 mL) was added dropwise and the resulting solid was stirred for 5 minutes, collected by filtration and rinsed with water to afford the title compound (1.26 g, 3.74 mmol, 82% yield) as a light orange solid. $^1$H NMR (400 MHz, $CDCl_3$) δ (ppm) 7.80 (d, J=1.8 Hz, 1H), 7.76 (d, J=1.8 Hz, 1H), 7.43 (d, J=8.6 Hz, 2H), 6.98 (d, J=8.6 Hz, 2H), 6.13 (br. s., 1H), 5.82 (br. s., 1H), 5.25 (s, 2H), 3.87 (s, 3H); LCMS (LCMS Method D): Rt=1.03, [M+H]$^+$=337.1.

Step 2: (E)-1-(4-((4-carbamoyl-2-((4-methoxybenzyl)oxy)-6-nitrophenyl)amino)but-2-en-1-yl)-2-(1-ethyl-3-methyl-1H-pyrazole-5-carboxamido)-1H-benzo[d]imidazole-5-carboxamide

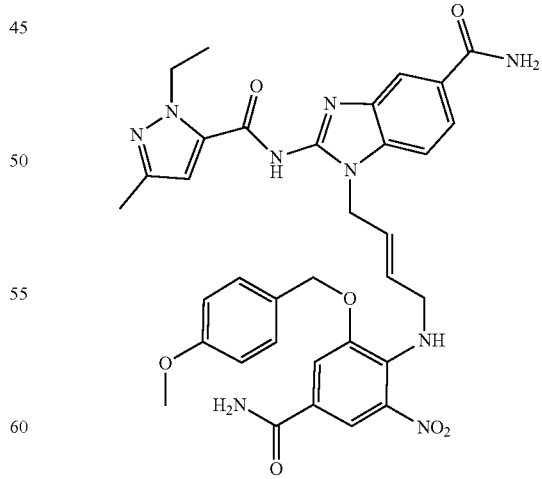

To a mixture of (E)-1-(4-aminobut-2-en-1-yl)-2-(1-ethyl-3-methyl-1H-pyrazole-5-carboxamido)-1H-benzo[d]imidazole-5-carboxamide, Hydrochloride (1.543 g, 3.69 mmol, Intermediate 6) and TEA (1.871 mL, 13.42 mmol) stirred in EtOH (7 mL) for 5 minutes was added 4-chloro-3-((4-methoxybenzyl)oxy)-5-nitrobenzamide (1.13 g, 3.36 mmol) and the mixture was heated in a sealed microwave vial at 120° C. for 18 hours. After cooling to RT, the mixture was diluted with DCM (50 mL) and water (50 mL) and a dark residue appeared. The layers were separated and the residue was combined with the organics and concentrated. To the crude mixture was added 10% MeOH in DCM and the resulting solid was collected by filtration and rinsed with DCM. To the concentrated filtrate 10% MeOH in DCM was again added and the resulting solid was collected by filtration and rinsed with DCM. Both batches of solid were combined to afford the title compound (559 mg, 0.82 mmol, 22% yield) as an orange solid. $^1$H NMR (400 MHz, DMSO-$d_6$) δ (ppm) 12.86 (br. s., 1H), 8.19 (d, J=2.0 Hz, 1H), 7.93-8.05 (m, 3H), 7.86 (t, J=6.3 Hz, 1H), 7.72 (dd, J=8.4, 1.3 Hz, 1H), 7.62 (s, 1H), 7.29-7.40 (m, 3H), 7.25 (d, J=8.6 Hz, 2H), 6.83 (d, J=8.6 Hz, 2H), 6.62 (s, 1H), 5.65-5.75 (m, 1H), 5.49-5.58 (m, 1H), 4.93 (s, 2H), 4.75 (d, J=5.1 Hz, 2H), 4.58 (q, J=7.1 Hz, 2H), 4.05 (t, J=5.6 Hz, 2H), 3.69 (s, 3H), 2.16 (s, 3H), 1.31 (t, J=7.1 Hz, 3H); LCMS (LCMS Method D): Rt=0.98, [M+H]$^+$=682.5.

Step 3: (E)-1-(4-((2-amino-4-carbamoyl-6-((4-methoxybenzyl)oxy)phenyl)amino)but-2-en-1-yl)-2-(1-ethyl-3-methyl-1H-pyrazole-5-carboxamido)-1H-benzo[d]imidazole-5-carboxamide

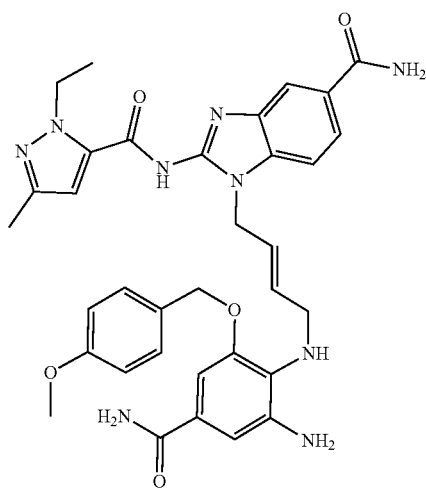 [SMILES: CCn1nc(C)cc1C(=O)Nc1nc2cc(C(N)=O)ccc2n1C/C=C/CNc1c(N)cc(C(N)=O)cc1OCc1ccc(OC)cc1]

To (E)-1-(4-((4-carbamoyl-2-((4-methoxybenzyl)oxy)-6-nitrophenyl)amino)but-2-en-1-yl)-2-(1-ethyl-3-methyl-1H-pyrazole-5-carboxamido)-1H-benzo[d]imidazole-5-carboxamide (557 mg, 0.817 mmol) in DMF (10 mL) was added ammonium hydroxide (1.136 mL, 8.17 mmol) followed by a dropwise addition of sodium hydrosulfite (837 mg, 4.09 mmol) in water (5 mL). After 1 hour at RT, the reaction was diluted with EtOAc and water. The aqueous was extracted with EtOAc, the combined organics were washed with saturated NH$_4$Cl and brine and concentrated to afford the title compound (335 mg, 0.51 mmol, 57% yield) as an orange solid. $^1$H NMR (400 MHz, DMSO-$d_6$) δ (ppm) 12.85 (br. s., 1H), 8.00 (s, 2H), 7.75 (dd, J=8.4, 1.5 Hz, 1H), 7.66 (br. s., 1H), 7.36 (br. s., 2H), 7.25-7.31 (m, 4H), 7.03 (br. s., 1H), 6.83-6.91 (m, 4H), 6.64 (s, 1H), 5.75-5.84 (m, 1H), 5.64-5.73 (m, 1H), 4.89 (s, 2H), 4.78 (d, J=5.1 Hz, 2H), 4.69 (br. s., 2H), 4.59 (q, J=7.0 Hz, 2H), 3.91 (t, J=7.0 Hz, 1H), 3.71 (s, 3H), 3.56 (br. m., 2H), 2.17 (s, 3H), 1.32 (t, J=7.1 Hz, 3H); LCMS (LCMS Method D): Rt=0.76, [M+H]$^+$=652.5.

Step 4: (E)-2-amino-1-(4-(5-carbamoyl-2-(1-ethyl-3-methyl-1H-pyrazole-5-carboxamido)-1H-benzo[d]imidazol-1-yl)but-2-en-1-yl)-7-((4-methoxybenzyl)oxy)-1H-benzo[d]imidazole-5-carboxamide Dihydrobromide

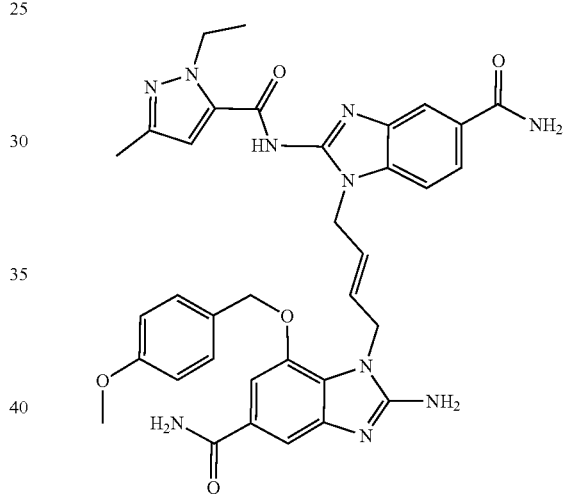

To a suspension of (E)-1-(4-((2-amino-4-carbamoyl-6-((4-methoxy-benzyl)oxy)phenyl)amino)but-2-en-1-yl)-2-(1-ethyl-3-methyl-1H-pyrazole-5-carboxamido)-1H-benzo-[d]imidazole-5-carboxamide (333 mg, 0.460 mmol) in MeOH (3 mL) was added cyanogen bromide (97 mg, 0.920 mmol) and the reaction was stirred at RT for 2 hours. The resulting solid was collected by filtration and rinsed with MeOH to afford the title compound (235 mg, 0.28 mmol, 58% yield) as a light orange solid. $^1$H NMR (400 MHz, DMSO-$d_6$) δ (ppm) 13.07 (br. s., 1H), 12.90 (s, 1H), 8.70 (br. s., 1H), 8.09 (br. s., 1H), 7.98-8.04 (m, 2H), 7.73 (d, J=8.6 Hz, 1H), 7.51 (s, 2H), 7.46 (br. s., 1H), 7.32-7.40 (m, 2H), 7.21 (d, J=8.6 Hz, 2H), 6.77 (d, J=8.4 Hz, 2H), 6.54 (s, 1H), 5.83-5.92 (m, 1H), 5.53-5.62 (m, 1H), 5.01 (s, 2H), 4.79 (s, 2H), 4.78 (s, 2H), 4.53 (q, J=7.2 Hz, 2H), 3.66 (s, 3H), 2.13 (s, 3H), 1.27 (t, J=7.1 Hz, 3H); LCMS (LCMS Method D): Rt=0.72, [M+H]$^+$=677.5.

Step 5: (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide

Example 16

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-hydroxy-1H-benzo[d]imidazole-5-carboxamide Dihydrochloride

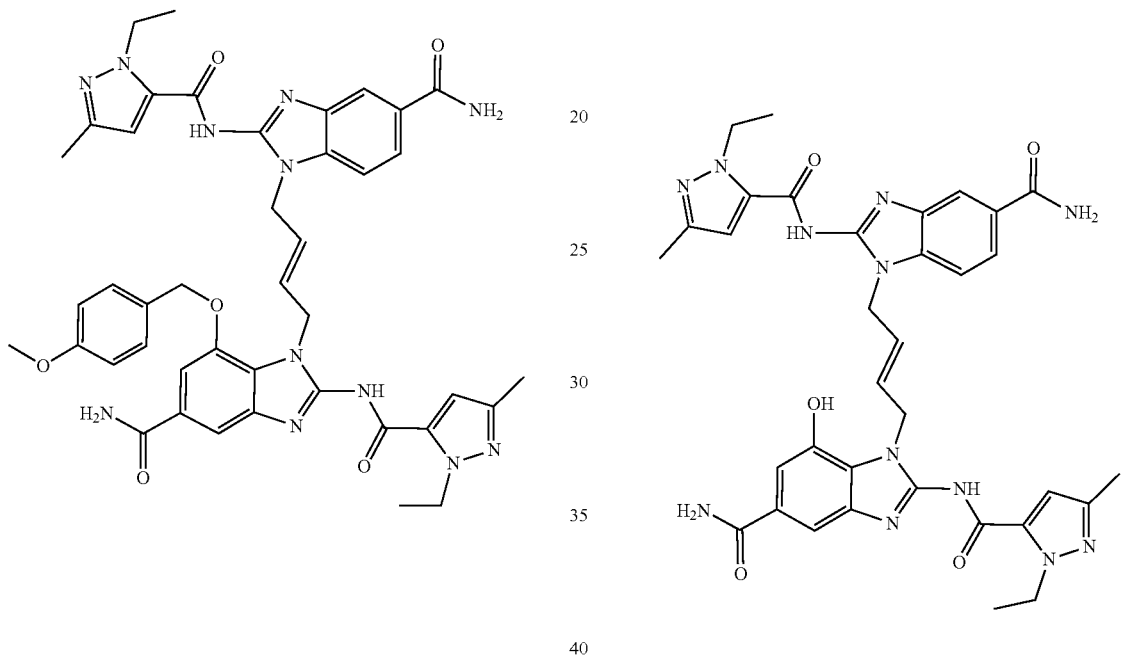

A solution of 1-ethyl-3-methyl-1H-pyrazole-5-carboxylic acid (51.4 mg, 0.333 mmol) and CDI (63.1 mg, 0.389 mmol) in DMF (3 mL) was stirred at 60° C. for 10 minutes, then (E)-1-(4-(2-amino-5-carbamoyl-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide dihydrobromide (233 mg, 0.278 mmol) and DIPEA (0.194 mL, 1.111 mmol) were added. After heating at 90° C. for 4 hours, additional CDI (20 mg) and 1-ethyl-3-methyl-1H-pyrazole-5-carboxylic acid (20 mg) were added and heating was continued for 1.5 hours. After cooling to RT and adding small ice chunks while stirring, water (5 mL) was added dropwise. The resulting solid was collected by filtration and rinsed with water to afford the title compound (225 mg, 0.27 mmol, 95% yield) as a light brown solid. $^1$H NMR (400 MHz, DMSO-$d_6$) δ (ppm) 12.88 (br. s., 2H), 8.00 (m, 2H), 7.64-7.72 (m, 2H), 7.46 (br. s., 1H), 7.29-7.42 (m, 3H), 7.20 (d, J=7.9 Hz, 2H), 6.75 (d, J=7.6 Hz, 2H), 6.54 (s, 2H), 5.94 (m, 1H), 5.49 (m, 1H), 4.97 (s, 2H), 4.85 (br. s., 2H), 4.78 (br. s., 2H), 4.53 (br. m., 4H), 3.65 (s, 3H), 2.13 (s, 3H), 2.10 (s, 3H), 1.22-1.33 (m, 6H); LCMS (LCMS Method F): Rt=2.27 min, [M+H]$^+$=813.9.

To (E)-1-(4-(5-carbamoyl-2-(1-ethyl-3-methyl-1H-pyrazole-5-carboxamido)-1H-benzo[d]-imidazol-1-yl)but-2-en-1-yl)-2-(1-ethyl-3-methyl-1H-pyrazole-5-carboxamido)-7-((4-methoxy-benzyl)oxy)-1H-benzo[d]imidazole-5-carboxamide (210 mg, 0.258 mmol) in dioxane (2 mL) was added 4N HCl in dioxane (0.258 mL, 1.03 mmol). After 30 min at RT, the reaction was heated to 50° C. for 18 hours. Additional 4N HCl in dioxane (0.2 mL) was added, and after heating another 5 hr, the reaction was cooled, and the resulting solid was collected by filtration and rinsed with DCM to afford the title compound (168 mg, 0.219 mmol, 81% yield) as a light tan solid. $^1$H NMR (400 MHz, MeOH-$d_4$) δ ppm 8.01 (d, J=1.3 Hz, 1H), 7.82 (dd, J=8.5, 1.6 Hz, 1H), 7.49-7.55 (m, 2H), 7.29 (d, J=1.5 Hz, 1H), 6.68 (s, 1H), 6.58 (s, 1H), 6.08-6.18 (m, 1H), 5.89-5.99 (m, 1H), 5.30 (d, J=5.6 Hz, 2H), 4.98-5.04 (m, 2H), 4.65 (dq, J=14.6, 7.2 Hz, 4H), 2.23 (s, 3H), 2.20 (s, 3H), 1.37-1.46 (m, 6H); LCMS (LCMS Method F): Rt=1.73 min, [M+H]$^+$=693.4.

Example 17
1,1'-(2,2,3,3-Tetrafluorobutane-1,4-diyl)bis(2-(1-ethyl-3-methyl-1H-pyrazole-5-carboxamido)-1H-benzo[d]imidazole-5-carboxamide)
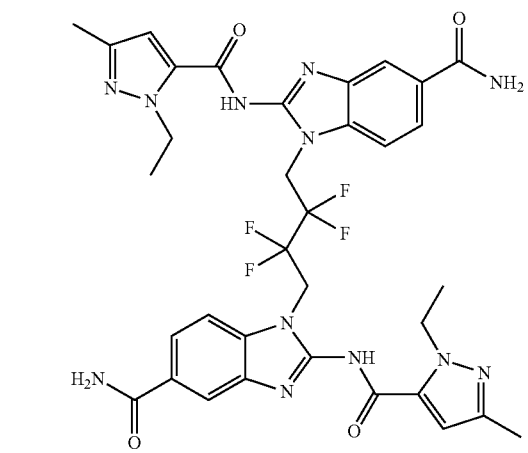
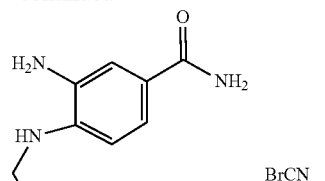
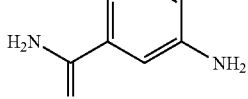
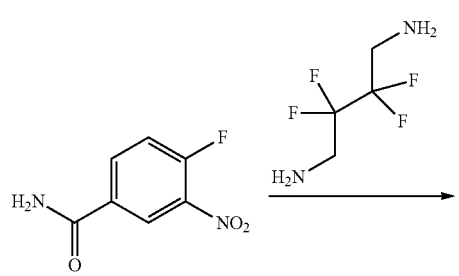
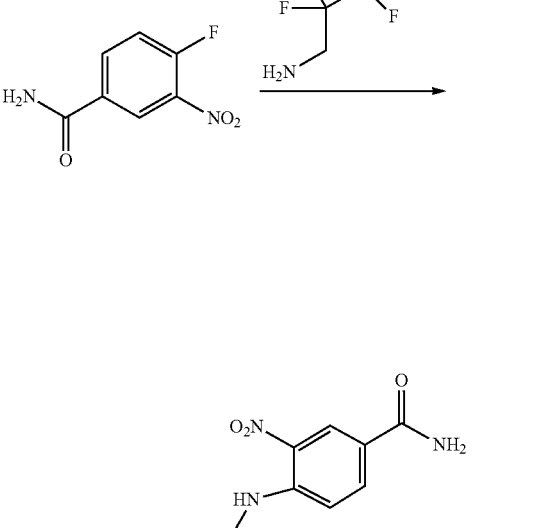
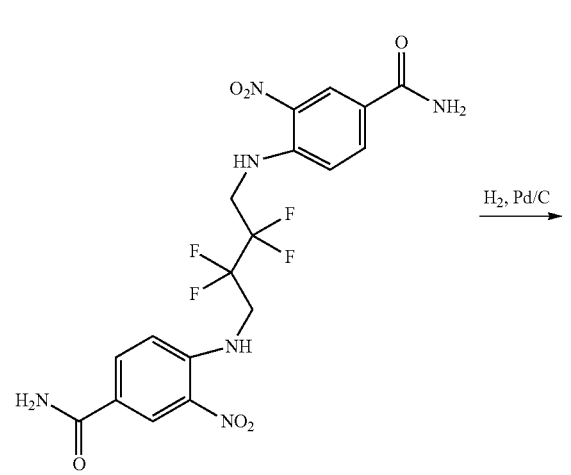
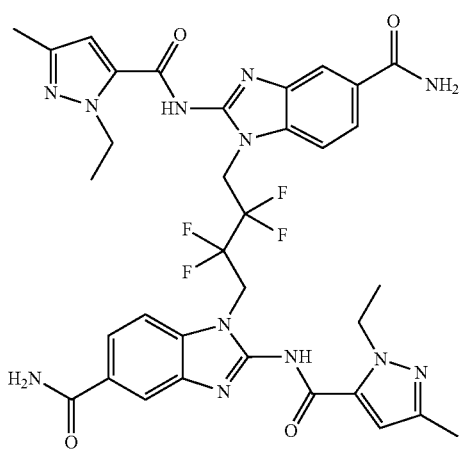

283

Step 1: 4,4-((2,2,3,3-Tetrafluorobutane-1,4-diyl)bis(azanediyl))bis(3-nitrobenzamide)

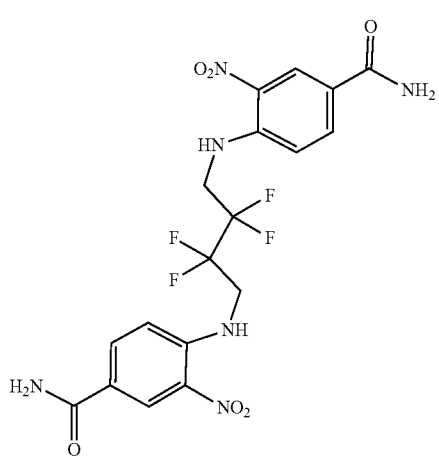

To 2,2,3,3-tetrafluorobutane-1,4-diamine (Intermediate 4) (1.25 g, 7.81 mmol), and potassium carbonate (3.24 g, 23.4 mmol) in DMF (50 mL) at RT was added 4-fluoro-3-nitrobenzamide (3.59 g, 19.5 mmol) over 5 min, and the reaction was stirred overnight. The mixture was quenched with water, and the resulting solid was collected by filtration and triturated with MeOH to afford the title compound (600 mg, 1.23 mmol, 16% yield) as a yellow solid. LCMS (LCMS Method A): Rt=1.367 min, [M+H]$^+$=489.0

Step 2: 4,4'-((2,2,3,3-Tetrafluorobutane-1,4-diyl)bis(azanediyl))bis(3-aminobenzamide)

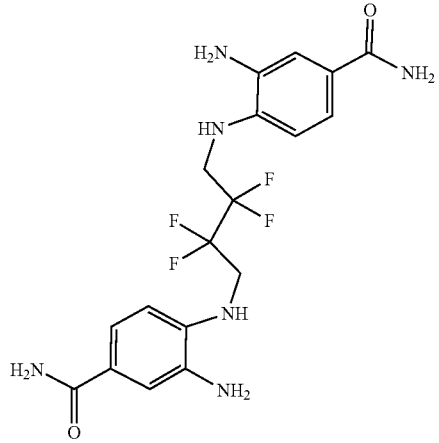 [SMILES: NC(=O)c1ccc(NCC(F)(F)C(F)(F)CNc2ccc(C(N)=O)cc2[N+](=O)[O-])c([N+](=O)[O-])c1]

4,4'-((2,2,3,3-Tetrafluorobutane-1,4-diyl)bis(azanediyl))bis(3-nitrobenzamide) (1.15 g, 2.36 mmol) and Pd on carbon (0.251 g, 2.36 mmol) in MeOH (100 mL) were stirred under H2 at 30° C. overnight. The reaction was filtered, and the filtrate concentrated to afford the title compound (250 mg, 0.584 mmol, 25% yield). LCMS (LCMS Method A): Rt=1.165 min, [M+H]$^+$=429.1

284

Step 3: 1,1'-(2,2,3,3-Tetrafluorobutane-1,4-diyl)bis(2-amino-1H-benzo[d]imidazole-5-carboxamide)

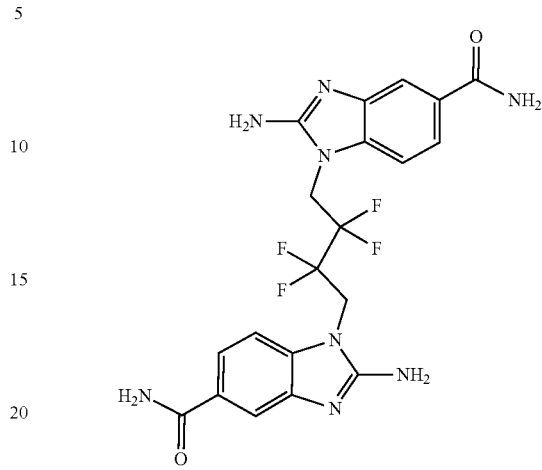

To 4,4'-((2,2,3,3-tetrafluorobutane-1,4-diyl)bis(azanediyl))bis(3-aminobenzamide) (20 mg, 0.047 mmol) in MeOH (1 mL) and water (2 mL) was added cyanogen bromide (29.7 mg, 0.280 mmol), and the reaction was stirred at 30° C. overnight. The MeOH was removed in vacuo and the resulting solid was collected by filtration to afford the title compound (15 mg, 0.031 mmol, 67% yield). LCMS (LCMS Method A): Rt=0.629 min, [M+H]$^+$=479.0

Step 4: 1,1'-(2,2,3,3-Tetrafluorobutane-1,4-diyl)bis(2-(1-ethyl-3-methyl-1H-pyrazole-5-carboxamido)-1H-benzo[d]imidazole-5-carboxamide)

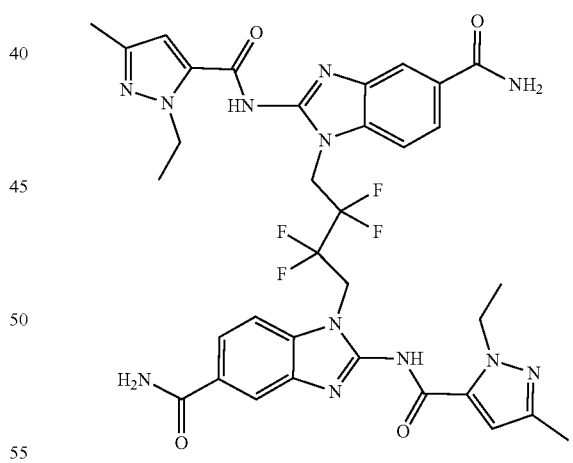

To HATU (763 mg, 2.01 mmol) and 1-ethyl-3-methyl-1H-pyrazole-5-carboxylic acid (227 mg, 1.47 mmol) in DMF (20 mL) at RT was added EDC (385 mg, 2.01 mmol), 1,1'-(2,2,3,3-tetrafluorobutane-1,4-diyl)bis(2-amino-1H-benzo[d]imidazole-5-carboxamide) (320 mg, 0.667 mmol) and DIEA (0.467 mL, 2.68 mmol) in one charge. The reaction was heated to 70° C. for 12 hr, concentrated and purified to yield the title compound (8 mg, 0.01 mmol, 2% yield). $^1$H NMR (400 MHz, DMSO-d$_6$) δ ppm 13.05 (s, 2H), 8.01 (d, J=8.6 Hz, 4H), 7.81 (d, J=8.2 Hz, 2H), 7.53 (d, J=8.3 Hz, 2H), 7.38 (s, 2H), 6.73 (s, 2H), 5.32 (t, J=16.0 Hz, 4H), 4.59 (dd, J=14.0, 6.9 Hz, 4H), 2.06 (s, 6H), 1.33 (t, J=7.1 Hz, 6H); LCMS (LCMS Method A): Rt=1.367 min, [M+H]⁺=751.1

Example 18

Di-tert-butyl (3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-H-benzo[d]imidazol-4-yl)oxy)propyl) Phosphate

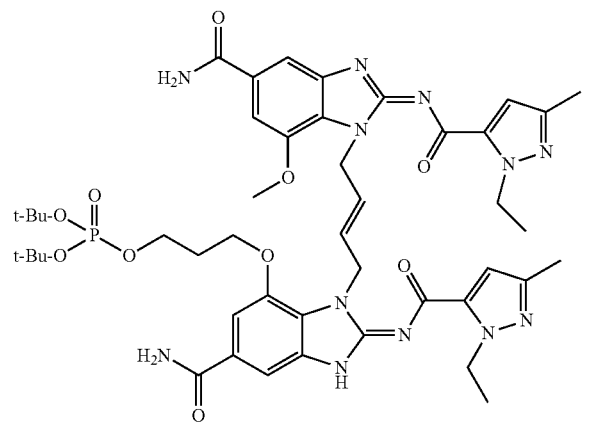

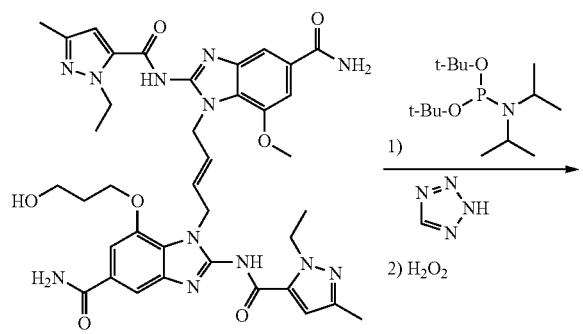

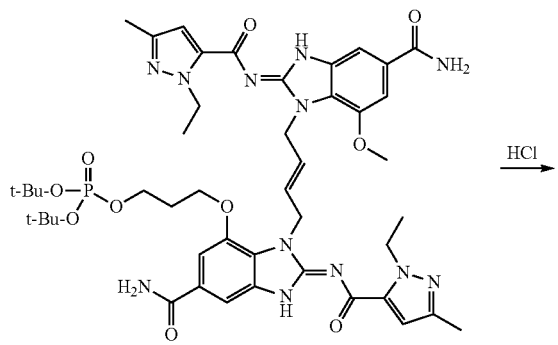

Example 18

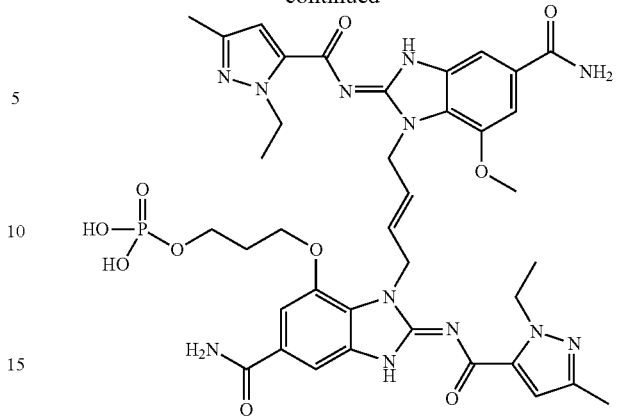

Example 19

Di-tert-butyl (3-(((2-6-carbamoyl-3-((E)-4-((Z)-5-carbamoyl-2-((i-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl) Phosphate

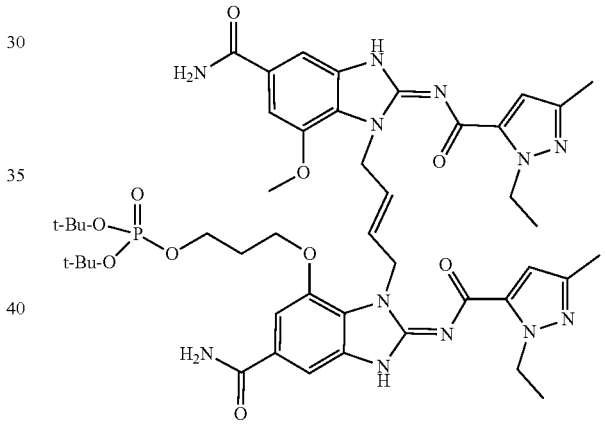

A suspension of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (1.00 g, 1.28 mmol) and 0.45 M 2H-tetrazole in acetonitrile (14.2 mL, 6.40 mmol) in DMF (5 mL) was concentrated on a rotary evaporator to remove acetonitrile. The resulting heterogeneous mixture in DMF was cooled to 0° C. then a solution of di-tert-butyl diisopropylphosphoramidite (1.617 mL, 5.12 mmol) in 5 mL DMF was added. Soon after addition, the solution becomes homogeneous but again becomes heterogeneous as the reaction is stirred at RT for 2 additional hours. The temperature was lowered to 0° C. and $H_2O_2$ (30/% Wt in water, 2.62 mL, 25.6 mmol) was added. After stirring for 20 min, an additional 10 eq of $H_2O_2$ was added and the reaction stirred until homogeneous (30 min). A 2 mL portion of aqueous $NaHCO_3$ and $Na_2S_2O_3$ (0.4M in $NaHCO_3$, 2M in $Na_2S_2O_3$) was added to 200 mL water. When the reaction mixture was poured into this solution, a precipitate was formed. The precipitate was then collected on a filter, dissolved in 200 mL TH, dried with MgSO₄ and concentrated to provide the title compound as an off-white solid (1.1 g, 1.13 mmol, 88% yield. ¹H NMR (400 MHz, DMSO-d₆) δ ppm 12.8 (s, 2H), 10.2 (s, 1H), 7.98 (m, 2H), 7.65 (d, J=2.5 Hz, 2H), 7.34 (m, 4H), 6.51 (d, J=2.5 Hz, 2H), 5.83 (m, 2H), 4.91 (m, 4H), 4.52 (m, 4H), 4.09 (m, 2H), 3.93 (m, 2H), 3.74 (s, 3H), 3.60 (n, 2H), 2.11 (s, 6H), 1.90 (m, 2H), 1.76 (m, 2H), 1.4-1.3 (m, 18H, 1.27 (m, 6H); LCMS (LCMS Method I): Rt=1.09 min [M+H]⁺=973.3.

Example 19

3-(((Z)-6-Carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl Dihydrogen Phosphate

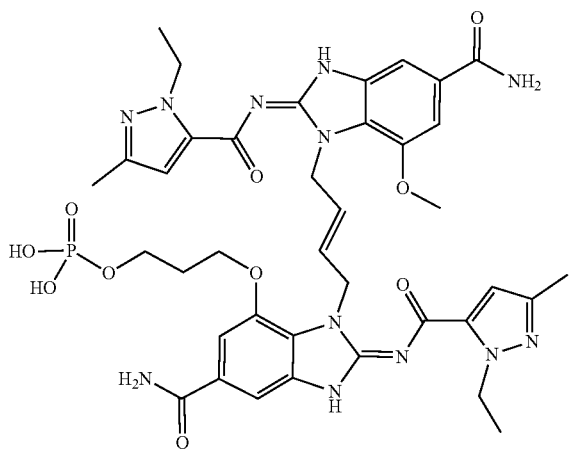 [SMILES: CCn1nc(C)cc1C(=O)/N=c1/[nH]c2cc(C(N)=O)cc(OC)c2n1C/C=C/Cn1/c(=N\C(=O)c2cc(C)nn2CC)[nH]c2cc(C(N)=O)cc(OCCCOP(=O)(O)O)c21]

To di-tert-butyl (3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)-propyl) phosphate (18 mg, 0.018 mmol) suspended in dioxane (1 mL) at RT was added 4N HCl in dioxane (0.028 mL, 0.11 mmol). Some precipitate formed immediately. The reaction was stirred for 2 hr and additional 4N HCl in dioxane (0.028 mL, 0.11 mmol) was added. After 2 hr, the reaction was placed in freezer, and after 16 hr, the reaction was diluted with diethyl ether. The mixture was adjusted to pH of 2-3 with conc. ammonium hydroxide. The precipitate was collected by filtration and washed with ether to yield the title compound (15 mg, 0.017 mmol, 92% yield) as a white solid. ¹H NMR (600 MHz, DMSO-d₆) δ ppm 12.85 (br s, 1H), 8.02 (br, d, J=6.6 Hz, 2H), 7.65 (d, J=5.7 Hz, 2H), 7.35-7.41 (m, 2H), 7.34 (br. d, J=10.6 Hz, 2H), 6.51 (d, J=12.8 Hz, 2H), 5.74-5.89 (m, 2H), 4.92 (br. dd, J=12.0, 4.9 Hz, 4H), 4.50 (quin, J=7.0 Hz, 4H), 4.10 (br. t, J=6.1 Hz, 2H), 3.91-3.94 (m, 2H), 3.75 (s, 3H), 2.10 (d, J=3.1 Hz, 6H), 1.84-1.93 (m, 2H), 1.22-1.28 (m, 6H); LCMS (LCMS Method I): Rt=0.68 min, [M+H]⁺=861.2

The compound prepared by the above process may exist in a tautomeric or an isomeric form, e.g., as (E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate

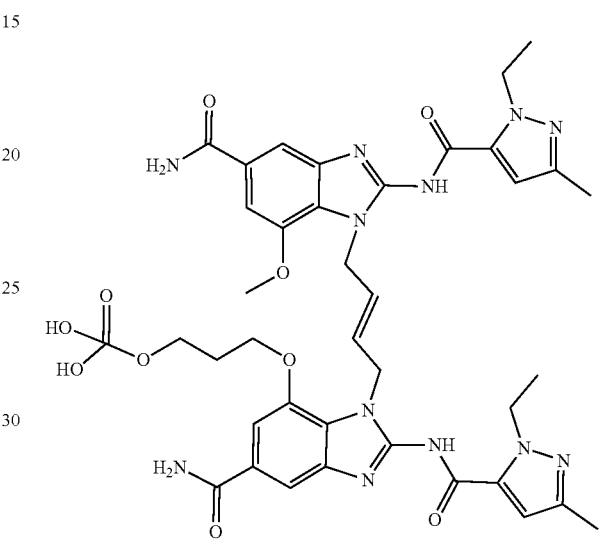

or 3-(((E)-6-carbamoyl-3-((E)-4-((E)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate

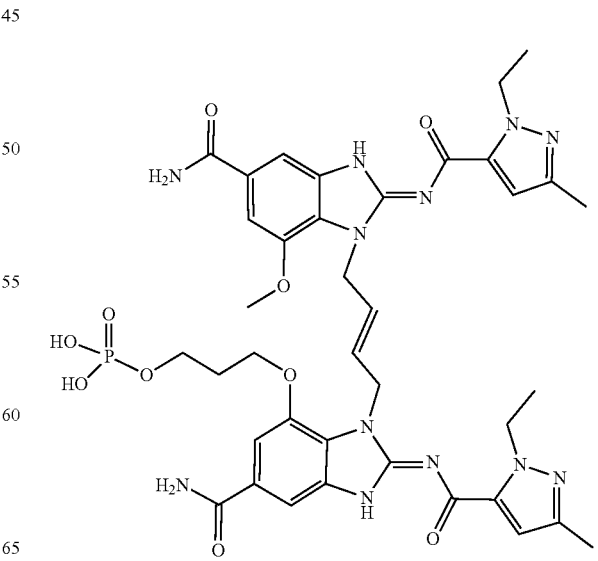

Example 20
Step 8: (E)-7-Bromo-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazole-5-carboxamide
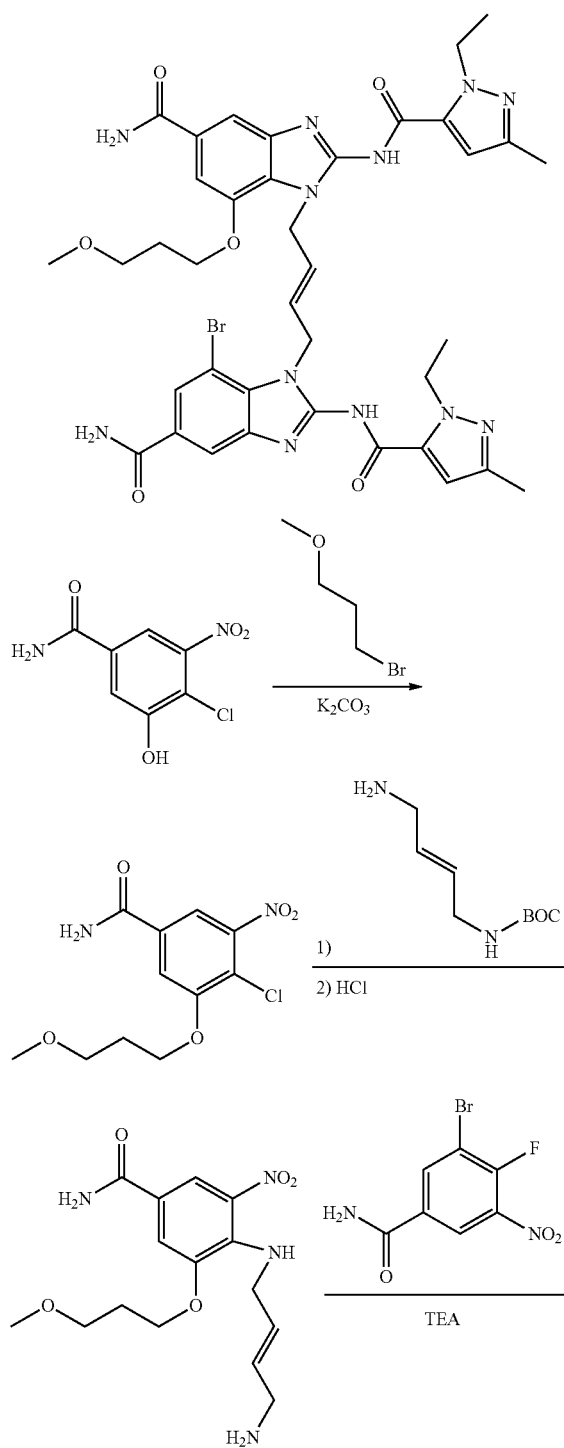
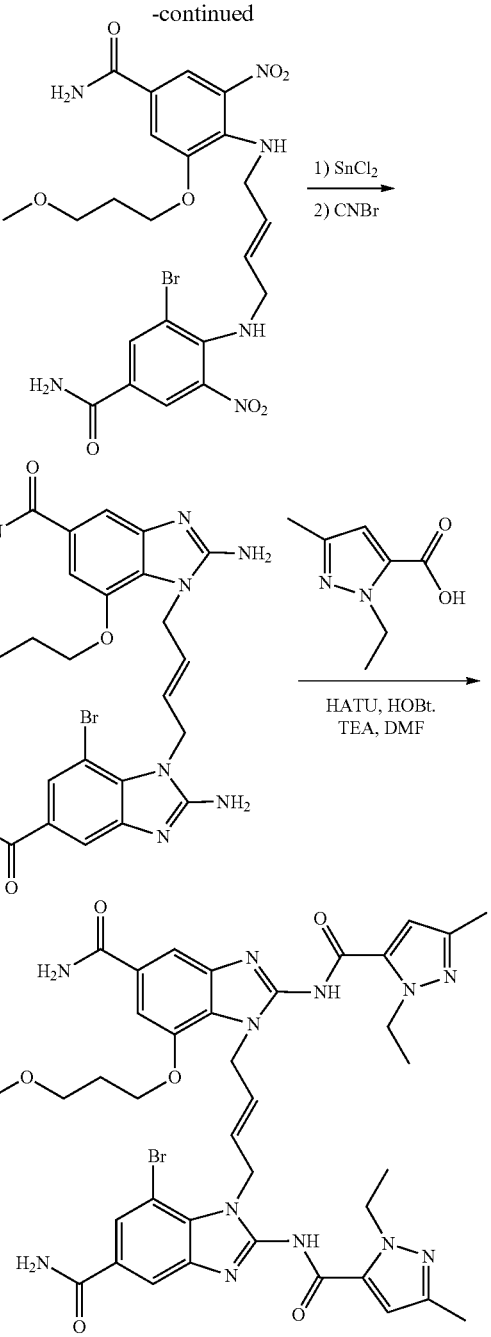
Step 1: 4-Chloro-3-(3-methoxypropoxy)-5-nitrobenzamide
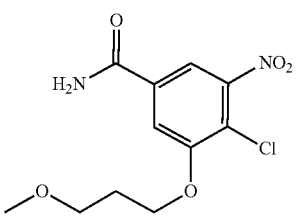 [SMILES: COCCCOc1cc(C(N)=O)cc([N+](=O)[O-])c1Cl]

To a suspension of 4-chloro-3-hydroxy-5-nitrobenzamide (1.00 g, 4.62 mmol) in DMF (15 mL) was added 1-bromo-3-methoxypropane (1.06 g, 6.93 mmol) and K$_2$CO$_3$ (1.91 mg, 13.9 mmol). The reaction mixture was stirred at 60° C. in a sealed tube. After 3 hr, the reaction was cooled to RT and poured into water. The resulting light yellow precipitate was collected by filtration and washed with diethyl ether to provide the title compound (1.1 g, 3.8 mmol, 83% yield). LCMS (LCMS Method D): Rt=0.84 min, [M+H]$^+$=289.0

Step 2: (E)-tert-Butyl (4-((4-carbamoyl-2-(3-methoxypropoxy)-6-nitrophenyl)amino)but-2-en-1-yl)carbamate

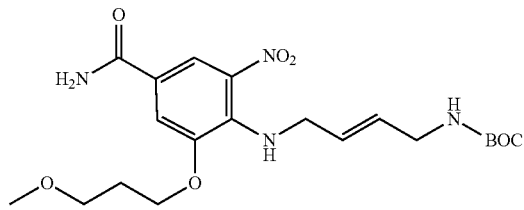 [SMILES: COCCCOc1cc(C(N)=O)cc([N+](=O)[O-])c1NC/C=C/CNC(=O)OC(C)(C)C]

To a suspension of 4-chloro-3-methoxy-5-nitrobenzamide (1.50 g, 6.50 mmol) in EtOH (25 mL) was added (E)-tert-butyl (4-aminobut-2-en-1-yl)carbamate (1.45 g, 7.81 mmol) and DIEA (3.41 mL, 19.5 mmol). The reaction was heated to 120° C. in a sealed tube overnight and allowed to cool to RT. The resulting orange precipitate was collected by filtration and washed with EtOH to provide the title compound (2.1 g, 5.5 mmol, 85% yield). LCMS (LCMS Method D): Rt=0.96 min, [M+H]$^+$=439.2

Step 3: (E)-4-((4-Aminobut-2-en-1-yl)amino)-3-(3-methoxypropoxy)-5-nitrobenzamide dihydrochloride

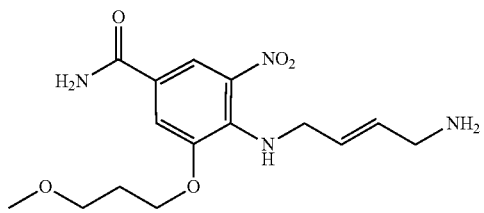 [SMILES: COCCCOc1cc(C(N)=O)cc([N+](=O)[O-])c1NC/C=C/CN]

To (E)-tert-butyl(4-((4-carbamoyl-2-(3-methoxy-propoxy)-6-nitrophenyl)amino)but-2-en-1-yl)carbamate (1.43 g, 3.26 mmol) in dioxane (10 mL) was added 4N HCl in dioxane (12.2 mL, 48.9 mmol). After 1 hr at RT, the reaction was concentrated, and the residue was triturated with diethyl ether to provide the title compound (1.3 g, 3.1 mmol, 96% yield). LCMS (LCMS Method D): Rt=0.52 min, [M+H]$^+$=339.2

Step 4: (E)-3-Bromo-4-((4-((4-carbamoyl-2-(3-methoxypropoxy)-6-nitrophenyl)amino)but-2-en-1-yl)amino)-5-nitrobenzamide

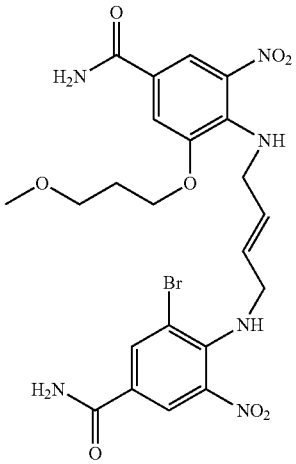 [SMILES: COCCCOc1cc(C(N)=O)cc([N+](=O)[O-])c1NC/C=C/CNc1c(Br)cc(C(N)=O)cc1[N+](=O)[O-]]

To a solution of (E)-4-((4-aminobut-2-en-1-yl)amino)-3-(3-methoxypropoxy)-5-nitrobenzamide dihydrochloride (361 mg, 0.878 mmol) in DMF (5 mL) was added 3-bromo-4-fluoro-5-nitrobenzamide (220 mg, 0.836 mmol) and TEA (0.47 mL, 3.4 mmol). After stirring at RT overnight, water (20 mL) was added, and the resulting light brown solid was collected by filtration to provide the title compound (475 mg, 0.719 mmol, 86% yield). LCMS (LCMS Method D): Rt=0.91 min, [M+H]$^+$=583.2

Step 5: (E)-3-Amino-4-((4-((2-amino-4-carbamoyl-6-(3-methoxypropoxy)phenyl)amino)but-2-en-1-yl)amino)-5-bromobenzamide

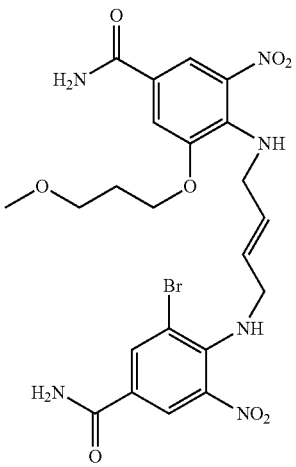 [SMILES: COCCCOc1cc(C(N)=O)cc([N+](=O)[O-])c1NC/C=C/CNc1c(Br)cc(C(N)=O)cc1[N+](=O)[O-]]

To a solution of (E)-3-bromo-4-((4-((4-carbamoyl-2-(3-methoxypropoxy)-6-nitrophenyl)amino)but-2-en-1-yl)amino)-5-nitrobenzamide (400 mg, 0.585 mmol) in conc. aq 12M HCl (5 mL, 60 mmol) was added tin (II) chloride (665 mg, 3.51 mmol). After 5 min at RT, 6N aq NaOH was added to neutralize the reaction, and the resulting solid was collected by filtration to provide the title compound (150 mg, 0.288 mmol, 49% yield). LCMS (LCMS Method D): Rt=0.55 min, [M+H]$^+$=521.2

Step 6: (E)-2-Amino-1-(4-(2-amino-5-carbamoyl-7-(3-methoxypropoxy)-1H-benzo[d]imidazol-1-yl)but-2-en-1-yl)-7-bromo-1H-benzo[d]imidazole-5-carboxamide

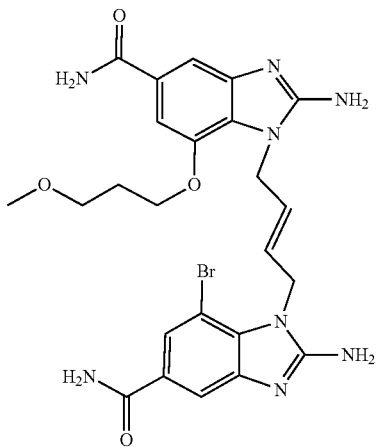 [SMILES: COCCCOc1cc(C(N)=O)cc2nc(N)n(C/C=C/Cn3c(N)nc4cc(C(N)=O)cc(Br)c43)c12]

To a solution of (E)-3-amino-4-((4-((2-amino-4-carbamoyl-6-(3-methoxypropoxy)phenyl)amino)but-2-en-1-yl)amino)-5-bromobenzamide (150 mg, 0.288 mmol) in MeOH (3 mL) and DMSO (1 mL) was added cyanogen bromide (183 mg, 1.73 mmol). The reaction mixture was stirred at RT overnight, during which time a solid precipitated out. This solid was collected by filtration to provide the crude title compound (120 mg, 0.210 mmol, 73% yield). LCMS (LCMS Method D): Rt=0.47 min, [M+H]$^+$=573.2

Step 8: (E)-7-Bromo-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazole-5-carboxamide

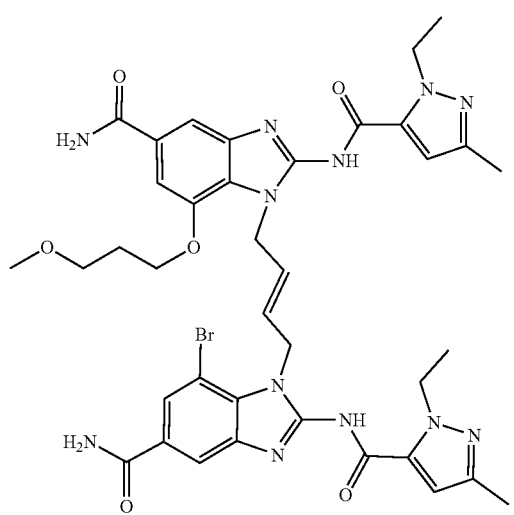

To 1-ethyl-3-methyl-1H-pyrazole-5-carboxylic acid (97 mg, 0.63 mmol) in DMF (2 mL) was added HATU (240 mg, 0.630 mmol) and HOBt (48 mg, 0.32 mmol). After 15 min at RT, TEA (0.18 mL, 1.3 mmol) was added, followed by (E)-2-amino-1-(4-(2-amino-5-carbamoyl-7-(3-methoxypropoxy)-1H-benzo[d]imidazol-1-yl)but-2-en-1-yl)-7-bromo-1H-benzo[d]imidazole-5-carboxamide (120 mg, 0.210 mmol). After stirring overnight, water (5 mL) was added, and the resulting light yellow precipitate was collected by filtration. This crude material was purified over silica gel (Isco Rf 25 g column eluting with 0-20% MeOH in DCM) to provide the title compound (45 mg, 0.050 mmol, 24% yield). $^1$H NMR (400 MHz, DMSO-d$_6$) δ ppm 13.06 (br. s., 1H), 12.83 (br. s., 1H), 8.07 (br. s., 1H), 8.00 (d, J=8.62 Hz, 2H), 7.88-7.96 (m, 1H), 7.64 (s, 1H), 7.47 (br. s., 1H), 7.28-7.39 (m, 2H), 6.49-6.59 (m, 2H), 5.70-5.92 (m, 2H), 5.09 (br. s., 2H), 4.93 (br. s., 2H), 4.44-4.60 (m, 4H), 4.03 (t, J=6.46 Hz, 2H), 3.23-3.30 (m, 2H), 3.14 (s, 3H), 2.11 (d, J=12.17 Hz, 6H), 1.71-1.83 (m, 2H), 1.27 (q, J=7.10 Hz, 6H); LCMS (LCMS Method D): Rt=0.96 min, [M/2+H]$^+$=422.1.

The compound prepared by the above process may exist in a tautomeric or an isomeric form, e.g., as (E)-7-bromo-1-((E)-4-((E)-5-carbamoyl-2-((1-ethyl-3-methyl-1H-pyrazole-5-carbonyl)imino)-7-(3-methoxypropoxy)-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazole-5-carboxamide

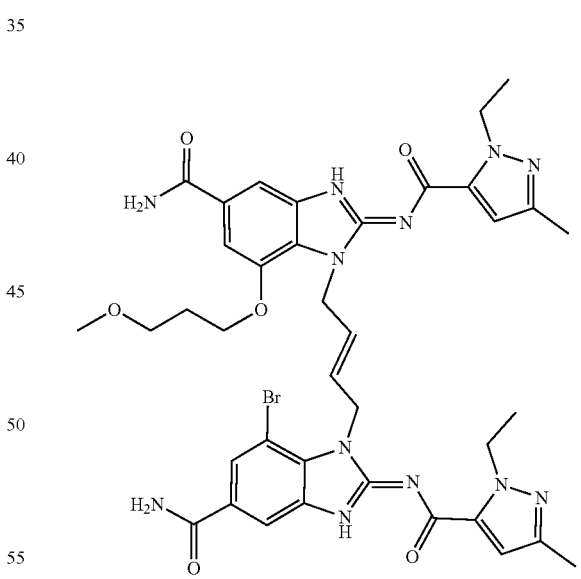

or (Z)-7-bromo-1-((E)-4-((Z)-5-carbamoyl-2-((1-ethyl-3-methyl-1H-pyrazole-5-carbonyl)imino)-7-(3-methoxypropoxy)-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazole-5-carboxamide

Example 21

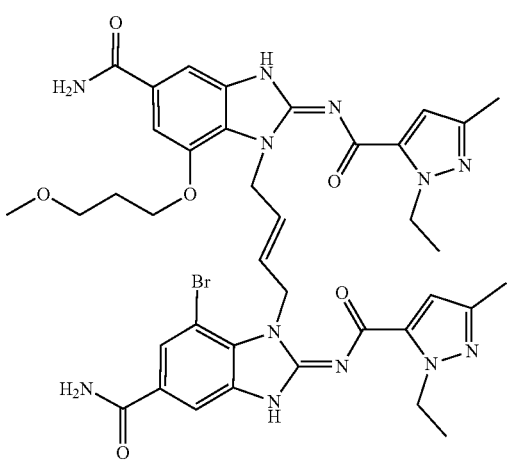

Step 9: Ethyl (E)-3-(5-carbamoyl-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate

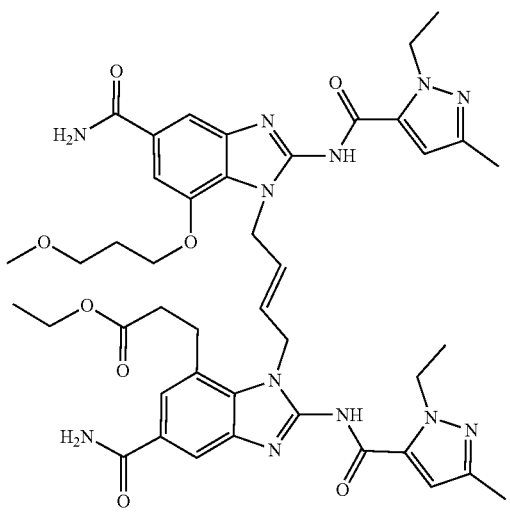

A mixture of (E)-7-bromo-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazole-5-carboxamide (50 mg, 0.059 mmol), Pd(amphos)Cl$_2$ (20 mg, 0.028 mmol) and (3-ethoxy-3-oxopropyl)zinc(II) bromide (1.5 ml, 0.750 mmol) was heated in the microwave at 100° C. After 15 min, the reaction was cooled, concentrated and the crude material was purified by reverse phase HPLC (Gilson HPLC (CH$_3$CN/H$_2$O 10 to 60%) to provide the title compound (20 mg, 0.023 mmol, 38.2% yield). $^1$H NMR (400 MHz, MeOH-d$_4$) δ ppm 7.85 (d, J=1.52 Hz, 1H), 7.59 (d, J=1.01 Hz, 1H), 7.54 (d, J=1.52 Hz, 1H), 7.32 (d, J=1.01 Hz, 1H), 6.61 (d, J=7.10 Hz, 2H), 5.92 (d, J=15.72 Hz, 1H), 5.61-5.77 (m, 1H), 4.99-5.23 (m, 4H), 4.50-4.69 (m, 4H), 4.08 (t, J=6.34 Hz, 2H), 4.00 (q, J=7.18 Hz, 2H), 3.41 (t, J=6.21 Hz, 2H), 3.28 (s, 3H), 3.12 (t, J=7.86 Hz, 2H), 2.53-2.65 (m, 2H), 2.22 (s, 6H), 1.85 (quin, J=6.27 Hz, 2H), 1.24-1.47 (m, 9H), 1.15 (t, J=7.10 Hz, 3H); LCMS (LCMS Method K): Rt=0.87 min, [M+H]$^+$=865.2

Example 22

Step 10: Ethyl (E)-3-(5-Carbamoyl-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazol-7-yl)propanoic Acid

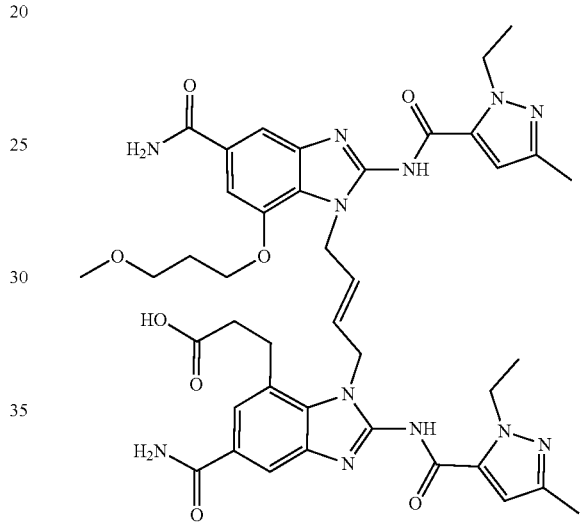

To (E)-ethyl 3-(5-carbamoyl-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate (15 mg, 0.014 mmol, Example 21) in THF (0.3 mL) was added 1M aq LiOH (0.042 mL, 0.042 mmol) in water (0.3 mL). After 1 hr at RT, the THF was removed in vacuo, and 5N aq HCl was added to neutralize the reaction. The resulting white solid was collected by filtration, and this crude material was purified by HPLC (Gilson, Sunfire C18 OBD 30×100 mm column with a gradient of 10-60% acetonitrile (0.1% TFA)/water (0.1% TFA) and a flow rate of 30 mL/min., gradient time:15 min.) to provide the title compound (2.4 mg, 3 μmol, 20% yield). $^1$H NMR (400 MHz, methanol-d$_4$) δ ppm 7.86 (d, J=1.52 Hz, 1H), 7.58 (dd, J=3.55, 1.27 Hz, 2H), 7.31 (d, J=1.01 Hz, 1H), 6.60 (d, J=5.83 Hz, 2H), 5.92 (d, J=15.46 Hz, 1H), 5.69 (d, J=15.46 Hz, 1H), 5.12 (br. s., 2H), 5.06 (d, J=4.82 Hz, 2H), 4.60 (dq, J=14.61, 7.21 Hz, 4H), 4.09 (t, J=6.46 Hz, 2H), 3.42 (t, J=6.08 Hz, 2H), 3.28 (s, 3H), 3.09-3.18 (m, 2H), 2.56-2.65 (m, 2H), 2.21 (d, J=4.82 Hz, 6H), 1.86 (t, J=6.21 Hz, 2H), 1.35 (dt, J=12.42, 7.10 Hz, 6H); LCMS (LCMS Method D): Rt=1.90 min, [M+H]$^+$=838.0

Example 23
Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate, bis Trifluoroacetic Acid Salt
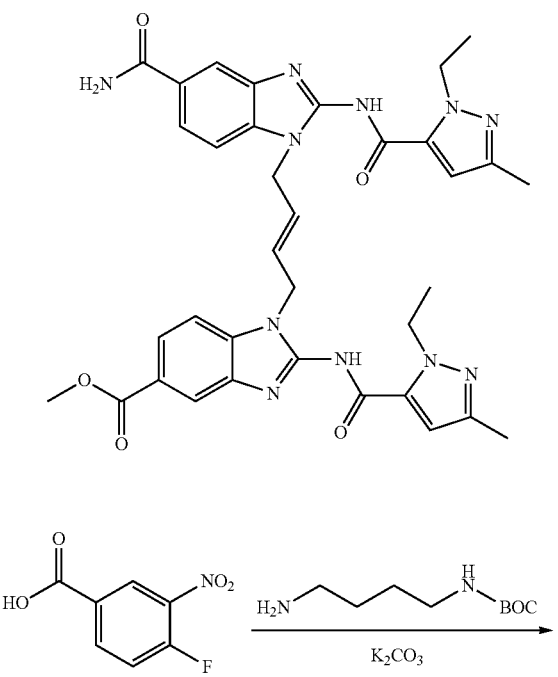
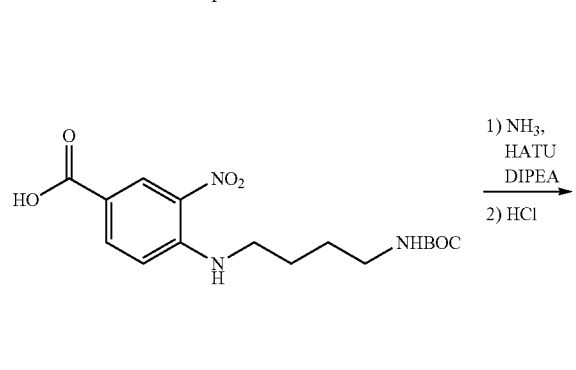
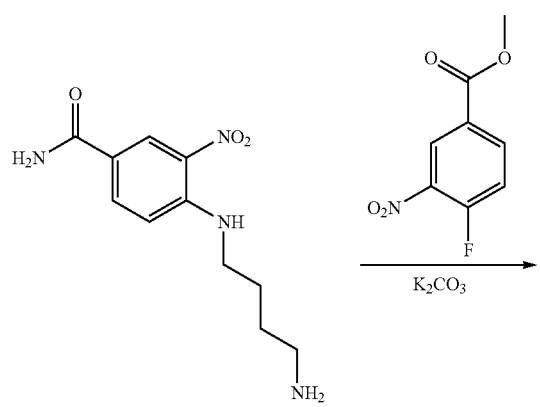
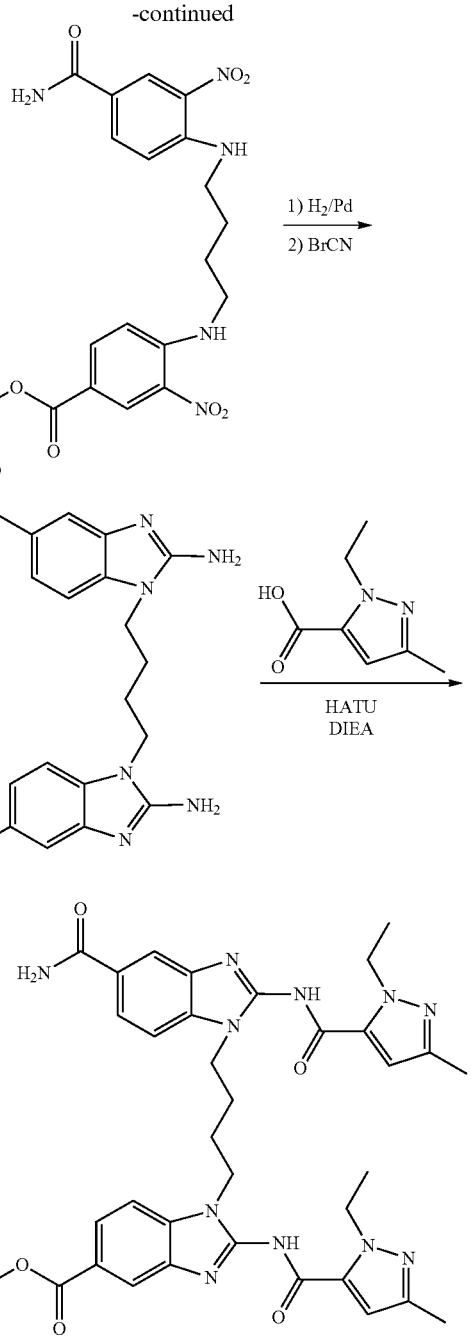
Step 1: 4-((4-((tert-Butoxycarbonyl)amino)butyl)amino)-3-nitrobenzoic Acid Hydrochloride
To tert-butyl (4-aminobutyl)carbamate (4.00 g, 21.3 mmol) and potassium carbonate (8.81 g, 63.7 mmol) in DMSO (70.8 ml) at RT was added 4-fluoro-3-nitrobenzoic acid (3.93 g, 21.3 mmol). The reaction was heated to 80° C. for 18 hr, cooled to RT and diluted with EtOAc and water. The mixture was stirred vigorously and carefully brought to pH 5 with HCl. The organic layer was isolated, washed with water and brine, dried over sodium sulfate, filtered and concentrated to afford the crude title compound (11.86 g, 21.3 mmol, quantitative yield) as a yellow amorphous solid, which was used without further purification. $^1$H NMR (400 MHz, DMSO-d δ ppm 12.89 (br. s., 1H), 8.63 (d, J=2.02 Hz, 1H), 8.50-8.60 (m, 1H), 7.97 (d, J=9.09 Hz, 1H), 7.16 (d, J=9.35 Hz, 1H), 6.88 (br. s., 1H), 3.44 (q, J=6.57 Hz, 2H), 3.38 (br. s., 1H), 2.98 (d, J=6.06 Hz, 2H), 1.61 (d, J=6.57 Hz, 2H), 1.43-1.54 (m, 2H), 1.39 (s, 9H); LCMS (LCMS Method C): Rt=0.91 min, [M+H]$^+$=354.1

Step 2: tert-Butyl (4-((4-carbamoyl-2-nitrophenyl) amino)butyl)carbamate

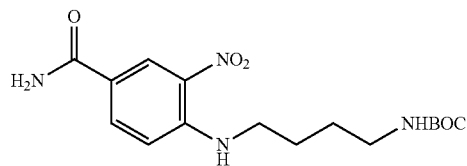

To 4-((4-((tert-butoxycarbonyl)amino)butyl)amino)-3-nitrobenzoic acid hydrochloride (10.7 g, 27.4 mmol) and HATU (12.5 g, 32.9 mmol) in DCM (91 ml) at RT was added DIEA (10.5 ml, 60.3 mmol) followed by 7 M ammonia in MeOH (7.83 ml, 54.8 mmol). After 3 hr, the resulting yellow solid was collected by filtration and washed with DCM to yield the title compound (8.52 g, 21.8 mmol, 79% yield). $^1$H NMR (400 MHz, DMSO-d δ ppm 8.41 (t, J=5.68 Hz, 1H), 8.34 (dd, J=4.04, 1.26 Hz, 1H), 8.13 (dd, J=8.34, 1.26 Hz, 1H), 7.31 (br. s., 2H), 7.07-7.15 (m, 1H), 3.39-3.46 (m, 2H), 3.36 (br. s., 1H), 2.97 (q, J=6.57 Hz, 2H), 1.55-1.67 (m, 2H), 1.42-1.53 (m, 2H), 1.38 (s, 9H); LCMS (LCMS Method C): Rt=0.84 min, [M+H]$^+$=353.1

Step 3: 4-((4-Aminobutyl)amino)-3-nitrobenzamide Dihydrochloride

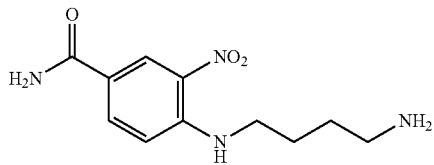 [SMILES: NCCCCNc1ccc(C(N)=O)cc1[N+](=O)[O-]]

To tert-butyl (4-((4-carbamoyl-2-nitrophenyl)amino) butyl)carbamate (4.42 g, 12.6 mmol) in dioxane (126 ml) at RT was added 4 M HCl in dioxane (62.8 ml, 251 mmol). After 24 hr, the reaction was concentrated to yield the title compound (4.08 g, 11.9 mmol, 95% yield) as a yellow-orange solid. $^1$H NMR (400 MHz, DMSO-d$_6$) δ ppm 8.78 (dd, J=4.42, 1.39 Hz, 1H), 8.68 (d, J=2.02 Hz, 1H), 8.55 (dd, J=8.34, 1.52 Hz, 1H), 8.03 (dd, J=9.09, 2.02 Hz, 2H), 7.90 (br. s., 3H), 7.09-7.17 (m, 2H), 3.46 (d, J=6.06 Hz, 2H), 2.78-2.91 (m, 2H), 1.67 (br. s., 4H); LCMS (LCMS Method C): Rt=0.40 min, [M+H]$^+$=253.0

Step 4: Methyl 4-((4-((4-carbamoyl-2-nitrophenyl) amino)butyl)amino)-3-nitrobenzoate

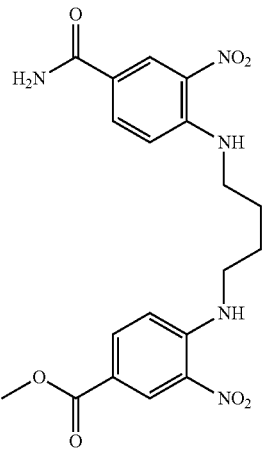 [SMILES: COC(=O)c1ccc(NCCCCNc2ccc(C(N)=O)cc2[N+](=O)[O-])c([N+](=O)[O-])c1]

To a suspension of 4-((4-aminobutyl)amino)-3-nitrobenzamide dihydrochloride (1.84 g, 5.66 mmol) and K$_2$CO$_3$ (2.346 g, 16.97 mmol) in DMSO (11.32 ml) at 23° C. was added methyl 4-fluoro-3-nitrobenzoate (1.13 g, 5.66 mmol). After 30 min, a bright yellow precipitate formed. The reaction was diluted with water (25 mL), and the solid was collected by filtration and dried under vacuum to yield the title compound (4.1 g, 5.6 mmol, 99% yield). $^1$H NMR (400 MHz, DMSO-d$_6$) δ ppm 8.64 (d, J=2.28 Hz, 1H), 8.61 (d, J=2.28 Hz, 2H), 8.42 (t, J=5.70 Hz, 1H), 7.93-8.03 (m, 3H), 7.30 (br. s., 1H), 7.17 (d, J=9.38 Hz, 1H), 7.12 (d, J=9.12 Hz, 1H), 3.83 (s, 3H), 3.48 (d, J=6.08 Hz, 4H), 1.73 (br. s., 4H); LCMS (LCMS Method D): Rt=0.97 min, [M+H]$^+$=432.2

Step 5: Methyl 2-amino-1-(4-(2-amino-5-carbamoyl-1H-benzo[d]imidazol-1-yl)butyl)-1H-benzo[d] imidazole-5-carboxylate Dihydrobromide

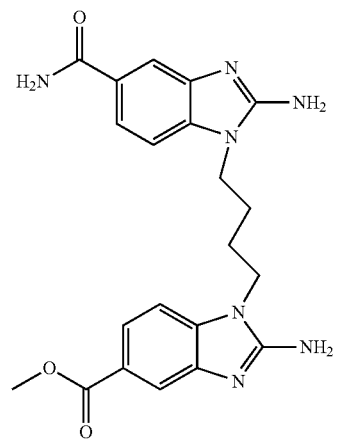 [SMILES: COC(=O)c1ccc2c(c1)nc(N)n2CCCCn1c(N)nc2cc(C(N)=O)ccc21]

To methyl 4-((4-((4-carbamoyl-2-nitrophenyl)amino) butyl)amino)-3-nitrobenzoate (3.18 g, 7.37 mmol) and 10% Pd/C (1.2 g, 1.128 mmol) at RT was added NMP (35 ml). The flask was evacuated and charged with nitrogen, then evacuated once more and charged with 1 atm H2 delivered via balloon. The mixture was stirred at 70° C. for 18 hr, then filtered through Celite warm. The filtrate was cooled to RT and treated with cyanic bromide (2.95 ml, 14.7 mmol). After 2 hr, the reaction was heated to 70° C. for 2 hr, cooled to RT and diluted with EtOAc (120 mL) with vigorous stirring. The resulting grey solid was collected by filtration to yield the title compound (4.91 g, 5.90 mmol, 80% yield). $^1$H NMR (400 MHz, DMSO-$d_6$) δ ppm 12.85 (br. s., 2H), 8.91 (br. s., 2H), 8.78 (s, 2H), 8.08 (br. s., 1H), 7.82-7.99 (m, 4H), 7.60-7.75 (m, 2H), 7.47 (br. s., 1H), 4.13-4.28 (m, 4H), 3.89 (s, 3H), 1.74-1.84 (m, 4H); LCMS (LCMS Method C): Rt=0.49 min, [M+H]$^+$=422.2

Example 23

Step 6: Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate, Bis Trifluoroacetic Acid Salt

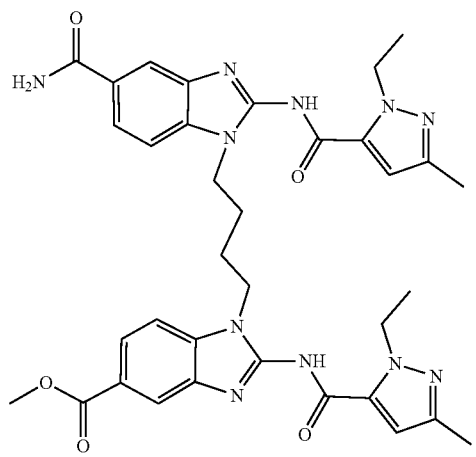

A microwave vial of 1-ethyl-3-methyl-1H-pyrazole-5-carboxylic acid (0.502 g, 3.26 mmol), HATU (1.27 g, 3.34 mmol) and DIEA (1.497 ml, 8.57 mmol) in NMP (5.71 ml) was allowed to stir at RT for 10 min. A separate solution of methyl 2-amino-1-(4-(2-amino-5-carbamoyl-1H-benzo[d]imidazol-1-yl)butyl)-1H-benzo[d]imidazole-5-carboxylate dihydrobromide (1.0 g, 1.7 mmol) dissolved in a minimal amount of NMP was added, and the vial was sealed and microwaved to 140° C. After 30 min, the reaction was cooled to RT and diluted with water (50 mL). The resulting grey solid was collected by filtration, dissolved in a minimal amount of DMSO and purified by reverse-phase HPLC (C18 50×30 mm Luna column, 47 mL/min), eluting with 10-40% acetonitrile in water (0.1% TFA) to yield the title compound (400 mg, 0.412 mmol, 24% yield) as an off-white solid. $^1$H NMR (400 MHz, DMSO-$d_6$) δ ppm 12.89 (s, 1H), 12.83 (s, 1H), 8.09 (s, 1H), 7.93-8.01 (m, 2H), 7.84 (d, J=8.59 Hz, 1H), 7.77 (d, J=8.08 Hz, 1H), 7.58 (dd, J=17.68, 8.34 Hz, 2H), 7.35 (br. s., 1H), 6.60 (d, J=7.83 Hz, 2H), 4.58 (q, J=6.74 Hz, 4H), 4.22-4.34 (m, 4H), 3.88 (s, 3H), 2.11 (s, 6H), 1.82-1.94 (m, 4H), 1.31 (t, J=6.82 Hz, 6H); LCMS (LCMS Method C): Rt=0.86 min, [M+H]$^+$=694.6

Example 24

(E)-1,1'-(But-2-ene-1,4-diyl)bis(2-(1-ethyl-3-methyl-1H-pyrazole-5-carboxamido)-7-methoxy-1H-benzo[d]imidazole-5-carboxamide)

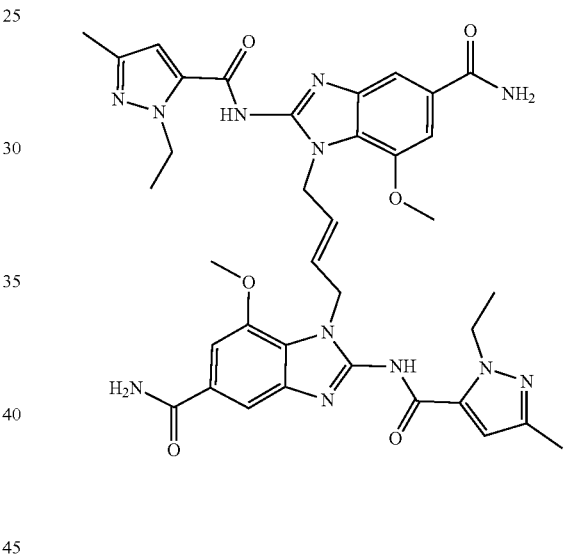

Example 24 can be prepared according to method 1 with modifications known to one of ordinary skill in the art. The last step of the preparation is provided:

A solution of 1-allyl-2-(1-ethyl-3-methyl-1H-pyrazole-5-carboxamido)-7-methoxy-1H-benzo[d]imidazole-5-carboxamide (20 mg, 0.052 mmol) in 1,2-dichloroethane (2.1 ml) was degassed with $N_2$ at 90° C. (heat was needed for dissolution) for 5 min., then Zhan catalyst 1B (CAS 918870-76-5, 5.76 mg, 7.84 µmol) was added. After heating 18 hr, the reaction was stirred at RT 2 days. Another 10 mg Zhan catalyst 1B was added, and the reaction was re-heated to 90° C. After 1 hr, the mixture was cooled and the resulting solid was collected by filtration to yield the title compound (4 mg, 5 µmole, 10% yield). $^1$H NMR (400 MHz, DMSO-$d_4$) δ ppm 12.84 (s, 2H), 7.91-8.24 (m, 2H), 7.64 (s, 2H), 7.33 (s, 4H), 6.53 (s, 2H), 5.70-6.16 (m, 2H), 4.91 (br. s., 4H), 4.29-4.64 (m, 4H), 3.77 (s, 6H), 2.10 (s, 6H), 1.27 (s, 6H); LCMS (LCMS Method L): Rt=0.85 min, [M+H]$^+$=737.5.

Example 25

1,1'-(Butane-1,4-diyl)bis(2-(1-ethyl-3-methyl-1H-pyrazole-5-carboxamido)-7-(3-hydroxypropoxy)-1H-benzo[d]imidazole-5-carboxamide), Dihydrochloride

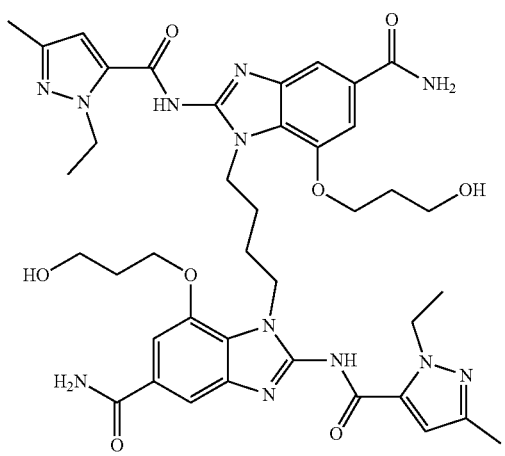

Example 25 can be prepared according to method 2 with modifications known to one of ordinary skill in the art. The last step of the preparation is provided:

To 1,1'-(butane-1,4-diyl)bis(7-(3-((tert-butyldimethylsilyl)oxy)propoxy)-2-(1-ethyl-3-methyl-1H-pyrazole-5-carboxamido)-1H-benzo[d]imidazole-5-carboxamide) (12 mg, 0.011 mmol) in 1,4-dioxane (1.5 mL) was added 4N HCl in dioxane (0.011 mL, 0.045 mmol). After 60 min, the reaction was concentrated and triturated with EtOAc, then the solid was isolated by filtration and dried to afford the title compound (10 mg, 0.011 mmol, 98% yield) as a white solid. $^1$H NMR (400 MHz, DMSO-$d_6$) δ ppm 12.77 (br. s., 2H), 8.02 (br. s., 2H), 7.57 (s, 2H), 7.29-7.39 (m, 4H), 6.58 (s, 2H), 4.56 (d, J=7.10 Hz, 4H), 4.36 (br. s., 4H), 4.15 (t, J=6.21 Hz, 4H), 3.48-3.54 (m, 6H), 2.10 (s, 6H), 1.86 (br. s., 4H), 1.74-1.83 (m, 4H), 1.30 (t, J=7.10 Hz, 6H); LCMS (LCMS Method D): Rt=0.78 min, [M+H]$^+$=827.4.

Example 26

(E)-8-ethyl-1,26-bis(3-hydroxypropoxy)-10,18-dimethyl-7,20-dioxo-6,7,8,11,12,-13,14,15,20,21,28,31-dodecahydrobenzo[4,5]imidazo[1,2-a]benzo[4,5]imidazo[2,1-p]dipyrazolo-[5,1-e:4',3'-l][1,3,6,15,17]pentaazacyclohenicosine-3,24-dicarboxamide, Bis Hydrochloride

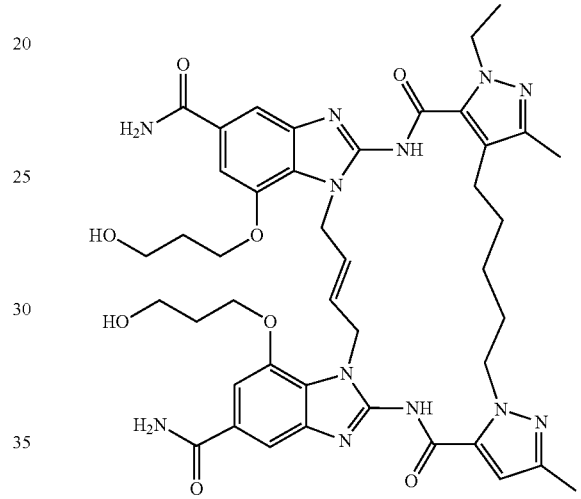

Example 26 can be prepared according to method 6 with modifications known to one of ordinary skill in the art. The last step of the preparation is provided:

To (E)-4,26-bis(3-((tert-butyldimethylsilyl)oxy)propoxy)-8-ethyl-10,18-dimethyl-7,20-dioxo-6,7,8,11,12, 13,14,15,20,21,28,31-dodecahydrobenzo[4,5]imidazo[1,2-a]benzo[4,5]imidazo[2,1-p]dipyrazolo[5,1-e:4',3'-l][1,3,6, 15,17]pentaazacyclohenicosine-2,24-dicarboxamide (269 mg, 0.246 mmol) in THF (20 mL) at 0° C. was added dropwise 4N HCl in dioxane (0.31 mL, 1.23 mmol). After 2 hr, the resulting white solid was collected by filtration and washed with Et$_2$O to afford the title compound (226 mg, 0.241 mmol, 98% yield). $^1$H NMR (600 MHz, MeOH-$d_4$) δ ppm 7.71-7.74 (m, 2H), 7.38-7.41 (m, 2H), 6.82 (s, 1H), 5.72 (s, 2H), 5.00-5.07 (m, 4H), 4.77-4.83 (m, 2H), 4.67 (q, J=7.2 Hz, 2H), 3.88-3.98 (m, 4H), 3.39-3.44 (m, 4H), 2.85-2.92 (m, 2H), 2.41 (s, 3H), 2.38 (s, 3H), 1.93-2.02 (m, 2H), 1.67 (br. t., J=7.6 Hz, 2H), 1.49 (t, J=7.2 Hz, 5H), 1.34-1.44 (m, 4H); LCMS (LCMS Method L): Rt=0.73 min, [M+H]$^+$=865.7017.

Example 27

(E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-(3-methoxypropoxy)-1H-benzo[d]imidazole-5-carboxamide, Dihydrochloride

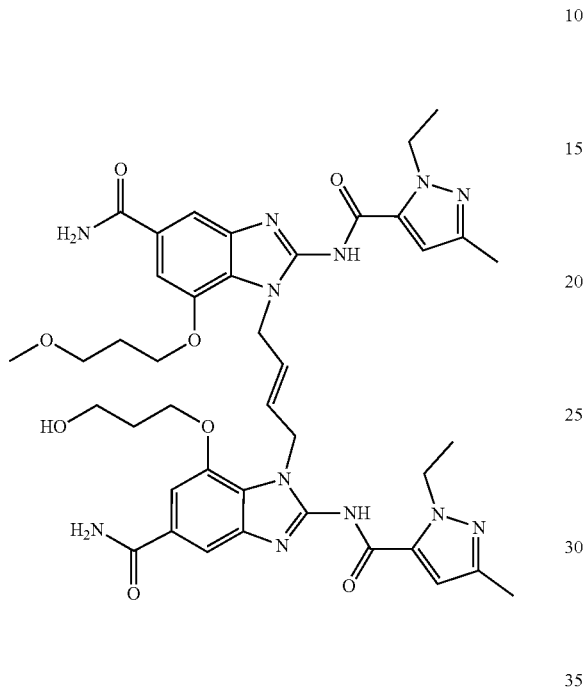

Example 27 can be prepared according to a combination of methods 2, 3 and 4 with modifications known to one of ordinary skill in the art. The last step of the preparation is provided:

1-Ethyl-3-methyl-1H-pyrazole-5-carboxylic acid (216 mg, 1.40 mmol) and CDI (227 mg, 1.40 mmol) were stirred in DMF (0.7 mL) at 100° C. After 10 min, (E)-2-amino-1-(4-(2-amino-5-carbamoyl-7-(3-hydroxypropoxy)-1H-benzo[d]imidazol-1-yl)but-2-en-1-yl)-7-(3-methoxypropoxy)-1H-benzo[d]imidazole-5-carboxamide dihydrobromide (255 mg, 0.350 mmol) was added, and the reaction was heated at 110° C. After 18 hr, a solution of 10M NaOH (350 µl, 3.50 mmol) was added and the reaction mixture heated for 1 h at 75° C. to hydrolyze a small amount of ester byproduct (15%). The mixture was then poured into sat'd aq NH$_4$Cl (10 mL) and the resulting solid was collected by filtration. The solid was suspended in hot MeOH and filtered to give a white powder. This solid was suspended in dioxane (10 mL), and 4N HCl in dioxane (74 µL, 0.30 mmol) was added. After 10 min, the solid was collected by filtration and washed with diethyl ether to afford the title compound (110 mg, 0.121 mmol, 35% yield). $^1$H NMR (400 MHz, MeOH-d$_4$) δ ppm 7.66 (dd, J=5.32, 1.01 Hz, 2H), 7.39 (dd, J=13.18, 1.27 Hz, 2H), 6.68 (d, J=17.24 Hz, 2H), 5.93 (br. s., 2H), 5.17 (br. s., 4H), 4.61-4.75 (m, 4H), 4.06-4.22 (m, 4H), 3.61-3.72 (m, 2H), 3.45 (t, J=6.08 Hz, 2H), 3.31 (s, 3H), 2.28 (d, J=4.06 Hz, 6H), 1.88 (td, J=6.21, 2.28 Hz, 4H), 1.35-1.50 (m, 6H); LCMS (LCMS Method L): Rt=0.78 min, [M+H]$^+$=839.6204.

Example 28

(E)-1-(4-(5-Carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-(2-methoxyethoxy)-1H-benzo[d]imidazole-5-carboxamide

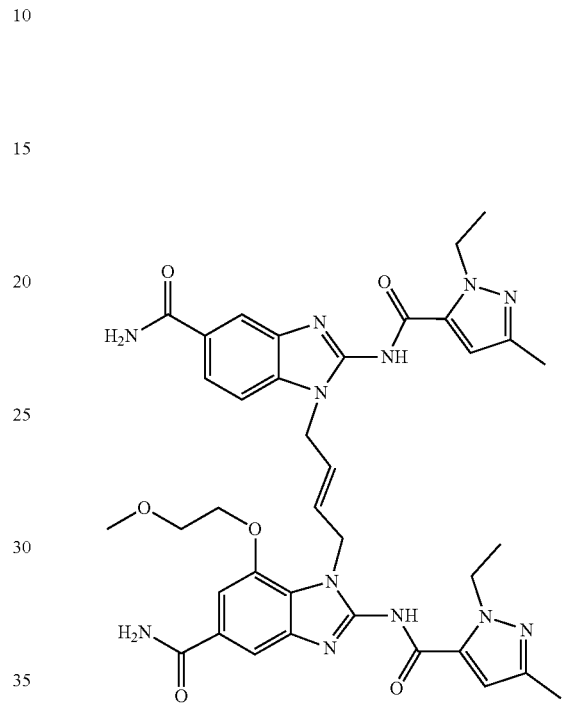

Example 28 can be prepared according to a combination of methods 2 and 3 with modifications known to one of ordinary skill in the art. The last step of the preparation is provided:

A mixture of HATU (894 mg, 2.35 mmol), DIEA (425 mg, 3.29 mmol), (E)-2-amino-1-(4-(2-amino-5-carbamoyl-1H-benzo[d]imidazol-1-yl)but-2-en-1-yl)-7-(2-methoxyethoxy)-1H-benzo[d]imidazole-5-carboxamide (450 mg, 0.940 mmol) and 1-ethyl-3-methyl-1H-pyrazole-5-carboxylic acid (362 mg, 2.35 mmol) in DMF (8 mL) was stirred at 65° C. After 12 hr, the reaction was cooled and treated with water. The resulting solid was collected by filtration and further purified by HPLC to yield the title compound (350 mg, 0.466 mmol, 50% yield). $^1$H NMR (400 MHz, DMSO-d$_6$) δ ppm 12.85 (s, 2H), 7.95-7.99 (m, 4H), 7.65-7.67 (m, 1H), 7.60 (s, 1H), 7.45-7.48 (m, 1H), 7.28-7.35 (m, 2H), 6.55 (d, J=4.0 Hz, 2H), 5.99 (dd, J=13.2, 7.7 Hz, 1H), 5.85 (dd, J=13.3, 7.5 Hz, 1H), 4.94 (d, J=5.3 Hz, 2H), 4.83 (d, J=4.9 Hz, 2H), 4.58-4.49 (m, 4H), 4.15-4.12 (m, 2H), 3.58-3.49 (m, 2H), 3.16 (s, 3H), 2.12 (s, 6H), 1.26-1.35 (m, 6H); LCMS (LCMS Method A): Rt=1.353 min, [M+H]$^+$=751.1.

Example 29

(E)-1,1'-(But-2-ene-1,4-diyl)bis(2-(1-ethyl-3-methyl-1H-pyrazole-5-carboxamido)-7-isopropoxy-1H-benzo[d]imidazole-5-carboxamide)

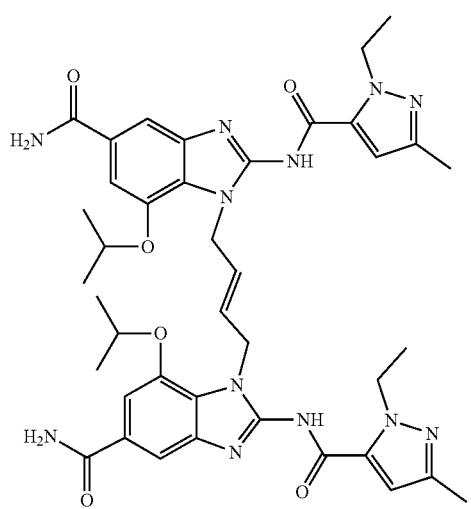 [SMILES: CCn1nc(C)cc1C(=O)Nc1nc2cc(C(N)=O)cc(OC(C)C)c2n1C/C=C/Cn1c(NC(=O)c2cc(C)nn2CC)nc2cc(C(N)=O)cc(OC(C)C)c21]

Example 29 can be prepared according to method 2 with modifications known to one of ordinary skill in the art. The last step of the preparation is provided:

1-Ethyl-3-methyl-1H-pyrazole-5-carboxylic acid (89 mg, 0.58 mmol) and CDI (107 mg, 0.659 mmol) in DMF (2 mL) were stirred for 10 minutes. (E)-1,1'-(But-2-ene-1,4-diyl)bis(2-amino-7-isopropoxy-1H-benzo[d]imidazole-5-carboxamide) dihydrobromide (180 mg, 0.264 mmol) and DIEA (0.18 mL, 1.1 mmol) were added, and the reaction was heated at 90° C. After 3 hr, ice was added, and the resulting solid was collected by filtration, stirred vigorously for 3 hr in EtOAc and isolated. The solid was found by LC/MS to contain~5% mono-amide and was treated with CDI (14 mg, 0.086 mmol), 1-ethyl-3-methyl-H-pyrazole-5-carboxylic acid (12 mg, 0.078 mmol) and DIEA (0.1 mL, 0.6 mmol) in DMF (1.5 mL). The reaction was heated to 90° C. 2 hr, and another portion of reagents was added. After 4 more hr, the reaction was cooled to RT, ice was added, and the resulting solid was collected by filtration to yield the title compound (122 mg, 0.154 mmol, 58% yield). $^1$H NMR (400 MHz, DMSO-$d_6$) δ ppm 12.80 (s, 2H), 7.94 (br. s., 2H), 7.59 (s, 2H), 7.32 (s, 2H), 7.28 (s, 2H), 6.55 (s, 2H), 5.85 (br. s., 2H), 4.94 (br. s., 4H), 4.74 (dt, J=12.0, 5.8 Hz, 2H), 4.55 (q, J=7.0 Hz, 4H), 2.14 (s, 6H), 1.28 (t, J=7.0 Hz, 6H), 1.10 (d, J=6.1 Hz, 12H); LCMS (LCMS Method D): Rt=1.03 min, [M/2+H]$^+$=397.4557.

Example 30

(E)-7-(Benzyloxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

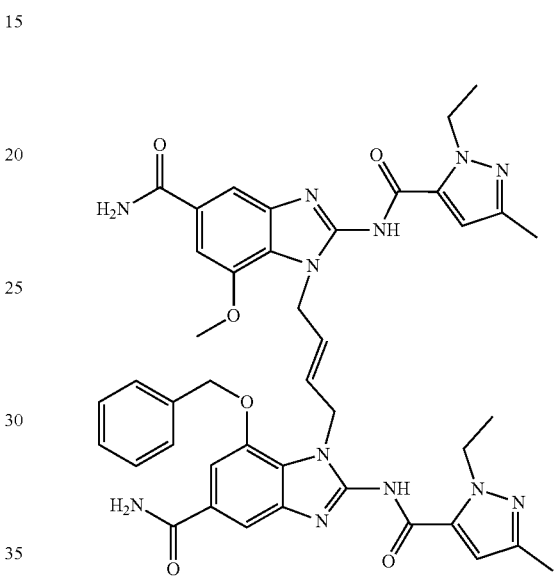

Example 30 can be prepared according to a combination of methods 2, 3 and 4 with modifications known to one of ordinary skill in the art. The last step of the preparation is provided:

1-Ethyl-3-methyl-1H-pyrazole-5-carboxylic acid (20.2 mg, 0.131 mmol) and CDI (23.1 mg, 0.142 mmol) in DMF (1 mL) were stirred for 10 minutes. (E)-2-Amino-1-(4-(2-amino-5-carbamoyl-7-methoxy-1H-benzo[d]imidazol-1-yl)but-2-en-1-yl)-7-(benzyloxy)-1Hbenzo[d]imidazole-5-carboxamide dihydrobromide (40 mg, 0.057 mmol) and DIEA (0.07 mL, 0.4 mmol) were added, and the reaction was heated at 90° C. After 22 hr, ice was added with vigorous stirring, and the resulting solid was collected by filtration, rinsed with water and triturated sequentially with ethyl acetate and methanol to yield the title compound (10 mg, 0.012 mmol, 21% yield) as a tan solid. $^1$H NMR (400 MHz, DMSO-$d_6$) δ ppm 12.86 (d, J=5.8 Hz, 2H), 7.99 (br. s., 2H), 7.67 (d, J=2.3 Hz, 2H), 7.45 (s, 1H), 7.37 (br. s., 2H), 7.19-7.30 (m, 6H), 6.53 (s, 1H), 6.49 (s, 1H), 5.74-5.84 (m, 1H), 5.53-5.62 (m, 1H), 5.05 (s, 2H), 4.86 (dd, J=11.8, 4.9 Hz, 4H), 4.44-4.58 (m, 4H), 3.64 (s, 3H), 2.12 (s, 3H), 2.09 (s, 3H), 1.19-1.31 (m, 6H); LCMS (LCMS Method D): Rt=1.02 min, [M/2+H]$^+$=407.4811.

Example 31

(E)-1-(4-(5-Carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-methyl-1Hbenzo[d]imidazole-5-carboxamide

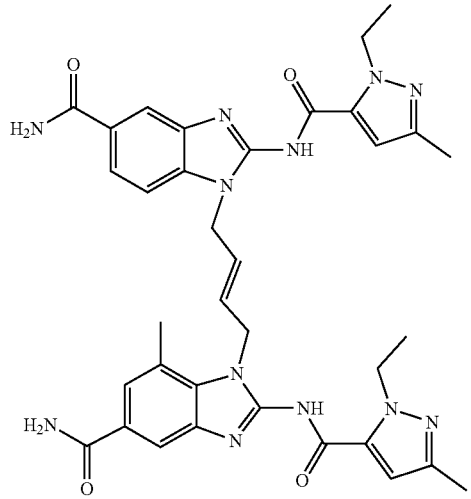 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(C)c21]

Example 32

(E)-1,1'-(But-2-ene-1,4-diyl)bis(7-butoxy-2-(1-ethyl-3-methyl-1H-pyrazole-5-carboxamido)-1H-benzo[d]imidazole-5-carboxamide)

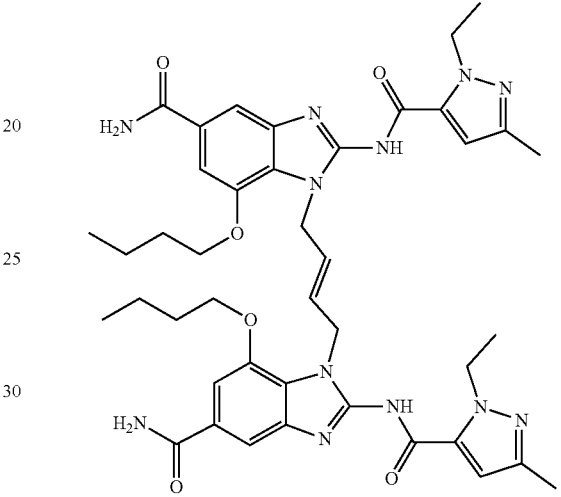

Example 31 can be prepared according to a combination of methods 2 and 4 with modifications known to one of ordinary skill in the art. The last step of the preparation is provided:

A mixture of HATU (568 mg, 1.49 mmol), DIEA (0.31 mL, 1.8 mmol) and 1-ethyl-3-methyl-1H-pyrazole-5-carboxylic acid (203 mg, 1.31 mmol) in NMP (5 mL) was stirred at RT. After 1 hr, (E)-2-amino-1-(4-(2-amino-5-carbamoyl-1H-benzo[d]imidazol-1-yl)but-2-en-1-yl)-7-methyl-1H-benzo[d]imidazole-5-carboxamide (250 mg, 0.597 mmol) was added, and the mixture was stirred at 60° C. overnight. The reaction was treated with water, and the resulting solid was collected by filtration and further purified by HPLC (Gemini-C18, 150×21.2 mm, 5 um, 20-50% $CH_3CN$ in $H_2O$, 0.1% TFA) to yield the title compound (3 mg, 4 μmol, 0.7% yield). $^1$H NMR (400 MHz, DMSO-$d_6$) δ ppm 13.08-12.70 (m, 2H), 7.97 (d, J=10.4 Hz, 2H), 7.87 (d, J=13.0 Hz, 2H), 7.73 (d, J=8.6 Hz, 1H), 7.50 (s, 1H), 7.45 (d, J=8.4 Hz, 1H), 7.32 (d, J=17.7 Hz, 2H), 6.54 (d, J=7.9 Hz, 2H), 5.96 (d, J=15.3 Hz, 1H), 5.52 (d, J=15.6 Hz, 1H), 4.99 (s, 2H), 4.83 (s, 2H), 4.53 (d, J=4.7 Hz, 4H), 2.51 (s, 3H), 2.12 (d, J=2.8 Hz, 6H), 1.27 (t, J=7.1 Hz, 6H); LCMS (LCMS Method A): Rt=1.321 min, [M+H]$^+$=691.3.

Example 32 can be prepared according to method 2 with modifications known to one of ordinary skill in the art. The last step of the preparation is provided:

To 1-ethyl-3-methyl-1H-pyrazole-5-carboxylic acid (17.4 mg, 0.113 mmol) and CDI (18.3 mg, 0.113 mmol) in DMF (650 uL) at 60° C. were added (E)-1,1'-(but-2-ene-1,4-diyl)bis(2-amino-7-(3-hydroxypropoxy)-1H-benzo[d]imidazole-5-carboxamide) (25 mg, 0.045 mmol) and TEA (38 μL, 0.27 mmol), and the reaction was heated to 120° C. After 18 hr, a solution of additional CDI (30 mg, 0.19 mmol) and 1-ethyl-3-methyl-H-pyrazole-5-carboxylic acid (30 mg, 0.19 mmol) (heated in DMF for 10 min at 60° C.) was then added to the reaction. The reaction was cooled, water was added, and the resulting precipitate was collected by filtration and triturated with hot MeOH (1 mL) to yield the title compound (6.9 mg, 8.4 μmol, 13% yield) as a tan solid. $^1$H NMR (400 MHz, DMSO-$d_6$) δ ppm 12.87 (s, 2H), 7.96 (br. s., 2H), 7.65 (s, 2H), 7.35 (br. s., 2H), 7.26 (s, 2H), 6.56 (s, 2H), 5.81 (br. s., 2H), 4.91 (br. s., 4H), 4.49-4.62 (m, 4H), 3.84 (t, J=6.46 Hz, 4H), 2.14 (s, 6H), 1.37-1.48 (m, 5H), 1.30 (t, J=6.97 Hz, 6H), 1.20 (dd, J=14.95, 7.60 Hz, 4H), 0.74 (t, J=7.48 Hz, 6H); LCMS (LCMS Method L): Rt=1.06 min, [M+H]$^+$=821.7039.

Example 33

(E)-1-(4-(5-Carbamoyl-2-(1-ethyl-3-methyl-1H-pyrazole-5-carboxamido)-1Hbenzo[d]imidazol-1-yl)but-2-en-1-yl)-2-(1-ethyl-3-methyl-1H-pyrazole-5-carboxamido)-7-isopropoxy-1H-benzo[d]imidazole-5-carboxamide

Example 34

(E)-1,1'-(But-2-ene-1,4-diyl)bis(2-(1-ethyl-3-methyl-1H-pyrazole-5-carboxamido)-7-(3-isopropoxypropoxy)-1H-benzo[d]imidazole-5-carboxamide) dihydrochloride

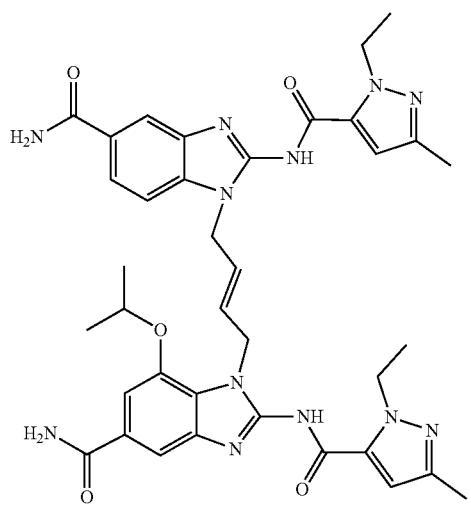 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OC(C)C)c21]

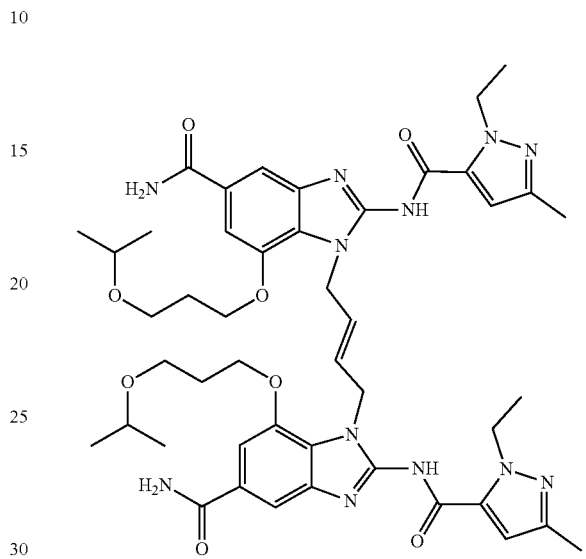

Example 33 can be prepared according to a combination of methods 2 and 4 with modifications known to one of ordinary skill in the art. The last step of the preparation is provided:

A mixture of HATU (190 mg, 0.500 mmol), DIEA (0.16 mL, 0.93 mmol) and 1-ethyl-3-methyl-1H-pyrazole-5-carboxylic acid (70 mg, 0.45 mmol) in NMP (3 mL) was stirred at RT. After 15 min, (E)-2-amino-1-(4-(2-amino-5-carbamoyl-1H-benzo[d]imidazol-1-yl)but-2-en-1-yl)-7-isopropoxy-1H-benzo[d]imidazole-5-carboxamide (86 mg, 0.19 mmol) was added, and the mixture was stirred at 60° C. 16 hr. The reaction was treated with water, and the resulting solid was collected by filtration and further purified by HPLC (Gemini-C18, 150×21.2 mm, 5 um, 30-50% CH$_3$CN in H$_2$O, 0.1% TFA, 15 min run) to yield the title compound (23 mg, 0.031 mmol, 17% yield) as an off-white solid. $^1$H NMR (400 MHz, DMSO-d$_6$) δ ppm 12.82 (s, 2H), 7.96 (d, J=14.3 Hz, 3H), 7.72 (d, J=8.5 Hz, 1H), 7.61 (s, 1H), 7.44 (d, J=8.4 Hz, 1H), 7.31 (d, J=11.6 Hz, 3H), 6.55 (s, 2H), 5.96 (dd, J=13.5, 7.7 Hz, 1H), 5.80 (d, J=15.7 Hz, 1H), 4.94 (d, J=5.4 Hz, 2H), 4.84 (d, J=4.9 Hz, 2H), 4.73-4.79 (m, 1H), 4.54 (td, J=14.3, 7.1 Hz, 4H), 2.13 (d, J=5.8 Hz, 6H), 1.28 (dt, J=12.1, 7.1 Hz, 6H), 1.14 (d, J=6.0 Hz, 6H); LCMS (LCMS Method A): Rt=1.413 min, [M+H]$^+$=735.2.

Example 34 can be prepared according to method 2 with modifications known to one of ordinary skill in the art. The last step of the preparation is provided:

To a solution of 1-ethyl-3-methyl-1H-pyrazole-5-carboxylic acid (110 mg, 0.711 mmol), HATU (271 mg, 0.711 mmol) and HOBt (54.5 mg, 0.356 mmol) in DMF (0.9 mL) was added a suspension of (E)-1,1'-(but-2-ene-1,4-diyl)bis(2-amino-7-(3-isopropoxypropoxy)-1H-benzo[d]-imidazole-5-carboxamide) (151 mg, 0.237 mmol) and TEA (0.20 mL, 1.4 mmol) in DMF (3.8 mL). After stirring at RT overnight, the reaction was diluted with water, extracted with EtOAc (2×), and the combined organic extracts were washed with brine and concentrated. The resulting residue was purified over silica gel (Isco Rf 40 g column), eluting with 0-20% MeOH in DCM to yield the free base of title compound (105 mg, 0.116 mmol, 49% yield) as a pale yellow solid. A portion of this material (80 mg, 0.088 mmol) was dissolved in MeOH (2 mL) and DCM (2 mL) and treated with 4N HCl in dioxane (0.044 mL, 0.18 mmol). After 5 min, the reaction was added to MeCN (A very small amount of solid precipitated), and the mixture was concentrated. The resulting residue was triturated with EtOAc to give the title compound (68 mg, 0.069 mmol, 79% yield) as a white solid. $^1$H NMR (400 MHz, DMSO-d$_6$) δ ppm 8.00 (br. s., 2H), 7.65 (d, J=1.01 Hz, 2H), 7.35 (br. s., 2H), 7.30 (d, J=1.01 Hz, 2H), 6.55 (s, 2H), 5.83 (br. s., 2H), 4.94 (br. s., 4H), 4.54 (q, J=7.10 Hz, 4H), 4.00 (t, J=6.21 Hz, 4H), 3.32-3.41 (m, 2H), 3.21-3.31 (m, 4H), 2.13 (s, 6H), 1.69 (t, J=6.21 Hz, 4H), 1.29 (t, J=7.10 Hz, 6H), 0.98 (d, J=6.08 Hz, 12H); LCMS (LCMS Method D): Rt=1.10 min, [M/2+H]$^+$=455.5857.

Example 35

(E)-2-(1-Ethyl-3-methyl-1H-pyrazole-5-carbox-amido)-1-(4-(2-(1-ethyl-3-methyl-1H-pyrazole-5-carboxamido)-7-(morpholinomethyl)-1H-benzo[d]imidazol-1-yl)but-2-en-1-yl)-1H-benzo[d]imidazole-5-carboxamide, Trifluoroacetic Acid Salt

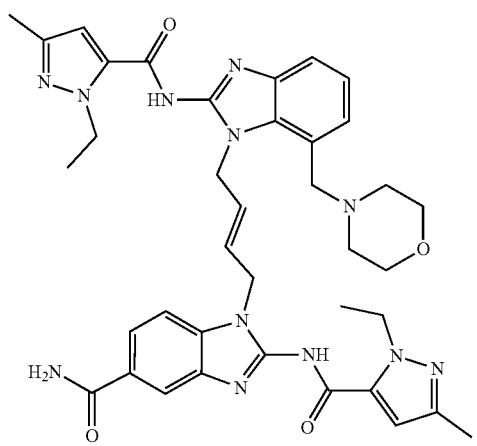

Example 35 can be prepared according to a combination of methods 2 and 3 with modifications known to one of ordinary skill in the art. The last step of the preparation is provided:

A mixture of 1-ethyl-3-methyl-1H-pyrazole-5-carboxylic acid (117 mg, 0.760 mmol), HATU (347 mg, 0.912 mmol) and DIEA (0.319 mL, 1.824 mmol) in DMF (6 mL) was stirred at RT. After 30 min, (E)-2-amino-1-(4-(2-amino-7-(morpholinomethyl)-1H-benzo[d]imidazol-1-yl)but-2-en-1-yl)-1H-benzo[d]imidazole-5-carboxamide (140 mg, 0.304 mmol) was added, and the reaction was stirred at 50° C. overnight. Water was added, and the resulting solid was collected by filtration and purified by prep-HPLC to afford the title compound (10 mg, 12 µmole, 3.9% yield) as a gray solid. $^1$H NMR (400 MHz, DMSO-d$_6$) δ ppm 12.98 (br. s., 2H), 10.59 (br. s., 1H), 7.91-8.01 (m, 2H), 7.74 (d, J=8.4 Hz, 1H), 7.64 (d, J=7.6 Hz, 1H), 7.42 (d, J=8.4 Hz, 1H), 7.24-7.39 (m, 3H), 6.56 (d, J=5.6 Hz, 2H), 5.93 (d, J=16 Hz, 2H), 5.38-5.50 (m, 2H), 5.10 (br. s., 2H), 4.79 (br. s., 2H), 4.48-4.55 (m, 4H), 3.69-3.85 (m, 4H), 3.03-3.32 (m, 4H), 2.13 (s, 6H), 1.21-1.40 (m, 6H); LCMS (LCMS Method A): Rt=1.328 min, [M+H]$^+$=733.2

Example 36

(E)-1-(4-(5-carbamoyl-2-(1-ethyl-3-methyl-1H-pyrazole-5-carboxamido)-7-(3-(piperidin-4-yl)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, Hydrochloride

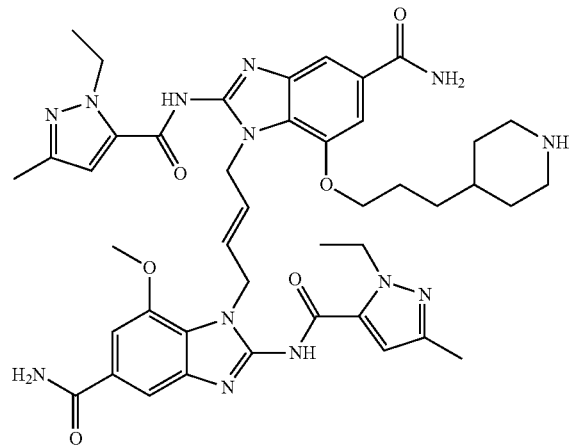

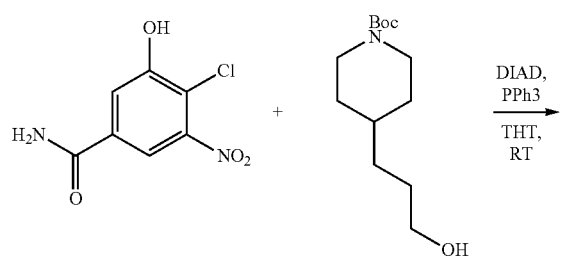

-continued
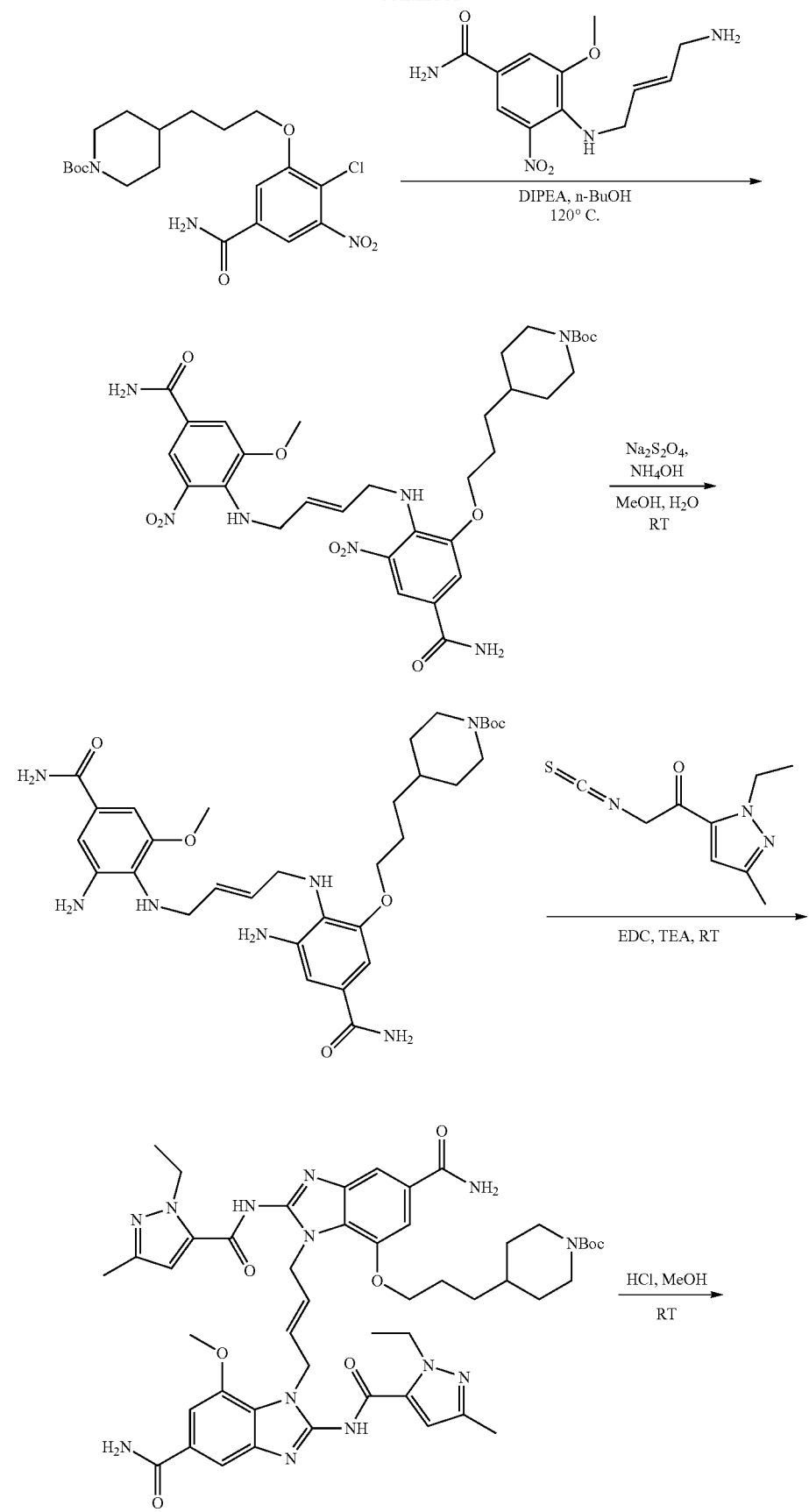

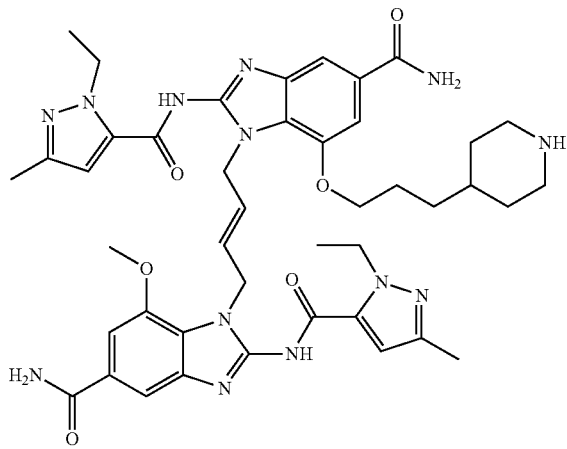

Step 1: tert-butyl 4-(3-(5-carbamoyl-2-chloro-3-nitrophenoxy)propyl)piperidine-1-carboxylate

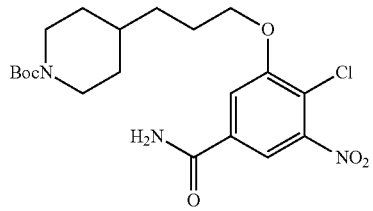 [SMILES: CC(C)(C)OC(=O)N1CCC(CCCOc2cc(C(N)=O)cc([N+](=O)[O-])c2Cl)CC1]

4-chloro-3-hydroxy-5-nitrobenzamide (1 g, 4.62 mmol)), tert-butyl 4-(3-hydroxypropyl) piperidine-1-carboxylate (1.348 g, 5.54 mmol) and triphenylphosphine (2.059 g, 7.85 mmol) were mixed in THE (20 mL) at 0° C., and then diisopropyl (E)-diazene-1,2-dicarboxylate (1.545 ml, 7.85 mmol) was added. The reaction was maintained at RT for 16 hrs, then the yellow solution was then concentrated and the residue was partitioned between sat. aq. NaHCO$_3$ and EtOAc. The organic layer was washed by brine, dried over MgSO$_4$ and concentrated to a yellow residue. This residue was purified by Isco Combiflash (10%-50% (3:1 EtOAc/EtOH)/Hexane, with 2% NH$_4$OH; 40 g RediSep column). Collected fractions containing the product were combined and concentrated to give the title compound as a yellow solid (2.83 g, 61% pure, 3.91 mmol, 85% yield). $^1$H NMR (400 MHz, DMSO-d$_6$) δ ppm 8.29 (s, 1H), 8.04 (d, J=1.77 Hz, 1H,) 7.87 (d, J=1.52 Hz, 1H), 7.80 (s, 1H), 4.22 (t, J=6.34 Hz, 2H), 3.93 (d, J=10.90 Hz, 2H), 2.68 (br. s., 2H), 1.77-1.88 (m, 2H), 1.67 (d, J=11.41 Hz, 2H), 1.47 (br. s., 1H), 1.34-1.42 (m, 11H), 0.89-1.05 (m, 2H); LCMS (LCMS Method K): Rt=1.25 min, [M−100]$^+$=342.0.

Step 2: tert-butyl (E)-4-(3-(5-carbamoyl-2-((4-((4-carbamoyl-2-methoxy-6-nitrophenyl)amino)but-2-en-1-yl)amino)-3-nitrophenoxy)propyl)piperidine-1-carboxylate

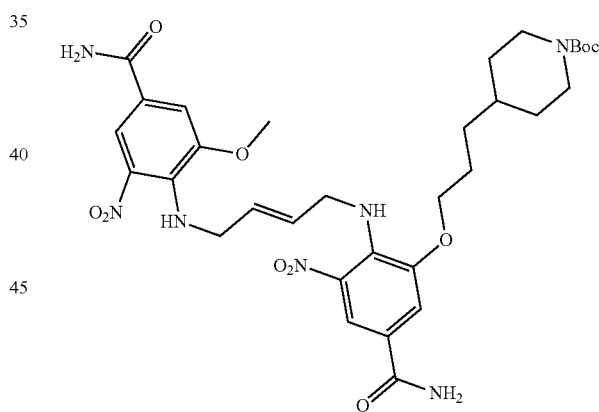

(E)-4-((4-aminobut-2-en-1-yl)amino)-3-methoxy-5-nitrobenzamide, Trifluoroacetic acid salt (1 g, 2.54 mmol) was suspended in n-butanol (10 mL) at RT, and then DIPEA (2.66 ml, 15.22 mmol) and tert-butyl 4-(3-(5-carbamoyl-2-chloro-3-nitrophenoxy)propyl)piperidine-1-carboxylate (2.021 g, 2.79 mmol) were added. The reaction mixture was then maintained at 120° C. for 48 hrs, then the reaction mixture was cooled to RT. The brown solid was collected by filtration, and purified by Isco Combiflash (20%-80% (3:1 EtOAc/EtOH)/Hexane, with 2% NH$_4$OH; 40 g RediSep column). Collected fractions containing the product were combined and concentrated to give the title compound as a red solid (204 mg, 12% yield). LCMS (LCMS Method K): Rt=1.25 min, [M−100]$^+$=586.2.

319

Step 3: tert-butyl (E)-4-(3-(3-amino-2-((4-((2-amino-4-carbamoyl-6-methoxyphenyl)amino)but-2-en-1-yl)amino)-5-carbamoylphenoxy)propyl)piperidine-1-carboxylate

320

Step 4: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperidine-1-carboxylate

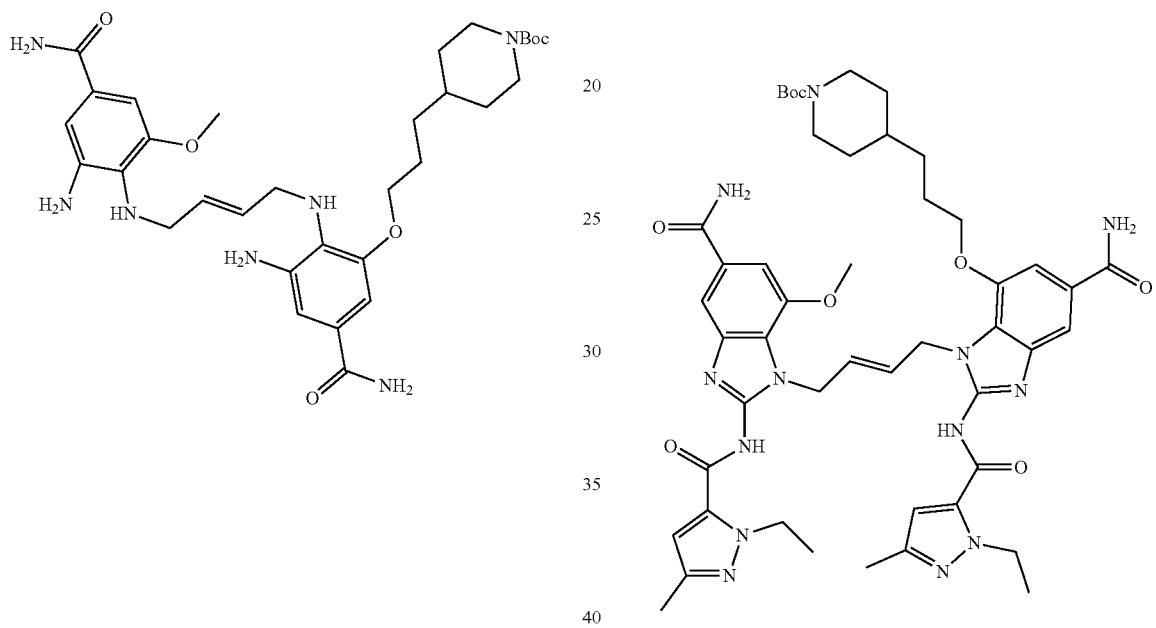

Sodium hydrosulfite (609 mg, 2.97 mmol) was dissolved in H₂O (5 mL) at rt, and then this solution was added to a stirring solution of tert-butyl (E)-4-(3-(5-carbamoyl-2-((4-((4-carbamoyl-2-methoxy-6-nitrophenyl)amino)but-2-en-1-yl)amino)-3-nitrophenoxy)propyl)piperidine-1-carboxylate (204 mg, 0.297 mmol) and ammonium hydroxide (0.799 mL, 5.95 mmol) in 20 ml MeOH. The reaction mixture was then maintained at RT for 2 hrs then the mixture was filtered and the filtrate was partially concentrated to remove MeOH.

The resulting yellow aqueous mixture was partitioned between sat. NaHCO₃ (aq) and EtOAc. The organic layer was washed by brine, dried over MgSO₄, concentrated and purified by Isco Combiflash (2%-20% MeOH/CH₂Cl₂, 10% TEA in MeOH; 40 g RediSep column). Collected fractions containing the product were combined and concentrated to give the title compound as a colorless oil (77 mg, 42% yield). ¹H NMR (400 MHz, METHANOL-d₄) δ ppm 6.94 (t, J=2.15 Hz, 2H), 6.89 (dd, J=4.56, 1.77 Hz, 2H), 5.74 (d, J=4.56 Hz, 2H), 4.05 (d, J=13.43 Hz, 2H), 3.96 (t, J=6.34 Hz, 2H), 3.80 (s, 3H), 3.52-3.62 (m, 4H), 2.62-2.83 (m, 2H), 1.77-1.88 (m, 2H), 1.71 (d, J=11.91 Hz, 2H), 1.35-1.52 (m, 12H), 0.99-1.16 (m, 2H). LCMS (LCMS Method K): Rt=0.64 min, [M+H]⁺=626.3.

tert-Butyl(E)-4-(3-(3-amino-2-((4-((2-amino-4-carbamoyl-6-methoxyphenyl)amino)but-2-en-1-yl)amino)-5-carbamoylphenoxy)propyl)piperidine-1-carboxylate (77 mg, 0.123 mmol) was dissolved in DMF (3 mL) at 0° C., and then 1-ethyl-3-methyl-1H-pyrazole-5-carbonyl isothiocyanate (0.308 ml, 0.123 mmol) was added. The reaction mixture was then maintained at 0° C. for 15 min. then EDC (28.3 mg, 0.148 mmol) and TEA (0.043 ml, 0.308 mmol) were then added to the reaction mixture. The reaction mixture was then maintained at RT for 16 hrs. The reaction mixture was concentrated and the yellow residue was purified on silica gel (20%-50% MeOH/CH₂Cl₂, 10% TEA in MeOH; 40 g RediSep column). Collected fractions containing the product were combined and concentrated to afford the title compound as a white solid (87 mg, 52% yield). LCMS (LCMS Method K): Rt=1.11 min, [M+H]⁺=948.3.

Example 36

(E)-1-(4-(5-carbamoyl-2-(1-ethyl-3-methyl-1H-pyrazole-5-carboxamido)-7-(3-(piperidin-4-yl)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, Hydrochloride

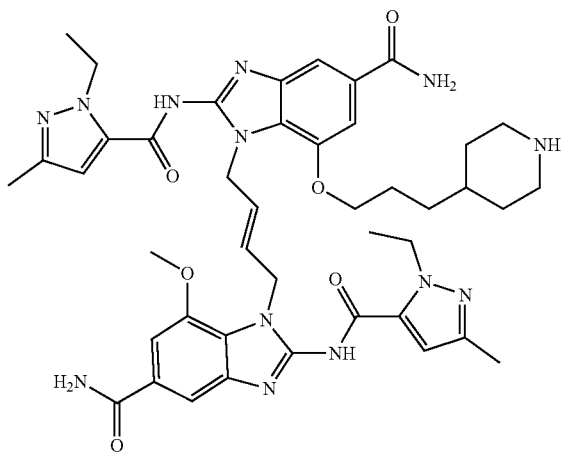 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCC3CCNCC3)c21]

Step 5: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperidine-1-carboxylate (87 mg, 0.092 mmol) was suspended in MeOH (40 ml), and HCl (4N in 1,4-dioxane) (0.575 ml, 2.30 mmol) was added. The reaction mixture was maintained at RT for 48 hrs, then the mixture was concentrated and the residue was purified by HPLC (XSELECT CSH C18 column, 150 mm×30 mm, i.d. 5 um packing diameter, 15%-85% 10 mM ammonium bicarbonate in water with acetonitrile). The desired fractions were combined and partially concentrated and the white precipitate collected to yield the title compound as a white solid (30 mg, 37% yield). $^1$H NMR (400 MHz, METHANOL-$d_4$) δ ppm 8.57 (s, 1H), 7.63 (d, J=1.01 Hz, 1H), 7.57 (s, 1H), 7.29 (s, 1H), 7.20 (s, 1H), 6.67 (s, 1H), 6.58 (s, 1H), 5.85 (br. s., 2H), 5.03 (br. s., 4H), 4.54-4.73 (m, 4H), 3.81 (t, J=6.46 Hz, 2H), 3.71 (s, 3H), 3.23 (d, J=12.93 Hz, 2H), 2.72-2.85 (m, 2H), 2.24 (d, J=12.17 Hz, 6H), 1.74 (d, J=13.69 Hz, 2H), 1.12-1.54 (m, 13H). LCMS (LCMS Method K): Rt=0.72 min, [M+H]$^+$=848.6.

Example 37

(E)-1-(4-(5-carbamoyl-2-(1-ethyl-3-methyl-1H-pyrazole-5-carboxamido)-7-(3-(piperazin-1-yl)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

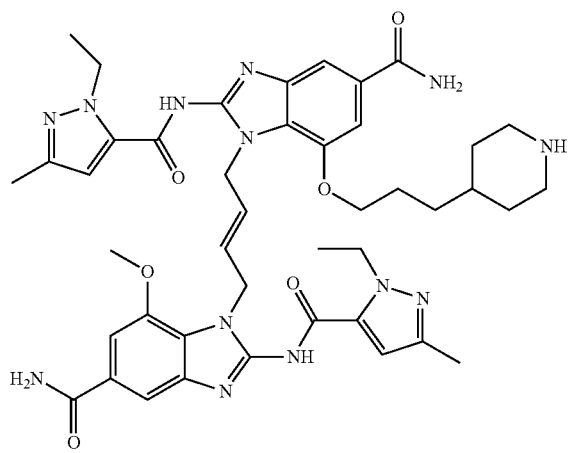

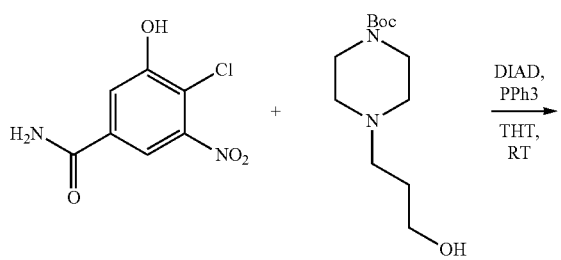

-continued
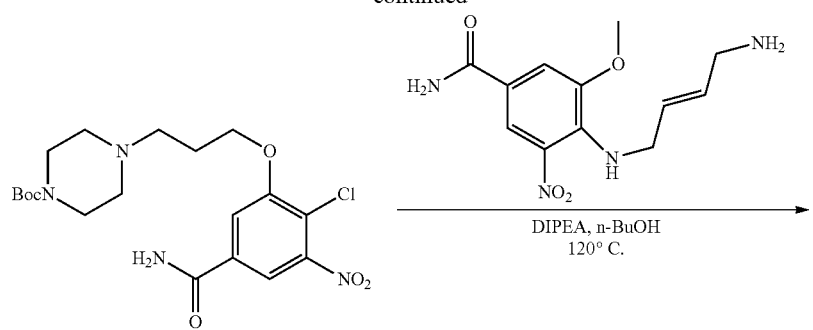
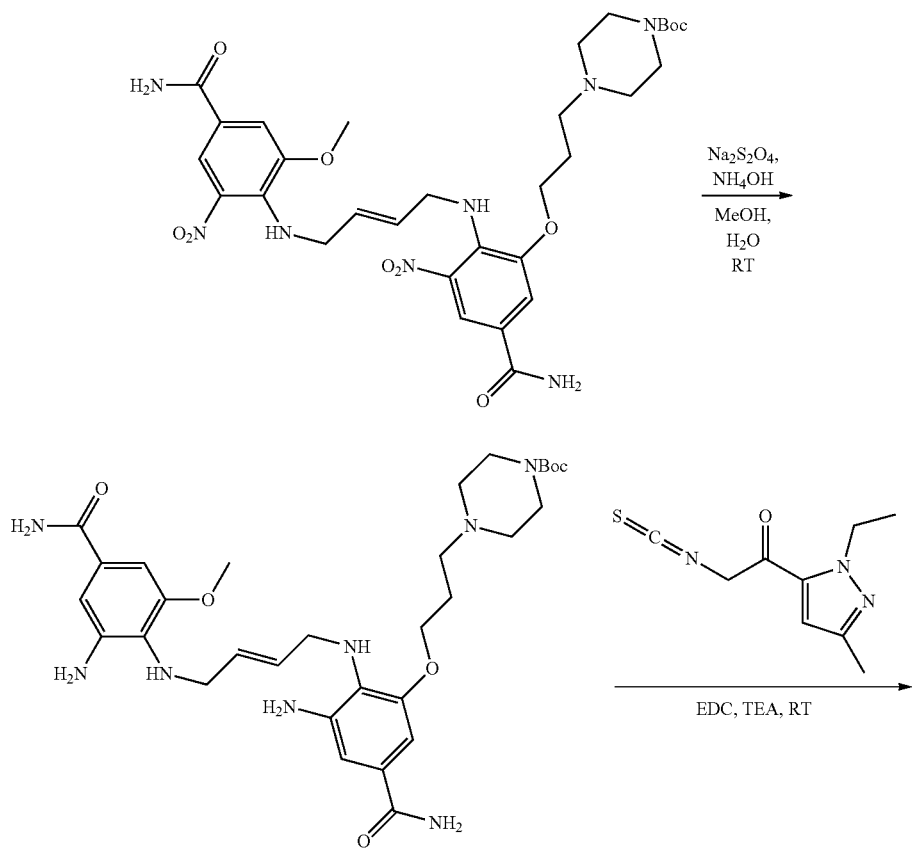
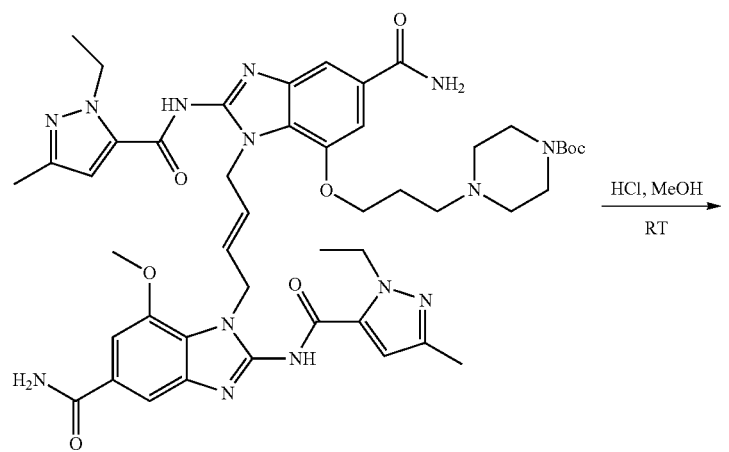

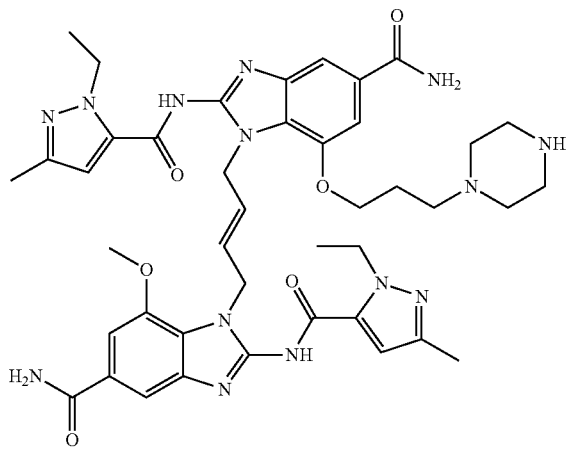

Step 1: tert-butyl 4-(3-(5-carbamoyl-2-chloro-3-nitrophenoxy)propyl)piperazine-1-carboxylate Step 2: tert-butyl (E)-4-(3-(5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)-3-nitrophenoxy) propyl) piperazine-1-carboxylate

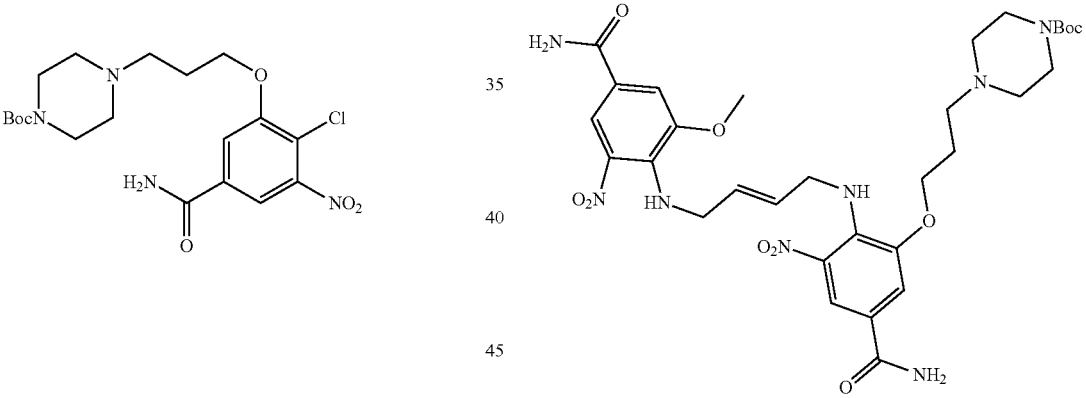

Triphenylphosphine (2.059 g, 7.85 mmol), tert-butyl 4-(3-hydroxypropyl)piperazine-1-carboxylate (1.692 g, 6.93 mmol) and diisopropyl (E)-diazene-1,2-dicarboxylate (1.587 g, 7.85 mmol) were mixed in THF (20 mL) at 0° C., and then 4-chloro-3-hydroxy-5-nitrobenzamide (1 g, 4.62 mmol) was added. The reaction solution was maintained at RT for 16 hrs then the brown reaction solution was partitioned between sat. NaHCO$_3$ (aq) and EtOAc. The organic layer was washed with brine, dried over MgSO$_4$, concentrated and purified on silica gel (20%-80% (3:1 EtOAc/EtOH)/Hexane, with 2% NH$_4$OH; 330 g RediSep column). Desired fractions were combined and concentrated to give the title compound as a white solid (970 mg, 47% yield). $^1$H NMR (400 MHz, DMSO-d$_6$) δ ppm 8.30 (s, 1H), 8.05 (d, J=1.77 Hz, 1H), 7.88 (d, J=1.77 Hz, 1H), 7.80 (s, 1H), 4.28 (t, J=6.21 Hz, 2H), 3.31 (br. s., 4H), 2.48 (t, J=7.10 Hz, 2H), 2.33 (t, J=4.94 Hz, 4H), 1.96 (t, J=6.59 Hz, 2H), 1.40 (s, 9H). LCMS (LCMS Method K): Rt=0.69 min, [M+H]$^+$=443.4.

(E)-1-(4-aminobut-2-en-1-yl)-2-(1-ethyl-3-methyl-1H-pyrazole-5-carboxamido)-7-methoxy-1H-benzo[d]imidazole-5-carboxamide, 2Hydrochloride (242 mg, 0.499 mmol) was dissolved in n-butanol (10 mL) at RT, and then DIPEA (0.476 mL, 2.72 mmol) was added, followed by tert-butyl 4-(3-(5-carbamoyl-2-chloro-3-nitrophenoxy)propyl)piperazine-1-carboxylate (201 mg, 0.454 mmol). The reaction mixture was maintained at 120° C. for 16 hrs. The reaction mixture was cooled to RT and the red solid was collected by filtration (296 mg, 73% yield). $^1$H NMR (400 MHz, DMSO-d$_6$) δ ppm 8.14 (d, J=1.77 Hz, 1H), 8.00 (br. s., 2H), 7.84 (t, J=6.46 Hz, 1H), 7.66 (s, 1H), 7.44 (s, 1H), 7.30-7.41 (m, 3H), 6.59 (s, 1H), 5.61-5.87 (m, 2H), 4.89 (d, J=5.58 Hz, 2H), 4.58 (q, J=7.35 Hz, 2H), 4.14 (br. s., 2H), 3.89 (t, J=6.34 Hz, 2H), 3.84 (s, 3H), 3.25 (br. s., 4H), 2.27 (t, J=6.72 Hz, 2H), 2.21 (br. s., 4H), 2.16 (s, 3H), 1.75 (d, J=6.08 Hz, 2H), 1.39 (s, 9H) 1.23-1.35 (m, 3H). LCMS (LCMS Method K): Rt=0.78 min, [M+H]$^+$=818.4.

327

Step 3: tert-butyl (E)-4-(3-(3-amino-5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)phenoxy)propyl) piperazine-1-carboxylate

328

Step 4: tert-butyl(E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperazine-1-carboxylate

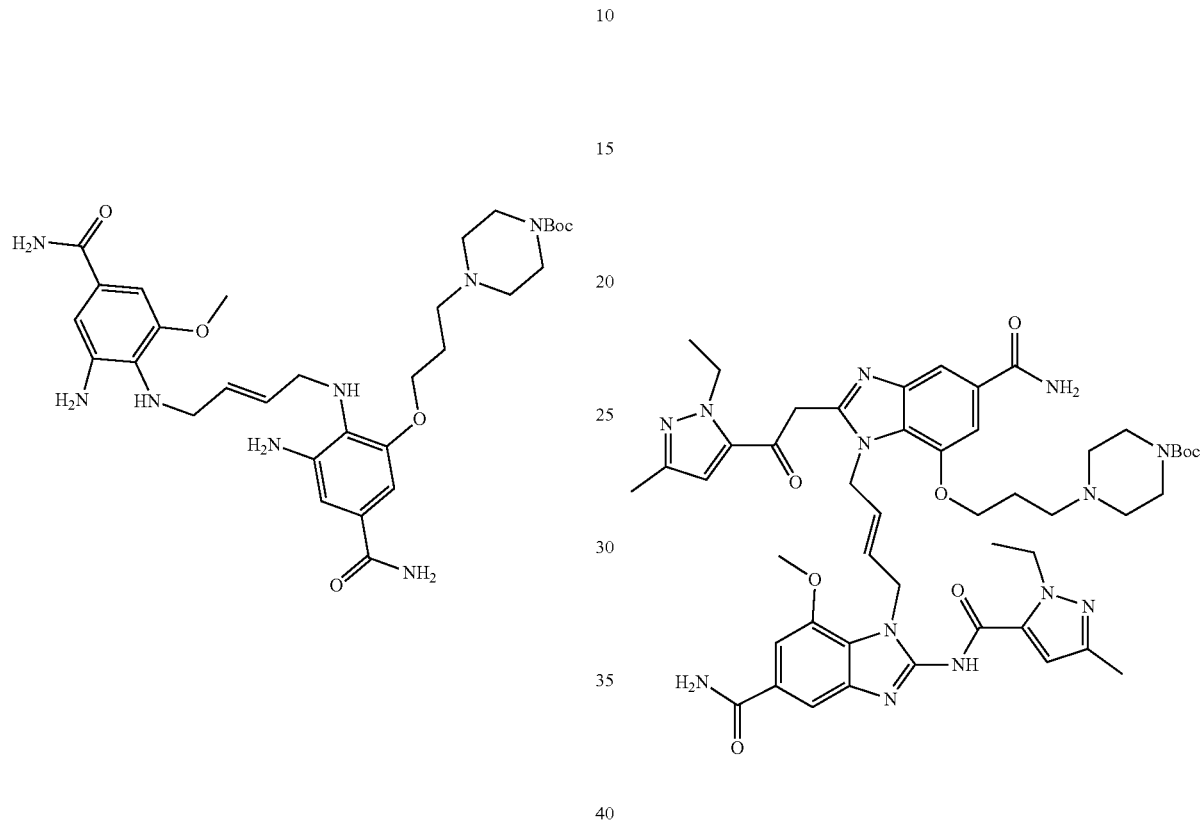

Sodium hydrosulfite (371 mg, 1.81 mmol) was dissolved in H₂O (2 mL) at RT, and then a solution of tert-butyl (E)-4-(3-(5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)-3-nitrophenoxy)propyl)piperazine-1-carboxylate (296 mg, 0.362 mmol) and ammonium hydroxide (0.486 mL, 3.62 mmol) in 5 mL MeOH was added. The reaction mixture was maintained at room temperature for 2 hrs, then the reaction mixture was filtered and the filtrate was partially concentrated to remove MeOH. The resulting yellow aqueous mixture was then extracted with EtOAc 3 times, the organic extracts were combined and concentrated to provide the title compound as a yellow solid (114 mg, 40% yield). $^1$H NMR (400 MHz, METHANOL-$d_4$) δ ppm 7.60 (d, J=1.27 Hz, 1H), 7.31 (d, J=1.27 Hz, 1H), 6.81 (d, J=1.77 Hz, 1H), 6.67 (s, 1H), 6.59 (d, J=1.77 Hz, 1H), 5.74-5.84 (m, 1H), 5.53-5.65 (m, 1H), 4.12 (q, J=7.18 Hz, 2H), 3.84-3.91 (m, 3H), 3.61-3.71 (m, 4H), 3.38 (br. s., 4H), 2.31-2.36 (m, 6H), 2.26 (s, 3H), 2.03 (s, 2H), 1.68-1.78 (m, 2H), 1.47 (s, 9H), 1.42 (t, J=7.10 Hz, 3H). LCMS (LCMS Method K): Rt=0.65 min, [M+H]⁺=788.5.

Tert-butyl(E)-4-(3-(3-amino-5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)phenoxy)propyl) piperazine-1-carboxylate (114 mg, 0.145 mmol) was dissolved in DMF (10 mL) at 0° C., and then 1-ethyl-3-methyl-1H-pyrazole-5-carbonyl isothiocyanate (0.362 mL, 0.145 mmol) was added. The reaction mixture was maintained at 0° C. for 15 min. then TEA (0.050 ml, 0.362 mmol) and EDC (33.3 mg, 0.174 mmol) were added to the reaction mixture. The reaction mixture was maintained at RT for 16 hrs. The reaction mixture was then added into a stirring solution of sat. NaHCO₃ (aq). The resulting white precipitate was collected by filtration to provide the title compound (103 mg, 75% yield). LCMS (LCMS Method K): Rt=0.82 min, [M+H]⁺=950.5.

Example 37

(E)-1-(4-(5-carbamoyl-2-(1-ethyl-3-methyl-1H-pyrazole-5-carboxamido)-7-(3-(piperazin-1-yl)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

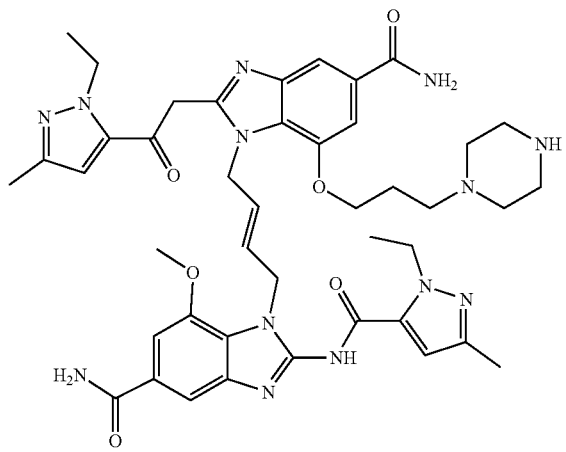 [SMILES: CCn1nc(C)cc1C(=O)Cc1nc2cc(C(N)=O)cc(OCCCN3CCNCC3)c2n1C/C=C/Cn1c(NC(=O)c2cc(C)nn2CC)nc2cc(C(N)=O)cc(OC)c21]

Step 5: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperazine-1-carboxylate (103 mg, 0.109 mmol) was dissolved in MeOH (2 mL) and DCM (2 mL), and then HCl (4N in 1,4-dioxane) (0.271 mL, 1.085 mmol) was added. The reaction mixture was maintained at RT for 16 hrs. DMSO (2 mL) was then added to the reaction mixture, and this mixture was filtered and the filtrate was concentrated and purified by HPLC (XSELECT CSH C18 column, 150 mm×30 mm, i.d. 5 um packing diameter, 30%-85% 10 mM ammonium bicarbonate in water with acetonitrile). The clean fractions after HPLC were combined and partially concentrated to yield the title compound as a white precipitate (25 mg, 27% yield). $^1$H NMR (400 MHz, METHANOL-$d_4$) δ ppm 7.57 (d, J=16.48 Hz, 2H), 7.14-7.30 (m, 2H), 6.50-6.70 (m, 2H), 5.81 (d, J=3.04 Hz, 2H), 4.99 (br. s., 4H) 4.50-4.69 (m, 4H) 3.86 (t, J=5.70 Hz, 2H) 3.69 (s, 3H) 2.81 (t, J=4.69 Hz, 4H) 2.32-2.36 (m, 6H) 2.20 (d, J=12.93 Hz, 6H), 1.70 (br. s., 2H), 1.25-1.45 (m, 6H). LCMS (LCMS Method K): Rt=0.67 min, [M+H]$^+$=849.8.

Example 38

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-7-ethoxy-2-(1-ethyl-3-methyl-1H-pyrazole-5-carboxamido)-1H-benzo[d]imidazole-5-carboxamide

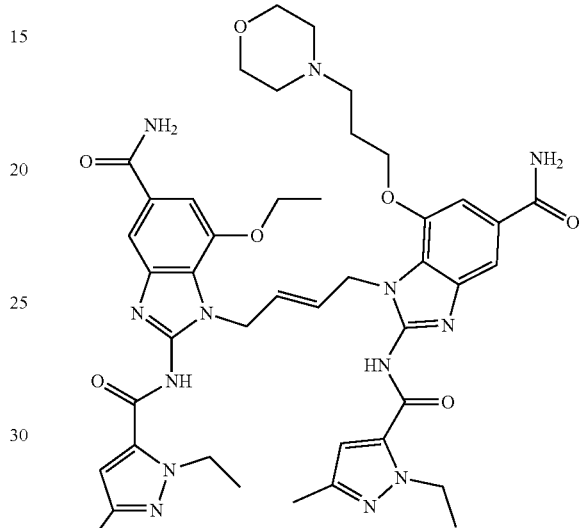

Example 38 can be prepared according to method 20 with modifications known to one of ordinary skill in the art. The last step of the preparation is provided: (E)-1-(4-((2-amino-4-carbamoyl-6-(3-morpholinopropoxy)phenyl)amino)but-2-en-1-yl)-7-ethoxy-2-(1-ethyl-3-methyl-1H-pyrazole-5-carboxamido)-1H-benzo[d]imidazole-5-carboxamide (46 mg, 0.065 mmol) was dissolved in DMF (655 uL) at 0° C., and then 1-ethyl-3-methyl-1H-pyrazole-5-carbonyl isothiocyanate (196 μl, 0.079 mmol) was added. The reaction solution was maintained at 0° C. for 15 min., then EDC (15.06 mg, 0.079 mmol) and TEA (22.81 μl, 0.164 mmol) were added and the reaction solution was maintained at RT. After 16 hrs, the reaction was concentrated and the yellow residue was purified by HPLC (XSELECT CSH C18 column, 150 mm×30 mm, i.d. 5 um packing diameter, 15%-55% 10 mM ammonium bicarbonate in water with acetonitrile). The desired fractions were combined and concentrated to provide the title compound as a white solid (19.2 mg, 34% yield). $^1$H NMR (400 MHz, METHANOL-$d_4$) δ ppm 7.62 (d, J=1.27 Hz, 1H), 7.58 (d, J=1.27 Hz, 1H), 7.24 (d, J=1.27 Hz, 1H), 7.20 (d, J=1.27 Hz, 1H), 6.64 (s, 1H), 6.62 (s, 1H), 5.78 (d, J=3.30 Hz, 2H), 5.01 (d, J=2.79 Hz, 4H), 4.63 (q, J=7.10 Hz, 4H), 3.86-4.08 (m, 6H), 3.69-3.81 (m, 2H), 3.37 (br. s., 2H), 3.16-3.23 (m, 2H), 2.97-3.13 (m, 2H), 2.23 (s, 6H), 1.96-2.04 (m, 2H), 1.39 (t, J=7.10 Hz, 6H), 1.15 (t, J=6.97 Hz, 3H). LCMS (LCMS Method K): Rt=0.76 min, [M+H]$^+$=864.5.

Example 39

(E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-(dimethylamino)propoxy)-2-(1-ethyl-3-methyl-1H-pyrazole-5-carboxamido)-1H-benzo[d]imidazole-5-carboxamide, 2Hydrochloride

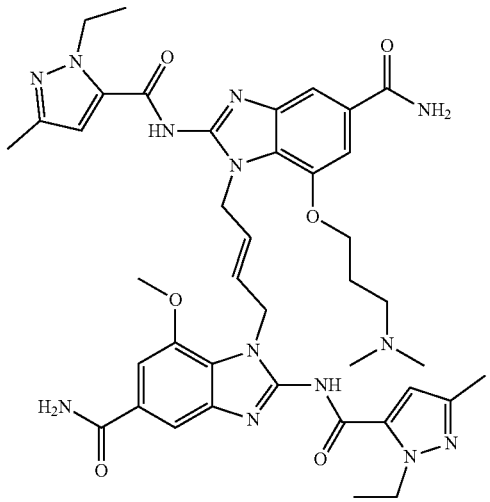

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, hydrochloride (150 mg, 0.184 mmol) in DMF (2 mL) was added TEA (0.20 mL, 1.435 mmol). The solution was cooled to 0° C. Methanesulfonyl chloride (42.0 mg, 0.367 mmol) was added at this temperature. The reaction mixture was stirred at this temperature for 1 hr then another 1 eq. of methanesulfonyl chloride (21.0 mg, 0.183 mmol) was then added, and the reaction was continued at 0° C. for 1 hr. $K_2CO_3$ (127 mg, 0.918 mmol) was then added to reaction mixture followed by 1 ml of dimethyl amine (2 M in THF, 2.0 mmol). The reaction mixture was stirred at 80° C. in a sealed tube for 2 hours then allowed to cool to room temperature, and the crude material was purified by mass directed HPLC. The HPLC analysis was conducted on an XSELECT SCH C18 column. Solvent condition: A=10 mM Ammonium Bicarbonate in H2O adjusted to pH 10 with Ammonia, B=MeCN B %: 15-55. Collected desired MW peaks. Solvent was removed and the residue was dissolved in 1 mL MeOH. 4N HCl in dioxane (1 mL) was added. The solution was stirred at room temperature for 10 min. Removed solvent and the solid washed with ethyl ether (5 ml×2) to provide the title compound (76 mg, 0.082 mmol, 44.7% yield). $^1$H NMR (DMSO-d6, 600 MHz): δ (ppm) 12.89 (br s, 2H), 10.18-10.41 (m, 1H), 7.96-8.04 (m, 2H), 7.66 (d, J=10.0 Hz, 2H), 7.35-7.41 (m, 2H), 7.28-7.35 (m, 2H), 6.53 (d, J=2.8 Hz, 2H), 5.82 (dt, J=15.5, 5.3 Hz, 1H), 5.71 (dt, J=15.4, 5.6 Hz, 1H), 4.85-4.98 (m, 4H), 4.52 (quin, J=6.5 Hz, 4H), 3.96-4.04 (m, 2H), 3.70 (s, 3H), 3.00-3.09 (m, 2H), 2.66 (d, J=4.8 Hz, 6H), 2.11 (d, J=4.4 Hz, 6H), 1.85-2.03 (m, 2H), 1.20-1.32 (m, 6H); LCMS Method K: Rt=0.67 min [M+H]$^+$=808.5

Example 40

(E)-1-(4-(5-carbamoyl-2-(1-ethyl-3-methyl-1H-pyrazole-5-carboxamido)-7-(3-(methylamino)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2Hydrochloride

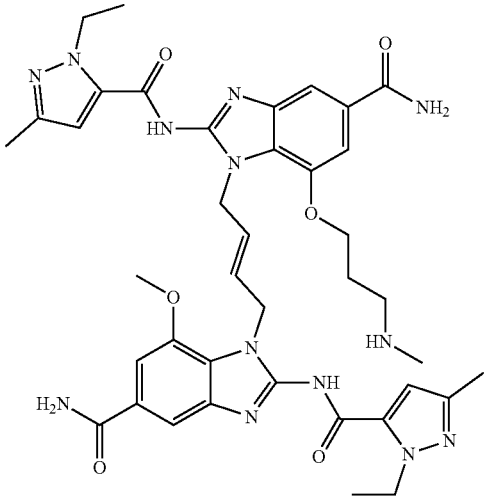

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, hydrochloride (100 mg, 0.122 mmol) was added TEA (0.102 mL, 0.734 mmol). The solution was cooled to 0° C. Methanesulfonyl chloride (28.0 mg, 0.245 mmol) was added. The reaction mixture was stirred at 0° C. for 1 hr then another 1 eq of MsCl was then added, and the reaction was continued at 0° C. for 2 hrs. $K_2CO_3$ (85 mg, 0.612 mmol) was then added to reaction mixture followed by 1 mL methanamine (2 M in THF, 2.0 mmol). The reaction mixture was stirred at 80° C. in a sealed tube for 2 h, then the reaction mixture was allowed to cool to RT and filtered. The crude filtrate was purified by mass directed HPLC. The HPLC analysis was conducted on an XSELECT SCH C18 column. Solvent condition: A=10 mM Ammonium Bicarbonate in $H_2O$ adjusted to pH 10 with Ammonia, B=MeCN B %: 15-55. Collected desired MW peaks and removed the solvent. The material was dissolved in 2 mL of MeOH, and 1 mL 4N HCl in dioxane was added. The mixture was stirred at RT for 15 min then concentrated to afford the title compound (33 mg, 0.037 mmol, 30.2% yield). $^1$H NMR (400 MHz, DMSO-d$_6$) δ ppm 12.90 (br, s, 1H), 8.79 (br. s., 2H) 8.03 (br. s., 2H) 7.66 (d, J=7.10 Hz, 2H) 7.26-7.48 (m, 4H) 6.52 (s, 2H) 5.68-5.90 (m, 2H) 4.92 (dd, J=17.24, 4.06 Hz, 4H) 4.52 (q, J=6.76 Hz, 4H) 4.09 (t, J=5.58 Hz, 2H) 3.73 (s, 3H) 2.90 (d, J=5.58 Hz, 2H) 2.46 (t, J=5.32 Hz, 3H) 2.11 (s, 6H) 1.88-2.01 (m, 2H) 1.27 (t, J=6.97 Hz, 6H); LCMS Method K: Rt=0.66 min, [M+H]$^+$=794.4.

Example 41

(E)-7-(3-aminopropoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide, 2Trifluoroacetic Acid Salt

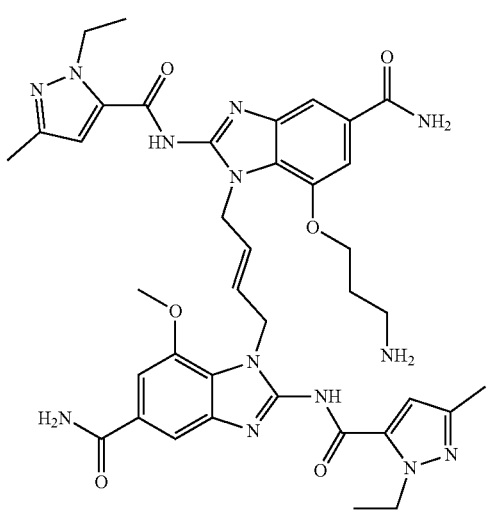

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2Hydrochloride (100 mg, 0.117 mmol) was added TEA (0.049 mL, 0.351 mmol). The solution was cooled to 0° C. Methanesulfonyl chloride (0.014 mL, 0.176 mmol) was added and the reaction mixture was allowed to warm to RT and stirred at RT for 1 h. Another 0.5 eq of MsCl was then added and stirred at RT for 2 hrs, then another 0.5 eq of MsCl was added and the reaction stirred for another 1 hr. $K_2CO_3$ (81 mg, 0.586 mmol) was then added to reaction mixture followed by 7M ammonia in MeOH (0.167 mL, 1.171 mmol). The reaction mixture was stirred at 50° C. in a sealed tube overnight. The reaction was then filtered and the crude filtrate was purified by mass directed HPLC to afford the title compound (15.6 mg, 13.2%). The HPLC analysis was conducted on an XSELECT SCH C18 column. Solvent condition: A=$H_2O$ (0.1% TFA), B=MeCN (0.1% TFA) B %: 15-55. $^1$H NMR (400 MHz, DMSO-$d_6$) δ ppm 12.86 (br. s., 1H), 7.99 (br. s., 2H), 7.76 (br. s., 2H), 7.65 (dd, 6.21, 0.89 Hz, 2H), 7.40 (br. s., 2H), 7.28-7.36 (m, 2H), 6.51 (d, J=8.87 Hz, 2H), 5.72-5.88 (m, 4H), 4.91 (dd, J=9.50, 4.44 Hz, 4H), 4.43-4.59 (m, 4H), 4.10 (t, J=5.96 Hz, 2H), 3.72 (s, 3H), 2.83-2.97 (m, 2H), 2.11 (d, J=5.07 Hz, 6H), 1.90 (quin, J=6.40 Hz, 2H), 1.26 (td, J=7.10, 4.82 Hz, 6H); LCMS Method K: Rt=0.65 min, [M+H]$^+$=780.5

Example 42

(E)-1-(4-(5-carbamoyl-2-(1-ethyl-3-methyl-1H-pyrazole-5-carboxamido)-7-(3-(3-hydroxypyrrolidin-1-yl)propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

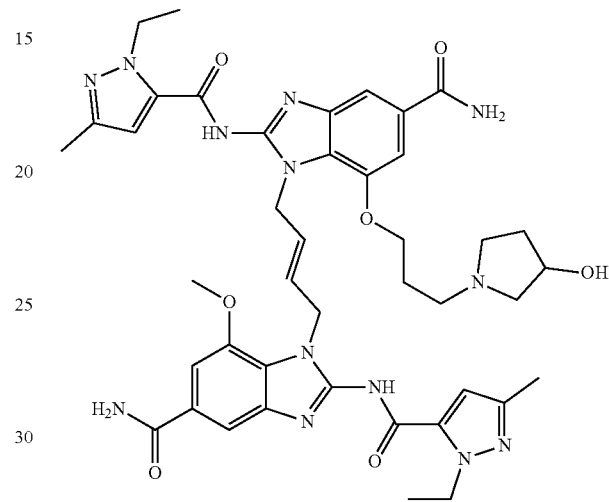

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2Hydrochloride (100 mg, 0.117 mmol) in DMF (2 mL) was added TEA (71.1 mg, 0.703 mmol). The solution was cooled to 0° C. Methanesulfonyl chloride (26.8 mg, 0.234 mmol) was added at this temperature. The reaction mixture was stirred at this temperature for 45 min. Another 1 eq of MsCl (13.5 mg) was then added, continued to stir at 0° C. for 2 hrs. $K_2CO_3$ (97 mg, 0.703 mmol) was then added to reaction mixture followed by pyrrolidin-3-ol (102 mg, 1.17 mmol). The reaction mixture was stirred at 80° C. in a sealed tube for 1 hr, then the reaction mixture was allowed to cool to RT and the reaction mixture was filtered. The crude filtrate was purified by mass directed HPLC to provide the title compound (56.6 mg, 0.063 mmol, 54.0% yield). The HPLC analysis was conducted on an XSELECT SCH C18 column. Solvent condition: A=10 mM Ammonium Bicarbonate in $H_2O$ adjusted to pH 10 with Ammonia, B=MeCN B %: 15-55. $^1$H NMR (400 MHz, DMSO-$d_6$) δ ppm 12.84 (br. s., 2H) 7.92-8.06 (m, 2H) 7.61-7.69 (m, 2H) 7.23-7.44 (m, 4H) 6.46-6.61 (m, 2H) 5.72-5.96 (m, 2H) 4.91 (dd, J=13.05, 4.18 Hz, 4H) 4.67 (br. s., 1H) 4.52 (q, J=7.18 Hz, 4H) 4.12 (br. s., 1H) 3.97 (t, J=5.96 Hz, 2H) 3.35 (br. s., 2H) 2.54-2.65 (m, 1H) 2.33-2.47 (m, 4H) 2.26 (br. s., 2H) 2.12 (d, J=8.36 Hz, 6H) 1.81-1.96 (m, 1H) 1.60-1.76 (m, 2H) 1.46 (dd, J=8.24, 4.69 Hz, 1H) 1.19-1.37 (m, 6H); LCMS Method K: Rt=0.72 min, [M+H]$^+$=850.9

Example 43

(E)-1-((E)-4-((E)-5-carbamoyl-2-((1-ethyl-3-methyl-1H-pyrazole-5-carbonyl)imino)-7-(3-(4-(2-hydroxyethyl)piperazin-1-yl)propoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

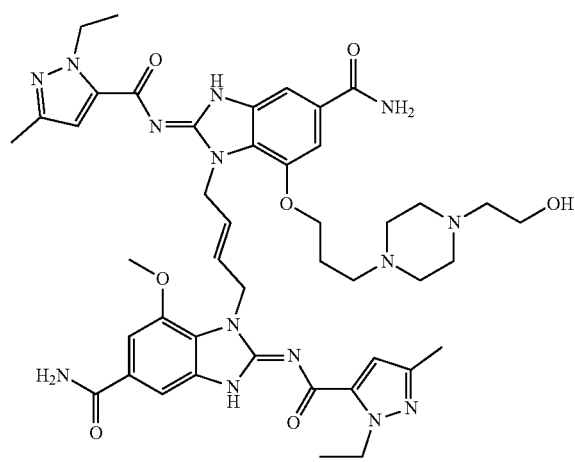 [SMILES: CCn1nc(C)cc1C(=O)/N=c1\[nH]c2cc(C(N)=O)cc(OC)c2n1C/C=C/Cn1/c(=N/C(=O)c2cc(C)nn2CC)[nH]c2cc(C(N)=O)cc(OCCCN3CCN(CCO)CC3)c21]

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, Hydrochloride (80 mg, 0.098 mmol) in DMF (2 mL) was added TEA (0.136 mL, 0.979 mmol) at RT. The solution was stirred at RT for 15 min. then methanesulfonic anhydride (51.1 mg, 0.294 mmol) was added at this temperature. The reaction mixture was stirred at this temperature for 45 min. $K_2CO_3$ (200 mg, 1.447 mmol) was then added to reaction mixture followed by 2-(piperazin-1-yl)ethan-1-ol (127 mg, 0.979 mmol). The reaction mixture was stirred at 80° C. in a sealed tube for 1 h and at 50° C. overnight, then the reaction mixture was allowed to cool to RT and filtered. The crude filtrate was purified by mass directed HPLC. Collected desired MW peaks. Removed solvent to provide the title compound (45.1 mg, 0.051 mmol, 51.6% yield). The HPLC analysis was conducted on an XSELECT SCH C18 column. Solvent condition: A=10 mM Ammonium Bicarbonate in $H_2O$ adjusted to pH 10 with Ammonia, B=MeCN B %: 15-55. $^1$H NMR (400 MHz, DMSO-$d_6$) δ ppm 12.85 (br. s., 2H) 7.98 (br. s., 2H) 7.61-7.71 (m, 2H) 7.21-7.45 (m, 4H) 6.47-6.65 (m, 2H) 5.75-5.92 (m, 2H) 4.85-5.01 (m, 4H) 4.48-4.65 (m, 4H) 4.34 (br. s., 1H) 3.91 (t, J=5.96 Hz, 2H) 3.70 (s, 3H) 3.44 (q, J=6.08 Hz, 2H) 2.18-2.39 (m, 10H) 2.14 (s, 3H) 2.11 (s, 3H) 1.57-1.70 (m, 2H) 1.29 (q, J=7.10 Hz, 6H); LCMS Method K: Rt=0.66 min, [M+H]$^+$=893.4

Example 44

(E)-1-((E)-4-((E)-5-carbamoyl-2-((1-ethyl-3-methyl-1H-pyrazole-5-carbonyl)imino)-7-(3-(3-(hydroxymethyl)morpholino)propoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide, 2Trifluoroacetic Acid Salt

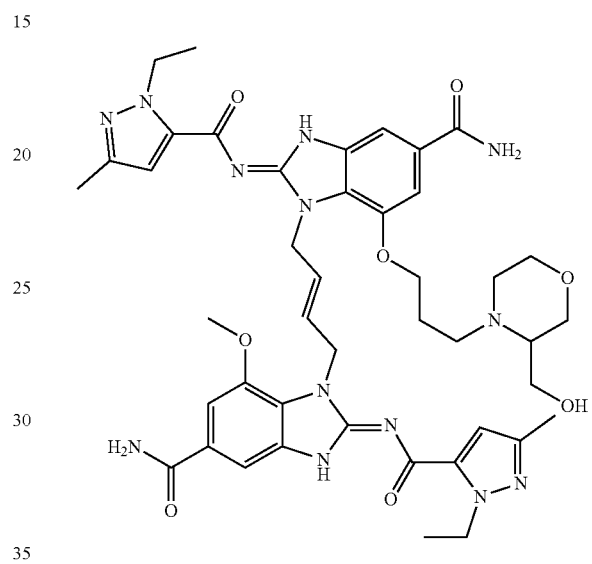

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, Hydrochloride (100 mg, 0.122 mmol) in DMF (2 mL) was added TEA (0.20 mL, 1.435 mmol). The solution was cooled to 0° C. and methanesulfonyl chloride (28.0 mg, 0.245 mmol) was added at this temperature. The reaction mixture was stirred at this temperature for 1 hr. Another 1 eq of MsCl was then added, continued to stir at 0° C. for another 3 hrs. $K_2CO_3$ (85 mg, 0.612 mmol) was then added to reaction mixture followed by morpholin-3-ylmethanol (86 mg, 0.734 mmol). The reaction mixture was stirred at 50° C. in a sealed tube overnight then reaction mixture was allowed to cool to RT and filtered. The crude filtrate was purified by mass directed HPLC to provide the title compound (13.1 mg, 9.66%). The HPLC analysis was conducted on an XSELECT SCH C18 column. Solvent condition: A=$H_2O$ (0.1% TEA), B=MeCN (0.1% TEA) B %: 15-55. $^1$H NMR (400 MHz, DMSO-$d_6$) δ ppm 12.49-13.47 (m, 1H) 9.64 (br. s., 1H) 7.99 (d, J=9.89 Hz, 2H) 7.67 (d, J=7.60 Hz, 2H) 7.40 (br. s., 2H) 7.31 (d, J=8.11 Hz, 2H) 6.54 (d, J=1.77 Hz, 2H) 5.70-5.85 (m, 2H) 4.80-5.01 (m, 6H) 4.54 (dd, 3-6.72, 3.68 Hz, 4H) 3.84-4.13 (m, 5H) 3.73-3.81 (m, 1H) 3.54-3.66 (m, 2H) 3.43 (d, J=11.91 Hz, 2H) 2.91-3.32 (m, 5H) 2.12 (d, J=4.82 Hz, 6H) 1.89 (br. s., 2H) 1.21-1.33 (m, 6H); LCMS Method K: Rt=0.72 min, [M+H]$^+$=880.5.

Example 45

(E)-1-((E)-4-((E)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-7-(3-(ethyl(2-methoxyethyl)amino)propoxy)-2-((1-ethyl-3-methyl-1H-pyrazole-5-carbonyl)imino)-2,3-dihydro-1H-benzo[d]imidazole-5-carboxamide

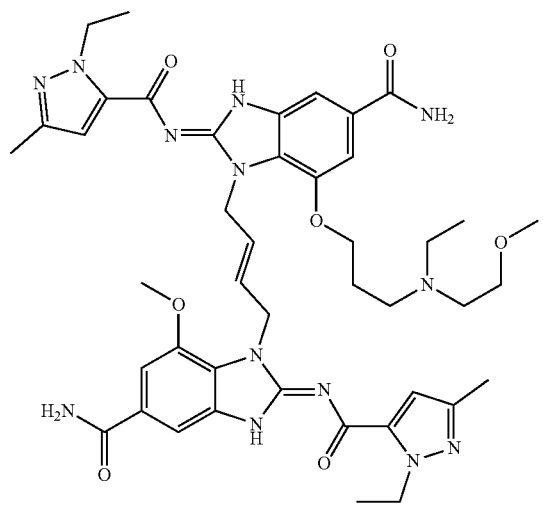

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, Hydrochloride (100 mg, 0.122 mmol) in DMF (2 mL) was added TEA (0.171 mL, 1.224 mmol) at RT. Methanesulfonic anhydride (42.6 mg, 0.245 mmol) was added at this temperature. The reaction mixture was stirred at this temperature for 1 hr. Another 1 eq of methanesulfonic anhydride was then added, continued to stir at RT for 30 min. K$_2$CO$_3$ (169 mg, 1.224 mmol) was then added to reaction mixture followed by N-ethyl-2-methoxyethan-1-amine (126 mg, 1.224 mmol). The reaction mixture was stirred at 80° C. in a sealed tube for 2 hrs then reaction mixture was allowed to cool to RT and filtered. The crude filtrate was purified by mass directed HPLC (2 injections). Collected desired MW peaks and removed solvent to provide the title compound (21.1 mg, 0.024 mmol, 19.52% yield). The HPLC analysis was conducted on an XSELECT SCH C18 column. Solvent condition: A=10 mM Ammonium Bicarbonate in H$_2$O adjusted to pH 10 with Ammonia, B=MeCN B %: 15-55. $^1$H NMR (400 MHz, DMSO-d$_6$) δ ppm 12.81 (br. s., 2H) 7.98 (br. s., 2H) 7.59-7.71 (m, 2H) 7.24-7.42 (m, 4H) 6.46-6.61 (m, 2H) 5.75-5.94 (m, 2H) 4.92 (dd, J=16.73, 4.06 Hz, 4H) 4.47-4.62 (m, 4H) 3.96 (t, J=5.83 Hz, 2H) 3.72 (s, 3H) 3.24 (t, J=6.08 Hz, 2H) 3.11 (s, 3H) 2.41 (t, J=5.96 Hz, 4H) 2.34 (q, J=7.10 Hz, 2H) 2.12 (d, J=10.39 Hz, 6H) 1.55-1.66 (m, 2H) 1.29 (q, J=7.10 Hz, 6H) 0.82 (t, J=6.97 Hz, 3H); LCMS Method K: Rt=0.69 min, [M+H]$^+$=866.4.

Example 46

(E)-1-((E)-4-((E)-5-carbamoyl-2-((1-ethyl-3-methyl-1H-pyrazole-5-carbonyl)imino)-7-(3-(4-(2-methoxyethyl)piperazin-1-yl)propoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide, 3 Trifluoroacetic Acid Salt

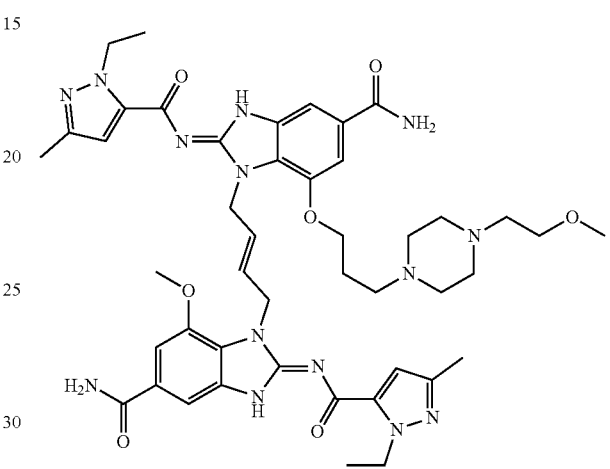

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, hydrochloride (100 mg, 0.122 mmol) in DMF (2 mL) was added TEA (0.171 mL, 1.224 mmol). The solution was cooled to 0° C. Methanesulfonic anhydride (42.6 mg, 0.245 mmol) was added at this temperature. The reaction mixture was stirred at this temperature for 1 hr. Another 1 eq. of MsCl was then added, continued to stir at 0° C. for 2 hrs. K$_2$CO$_3$ (85 mg, 0.612 mmol) was then added followed by 1-(2-methoxyethyl)piperazine (176 mg, 1.224 mmol) and the reaction mixture was stirred at 50° C. in a sealed tube for overnight. The reaction was then allowed to cool to RT and filtered. The crude filtrate was purified by mass directed HPLC. Collected desired MW peaks and removed solvent to provide the title compound (39.6 mg, 0.032 mmol, 25.9% yield). The HPLC analysis was conducted on an XSELECT SCH C18 column. Solvent condition: A=H$_2$O (0.1% TFA), B=MeCN (0.1% TFA) B %: 15-55. $^1$H NMR (400 MHz, DMSO-d$_6$) δ ppm 12.90 (br, s, 2H) 8.00 (d, J=9.89 Hz, 2H) 7.66 (s, 2H) 7.40 (d, J=4.06 Hz, 2H) 7.22-7.35 (m, 2H) 6.53 (d, J=4.06 Hz, 2H) 5.70-5.89 (m, 2H) 4.91 (dd, J=9.63, 4.56 Hz, 4H) 4.53 (dd, J=7.10, 3.55 Hz, 6H) 3.94-4.04 (m, 3H) 3.70 (s, 3H) 3.60 (d, J=4.06 Hz, 2H) 3.31 (s, 3H) 3.09-3.25 (m, 5H) 2.86 (br. s., 4H) 2.12 (d, J=5.07 Hz, 6H) 1.74-1.88 (m, 2H) 1.28 (td, J=7.10, 3.30 Hz, 6H); LCMS Method K: Rt=0.66 min, [M+H]$^+$=907.4

Example 47
8-ethyl-23-((4-methoxybenzyl)(methyl)amino)-10,
18-dimethyl-7,20-dioxo-6,7,8,11,12,13,14,15,20,21,
28,29,30,31-tetradecahydrobenzo[4,5]imidazo[1,2-a]
benzo[4,5]imidazo[2,1-p]dipyrazolo[5,1-e:4',3'-l][1,
3,6,15,17]pentaazacyclohenicosine-3-carboxamide
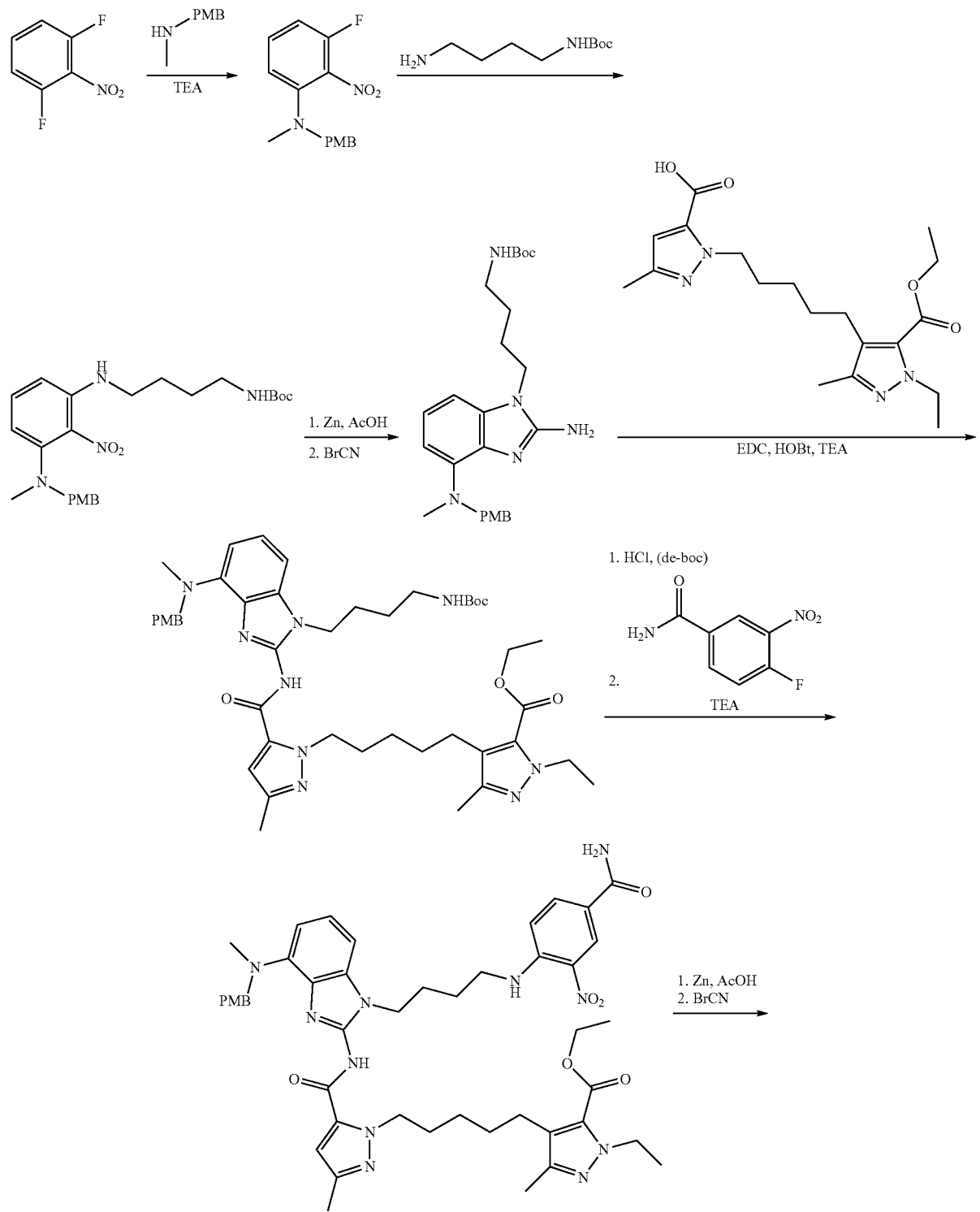

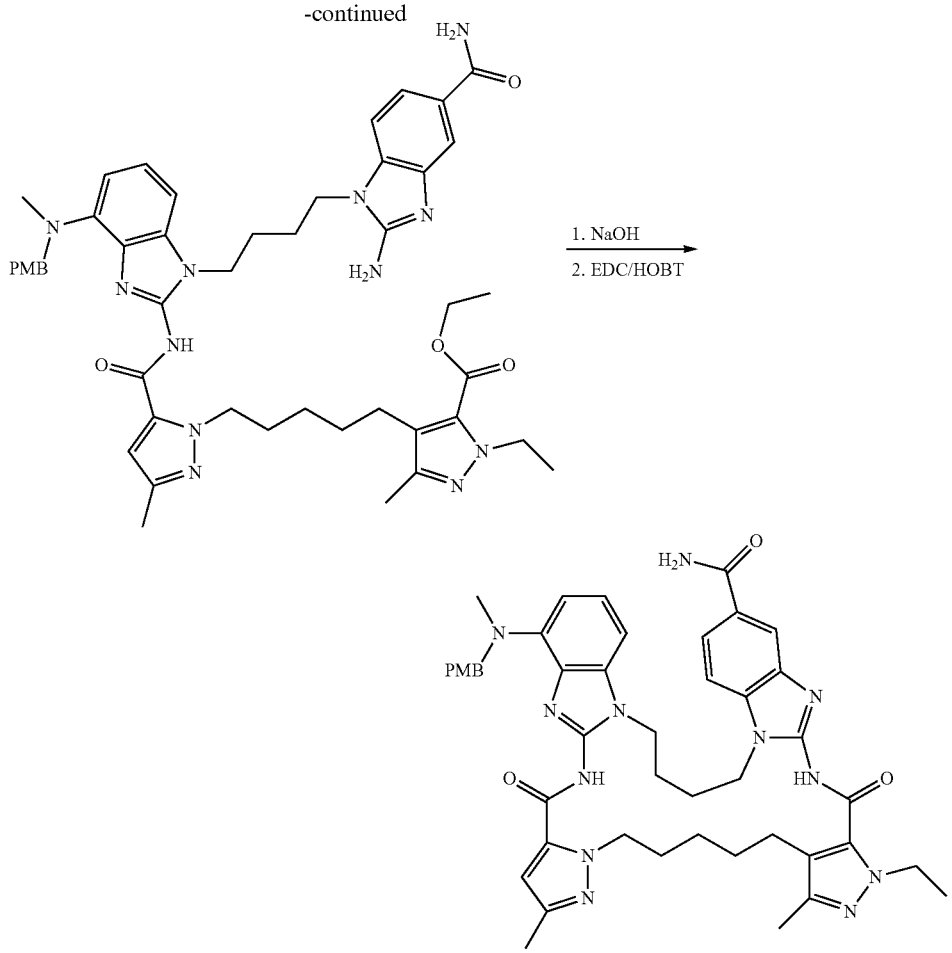

1. NaOH
2. EDC/HOBT

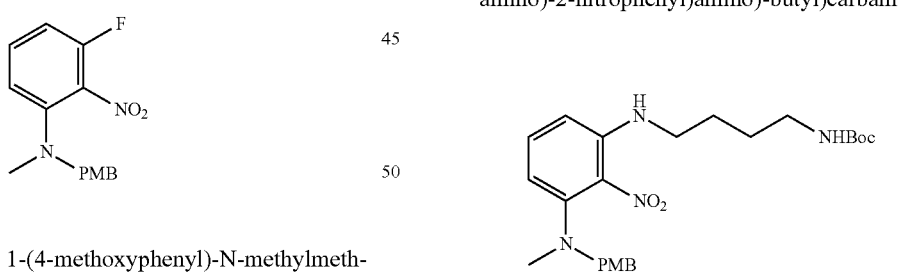

Step 1: 3-fluoro-N-(4-methoxybenzyl)-N-methyl-2-nitroaniline

A solution of 1-(4-methoxyphenyl)-N-methylmethanamine (5.23 g, 34.6 mmol) in CHCl₃ (20 ml) was added to a stirring solution of 1,3-difluoro-2-nitrobenzene (5.5 g, 34.6 mmol) and TEA (5.78 mL, 41.5 mmol) in CHCl₃ (250 mL) at RT under $N_2$. The mixture was stirred at RT for 30 min and then heated to 50° C. overnight. Saturated NaHCO₃ was added, the organic layer was separated, the aqueous layer was as extracted with DCM, and the combined extracts were washed with brine, dried over Na₂SO₄ filtered and concentrated. The residue was purified by silica column chromatography (0-12% EtOAc in hexanes) to afford the title compound (8.5 g, 29.3 mmol, 85% yield) as an orange oil. ¹H NMR (400 MHz, CHLOROFORM-d₆) δ ppm 7.29-7.34 (m, 1H) 7.20 (d, J=8.28 Hz, 2H) 6.86-6.93 (m, 3H) 6.78 (t, J=8.78 Hz, 1H) 4.29 (s, 2H) 3.82 (s, 3H) 2.80 (s, 3H); LCMS (LCMS Method D): Rt=1.28, $[M+H]^+$=120.5

Step 2: tert-butyl(4-((3-((4-methoxybenzyl)(methyl)amino)-2-nitrophenyl)amino)-butyl)carbamate To a solution of 3-fluoro-N-(4-methoxybenzyl)-N-methyl-2-nitroaniline (8.5 g, 29.3 mmol) in N,N-Dimethylformamide (DMF) (60 mL) was added tert-butyl (4-aminobutyl)carbamate (8.27 g, 43.9 mmol) at RT and the mixture was stirred for 10 min; K₂CO₃ (8.09 g, 58.6 mmol) was then added and the mixture was stirred 80° C. overnight. The reaction was cooled to RT, diluted with EtOAc (200 mL) and washed successively with water (300 mL), 5% LiCl, and brine. The organic layer was dried over Na₂SO₄, filtered, concentrated and the resulting residue was purified by silica column chromatography (0-30% EtOAc in hexane) to afford the title compound (10.68 g, 23.29 mmol, 80% yield) as a red oil. ¹H NMR (400 MHz, CHLOROFORM-d₆) δ ppm 7.09-7.28 (m, 3H) 6.87 (d, J=7.53 Hz, 2H) 6.40 (br. s., 1H) 6.29 (d, J=7.03 Hz, 1H) 4.57 (br. s., 1H) 4.32 (br. s., 2H) 3.81 (s, 3H) 3.11-3.30 (m, 4H) 2.77 (br. s., 3H) 1.67-1.79 (m, 2H) 1.55-1.67 (m, 2H) 1.47 (s, 9H). LCMS (LCMS Method D): Rt=1.37, [M+H]⁺=459.2.

Step 3: tert-butyl (4-((2-amino-3-((4-methoxybenzyl)(methyl)amino)phenyl)amino)butyl)carbamate

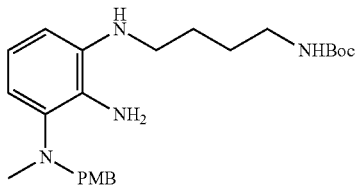

Zinc (4.66 g, 71.3 mmol) was added portionwise to a stirring solution of tert-butyl (4-((3-((4-methoxybenzyl)(methyl)amino)-2-nitrophenyl)amino)butyl)carbamate (10.9 g, 23.77 mmol) in acetic acid (200 mL). The mixture was stirred for 3 h and another portion of zinc (4.66 g, 71.3 mmol) was added. The mixture was stirred for another 30 min. The solid was filtered off and the filtrate was concentrated in vacuo. The residue was taken up in DCM (200 mL), washed with 15% K₂CO₃ and brine. The organic layer were dried over Na₂SO₄, filtered and then concentrated in vacuo to give the title compound (9.95 g, 23.22 mmol, 98% yield) as brown foam which was used for the next step without purification. ¹H NMR (400 MHz, METHANOL-d₄) δ ppm 7.24 (d, J=8.53 Hz, 2H) 6.85 (d, J=8.28 Hz, 2H) 6.66-6.73 (m, 1H) 6.57-6.63 (m, 1H) 6.47 (d, J=7.78 Hz, 1H) 3.90 (s, 2H) 3.78 (s, 3H) 3.13 (dt, J=13.30, 6.65 Hz, 4H) 2.53 (s, 3H) 1.58-1.76 (m, 4H) 1.45 (s, 9H). LCMS (LCMS Method D): Rt=1.00, [M+H]⁺=429.2

Step 4: tert-butyl (4-(2-amino-4-((4-methoxybenzyl)(methyl)amino)-1H-benzo[d]imidazol-1-yl)butyl)carbamate, Hydrobromide

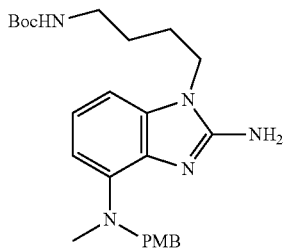

Tert-butyl(4-((2-amino-3-((4-methoxybenzyl)(methyl)amino)phenyl)amino)butyl)carbamate (9.95 g, 23.22 mmol) was dissolved in methanol (80 mL), cyanogen bromide (4.64 mL, 23.22 mmol) was added. The mixture was stirred for 18 hours at RT, concentrated in vacuo to ~1/4 of the original volume and MeCN (50 mL) and toluene (50 mL) were added. The mixture was concentrated to dryness and dried in vacuo for 16 hr to afford the title compound (12.54 g, quantitative yield) as a dark brown solid. LCMS (LCMS Method D): Rt=1.04, [M+H]⁺=454.2.

Step 5: ethyl 4-(5-(5-((1-(4-((tert-butoxycarbonyl)amino)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate

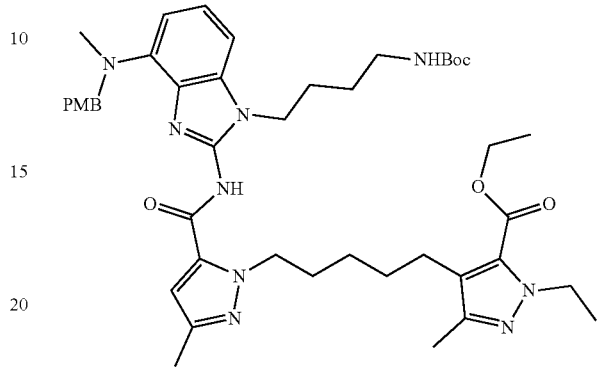

A mixture of 1-(5-(5-(ethoxycarbonyl)-1-ethyl-3-methyl-1H-pyrazol-4-yl)pentyl)-3-methyl-1H-pyrazole-5-carboxylic acid (1 g, 2.66 mmol), tert-butyl (4-(2-amino-4-((4-methoxy-benzyl)(methyl)amino)-1H-benzo[d]imidazol-1-yl)butyl)carbamate, hydrobromide (1.704 g, 3.19 mmol), TEA (1.111 mL, 7.97 mmol), EDC (0.662 g, 3.45 mmol) and HOBt (0.610 g, 3.98 mmol) in NMP (25 mL) was stirred overnight at RT under nitrogen. The reaction was diluted with EtOAc (100 mL), washed with saturated NaHCO₃, 5% LiCl, and brine. The organic layer was dried over Na₂SO₄, filtered, concentrated, and the residue was purified by silica column chromatography (0-45% EtOAc in DCM) to afford ethyl the title compound (1.3 g, 1.601 mmol, 60.3% yield) as a pink solid. LCMS (LCMS Method E): Rt=1.56, [M+H]⁺=812.6.

Step 6: ethyl 4-(5-(5-((1-(4-aminobutyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate, 2Hydrochloride

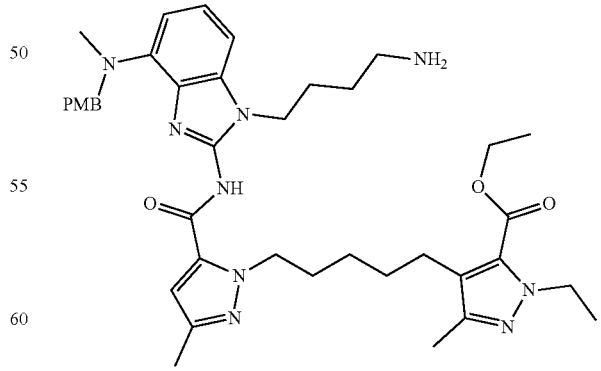

4N HCl (2.232 mL, 8.93 mmol) was added to a stirring solution of ethyl 4-(5-(5-((1-(4-((tert-butoxycarbonyl)amino)butyl)-4-((4-methoxybenzyl)(methyl)amino)-1H-benzo[d]imidazol-2-yl)carbamoyl)-3-methyl-1H-pyrazol-1-

Step 8: ethyl 4-(5-(5-((1-(4-((2-amino-4-carbam-oylphenyl)amino)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate yl)pentyl)-1-ethyl-3-methyl-1H-pyrazole-5-carboxylate (1.45 g, 1.786 mmol) in methanol (15 mL). The mixture was stirred overnight at room temperature under nitrogen. The reaction was concentrated in vacuo to ~1/5 of the original volume and MeCN (10 mL) and toluene (10 mL) were added. The mixture was concentrated to dryness and dried in vacuo to afford the title compound (1.45 g, 1.792 mmol, 100% yield) as an orange-red solid which was used for the next step without purification. Assumed quantitative yield. LCMS (LCMS Method E): Rt=1.19, [M+H]$^+$=712.6

Step 7: ethyl 4-(5-(5-((1-(4-((4-carbamoyl-2-nitrophenyl)amino)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate

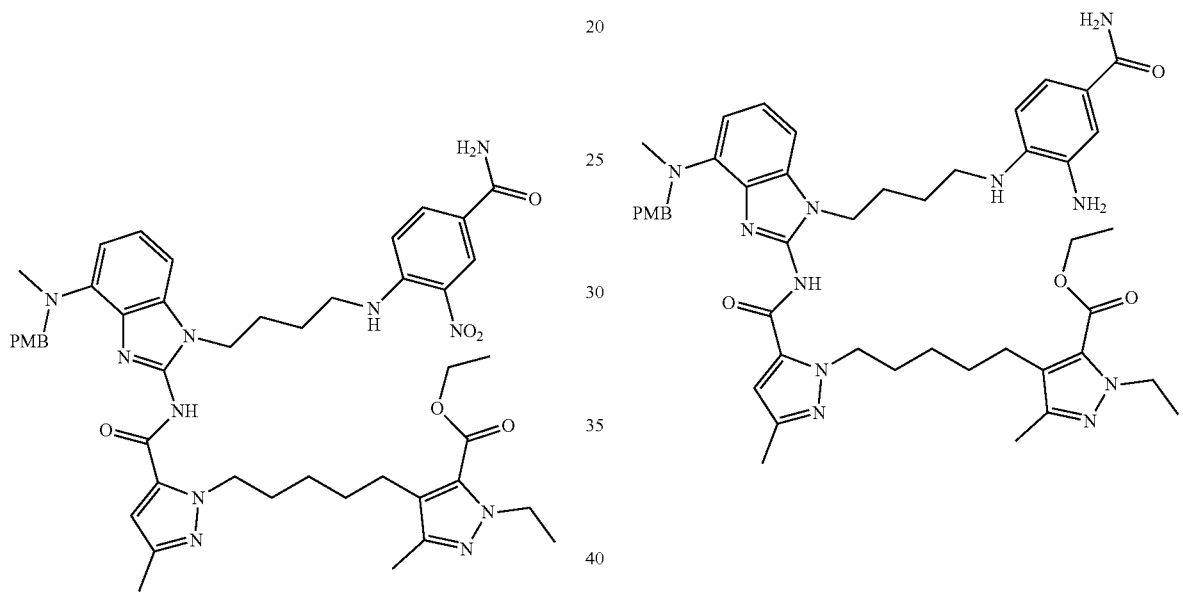

To a solution of ethyl 4-(5-(5-((1-(4-aminobutyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate, 2Hydrochloride (100 mg, 0.124 mmol) in DMSO (1 mL) was added TEA (0.086 mL, 0.618 mmol) followed by 4-fluoro-3-nitrobenzamide (22.76 mg, 0.124 mmol) and the mixture was stirred at 70° C. overnight. The reaction was diluted with water, extracted three times with EtOAc, washed with brine, dried over Na$_2$SO$_4$, filtered and concentrated. The residue was purified by flash silica chromatography (EtOH/EtOAc 0-5%) to afford the title compound (74 mg, 0.084 mmol, 68.3% yield) as a yellow solid. $^1$H NMR (400 MHz, METHANOL-d$_4$) δ ppm 8.69 (s, 1H) 7.91 (d, J=9.03 Hz, 1H) 7.18-7.31 (m, 3H) 7.09 (d, J=8.03 Hz, 1H) 6.96 (d, J=9.04 Hz, 1H) 6.82-6.92 (m, 3H) 6.66 (s, 1H) 4.65 (t, J=6.53 Hz, 2H) 4.20-4.43 (m, 8H) 3.76 (s, 3H) 3.48 (t, J=6.27 Hz, 2H) 2.88 (s, 3H) 2.59 (t, J=7.40 Hz, 2H) 2.21 (s, 3H) 2.11 (s, 3H) 2.03-2.08 (m, 2H) 1.72-1.90 (m, 4H) 1.41-1.55 (m, 2H) 1.22-1.35 (m, 9H). LCMS (LCMS Method E): Rt=1.41, [M+H]$^+$=877.5

Zinc (0.240 g, 3.66 mmol) was added portionwise to a stirring solution of ethyl 4-(5-(5-((1-(4-((4-carbamoyl-2-nitrophenyl)amino)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate (1.07 g, 1.221 mmol) in acetic Acid (10 mL). The mixture was stirred for 30 min and another portion of zinc (0.240 g, 3.66 mmol) was added. The mixture was stirred for another 30 min, the solid was filtered off and the filtrate was concentrated in vacuo. The residue was taken up in DCM (50 mL) and washed with 15% K$_2$CO$_3$ and then brine. The organic layer was dried over Na$_2$SO$_4$, filtered and then concentrated in vacuo to give the title compound (1.16 g, 1.234 mmol) as brown foam which was used for the next step without purification. Assumed quantitative yield. LCMS (LCMS Method E): Rt=1.29, [M+H]$^+$=847.6

Step 9: ethyl 4-(5-(5-((1-(4-(2-amino-5-carbamoyl-1H-benzo[d]imidazol-1-yl)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate Step 10: 4-(5-(5-((1-(4-(2-amino-5-carbamoyl-1H-benzo[d]imidazol-1-yl)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylic Acid

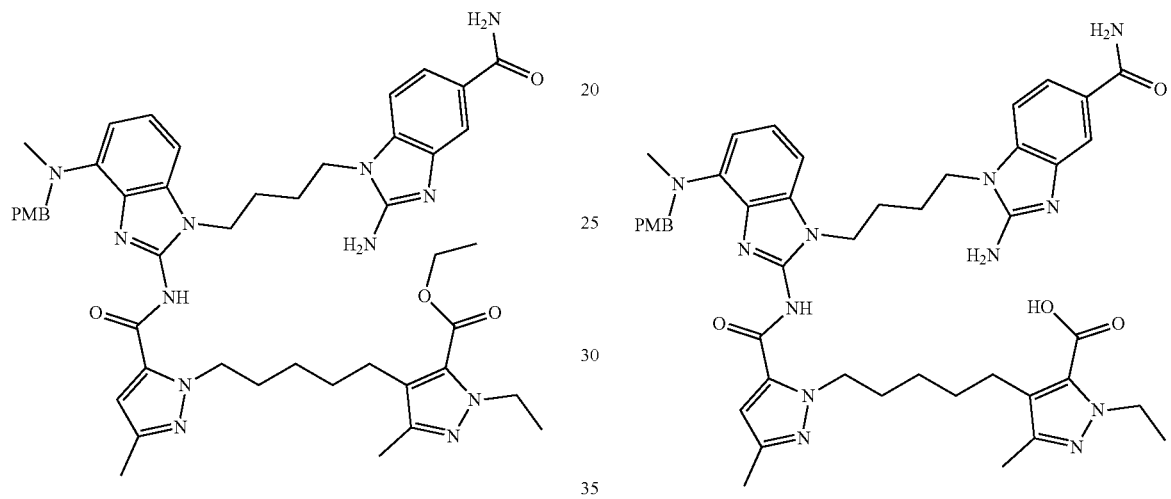

Ethyl-4-(5-(5-((1-(4-((2-amino-4-carbamoylphenyl)amino)butyl)-4-((4-methoxybenzyl)-(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate (1.03 g, 1.217 mmol) was dissolved in methanol (5 mL) and cyanogen bromide (0.243 mL, 1.217 mmol) was added. The mixture was stirred for 18 hours at RT. The reaction was concentrated, the residue was taken up in 10% MeOH in DCM (100 mL) and washed with 10% $K_2CO_3$ and brine. The organic layer was dried over $Na_2SO_4$, filtered and concentrated. The residue was purified by flash silica chromatography (2M $NH_3$ in MeOH/DCM 0-10%) to afford the title compound (870 mg, 0.999 mmol, 82% yield) as a light-purple foam. $^1$H NMR (400 MHz, METHANOL-$d_4$) δ ppm 7.75 (s, 1H) 7.55 (d, J=8.28 Hz, 1H) 7.18-7.29 (m, 3H) 7.15 (d, J=8.28 Hz, 1H) 7.00 (d, J=8.28 Hz, 1H) 6.81-6.93 (m, 3H) 6.65 (s, 1H) 4.62 (t, J=6.65 Hz, 2H) 4.19-4.41 (m, 8H) 4.03-4.13 (m, 2H) 3.75 (s, 3H) 3.37 (s, 1H) 2.88 (s, 3H) 2.58 (t, J=7.40 Hz, 2H) 2.24 (s, 3H) 2.10 (s, 3H) 1.77-2.00 (m, 6H) 1.42-1.54 (m, 2H) 1.27 (t, J=7.03 Hz, 9H). LCMS (LCMS Method E): Rt=1.20, [M+H]$^+$=872.5

To a suspension of ethyl 4-(5-(5-((1-(4-(2-amino-5-carbamoyl-1H-benzo[d]imidazol-1-yl)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylate (870 mg, 0.999 mmol) in methanol (8 mL) was added NaOH (4.99 mL, 4.99 mmol) and the resulting clear homogeneous solution was stirred overnight at rt. Methanol (8 mL) was added followed by dropwise addition of 1 M HCl (5 mL). The mixture was concentrated to remove most of the methanol, and water was added. The precipitates were filtered, washed with water, air dried, and then dried in vacuo to give the title compound (782 mg, 0.928 mmol, 93% yield) as a light pink solid. $^1$H NMR (400 MHz, DMSO-$d_6$) δ ppm 7.83 (br. s., 1H) 7.71 (s, 1H) 7.53 (d, J=8.07 Hz, 1H) 7.01-7.22 (m, 7H) 6.84 (d, J=8.31 Hz, 2H) 6.67 (br. s., 1H) 4.42 (br. s., 2H) 4.34 (q, J=7.09 Hz, 2H) 4.12 (br. s., 2H) 3.97-4.06 (m, 2H) 2.85 (s, 3H) 2.52-2.56 (m, 2H) 2.15 (s, 3H) 2.04 (s, 3H) 1.81 (br. s., 2H) 1.70 (d, J=6.36 Hz, 4H) 1.34-1.46 (m, 2H) 1.14-1.27 (m, 6H). LCMS (LCMS Method E): Rt=1.02, [M+H]$^+$=843.5

Example 47

8-ethyl-23-((4-methoxybenzyl)(methyl)amino)-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3-carboxamide

Examples 48-50

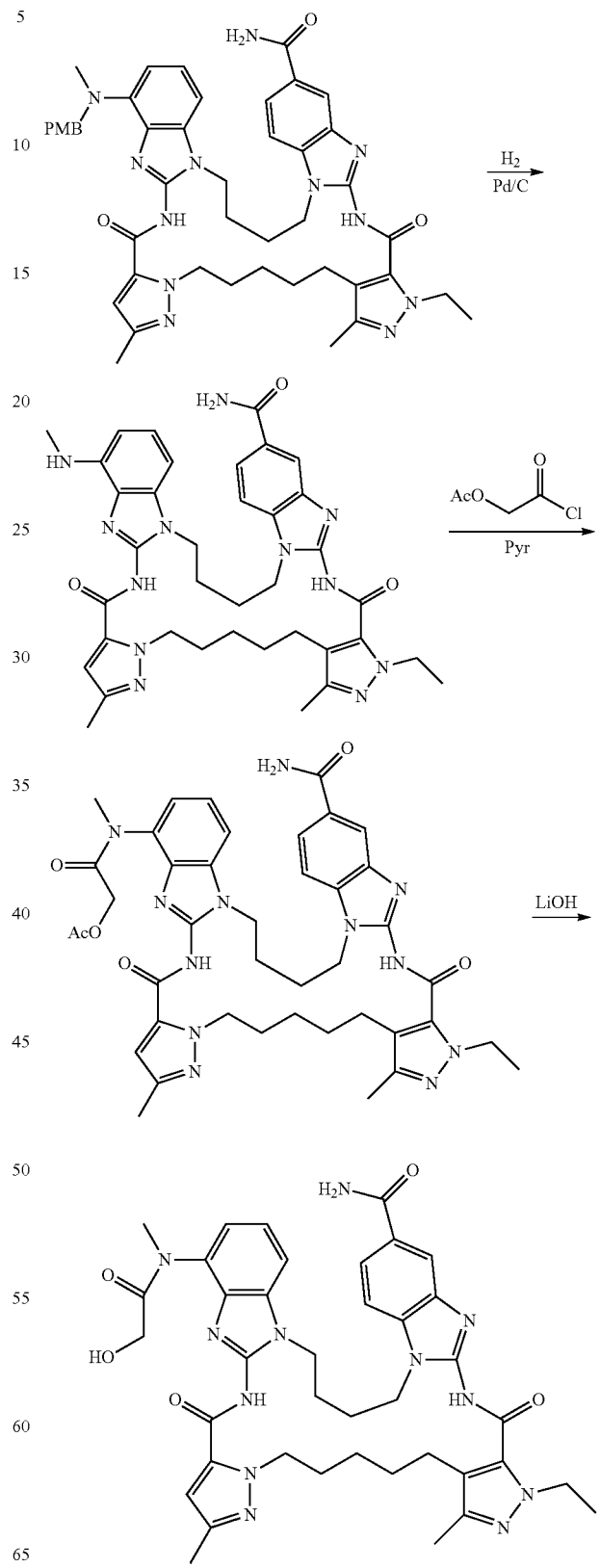

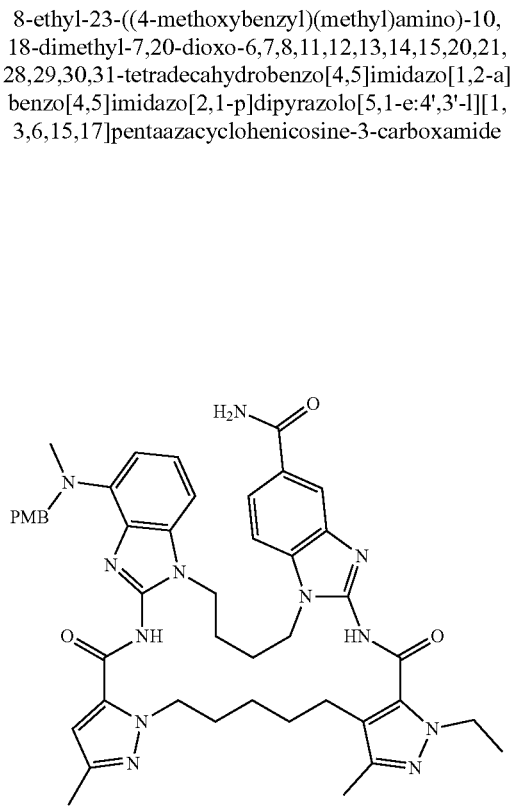

A solution of 4-(5-(5-((1-(4-(2-amino-5-carbamoyl-1H-benzo[d]imidazol-1-yl)butyl)-4-((4-methoxybenzyl)(methyl)amino)-1H-benzo[d]imidazol-2-yl)carbamoyl)-3-methyl-1H-pyrazol-1-yl)pentyl)-1-ethyl-3-methyl-1H-pyrazole-5-carboxylic acid (200 mg, 0.237 mmol) in DMF (5 mL) was slowly added (8 hours) by a syringe pump to a mixture of 1Hbenzo[d][1,2,3]triazol-1-ol (64.1 mg, 0.475 mmol), DMAP (2.90 mg, 0.024 mmol) and EDC (68.2 mg, 0.356 mmol) in DMF (5 mL) at 60° C. under nitrogen. The reaction was stirred for an additional 24 hrs, concentrated under vacuum, and the residue was dissolved in 10% MeOH in DCM. Saturated aqueous $NaHCO_3$ was added and the mixture was extracted with 10% MeOH in DCM. The combined extracts were washed with brine, dried over $Na_2SO_4$, filtered, concentrated, and the residue was purified by flash silica chromatography (2M $NH_3$ in MeOH/DCM 0-10%) to afford the title compound (40 mg, 0.048 mmol, 20.44% yield) as a off-white solid. $^1$H NMR (400 MHz, DMSO-$d_6$) δ ppm 12.88 (s, 2H) 8.02 (d, J=1.47 Hz, 2H) 7.82 (d, J=8.56 Hz, 1H) 7.49-7.65 (m, 1H) 7.38 (br. s., 1H) 7.20 (br. s., 3H) 6.85 (br. s., 3H) 6.50-6.64 (m, 1H) 4.54-5.18 (m, 3H) 4.48 (d, J=7.09 Hz, 2H) 4.20 (br. s., 5H) 3.71 (s, 3H) 2.72-2.91 (m, 5H) 2.18 (br. s., 3H) 2.09 (s, 3H) 1.77-1.97 (m, 6H) 1.49 (br. s., 2H) 1.30 (t, J=7.09 Hz, 5H). LCMS (LCMS Method D): Rt=1.18, [M+H]$^+$=825.8.

Example 48

8-ethyl-10,18-dimethyl-23-(methylamino)-7,20-di-oxo-6,7,8,11,12,13,14,-15,20,21,28,29,30,31tetra-deca-hydrobenzo[4,5]imidazo[1,2-a]benzo[4,5]imi-dazo[2,1-p]dipyrazolo[5,1-e:4',3'-l][1,3,6,15,17] pentaazacyclohenicosine-3-carboxamide

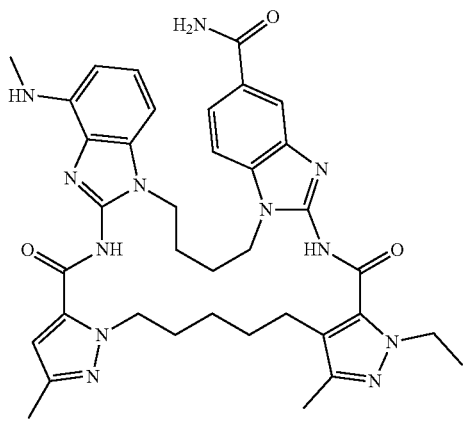 [SMILES: CCn1nc(C)c2c1C(=O)Nc1nc3cc(C(N)=O)ccc3n1CCCCn1c(nc3c(NC)cccc31)NC(=O)c1cc(C)nn1CCCCC2]

Pd—C(0.258 g, 0.242 mmol) was added a solution of 8-ethyl-23-((4-methoxybenzyl)(methyl)amino)-10,18-dimethyl-7,20-dioxo-6,7,8,11,12,13,14,15,20,21,28,29,30,31-tetradecahydrobenzo-[4,5]imidazo[1,2-a]benzo[4,5]imidazo[2,1-p]dipyrazolo[5,1-e:4',3'-l][1,3,6,15,17]-pentaazacyclohenicosine-3-carboxamide (2.0 g, 2.424 mmol) in MeOH (20 mL) and DCM (20 mL). The flask was purged with nitrogen, then hydrogen and the mixture was stirred under H2. After 8 hrs Pd/C was filtered off and the filtrate was concentrated in vacuo to give a white solid which was washed with MeOH to afford the title compound (1.25 g, 1.773 mmol, 73.2% yield) as a white solid. 1H NMR (400 MHz, DMSO-$d_6$) δ ppm 12.86 (br. s., 1H) 12.53 (br. s., 1H) 8.02 (br. s., 1H) 7.99 (br. s., 1H) 7.81 (d, J=8.07 Hz, 1H) 7.58 (d, J=8.07 Hz, 1H) 7.34 (br. s., 1H) 7.13 (t, J=7.70 Hz, 1H) 6.83 (d, J=7.82 Hz, 1H) 6.72 (d, J=4.16 Hz, 1H) 6.55 (s, 1H) 6.41 (d, J=7.83 Hz, 1H) 4.75 (br. s., 2H) 4.48 (d, J=6.85 Hz, 2H) 4.22 (br. s., 4H) 2.82 (d, J=3.91 Hz, 5H) 2.16 (br. s., 3H) 2.09 (br. s., 3H) 1.90 (br. s., 4H) 1.81 (br. s., 2H) 1.49 (br. s., 2H) 1.38 (br. s., 2H) 1.30 (t, J=6.85 Hz, 3H); LCMS (LCMS Method D): Rt=1.01, [M+H]$^+$=705.5

Example 49

2-((3-carbamoyl-8-ethyl-10,18-dimethyl-7,20-dioxo-6,7,8,11,12,13,14,15,20,21,28,29,30,31-tetradecahy-drobenzo[4,5]imidazo[1,2-a]benzo[4,5]imidazo[2,1-p]dipyrazolo[5,1-e:4',3'-l][1,3,6,15,17] pentaazacyclohenicosin-23-yl)(methyl)amino)-2-oxoethylacetate

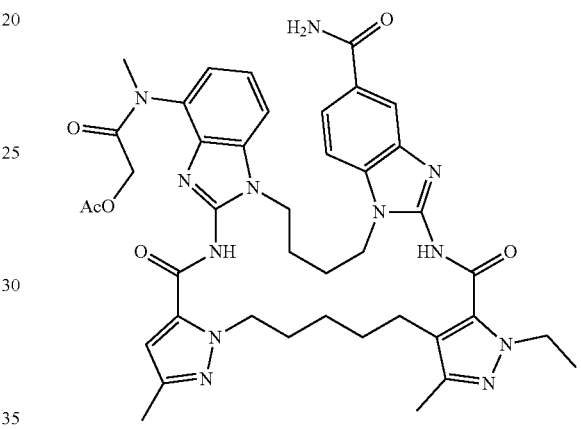

2-chloro-2-oxoethyl acetate (0.069 mL, 0.638 mmol) was added to a suspension of 8-ethyl-10,18-dimethyl-23-(methylamino)-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17] pentaazacyclohenicosine-3-carboxamide (300 mg, 0.426 mmol) in pyridine (5 mL) at RT. The mixture was stirred overnight then concentrated, and the residue was taken up in 10% MeOH in DCM (100 mL) and washed with water and brine. The organic layer was dried over $Na_2SO_4$, filtered and concentrated. The residue was purified by flash silica chromatography (2M $NH_3$ in MeOH/DCM 0-10%) to afford the title compound (198 mg, 0.246 mmol, 57.8% yield) as a light-pink solid. $^1$H NMR (400 MHz, METHANOL-$d_4$) δ ppm 7.97 (s, 1H) 7.86 (d, J=8.28 Hz, 1H) 7.59 (d, J=6.78 Hz, 1H) 7.38-7.53 (m, 2H) 7.34 (d, J=7.78 Hz, 1H) 6.60-6.75 (m, 1H) 4.76 (br. s., 2H) 4.48-4.60 (m, 3H) 4.31 (br. s., 5H) 3.54 (br. s., 1H) 3.36 (s, 2H) 2.89 (br. s., 2H) 2.26 (br. s., 3H) 2.18 (s, 3H) 2.04 (br. s., 6H) 1.96 (s, 1H) 1.88 (d, J=6.53 Hz, 2H) 1.60 (br. s., 2H) 1.33-1.49 (m, 5H); LCMS (LCMS Method D): Rt=0.94, [M+H]$^+$=805.6

Example 50

8-ethyl-23-(2-hydroxy-N-methylacetamido)-10,18-dimethyl-7,20-dioxo-6,7,8,11,12,13,14,-15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3-carboxamide

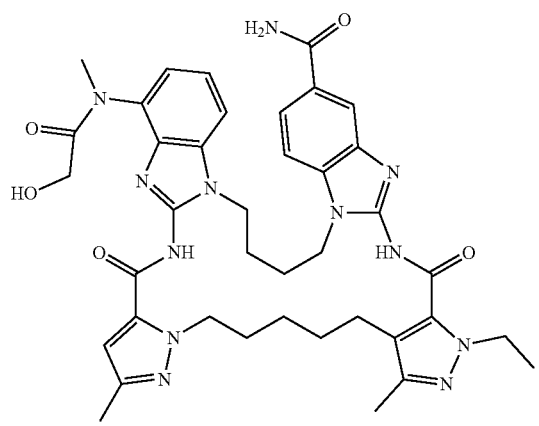 [SMILES: CCn1nc(C)c2c1C(=O)Nc1nc3cc(C(N)=O)ccc3n1CCCCn1c(nc3c(N(C)C(=O)CO)cccc31)NC(=O)c1cc(C)nn1CCCCC2]

To a solution of 2-((3-carbamoyl-8-ethyl-10,18-dimethyl-7,20-dioxo-6,7,8,11,12,13,14,-15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosin-23-yl)(methyl)amino)-2-oxoethyl acetate (132 mg, 0.164 mmol) in MeOH (4 mL) was added lithium hydroxide (1.640 mL, 1.640 mmol) and the mixture was stirred at RT. After 3 hours 1.64 mL of 1M HCl was added to the suspension to give a clear solution. Most of the MeOH was removed in vacuo, water was added, and the solid was isolated by filtration, washed with water, air dried, and then dried in vacuo to afford the title compound (119 mg, 0.156 mmol, 95% yield) as white solid. $^1$H NMR (400 MHz, DMSO-$d_6$) δ ppm 12.87 (s, 2H) 7.93-8.06 (m, 2H) 7.83 (d, J=7.58 Hz, 1H) 7.50-7.71 (m, 2H) 7.35 (br. s., 2H) 7.25 (d, J=7.09 Hz, 1H) 6.56 (br. s., 1H) 4.54-4.88 (m, 3H) 4.49 (q, J=7.01 Hz, 2H) 4.24 (br. s., 5H) 3.49-3.88 (m, 2H) 3.22 (br. s., 2H) 2.82 (br. s., 2H) 2.16 (br. s., 3H) 2.10 (s, 3H) 1.69-2.02 (m, 6H) 1.50 (br. s., 2H) 1.31 (t, J=7.09 Hz, 5H); LCMS Method D: Rt=0.88 min, [M+H]$^+$=763.6.

Example 51

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(2-(tetrahydro-2H-pyran-4-yl)ethoxy)-1H-enzo[d]imidazole-5-carboxamide

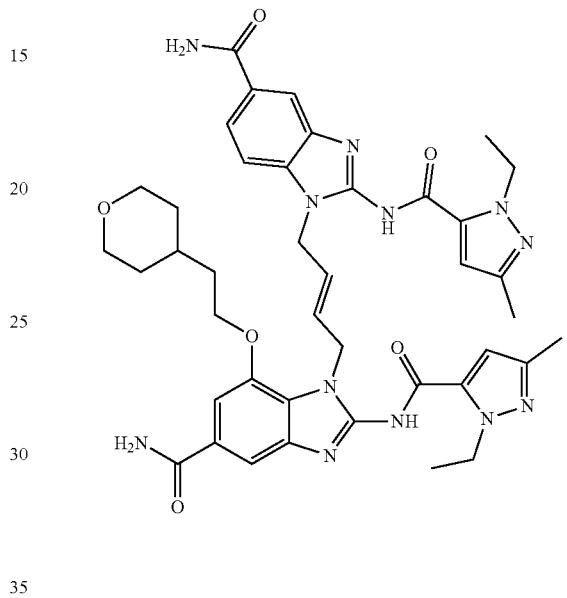

Example 51 can be prepared according to method 14 with modifications known to one of ordinary skill in the art. The last step of the preparation is provided: A mixture of 4-(2-bromoethyl)tetrahydro-2H-pyran (12.54 mg, 0.065 mmol), (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-hydroxy-1H-benzo[d]imidazole-5-arboxamide (45 mg, 0.065 mmol) and potassium carbonate (22.44 mg, 0.162 mmol) was heated for 3 hr at 85° C. in DMSO (650 µl) and NMP (650 µl), then cooled. The residue was purified via acidic reverse phase chromatography (5% to 50% in 0.1% TFA in MeCN to 0.1% TFA in water; 50×30 mm Phenomenex Eclipse, 5 µM C18 column, 20 min gradient). The pure fractions were partitioned between EtOAc and aqueous saturated sodium bicarbonate, the organic layer was separated, dried over sodium sulfate and evaporated in vacuo to provide the title compound (8 mg, 15.3% yield) as a white solid. $^1$H NMR (DMSO-$d_6$, 600 MHz): δ (ppm) 12.83 (br s, 2H), 7.97-8.00 (m, 1H), 7.93 (br s, 2H), 7.69 (dd, J=8.4, 1.5 Hz, 1H), 7.63 (s, 1H), 7.41 (d, J=8.3 Hz, 1H), 7.33 (br d, J=11.4 Hz, 2H), 7.29 (s, 1H), 6.55 (s, 1H), 6.52 (s, 1H), 5.96-6.02 (m, 1H), 5.70-5.79 (m, 1H), 4.93 (br d, J=5.0 Hz, 2H), 4.82 (br d, J=5.3 Hz, 2H), 4.49-4.58 (m, 4H), 3.96 (br t, J=6.7 Hz, 2H), 3.75 (br dd, J=11.2, 2.9 Hz, 2H), 3.16-3.23 (m, 2H), 2.12 (d, J=12.7 Hz, 6H), 1.50-1.53 (m, 1H), 1.45-1.49 (m, 2H), 1.43 (br d, J=11.9 Hz, 2H), 1.28 (m, 6H), 1.08 (br dd, J=12.0, 3.6 Hz, 2H); LCMS (LCMS Method K): Rt=0.90 min, [M+H]$^+$=805.5.

Example 52

(E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)butanoic Acid

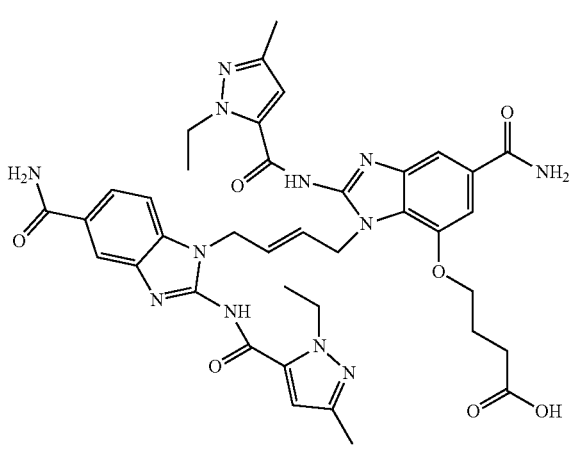 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCC(=O)O)c21]

Example 52 can be prepared according to a combination of method 14 and 16 with modifications known to one of ordinary skill in the art. The last step of the preparation is provided: Methyl (E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)butanoate (40 mg, 0.050 mmol) was dissolved in MeOH and THF (1 mL each) and sodium hydroxide (101 µl, 0.505 mmol, 5N) was added, and the mixture stirred at 25° C. for 18 hr. The reaction was then partitioned between EtOAc and 10% aqueous potassium hydrogen sulfate. The resulting gummy gel mixture was evaporated to near dryness, dissolved in 2 mL MeOH with aqueous sodium hydroxide (5N) to dissolve. The residue was purified via basic reverse phase chromatography (10% to 55% in 0.1% NH₄OH in water to MeCN; 50×30 mm Phenomenex Gemini, 5 µM C18 110A column, 10 min gradient). The pure fractions were collected and the product isolated by concentration in vacuo then dried under high vacuum to give the title compound as a white solid. ¹H NMR (400 MHz, Methanol-$d_4$) δ ppm 8.45-8.76 (m, 1H), 7.85-8.12 (m, 1H), 7.49-7.78 (m, 2H), 6.92-7.30 (m, 2H), 6.31-6.58 (m, 2H), 5.83-6.02 (m, 1H), 5.56-5.75 (m, 1H), 4.45-4.66 (m, 5H), 3.91-4.16 (m, 4H), 3.6 (q, J=6.3 Hz, 4H), 2.31 (m, 2H), 2.18 (s, 6H), 1.29 (q, J=6.1 Hz, 4H), 1.13 (t, J=6.1 Hz, 6H); LCMS Method K: Rt=0.75 min, [M+H]⁺=779.4.

Example 53

3-(((Z)-6-carbamoyl-3-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate, 2Hydrochloride

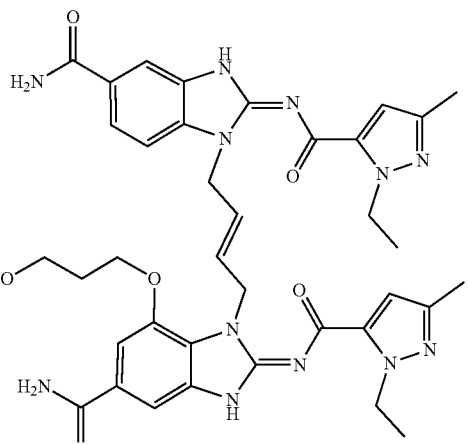

Step 1: Di-tert-butyl (3-(((Z)-6-carbamoyl-3-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-2,3-dihydro-H-benzo[d]imidazol-4-yl)oxy)propyl) Phosphate

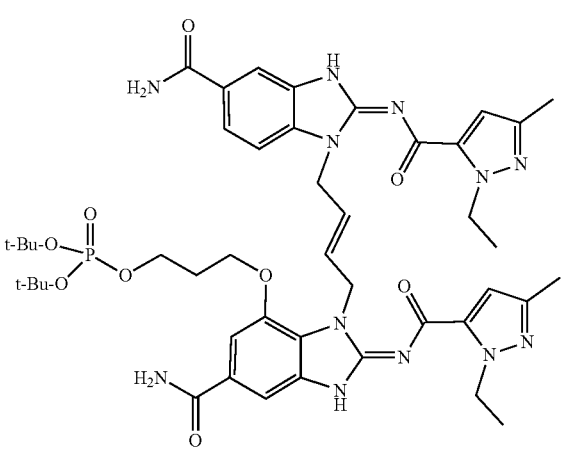

(E)-1-(4-(5-carbamoyl-2-(1-ethyl-3-methyl-1H-pyrazole-5-carboxamido)-1H-benzo[d]-imidazol-1-yl)but-2-en-1-yl)-2-(1-ethyl-3-methyl-1H-pyrazole-5-carboxamido)-7-(3-hydroxy-propoxy)-1H-benzo[d]imidazole-5-carboxamide (100 mg, 0.133 mmol) was suspended in DMF (1 mL), 2H-tetrazole in MeCN (1.480 mL, 0.666 mmol) was added, and the mixture was concentrated on rotovap to remove MeCN. The reaction mixture was cooled in an ice-water bath, and then a solution of di-tert-butyl diisopropylphosphoramidite (148 mg, 0.533 mmol) in DMF (1 mL) was added. The mixture was stirred for 1 hr, slowly warmed to RT and left over night for 16 hrs, then cooled with an ice-water bath, and an additional 2 eq of 2H-tetrazole in MeCN and 2 eq. of di-tert-butyl diisopropylphosphoramidite were added and the reaction stirred for 2 hrs. Additional 2 eq of 2H-tetrazole in MeCN and 2 eq of di-tert-butyl diisopropylphosphoramidite were then added and the reaction stirred for 2 hrs. The reaction was then cooled in an ice-water bath, $H_2O_2$ (0.272 mL, 2.66 mmol, 30%) was added, and stirring was continued for 30 min. The reaction mixture was poured into water (50 ml) containing a mixture of $NaHCO_3$ and $Na_2S_2O_3$ (1:1, 2M, 1 ml). The sticky paste was filtered, washed with water, and dried on the filter for 2 days. The residue was dissolved in THF, combined with the extracts from the filtrate using 3:1 $CHCl_3$:EtOH, organics were dried with $MgSO_4$, concentrated, dry-loaded on silica gel (12 g column), and purified by silica gel chromatography using 1-10% MeOH in DCM (+1% $NH_4OH$) for 5 min then 10% for 15 min to the title compound (23 mg, 0.024 mmol, 18.31% yield) as a white solid. The compound was used for next step directly without purification. LCMS (LCMS Method I): Rt=1.03 min, $[M+H]^+$=943.3

Example 53

3-(((Z)-6-carbamoyl-3-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyldihydrogen phosphate, 2Hydrochloride

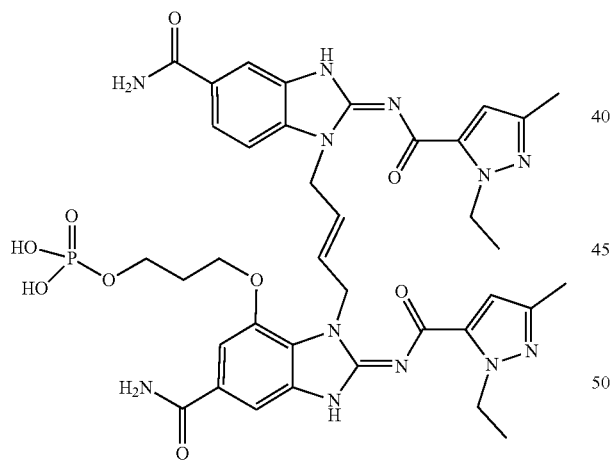

Di-tert-butyl(3-(((Z)-6-carbamoyl-3-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl)phosphate (22 mg, 0.023 mmol) was suspended in dioxane (1 mL), HCl 3M in CPME (0.156 mL, 0.467 mmol) was added at RT. After 2 hrs., diethyl ether (50 ml) was added, precipitate was filtered under $N_2$, washed with ether, dried in vacuum oven at 40° C. for 2 hrs to give the title compound (18 mg, 0.020 mmol, 85% yield) as a white solid. $^1H$ NMR (700 MHz, DMSO-$d_6$) δ (ppm) 12.83 (br s, 2H), 7.92-8.05 (m, 4H), 7.73 (dd, J=8.4, 1.4 Hz, 1H), 7.64-7.67 (m, 1H), 7.43 (d, J=8.3 Hz, 2H), 7.30-7.39 (m, 4H), 6.55 (s, 1H), 6.49 (s, 1H), 6.02 (dt, J=15.4, 5.5 Hz, 1H), 5.62-5.77 (m, 1H), 4.95 (br d, J=4.8 Hz, 3H), 4.83 (br d, J=5.4 Hz, 3H), 4.44-4.59 (m, 9H), 4.15 (br t, J=6.1 Hz, 5H), 3.94-3.99 (m, 4H), 2.11 (s, 4H), 2.09 (s, 3H), 1.96 (quin, J=6.0 Hz, 3H), 1.25 (q, J=7.3 Hz, 8H); LCMS (LCMS Method I): Rt=0.64 min, $[M+H]^+$=831.2.

Example 54

3-Carbamoyl-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxylic Acid

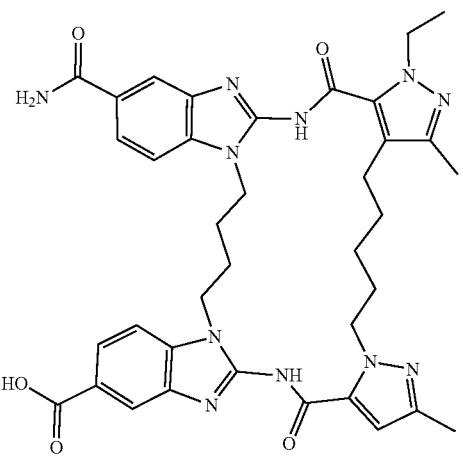 [SMILES: CCn1nc(C)c2c1C(=O)Nc1nc3cc(C(N)=O)ccc3n1CCCCn1c(nc3cc(C(=O)O)ccc31)NC(=O)c1cc(C)nn1CCCCC2]

Step 1: Methyl 3-carbamoyl-8-ethyl-10,18-dimethyl-7,20-dioxo-6,7,8,11,12,13,-14,15,20,21,28,29,30,31-tetradecahydrobenzo-[4,5]imidazo[1,2a]benzo[4,5]imidazo[2,1-p]dipyrazolo[5,1-e:4',3'-l][1,3,6,15,17]pentaazacyclohenicosine-24-carboxylate

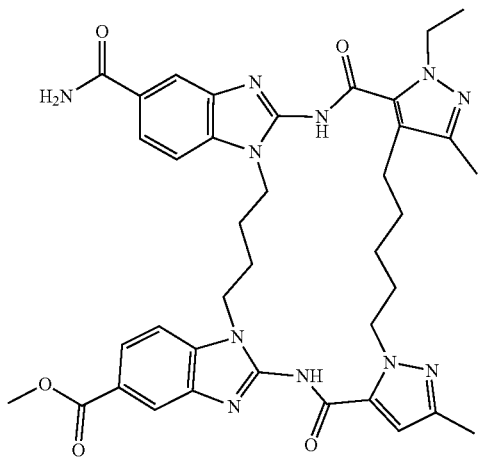

Example 55 can be prepared according to method 13 with modifications known to one of ordinary skill in the art. The last two steps step of the preparation are provided:

To a suspension of 24-cyano-8-ethyl-10,18-dimethyl-7,20-dioxo-6,7,8,11,12,13,-14,15,20,21,28,29,30,31-tetradecahydrobenzo[4,5]imidazo[1,2-a]benzo[4,5]imidazo-[2,1-p]dipyrazolo[5,1-e:4',3'-l][1,3,6,15,17]pentaazacyclohenicosine-3-carboxamide (900 mg, 1.284 mmol) in MeOH (40 mL) was added boron trifluoride etherate (0.814 mL, 6.42 mmol). The reaction mixture was stirred at 80° C. for 48 hrs then concentrated under vacuum and poured into ice water. The precipitate was collected by filtration, washed with water and dried to afford the title compound (600 mg, 0.818 mmol, 63.7% yield) as a gray solid. LCMS (LCMS Method A): Rt=1.406 min, [M+H]$^+$=733.7

Example 54

3-Carbamoyl-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxylic Acid

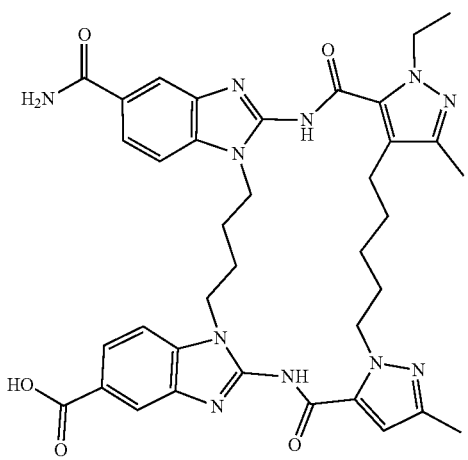 [SMILES: CCn1nc(C)c2c1C(=O)Nc1nc3cc(C(N)=O)ccc3n1CCCCn1c(nc3cc(C(=O)O)ccc31)NC(=O)c1cc(C)nn1CCCCC2]

To a suspension of methyl 3-carbamoyl-8-ethyl-10,18-dimethyl-7,20-dioxo-6,7,8,11,12,13,14,15,20,21,28,29,30,31-tetradecahydrobenzo[4,5]imidazo[1,2a]benzo[4,5]imidazo[2,1-p]dipyrazolo[5,1-e:4',3'-l][1,3,6,15,17]pentaazacyclohenicosine-24-carboxylate (420 mg, 0.572 mmol) in MeOH (15 mL) and Water (15 mL) was added NaOH (229 mg, 5.72 mmol). The reaction mixture was stirred at 25° C. for 16 hrs. The mixture was diluted with water (20 mL), acidified to pH=3 with 2N HCl and the precipitate was collected by filtration to afford crude product. The crude product was purified by preparative HPLC (Gemini Prep C18 OBD column, 5µ silica, 21.2 mm diameter, 150 mm length), using decreasingly polar mixtures of water (containing 0.1% TFA) and MeCN as eluents. Fractions containing the desired compound were evaporated to dryness to afford the title compound (190 mg, 0.264 mmol, 46.1% yield) as an off white solid. $^1$H NMR (400 MHz, DMSO-d δ (ppm) 12.89 (s, 1H), 8.13 (d, J=9.5 Hz, 1H), 7.87 (d, J=8.4 Hz, 1H), 7.71-7.52 (m, 3H), 7.45 (d, J=4.7 Hz, 1H), 6.55 (s, 1H), 4.51 (q, J=6.8 Hz, 2H), 4.36 (t, J=7.0 Hz, 2H), 4.17 (s, 2H), 4.10 (d, J=6.8 Hz, 2H), 2.65 (t, J=7.3 Hz, 2H), 2.10 (t, J=9.2 Hz, 6H), 1.87-1.61 (m, 6H), 1.46 (s, 2H), 1.28 (t, J=7.0 Hz, 3H), 1.19 (s, 2H); LCMS Method A: Rt=1.295 min, [M+H]$^+$=720.2

Example 55

Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-hydroxy-1H-benzo[d]imidazole-5-carboxylate, 2Trifluoroacetic Acid Salt

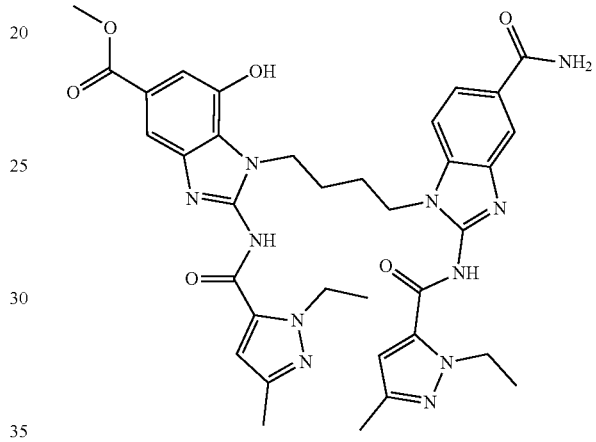

Example 55 can be prepared according to method 11 with modifications known to one of ordinary skill in the art. The last step of the preparation is provided: In a 50 mL RB flask, methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate (35 mg, 0.048 mmol) was stirred in DCM. Boron tribromide (58.0 µl, 0.058 mmol) was then added in portions. The reaction mixture was stirred at RT overnight (approximately 18 hrs), after which the reaction was quenched with MeOH and concentrated in vacuo. The crude containing both methoxy and phenol compounds purified on reverse phase HPLC (Gilson 115 liquid handler, Gilson 333 Aquious pump, Gilson 334 Organic pump, Gilson UV/VIS-155 detector, running Trilution v1.4 software. Lunar column: acetonitrile, 0.1% TFA/water eluent, 0-20% gradient. The desired fractions were combined and dried under vacuum to afford the title compound (5 mg, 5.07 umol, 10.47% yield). $^1$H NMR (400 MHz, DMSO-d$_6$) δ ppm 12.62-13.04 (m, 2H) 10.69 (s, 1H) 7.99 (s, 2H) 7.72-7.82 (m, 1H) 7.65 (s, 1H) 7.54 (d, J=8.34 Hz, 1H) 7.34 (d, J=2.27 Hz, 2H) 6.59 (s, 2H) 4.57 (dd, J=6.82, 4.04 Hz, 5H) 4.44 (br. s., 3H) 3.80-3.90 (m, 3H) 2.10 (d, J=4.55 Hz, 6H) 1.89 (br. s., 4H) 1.31 (t, J=7.07 Hz, 6H); LCMS (LCMS Method C): Rt=0.87 min, [M+H]$^+$=710.6

Example 56

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-4-fluoro-3-methyl-1H-pyrazole-5-carboxamido)-7-(3-morpholinopropoxy)-1H-benzo[d]imidazole-5-carboxamide

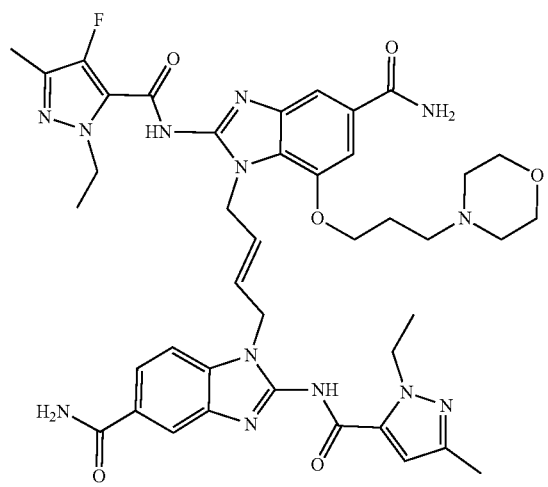 [SMILES: CCn1nc(C)cc1C(=O)Nc1nc2cc(C(N)=O)ccc2n1C/C=C/Cn1c(NC(=O)c2c(F)c(C)nn2CC)nc2cc(C(N)=O)cc(OCCCN3CCOCC3)c21]

Example 56 can be prepared according to method 20 with modifications known to one of ordinary skill in the art. The last step of the preparation is provided: To a suspension of (E)-2-amino-1-(4-(5-carbamoyl-2-(1-ethyl-3-methyl-1H-pyrazole-5-carboxamido)-1H-benzo[d]imidazol-1-yl)but-2-en-1-yl)-7-(3-morpholinopropoxy)-1H-benzo[d]imidazole-5-carboxamide (50 mg, 0.073 mmol) in DMF (2 mL) was added a solution of 1-ethyl-3-fluoro-4-methyl-1H-pyrazole-5-carboxylic acid (31.5 mg, 0.183 mmol), HOBt (16.8 mg, 0.110 mmol), HATU (69.5 mg, 0.183 mmol) and triethylamine (0.04 mL, 0.3 mmol) in DMF (2 mL) at RT. The mixture was stirred overnight, then heated to 50° C. for 30 min. Water was added, and the cloudy solution was chilled in a refrigerator until a precipitate formed. The solid was collected by filtration and purified over silica gel (Isco 4 g silica column), eluting with 0-20% MeOH in DCM to afford the title compound (4 mg, 4.77 µmole, 6.5% yield) as a white solid. $^1$H NMR (400 MHz, DMSO-$d_6$) δ ppm 12.81 (br. s., 2H), 7.99-8.03 (m, 2H), 7.92-7.97 (m, 1H), 7.67-7.73 (m, 1H), 7.64 (s, 1H), 7.30-7.44 (m, 4H), 6.53 (br. s., 1H), 5.93-6.04 (m, 1H), 5.68-5.82 (m, 1H), 4.90-4.97 (m, 2H), 4.76-4.84 (m, 1H), 4.45-4.57 (m, 4H), 3.98 (br. s., 2H), 3.44-3.49 (m, 4H), 2.21-2.29 (m, 2H), 2.17-2.21 (m, 4H), 2.07-2.15 (m, 6H), 1.63-1.74 (m, 2H), 1.13-1.21 (m, 6H); LCMS (LCMS Method J): Rt=0.65 min, [M+H]$^+$=838.3

Example 57

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-hydroxy-1H-benzo[d]imidazole-5-carboxamide, Trifluoroacetic Acid Salt

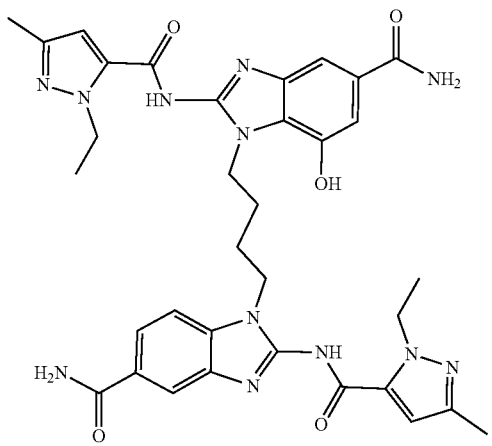

Example 57 can be prepared according to method 20 with modifications known to one of ordinary skill in the art. The last step of the preparation is provided: To 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide, bis trifluoroacetic acid salt (17 mg, 0.018 mmol) in DCM (2 mL) at −78° C. was added 1M BBr$_3$ in DCM (50 µL, 0.050 mmol). After 1 hr, the reaction was warmed to RT, and LC/MS analysis showed no reaction progression. The reaction was cooled to 0° C., and another 100 µL 1M BBr$_3$ in DCM was added. The reaction was allowed to slowly warm to RT over 72 hr, was returned to 0° C., and then another 100 µL 1M BBr$_3$ in DCM was added. After an additional 24 hr, MeOH (~2 mL) was added, and the reaction was concentrated. The residue was purified via reverse phase HPLC, eluting with 20-45% MeCN in H$_2$O (with 0.1% TFA) to afford the title compound (8 mg, 0.01 mmol, 55% yield). $^1$H NMR (400 MHz, DMSO-$d_6$) δ ppm 12.80 (br. s, 1H), 10.48 (s, 1H), 7.98 (d, J=1.27 Hz, 2H), 7.83 (br. s., 1H), 7.75 (dd, J=8.36, 1.52 Hz, 1H), 7.53 (d, J=8.36 Hz, 1H), 7.43 (d, J=1.27 Hz, 1H), 7.22 (s, 1H), 7.34 (br. s., 1H), 7.14 (d, J=1.52 Hz, 1H), 7.10 (s, 1H), 6.97 (s, 1H), 6.58 (d, J=9.63 Hz, 2H), 4.49-4.65 (m, 4H), 4.43 (t, J=6.40 Hz, 2H), 4.27 (t, J=7.00 Hz, 2H), 2.10 (d, J=6.34 Hz, 6H), 1.82-1.95 (m, 4H), 1.30 (td, J=7.03, 3.68 Hz, 6H); LCMS (LCMS Method D): Rt=0.78 min, [M+H]$^+$=695.4

Example 58

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(2-hydroxyethoxy)-1H-benzo[d]imidazole-5-carboxamide

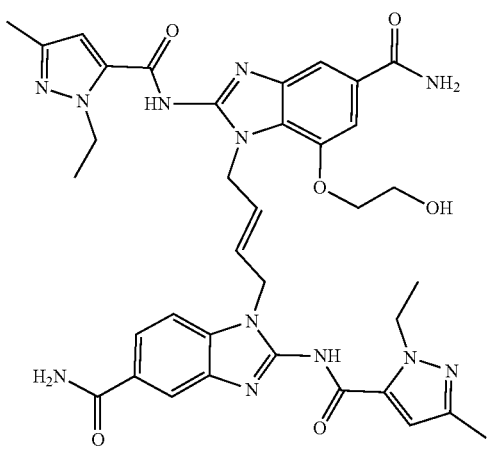

Example 58 can be prepared according to method 9 with modifications known to one of ordinary skill in the art. The last step of the preparation is provided: To (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(2-methoxyethoxy)-1H-benzo[d]imidazole-5-carboxamide (300 mg, 0.400 mmol) in DCM (5 mL) at 0° C. was added $BBr_3$ (501 mg, 2.00 mmol). After 3 hr, the reaction was quenched with water (5 mL), and the resulting solid was collected by filtration. This solid was purified via prep HPLC to afford the title compound (21 mg, 0.029 mmol, 7% yield) as a gray solid. $^1$H NMR (400 MHz, DMSO-$d_6$) δ ppm 12.83 (s, 2H), 7.97 (d, J=12.2 Hz, 3H), 7.62-7.78 (m, 2H), 7.29-7.50 (m, 4H), 6.54 (d, J=14.1 Hz, 2H), 5.99 (s, 1H), 5.86 (s, 1H), 4.99 (s, 3H), 4.82 (s, 2H), 4.53 (d, J=6.8 Hz, 4H), 4.07 (s, 2H), 3.63 (s, 2H), 2.11 (s, 6H), 1.27 (s, 6H); LCMS (LCMS Method A): Rt=1.333 min, [M+H]$^+$=737.1

Example 59

(E)-1-(4-(5-Carbamoyl-2-(1-ethyl-3-methyl-1H-pyrazole-5-carboxamido)-1H-benzo[d]imidazol-1-yl)but-2-en-1-yl)-7-ethoxy-2-(1-ethyl-3-methyl-1H-pyrazole-5-carboxamido)-1H-benzo[d]imidazole-5-carboxamide

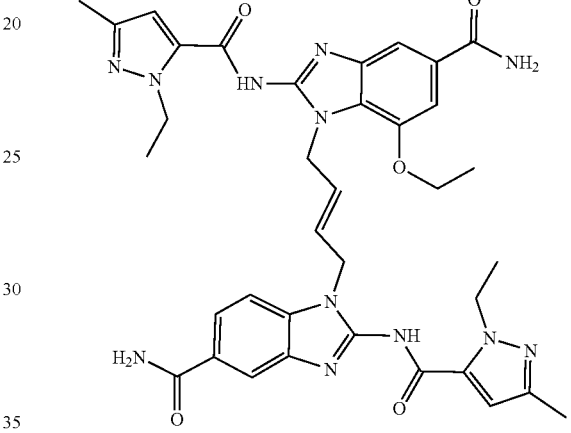

Example 59 can be prepared according to method 9 with modifications known to one of ordinary skill in the art. The last step of the preparation is provided: To 1-ethyl-3-methyl-1H-pyrazole-5-carboxylic acid (58 mg, 0.38 mmol) in NMP (3 ml) at RT was added HATU (171 mg, 0.450 mmol) and DIEA (0.14 mL, 0.77 mmol). After 15 min, (E)-2-amino-1-(4-(2-amino-5-carbamoyl-1H-benzo[d]imidazol-1-yl)but-2-en-1-yl)-7-ethoxy-1H-benzo[d]imidazole-5-carboxamide (65 mg, 0.15 mmol) was added, and the mixture was heated to 60° C. After 16 hr, water was added, and the resulting solid was collected by filtration. This material was purified by prep HPLC to afford the title compound (35 mg, 0.047 mmol, 33% yield) as a yellow solid. $^1$H NMR (400 MHz, DMSO-$d_6$) δ ppm 12.85 (s, 2H), 7.97 (d, J=11.7 Hz, 3H), 7.72 (d, J=8.4 Hz, 1H), 7.64 (s, 1H), 7.43 (d, J=8.4 Hz, 1H), 7.32 (d, J=12.3 Hz, 3H), 6.55 (s, 2H), 5.91-6.02 (m, 1H), 5.78 (dd, J=13.3, 7.7 Hz, 1H), 4.94 (d, J=4.7 Hz, 2H), 4.83 (d, J=4.9 Hz, 2H), 4.50-4.57 (m, 4H), 3.99-4.06 (s, 2H), 2.12 (d, J=3.8 Hz, 6H), 1.28 (dd, J=12.7, 6.9 Hz, 6H), 1.18 (t, J=6.9 Hz, 3H); LCMS (LCMS Method A): Rt=1.382 min, [M+H]$^+$=721.2

Example 60

(E)-7-Bromo-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

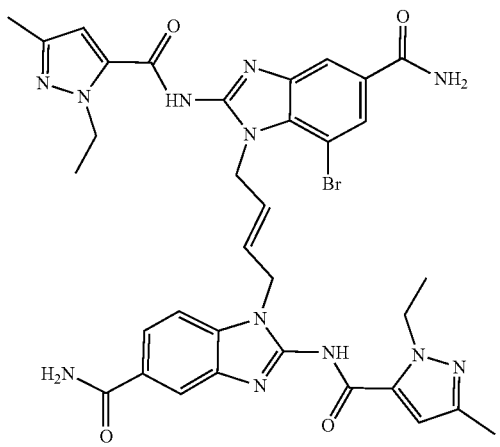

Example 60 can be prepared according to method 9 with modifications known to one of ordinary skill in the art. The last step of the preparation is provided: 1-Ethyl-3-methyl-1H-pyrazole-5-carboxylic acid (1.12 g, 7.28 mmol), (E)-2-amino-1-(4-(2-amino-5-carbamoyl-1H-benzo[d]imidazol-1-yl)but-2-en-1-yl)-7-bromo-1H-benzo[d]imidazole-5-carboxamide (1.6 g, 3.3 mmol), HATU (3.14 g, 8.28 mmol) and triethylamine (1.01 g, 9.93 mmol) were heated to 60° C. in DMF (30 mL). After 12 hr, water (5 mL) was added, and the resulting solid was collected by filtration. This material was purified by prep HPLC to afford the title compound (700 mg, 0.926 mmol, 28% yield) as a brown solid. $^1$H NMR (400 MHz, DMSO-$d_6$) δ ppm 13.05 (br. s., 1H), 12.80 (s, 1H), 8.06 (s, 1H), 7.91-8.00 (m, 4H), 7.72 (d, J=8 Hz, 1H), 7.43-7.47 (m, 2H), 7.33 (s, 1H), 6.54 (d, J=4 Hz, 2H), 5.95-6.05 (m, 1H), 5.60-5.70 (m, 1H), 5.06-5.13 (m, 2H), 4.75-4.81 (m, 2H), 4.45-4.61 (m, 4H), 2.12 (d, J=4 Hz, 6H), 1.18-1.35 (m, 6H); LCMS (LCMS Method A): Rt=1.367 min, [M+H]$^+$=755.1

Example 61

(E)-7-(Aminomethyl)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide, Trifluoroacetic Acid Salt

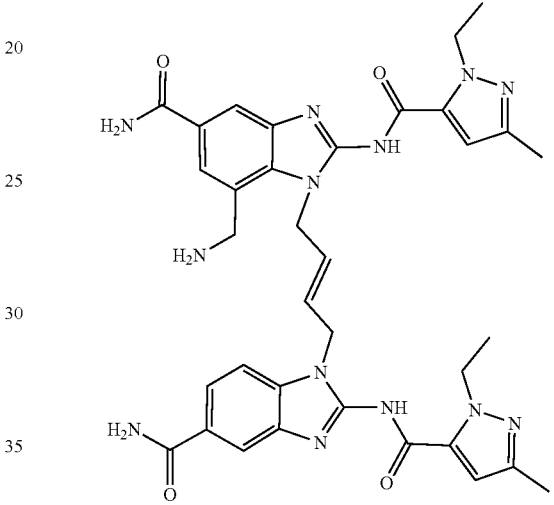

Example 61 can be prepared according to method 9 with modifications known to one of ordinary skill in the art. The last step of the preparation is provided:

To (E)-tert-butyl ((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)methyl)carbamate (410 mg, 0.509 mmol) in MeOH (10 mL) at RT was added 36.5% HCl (0.5 mL, 0.51 mmol). The reaction was heated to 40° C. and concentrated after 3 hr. The residue was purified by prep-HPLC to afford the title compound (9 mg, 11 μmol, 2% yield). $^1$H NMR (400 MHz, DMSO-$d_6$) δ ppm 13.07-12.88 (m, 1H), 8.34 (s, 3H), 8.00 (d, J=7.3 Hz, 2H), 7.95 (s, 1H), 7.88 (s, 1H), 7.74 (d, J=8.4 Hz, 1H), 7.43 (d, J=8.4 Hz, 2H), 7.35 (s, 1H), 6.56 (d, J=15.5 Hz, 2H), 5.92 (d, J=15.9 Hz, 1H), 5.58 (d, J=16.0 Hz, 1H), 5.23-5.29 (m, 2H), 5.00 (s, 2H), 4.82 (s, 2H), 4.53 (dd, J=13.6, 6.6 Hz, 4H), 4.15 (d, J=4.6 Hz, 2H), 2.12 (d, J=3.9 Hz, 6H), 1.28 (d, J=4.2 Hz, 6H); LCMS (LCMS Method A): Rt=1.183 min, [M+H]$^+$=706.3

Example 62

(E)-8-Ethyl-1,26-dimethoxy-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide, bis Trifluoroacetic Acid Salt

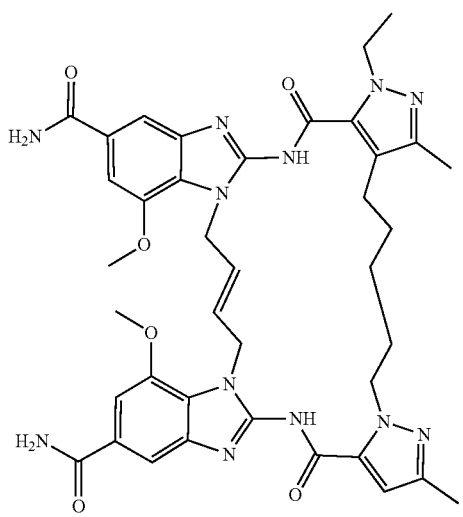 [SMILES: CCn1nc(C)c2c1C(=O)Nc1nc3cc(C(N)=O)cc(OC)c3n1C/C=C/Cn1c(nc3cc(C(N)=O)cc(OC)c31)NC(=O)c1cc(C)nn1CCCCC2]

Example 63

8-Ethyl-1,26-bis(3-hydroxypropoxy)-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide Dihydrochloride

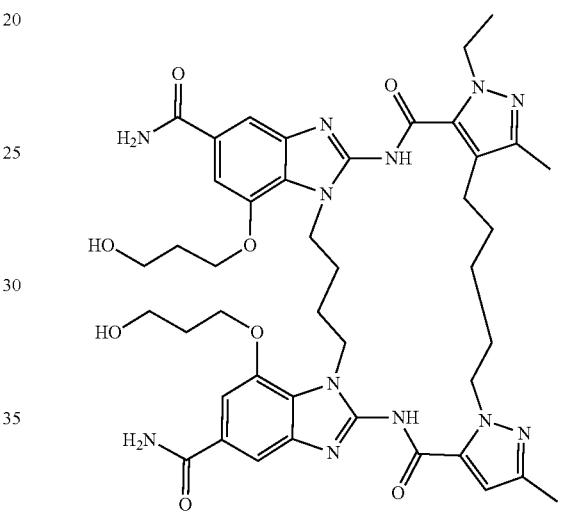

Example 62 can be prepared according to methods 6 with modifications known to one of ordinary skill in the art. The last step of the preparation is provided: To a solution of 4-(5-(5-carboxy-3-methyl-1H-pyrazol-1-yl)pentyl)-1-ethyl-3-methyl-1H-pyrazole-5-carboxylic acid (37.5 mg, 0.108 mmol), HATU (101 mg, 0.267 mmol) and TEA (86 μL, 0.62 mmol) in DMF (4.1 ml) was added (E)-4,4'-(but-2-ene-1,4-diylbis(azanediyl))bis(3-amino-5-methoxybenzamide) dihydrochloride (50 mg, 0.10 mmol). The reaction was heated to 100° C., and after 3 hr, water was added. The resulting solid was collected by filtration and purified by HPLC to afford the title compound (1 mg, 1 μmol, 1% yield; low yield partially due to an injection port malfunction during HPLC purification). $^1$H NMR (400 MHz, MeOH-d$_4$) δ ppm 7.68 (s, 1H), 7.64 (s, 1H), 7.37 (d, J=4.56 Hz, 2H), 6.63 (s, 1H), 5.76 (d, J=12.67 Hz, 2H), 5.05 (d, J=12.93 Hz, 4H), 4.70 (br. s., 2H), 4.46-4.57 (m, 2H), 3.72 (d, J=8.36 Hz, 6H), 2.81 (d, J=6.59 Hz, 2H), 2.26 (s, 3H), 2.20 (s, 3H), 1.86 (br. s., 2H), 1.58 (br. s., 2H), 0.89-0.96 (m, 5H); LCMS (LCMS Method D): Rt=0.91 min, [M/2+H]$^+$=389.5

Example 63 can be prepared according to method 6 with modifications known to one of ordinary skill in the art. The last step of the preparation is provided: To 1,26-bis(3-((tert-butyldimethylsilyl)oxy)propoxy)-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide (18 mg, 0.016 mmol) in THF (0.5 ml) at 0° C. was added 4 N HCl (0.025 mL, 0.099 mmol). After 60 min, the resulting precipitate was collected by filtration and washed with EtOAc to afford the title compound (15 mg, 0.016 mmol, 97% yield). $^1$H NMR (400 MHz, DMSO-d$_6$) δ ppm 7.95-8.08 (m, 2H), 7.64-7.70 (m, 2H), 7.29-7.42 (m, 4H), 6.51-6.58 (m, 1H), 4.63-4.72 (m, 2H), 4.31-4.50 (m, 6H), 4.11-4.20 (m, 4H), 3.42-3.48 (m, 4H), 2.74-2.85 (m, 2H), 2.15 (s, 3H), 2.10 (s, 3H), 1.78-1.91 (m, 6H), 1.64-1.74 (m, 4H), 1.48-1.58 (m, 2H), 1.37-1.47 (m, 2H), 1.26-1.32 (m, 3H); LCMS (LCMS Method D): Rt=0.82 min, [M+H]$^+$=867.5

Example 64

(29R,30R)-8-Ethyl-29,30-dihydroxy-10,18-dimethyl-7,20-dioxo-6,7,8,11,12,-13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

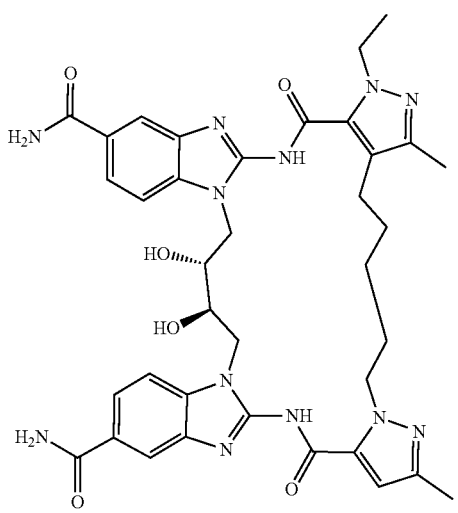 [SMILES: CCn1nc(C)c2c1C(=O)Nc1nc3cc(C(N)=O)ccc3n1C[C@@H](O)[C@H](O)Cn1c(nc3cc(C(N)=O)ccc31)NC(=O)c1cc(C)nn1CCCCC2]

Example 65

8-Ethyl-10,13,13,18-tetramethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

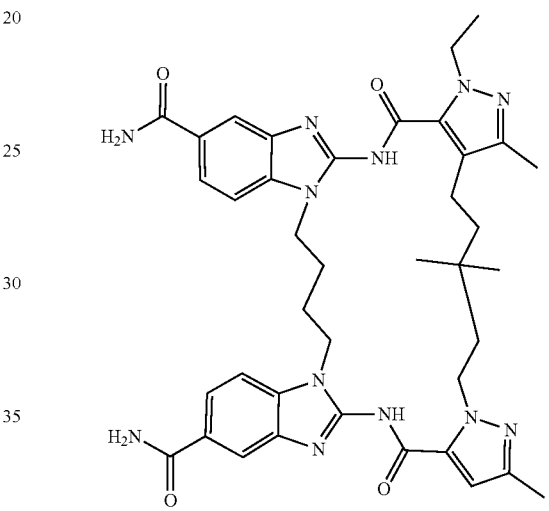

Example 64 can be prepared according to method 19 with modifications known to one of ordinary skill in the art. The last step of the preparation is provided: (28aR,31aR)-8-Ethyl-10,18,30,30-tetramethyl-7,20-dioxo-6,7,8,11,12,13,14,15,-20,21,28,28a,31a,32-tetradecahydrobenzo[4,5]imidazo[1,2-a]benzo[4,5]imidazo[2,1-p][1,3]dioxolo[4,5-s]dipyrazolo[5,1-e:4',3'-l][1,3,6,15,17]-pentaazacyclohenicosine-3,24-dicarboxamide (500 mg, 0.632 mmol), formic acid (15 mL, 391 mmol) and water (1.5 mL) were stirred at 25° C. After 48 hr, the mixture was concentrated and the residue was purified by prep HPLC (Gemini-C18 column, 5μ silica, 21 mm diameter, 150 mm length), eluting with 10-30% water in MeCN (with 0.1% formic acid) to afford the title compound (7.5 mg, 9.5 μmol, 1.5% yield) as a white solid. $^1$H NMR (400 MHz, MeOH-d$_4$) δ ppm 8.01 (d, J=13.1 Hz, 2H), 7.81-7.93 (m, 2H), 7.63-7.76 (m, 2H), 6.66 (s, 1H), 4.83 (s, 1H), 4.62-4.74 (m, 1H), 4.42-4.63 (m, 6H), 4.12-4.33 (m, 2H), 2.90-3.00 (m, 1H), 2.71-2.82 (m, 1H), 2.23 (d, J=18.2 Hz, 6H), 1.84-2.00 (m, 2H), 1.61-1.73 (m, 2H), 1.37-1.47 (m, 2H), 1.38 (t, J=7.1 Hz, 3H); LCMS (LCMS Method A): Rt=1.295 min, [M+H]$^+$=751.2

Example 65 can be prepared according to method 19 with modifications known to one of ordinary skill in the art. The last step of the preparation is provided: To 4-(5-(5-carboxy-3-methyl-1H-pyrazol-1-yl)-3,3-dimethylpentyl)-1-ethyl-3-methyl-1H-pyrazole-5-carboxylic acid (192 mg, 0.510 mmol) in NMP (10 mL) was added HATU (194 mg, 0.510 mmol). The reaction was heated to 40° C., and 1,1'-(propane-1,3-diyl)bis(2-amino-1H-benzo[d]imidazole-5-carboxamide) (200 mg, 0.510 mmol) was added. After heating overnight, the reaction was purified by prep HPLC to afford the title compound (13 mg, 0.017 mmol, 3.4% yield). $^1$H NMR (400 MHz, MeOH-d$_4$) δ ppm 8.01 (d, J=8.4 Hz, 2H), 7.85 (d, J=8.4 Hz), 7.51 (t, J=8.4 Hz, 2H), 6.65 (s, 1H), 4.73-4.77 (m, 2H), 4.45-4.53 (m, 2H), 4.28-4.33 (m, 4H), 2.78-2.87 (m, 2H), 2.29 (d, J=11.6 Hz, 6H), 1.98 (br. s., 4H), 1.88 (t, J=7.6 Hz, 2H), 1.45-1.54 (m, 2H), 1.27-1.39 (m, 5H), 1.07 (s, 6H); LCMS (LCMS Method A): Rt=1.397 min, [M+H]$^+$=747.3

Example 66

8-Ethyl-12,13-dihydroxy-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

Example 67

(1r,39r)-14-ethyl-16,25-dimethyl-12,28-dioxo-2,9,11,14,15,23,24,29,31,38-decaazaoctacyclo[37.2.2.0², ¹⁰0.0³,⁸.0¹³,¹⁷0.0²³,²⁷0.0³⁰,³⁸0.0³²,³⁷]tritetraconta-3,5,7,9,13(17), 15,24,26,30,32,34,36-dodecaene-6,34-Dicarboxamide

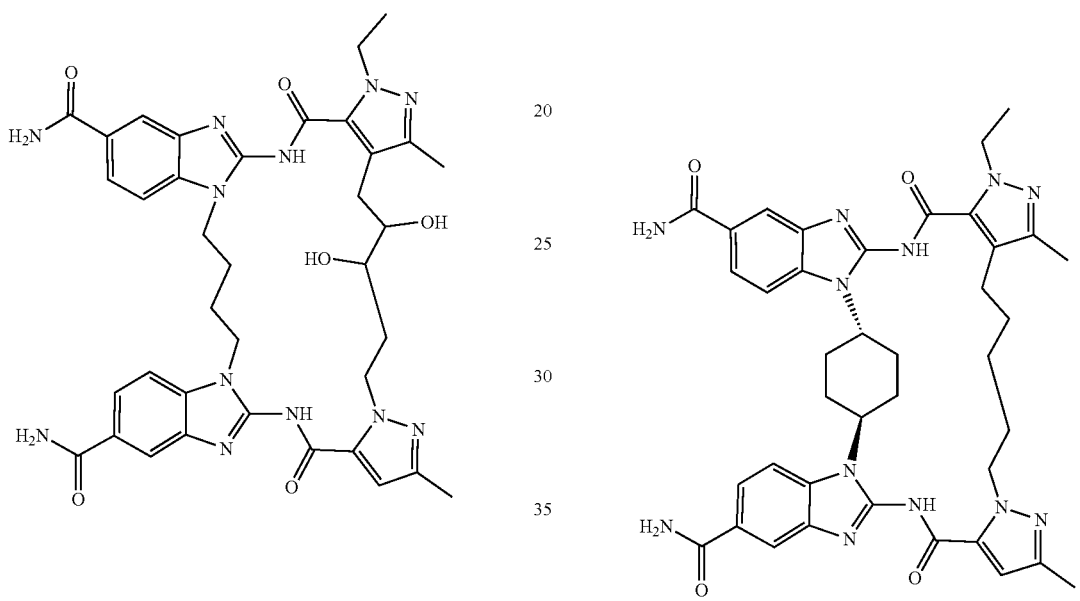

Example 66 can be prepared according to method 19 with modifications known to one of ordinary skill in the art. The last step of the preparation is provided: To 8-ethyl-10,18-dimethyl-7,20-dioxo-6,7,8,11,14,15,20,21,28,29,30,31-dodecahydrobenzo[4,5]imidazo[1,2-a]benzo[4,5]imidazo[2,1-p]dipyrazolo[5,1-e:4',3'-l][1,3,6,15,17]-pentaazacyclohenicosine-3,24-dicarboxamide (350 mg, 0.488 mmol) and NMO (114 mg, 0.977 mmol) in tert-BuOH (9 mL) and water (3 mL) was added osmium tetroxide (7.7 µL, 0.024 mmol). After 4 hr at 25° C., the reaction was quenched with $Na_2SO_3$ and diluted with DCM (50 mL). The mixture was washed with water (30 mL) and brine (30 mL), and the organic layer was dried over $Na_2SO_4$ and concentrated. The residue was purified by prep HPLC (Gemini-C18 column, 5µ silica, 21 mm diameter, 150 mm length), eluting with 20-40% MeCN in water (with 0.1% TFA) to afford the title compound (11 mg, 0.015 mmol, 3.0% yield) as a white solid. ¹H NMR (400 MHz, MeOH-$d_4$) δ ppm 8.14 (s, 1H), 8.04 (s, 1H), 7.94 (dd, J=27.0, 8.4 Hz, 2H), 7.68 (dd, J=37.9, 8.5 Hz, 2H), 6.68 (s, 1H), 5.29-5.41 (m, 1H), 4.38-4.61 (m, 6H), 4.20-4.29 (m, 1H), 3.74 (t, J=12.4 Hz, 2H), 3.16 (dd, J=14.1, 10.2 Hz, 1H), 2.95 (d, J=11.2 Hz, 1H), 2.38-2.49 (m, 1H), 2.29 (s, 1H), 2.29 (s, 3H), 2.27 (s, 3H), 2.04-2.15 (m, 3H), 1.92-1.99 (m, 1H), 1.45 (t, J=8 Hz, 3H); LCMS (LCMS Method A): Rt=1.270 min, [M+H]⁺=750.9

Example 67 can be prepared according to method 19 with modifications known to one of ordinary skill in the art. The last step of the preparation is provided: To 4-(5-(5-carboxy-3-methyl-1H-pyrazol-1-yl)pentyl)-1-ethyl-3-methyl-1H-pyrazole-5-carboxylic acid (483 mg, 1.39 mmol) in DMF (10 mL) at 25° C. was added HATU (1.10 g, 2.89 mmol) and DIEA (1.01 mL, 5.78 mmol). After 4 hr, 1,1'-((1R,4R)-cyclohexane-1,4-diyl)bis(2-amino-1H-benzo[d]imidazole-5-carboxamide) (500 mg, 1.16 mmol) was added, and the reaction was stirred at 80° C. for 16 hr. Water was added, a brown solid appeared and was collected. The solid was subjected to purification twice to give the product (3 mg, 4 µmol, 0.3% yield). ¹H NMR (400 MHz, DMSO-$d_6$) δ ppm 13.04 (s, 2H), 8.07 (d, J=8.2 Hz, 6H), 7.88 (d, J=8.2 Hz, 2H), 7.39 (s, 2H), 6.58 (s, 1H), 4.95 (br, s., 2H), 4.69 (br. s., 2H), 4.48 (br. s., 2H), 2.60-2.85 (m, 6H), 1.99-2.24 (m, 10H), 1.80-2.01 (m, 3H), 1.49-1.65 (m, 4H), 1.34 (br. s., 4H); LCMS (LCMS Method A): Rt=1.413 min, [M+H]⁺=745.3

Example 68

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-isopropoxy-1Hbenzo[d]imidazole-5-carboxamide

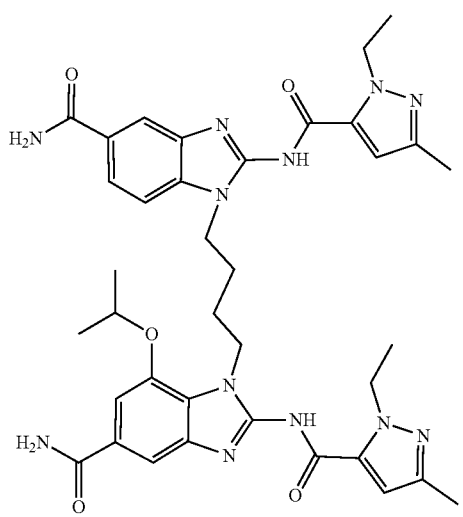 [SMILES: CCn1nc(C)cc1C(=O)Nc1nc2cc(C(N)=O)ccc2n1CCCCn1c(NC(=O)c2cc(C)nn2CC)nc2cc(C(N)=O)cc(OC(C)C)c21]

Example 68 can be prepared according to method 9 with modifications known to one of ordinary skill in the art. The last step of the preparation is provided: To 1-ethyl-3-methyl-1H-pyrazole-5-carboxylic acid (215 mg, 1.40 mmol) in DMF (5 mL) at 25° C. was added DIEA (0.489 mL, 2.80 mmol) and HATU (638 mg, 1.68 mmol). After 30 min, 2-amino-1-(4-(2-amino-5-carbamoyl-1H-benzo[d]imidazol-1-yl)butyl)-7-isopropoxy-1H-benzo[d]imidazole-5-carboxamide (260 mg, 0.560 mmol) was added. After 16 hr, water was added, and the resulting precipitate was collected by filtration and washed with MeOH to afford the title compound (55 mg, 0.075 mmol, 13% yield) as a brown solid. $^1$H NMR (400 MHz, DMSO-$d_6$) δ ppm 12.80 (d, J=12.5 Hz, 2H), 7.88-8.01 (m, 3H), 7.75 (d, J=7.8 Hz, 1H), 7.55-7.60 (m, 2H), 7.30 (br. s., 3H), 6.59 (s, 2H), 4.74-4.84 (m, 1H), 4.52-4.63 (m, 4H), 4.29-4.36 (m, 4H), 2.11 (d, J=6.5 Hz, 6H), 1.77-1.94 (m, 4H), 0.98-1.44 (m, 12H); LCMS (LCMS Method A): Rt=1.428 min, [M+H]$^+$=737.2

Example 69

1-(4-(5-Carbamoyl-2-(1-ethyl-3-methyl-1H-pyrazole-5-carboxamido)-1H-benzo[d]imidazol-1-yl)butyl)-7-ethoxy-2-(1-ethyl-3-methyl-1H-pyrazole-5-carboxamido)-1H-benzo[d]imidazole-5-carboxamide

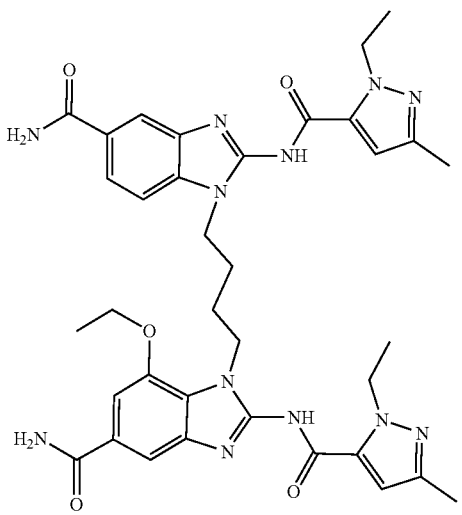 [SMILES: CCOc1cc(C(N)=O)cc2nc(NC(=O)c3cc(C)nn3CC)n(CCCCn3c(NC(=O)c4cc(C)nn4CC)nc4cc(C(N)=O)ccc43)c12]

Example 69 can be prepared according to method 9 with modifications known to one of ordinary skill in the art. The last step of the preparation is provided: To 1-ethyl-3-methyl-1H-pyrazole-5-carboxylic acid (191 mg, 1.24 mmol) in DMF (10 mL) at 25° C. was added DIEA (0.550 mL, 3.15 mmol) and HATU (600 mg, 1.58 mmol). After 30 min, 2-amino-1-(4-(2-amino-5-carbamoyl-1H-benzo[d]imidazol-1-yl)butyl)-7-ethoxy-1H-benzo[d]imidazole-5-carboxamide (270 mg, 0.599 mmol) was added. After 16 hr, water was added, and the resulting precipitate was collected by filtration and washed with MeOH to afford the title compound (28 mg, 0.039 mmol, 6% yield). $^1$H NMR (400 MHz, DMSO-$d_6$) δ ppm 8.00 (s, 2H), 7.94 (s, 1H), 7.74 (d, J=8.4 Hz, 1H), 7.59 (s, 1H), 7.50 (d, J=8.4 Hz, 1H), 7.35 (s, 2H), 7.30 (s, 1H), 6.59 (s, 2H), 4.50-4.64 (m, 4H), 4.31 (d, J=36.9 Hz, 4H), 4.12 (d, J=7.0 Hz, 2H), 2.10 (d, J=71.7 Hz, 6H), 1.86 (s, 4H), 1.29 (dd, J=7.7, 6.6 Hz, 6H), 1.24 (d, 77.0 Hz, 3H); LCMS (LCMS Method A): Rt=1.426 min, [M+H]$^+$=723.2

Example 70

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methyl-1H-benzo[d]imidazole-5-carboxamide

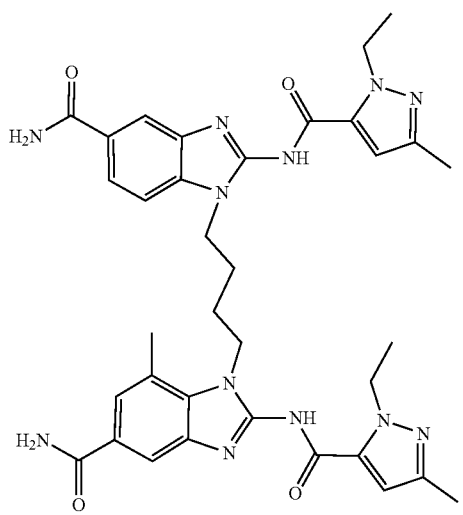 [SMILES: CCn1nc(C)cc1C(=O)Nc1nc2cc(C(N)=O)ccc2n1CCCCn1c(NC(=O)c2cc(C)nn2CC)nc2cc(C(N)=O)cc(C)c21]

Example 70 can be prepared according to method 9 with modifications known to one of ordinary skill in the art. The last step of the preparation is provided: To 1-ethyl-3-methyl-1H-pyrazole-5-carboxylic acid (331 mg, 2.15 mmol) in NMP (10 mL) at RT was added DIEA (0.900 mL, 5.15 mmol) and HATU (979 mg, 2.58 mmol). After 30 min, 2-amino-1-(4-(2-amino-5-carbamoyl-1H-benzo[d]imidazol-1-yl)butyl)-7-methyl-1H-benzo[d]imidazole-5-carboxamide dihydrobromide (500 mg, 0.859 mmol) was added, and the reaction was heated to 60° C. overnight. Water was added, and the resulting precipitate was collected by filtration and purified by prep HPLC to afford the title compound (45 mg, 0.065 mmol, 7.6% yield) as a white solid. $^1$H NMR (400 MHz, DMSO-$d_6$) δ ppm 12.85 (s, 2H), 7.98 (s, 2H), 7.91 (s, 1H), 7.85 (s, 1H), 7.77 (d, J=8.4 Hz, 1H), 7.54-7.64 (m, 2H), 7.32 (d, J=9.9 Hz, 2H), 6.60 (d, J=15.5 Hz, 2H), 4.56 (dd, J=10.8, 7.1 Hz, 4H), 4.39 (s, 2H), 4.29 (s, 2H), 2.62 (s, 3H), 2.09 (d, J=13.4 Hz, 6H), 1.89 (d, J=22.1 Hz, 4H), 1.30 (q, J=7.3 Hz, 6H); LCMS (LCMS Method A): Rt=1.341 min, [M+H]$^+$=693.3

Example 71

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-(morpholinomethyl)-1H-benzo[d]imidazole-5-carboxamide

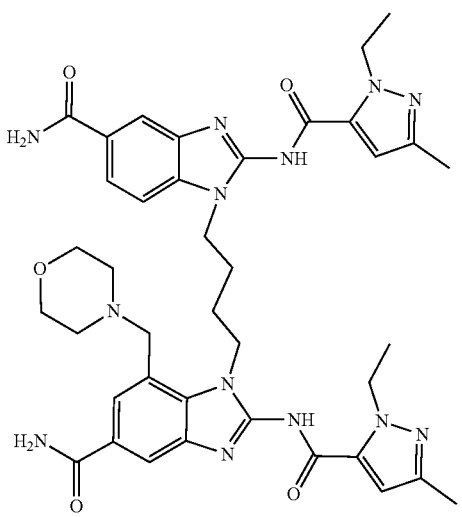 [SMILES: CCn1nc(C)cc1C(=O)Nc1nc2cc(C(N)=O)ccc2n1CCCCn1c(NC(=O)c2cc(C)nn2CC)nc2cc(C(N)=O)cc(CN3CCOCC3)c21]

Example 71 can be prepared according to method 9 with modifications known to one of ordinary skill in the art. The last step of the preparation is provided: To 1-ethyl-3-methyl-1H-pyrazole-5-carboxylic acid (302 mg, 1.96 mmol) in NMP (3 mL) at RT was added DIEA (0.777 mL, 4.45 mmol) and HATU (846 mg, 2.23 mmol). After 1 hr, 2-amino-1-(4-(2-amino-5-carbamoyl-1H-benzo[d]imidazol-1-yl)butyl)-7-(morpholinomethyl)-1H-benzo[d]-imidazole-5-carboxamide (450 mg, 0.890 mmol) was added, and the reaction was heated to 60° C. overnight. Water was added, and the resulting precipitate was collected by filtration to afford the title compound (70 mg, 0.090 mmol, 10% yield) as a white solid. $^1$H NMR (400 MHz, DMSO-$d_6$) δ ppm 12.99 (br. s., 2H), 9.89 (br. s., 2H), 7.99-8.11 (m, 5H), 7.87 (s, 1H), 7.76 (d, J=8.4 Hz, 1H), 7.51 (d, J=8.4 Hz, 2H), 7.35 (s, 1H), 6.66 (s, 1H), 6.62 (s, 1H), 4.53-4.61 (m, 5H), 4.47 (s, 2H), 4.26 (s, 2H), 3.92 (br. s., 2H), 3.60 (br. s., 2H), 3.36 (br. s., 2H), 2.10 (s, 3H), 2.07 (s, 3H), 1.83 (d, J=22.7 Hz, 4H), 1.23-1.45 (m, 6H); LCMS (LCMS Method A): Rt=1.255 min, [M+H]$^+$=778.3

Example 72

4-(2-(Dimethylamino)acetamido)-8-ethyl-10,18-dimethyl-7,20-dioxo-6,7,8,11,12,13,14,-15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide

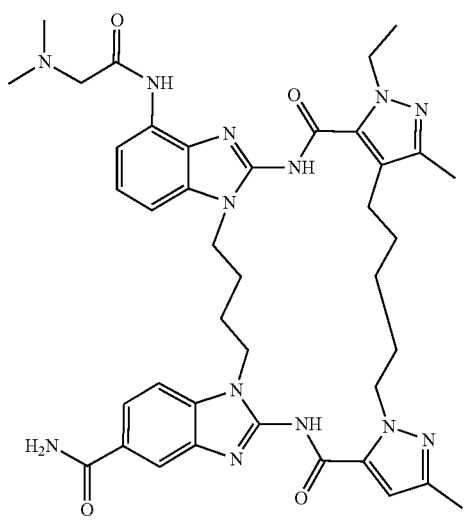

Example 72 can be prepared according to method 13 with modifications known to one of ordinary skill in the art. The last step of the preparation is provided: To 4-amino-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l]-[1,3,6,15,17]pentaazacyclohenicosine-24-carboxamide (200 mg, 0.290 mmol), 2-(dimethylamino)acetic acid (119 mg, 1.158 mmol), HOBt (44.3 mg, 0.290 mmol), DIEA (0.405 mL, 2.32 mmol) and DMAP (17.7 mg, 0.145 mmol) in DMF (5 mL) at 60° C. was added HATU (661 mg, 1.74 mmol) in 10 portions at 30 min intervals. The reaction was cooled to RT, diluted with water, and the resulting solid was collected by filtration, washed with water and air dried. The solid was then purified over silica gel (Combiflash Rf 120 g column, 85 mL/min), eluting with 0-20% MeOH in DCM to afford the title compound (205 mg, 0.251 mmol, 87% yield) as an off white solid. $^1$H NMR (400 MHz, DMSO-$d_6$) δ ppm 12.90 (br. s., 1H), 12.55 (br. s., 1H), 10.37 (br. s., 1H), 8.02 (s, 1H), 7.99 (br. s., 1H), 7.83 (dd, J=8.6, 1.5 Hz, 1H), 7.66 (d, J=8.6 Hz, 1H), 7.58 (d, J=7.8 Hz, 1H), 7.35 (d, J=7.6 Hz, 2H), 7.22-7.29 (m, 1H), 6.57 (s, 1H), 4.69-4.80 (m, 2H), 4.47 (d, J=7.1 Hz, 2H), 4.14-4.34 (m, 4H), 3.25 (s, 2H), 2.81 (br. s., 2H), 2.33 (s, 6H), 2.16 (s, 3H), 2.08 (s, 3H), 1.91 (br. s., 4H), 1.76-1.86 (m, 2H), 1.48 (d, J=5.9 Hz, 2H), 1.38 (d, J=5.1 Hz, 2H), 1.29 (t, J=7.1 Hz, 3H); LCMS (LCMS Method D): Rt=0.82 min, [M+H]$^+$=776.7

Example 73

7-(Aminomethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide

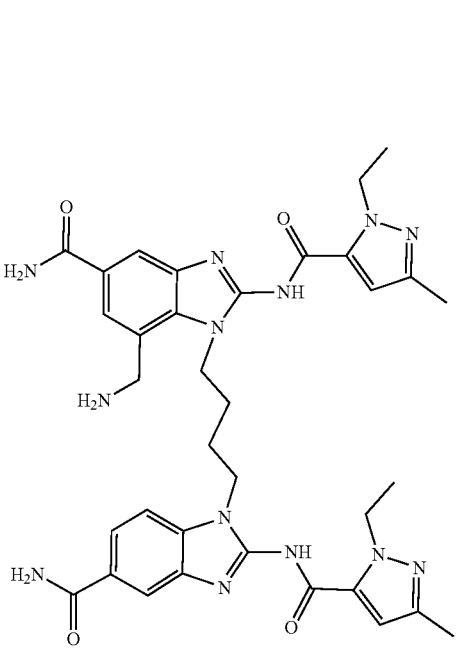 [SMILES: CCn1nc(C)cc1C(=O)Nc1nc2cc(C(N)=O)ccc2n1CCCCn1c(NC(=O)c2cc(C)nn2CC)nc2cc(C(N)=O)cc(CN)c21]

Example 73 can be prepared according to method 9 with modifications known to one of ordinary skill in the art. The last step of the preparation is provided: To tert-butyl ((5-carbamoyl-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazol-7-yl)methyl)carbamate (200 mg, 0.248 mmol) in MeOH (10 mL) at RT was added 12 M HCl (0.5 ml, 16.5 mmol). After stirring overnight, the mixture was concentrated and purified by prep-HPLC to afford the title compound (50 mg, 0.071 mmol, 29% yield) as an off white solid. $^1$H NMR (400 MHz, DMSO-$d_6$) δ ppm 8.21 (s, 1H), 7.89-8.01 (m, 5H), 7.76 (d, J=6.5 Hz, 2H), 7.56 (d, J=8.4 Hz, 1H), 7.33 (s, 2H), 6.59 (d, J=12.7 Hz, 2H), 4.47-4.62 (m, 6H), 4.28 (s, 2H), 4.07 (s, 2H), 2.08 (d, J=10.8 Hz, 6H), 1.89 (d, J=17.6 Hz, 4H), 1.29 (q, J=6.9 Hz, 6H); LCMS (LCMS Method A): Rt=1.176 min, [M+H]$^+$=708.3

Example 74

(E)-1,26-Dibromo-8-ethyl-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

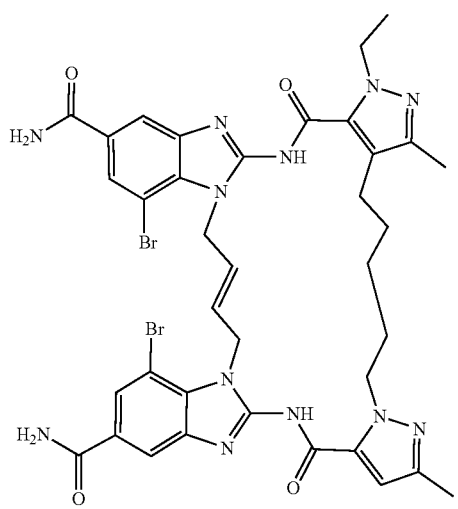 [SMILES: CCn1nc(C)c2c1C(=O)Nc1nc3cc(C(N)=O)cc(Br)c3n1C/C=C/Cn1c(nc3cc(C(N)=O)cc(Br)c31)NC(=O)c1cc(C)nn1CCCCC2]

Example 74 can be prepared according to method 6 with modifications known to one of ordinary skill in the art. The last step of the preparation is provided: To (E)-1,1'-(but-2-ene-1,4-diyl)bis(2-amino-7-bromo-1H-benzo[d]imidazole-5-carboxamide) (500 mg, 0.889 mmol), 4-(5-(5-carboxy-3-methyl-1H-pyrazol-1-yl)pentyl)-1-ethyl-3-methyl-1H-pyrazole-5-carboxylic acid (310 mg, 0.889 mmol) and HATU (1.01 g, 2.67 mmol) in DMF (15 mL) was added DIEA (0.466 mL, 2.67 mmol), and the reaction was heated to 90° C. After 1.5 hr, the mixture was poured into water, and the resulting solid was collected by filtration. The crude material was purified over silica gel, eluting with 5:1 DCM:MeOH with 0.1% aq $NH_3$ to afford the title compound (250 mg, 0.215 mmol, 24% yield) as a brown solid. $^1H$ NMR (400 MHz, DMSO-$d_6$) δ ppm 13.04 (br. s., 2H), 8.02-8.10 (m, 4H), 7.92 (s, 2H), 7.47 (s, 2H), 6.51 (s, 1H), 5.72-5.78 (m, 2H), 5.01-5.25 (m, 4H), 4.52-4.66 (m, 2H), 4.39-4.50 (m, 2H), 2.71-2.76 (m, 2H), 2.17 (s, 3H), 2.10 (s, 3H), 1.62-1.76 (m, 2H), 1.45-1.54 (m, 2H), 1.24-1.40 (m, 5H); LCMS (LCMS Method A): Rt=1.448 min, [M+H]$^+$=873.2

Example 75

Example 75 is Mixture of Two Isomers 28-ethyl-17,26-dimethyl-14,30-dioxo-4,11,13,18,19,27,28,31,33,40-decaazaoctacyclo[42.3.1.0$^{4,12}$.0$^{5,10}$.0$^{15,19}$.0$^{25,29}$.0$^{32,40}$.0$^{34,39}$]octatetraconta-1(48),5,7,9,11,15,17,25(29),26,32,34,36,38,44,46-pentadecaene-8,36-dicarboxamide and 16-ethyl-18,27-dimethyl-14,30-dioxo-4,11,13,16,17,25,26,31,33,40-decaazaoctacyclo[42.3.1.0$^{4,12}$.0$^{5,10}$.0$^{15,19}$.0$^{25,29}$.0$^{32,40}$.0$^{34,39}$]octatetraconta-1(48),5,7,9,11,15(19),17,26,28,32,34,36,38,44,46-pentadecaene-8,36-dicarboxamide

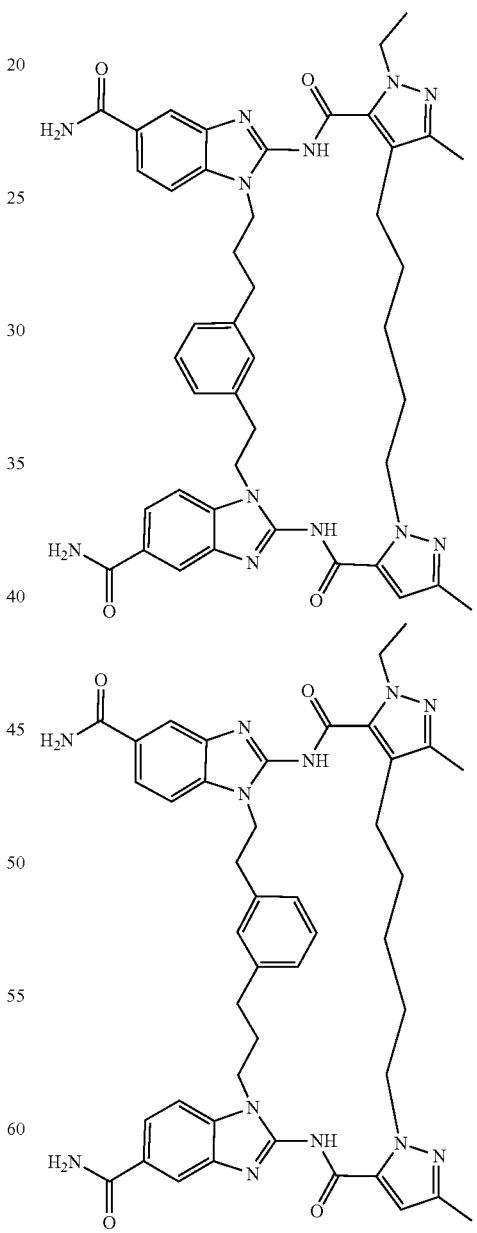

Example 75 can be prepared according to method 19 with modifications known to one of ordinary skill in the art. The last step of the preparation is provided: To 4-(5-(5-carboxy-3-methyl-1H-pyrazol-1-yl)pentyl)-1-ethyl-3-methyl-1H-pyrazole-5-carboxylic acid (140 mg, 0.403 mmol) in NMP (10 mL) at 40° was added HATU (153 mg, 0.403 mmol) and 2-amino-1-(3-(3-(2-(2-amino-5-carbamoyl-1H-benzo[d]imidazol-1-yl)ethyl)phenyl)-propyl)-1H-benzo[d]imidazole-5-carboxamide (200 mg, 0.403 mmol). After stirring overnight, the reaction was purified by prep HPLC to afford the title compounds as a mixture (2 mg, 2 μmol, 0.6% yield). $^1$H NMR (400 MHz, MeOH-d$_4$) δ ppm 7.97 (s, 1H), 7.84-7.91 (m, 2H), 7.73 (d, J=8.4 Hz, 1H), 7.51 (d, J=8.4 Hz, 1H), 7.20 (d, J=8.4 Hz, 1H), 6.93-6.98 (m, 2H), 6.81-6.89 (m, 2H), 6.64 (s, 1H), 4.66-4.72 (m, 2H), 4.49-4.57 (m, 2H), 4.40-4.47 (m, 2H), 4.25-4.31 (m, 2H), 2.96-3.02 (m, 2H), 2.78-2.84 (m, 2H), 2.60-2.66 (m, 2H), 2.28 (s, 3H), 2.18 (s, 3H), 1.83-1.92 (m, 2H), 1.56-1.64 (m, 2H), 1.29-1.39 (m, 7H); LCMS (LCMS Method A): Rt=1.428 min, [M+H]$^+$=809.3

Example 76

4-Amino-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide

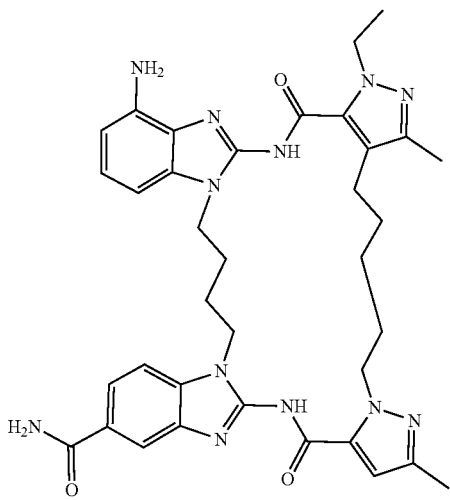 [SMILES: CCn1nc(C)c2c1C(=O)Nc1nc3c(N)cccc3n1CCCCn1c(nc3cc(C(N)=O)ccc31)NC(=O)c1cc(C)nn1CCCCC2]

Example 76 can be prepared according to method 13 with modifications known to one of ordinary skill in the art. The last step of the preparation is provided: To neat tert-butyl (24-carbamoyl-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosin-4-yl)carbamate (2.85 g, 3.60 mmol) was slowly added TFA (10 mL, 130 mmol). After 30 min, the reaction was concentrated. The residue was suspended in water, treated with NaHCO$_3$ until basic, filtered and washed with water. This material was purified over silica gel (120 g column), eluting with 0-20% MeOH in DCM to afford the title compound (2.35 g, 3.23 mmol, 90% yield) as an off white solid. $^1$H NMR (400 MHz, DMSO-d$_6$) δ ppm 12.90 (s, 1H), 12.36 (s, 1H), 8.02 (d, J=1.2 Hz, 1H), 7.99 (br. s., 1H), 7.83 (dd, J=8.4, 1.3 Hz, 1H), 7.64 (d, J=8.3 Hz, 1H), 7.34 (br. s., 1H), 6.91-7.03 (m, 1 H), 6.70 (d, J=7.8 Hz, 1H), 6.57 (s, 1H), 6.48 (d, J=7.8 Hz, 1H), 5.92 (s, 2H), 4.74 (t, J=7.1 Hz, 2H), 4.48 (q, J=7.1 Hz, 2H), 4.26 (br. s., 2H), 4.14 (br. s., 2H), 2.74-2.88 (m, 2H), 2.16 (s, 3H), 2.08 (s, 3H), 1.72-1.96 (m, 6H), 1.48 (d, J=5.4 Hz, 2H), 1.38 (d, J=5.6 Hz, 2H), 1.29 (t, J=7.1 Hz, 3H); LCMS (LCMS Method D): Rt=0.91 min, [M+H]$^+$=691.5

Example 77

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-(2-hydroxyethoxy)-1H-benzo[d]imidazole-5-carboxamide

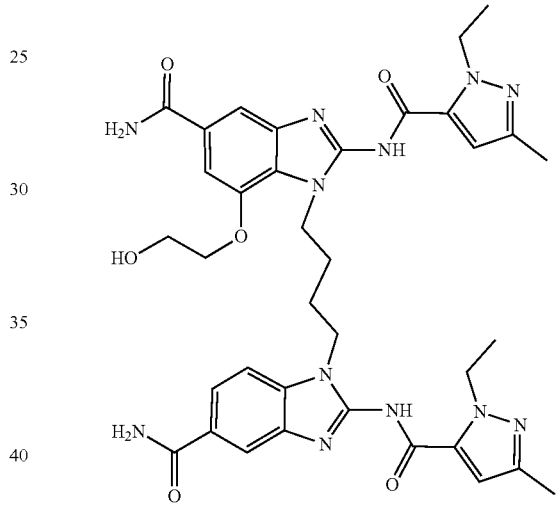

Example 77 can be prepared according to method 4 with modifications known to one of ordinary skill in the art. The last step of the preparation is provided: To a suspension of 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-(2-methoxyethoxy)-1H-benzo[d]imidazole-5-carboxamide (100 mg, 0.133 mmol) in DCM (5 mL) at RT was added, dropwise, BBr$_3$ (0.126 mL, 1.33 mmol). After 2 hr the reaction was quenched with MeOH, concentrated, and the residue was purified by prep HPLC to afford the title compound (15 mg, 0.020 mmol, 15% yield) as a white solid. $^1$H NMR (400 MHz, DMSO-d$_6$) δ ppm 12.81 (br. s., 2H), 7.93-8.01 (m, 3H), 7.75 (d, J=8.8 Hz, 1H), 7.63 (s, 1H), 7.51 (d, J=8.4 Hz, 1H), 7.31-7.38 (m, 3H), 6.59 (d, J=11.6 Hz, 2H), 4.94 (br. s., 1H), 4.54-4.61 (m, 4H), 4.40-4.49 (m, 2H), 4.21-4.32 (m, 2H), 4.12-4.20 (m, 2H), 3.70-3.76 (m, 2H), 2.08 (d, J=5.6 Hz, 6H), 1.77-1.91 (m, 4H), 1.22-1.35 (m, 6H); LCMS (LCMS Method A): Rt=1.290 min, [M+H]$^+$=739.2

Example 78

(E)-2-(1-Ethyl-3-methyl-1H-pyrazole-5-carboxamido)-1-(4-(2-(1-ethyl-3-methyl-1H-pyrazole-5-carboxamido)-7-methoxy-1H-benzo[d]imidazol-1-yl)but-2-en-1-yl)-7-methoxy-1H-benzo[d]imidazole-5-carboxamide Bis Trifluoroacetic Acid Salt

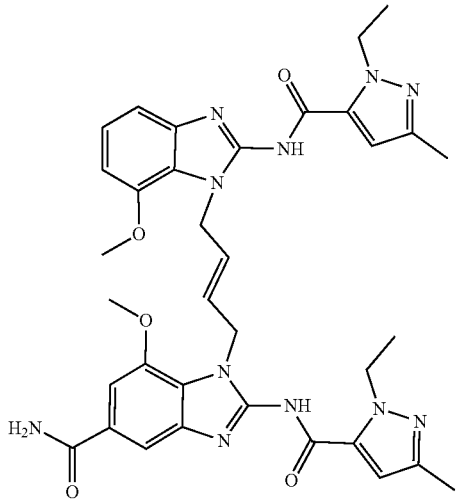 [SMILES: CCn1nc(C)cc1C(=O)Nc1nc2cccc(OC)c2n1C/C=C/Cn1c(NC(=O)c2cc(C)nn2CC)nc2cc(C(N)=O)cc(OC)c21]

Example 78 can be prepared according to method 11 with modifications known to one of ordinary skill in the art. The last step of the preparation is provided: To (E)-2-amino-1-(4-(2-amino-7-methoxy-1H-benzo[d]imidazol-1-yl)but-2-en-1-yl)-7-methoxy-1H-benzo[d]imidazole-5-carboxamide (250 mg, 0.178 mmol), HATU (203 mg, 0.534 mmol), HOBt (40.9 mg, 0.267 mmol) and 1-ethyl-3-methyl-1H-pyrazole-5-carboxylic acid (82 mg, 0.53 mmol) in DMF (3 mL) was added TEA (0.149 mL, 1.07 mmol). After stirring over the weekend, the reaction was passed through a syringe filter and purified via reverse phase HPLC (Gilson, Sunfire Prep C18 OBD 5 μm 30×100 mm column), eluting with 20-90% MeCN in water (0.1% TFA) to afford the title compound (18 mg, 0.020 mmol, 11% yield). $^1$H NMR (400 MHz, MeOH-d$_4$) δ ppm 7.60 (d, J=1.27 Hz, 1H), 7.33 (d, J=1.27 Hz, 1H), 7.26 (s, 1H), 7.13 (d, J=8.11 Hz, 1H), 6.87 (d, J=8.11 Hz, 1H), 6.58 (s, 1H), 6.54-6.57 (m, 1H), 5.85-5.93 (m, 2H), 5.14 (br. s., 2H), 5.06 (d, J=3.80 Hz, 2H), 4.59 (dd, J=13.81, 6.97 Hz, 4H), 3.79 (s, 6H), 2.20 (d, J=1.77 Hz, 6H), 1.36 (td, J=7.16, 2.91 Hz, 6H); LCMS (LCMS Method D): Rt=1.02 min, [M+H]$^+$=694.5

Example 79

8-4-(2-Aminoacetamido)-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide

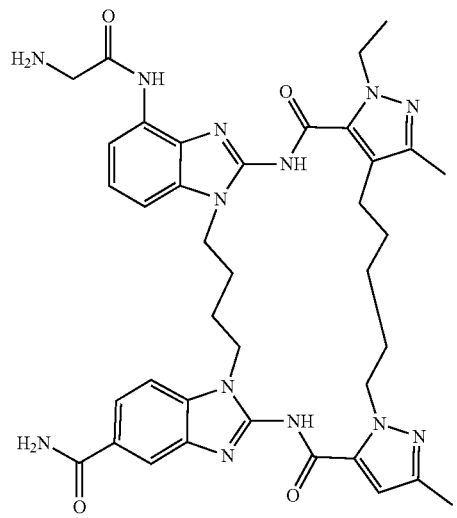 [SMILES: CCn1nc(C)c2c1C(=O)Nc1nc3c(NC(=O)CN)cccc3n1CCCCn1c(nc3cc(C(N)=O)ccc31)NC(=O)c1cc(C)nn1CCCCC2]

Example 79 can be prepared according to method 13 with modifications known to one of ordinary skill in the art. The last step of the preparation is provided: To tert-butyl (2-((24-carbamoyl-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosin-4-yl)amino)-2-oxoethyl)carbamate (350 mg, 0.413 mmol) was slowly added TFA (3.00 mL, 38.9 mmol). After 30 min the reaction was concentrated. The resulting residue was suspended in water and treated with NaHCO$_3$ until basic. The solid was collected by filtration and washed with water. This material was purified over silica gel (80 g column), eluting with 0-20% (2N NH$_3$ in MeOH) in DCM to afford the title compound (270 mg, 0.343 mmol, 83% yield) as an off white solid. $^1$H NMR (400 MHz, DMSO-d$_6$) δ ppm 8.03 (d, J=1.2 Hz, 1H), 7.99 (br. s., 1H), 7.83 (dd, J=8.3, 1.5 Hz, 1H), 7.58-7.69 (m, 2H), 7.34 (d, J=7.3 Hz, 2H), 7.20-7.31 (m, 1H), 6.57 (s, 1H), 4.74 (t, J=7.1 Hz, 2H), 4.47 (q, J=7.1 Hz, 2H), 4.14-4.34 (m, 4H), 3.54 (s, 2H), 2.76-2.85 (m, 2H), 2.16 (s, 3H), 2.09 (s, 3H), 1.91 (br. s., 4H), 1.82 (d, J=6.6 Hz, 2H), 1.48 (d, J=5.6 Hz, 2H), 1.38 (d, J=4.9 Hz, 2H), 1.29 (t, J=7.1 Hz, 3H); LCMS (LCMS Method D): Rt=0.78 min, [M+H]$^+$=748.6

Example 80

8-Ethyl-10,17-dimethyl-7,19-dioxo-7,8,11,12,13,14,19,20,27,28,29,30-dodecahydro-6H-benzo[4,5]imidazo[1,2-a]benzo[4,5]imidazo[2,1-o]dipyrazolo[5,1-e:4',3'-k][1,3,6,14,16]pentaazacycloicosine-3,23-dicarboxamide

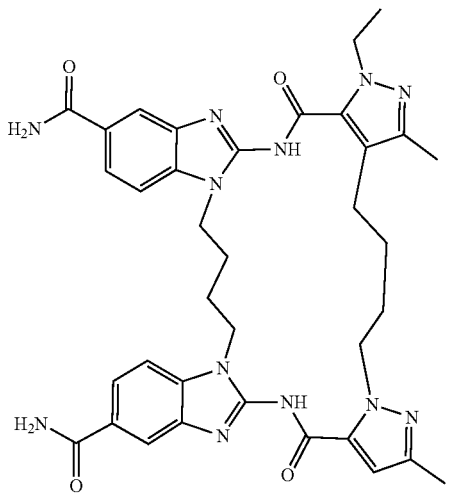 [SMILES: CCn1nc(C)c2c1C(=O)Nc1nc3cc(C(N)=O)ccc3n1CCCCn1c(nc3cc(C(N)=O)ccc31)NC(=O)c1cc(C)nn1CCCC2]

Example 80 can be prepared according to method 19 with modifications known to one of ordinary skill in the art. The last step of the preparation is provided: A mixture of 4-(4-(5-carboxy-3-methyl-1H-pyrazol-1-yl)butyl)-1-ethyl-3-methyl-1H-pyrazole-5-carboxylic acid (165 mg, 0.492 mmol), 1,1'-(butane-1,4-diyl)bis(2-amino-1H-benzo[d]imidazole-5-carboxamide) (200 mg, 0.492 mmol), HATU (561 mg, 1.48 mmol) and DIEA (382 mg, 2.95 mmol) in NMP (8 mL) was stirred at 120° C. for 18 hr. The mixture was concentrated, and the residue was purified over silica gel, eluting with 80:20:1 DCM:MeOH:NH$_4$OH(aq). The partially pure product was further purified prep-HPLC to afford the title compound (7 mg, 10 μmol, 2% yield). $^1$H NMR (400 MHz, DMSO-d$_6$) δ ppm 12.83 (br. s., 2H), 7.90-8.01 (m, 4H), 7.79 (t, J=6 Hz, 2H), 7.52-7.62 (m, 2H), 7.35 (br. s., 2H), 6.56 (s, 1H), 4.80 (br. s., 2H), 4.46-4.54 (m, 2H), 4.25 (br. s., 4H), 2.90-3.01 (m, 2H), 2.17 (s, 3H), 2.08 (s, 3H), 1.78-1.89 (br. m., 6H), 1.53-1.57 (m, 2H), 1.30 (t, J=6 Hz, 3H); LCMS (LCMS Method A): Rt=1.316 min, [M+H]$^+$=704.7

Example 81

8-Ethyl-10,18-dimethyl-7,20-dioxo-6,7,8,11,14,15,20,21,28,29,30,31-dodecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide

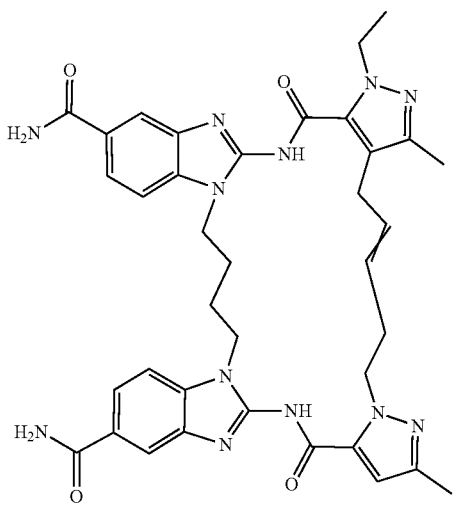 [SMILES: CCn1nc(C)c2c1C(=O)Nc1nc3cc(C(N)=O)ccc3n1CCCCn1c(nc3cc(C(N)=O)ccc31)NC(=O)c1cc(C)nn1CCC=CC2]

Example 81 can be prepared according to method 19 with modifications known to one of ordinary skill in the art. The last step of the preparation is provided: To 4-(5-(5-carboxy-3-methyl-1H-pyrazol-1-yl)pent-2-en-1-yl)-1-ethyl-3-methyl-1H-pyrazole-5-carboxylic acid (320 mg, 0.924 mmol), 1,1'-(butane-1,4-diyl)bis(2-amino-1H-benzo[d]imidazole-5-carboxamide) (488 mg, 1.20 mmol) and DIEA (0.484 mL, 2.77 mmol) in NMP (10 mL) was added HATU (878 mg, 2.31 mmol). The reaction was stirred at 80° C. for 16 hr, then poured into Et$_2$O (50 mL). The resulting precipitate was collected by filtration and washed with Et$_2$O and water. The crude product was purified by preparative HPLC (Gemini-C18 column, 5μ silica, 21 mm diameter, 150 mm length), eluting with 20-40% MeCN in water (containing 0.1% TFA) to afford the title compound (11 mg, 15 μmol, 1.7% yield) as a white solid. $^1$H NMR (400 MHz, MeOH-d$_4$) δ ppm 8.00 (s, 1H), 7.93 (s, 1H), 7.81 (t, J=9.7 Hz, 2H), 7.56-7.40 (m, 2H), 6.66 (s, 1H), 5.77 (d, J=15.2 Hz, 1H), 5.42 (d, J=15.5 Hz, 1H), 4.78-4.85 (m, 1H), 4.68-4.52 (m, 2H), 4.37-4.22 (m, 4H), 3.62 (d, J=5.8 Hz, 2H), 2.82-2.49 (m, 2H), 2.23 (s, 3H), 2.13 (s, 3H), 2.09-1.93 (m, 5H), 1.41 (t, J=8.0 Hz, 3H); LCMS (LCMS Method A): Rt=1.376 min, [M+H]$^+$=716.9

Example 82

35-ethyl-5,37-dimethyl-8,33-dioxo-3,4,9,11,18,23, 30,32,35,36-decaazaoctacyclo[38.1.1.0$^{3,7}$0.0$^{10,18}$0.0$^{12,17}$0.0$^{23,31}$0.0$^{24,29}$0.0$^{34,38}$]dotetraconta-4,6, 10,12,14,16,24,26,28,30,34(38), 36-dodecaene-14, 27-dicarboxamide

Example 83

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxylic Acid

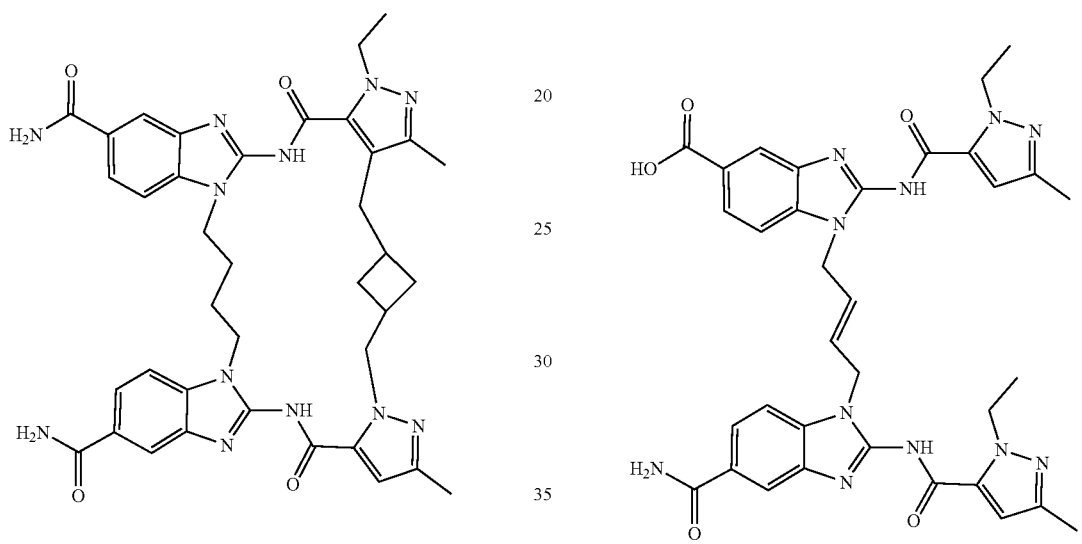

Example 82 can be prepared according to method 19 with modifications known to one of ordinary skill in the art. The last step of the preparation is provided: To 4-((3-((5-carboxy-3-methyl-1H-pyrazol-1-yl)methyl)cyclobutyl)methyl)-1-ethyl-3-methyl-1H-pyrazole-5-carboxylic acid (175 mg, 0.486 mmol), 1,1'-(butane-1,4-diyl)bis(2-amino-1H-benzo[d]imidazole-5-carboxamide) (220 mg, 0.541 mmol), and HATU (559 mg, 1.47 mmol) in NMP (2 mL) at RT was slowly added DIEA (0.514 mL, 2.94 mmol). The mixture was heated to 70° C. for 4 hr and poured into water. The crude product was collected by filtration, and the filtrate was concentrated to yield a second batch of crude product, which was washed with water. The combined crude product was purified by prep-HPLC (Gemini-C18 column, 5μ silica, 21 mm diameter, 150 mm length), eluting with 30-60% MeCN in water (containing 0.1% TFA) to afford the title compound as a white solid. $^1$H NMR (400 MHz, MeOH-d$_4$) δ ppm 12.87 (s, 2H), 8.02 (t, J=9.0 Hz, 4H), 7.83 (dd, J=19.9, 8.4 Hz, 2H), 7.65 (dd, J=23.0, 8.2 Hz, 2H), 7.37 (d, J=2.1 Hz, 2H), 6.52 (s, 1H), 4.64 (d, J=5.3 Hz, 2H), 4.44 (m, 2H), 4.28 (s, 4H), 2.91 (d, J=7.3 Hz, 2H), 2.47 (m, 2H), 2.14 (s, 3H), 2.08 (s, 3H), 1.96 (s, 6H), 1.53 (m, 2H), 1.28 (t, J=7.1 Hz, 3H); LCMS (LCMS Method A): Rt=1.351 min, [M+H]$^+$=731.3

Example 83 can be prepared according to method 11 with modifications known to one of ordinary skill in the art. The last step of the preparation is provided: To (E)-methyl 1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxylate (1.26 g, 1.82 mmol) in MeOH (10 mL), DMF (10 mL) and water (10 mL) at RT was added NaOH (0.729 g, 18.2 mmol). After 3 hr, another portion of NaOH (0.729 g, 18.2 mmol) was added, and the reaction was stirred overnight. The mixture was concentrated, and the residue diluted with water (100 mL) and acidified with 3N HCl to pH=3. The resulting precipitate was collected by filtration to afford the title compound (1.06 g, 1.56 mmol, 86% yield) as a yellow-white solid. $^1$H NMR (400 MHz, DMSO-d$_6$) δ ppm 12.80-12.87 (m, 2H), 7.93-7.98 (m, 3H), 7.85 (d, J=8.3 Hz, 1H), 7.71 (d, J=8.2 Hz, 1H), 7.55 (d, J=8.3 Hz, 1H), 7.43 (d, J=8.4 Hz, 1H), 7.33 (s, 1H), 6.54 (d, J=6.6 Hz, 2H), 5.90-5.98 (m, 2H), 4.86 (d, J=20.0 Hz, 4H), 4.52 (d, J=6.7 Hz, 4H), 2.12 (s, 6H), 1.27 (d, J=6.8, 4.6 Hz, 6H); LCMS (LCMS Method A): Rt=1.376 min, [M+H]$^+$=677.9

Example 84

23-(Aminomethyl)-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3-carboxamide

Example 85

(E)-2-(1-Ethyl-3-methyl-1H-pyrazole-5-carboxamido)-1-(4-(2-(1-ethyl-3-methyl-1H-pyrazole-5-carboxamido)-4-methyl-1H-benzo[d]imidazol-1-yl)but-2-en-1-yl)-1H-benzo[d]imidazole-5-carboxamide

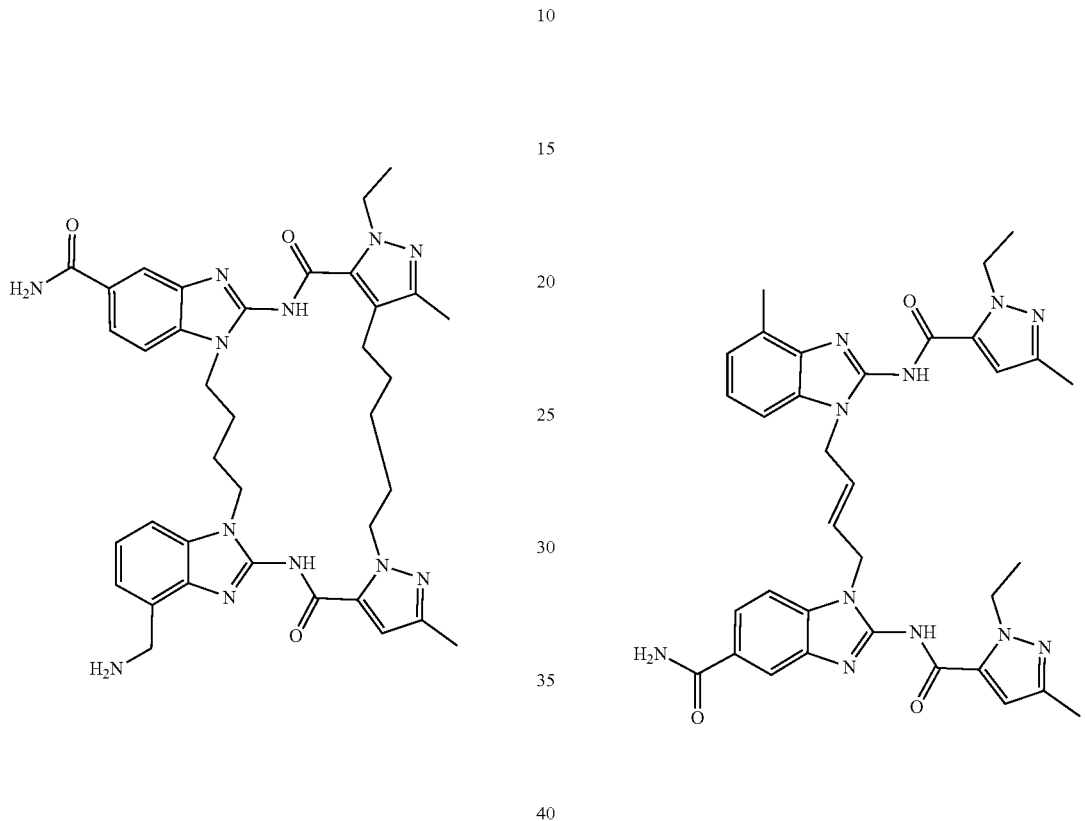

Example 84 can be prepared according to method 13 with modifications known to one of ordinary skill in the art. The last step of the preparation is provided: To tert-butyl ((3-carbamoyl-8-ethyl-10,18-dimethyl-7,20-dioxo-6,7,8,11,12,13,14,15,20,21,-28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosin-23-yl)methyl)carbamate (410 mg, 0.509 mmol) was slowly added TFA (3 mL, 38.9 mmol). After 30 min the reaction was concentrated. The resulting residue was suspended in water and treated with NaHCO$_3$ until basic. The solid was collected by filtration and washed with water. This material was purified over silica gel (80 g column), eluting with 0-20% (2N NH$_3$ in MeOH) in DCM to afford the title compound (340 mg, 0.458 mmol, 90% yield) as an off white solid. $^1$H NMR (400 MHz, DMSO-d$_6$) δ ppm 8.02 (d, J=1.2 Hz, 1H), 7.98 (br. s., 1H), 7.82 (dd, J=8.3, 1.5 Hz, 1H), 7.60 (d, J=8.3 Hz, 1H), 7.48 (d, J=8.1 Hz, 1H), 7.34 (br. s., 1H), 7.24 (t, J=7.8 Hz, 1H), 7.14 (d, J=7.6 Hz, 1H), 6.55 (s, 1H), 4.74 (t, J=7.1 Hz, 2H), 4.47 (q, J=7.0 Hz, 2H), 4.18-4.32 (m, 4H), 4.12 (s, 2H), 2.77-2.88 (m, 2H), 2.15 (s, 3H), 2.05-2.11 (m, 3H), 1.91 (br. s., 4H), 1.77-1.86 (m, 2H), 1.43-1.56 (m, 2H), 1.38 (m, 2H), 1.30 (t, J=7.1 Hz, 3H); LCMS (LCMS Method D): Rt=0.77 min, [M+H]$^+$=705.6

Example 85 can be prepared according to method 11 with modifications known to one of ordinary skill in the art. The last step of the preparation is provided: To 1-ethyl-3-methyl-1H-pyrazole-5-carboxylic acid (208 mg, 1.35 mmol) in NMP (8 mL) was added HATU (616 mg, 1.62 mmol) and DIEA (0.57 mL, 3.2 mmol). After 30 min, (E)-2-amino-1-(4-(2-amino-4-methyl-1H-benzo[d]imidazol-1-yl)but-2-en-1-yl)-1H-benzo[d]imidazole-5-carboxamide dihydrobromide (290 mg, 0.540 mmol) was added, and the reaction was heated to 60° C. After stirring overnight, water was added, and the mixture was extracted with EtOAc. The organic layer was concentrated and purified by prep-HPLC to afford the title compound (45 mg, 0.069 mmol, 13% yield) as an off white solid. $^1$H NMR (400 MHz, DMSO-d$_6$) δ ppm 12.79 (br. s., 1H), 12.19 (br. s., 1H), 7.97 (s, 1H), 7.96 (s, 1H), 7.72-7.75 (m, 1H), 7.44-7.47 (m, 1H), 7.37 (s, 1H), 7.24-7.27 (m, 1H), 7.00-7.12 (m, 2H), 6.56 (s, 2H), 5.78-5.89 (m, 2H), 4.75-4.85 (m, 4H), 4.49-4.56 (m, 4H), 2.48-2.52 (m, 3H), 2.13 (s, 6H), 1.21-1.29 (m, 6H); LCMS (LCMS Method A): Rt=1.507 min, [M+H]$^+$=648.2

Example 86

(E)-2-(1-Ethyl-3-methyl-1H-pyrazole-5-carbox-amido)-1-(4-(2-(1-ethyl-3-methyl-1H-pyrazole-5-carboxamido)-7-methoxy-1H-benzo[d]imidazol-1-yl)but-2-en-1-yl)-1H-benzo[d]imidazole-5-carboxamide

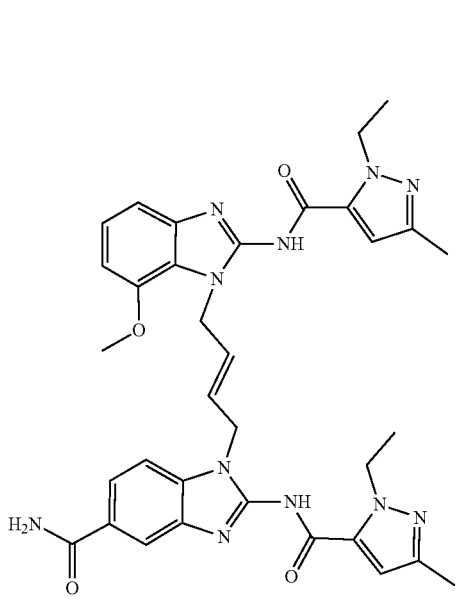 [SMILES: CCn1nc(C)cc1C(=O)Nc1nc2cc(C(N)=O)ccc2n1C/C=C/Cn1c(NC(=O)c2cc(C)nn2CC)nc2cccc(OC)c21]

Example 86 can be prepared according to method 11 with modifications known to one of ordinary skill in the art. The last step of the preparation is provided: To 1-ethyl-3-methyl-1H-pyrazole-5-carboxylic acid (295 mg, 1.92 mmol) in NMP (8 mL) at RT was added HATU (874 mg, 2.30 mmol) and DIPEA (0.803 mL, 4.60 mmol). After 30 min (E)-2-amino-1-(4-(2-amino-7-methoxy-1H-benzo[d]imidazol-1-yl)but-2-en-1-yl)-1H-benzo[d]imidazole-5-carboxamide (300 mg, 0.766 mmol) was added, and the reaction was heated to 60° C. overnight. Water was added, and the resulting solid was collected by filtration and purified by prep-HPLC to afford the title compound (78 mg, 0.12 mmol, 15% yield). $^1$H NMR (400 MHz, DMSO-$d_6$) δ ppm 12.75 (s, 2H), 7.95 (d, J=12.1 Hz, 2H), 7.70 (d, J=8.4 Hz, 1H), 7.40 (d, J=8.4 Hz, 1H), 7.33 (s, 1H), 7.17-7.09 (m, 2H), 6.80 (dd, J=6.8, 2.4 Hz, 1H), 6.53 (d, J=17.1 Hz, 2H), 5.92-5.96 (m, 1H), 5.71-5.75 (m, 1H), 4.91 (d, J=4.9 Hz, 2H), 4.81 (d, J=5.4 Hz, 2H), 4.52 (q, J=7.1 Hz, 4H), 3.69 (s, 3H), 2.11 (d, J=4.0 Hz, 6H), 1.26 (td, J=7.1, 2.0 Hz, 6H); LCMS (LCMS Method A): Rt=1.494 min, [M+H]$^+$=664.2

Example 87

4-((Dimethylamino)methyl)-8-ethyl-10,18-dimethyl-7,20-dioxo-6,7,8,11,12,13,14,-15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide

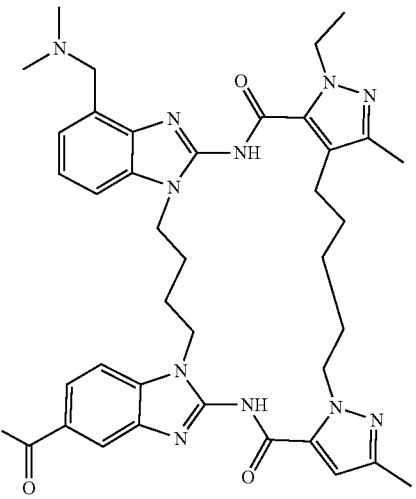

Example 87 can be prepared according to method 13 with modifications known to one of ordinary skill in the art. The last step of the preparation is provided: A mixture of 4-(aminomethyl)-8-ethyl-10,18-dimethyl-7,20-dioxo-6,7,8,11,12,13,14,-15,20,21,28,29,30,31-tetradecahydrobenzo[4,5]imidazo[1,2-a]benzo[4,5]imidazo-[2,1-p]dipyrazolo[5,1-e:4',3'-l][1,3,6,15,17]pentaazacyclohenicosine-24-carboxamide (100 mg, 0.142 mmol) and formaldehyde (37% in water) (0.106 mL, 1.42 mmol) in acetic acid (5 mL) was stirred at RT for 20 min and then cooled to 0° C. Sodium triacetoxyborohydride (301 mg, 1.42 mmol) was added, the reaction was stirred at 0° C. for 1 hr and then at RT overnight. The solvent was removed, and the residue was suspended in water and treated with NaHCO$_3$ until basic. The mixture was extracted with EtOAc (3×), and the combined organic layers were washed with brine (2×), dried over Na$_2$SO$_4$, filtered and concentrated. The residue was purified over silica gel (40 g column), eluting with 0-20% MeOH in DCM to afford the title compound (30 mg, 0.039 mmol, 27% yield) as an off white solid. $^1$H NMR (400 MHz, DMSO-$d_6$) δ ppm 12.89 (br. s., 1H), 12.24 (br. s., 1H), 7.96-8.09 (m, 2H), 7.84 (dd, J=8.44, 1.59 Hz, 1H), 7.65 (d, J=8.31 Hz, 1H), 7.51 (d, J=7.82 Hz, 1H), 7.35 (br. s., 1H), 7.26 (t, J=7.83 Hz, 1H), 7.14 (d, J=7.58 Hz, 1H), 6.58 (s, 1H), 4.74 (t, J=7.09 Hz, 2H), 4.47 (q, J=7.01 Hz, 2H), 4.13-4.34 (m, 4H), 3.73 (s, 2H), 2.74-2.88 (m, 2H), 2.23 (s, 6H), 2.16 (s, 3H), 2.09 (s, 3H), 1.92 (br. s., 4H), 1.81 (m, 4H), 1.49 (m, 2H), 1.39 (m, 2H), 1.29 (t, J=7.09 Hz, 3H); LCMS (LCMS Method D): Rt=0.80 min, [M+H]$^+$=733.6

Example 88 tert-Butyl((3-carbamoyl-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosin-23-yl)methyl)carbamate

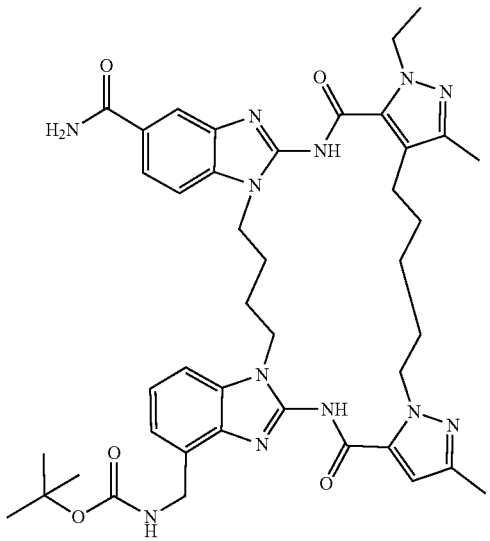 [SMILES: CCn1nc(C)c2c1C(=O)Nc1nc3cc(C(N)=O)ccc3n1CCCCn1c(nc3c(CNC(=O)OC(C)(C)C)cccc31)NC(=O)c1cc(C)nn1CCCCC2]

Example 88 can be prepared according to method 13 with modifications known to one of ordinary skill in the art. The last step of the preparation is provided: To 4-(5-(5-((1-(4-(2-amino-5-carbamoyl-1H-benzo[d]imidazol-1-yl)butyl)-4-(((tert-butoxycarbonyl)amino)methyl)-1H-benzo[d]imidazol-2-yl)carbamoyl)-3-methyl-1H-pyrazol-1-yl)pentyl)-1-ethyl-3-methyl-1H-pyrazole-5-carboxylic acid (1.50 g, 1.82 mmol), HOBt (0.335 g, 2.19 mmol) and EDC (0.524 g, 2.73 mmol) in DMF (100 mL) was added DIEA (1.27 mL, 7.29 mmol) and DMAP (22 mg, 0.18 mmol). The reaction was heated to 60° C. After 6 hr, the mixture was cooled to RT, diluted with water and extracted with EtOAc (3×). The combined organics were washed with saturated $NH_4Cl$ (2×) and brine (2×), dried over $Na_2SO_4$, filtered and concentrated. This residue was purified over silica gel (120 g column), eluting with 0-20% MeOH in DCM to afford the title compound (860 mg, 1.0 mmol, 56% yield) as an off white solid. $^1$H NMR (400 MHz, DMSO-$d_6$) δ ppm 12.85 (s, 1H), 12.41 (s, 1H), 8.02 (d, J=1.5 Hz, 1H), 7.98 (br. s., 1H), 7.82 (dd, J=8.6, 1.5 Hz, 1H), 7.60 (d, J=8.6 Hz, 1H), 7.57 (br. s., 1H), 7.54 (d, J=8.1 Hz, 1H), 7.34 (br. s., 1H), 7.27 (t, J=7.8 Hz, 1H), 7.15 (d, J=7.6 Hz, 1H), 6.55 (s, 1H), 4.74 (t, J=7.1 Hz, 2H), 4.48 (q, J=7.1 Hz, 2H), 4.37 (d, J=5.9 Hz, 2H), 4.25 (m, 4H), 2.75-2.87 (m, 2H), 2.15 (s, 3H), 2.08 (s, 3H), 1.91 (br. s., 4H), 1.75-1.86 (m, 2H), 1.49 (br. s., 2H), 1.39 (m, 11H), 1.30 (t, J=7.1 Hz, 3H); LCMS (LCMS Method D): Rt=1.11 min, [M+H]$^+$=805.7

Table 1 provides Example 89 to Example 197. The compounds can be prepared by using synthetic methods described above.

| Example | Structure/Name | Synthetic Method | NMR | LCMS |
|---|---|---|---|---|
| Example 89 | 1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-7-(3-hydroxypropoxy)-1H-benzo[d]imidazole-5-carboxamide | Method 9 | $^1$H NMR (400 MHz, Methanol-d4) δ 7.58 (s, 1H), 7.48 (d, J = 8.4 Hz, 1H), 7.33 (s, 1H), 7.17 (d, J = 8.4 Hz, 1H), 6.89 (s, 1H), 6.58 (s, 2H), 5.11-4.99 (m, 1H), 4.93 (s, 1H), 4.61 (m, 5H), 4.46-4.36 (m, 1H), 4.31 (dd, J = 13.4, 3.2 Hz, 1H), 4.19 (dd, J = 14.0, 3.4 Hz, 1H), 4.03 (dd, J = 15.1, 6.4 Hz, 1H), 3.88 (dd, J = 14.9, 6.4 Hz, 1H), 3.83-3.72 (m, 1H), 2.23 (s, 3H), 2.18 (s, 3H), 2.05 (dd, J = 11.5, 5.9 Hz, 2H), 1.64 (d, J = 10.3 Hz, 6H), 1.50-1.28 (m, 6H) | LCMS Method A: Rt = 1.338 min, [M + H]$^+$ = 824.8 |

Table 1 provides Example 89 to Example 197. The compounds can be prepared by using synthetic methods described above.

| Example | Structure/Name | Synthetic Method | NMR | LCMS |
|---|---|---|---|---|
| Example 90 | 1-(4-(4-((dimethylamino)methyl)-2-(1-ethyl-3-methyl-1H-pyrazole-5-carboxamido)-1Hbenzo[d]imidazol-1-yl)butyl)-2-(1-ethyl-3-methyl-1H-pyrazole-5-carboxamido)-1Hbenzo[d]imidazole-5-carboxamide, trifluoroacetic acid salt | Method 11 | $^1$H NMR (400 MHz, DMSO-$d_6$) δ ppm 12.86 (s, 2H), 9.55 (s, 1H), 7.99 (s, 2H), 7.78 (s, 1H), 7.65 (dd, J = 6.7, 2.2 Hz, 1H), 7.55 (d, J = 8.4 Hz, 1H), 7.33 (t, J = 7.9 Hz, 3H), 6.61 (d, J = 9.9 Hz, 2H), 4.68 (d, J = 4.9 Hz, 2H), 4.56 (dd, J = 13.9, 6.8 Hz, 4H), 4.28 (s, 4H), 2.77 (d, J = 4.5 Hz, 6H), 2.11 (s, 6H), 1.87 (s, 4H), 1.30 (t, J = 7.0 Hz, 6H) | LCMS Method A: Rt = 1.275 min, [M + H]$^+$ = 693.3 |
| Example 91 | (E)-1,1'-(but-2-ene-1,4-diyl)bis(2-(1-ethyl-3-methyl-1H-pyrazole-5-carboxamido)-7-(3-methoxypropoxy)-1H-benzo[d]imidazole-5-carboxamide) | Method 2 | $^1$H NMR (400 MHz, Methanol-d4) δ ppm 7.52-7.65 (m, 2H), 7.23-7.37 (m, 2 H), 6.55-6.69 (m, 2H), 5.78-5.93 (m, 2H), 5.03-5.10 (m, 4 H), 4.49-4.70 (m, 4H), 3.98-4.10 (m, 4H), 3.36-3.46 (m, 6 H), 2.24 (s, 6H), 1.71-1.90 (m, 4 H), 1.35-1.47 (m, 6H). | LCMS Method F: Rt = 0.87 min, [M + H]$^+$ = 853.7 |
| Example 92 | 1,1'-(cyclopentane-1,3-diyl)bis(2-(1-ethyl-3-methyl-1H-pyrazole-5-carboxamido)-7-(3-hydroxypropoxy)-1H-benzo[d]imidazole-5-carboxamide) | 15 | $^1$H NMR (400 MHz, Methanol-$d_4$) δ ppm 7.59-7.78 (m, 2H), 7.46-7.55 (m, 2 H), 6.57-6.72 | LCMS Method F: Rt = 0.80 min, [M + H]$^+$ = 839.7 |

Table 1 provides Example 89 to Example 197. The compounds can be prepared by using synthetic methods described above.

| Example | Structure/Name | Synthetic Method | NMR | LCMS |
|---|---|---|---|---|
| | | | (m, 2H), 5.78-6.04 (m, 2H), 4.48-4.71 (m, 4 H), 4.32-4.45 (m, 4H), 3.74-3.89 (m, 4H), 2.92-3.02 (m, 2 H), 2.29-2.44 (m, 2H), 2.15-2.26 (m, 4H), 2.09 (s, 6H), 1.32 (m, 6H), 0.84-0.99 (m, 2 H) | |
| Example 93 | ethyl (E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate | Method 10 | $^1$H NMR (400 MHz, DMSO-d$_6$) δ ppm 12.66-13.00 (m, 2H), 7.89-8.05 (m, 2 H), 7.88 (s, 1H), 7.71 (d, J = 8.11 Hz, 1H), 7.53 (s, 1H), 7.42 (d, J = 8.36 Hz, 1H), 7.34 (d, J = 9.38 Hz, 2H), 6.53 (d, J = 3.55 Hz, 2H), 5.95-6.07 (m, 1 H), 5.49-5.65 (m, 1H), 4.96-5.08 (m, 2H), 4.79-4.88 (m, 2 H), 4.37-4.63 (m, 4H), 3.97 (q, J = 7.10 Hz, 2H), 3.03-3.15 (m, 2 H), 2.63 (t, J = 7.73 Hz, 3H), 2.12 (d, J = 6.08 Hz, 6H), 1.28 (d, J = 3.80 Hz, 6H), 1.09 (t, J = 7.10 Hz, 3H) | LCMS Method F: Rt = 0.86 min, [M + H]$^+$ = 777.5 |
| Example 94 | methyl (E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)butanoate | Method 10 | $^1$H NMR (400 MHz, DMSO-d$_6$) δ ppm 12.71-12.97 (m, 2H), 7.98 (d, J = 1.27 Hz, 2H), 7.91-7.96 (m, 1H), 7.67-7.76 (m, 1 H), 7.59-7.66 | LCMS Method K: Rt = 0.85 min, [M + H]$^+$ = 793.5 |

Table 1 provides Example 89 to Example 197. The compounds can be prepared by using synthetic methods described above.

| Example | Structure/Name | Synthetic Method | NMR | LCMS |
|---|---|---|---|---|
| | | | (m, 1H), 7.42 (d, J = 7.60 Hz, 1H), 7.33-7.39 (m, 2 H), 7.28-7.32 (m, 1H), 6.47-6.58 (m, 2H), 5.92-6.05 (m, 1 H), 5.67-5.80 (m, 1H), 4.91-4.99 (m, 2H), 4.78-4.87 (m, 2 H), 4.46-4.58 (m, 4H), 4.03 (s, 2H), 3.55 (s, 3 H), 2.29-2.39 (m, 2H), 2.12 (d, J = 3.80 Hz, 6H), 1.71-1.93 (m, 2 H), 1.22-1.32 (m, 6H) | |
| Example 95 | (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxy-2-methylpropoxy)-2,3-dihydro-1H-benzo[d]imidazole-5-carboxamide | Method 14 | $^1$H NMR (400 MHz, DMSO-d$_6$) δ ppm 12.62-12.93 (m, 1H), 7.91-8.05 (m, 3 H), 7.71 (d, J = 8.11 Hz, 1H), 7.58-7.68 (m, 1 H), 7.41 (d, J = 7.86 Hz, 1H), 7.28-7.37 (m, 3 H), 6.47-6.55 (m, 2H), 5.93-6.08 (m, 1H), 5.70-5.84 (m, 1 H), 4.90-5.00 (m, 2H), 4.77-4.87 (m, 2H), 4.62 (t, J = 5.80 Hz, 1H), 4.45-4.58 (m, 4H), 3.99-4.08 (m, 2 H), 3.84-3.93 (m, 1H), 2.11 (s, 6H), 1.87 (m, 1H), 1.27 (d, J = 6.84 Hz, 6H), 0.80-0.89 (m, 3 H) | LCMS Method K: Rt = 0.81 min, [M + H]$^+$ = 765.5 |
| Example 96 | (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3- | Method 14 | $^1$H NMR (400 MHz, DMSO-d$_6$) δ 12.64-13.10 (m, 2H), 7.97-8.13 (m, 1H), 7.86-7.97 (m, 1H), | LCMS Method K: Rt = 0.85 min, [M + H]$^+$ = 779.5 |

Table 1 provides Example 89 to Example 197. The compounds can be prepared by using synthetic methods described above.

| Example | Structure/Name | Synthetic Method | NMR | LCMS |
|---|---|---|---|---|
| | hydroxy-3-methylbutoxy)-1H-benzo[d]imidazole-5-carboxamide | | 7.66-7.76 (m, 1 H), 7.58-7.66 (m, 1H), 7.37-7.47 (m, 1H), 7.21-7.37 (m, 3 H), 6.53 (s, 2H), 5.87-6.09 (m, 1 H), 5.60-5.87 (m, 1H), 4.98 (d, J = 4.82 Hz, 2H), 4.81 (d, J = 4.80 Hz, 2H), 4.44-4.67 (m, 5H), 4.40 (s, 1H), 3.98-4.19 (m, 2 H), 2.11 (s, 6H), 1.70 (t, J = 7.10 Hz, 2H), 1.28 (m, 6H), 1.07 (s, 6H) | |
| Example 97 | (E)-1-(4-(5-carbamoyl-2-(1-ethyl-3-methyl-1H-pyrazole-5-carboxamido)-7-(3-methoxypropoxy)-1H-benzo[d]imidazol-1-yl)but-2-en-1-yl)-2-(1-ethyl-3-methyl-1H-pyrazole-5-carboxamido)-7-isobutyl-1H-benzo[d]imidazole-5-carboxamide, trifluoroacetic acid salt | Method 9 | $^1$H NMR (400 MHz, DMSO-d$_6$) δ ppm 12.91 (br, 1H), 7.89-8.16 (m, 4H) 7.64 (s, 1H) 7.47 (br. s., 1H) 7.25-7.40 (m, 2H) 6.47-6.60 (m, 2H) 5.82 (d, J = 15.72 Hz, 1H) 5.54 (d, J = 15.72 Hz, 1 H), 4.91 (br. s., 4 H) 4.41-4.65 (m, 4H) 4.03 (t, J = 6.46 Hz, 2H) 3.29 (t, J = 6.08 Hz, 2H) 3.14 (s, 3H), 2.55(br, 2H), 2.11 (d, J = 12.17 Hz, 6H) 1.69-1.84 (m, 2 H), 1.36(m, 1H), 1.27 (q, J = 7.10 Hz, 6H), 0.69 (s, J = 6.3 Hz, 6H) | LCMS Method F: Rt = 2.33 min, [M + H]$^+$ = 822.1 |
| Example 98 | (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1Hpyrazole-5-carboxamido)-7-(methoxymethyl)-1H-benzo[d]imidazole-5-carboxamide | Method 9 | $^1$H NMR (400 MHz, DMSO) δ 12.98 (s, 1H), 7.98 (m, 4H), 7.77-7.65 (m, 2H), 7.44 (d, J = 8.4 Hz, 2H), 7.35 (s, 2H), 6.53 (d, J = 6.8 Hz, 2H), | LCMS Method A: Rt = 1.30 min, [M + H]$^+$ = 721.4 |

| Example | Structure/Name | Synthetic Method | NMR | LCMS |
|---|---|---|---|---|
| | | | 5.95 (d, J = 15.8 Hz, 1H), 5.52 (d, J = 15.8 Hz, 1H), 4.95 (s, 2H), 4.81 (s, 2H), 4.52 (d, J = 7.0 Hz, 6H), 3.15 (s, 3H), 2.11 (s, 6H), 1.26 (td, J = 7.1, 3.7 Hz, 6H) | |
| Example 99 | (E)-2-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)acetic acid | Method 9 | $^1$H NMR (400 MHz, DMSO) δ 12.87 (s, 3H), 8.02-7.87 (m, 4H), 7.71 (d, J = 8.4 Hz, 1H), 7.57 (s, 1H), 7.41 (d, J = 8.4 Hz, 1H), 7.32 (s, 2H), 6.52 (d, J = 14.4 Hz, 2H), 5.95 (d, J 15.0 Hz, 1H), 5.48 (d, J = 15.5 Hz, 1H), 4.97 (s, 2H), 4.79 (s, 2H), 4.59-4.46 (m, 4H), 3.71 (s, 2H), 2.08 (t, J = 12.1 Hz, 6H), 1.25 (td, J = 7.1, 2.6 Hz, 6H) | Method A: Rt = 1.30 min, [M + H]$^+$ = 735.4 |
| Example 100 | 1-(4-(5-carbamoyl-2-(1-ethyl-3-methyl-1H-pyrazole-5-carboxamido)-1H-benzo[d]imidazol-1-yl)-2,3-dimethylbutyl)-2-(1-ethyl-3-methyl-1H-pyrazole-5-carboxamido)-7-(3-hydroxypropoxy)-1H-benzo[d]imidazole-5-carboxamide | Method 16 | $^1$H NMR (400 MHz, DMSO-d$_6$) D$_2$O) δ ppm 7.76 (d, J = 9.6 Hz, 1H), 7.55-7.47 (m, 2H), 7.14 (s, 1H), 7.03 (d, J = 9.7 Hz, 2H), 6.62 (s, 1H), 6.56 (s, 1H), 4.62-4.50 | LCMS Method A: Rt = 1.335 & 1.362 min, [M + H]$^+$ = 780.7 |

Table 1 provides Example 89 to Example 197. The compounds can be prepared by using synthetic methods described above.

| Example | Structure/Name | Synthetic Method | NMR | LCMS |
|---|---|---|---|---|
| | 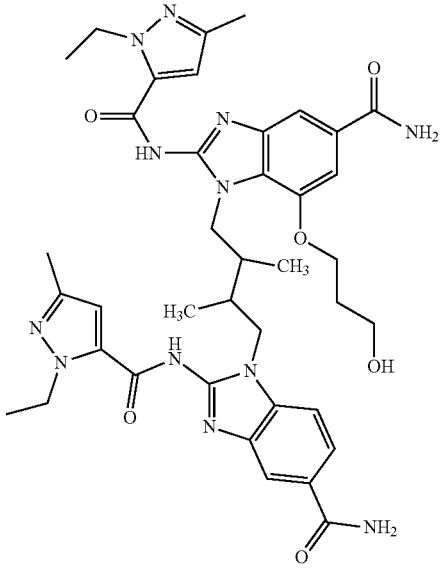 [SMILES: CCn1nc(C)cc1C(=O)Nc1nc2cc(C(N)=O)ccc2n1CC(C)C(C)Cn1c(NC(=O)c2cc(C)nn2CC)nc2cc(C(N)=O)cc(OCCCO)c21] | | (m, 4H), 4.35-4.17 (m, 3H), 4.05-3.97 (m, 1H), 3.78-3.70 (m, 2H), 3.38-3.32 (m, 2H), 2.68 (s, 1H), 2.34 (s, 1H), 2.16 (s, 3H), 2.14 (s, 3H), 2.08-1.96 (m, 2H), 1.66-1.48 (m, 2H), 1.38-1.28 (m, 4H), 1.22 (s, 2H), 1.04 (d, J = 6.7 Hz, 3H), 0.97 (d, J = 6.7 Hz, 3H), 0.91-0.80 (m, 2H) (NMR analysis is based on the major peaks from the major diastereomer) | |
| Example 101 | (E)-7-(2-aminoethyl)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide, Formic acid salt | Similar to Method 15 | $^1$H NMR (400 MHz, DMSO-$d_6$) δ ppm 8.41 (br s, 3H), 8.00 (br d, J = 14.1 Hz, 3H), 7.90 (s, 1H), 7.73 (d, J = 7.5 Hz, 2H), 7.56 (s, 1H), 7.41-7.34 (m, 3H), 6.53 (br s, 2H), 5.98 (d, J = 16.4 Hz, 1H), 5.56 (s, 1H), 4.99 (br s, 2H), 4.81 (br s, 2H), 4.51 (d, J = 5.7 Hz, 4H), 3.03 (br s,4H), 2.11 (s, 6H), 2.05 (br t, 2H), 1.32-1.13 (m, 6H) | LCMS Method A: Rt = 1.168 min, [M + H]$^+$ = 719.9 |
| Example 102 | 8-ethyl-10,18-dimethyl-7,20-dioxo-7,8,11,12,13,-14,15,20,21,28,29,30,31,32-tetradecahydro-6H-benzo[4,5]imidazo[2,1-b]benzo[4,5]imidazo[1,2-i]dipyrazolo[5,1-m:4',3'-t][1,3,6,9,11,14]hexaazacyclocosine-3-carboxamide | Method 13 | $^1$H NMR (400 MHz, Methanol-d4) δ ppm 8.02 (d, J = 1.2 Hz, 1H), 7.97-7.93 (m, 1H), 7.68 (d, J = 8.5 Hz, 1H), 7.56 (td, J = 6.6, 3.4 Hz, 2H), 7.42- | LCMS Method A: Rt = 1.274 min, [M + H]$^+$ = 691.3 |

Table 1 provides Example 89 to Example 197. The compounds can be prepared by using synthetic methods described above.

| Example | Structure/Name | Synthetic Method | NMR | LCMS |
|---|---|---|---|---|
| | | | 7.34 (m, 2H), 6.84 (s, 1H), 4.73 (t, J = 5.8 Hz, 4H), 4.52 (q, J = 7.1 Hz, 2H), 4.34 (t, J = 6.9 Hz, 2H), 3.76 (t, J = 6.7 Hz, 2H), 3.68-3.63 (m, 2H), 2.84-2.78 (m, 2H), 2.24 (s, 3H), 2.18 (s, 3H), 1.89-1.82 (m, 2H), 1.42 (dd, J = 13.9, 6.4 Hz, 2H), 1.34 (t, 7.1 Hz, 3H), 1.27-1.19 (m, 2H) | |
| Example 103 | 8-ethyl-10,18-dimethyl-7,20-dioxo-7,8,11,12,13,-14,15,20,21,28,29,30,31,32-tetradecahydro-6H-benzo[4,5]imidazo[2,1-b]benzo[4,5]imidazo[1,2-i]dipyrazolo[5,1-m:4',3'-t][1,3,6,9,11,14]hexaazacyclodocosine-24-carboxamide | Method 13 | $^1$H NMR (400 MHz, Methanol-d4) 8.08-8.06 (m, 1H), 7.94-7.90 (m, 1H), 7.63-7.59 (m, 2H), 7.55-7.51 (m, 1H), 7.42-7.34 (m, 2H), 6.85-6.82 (m, 1H), 4.75-4.69 (m, 4H), 4.53-4.46 (m, 3H), 4.36-4.30 (m, 2H), 3.82-3.77 (m, 2H), 3.69-3.65 (m, 2H), 2.83-2.76 (m, 2H), 2.25-2.21 (m, 3H), 2.19-2.17 (m, 3H), 1.87 (s, 2H), 1.46-1.41 (m, 2H), 1.33-1.32 (m, 3H), 1.25-1.19 (m, 2H) | LCMS Method A: Rt = 1.297 min, [M + H]$^+$ = 691.3 |
| Example 104 | 8-ethyl-10,18,30-trimethyl-7,20-dioxo-7,8,11,12,13,-14,15,20,21,28,29,30,31,32-tetradecahydro-6H-benzo[4,5]imidazo[2,1-b]benzo[4,5]imidazo[1,2-i]dipyrazolo[5,1-m:4',3'-t][1,3,6,9,11,14]hexaazacyclodocosine-3-carboxamide | Method 19 | $^1$H NMR (400 MHz, Methanol-d4) δ 8.00 (s, 1H), 7.93 (d, 7 8.4 Hz, 1H), 7.56 (dd, J = 15.9, 7.1 Hz, 3H), 7.39-7.35 (m, 2H), 6.75 (s, 1H), 4.78 | LCMS Method A: Rt = 1.32 min, [M + H]$^+$ = 705.3 |

| Example | Structure/Name | Synthetic Method | NMR | LCMS |
|---|---|---|---|---|
| | | | (s, 2H), 4.68 (s, 2H), 4.53 (dd, J = 14.3, 7.2 Hz, 4H), 4.00 (s, 2H), 3.78 (s, 2H), 3.15 (s, 3H), 2.83 (s, 3H), 2.35 (d, 7 7.8 Hz, 2H), 2.17 (s, 6H), 1.77 (s, 2H), 1.36 (dd, 7 15.7, 8.6 Hz, 6H), 1.14 (s, 2H) | |
| Example 105 | 35-ethyl-5,37-dimethyl-8,33-dioxo-3,4,9,11,18,23,-30,32,35,36-Decaaza-octacyclo[38.3.1.0$^{37}$,.0$^{10}$,1$^8$.0$^{12}$, 1$^7$.0$^{23}$,$^{31}$.0$^{24}$,$^{29}$.0$^{34}$,3$^8$] tetratetraconta-1(44),4,6,10,-12(17),13,15,24(29),25,27,30,34 (38),36,40,42-pentadecaene-14,27-dicarboxamide | Method 19 | $^1$H NMR (400 MHz, DMSO-d$_6$) δ ppm 12.86 (br. s., 2H) 8.00-8.01 (m, 4H) 7.77-7.81 (m, 2H) 7.52-7.58 (m, 2H) 7.36 (s, 2H) 7.14 (t, J = 8.0 Hz, 2H) 6.98-7.00 (m, 1H) 6.61-6.65 (m, 2H) 5.99 (s, 2H) 4.56 (q, J = 6.7 Hz, 2H) 4.28 (s, 2H) 3.85-3.96 (m, 4H) 2.15 (s, 3H) 1.93 (m, 3H) 1.40-1.56 (m, 4H) 1.35 (t, J = 6.0 Hz, 3H) | LCMS Method A: Rt = 1.386 min, [M + H]$^+$ = 753.2 |
| Example 106 | 1,1'-((2R,3R)-2,3-diethoxybutane-1,4-diyl)bis(2-(1-ethyl-3-methyl-1H-pyrazole-5-carboxamido)-1H-benzo[d]imidazole-5-carboxamide) | Method 15 | $^1$H NMR (400 MHz, DMSO-d$_6$) δ ppm 12.93 (br. s., 2H) 8.02 (s, 4H) 7.81 (dd, J = 8.0.1.2 Hz, 2H) | LCMS Method A: Rt = 1.372 min, [M + H]$^+$ = |

Table 1 provides Example 89 to Example 197. The compounds can be prepared by using synthetic methods described above.

| Example | Structure/Name | Synthetic Method | NMR | LCMS |
|---|---|---|---|---|
| | | | 7.56 (d, J = 8.4 Hz, 2H) 7.35 (s, 2H) 6.68 (s, 2H) 4.55-4.69 (m, 6H) 4.43-4.48 (m, 2H) 4.05-4.07 (m, 2H) 3.49-3.57 (m, 2H) 3.13-3.20 (m, 2H) 2.11 (s, 6H) 1.36 (t, J = 7.2 Hz, 6H) 0.77 (t, J = 7.0 Hz, 6H) | 766.8 |
| Example 107 | 1,1'-(butane-1,4-diyl)bis(2-(1-ethyl-3-methyl-1H-pyrazole-5-carboxamido)-1H-benzo[d]imidazole-5-carboxamide), 2Trifluoroacetic acid salt | Method 2 | $^1$H NMR (400 MHz, DMSO-d$_6$) δ ppm 12.85 (br. s., 2H) 7.99 (s, 4 H) 7.77 (d, J = 8.34 Hz, 2H) 7.56 (d, J = 8.34 Hz, 2H) 7.36 (br. s., 2H) 6.61 (s, 2 H) 4.51-4.69 (m, 4H) 4.28 (br. s., 4H) 2.04-2.21 (m, 6H) 1.88 (br. s., 4H) 1.31 (t, J = 7.07 Hz, 6H) | LCMS Method C: Rt = 0.76 min., [M + H]$^+$ = 679.6 |
| Example 108 | 1-(4-(5-carbamoyl-2-(1,3-dimethyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, 2Trifluoroacetic acid salt | Method 20 | $^1$H NMR (400 MHz, DMSO-d$_6$) δ ppm 12.82 (br. s., 2H) 7.98 (s, 4 H) 7.76 (dd, J = 8.31, 1.47 Hz, 2H) 7.55 (d, J = 8.31 Hz, 2H) 7.35 (br. s., 2H) | LCMS Method D: Rt = 0.77 min., [M + H]$^+$ = 665.6 |

Table 1 provides Example 89 to Example 197. The compounds can be prepared by using synthetic methods described above.

| Example | Structure/Name | Synthetic Method | NMR | LCMS |
|---|---|---|---|---|
| | | | 6.60 (s, 2H) 4.57 (q, J = 7.01 Hz, 2H) 4.28 (d, J = 5.87 Hz, 4H) 4.09 (s, 3H) 2.10 (d, J = 4.65 Hz, 6H) 1.87 (br. s., 4H) 1.30 (t, J = 7.09 Hz, 3H) | |
| Example 109 | 1-(4-(5-carbamoyl-2-(1-ethyl-3-methyl-1H-pyrazole-5-carboxamido)-1H-benzo[d]imidazol-1-yl)butyl)-2-(3-cyclopropyl-1-methyl-1H-pyrazole-5-carboxamido)-1H-benzo[d]imidazole-5-carboxamide, 2Trifluoroacetic acid salt | Method 20 | $^1$H NMR (400 MHz, DMSO-$d_6$) δ ppm 12.84 (br. s., 2H) 7.99 (s, 4H) 7.76 (dd, J = 8.56, 1.47 Hz, 2H) 7.54 (d, J = 8.31 Hz, 2H) 7.35 (br. s., 2H) 6.66 (s, 1H) 6.60 (s, 1H) 4.57 (q, J = 7.01 Hz, 2H) 4.26-4.39 (m, 4H) 4.09 (s, 3H) 2.09 (s, 3H) 1.70-1.90 (m, 5H) 1.31 (t, J = 7.09 Hz, 3H) 0.72-0.83 (m, 2H) 0.46-0.57 (m, 2H) | LCMS Method D: Rt = 0.84 min., [M + H]$^+$ = 691.6 |
| Example 110 | (11Z,29E)-8-ethyl-1,26-bis(3-hydroxypropoxy)-10,18-dimethyl-7,20-dioxo-6,7,8,13,14,15,20,21,28,31-decahydrobenzo[4,5]imidazo[1,2-a]benzo[4,5]imidazo[2,1-p]dipyrazolo[5,1-e:4',3'l][1,3,6,15,17]pentaazacyclohenicosine-3,24-dicarboxamide, 2Hydrochloride | Method 19 | $^1$H NMR (400 MHz, METHANOL) δ ppm 7.71 (dd, J = 5.32, 1.01 Hz, 2H), 7.44 (dd, J = 8.74, 1.14 Hz, 2H), 6.82 (s, 1H), 6.46 (d, J = 11.15 Hz, 1 | LCMS Method L: Rt = 0.75 min, [M + H]$^+$ = 863.7 |

Table 1 provides Example 89 to Example 197. The compounds can be prepared by using synthetic methods described above.

| Example | Structure/Name | Synthetic Method | NMR | LCMS |
|---|---|---|---|---|
| | 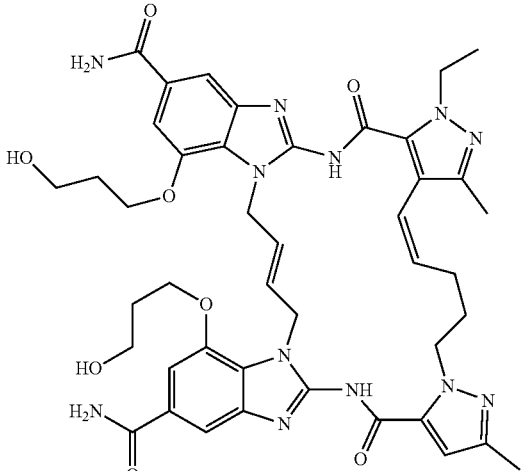 | | H), 5.84-5.96 (m, 1H), 5.58 (s, 2H), 5.09 (br. s., 4H), 4.62-4.75 (m, 2H), 4.07-4.23 (m, 4H), 3.72-3.79 (m, 4 H), 3.53-3.58 (m, 2H), 2.33 (s, 3H), 2.26 (s, 3 H), 1.93-2.11 (m, 4H), 1.54-1.71 (m, 4H), 1.49 (t, J = 7.10 Hz, 3H); | |
| Example 111 | (E)-1,1'-(but-2-ene-1,4-diyl)bis(2-(1-ethyl-4-fluoro-3-methyl-1H-pyrazole-5-carboxamido)-7-(3-hydroxypropoxy)-1H-benzo[d]imidazole-5-carboxamide), | Method 2 | $^1$H NMR (400 MHz, DMSO-$d_6$) δ ppm 12,90 (s, 2H), 7.99 (br. s., 2H), 7.64 (d, J = 1.27 Hz, 2H), 7.29-7.38 (m, 4 H), 5.87 (br. s., 2 H), 4.91 (br. s., 4 H), 4.40-4.62 (m, 6H), 4.04 (t, J = 6.08 Hz, 4H), 3.43 (d, J = 5.07 Hz, 4H), 2.10 (s, 6H), 1.67 (t, J = 6.08 Hz, 4H), 1.24 (t, J = 7.10 Hz, 6H); | LCMS Method D: Rt = 0.89 min [M + H]$^+$ /2 = 431.5 |
| Example 112 | 2-(1-ethyl-3-methyl-1H-pyrazole-5-carboxamido)-1-(4-(2-(1-ethyl-3-methyl-1H-pyrazole-5-carboxamido)-4-(morpholinomethyl)-1H-benzo[d]imidazol-1-yl)butyl)-1H-benzo[d]imidazole-5-carboxamide | Method 16 | $^1$H NMR (400 MHz, DMSO-$d_6$) δ ppm 12.80 (s, 1H), 12.57 (s, 1H), 7.98 (s, 2H), 7.77 (d, J = 8.2 Hz, 1H), 7.54 (d, J = 8.4 Hz, 1H), | LCMS Method A: Rt = 1.275 min, [M + H]$^+$ = 735.3 |

Table 1 provides Example 89 to Example 197. The compounds can be prepared by using synthetic methods described above.

| Example | Structure/Name | Synthetic Method | NMR | LCMS |
|---|---|---|---|---|
| | | | 7.30-7.48 (m, 2H), 7.14 (d, J = 27.8 Hz, 2H), 6.59 (s, 2H), 4.48-4.67 (m, 4H), 4.27 (s, 4H), 3.81 (s, 2H), 3.70 (s, 4H), 2.42 (s, 4H), 2.11 (s, 6H), 1.88 (s, 4H), 1.30 (td, J = 7.0, 3.4 Hz, 6H) | |
| Example 113 | tert-butyl ((1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1Hpyrazole-5-carboxamido)-1H-benzo[d]imidazol-4-yl)methyl)(methyl)carbamate | Method 16 | $^1$H NMR (400 MHz, DMSO-d$_6$) δ ppm 12.81 (s, 2H), 7.99 (t, J = 5.1 Hz, 2H), 7.78 (d, J = 8.4 Hz, 1H), 7.55 (d, J = 8.4 Hz, 2H), 7.48 (d, J = 8.2 Hz, 1H), 7.34 (s, 1H), 7.21 (d, J = 7.7 Hz, 2H), 6.60 (d, J = 12.2 Hz, 2H), 4.48-4.77 (m, 6H), 4.27 (d, J = 5.9 Hz, 4H), 2.72 (s, 3H), 2.09 (t, J = 4.3 Hz, 6H), 1.87 (s, 4H), 1.44 (s, 9H), 1.28 (td, J = 7.0, 2.4 Hz, 6H) | LCMS Method A: Rt = 1.646 min, [M + H]$^+$ = 779.3 |
| Example 114 | 2-(1-ethyl-3-methyl-1H-pyrazole-5-carboxamido)-1-(4-(2-(1-ethyl-3-methyl-1H-pyrazole-5-carboxamido)-4-isopropyl-1H-benzo[d]imidazol-1-yl)butyl)-1H-benzo[d]imidazole-5-carboxamide | Method 16 | $^1$H NMR (400 MHz, DMSO-d$_6$) δ ppm 12.83 (s, 1H), 12.21 (s, 1H), 7.98 (d,J = 8.2 Hz, 2H), 7.77 (d, J = 8.3 Hz, 1H), 7.55 (d, J = | LCMS Method A: Rt = 1.601 min, [M + H]$^+$ = 678.5 |

-continued

Table 1 provides Example 89 to Example 197. The compounds can be prepared by using synthetic methods described above.

| Example | Structure/Name | Synthetic Method | NMR | LCMS |
|---|---|---|---|---|
| | | | 8.4 Hz, 1H), 7.30-7.41 (m, 2H), 7.07-7.28 (m, 2H), 6.60 (d, J = 10.0 Hz, 2H), 4.57 (d, J = 6.8 Hz, 4H), 4.28 (s, 4H), 3.40-3.54 (m, 1H), 2.11 (s, 6H), 1.87 (s, 4H), 1.05-1.47 (m, 12H) | |
| Example 115 | 1,1'-((2R,3R)-2,3-dimethoxybutane-1,4-diyl)bis(2-(1-ethyl-3-methyl-1H-pyrazole-5-carboxamido)-1H-benzo[d]imidazole-5-carboxamide) | Method 15 | $^1$H NMR (400 MHz, DMSO-$d_6$) δ (ppm) 12.99 (br. s. 2H) 8.01 (s, 4 H), 7.81 (d, J = 8.56 Hz, 2H), 7.55 (d, J = 8.80 Hz, 2H), 7.36 (br. s., 2H), 6.64 (s, 2H), 4.53-4.70 (m, 6H), 4.46 (dd, J = 14.06, 8.68 Hz, 2H), 4.04 (br. s., 2H), 3.21 (s, 6 H), 2.11 (s, 6H), 1.35 (t, J = 7.09 Hz, 6H). | LCMS Method A: Rt = 1.29 min, [M + H]$^+$ = 739.8 |
| Example 116 | (E)-1-(4-(6-carbamoyl-2-(1,3-diethyl-1H-pyrazole-5-carboxamido)-1H-benzo[d]imidazol-1-yl)but-2-en-1-yl)-2-(1,3-diethyl-1H-pyrazole-5-carboxamido)-7-(3-hydroxypropoxy)-1H-benzo[d]imidazole-5-carboxamide | Method 16 | $^1$H NMR (400 MHz, DMSO-$d_6$) δ ppm 12.56-13.10 (m, 1H), 7.99 (s, 2H), 7.94 (br. s., 1H), 7.71 (d, J = 8.56 Hz, 1H), 7.64 (s, 1H), 7.41 (d, J = | Method A: Rt = 1.339 min, [M + H]$^+$ = 779.8 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 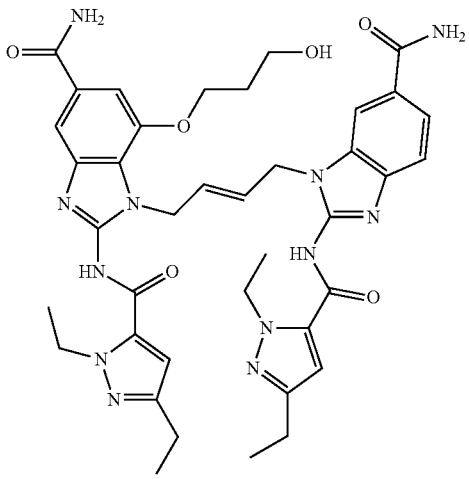 [SMILES: CCc1cc(C(=O)Nc2nc3ccc(C(N)=O)cc3n2C/C=C/Cn2c(NC(=O)c3cc(CC)nn3CC)nc3cc(C(N)=O)cc(OCCCO)c32)n(CC)n1] | | 8.31 Hz, 1H), 7.34 (br. s., 3H), 6.57 (d, J = 13.20 Hz, 2H), 5.98 (s, 1H), 5.71-5.82 (m, 1H), 4.95 (d, J = 4.65 Hz, 2H), 4.84 (d, J = 4.89 Hz, 2H), 4.49-4.62 (m, 5H), 4.11 (t, J = 6.36 Hz, 2H), 3.48 (q, J = 5.71 Hz, 2H), 2.43-2.49 (m, 2H), 1.75 (t, 7 6.24 Hz, 2H), 1.28 (t, J = 7.09 Hz, 6H), 1.13 (td, J = 7.64, 3.06 Hz, 6H) | |
| Example 117 | 2-(1-Ethyl-3-methyl-1Hpyrazole-5-carboxamido)-1-(4-(2-(1-ethyl-3-methyl-1Hpyrazole-5-carboxamido)-7-methoxy-1Hbenzo[d]imidazol-1-yl)butyl)-1H-benzo[d]imidazole-5-carboxamide | Method 16 | $^1$H NMR (400 MHz, DMSO-d$_6$) δ ppm 12.82 (s, 2H), 7.98 (t, J = 4.5 Hz, 2H), 7.73 -7.81 (m, 1H), 7.54 (d, J = 8.5 Hz, 1H), 7.33 (s, 1H), 7.11-7.18 (m, 2H), 6.86 (dd, J = 6.0, 3.2 Hz, 1H), 6.59 (d, J = 14.3 Hz, 2H), 4.57 (dt, J = 13.6, 6.8 Hz, 4H), 4.38 (s, 2H), 4.28 (s, 2H), 3.81 (s, 3H), 2.11 (d, J = 5.9 Hz, 6H), 1.85 (s, 4H), 1.30 (q, J = 7.0 Hz, 6H) | Method A: Rt = 1.468 min, [M + H]$^+$ = 666.3 |
| Example 118 | 2-(1-Ethyl-3-methyl-1H-pyrazole-5-carboxamido)-1-(4-(2-(1-ethyl-3-methyl-1H-pyrazole-5-carboxamido)-4-((methylamino)methyl)-1Hbenzo[d]imidazol-1yl)butyl)-1Hbenzo[d]imidazole-5-carboxamide | Method 16 | $^1$H NMR(400 MHz, DMSO-d$_6$) δ ppm 12.84 (s, 2H), 8.67 (s, 2H), 7.98 (d, J = 1.2 Hz, 2H), 7.77 (dd, J = 8.4,1.4 Hz, 1H), 7.60 (d, | Method A: Rt = 1.259 min, [M + H]$^+$ = 679.3 |

Table 1 provides Example 89 to Example 197. The compounds can be prepared by using synthetic methods described above.

| Example | Structure/Name | Synthetic Method | NMR | LCMS |
|---|---|---|---|---|
| | 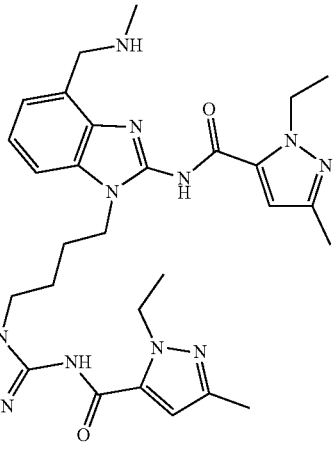 | | J = 6.6 Hz, 1H), 7.54 (d, J = 8.4 Hz, 1H), 7.31 (dt, J = 15.2, 6.7 Hz, 3H), 6.62 (d, J = 2.8 Hz, 2H), 4.54 (ddd, J = 30.5, 10.8, 6.4 Hz, 6H), 4.28 (s, 4H), 2.62 (t, J = 5.3 Hz, 3H), 2.11 (s, 6H), 1.86 (s, 4H), 1.30 (td, J = 7.1, 3.6 Hz, 6H). | |
| Example 119 | 1,1'-(2,2-Difluorobutane-1,4-diyl)bis(2-(1-ethyl-3-methyl-1H-pyrazole-5-carboxamido)-1H-benzo[d]imidazole-5-carboxamide) | Method 15 | $^1$H NMR (400 MHz, DMSO-$d_6$) δ ppm 12.91 (d, J = 31.5 Hz, 2H), 7.99 (s, 3H), 7.77 (d, J = 8.4 Hz, 2H), 7.51 (dd, J = 14.0, 8.4 Hz, 2H), 7.35 (s, 1H), 7.23 (s, 1H), 7.10 (s, 1H), 6.97 (s, 1H), 6.67 (d, J = 17.3 Hz, 2H), 4.89 (t, J = 14.3 Hz, 2H), 4.35-4.68 (m, 6H), 2.61-2.82 (m, 2H), 1.92-2.14 (m, 6H), 1.16-1.39 (m, 6H) | Method A: Rt = 1.298 min, [M + H]$^+$ = 715.7 |
| Example 120 | 1-(4-(4-(benzyloxy)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide | Method 11 | $^1$H NMR (DMSO-$d_6$) δ 12.80 (s, 1H), 12.07 (s, 1H), 7.98 (d, J = 1.5 Hz, 1H), 7.94 (br s, 1H), 7.75 (dd, J = 8.4, 1.3 Hz, 1H), | LCMS Method D: Rt = 1.18 min, [M + H]$^+$ = 742.5 |

-continued

Table 1 provides Example 89 to Example 197. The compounds can be prepared by using synthetic methods described above.

| Example | Structure/Name | Synthetic Method | NMR | LCMS |
|---------|----------------|------------------|-----|------|
| | 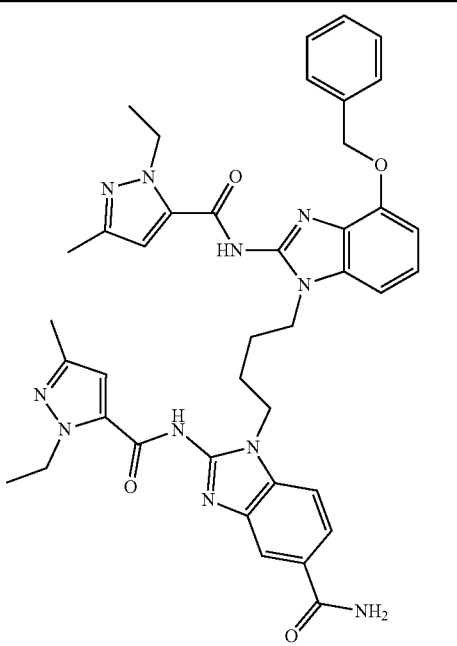 | | 7.47-7.59 (m, 3H), 7.39-7.45 (m, 2H), 7.33-7.39 (m, 1H), 7.26-7.32 (m, 1H), 7.14 (br s, 2H), 6.92-7.02 (m, 1H), 6.59 (s, 2H), 5.30 (s, 2H), 4.43-4.62 (m, 4H), 4.15-4.31 (m, 4H), 2.11 (s, 3H), 2.10 (s, 3H), 1.85 (br s, 4H), 1.28 (dt, J = 14.5, 7.2 Hz, 6H) | |
| Example 121 | tert-butyl ((24-carbamoyl-8-ethyl-10,18-dimethyl-7,20-dioxo-6,7,8,11,12,13,14,15,20,21,28,29,30,31-tetradeca-hydrobenzo[4,5]imidazo[1,2-a]benzo[4,5]imidazo[2,1-p]dipyrazolo[5,1-e:4',3'l][1,3,6,15,17]pentaazacyclohenicosin-4-yl)methyl)carbamate 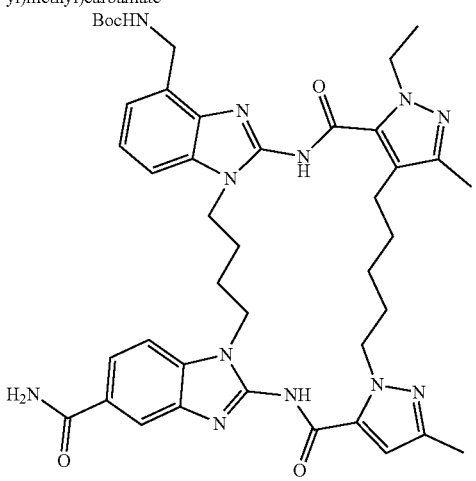 | 13 | $^1$H NMR DMSO-$d_6$) δ 12.90 (br. s., 1H), 12.36 (br. s., 1H), 8.02 (br. s., 2H), 7.84 (dd, J = 8.3,1.3 Hz, 1H), 7.66 (d, J = 8.5 Hz, 1H), 7.62 (t, J = 6.3 Hz, 1H), 7.50 (d, J = 8.0 Hz, 1H), 7.36 (br. s., 1H), 7.25 (t, J = 7.8 Hz, 1H), 7.12 (d, J = 7.8 Hz, 1H), 6.57 (s, 1H), 4.74 (t, J = 6.8 Hz, 2H), 4.47 (q, J = 7.0 Hz, 2H), 4.38 (d, J = 6.0 Hz, 2H), 4.15-4.33 (m, 4H), 2.74-2.87 (m, 2H), 2.15 (s, 3H), 2.08 (s, 3H), 1.90 (br. s., 4H), 1.80 (br. s., 2H), 1.32-1.54 (m, 2H), 1.40 (s, 9H), 1.28 (t, J = 7.0 Hz, 3H) | LCMS Method D: Rt = 1.10 min, [M + H]$^+$ = 805.6 |
| Example 122 | 2-(1-ethyl-3-methyl-1H-pyrazole-5-carboxamido)-1-(4-(2-(1-ethyl-3-methyl-1H-pyrazole-5-carboxamido)-4-hydroxy-1H-benzo[d]imidazol-1-yl)butyl)-1H-benzo[d]imidazole-5-carboxamide | Method 11 | $^1$H NMR (DMSO-$d_6$) δ 12.73 (br. s, 1H), 7.99 (d, J = 1.5 Hz, 1H), 7.81-7.92 (m, 1H), 7.61-7.74 (m, 1H), 7.36- | LCMS Method D: Rt = 0.91 min, [M + H]$^+$ = 652.2 |

Table 1 provides Example 89 to Example 197. The compounds can be prepared by using synthetic methods described above.

| Example | Structure/Name | Synthetic Method | NMR | LCMS |
|---|---|---|---|---|
| | 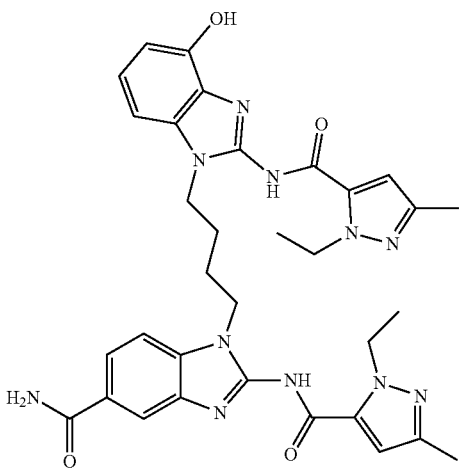 [SMILES: CCn1nc(C)cc1C(=O)Nc1nc2cc(C(N)=O)ccc2n1CCCCn1c(NC(=O)c2cc(C)nn2CC)nc2c(O)cccc21] | | 7.50 (m, 1H), 7.14-7.28 (m, 1H), 6.95-7.06 (m, 1H), 6.79-6.90 (m, 1H), 6.58-6.64 (m, 1H), 6.49-6.58 (m, 2H), 4.49-4.64 (m, 4H), 4.13-4.30 (m, 4H), 2.10 (s, 3H), 2.09 (s, 3H), 1.84 (br s, 4H), 1.18-1.37 (m, 6H) | |
| Example 123 | 2-(1-Ethyl-3-methyl-1H-pyrazole-5-carboxamido)-1-(4-(2-(1-ethyl-3-methyl-1H-pyrazole-5-carboxamido)-4-isopropoxy-1H-benzo[d]imidazol-1-yl)butyl)-1H-benzo[d]imidazole-5-carboxamide | Method 11 | $^1$H NMR (400 MHz, DMSO-d$_6$) δ ppm 12.81 (br. s., 1H), 11.96 (br. s., 1H), 7.98 (d, J = 1.0 Hz, 1 H), 7.96 (br. s., 1 H), 7.76 (dd, J = 8.6, 1.5 Hz, 1 H), 7.53 (d, J = 8.6 Hz, 1H), 7.33 (br. s., 1H), 7.08-7.21 (m, 2 H), 6.91 (d, J = 7.1 Hz, 1H), 6.51-6.63 (m, 2 H), 4.81 (br. s., 1 H), 4.45-4.62 (m, 4H), 4.24 (m, 4H), 2.11 (s, 6H), 1.85 (br. s., 4H), 1.20-1.41 (m, 12H) | LCMS Method C: Rt = 1.05 min, [M + H]$^+$ = 694.7 |
| | 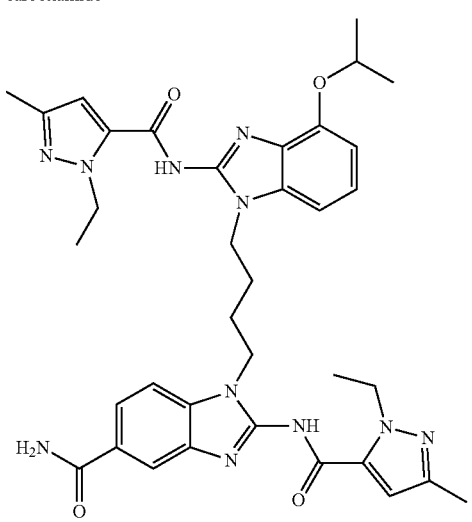 | | | |
| Example 124 | 2-(1-Ethyl-3-methyl-1H-pyrazole-5-carboxamido)-1-(4-(2-(1-ethyl-3-methyl-1H-pyrazole-5-carboxamido)-4-(methylamino)-1H-benzo[d]imidazol-1-yl)butyl)-1H-benzo[d]imidazole-5-carboxamide | Method 11 | $^1$H NMR (400 MHz, DMSO-d$_6$) δ ppm 12.83 (s, 1 H), 12.38 (s, 1 H), 7.97 (s, 1H), 7.96 (br. s., 1H), 7.75 (d, J = 8.6 Hz, 1H), 7.53 (d, | LCMS Method C: Rt = 0.92 min, [M + H]$^+$ = 665.6 |

Table 1 provides Example 89 to Example 197. The compounds can be prepared by using synthetic methods described above.

| Example | Structure/Name | Synthetic Method | NMR | LCMS |
|---|---|---|---|---|
| | | | J = 8.3 Hz, 1H) 7.33 (br. s., 1H), 7.04 (t, J = 8.1 Hz, 1H), 6.71 (d, J = 7.8 Hz, 2H), 6.60 (s, 1H), 6.55 (s, 1H), 6.35 (d, J = 8.1 Hz, 1H), 4.57 (q, J = 6.9 Hz, 4H), 4.27 (br. s., 2H), 4.19 (br. s., 2H), 2.79 (d, J = 4.5 Hz, 3H), 2.10 (s, 3H), 2.09 (s, 3H), 1.84 (br. s., 4H), 1.29 (q, J = 6.8 Hz, 6H) | |
| Example 125 | 1-(4-(4-Amino-2-(1-ethyl-3-methyl-1H-pyrazole-5-carboxamido)-1H-benzo[d]imidazol-1-yl)butyl)-2-(1-ethyl-3-methyl-1Hpyrazole-5-carboxamido)-1H-benzo[d]imidazole-5-carboxamide, tris trifluoroacetic acid salt | Method 11 | $^1$H NMR (400 MHz, DMSO-d$_6$) δ ppm 12.90 (br s, 1H), 12.30 (br s, 1H), 7.98 (d, J = 1.5 Hz, 1H), 7.96 (br. s., 1H), 7.76 (dd, J = 8.4, 1.6 Hz, 1H), 7.54 (d, J = 8.5 Hz, 1H), 7.33 (br. s., 1H), 6.95 (t, J = 8.0 Hz, 1H), 6.71 (d, J = 7.8 Hz, 1H), 6.61 (s, 1H), 6.56 (s, 1H), 6.49 (d, J = 8.0 Hz, 1H), 4.56 (q, J = 7.2 Hz, 4H), 4.27 (br. s., 2H), 4.14-4.23 (m, 2H), 2.10 (s, 3H), 2.09 (s, 3H), 1.84 (br. s., 4H), 1.22-1.36 (m, 6H) | LCMS Method D: Rt = 0.88 min, [M + H]$^+$ = 651.6 |
| Example 126 | 2-(1-Ethyl-3-methyl-1H-pyrazole-5-carboxamido)-1-(4-(2-(1-ethyl-3-methyl-1H-pyrazole-5-carboxamido)-4-(N-methylmethylsulfonamido)-1H-benzo[d]imidazol-1-yl)butyl)-1H-benzo[d]imidazole-5-carboxamide, bis trifluoroacetic acid salt | Method 11 | $^1$H NMR (400 MHz, DMSO-d$_6$) δ ppm 12.83 (br. s., 1H), 12.05 (br. s., 1H), 7.98 (s, 1H), 7.96 (br. s., 1H), 7.76 (d, J = 8.5 Hz, 1H), 7.55 (d, J = 7.5 | LCMS Method D: Rt = 0.98 min, [M + H]$^+$ = 743.7 |

Table 1 provides Example 89 to Example 197. The compounds can be prepared by using synthetic methods described above.

| Example | Structure/Name | Synthetic Method | NMR | LCMS |
|---|---|---|---|---|
| | 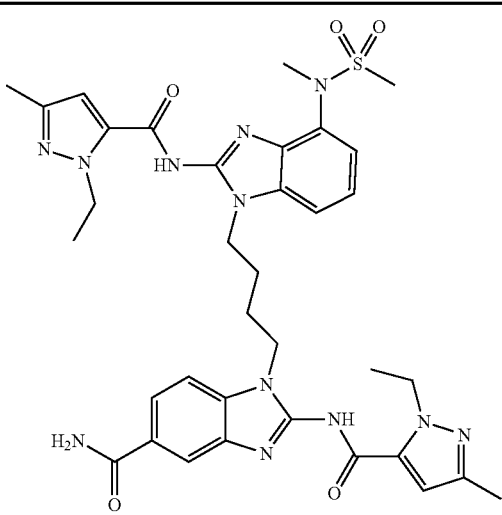 | | Hz, 2H), 7.41 (br. s., 1H), 7.27-7.37 (m, 2H), 6.62 (s, 2H), 4.46-4.62 (m, 4 H), 4.27 (br. s., 4 H), 3.31 (s, 3H), 3.05 (s, 3H), 2.11 (s, 6H), 1.86 (br. s., 4H), 1.20-1.34 (m, 6 H) | |
| Example 127 | 1-(4-(4-(2-Aminoethyl)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, tris trifluoroacetic acid salt 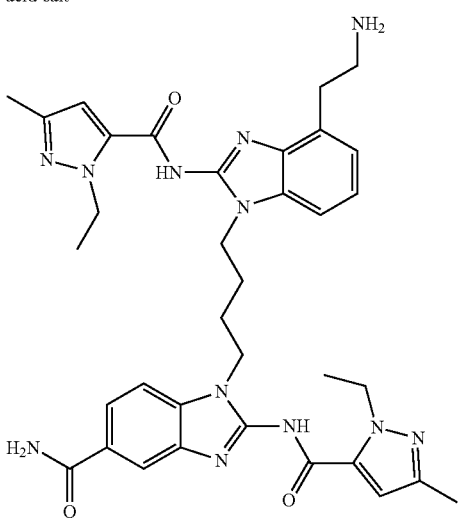 | Method 11 | $^1$H NMR (400 MHz, DMSO-$d_6$) δ ppm 7.98 (d, J = 1.3 Hz, 2H), 7.73-7.85 (m, 4 H), 7.54 (d, J = 8.3 Hz, 1H), 7.44 (d, J = 7.8 Hz, 1H), 7.35 (br. s., 1H), 7.17-7.24 (m, 1H), 7.09-7.15 (m, 1 H), 6.62 (s, 1H), 6.61 (s, 1H), 4.48-4.61 (m, 4 H), 4.20-4.31 (m, 4H), 3.05-3.19 (m, 4H), 2.11 (s, 6H), 1.86 (br. s., 4H), 1.29 (t, J = 7.0 Hz, 3H), 1.28 (t, J = 7.0 Hz, 3H) | LCMS Method D: Rt = 0.78 min, [M + H]$^+$ = 679.6 |
| Example 128 | 2-(1-Ethyl-3-methyl-1H-pyrazole-5-carboxamido)-1-(4-(2-(1-ethyl-3-methyl-1H-pyrazole-5-carboxamido)-4-(N-methylacetamido)-1H-benzo[d]imidazol-1-yl)butyl)-1H-benzo[d]imidazole-5-carboxamide | Method 11 | $^1$H NMR (400 MHz, DMSO-$d_6$) δ ppm 12.81 (br. s, 1H), 7.98 (s, 1 H), 7.97 (br. s., 1 H), 7.76 (dd, J = 8.3,1.5 Hz, 1 H), 7.52 (d, | LCMS Method N: Rt = 6.584 min, [M + H]$^+$ = 707.2 |

Table 1 provides Example 89 to Example 197. The compounds can be prepared by using synthetic methods described above.

| Example | Structure/Name | Synthetic Method | NMR | LCMS |
|---|---|---|---|---|
| | 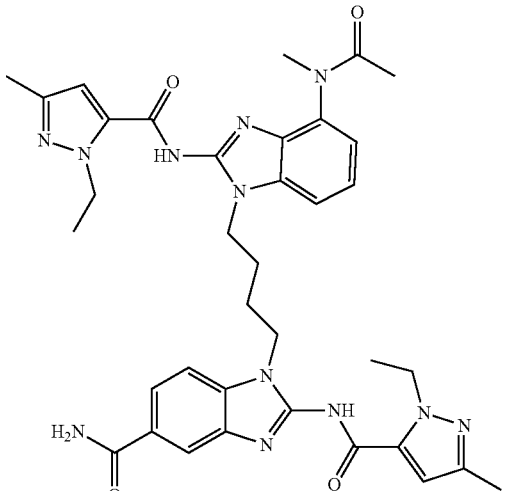 | | J = 8.3 Hz, 2H), 7.34 (br. s., 1H), 7.24 (t, J = 7.9 Hz, 1H), 7.16 (d, J = 8.0 Hz, 1H), 6.59 (s, 2H), 4.43-4.59 (m, 4 H), 4.24 (br. s., 4 H), 3.14 (s, 3H), 2.11 (br. s., 3H), 2.10 (s, 3H), 1.85 (br. s., 4H), 1.66 (s, 3H), 1.27 (m, 6H) | |
| Example 129 | 2-(1-Ethyl-3-methyl-1H-pyrazole-5-carboxamido)-1-(4-(2-(1-ethyl-3-methyl-1H-pyrazole-5-carboxamido)-4-(1-hydroxyethyl)-1H-benzo[d]imidazol-1-yl)butyl)-1H-benzo[d]imidazole-5-carboxamide<br/>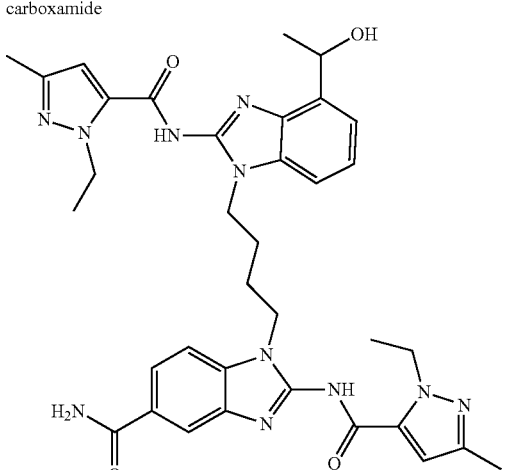 | Method 11 | $^1$H NMR (400 MHz, DMSO-d$_6$) δ ppm 12.83 (s, 1 H), 12.23 (s, 1 H), 7.92-8.02 (m, 2H), 7.76 (dd, J = 8.3, 1.3 Hz, 1H), 7.54 (d, J = 8.5 Hz, 1H), 7.40 (d, J = 8.0 Hz, 1H), 7.34 (br. s., 1H), 7.17 (t, J = 7.8 Hz, 1 H), 7.07 (d, J = 7.5 Hz, 1H), 6.61 (s, 1H), 6.58 (s, 1H), 5.88 (d, J = 3.3 Hz, 1H), 5.11 (d, J = 4.3 Hz, 1H), 4.56 (m, 4H), 4.27 (m, 4H), 2.10 (d, J = 1.3 Hz, 6H), 1.86 (br. s., 4H), 1.42 (d, J = 6.5 Hz, 3 H), 1.29 (q, J = 7.3 Hz, 6H) | LCMS Method D: Rt = 0.95 min, [M + H]$^+$ = 680.6 |
| Example 130 | 1-(4-(4-(2-Amino-N-methylacetamido)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, tris trifluoroacetic acid salt | Method 11 | $^1$H NMR (400 MHz, DMSO-d$_6$) δ ppm 12.81 (br. s, 1H), 8.16 (br. s., 1H), 7.99 (s, 2 H), 7.92 (br. s., 2 H), 7.77 (dd, J = 8.4, 1.4 Hz, 1 H), 7.64 (d, J = 7.8 Hz, 1H), | LCMS Method D: Rt = 0.78 min, [M + H]$^+$ = 722.6 |

Table 1 provides Example 89 to Example 197. The compounds can be prepared by using synthetic methods described above.

| Example | Structure/Name | Synthetic Method | NMR | LCMS |
|---|---|---|---|---|
| | 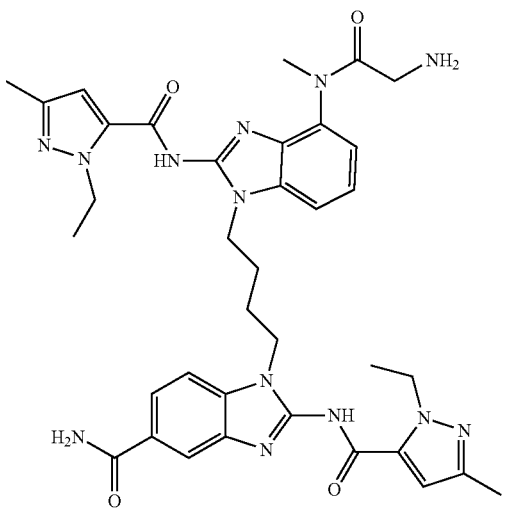 | | 7.48-7.59 (m, 1 H), 7.35 (m, 1 H), 7.31 (d, J = 8.0 Hz, 1H), 7.23-7.29 (m, 1 H), 6.68 (br. s., 1H), 6.61 (s, 1H), 4.56 (q, J = 6.9 Hz, 4H), 4.46 (br. s., 2H), 4.26 (br. s., 4H), 3.24 (s, 3H), 2.08-2.15 (m, 6H), 1.86 (br. s., 4H), 1.19-1.35 (m, 6 H) | |
| Example 131 | 2-(1-Ethyl-3-methyl-1H-pyrazole-5-carboxamido)-1-(4-(2-(1-ethyl-3-methyl-1H-pyrazole-5-carboxamido)-4-(methylsulfonamido)-1H-benzo[d]imidazol-1-yl)butyl)-1H-benzo[d]imidazole-5-carboxamide, bis trifluoroacetic acid salt 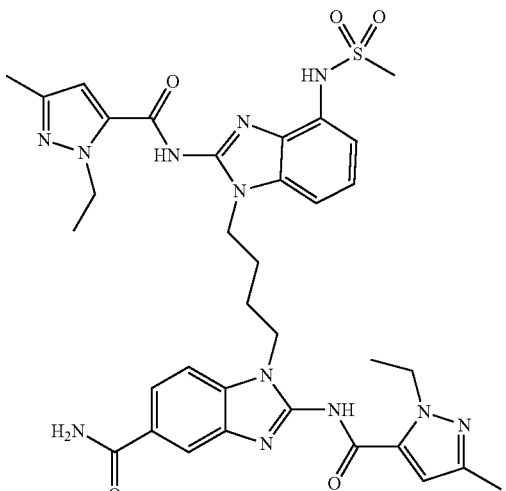 | Method 11 | $^1$H NMR (400 MHz, DMSO-$d_6$) δ ppm 10.37 (s, 1 H), 7.98 (d, J = 1.3 Hz, 1H), 7.96 (br. s., 1H), 7.76 (dd, J = 8.5, 1.5 Hz, 1H), 7.55 (d, J = 8.5 Hz, 1H), 7.34 (br. s., 1H), 7.31 (dd, J = 7.3,1.5 Hz, 1H), 7.17-7.27 (m, 2H), 6.61 (s, 1H), 6.59 (s, 1H), 4.51-4.61 (m, 4 H), 4.16-4.34 (m, 4H), 3.04 (s, 3H), 2.10 (s, 3 H), 2.09 (s, 3H), 1.86 (br. s., 4H), 1.30 (td, J = 7.2, 2.8 Hz, 6H) | LCMS Method D: Rt = 0.90 min, [M + H]$^+$ = 729.6 |
| Example 132 | 1-(4-(4-(2-(Dimethylamino)-N-methylacetamido)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, tris trifluoroacetic acid salt | Method 11 | $^1$H NMR (400 MHz, DMSO-$d_6$) δ ppm 12.8 (br. s, 1H), 9.50 (br. s., 1H), 7.99 (s, 2 H), 7.78 (dd, J = 8.4, 1.4 Hz, 1 H), 7.62 (d, J = 7.8 Hz, 1H), 7.55 (d, J = 8.5 | LCMS Method D: Rt = 0.79 min, [M + H]$^+$ = 750.7 |

Table 1 provides Example 89 to Example 197. The compounds can be prepared by using synthetic methods described above.

| Example | Structure/Name | Synthetic Method | NMR | LCMS |
|---|---|---|---|---|
| | 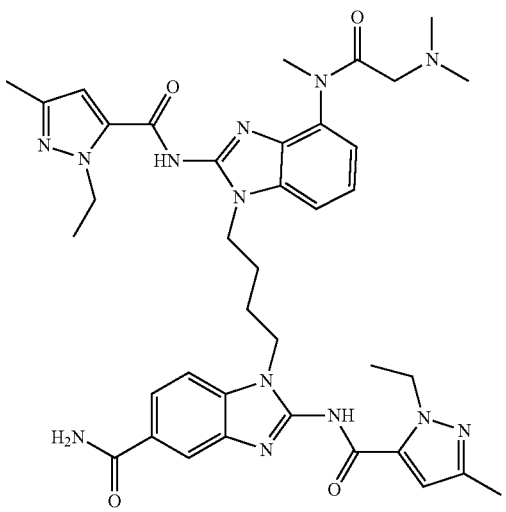 | | Hz, 1H), 7.35 (br. s., 1H), 7.21-7.33 (m, 2H), 6.62 (s, 2H), 4.52-4.63 (m, 6 H), 4.28 (m, 4 H), 3.23 (s, 3 H), 2.70 (d, J = 4.0 Hz, 6H), 2.11 (d, J = 1.5 Hz, 6H), 1.87 (br. s., 4H), 1.28 (dt, J = 14.1, 7.0 Hz, 6H) | |
| Example 133 | 1-(4-(4-(2-(Dimethylamino)acetamido)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, tris trifluoroacetic acid salt<br>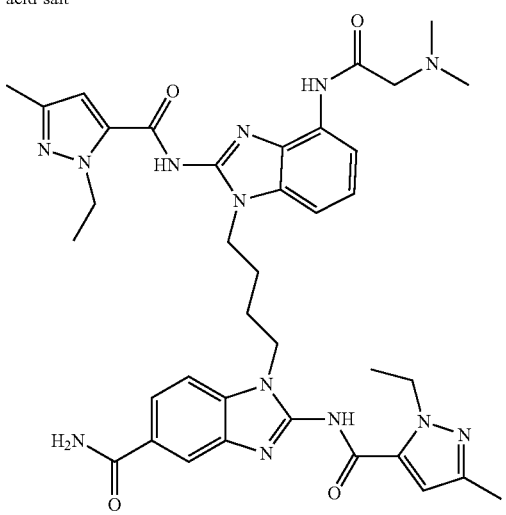 | Method 11 | $^1$H NMR (400 MHz, DMSO-$d_6$) δ ppm 12.82 (br. s, 1H), 12.7 (br. s, 1H), 10.91 (s, 1 H), 9.94 (br. s., 1 H), 7.97 (s, 2H), 7.76 (d, J = 8.3 Hz, 1H), 7.72 (d, J = 8.0 Hz, 1H), 7.52 (d, J = 8.5 Hz, 1H), 7.34 (d, J = 7.8 Hz, 2H), 7.18-7.28 (m, 1 H), 6.60 (s, 1H), 6.59 (s, 1H), 4.55 (q, J = 6.8 Hz, 4H), 4.27 (br. s., 6H), 2.92 (s, 6H), 2.10 (s, 6H), 1.87 (br. s., 4H), 1.29 (t, J = 7.0 Hz, 6H) | LCMS Method D: Rt = 0.80 min, [M + H]$^+$ = 369.0 |
| Example 134 | 2-(1-Ethyl-3-methyl-1H-pyrazole-5-carboxamido)-1-(4-(2-(1-ethyl-3-methyl-1H-pyrazole-5-carboxamido)-4-(2-hydroxyacetamido)-1H-benzo[d]imidazol-1-yl)butyl)-1H-benzo[d]imidazole-5-carboxamide, bis trifluoroacetic acid salt | Method 11 | $^1$H NMR (400 MHz, DMSO-$d_6$) δ ppm 12.83 (br. s., 1H), 12.52 (br. s., 1H), 10.32 (br. s., 1 H), 7.99 (s, 1H), 7.97 (br. s., 1H), 7.76 (d, J = 8.3 | LCMS Method D: Rt = 0.86 min, [M + H]$^+$ / 2 = 355.4 |

Table 1 provides Example 89 to Example 197. The compounds can be prepared by using synthetic methods described above.

| Example | Structure/Name | Synthetic Method | NMR | LCMS |
|---|---|---|---|---|
| | 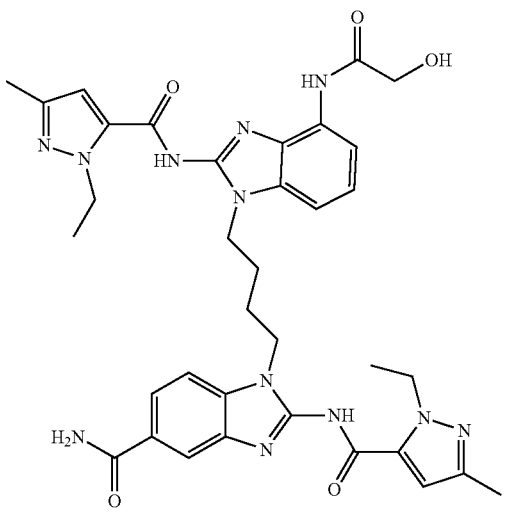 | | Hz, 1H), 7.54 (d, J = 8.3 Hz, 2H), 7.34 (br. s., 1H), 7.30 (d, J = 8.0 Hz, 1H), 7.16-7.23 (m, 1H), 6.61 (s, 2H), 4.50-4.62 (m, 4 H), 4.27 (br. s., 4 H), 4.14 (s, 2H), 2.68 (br. s., 1H), 2.11 (s, 6H), 1.87 (br. s., 4H), 1.30 (q, J = 7.0 Hz, 6H) | |
| Example 135 | 2-(1-Ethyl-3-methyl-1H-pyrazole-5-carboxamido)-1-(4-(2-(1-ethyl-3-methyl-1H-pyrazole-5-carboxamido)-4-(N-methyl-2-(methylamino)acetamido)-1H-benzo[d]imidazol-1-yl)butyl)-1H-benzo[d]imidazole-5-carboxamide, tris trifluoroacetic acid salt | Method 11 | $^1$H NMR (400 MHz, DMSO-d$_6$) δ ppm 12.83 (br. s., 1H), 8.61 (br. s., 1H), 7.91-8.04 (m, 2H), 7.77 (d, J = 8.5 Hz, 1H), 7.63 (br. s., 1H), 7.44-7.59 (m, 2H), 7.19-7.40 (m, 3 H), 6.55-6.64 (m, 2H), 4.48-4.63 (m, 4H), 4.26 (br. s., 6H), 3.33 (s, 1H), 3.24 (s, 2H), 2.63-2.71 (m, 1 H), 2.44 (t, J = 5.1 Hz, 2H), 2.05-2.19 (m, 6H), 1.76-1.95 (m, 4 H), 1.28 (q, J = 6.7 Hz, 6H) | LCMS Method D: Rt = 0.79 min, [M + H]$^+$ / 2 = 369.0 |
| | 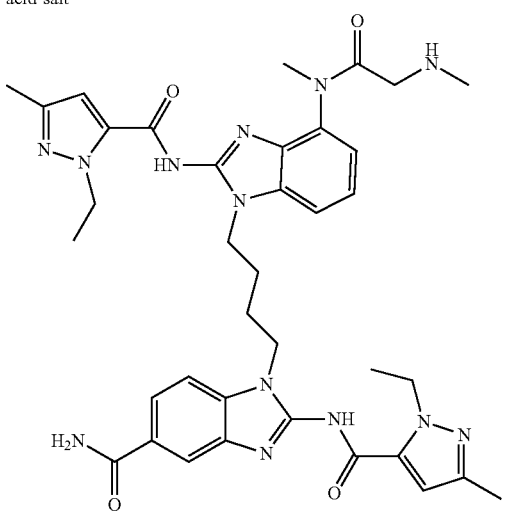 | | | |
| Example 136 | 1-(4-(4-(Aminomethyl)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, tris trifluoroacetic acid salt | Method 11 | $^1$H NMR (400 MHz, DMSO-d$_6$) δ ppm 12.82 (br. s., 1H), 12.53 (br. s., 1H), 8.05 (br. s., 3H), 7.97 (s, 2H), 7.76 (d, J = 8.3 Hz, 1H), 7.55 (t, J = 8.5 Hz, | LCMS Method D: Rt = 0.76 min, [M + H]$^+$ / 2 = 333.4 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 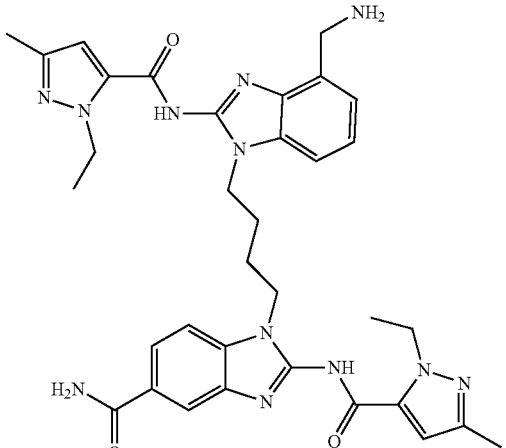 | | 2H), 7.25-7.39 (m, 3H), 6.61 (s, 2H), 4.56 (d, J = 7.0 Hz, 4H), 4.38 (m, 2H), 4.27 (br. s., 4H), 2.10 (s, 6H), 1.84 (br. s., 4H), 1.21-1.36 (m, 6 H) | |
| Example 137 | 2-(1-Ethyl-3-methyl-1H-pyrazole-5-carboxamido)-1-(4-(2-(1-ethyl-3-methyl-1H-pyrazole-5-carboxamido)-4-(2-(methylamino)acetamido)-1H-benzo[d]imidazol-1-yl)butyl)-1H-benzo[d]imidazole-5-carboxamide, tris trifluoroacetic acid salt | Method 11 | $^1$H NMR (400 MHz, DMSO-d$_6$) δ ppm 12.80 (br. s., 1H), 12.54 (br. s., 1H), 10.86 (br. s., 1 H), 8.88 (br. s., 2 H), 7.97 (s, 2H), 7.76 (d, J = 8.0 Hz, 1H), 7.69 (d, J = 8.0 Hz, 1H), 7.53 (d, J = 8.3 Hz, 1H), 7.33 (d, J = 7.8 Hz, 2H), 7.19-7.27 (m, 1 H), 6.59 (s, 2H), 4.55 (q, J = 7.0 Hz, 4H), 4.26 (m, 4H), 4.08 (t, J = 5.5 Hz, 2H), 2.63-2.72 (m, 3 H), 2.10 (s, 6H), 1.87 (br. s., 4H), 1.29 (t, J = 7.0 Hz, 6H) | LCMS Method D: Rt = 0.79 min, [M + H]$^+$/2 = 362.0 |
| | 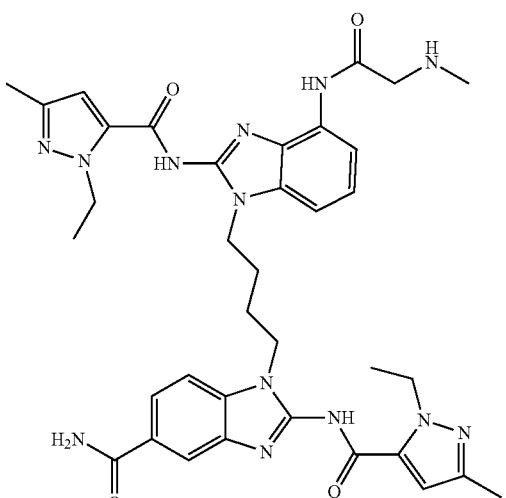 | | | |
| Example 138 | 2-(1-Ethyl-3-methyl-1H-pyrazole-5-carboxamido)-1-(4-(2-(1-ethyl-3-methyl-1H-pyrazole-5-carboxamido)-4-(2-hydroxy-N-methylacetamido)-1H-benzo[d]imidazol-1-yl)butyl)-1H-benzo[d]imidazole-5-carboxamide, bis trifluoroacetic acid salt | Method 11 | $^1$H NMR (400 MHz, DMSO-d$_6$) δ ppm 12.83 (br. s., 2H), 7.99 (d, J = 1.3 Hz, 1H), 7.96 (br. s., 1H), 7.76 (dd, J = 8.3, 1.5 Hz, 1H), 7.54 (br. s., 2H), | LCMS Method D: Rt = 0.86 min, [M + H]$^+$/2 = 362.4 |

Table 1 provides Example 89 to Example 197. The compounds can be prepared by using synthetic methods described above.

| Example | Structure/Name | Synthetic Method | NMR | LCMS |
|---|---|---|---|---|
| | 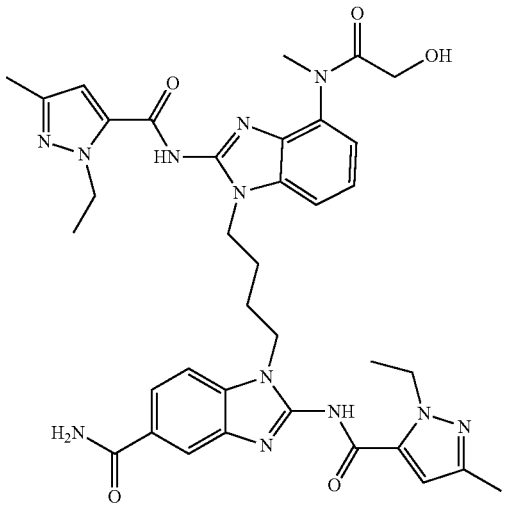 | | 7.33 (br. s., 1H), 7.26 (t, J = 7.9 Hz, 1H), 7.19 (d, J = 7.3 Hz, 1H), 6.61 (br. s., 2H), 4.45-4.63 (m, 4 H), 4.25 (br. s., 4 H), 3.44-3.86 (br. s., 2H), 3.29 (br. s., 1H), 3.18 (br. s., 3H), 2.11 (br. s., 3H), 2.10 (br. s., 3H), 1.86 (br. s., 4H), 1.21-1.35 (m, 6H) | |
| Example 139 | 1-(4-(4-(2-Aminoacetamido)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide 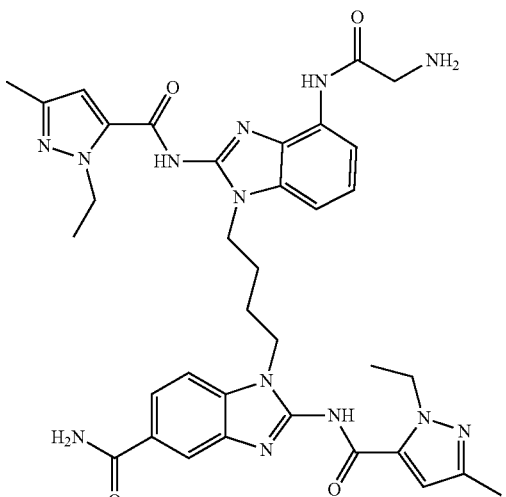 | Method 11 | $^1$H NMR (400 MHz, DMSO-$d_6$) δ ppm 12.82 (br. s, 1H), 12.6 (br. s, 1H), 10.81 (s, 1 H), 8.20 (br. s., 3 H), 7.97 (d, J = 1.3 Hz, 2H), 7.76 (dd, J = 8.5, 1.5 Hz, 1H), 7.69 (d, J = 8.0 Hz, 1H), 7.53 (d, J = 8.5 Hz, 1H), 7.33 (d, J = 8.0 Hz, 2H), 7.19-7.28 (m, 1H), 6.59 (s, 2H), 4.55 (q, J = 7.0 Hz, 4H), 4.26 (d, J = 6.3 Hz, 4H), 3.85-4.02 (m, 2 H), 2.10 (s, 6H), 1.87 (br. s.,4H), 1.29 (t, J = 7.2 Hz, 6H) | LCMS Method D: Rt = 0.79 min, [M + H]$^+$ = 708.6 |
| Example 140 | 2-(1-Ethyl-3-methyl-1H-pyrazole-5-carboxamido)-1-(4-(2-(1-ethyl-3-methyl-1H-pyrazole-5-carboxamido)-4-(5-oxoimidazolidin-1-yl)-1H-benzo[d]imidazol-1-yl)butyl)-1H-benzo[d]imidazole-5-carboxamide 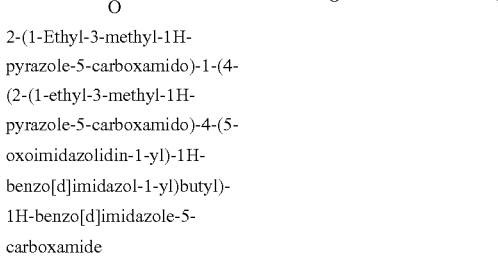 | Method 11 | $^1$H NMR (400 MHz, DMSO-$d_6$) δ ppm 12.7 (br. s, 1H), 12.4 (br. s, 1H), 7.96 (s, 2 H), 7.74 (dd, J = 8.4, 1.3 Hz, 1 H), 7.51 (d, | LCMS Method E: Rt = 0.73 min, [M + H]$^+$ = 720.9 |

Table 1 provides Example 89 to Example 197. The compounds can be prepared by using synthetic methods described above.

| Example | Structure/Name | Synthetic Method | NMR | LCMS |
|---|---|---|---|---|
| | 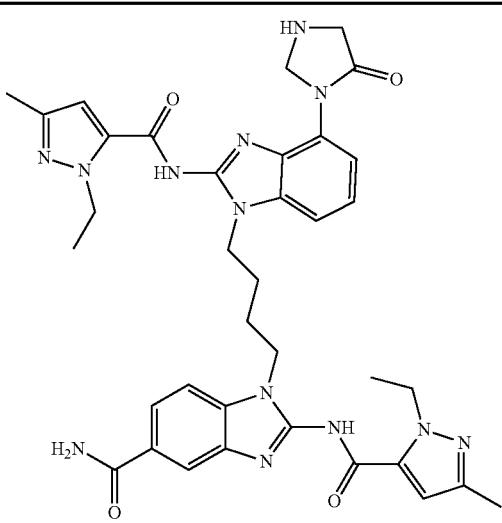 | | J = 8.6 Hz, 1H), 7.38 (d, J = 8.1 Hz, 1H), 7.35 (br. s., 1H), 7.23 (t, J = 8.1 Hz, 1 H), 6.98 (d, J = 7.8 Hz, 1H), 6.61 (s, 1H), 6.59 (s, 1H), 4.86 (br. s., 2H), 4.46-4.64 (m, 4 H), 4.26 (br. s., 4 H), 3.73 (br. s., 1 H), 3.55 (br. s., 2 H), 2.10 (s, 6H), 1.87 (br. s.,4H), 1.21-1.38 (m, 6 H) | |
| Example 141 | 2-(1-Ethyl-3-methyl-1H-pyrazole-5-carboxamido)-1-(4-(2-(1-ethyl-3-methyl-1H-pyrazole-5-carboxamido)-4-(3-methyl-5-oxoimidazolidin-1-yl)-1H-benzo[d]imidazol-1-yl)butyl)-1H-benzo[d]imidazole-5-carboxamide | Method 11 | $^1$H NMR (400 MHz, DMSO-d$_6$) δ ppm 12.81 (br. s., 1H), 12.24 (br. s., 1H), 7.97 (s, 2H), 7.75 (dd, J = 8.4,1.3 Hz, 1H), 7.53 (d, J = 8.6 Hz, 1H), 7.41 (d, J = 8.1 Hz, 1H), 7.34 (br. s., 1H), 7.25 (t, J = 8.1 Hz, 1 H), 7.00 (d, J = 7.8 Hz, 1H), 6.61 (s, 1H), 6.59 (br. s., 1H), 4.66 (br. s., 2H), 4.48-4.61 (m, 4 H), 4.27 (br. s., 4 H), 3.51 (br. s., 2 H), 2.46 (s, 3H), 2.10 (s, 6H), 1.80-1.93 (m, 4 H), 1.22-1.36 (m, 6H) | LCMS Method D: Rt = 0.82 min, [M + H]$^+$ = 734.6 |
| | 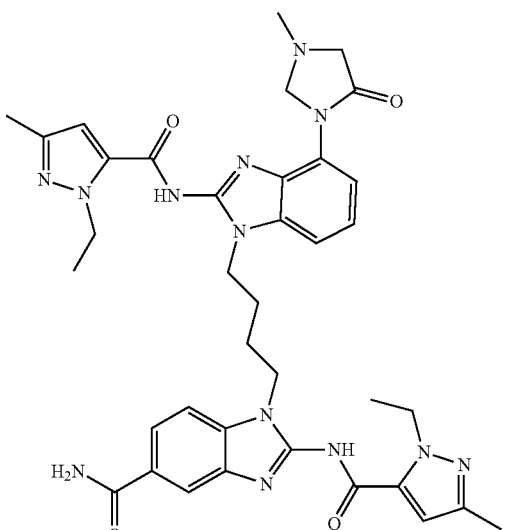 | | | |
| Example 142 | 2-(1-Ethyl-3-methyl-1H-pyrazole-5-carboxamido)-1-(4-(2-(1-ethyl-3-methyl-1H-pyrazole-5-carboxamido)-4-(3-methylbutanamido)-1H-benzo[d]imidazol-1-yl)butyl)-1H-benzo[d]imidazole-5-carboxamide | Method 11 | $^1$H NMR (400 MHz, DMSO-d$_6$) δ ppm 12.82 (br. s., 1H), 12.53 (s, 1H), 10.36 (s, 1 H), 7.91-8.01 (m, 2H), 7.76 (dd, J = 8.4, 1.3 | LCMS Method E: Rt = 0.99 min, [M + H]$^+$ = 736.1 |

Table 1 provides Example 89 to Example 197. The compounds can be prepared by using synthetic methods described above.

| Example | Structure/Name | Synthetic Method | NMR | LCMS |
|---|---|---|---|---|
| | 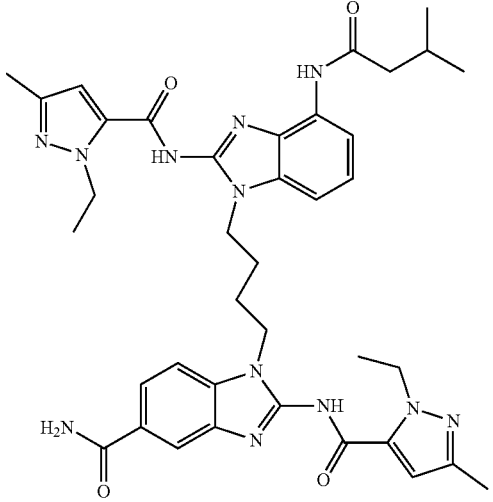 | | Hz, 1H), 7.65 (d, J = 8.1 Hz, 1H), 7.54 (d, J = 8.6 Hz, 1H), 7.34 (br. s., 1H), 7.22-7.30 (m, 1H), 7.12-7.21 (m, 1 H), 6.59 (s, 1H), 6.58 (s, 1H), 4.56 (q, J = 7.0 Hz, 4H), 4.18-4.32 (m, 4H), 2.33 (d, J = 7.1 Hz, 2H), 2.15 (m, 1H), 2.09 (s, 6H), 1.86 (br. s., 4H), 1.29 (td, J = 7.0, 4.6 Hz, 6 H), 0.98 (d, J = 6.6 Hz, 6H) | |
| Example 143 | 8-Ethyl-10,18-dimethyl-7,20-dioxo-23-(5-oxoimidazolidin-1-yl)-6,7,8,11,12,13,14,15,20,21,28,29,30,31-tetradecahydrobenzo[4,5]-imidazo[1,2-a]benzo[4,5]imidazo-[2,1-p]dipyrazolo[5,1-e:4',3'-l][1,3,6,15,17]pentaaza-cyclohenicosine-3-carboxamide 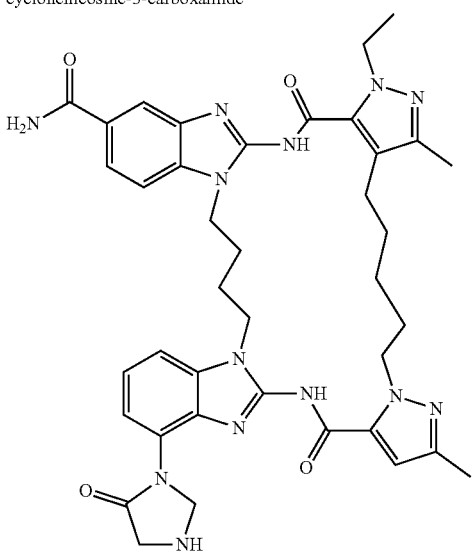 | Method 13. | $^1$H NMR (400 MHz, DMSO-d$_6$) δ ppm 8.02 (s, 1 H), 7.98 (br. s., 1 H), 7.82 (d, J = 8.5 Hz, 1H), 7.60 (d, J = 7.8 Hz, 1H), 7.52 (d, J = 8.0 Hz, 1H), 7.28-7.40 (m, 2 H), 7.06 (br. s., 1 H), 6.55 (br. s., 1 H), 4.87 (br. s., 2 H), 4.74 (br. s., 2 H), 4.47 (q, J = 7.3 Hz, 2H), 4.24 (br. s., 4H), 3.55 (br. s., 2H), 2.82 (br. s., 2H), 2.16 (s, 3H), 2.09 (s, 3H), 1.92 (br. s., 4H), 1.81 (br. s., 2H), 1.49 (br. s., 2H), 1.38 (br. s., 2H), 1.30 (t, J = 6.9 Hz, 3H) | LCMS Method C: Rt = 0.83 min, [M + H]$^+$ = 760.4 |
| Example 144 | 2-(1-Ethyl-3-methyl-1H-pyrazole-5-carboxamido)-1-(4-(2-(1-ethyl-3-methyl-1H-pyrazole-5-carboxamido)-4-(2-(methylamino)ethoxy)-1H-benzo[d]imidazol-1-yl)butyl)-1H-benzo[d]imidazole-6-carboxamide | Method 11 | $^1$H NMR (400 MHz, DMSO-d$_6$) δ ppm 12.81 (br. s., 1H), 11.98 (br. s., 1H), 8.90 (br. s., 2H), 7.97 (s, 2H), 7.76 (dd, J = 8.3,1.5 | LCMS Method C: Rt = 0.79 min, [M + H]$^+$ = 709.4 |

Table 1 provides Example 89 to Example 197. The compounds can be prepared by using synthetic methods described above.

| Example | Structure/Name | Synthetic Method | NMR | LCMS |
|---|---|---|---|---|
| | 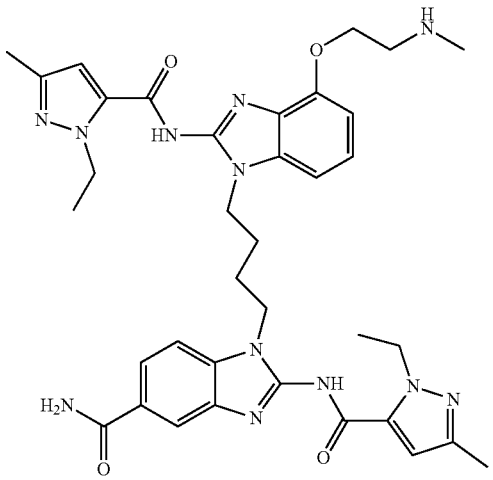 | | Hz, 1H), 7.53 (d, J = 8.6 Hz, 1H), 7.35 (br. s., 1H), 7.14-7.22 (m, 2 H), 6.91 (dd, J = 6.1, 2.9 Hz, 1 H), 6.59 (s, 2H), 4.55 (q, J = 6.7 Hz, 4H), 4.37 (t, J = 4.4 Hz, 2H), 4.25 (d, J = 7.6 Hz, 4H), 3.39 (s, 3H), 2.71 (t, J = 5.1 Hz, 3H), 2.10 (s, 6H), 1.85 (br. s., 4H), 1.28 (td, J = 7.1, 5.1 Hz, 6H) | |
| Example 145 | 8-ethyl-10,18-dimethyl-4-(methylamino)-7,20-dioxo-6,7,8,11,12,13,14,15,20,21,28,29,30,31-tetradecahydrobenzo[4,5]imidazo[1,2-a]benzo-[4,5]imidazo[2,1-p]dipyrazolo[5,1-e:4',3'-l][1,3,6,15,17]pentaazacyclohenicosine-24-carboxamide 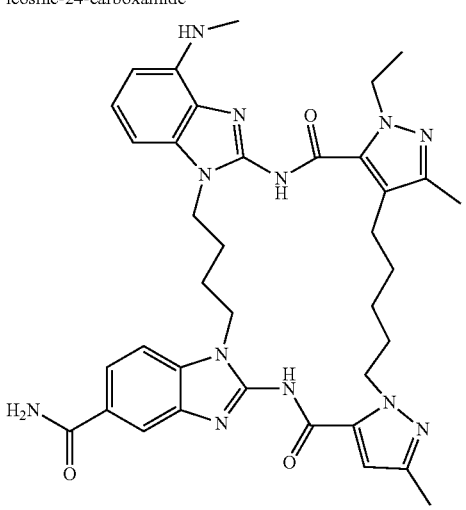 | Method 13 | $^1$H NMR (400 MHz, DMSO-d$_6$) δ ppm 12.92 (br. s., 1H) 12.45 (s, 1H) 8.02 (br. s., 2H) 7.84 (d, J = 8.56 Hz, 1H) 7.66 (d, J = 8.31 Hz, 1H) 7.39 (br. s., 1H) 7.12 (t, J = 8.07 Hz, 1H) 6.72-6.86 (m, 2 H) 6.58 (s, 1H) 6.39 (d, J = 8.07 Hz, 1H) 4.75 (br. s., 2H) 4.48 (q, J = 7.01 Hz, 2H) 4.27 (br. s., 2H) 4.16 (br. s., 2H) 2.82 (d, J = 4.65 Hz, 4H) 2.74-2.79 (m, 1H) 2.16 (s, 3H) 2.08 (s, 3H) 1.89 (br. s., 4H) 1.80 (br. s., 2H) 1.48 (br. s., 2H) 1.37 (br. s., 2H) 1.30 (t, J = 6.97 Hz, 3H) | LCMS Method D: Rt = 1.01 01 min, [M + H]$^+$ = 705.4 |
| Example 146 | 2-(1-ethyl-3-methyl-1H-pyrazole-5-carboxamido)-1-(4-(2-(1-ethyl-3-methyl-1H-pyrazole-5-carboxamido)-4-methyl-1H-benzo[d]imidazol-1-yl)butyl)-1H-benzo[d]imidazole-5-carboxamide, 2Trifluoroacetic acid salt | Method 11 | $^1$H NMR (400 MHz, DMSO-d$_6$) δ ppm 1.29 (m, 6 H) 1.85 (br. s., 4 H) 2.07-2.19 (m, 6H) 4.25 (d, J = 7.83 Hz, 4H) 4.55 (quin, | LCMS Method C: Rt = 0.98 min, [M + H]$^+$ = 650.5 |

Table 1 provides Example 89 to Example 197. The compounds can be prepared by using synthetic methods described above.

| Example | Structure/Name | Synthetic Method | NMR | LCMS |
|---|---|---|---|---|
| | 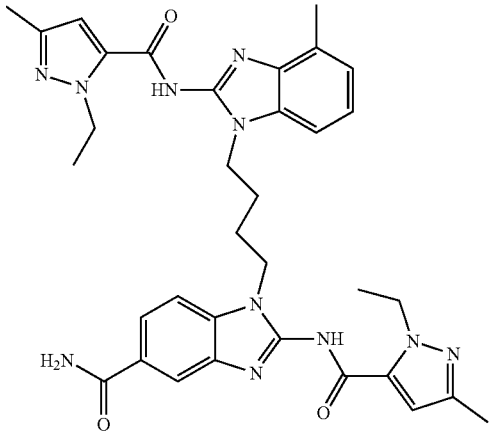 | | J = 6.69 Hz, 4H) 6.59 (s, 2H) 7.01-7.19 (m, 2 H) 7.30-7.41 (m, 2H) 7.53 (d, J = 8.34 Hz, 1H) 7.75 (dd, J = 8.46, 1.39 Hz, 1H) 7.92-8.05 (m, 2 H) 12.83 (br. s., 2H) | |
| Example 147 | methyl 2-((1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazol-4-yl)oxy)acetate, 2Trifluoroacetic acid salt | Method 11 | $^1$H NMR (400 MHz, DMSO-d$_6$) δ ppm 1.22-1.34 (m, 6H) 1.85 (br. s., 4H) 2.11 (d, J = 1.00 Hz, 6 H) 3.94 (s, 3H) 4.24 (d, J = 9.29 Hz, 4H) 4.45-4.60 (m, 4H) 6.56-6.64 (m, 2 H) 6.90 (d, J = 7.78 Hz, 1H) 7.12-7.23 (m, 2 H) 7.33 (br. s., 1 H) 7.51 (d, J = 8.53 Hz, 1H) 7.75 (dd, J = 8.53, 1.51 Hz, 1H) 7.97 (d, J = 1.51 Hz, 2H) 12.80 (br. s., 2H) | LCMS Method D: Rt = 1.03 min, [M + H]$^+$ = 666.5 |
| Example 148 | 2-(1-ethyl-3-methyl-1H-pyrazole-5-carboxamido)-1-(4-(2-(1-ethyl-3-methyl-1H-pyrazole-5-carboxamido)-4-methoxy-1H-benzo[d]imidazol-1-yl)butyl)-1H-benzo[d]imidazole-5-carboxamide, 2Trifluoroacetic acid salt | Method 16 | $^1$H NMR (400 MHz, DMSO-d$_6$) δ ppm 1.29 (m, 6 H) 1.86 (br. s., 4 H) 2.11 (s, 6H) 3.71 (s, 3H) 4.25 (br. s., 4H) 4.56 (q, J = 7.01 Hz, 4H) 6.58- | LCMS Method D: Rt = 0.97 min, [M + H]$^+$ = 724.5 |

Table 1 provides Example 89 to Example 197. The compounds can be prepared by using synthetic methods described above.

| Example | Structure/Name | Synthetic Method | NMR | LCMS |
|---|---|---|---|---|
| | | | 6.65 (m, 2H) 5.00 (s, 2H) 6.88 (br. s., 1H) 7.12-7.22 (m, 2 H) 7.30 (br. s., 1 H) 7.51 (d, J = 8.31 Hz, 1H) 7.75 (dd, J = 8.44, 1.59 Hz, 1H) 7.90-8.00 (m, 2 H) 12.79 (br. s., 2H) | |
| Example 149 | 2-(1-ethyl-3-methyl-1H-pyrazole-5-carboxamido)-1-(4-(2-(1-ethyl-3-methyl-1H-pyrazole-5-carboxamido)-4-(2-hydroxyethoxy)-1 H-benzo[d]imidazol-1-yl)butyl)-1H-benzo[d]imidazole-5-carboxamide, 2Trifluoroacetic acid salt | Method 16 | $^1$H NMR (400 MHz, DMSO-d$_6$) δ ppm 1.20-1.39 (m, 6H) 1.85 (br. s., 4H) 2.10 (d, J = 1.96 Hz, 6 H) 3.74-3.82 (m, 3H) 4.13 (t, J = 4.52 Hz, 2H) 4.20-4.31 (m, 4 H) 4.48-4.61 (m, 4H) 6.60 (s, 2H) 6.87 (d, J = 7.58 Hz, 1H) 7.10-7.20 (m, 2 H) 7.34 (br. s., 1 H) 7.53 (d, J = 8.31 Hz, 1H) 7.75 (dd, J = 8.56, 1.47 Hz, 1H) 7.97 (d, J = 1.47 Hz, 2H) 12.11 (br. s., 1H) 12.83 (br. s., 2 H) | LCMS Method D: Rt = 0.90 min, [M + H]$^+$ = 696.4 |
| Example 150 | 2-(1-ethyl-3-methyl-1H-pyrazole-5-carboxamido)-1-(4-(2-(1-ethyl-3-methyl-1H-pyrazole-5-carboxamido)-4-(hydroxymethyl)-1H-benzo[d]imidazol-1-yl)butyl)-1H-benzo[d]imidazole-5-carboxamide, 2Trifluoroacetic acid salt | Method 11 | $^1$H NMR (400 MHz, DMSO-d$_6$) δ ppm 1.24-1.35 (m, 6H) 1.87 (br. s., 4H) 2.00 -2.14 (m, 6H) 4.27 (d, J = 4.65 Hz, 4H) 4.56 (quin, J = 7.21 Hz, | LCMS Method D: Rt = 0.89 min, [M + H]$^+$ = 666.5 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 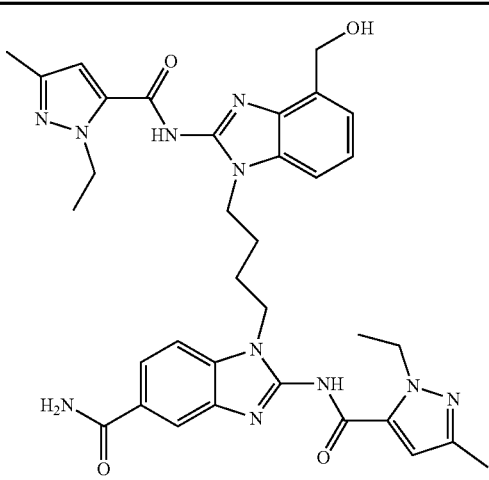 | | 4H) 4.83 (s, 2H) 6.60 (d, J = 8.56 Hz, 2H) 7.06-7.12 (m, 1H) 7.14-7.23 (m, 1 H) 7.31 (br. s., 1 H) 7.41 (d, J = 7.83 Hz, 1H) 7.53 (d, J = 8.31 Hz, 1H) 7.75 (dd, J = 8.56,1.47 Hz, 1H) 7.89-8.01 (m, 2H) 12.17 (br. s., 1 H) 12.80 (br. s., 2H) | |
| Example 151 | 1-(4-(4-(2-(dimethylamino)-2-oxoethoxy)-2-(1-ethyl-3-methyl 1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide | Method 16 | $^1$H NMR (400 MHz, DMSO-$d_6$) δ ppm 1.18-1.38 (m,6H) 1.80-1.94 (m, 4H) 2.11 (s, 6H) 2.85 (s, 3H) 3.00 (s, 3H) 4.26 (d, J = 10.27 Hz, 4H) 4.49-4.64 (m, 4H) 5.02 (s, 2H) 6.60 (d, J = 9.29 Hz, 2H) 6.81-6.92 (m, 1H) 7.10-7.20 (m, 2 H) 7.30 (br. s., 1 H) 7.52 (d, J = 8.31 Hz, 1H) 7.75 (dd, J = 8.44, 1.35 Hz, 1H) 7.87-8.03 (m, 2 H) 12.09 (br. s., 1H) 12.80 (s, 1 H) | LCMS Method E: Rt = 0.88 min, [M + H]$^+$ = 737.5 |
| Example 152 | 1-(4-(4-(2-amino-2-oxoethoxy)-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide, 2Trifluoroacetic acid salt | Method 16 | $^1$H NMR (400 MHz, DMSO-$d_6$) d ppm 1.26-1.33 (m, 6H) 1.86 (br. s., 4H) 2.07-2.14 (m, 6H) 4.25 (d, J = 9.54 Hz, 6H) 4.51-4.60 (m, 4H) | LCMS Method D: Rt = 0.86 min, [M + H]$^+$ = 709.4 |

Table 1 provides Example 89 to Example 197. The compounds can be prepared by using synthetic methods described above.

| Example | Structure/Name | Synthetic Method | NMR | LCMS |
|---|---|---|---|---|
| | 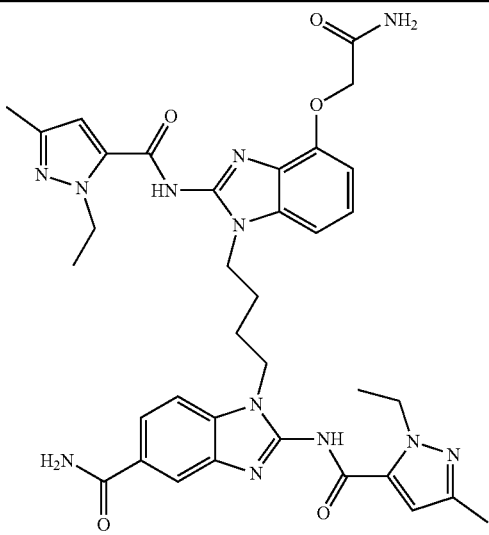 | | 6.59 (d, J = 7.09 Hz, 1H) 6.86 (dd, J = 5.62, 3.42 Hz, 1H) 7.13-7.16 (m, 2H) 7.30 (br. s., 1H) 7.50-7.59 (m, 2H) 7.76 (dd, J = 8.31,1.47 Hz, 1H) 7.89-8.01 (m, 2H) 8.44 (br. s., 1H) 12.77 (br. s., 2H) | |
| Example 153 | 2-(1-ethyl-3-methyl-1H-pyrazole-5-carboxamido)-1-(4-(2-(1-ethyl-3-methyl-1H-pyrazole-5-carboxamido)-4-(2-(methylamino)-2-oxoethoxy)-1H-benzo[d]imidazol-1-yl)butyl)-1H-benzo[d]imidazole-5-carboxamide | Method 16 | $^1$H NMR (400 MHz, DMSO-d$_6$) d ppm 1.25-1.35 (m, 6H) 1.86 (br. s., 4H) 2.04-2.18 (m, 6H) 2.75 (d, J = 4.40 Hz, 3H) 4.25 (br. s., 4H) 4.52-4.63 (m, 7H) 6.54-6.63 (m, 2H) 6.84-6.90 (m, 1H) 7.16 (d, J = 4.65 Hz, 2H) 7.31 (br. s., 1H) 7.53 (d, J = 8.31 Hz, 1H) 7.76 (d, J = 8.31 Hz, 1H) 7.90-8.01 (m, 2H) 8.64 (d, J = 4.40 Hz, 1H) 12.31 (br. s., 1H) 12.80 (br. s., 1H) | LCMS Method D: Rt = 0.89 min, [M + H]$^+$ = 723.5 |
| Example 154 | 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-N-(2-morpholinoethyl)-1H-benzo[d]imidazole-5-carboxamide, 3Trifluoroacetic acid salt | Method 11 | $^1$H NMR (400 MHz, DMSO-d$_6$) δ ppm 9.66 (br. s., 1H) 8.70-8.77 (m, 1H) 7.98 (s, 3H) 7.68-7.81 (m, 2H) 7.57 (dd, J = 19.20, 8.34 Hz, 2H) 7.38 (br. s., 1H) | LCMS Method C: Rt = 0.75 min, [M + H]$^+$ = 792.7 |

Table 1 provides Example 89 to Example 197. The compounds can be prepared by using synthetic methods described above.

| Example | Structure/Name | Synthetic Method | NMR | LCMS |
|---|---|---|---|---|
| | | | 6.61 (d, J = 9.60 Hz, 2H) 4.51-4.66 (m, 4H) 4.29 (br. s., 4H) 4.03 (d, J = 11.87 Hz, 2H) 3.54-3.75 (m, 6H) 3.35 (br. s., 2H) 3.16 (d, J = 9.60 Hz, 2H) 2.07-2.13 (m, 1H) 2.11 (s, 6H) 1.88 (br. s., 4H) 1.31 (m, J = 7.07 Hz, 6H). | |
| Example 155 | 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-N,N-dimethyl-1H-benzo[d]imidazole-5-carboxamide | Method 11 | ¹H NMR (400 MHz, DMSO-d₆) δ ppm 12.73-12.87 (m, 2H) 7.97 (s, 1H) 7.75 (d, J = 8.34 Hz, 1H) 7.48-7.58 (m, 3H) 7.34 (br. s., 1H) 7.24 (dd, J = 8.34, 1.26 Hz, 1H) 6.60 (d, J = 9.60 Hz, 2H) 4.56 (d, J = 7.07 Hz, 4H) 4.27 (d, J = 6.32 Hz, 4H) 2.95 (br. s., J = 15.66 Hz, 6 H) 2.09 (d, J = 1.77 Hz, 6H) 1.87 (br. s.,4H) 1.30 (m, J = 7.07 Hz, 6H) 1.23 (s, 1H) | LCMS Method C: Rt = 0.86 min, [M + H]⁺ = 707.7 |
| Example 156 | 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-N-methyl-1H-benzo[d]imidazole-5-carboxamide, 2Trifluoroacetic acid salt | Method 11 | ¹H NMR (400 MHz, DMSO-d₆) δ ppm 12.84 (br. s., 2H) 8.41 (d, J = 4.55 Hz, 1H) 7.95 (d, J = 14.15 Hz, 3H) 7.75 (d, J = 8.34 Hz, 1H) 7.69 (d, J = 8.34 | LCMS Method C: Rt = 0.80 min, [M + H]⁺ = 693.6 |

Table 1 provides Example 89 to Example 197. The compounds can be prepared by using synthetic methods described above.

| Example | Structure/Name | Synthetic Method | NMR | LCMS |
|---|---|---|---|---|

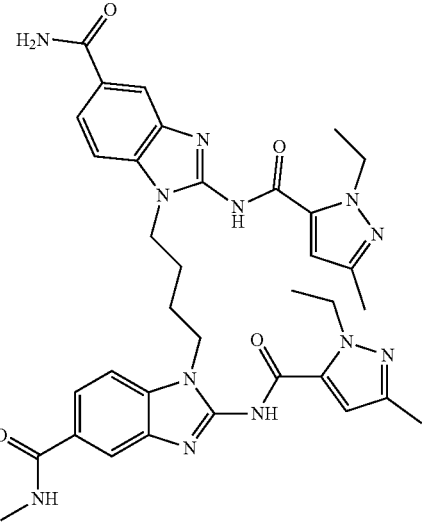

| Example 157 | 2-(1-ethyl-3-methyl-1H-pyrazole-5-carboxamido)-1-(4-(2-(1-ethyl-3-methyl-1H-pyrazole-5-carboxamido)-7-isopropoxy-1Hbenzo[d]imidazol-1-yl)butyl)-1H-benzo[d]imidazole-5-carboxamide | Method 11 | $^1$H NMR (400 MHz, DMSO-$d_6$) δ 12.78 (br s, 2H), 8.02-7.92 (m, 2H), 7.75 (dd, J = 8.4, 1.3 Hz, 1H), 7.53 (d, J = 8.4 Hz, 1H), 7.32 (br s, 1H), 7.14-7.03 (m, 2H), 6.85-6.75 (m, 1H), 6.59 (s, 2H), 4.74-4.63 (m, 1H), 4.62-4.51 (m, 4H), 4.43-4.22 (m, 4H), 2.11 (s, 3H), 2.10 (s, 3H), 1.97-1.69 (m, 4H), 1.35-1.23 (m, 6H), 1.15 (d, J = 6.0 Hz, 6H) | LCMS Method A: Rt = 1.518 min, [M + H]$^+$ = 694.5 |
| Example 158 | 23-(2-(dimethylamino)-N-methylacetamido)-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]-pentaazacyclohenicosine-3-carboxamide, Trifluoroacetic acid salt | Method 13 | $^1$H NMR (METHANOL-$d_4$) δ 8.35 (s, 1H), 7.99 (s, 2H), 7.88 (s, 1H), 7.72 (d, 1H), 7.46 (br. s., 2H), 7.35 (d, 1H), 6.75 (s, 1H), 4.47-4.62 (m, 3H), 4.35 (br. s., 6H), 3.71 (br. s., 2H), 3.43 (s, 2H), | LCMS Method A: Rt = 0.82 min, [M + H]$^+$ = 790.6 |

Hz, 1H) 7.54 (dd, J = 8.46, 2.65 Hz, 2H) 7.34 (br. s., 1H) 6.59 (s, 2H) 4.56 (q, J = 6.99 Hz, 4H) 4.27 (br. s., 4H) 2.79 (d, J = 4.29 Hz, 3H) 2.09 (s, 6H) 1.86 (br. s., 4H) 1.29 (t, J = 6.95 Hz, 6H)

Table 1 provides Example 89 to Example 197. The compounds can be prepared by using synthetic methods described above.

| Example | Structure/Name | Synthetic Method | NMR | LCMS |
|---|---|---|---|---|
| | 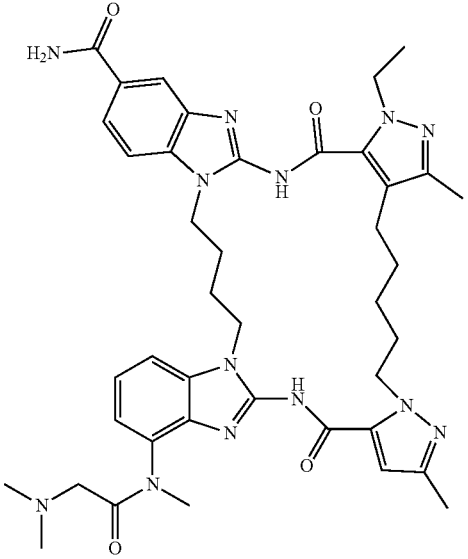 | | 3.12 (s, 1H), 2.79-2.92 (m, 6H), 2.29 (d, J = 6.3 Hz, 2H), 2.20 (br. s., 4H), 2.05 (br. s., 4H), 1.90 (br. s., 6H), 1.62 (br. s., 2H), 1.32-1.45 (m, 6H) | |
| Example 159 | 23-(2-amino-N-methylacetamido)-8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]-pentaazacyclohenicosine-3-carboxamide | Method 13 | $^1$H NMR (DMSO-d$_6$) δ 7.95-8.07 (m, 2H), 7.88-7.15 (m, 5H), 6.75 (br s, 1H), 4.69 (br. s, 2H), 4.35 (br. s, 6H), 4.49 (d, J = 7.1 Hz, 2H), 4.22 (br. s, 6H), 3.34 (s, 3H), 2.75-2.89 (m, 2H), 2.21 (s, 2H), 2.17 (s, 2H), 1.91 (br. s, 3H), 1.72-1.85 (m, 3H), 1.50 (br. s, 2H), 1.24-1.41 (m, 6H) | LCMS Method A: Rt = 0.81 min, [M + H]$^+$ = 762.7 |
| Example 160 | 8-ethyl-10,18-dimethyl-23-(N-methyl-2-(methylamino)acetamido)-7,20-dioxo-6,7,8,11,12,13,14,15,20,21,28,29,30,31-tetradecahydrobenzo[4,5]imidazo[1,2-a]benzo[4,5]imidazo[2,1- | Method 13 | $^1$H NMR (METHANOL-d$_4$) δ 7.99 (s, 2H), 7.88 (s, 1H), 7.72 (d, 1H), 7.46 (br. s., 2H), 7.35 (d, 1H), 6.75 (s, 1H), 4.47-4.62 (m, | LCMS Method A: Rt = 0.80 min, [M + H]$^+$ = 776.6 |

| Example | Structure/Name | Synthetic Method | NMR | LCMS |
|---|---|---|---|---|
| | p]dipyrazolo[5,1-e:4',3'-l][1,3,6,15,17]-pentaazacyclohenicosine-3-carboxamide Trifluoroacetic acid salt<br>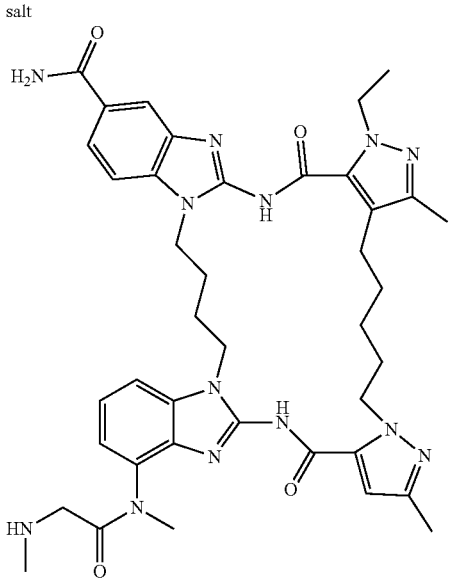 | | 3H), 4.35 (br. s., 6H), 3.71 (br. s., 2H), 3.43 (s, 2H), 3.12 (s, 1H), 2.79-2.92 (m, 3H), 2.29 (d, J = 6.3 Hz, 2H), 2.20 (br. s., 4H), 2.05 (br. s., 6H), 1.90 (br. s., 6H), 1.62 (br. s., 2H), 1.32-1.45 (m, 6H) | |
| Example 161 | (E)-1-(4-(5-carbamoyl-2-(1-ethyl-3-methyl-1H-pyrazole-5-carboxamido)-1H-benzo[d]imidazol-1-yl)but-2-en-1-yl)-7-(cyanomethyl)-2-(1-ethyl-3-methyl-1H-pyrazole-5-carboxamido)-1H-benzo[d]imidazole-5-carboxamide<br>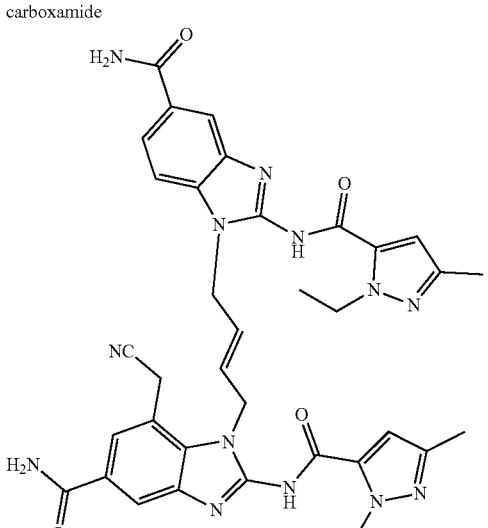 | Method 9 | $^1$H NMR (400 MHz, DMSO-$d_6$) δ 12.90 (br s, 2H), 8.12-7.80 (m, 4H), 7.73 (d, J = 6.5 Hz, 2H), 7.48-7.30 (m, 3H), 6.55 (s, 2H), 6.01-5.94 (m, 1H), 5.62-5.54 (m, 1H), 5.01 (s, 2H), 4.82 (s, 2H), 4.56-4.46 (m, 4H), 4.34 (s, 2H), 2.11 (s, 3H), 2.08 (s, 3H), 1.29-1.23 (m, 6H) | LCMS Method A: Rt = 1.29 min, [M + H]$^+$ = 716.4 |
| Example 162 | (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl- | Method 9 | $^1$H NMR (400 MHz, DMSO-$d_6$) δ 12.92 (br s, 2H), 8.02-7.91 (m, 4H), 7.72 (d, J = | LCMS Method A: Rt = 1.234 min, |

Table 1 provides Example 89 to Example 197. The compounds can be prepared by using synthetic methods described above.

| Example | Structure/Name | Synthetic Method | NMR | LCMS |
|---|---|---|---|---|
| | 1Hpyrazole-5-carboxamido)-7-(hydroxymethyl)-1H-benzo[d]imldazole-5-carboxamide | | 10.1 Hz, 2H), 7.71 (s, 1H) 7.43 (d, J = 8.4 Hz, 1H), 7.34 (br s, 2H), 6.52 (d,J = 6.7 Hz, 2H), 5.98 (d, 7 15.5 Hz, 1H), 5.51 (dd, J = 13.2, 8.0 Hz, 1H), 5.09 (s, 2H), 4.81 (d, J = 4.2 Hz, 2H), 4.61 (s, 2H), 4.55-4.48 (m, 4H), 2.12 (s, 3H), 2.11 (s, 3H), 1.29-1.25 (m, 6H) | [M + H]+ = 707.9 |
| Example 163 | (E)-2-(1-ethyl-3-methyl-1H-pyrazole-5-carboxamido)-1-(4-(2-(1-ethyl-3-methyl-1H-pyrazole-5-carboxamido)-4-(morpholinomethyl)-1H-benzo[d]imidazol-1-yl)but-2-en-1-yl)-1H-benzo[d]imidazole-5-carboxamide | Method 11 | $^1$H NMR (400 MHz, DMSO-d$_6$) δ 12.90 (br s, 2H), 9.81 (s, 1H), 7.97 (s, 2H), 7.72-7.23 (m, 6H), 6.56 (d, J = 15.7 Hz, 2H), 5.93-5.85 (m, 2H), 4.85 (br s, 4H), 4.72 (br s, 2H), 4.54-4.50 (m, 4H), 3.8 (brs, 2H), 3.5 (br s, 2H), 3.26 (br s, 4H), 2.13 (s, 6H), 1.30- 1.22 (m, 6H) | LCMS Method A: Rt = 1.308 min, [M + H]+ = 733 |
| Example 164 | 2-(1-ethyl-3-methyl-1Hpyrazole-5-carboxamido)-1-(4-(2-(1-ethyl-3-methyl-1H-pyrazole-5-carboxamido)-7-(morpholinomethyl)-1Hbenzo[d]imidazol-1-yl)butyl)- | Method 11 | $^1$H NMR (400 MHz, DMSO-d$_6$) δ ppm 12.84 (s, 2), 10.03 (s, 1), 7.97 (t, J = 4.4 Hz, 2), 7.75 (dd, J = 8.4, | LCMS Method A: Rt = 1.329 min, [M + H]+ = |

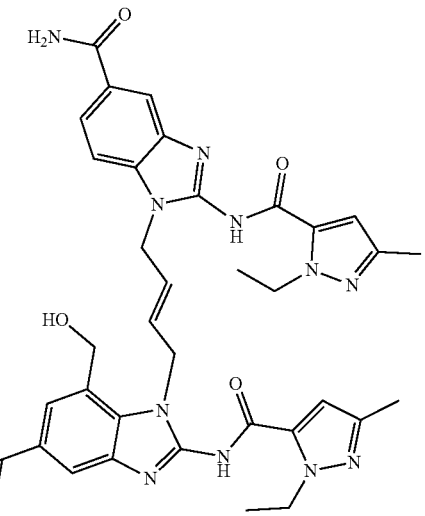

| Example | Structure/Name | Synthetic Method | NMR | LCMS |
|---|---|---|---|---|
| | 1Hbenzo[d]imidazole-5-carboxamide,Trifluoroacetic acid salt | | 1.3 Hz, 1), 7.66 (d, J = 7.6 Hz, 1), 7.51 (d, J = 8.4 Hz, 1), 7.32 (d, J = 12.3 Hz, 3), 6.60 (t, J = 11.2 Hz, 2), 4.52 (dd, J = 18.6, 13.6 Hz, 8H), 4.25 (d, J = 6.2 Hz, 2H), 3.89 (s, 2H), 3.61 (s, 2H, 3.25 (s, 4H, 2.08 (d, J = 15.6 Hz, 6H), 1.81 (d, J = 22.1 Hz, 4H), 1.30 (t, J = 7.0 Hz, 6H) | 735.3 |
| Example 165 | 2-(1-ethyl-3-methyl-1Hpyrazole-5-carboxamido)-1-(4-(2-(1-ethyl-3-methyl-1Hpyrazole-5-carboxamido)-7-methyl-1H-benzo[d]imidazol-1-yl)butyl)-1Hbenzo[d]imidazole-5-carboxamide | Method 11 | $^1$H NMR (400 MHz, DMSO-d$_6$) δ ppm 12.77 (s, 2H), 7.97 (t, J = 4.1 Hz, 2H), 7.76 (dd, J = 8.4,1.4 Hz, 1H), 7.58 (d, J = 8.4 Hz, 1H), 7.37 (m, 2H), 7.09 (t, J = 7.7 Hz, 1H), 7.00 (d, J = 7.5 Hz, 1H), 6.58 (d, J = 21.8 Hz, 2H), 4.56 (dq, J = 14.2, 7.0 Hz, 4H), 4.39 (t, J = 6.8 Hz, 2H), 4.28 (d, J = 6.9 Hz, 2H), 2.61 (d, 7 8.6 Hz, 3H), 2.09 (d, J = 14.8 Hz, 6H), 1.88 (dd, J = 29.7, 5.6 Hz, 4H), 1.29 (dt, J = 9.8, 7.1 Hz, 6H) | LCMS Method A: Rt = 1.470 min, [M + H]$^+$ = 650.3 |
| Example 166 | (E)-2-(1-ethyl-3-methyl-1Hpyrazole-5-carboxamido)-1-(4-(2-(1-ethyl-3-methyl-1Hpyrazole-5-carboxamido)-4-methoxy-1Hbenzo[d]imidazol-1-yl)but-2-en-1-yl)-1Hbenzo[d]imidazole-5-carboxamide | Method 11 | $^1$H NMR (400 MHz, DMSO-d6) δ ppm 7.97 (m, 2 H), 7.72 (d, J = 8.3 Hz, 1H), 7.43 (d, J = 8.3 Hz, 1H), 7.35 (s, 1H), 7.14 (t, | LCMS Method A: Rt = 1.496 min, [M + H]$^+$ = 664.2 |

Table 1 provides Example 89 to Example 197. The compounds can be prepared by using synthetic methods described above.

| Example | Structure/Name | Synthetic Method | NMR | LCMS |
|---|---|---|---|---|
| | | | J = 8.1 Hz, 1H), 7.06 (d, J = 8.0 Hz, 1H), 6.89 (s, 1H), 6.58 (m, 2 H), 5.90 (s, 2 H), 4.82 (m, 4H), 4.52 (m, 4H), 3.94 (s, 3H), 2.14 (s, 6H), 1.30-1.24 (m, 6 H) | |
| Example 167 | (E)-2-(1-ethyl-3-methyl-1Hpyrazole-5-carboxamido)-1-(4-(2-(1-ethyl-3-methyl-1Hpyrazole-5-carboxamido)-1H-benzo[d]imidazol-1-yl)but-2-en-1-yl)-1Hbenzo[d]imidazole-5-carboxamide | Method 11 | $^1$H NMR (400 MHz, DMSO-d6) δ ppm 12.76 (br. m., 2H), 7.96 (m, 2H), 7.71 (d, J = 8.5 Hz, 1H), 7.50 (s, 1H), 7.43 (d, J = 8.4 Hz, 1H), 7.38 (s, 1H), 7.33 (s, 1 H), 7.16 (m, 2H), 6.55 (d, J = 7.4 Hz, 2H), 5.91 (s, 2H), 4.83 (s, 4 H), 4.53 (q, J = 7.1 Hz, 4H), 2.13 (s, 6H), 1.28 (m, 6H) | LCMS Method A: Rt = 1.447 min, [M + H]$^+$ = 634.2 |
| Example 168 | (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1Hpyrazole-5-carboxamido)-7-(morpholinomethyl)-1H-benzo[d]imidazole-5-carboxamide | Method 16 | $^1$H NMR (400 MHz, DMSO-d6) δ ppm 13.10 (br. s., 2H), 8.01 (m, 4H), 7.75 (m, 2 H), 7.43 (m, 2 H), 7.36 (s, 1H), 6.58 (s, 2H), 5.92 (d, J = 16.3 | LCMS Method A: Rt = 1.255 min, [M + H]$^+$ = 776.8 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 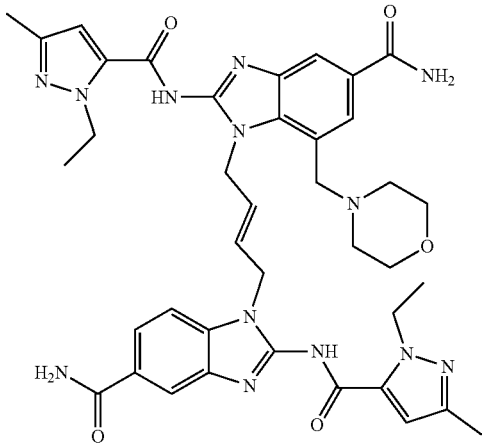 | | Hz, 1H), 5.46 (d, J = 15.6 Hz, 1H), 5.11 (s, 2H), 4.80 (s, 2H), 4.54 (br. s., 6H), 2.14 (s, 6H), 1.31-1.26 (m, 6 H) | |
| Example 169 | Structure not determined One of two possible structures 8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,9,15,17]-hexaazacyclohenicosine-24-carboxamide 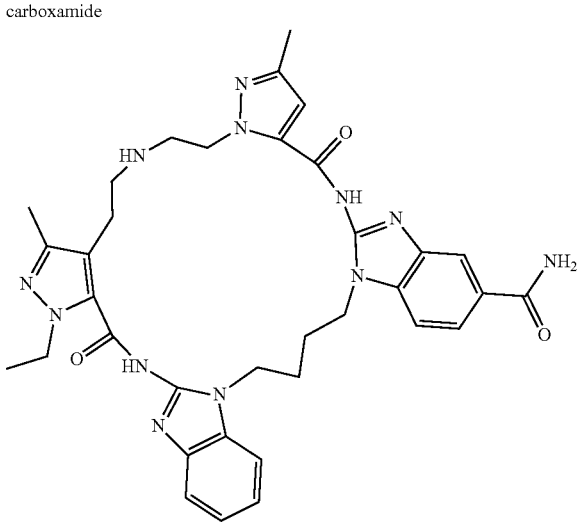 8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,9,15,17]-hexaazacyclohenicosine-3-carboxamide | Method 13 | $^1$H NMR (400 MHz, MeOD-d4) δ ppm 8.07 (d, J = 1.3 Hz, 1H), 7.89 (dd, J = 8.6, 1.4 Hz, 1H), 7.60 (d, J = 8.4 Hz, 1H), 7.52 (d, J = 7.4 Hz, 1H), 7.31-7.44 (m, 3 H), 6.06 (s, 1H), 4.87 (br. s., 2H), 4.26 (br. s., 2H), 4.20 (br. s., 2H), 4.08-4.16 (m, 2 H), 3.59 (t, J = 4.9 Hz, 2H), 3.36-3.42 (m, 2H), 3.08-3.14 (m, 2 H), 2.29 (s, 3H), 2.21 (s, 3H), 2.04 (br. s., 4H), 1.09 (t, J = 7.1 Hz, 3H) | LCMS Method A: Rt = 1.270 min, [M + H]$^+$ = 677.3 |

Table 1 provides Example 89 to Example 197. The compounds can be prepared by using synthetic methods described above.

| Example | Structure/Name | Synthetic Method | NMR | LCMS |
|---|---|---|---|---|
| Example 170 | 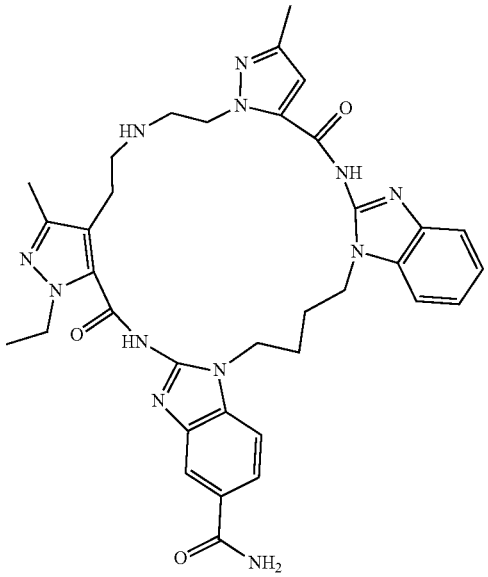 [SMILES: CCn1nc(C)c2c1C(=O)Nc1nc3cc(C(N)=O)ccc3n1CCCCn1c(nc3ccccc31)NC(=O)c1cc(C)nn1CCNCC2]<br>Structure not determined<br>One of two possible structures<br>8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,9,15,17]-hexaazacyclohenicosine-24-carboxamide<br><br>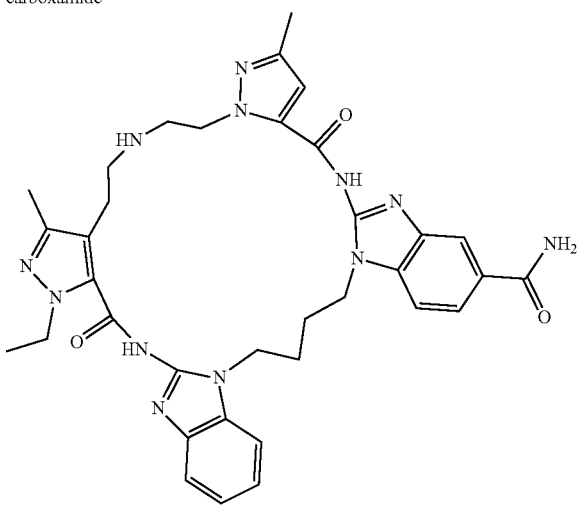<br>8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,9,15,17]-hexaazacyclohenicosine-3-carboxamide | Method 13 | $^1$H NMR (MeOD-d4) δ ppm 7.89-7.96 (m, 2H), 7.52-7.61 (m, 3H), 7.34-7.43 (m, 2H), 6.07 (s, 1H), 4.85-4.94 (br. m.( 2H), 4.19-4.26 (m, 1H), 4.13 (d, J = 7.3 Hz, 1H), 3.57 (t, J = 4.9 Hz, 2H), 3.39 (t, J = 6.3 Hz, 2H), 2.29 (s, 3H), 2.21 (s, 3H), 2.05 (br. s., 4H), 1.08 (t, J = 7.1 Hz, 3H) | LCMS Method A:<br>Rt = 1.289 min,<br>[M + H]$^+$ = 677.2 |

| Example | Structure/Name | Synthetic Method | ¹H NMR | LCMS |
|---|---|---|---|---|
| Example 171 | 1,1'-(2,3-difluorobutane-1,4-diyl)bis(2-(1-ethyl-3-methyl-1H-pyrazole-5-carboxamido)-1H-benzo[d]imidazole-5-carboxamide) | Method 15 | ¹H NMR (DMSO-d6) δ ppm 12.95 (s, 2H), 8.03 (s, 2H), 8.00 (br. s., 2H), 7.82 (d, J = 8.4 Hz, 2H), 7.59 (d, J = 8.4 Hz, 2H), 7.36 (br. s., 2H), 6.67 (s, 2H), 4.80-4.92 (m, 2H), 4.59 (q, J = 7.2 Hz, 4H), 2.06 (s, 6H), 1.33 (t, J = 7.1 Hz, 6H) | LCMS Method A: Rt = 1.268 min, [M + H]⁺ = 715.2 |
| Example 172 | N,N'-(4-carbamoyl-8,9,16,17,18,19-hexahydro-7H-6,10-dioxa-2,14,15a,19a-tetraaza-cyclopentadeca[l,2,3-cd:11,10,9-c'd']diindene-1,15-diyl)bis(1-ethyl-3-methyl-1H-pyrazole-5-carboxamide), 2Trifluoroacetic acid salt | Method 21 | ¹H NMR (400 MHz, DMSO-d₆) δ ppm 12.62-13.07 (m, 1H), 8.02 (br. s., 1H), 7.67 (s, 1H), 7.45 (s, 1H), 7.38 (br. s., 1H), 7.13-7.21 (m, 2 | LCMS Method D: Rt = 1.05 min, [M + H]⁺ = 708.9 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 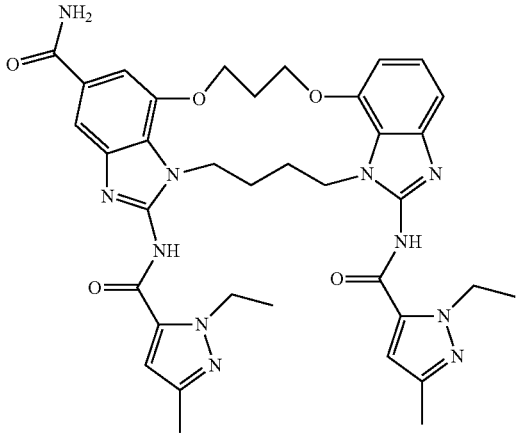 [SMILES: CCn1nc(C)cc1C(=O)Nc1nc2cccc3c2n1CCCCn1c(NC(=O)c2cc(C)nn2CC)nc2cc(C(N)=O)cc(c21)OCCCO3] | | H), 6.96 (dd, J = 6.24, 3.06 Hz, 1H), 6.59 (d, J = 10.51 Hz, 2 H), 4.54-4.67 (m, 6H), 4.32-4.53 (m, 10 H), 2.30-2.36 (m, 1 H), 2.14-2.25 (m, 1H), 2.08-2.14 (m, 6H), 2.05 (br. s., 3H), 1.26-1.39 (m, 6 H) | |
| Example 173 | 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-4-hydroxy-1H-benzo[d]imidazole-5-carboxamide 2,2,2-trifluoroacetate 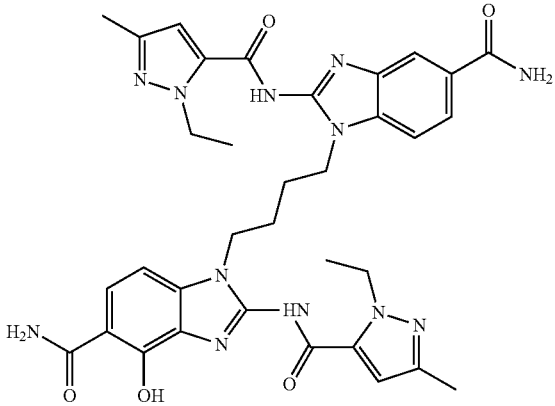 [SMILES: CCn1nc(C)cc1C(=O)Nc1nc2cc(C(N)=O)ccc2n1CCCCn1c(NC(=O)c2cc(C)nn2CC)nc2c(O)c(C(N)=O)ccc21] | Method 9 | $^1$H NMR (400 MHz, CD$_3$OD) δ ppm 7.88 (d, J = 1.2 Hz, 1H), 7.77 (dd, J = 8.4, 1.2 Hz, 1H), 7.65 (d, J = 8.8 Hz, 1H), 7.41 (d, J = 8.4 Hz, 1H), 6.91 (d, J = 8.4 Hz, 1H), 6.59 (d, J = 3.2 Hz, 2H), 4.68-4.59 (m, 4H), 4.29-4.26 (m, 4H), 2.22 (s, 3H), 2.21 (s, 3H), 2.05 (s, 4H), 1.42-1.38 (m, 6H) | LCMS Method A: Rt = 1.362 min, [M + H]$^+$ = 695.6 |
| Example 174 | 1,1'-(Ethane-1,2-diyl)bis(2-(1-ethyl-3-methyl-1H-pyrazole-5-carboxamido)-1H-benzo[d]imidazole-5-carboxamide) | Method 15 | $^1$H NMR (400 MHz, DMSO-d$_6$) δ ppm 12.53 (s, 2H), 8.01 (s, 2H), 7.9 (s, 2H), 7.89 (s, 2H), 7.59 (s, 2H), 7.35 (s, 2H), 7.25 (s, 1H), 7.12 (s, 1H), 6.99 (s, 1H), 5.34 (s, 2H), 4.43 (q, J = 6.7 Hz, 4H), 1.95 (s, 6H), 1.24 (t, J = 8.0 Hz, 6H) | LCMS Method A: Rt = 1.25 min, [M + H]$^+$ = 651.2 |

Table 1 provides Example 89 to Example 197. The compounds can be prepared by using synthetic methods described above.

| Example | Structure/Name | Synthetic Method | NMR | LCMS |
|---|---|---|---|---|
| Example 175 | 1-(2-(N-(2-(5-Carbamoyl-2-(1-ethyl-3-methyl-1H-pyrazole-5-carboxamido)-1H-benzo[d]imidazol-1-yl)ethyl)-2-hydroxyacetamido)ethyl)-2-(1-ethyl-3-methyl-1H-pyrazole-5-carboxamido)-1H-benzo[d]imidazole-5-carboxamide | Method 16 | $^1$H NMR (400 MHz, DMSO-$d_6$) δ ppm 12.86 (s, 1H), 12.77 (s, 1H), 7.98 (d, J = 8.0 Hz, 3H), 7.76 (d, J = 8.0 Hz, 2H), 7.51 7.54-7.48 (m, 2H), 7.35-7.32 (s, 2H), 6.64 (s, 1H), 6.59 (s, 1H), 4.59-4.51 (m, 4H), 4.41-4.38 (m, 4H), 3.85-4.82 (m, 2H), 3.70-3.64 (m, 4H), 2.09-2.08 (m, 5H), 1.33-1.30 (m, 5H) | LCMS Method A: Rt = 1.23 min, [M + H]$^+$ = 751.9 |
| Example 176 | 1-(2-(2-Amino-N-(2-(5-carbamoyl-2-(1-ethyl-3-methyl-1H-pyrazole-5-carboxamido)-1H-benzo[d]imidazol-1-yl)ethyl)acetamido)ethyl)-2-(1-ethyl-3-methyl-1H-pyrazole-5-carboxamido)-1H benzo[d]imidazole-5-carboxamide | Method 15 | $^1$H NMR (400 MHz, DMSO-$d_6$) δ ppm 12.91 (s, 2H), 8.03-7.99 (m, 6H), 7.81-7.78 (m, 2H), 7.63 (d, J = 8.0 Hz, 1H), 7.55 (d, J = 8.0 Hz, 1H), 7.37 (d, J = 4.0 Hz, 2H), 6.67 (s, 1H), 6.58 (s, 1H), 4.60-4.50 (m, 6H), 4.42 (d, J = 6.0 Hz, 2H), 3.95 (t, J = 6.0 Hz, 2H), 3.95 (t, J = 6.0 Hz, 2H), 3.56 (d, J = 4.0 Hz, 2H), 2.06 (d, J = 8.0 Hz, 5H), 1.34-1.30 (m, 5H) | LCMS Method A: Rt = 1.16 min, [M + H]$^+$ = 750.7 |

Table 1 provides Example 89 to Example 197. The compounds can be prepared by using synthetic methods described above.

| Example | Structure/Name | Synthetic Method | NMR | LCMS |
|---|---|---|---|---|
| Example 177 | 8-Ethyl-10,18-dimethyl-7,20-dioxo-6,7,8,11,12,13,14,15,20,21,28,29-dodecahydrobenzo[4,5]imidazo[2,1-b]benzo[4,5]imidazo[1,2-f]dipyrazolo[5,1-j:4',3'-q][1,3,6,8,11]pentaazacyclononadecine-3,24-dicarboxamide | Method 19 | $^1$H NMR (400 MHz, DMSO-$d_6$) δ ppm 12.74 (s, 2H), 8.06-7.90 (m, 4H), 7.61 (s, 2H), 7.34 (s, 2H), 6.90 (s, 2H), 6.28 (s, 1H), 4.69 (s, 4H), 4.56 (s, 2H), 4.27 (s, 2H), 2.69 (d, J = 12.7 Hz, 2H), 2.11 (d, J = 22.2 Hz, 6H), 1.87 (s, 2H), 1.58 (s, 2H), 1.34 (s, 2H), 1.21 (dd, J = 15.2, 8.2 Hz, 3H) | LCMS Method A: Rt = 1.299 min, [M + H]$^+$ = 691.2 |
| Example 178 | 3,24-dicarbamoyl-8-ethyl-10,18-dimethyl-7,20-dioxo-8,11,12,13,14,15,20,21,28,29,31,32-dodecahydro-1H-benzo[4,5]imidazo[2,1-b]benzo[4,5]imidazo[1,2-i]dipyrazolo[5,1-m:4',3'-t][1,3,6,9,11,14]hexaazacyclodocosine-30-carboxylate | Method 19 | $^1$H NMR (400 MHz, CD$_3$OD) δ ppm 8.01-7.95 (m, 2H), 7.86-7.80 (m, 2H), 7.50-7.36 (m, 2H), 6.72-6.59 (m, 1H), 4.76 (t, J = 6 Hz, 1H), 4.65 (t, J = 6 Hz, 1H), 4.45-4.42 (m, 4H), 4.32 (s, 1H), 3.78-3.65 (m, 4H), 2.84 (d, J = 8 Hz, 2H), 2.71 (d, J = 8 Hz, 2H), 2.27 (s, 1H), 2.72-2.20 (m, 2H), 2.16 (s, 1H), 1.88-1.78 (m, 2H), 1.52-1.43 (m, 2H), 1.37-1.32 (m, 3H), 1.23-1.16 (m, 2H), 0.80 (s, 4H), 0.72 (s, 3H) | LCMS Method A: Rt = 1.356 min, [M + H]$^+$ = 834.7 |
| Example 179 | 8-Ethyl-10,18-dimethyl-7,20-dioxo-7,8,11,12,13,14,15,20,21,28,29,30,31,32-tetradecahydro-1H-benzo[4,5]imidazo[2,1-b]benzo[4,5]imidazo[1,2-i]dipyrazolo[5,1-m:4',3'-t][1,3,6,9,11,14]hexaazacyclodocosine-3,24-dicarboxamide, trifluoroacetic acid salt | Method 19 | $^1$H NMR (400 MHz, CD$_3$OD) δ 8.06-8.06 (m, 1H), 8.01 (s, 1H), 7.95-7.90 (m, 2H), 7.68 (d, J = 8.0 Hz, 1H), 7.60 (d, J = 12 Hz, 1H), 6.85 (s, 1H), 4.74-4.71 (m, | LCMS Method A: Rt = 1.23 min, [M + H]$^+$ = 734.0 |

| Example | Structure/Name | Synthetic Method | NMR | LCMS |
|---|---|---|---|---|
| | 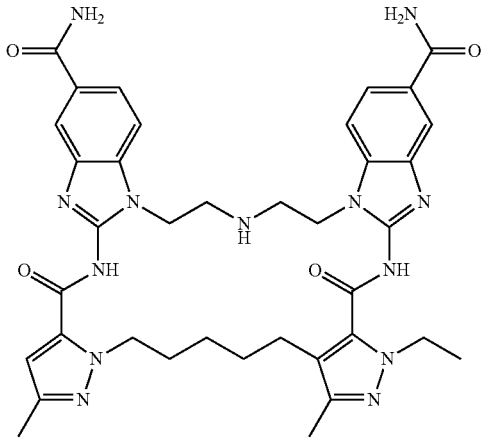 [SMILES: CCn1nc(C)c2c1C(=O)Nc1nc3cc(C(N)=O)ccc3n1CCNCCn1c(nc3cc(C(N)=O)ccc31)NC(=O)c1cc(C)nn1CCCCC2] | | 3H), 4.51 (q, J = 6.7 Hz, 2H), 4.35 (t, J = 8.0 Hz, 2H), 3.80-3.77 (m, 2H), 3.67 (t, J = 4 Hz, 2H), 2.80 (t, J = 8 Hz, 2H), 2.24 (s, 3H), 2.17 (s, 3H), 1.90-1.83 (m, 2H), 1.46-1.39 (m, 2H), 1.33 (t, J = 8.0 Hz, 3H), 1.26-1.18(s, 2H) | |
| Example 180 | 8-Ethyl-30-glycyl-10,18-dimethyl-7,20-dioxo-6,7,8,11,12,13,14,15,20,21,29,30,31,32-tetradecahydro-28H-benzo[4,5]imidazo[2,1-b]benzo[4,5]imidazo[1,2-i]dipyrazolo[5,1-m:4',3'-t][1,3,6,9,11,14]hexaazacyclodocosine-3,24-dicarboxamide trifluoroacetic acid salt | Method 19 | $^1$H NMR (400 MHz, CD$_3$OD) δ 8.01-7.98 (m, 2H), 7.95-7.88 (m, 2H), 7.65-7.50 (m, 2H), 6.67-6.53 (m, 1H), 4.76 (t, J = 6 Hz, 3H), 4.65-4.60 (m, 1H), 4.54-4.50 (m, 2H), 4.44-4.41 (m, 1H), 3.91-3.88 (m, 1H), 3.80-3.72 (m, 1H), 3.45-3.45 (m, 3H), 3.40-3.37 (m, 3H), 2.19 (t, J = 14 Hz, 3H), 2.05 (s, 1H), 1.85-1.76 (m, 2H), 1.36 (t, J = 6.0 Hz, 2H), 1.29 (t, J = 6.0 Hz, 2H), 1.19-1.12 (m, 2H) | LCMS Method A: Rt = 1.21 min, [M + H]$^+$ = 791.6 |
| Example 181 | Structure not determined, is one of the following compounds: 8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide | Method 19 | $^1$H NMR (400 MHz, DMSO-d$_6$) δ ppm 8.03 (s, 3H), 7.84 (d, J = 8.0 Hz, 1H), 7.66 (d, J = 8.0 Hz, 1H), 7.57-7.55 (s, 1H), 7.37 (s, 1H), 7.28-7.22 (m, 2H), 7.13 (s, 1H), 7.00 (s, 1H), 6.58 | LCMS Method A: Rt = 1.489 min, [M + H]$^+$ = 676.9 |

Table 1 provides Example 89 to Example 197. The compounds can be prepared by using synthetic methods described above.

| Example | Structure/Name | Synthetic Method | NMR | LCMS |
|---|---|---|---|---|
| | 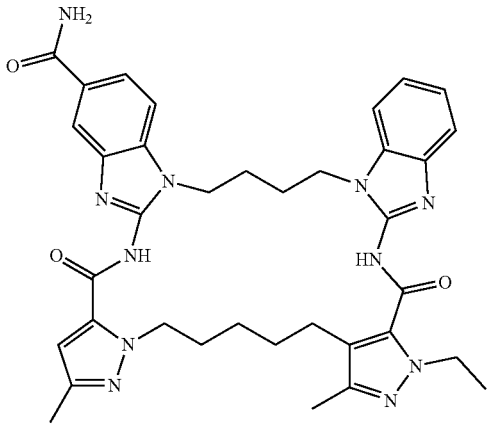 [SMILES: CCn1nc(C)c2c1C(=O)Nc1nc3ccccc3n1CCCCn1c(nc3cc(C(N)=O)ccc31)NC(=O)c1cc(C)nn1CCCCC2]<br>8-Ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3-carboxamide | | (s, 1H), 5.84 (s, 1H), 4.75 (t, 2H), 4.47 (q, J = 8.0 Hz, 2H), 4.28-4.22 (m, 4H), 2.82 (t, J = 8.0 Hz, 2H), 2.68-2.66 (m, 1H), 2.34-2.33 (m, 1H), 2.16 (s, 2H), 2.09 (s, 2H), 1.91 (s, 2H), 1.81 (s, 2H), 1.51-1.47 (m, 4H), 1.29 (t, J = 8.0 Hz, 2H), 1.23 (s, 2H) | |
| Example 182 | Structure not determined, is one of the following compounds:<br>8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-24-carboxamide<br>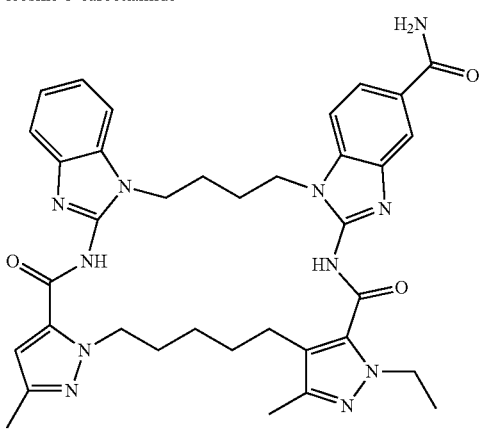 | Method 19 | $^1$H NMR (400 MHz, DMSO-d$_6$) δ ppm 8.03-7.99 (m, 2H), 7.84-7.80 (m, 1H), 7.62-7.54 (m, 3H), 7.38-7.35 (m, 1H), 7.61-7.54 (m, 2H), 7.10 (s, 1H), 6.97 (s, 1H), 6.57- | LCMS Method A: Rt = 1.489 min, [M + H]$^+$ = 677.0 |

Table 1 provides Example 89 to Example 197. The compounds can be prepared by using synthetic methods described above.

| Example | Structure/Name | Synthetic Method | NMR | LCMS |
|---|---|---|---|---|
| | 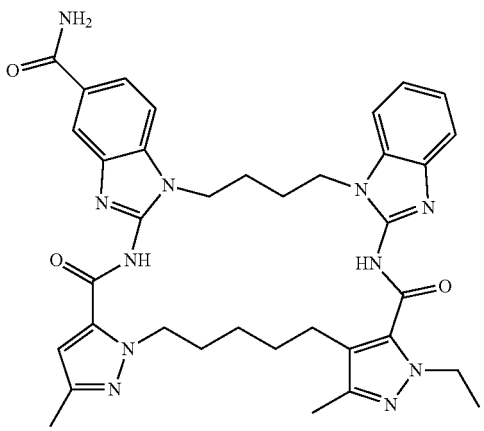 [SMILES: CCn1nc(C)c2c1C(=O)Nc1nc3ccccc3n1CCCCn1c(nc3cc(C(N)=O)ccc31)NC(=O)c1cc(C)nn1CCCCC2]<br>8-Ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3-carboxamide | | 6.55 (m, 1H), 4.77-4.72 (m, 2H), 4.50-4.45 (m, 2H), 4.27-4.22 (m, 3H), 2.85-2.80 (m, 2H), 2.69-2.67 (m, 1H), 2.34-2.32 (m, 1H), 2.17-2.13 (m, 3H), 2.10-2.07 (m, 3H), 1.93-1.89 (m, 3H), 1.83-1.79 (m, 2H), 1.51-1.46 (m, 2H), 1.40-1.35 (m, 2H), 1.29 (t, J = 6.0 Hz, 2H), 1.24-1.22 (m, 1H) | |
| Example 183 | 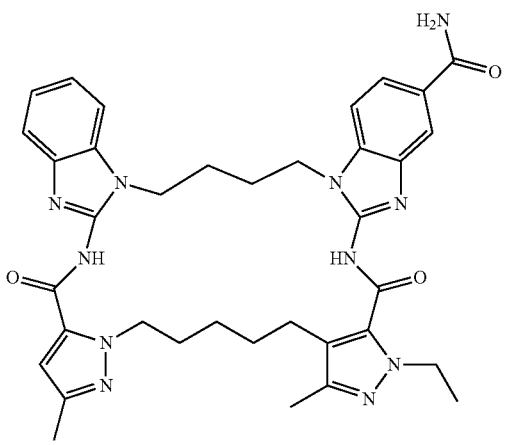<br>10,18-dimethyl-7,20-dioxo-6,7,8,11,12,13,14,-15,20,21,28,29,30,31-tetradecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide | Method 19 | $^1$H NMR (400 MHz, DMSO) δ 12.91 (s, 1H), 12.76 (s, 1H), 8.03 (s, 4H), 7.83 (m, 2H), 7.69-7.62 (m, 2H), 7.37 (br. s, 2H), | LCMS Method A: Rt = 1.283 min, [M + H]$^+$ = 691.2 |

-continued

Table 1 provides Example 89 to Example 197. The compounds can be prepared by using synthetic methods described above.

| Example | Structure/Name | Synthetic Method | NMR | LCMS |
|---|---|---|---|---|
| | 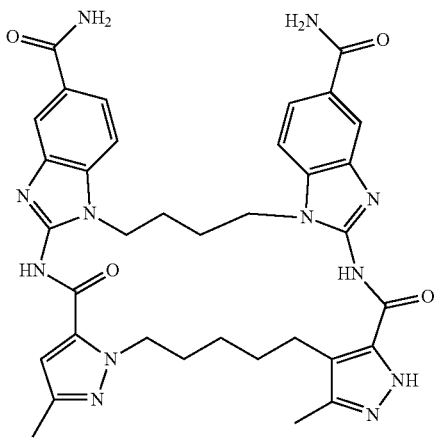 [SMILES: Cc1cc2n(n1)CCCCCc1c(C)n[nH]c1C(=O)Nc1nc3cc(C(N)=O)ccc3n1CCCCn1c(nc3cc(C(N)=O)ccc31)NC2=O] | | 6.57 (s, 1H), 4.75 (br. s, 2H), 4.26 (br. s, 4H), 2.87 (br. s, 2H), 2.16-1.24 (m, 17H) | |
| Example 184 | (E)-7-(aminomethyl)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide | Method 9 | $^1$H NMR (400 MHz, DMSO-d$_6$) δ ppm 8.15 (s, 1H), 7.95 (t, J = 14.8 Hz, 3H), 7.68 (d, J = 25.8 Hz, 2H), 7.35 (d, J = 18.1 Hz, 3H), 6.52 (d, J = 18.5 Hz, 2H), 5.76 (d, J = 15.9 Hz, 1H), 5.54 (d, J = 15.8 Hz, 1H), 5.08 (s, 2H), 4.88 (s, 2H), 4.51 (d, J = 6.7 Hz, 4H), 3.95 (s, 2H), 3.76 (s, 3H), 2.10 (d, J = 1.8 Hz, 6H), 1.26 (td, J = 7.1, 4.5 Hz, 6H) | LCMS Method A: Rt = 1.205 min, [M + H]$^+$ = 735.8 |
| Example 185 | (E)-7-(aminomethyl)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-1H-benzo[d]imidazole-5-carboxamide | Method 9 | $^1$H NMR (400 MHz, DMSO-d$_6$) δ ppm 8.15 (s, 1H), 7.95 (t, J = 17.8 Hz, 3H), 7.70 (s, 1H), 7.64 (s, 1H), 7.34 (m, 3H), 6.52 (d, J = 9.9 Hz, 2H), 5.78 (d, | LCMS Method A: Rt = 1.186 min, [M + H]$^+$ = 779.8 |

Table 1 provides Example 89 to Example 197. The compounds can be prepared by using synthetic methods described above.

| Example | Structure/Name | Synthetic Method | NMR | LCMS |
|---|---|---|---|---|
| | 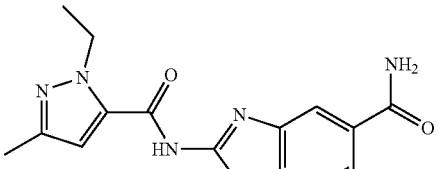 | | J = 15.9 Hz, 1H), 5.56 (d, J = 15.8 Hz, 1H), 5.09 (s, 2H), 4.90 (s, 2H), 4.52 (d, J = 6.6 Hz, 4H), 4.04 (s, 2H), 3.91 (s, 2H), 3.41 (s, 2H), 2.10 (s, 6H), 1.62 (m, 2H), 1.27 (t, J = 7.1 Hz, 6H) | |
| Example 186 | 1,1'-(butane-1,4-diyl)bis(2-(1-allyl-3-methyl-1H-pyrazole-5-carboxamido)-1H-benzo[d]imidazole-5-carboxamide)<br>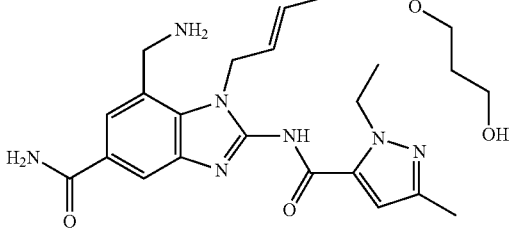 | Method 11 | $^1$H NMR (400 MHz, DMSO-d$_6$) δ ppm 12.81 (s, 2 H), 7.97 (s, 4H), 7.76 (d, J = 8.34 Hz, 2H), 7.53 (d, J = 8.34 Hz, 2H), 7.33 (br. s., 2H), 6.64 (s, 2H), 5.93-6.05 (m, 2 H), 5.21 (d, J = 4.80 Hz, 4H), 5.02 (dd, J = 10.36, 1.01 Hz, 2H), 4.89 (dd, J = 17.18, 1.01 Hz, 2H), 4.27 (br. s., 4H), 2.10 (s, 6H), 1.86 (br. s., 4H) | LCMS Method C: Rt = 0.83 min, [M + H]$^+$ = 703.6 |
| Example 187 | 1,1'-(butane-1,4-diyl)bis(2-(1-ethyl-4-iodo-3-methyl-1H-pyrazole-5-carboxamido)-1H-benzo[d]imidazole-5-carboxamide) | Method 11 | $^1$H NMR (400 MHz, DMSO-d$_6$) δ ppm 12.92 (s, 2 H), 8.00 (d, J = 1.01 Hz, 2H), 7.98 (br. s., 2H), | LCMS Method C: Rt = 1.01 min, [M + H]$^+$ = 931.5. |

Table 1 provides Example 89 to Example 197. The compounds can be prepared by using synthetic methods described above.

| Example | Structure/Name | Synthetic Method | NMR | LCMS |
|---|---|---|---|---|
| | 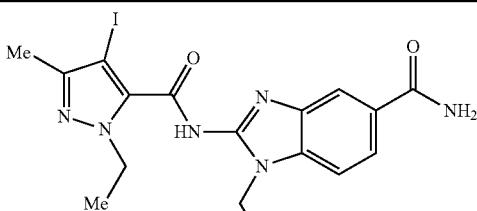 | | 7.78 (dd, J = 8.46, 1.39 Hz, 2H), 7.57 (d, J 8.34 Hz, 2H), 7.35 (br. s., 2H), 4.52 (q, J = 7.07 Hz, 4 H), 4.35 (br. s., 4 H), 2.14 (s, 6H), 1.91 (br. s., 4H), 1.28 (t, J = 7.07 Hz, 6H) | |
| Example 188 | 1-allyl-2-(1-(5-(5-((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide 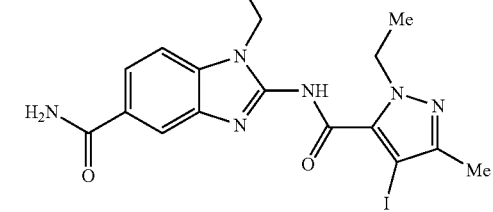 | Method 7 | $^1$H NMR (400 MHz, DMSO-d$_6$) δ ppm 12.88 (s, 1 H), 12.81 (s, 1 H), 7.99-8.02 (m, 2H), 7.97 (br. s., 2H), 7.77 (ddd, J = 8.34, 3.66, 1.39 Hz, 2 H), 7.41 (dd, J = 16.93, 8.34 Hz, 2H), 7.34 (br. s., 2H), 6.65 (s, 1H), 5.87-6.02 (m, 2H), 4.99-5.22 (m, 4 H), 4.82 (dd, J = 11.62, 4.80 Hz, 4H), 4.50-4.61 (m, 4H), 2.73 (t, J = 7.45 Hz, 2H), 2.15 (s, 3H), 2.08 (s, 3 H), 1.71-1.85 (m, 2H), 1.45-1.55 (m, 2H), 1.27-1.34 (m, 5 H) | LCMS Method C: Rt = 0.93 min, [M + H]$^+$ = 745.7 |
| Example 189 | 8-ethyl-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide 7:1 trans:cis mixture | Method 7 | Data provided for the trans-isomer $^1$H NMR (400 MHz, DMSO-d$_6$) δ ppm 12.87 (s, 1 H), 12.84 (s, 1 H), 7.98 (br. s., 4 H), 7.77 (dd, J = 7.71, 3.16 Hz, 2H), 7.33-7.48 (m, 4H), 6.55 (s, | Data provided for the trans-isomer LCMS Method C: Rt = 0.82 min, [M + H]$^+$ = 717.6. |

Table 1 provides Example 89 to Example 197. The compounds can be prepared by using synthetic methods described above.

| Example | Structure/Name | Synthetic Method | NMR | LCMS |
|---|---|---|---|---|
| | 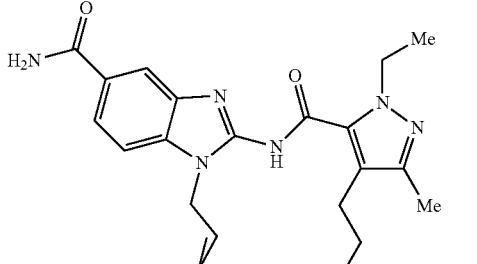 | | 1H), 5.89-5.98 (m, 1H), 5.66-5.75 (m, 1H), 4.90 (d, J = 7.83 Hz, 4H), 4.73 (t, J = 6.95 Hz, 2H), 4.47 (q, J = 6.99 Hz, 2H), 2.72-2.80 (m, 2H), 2.17 (s, 3H), 2.10 (s, 3H), 1.72 (br. s., 2H), 1.44 (br. s., 2H), 1.30 (t, J = 7.07 Hz, 5H) | |
| Example 190 | 2-(1-(5-(5-(((5-carbamoyl-1-propyl-1H-benzo[d]imidazol-2-yl)carbamoyl)-1-ethyl-3-methyl-1H-pyrazol-4-yl)pentyl)-3-methyl-1H-pyrazole-5-carboxamido)-1-propyl-1H-benzo[d]imidazole-5-carboxamide 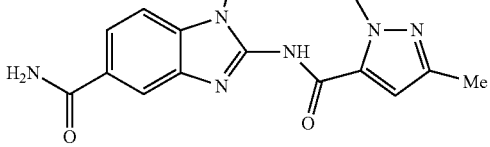 | Method 22 | $^1$H NMR (400 MHz, DMSO-d$_6$) δ ppm 12.84 (s, 1 H), 12.78 (s, 1 H), 8.00 (d, J = 2.27 Hz, 2H), 7.97 (br. s., 2H), 7.78 (d, J = 7.07 Hz, 2H), 7.49-7.58 (m, 2H), 7.33 (br. s., 2H), 6.63 (s, 1H), 4.51-4.65 (m, 4 H), 4.07-4.20 (m, 4H), 2.76 (t, J = 7.07 Hz, 2H), 2.15 (s, 3H), 2.08 (s, 3H), 1.69-1.83 (m, 6 H), 1.48-1.59 (m, 2H), 1.28-1.36 (m, 5H), 0.83-0.91 (m, 6 H) | LCMS Method C: Rt = 0.97 min, [M + H]$^+$ = 749.7 |
| Example 191 | ethyl 4-(2-(1-(5-(5-(((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-5-carbamoyl-1H-benzo[d]imidazol-1-yl)butanoate | Method 23 | $^1$H NMR (400 MHz, CDCl$_3$:METHANOL-d$_4$, 1:1) δ ppm 7.89 (s, 1H), 7.87 (s, 1H), 7.82 (d, J = 8.28 | LCMS Method D: Rt = 1.01 min, [M + H]$^+$ = 819.7 |

Table 1 provides Example 89 to Example 197. The compounds can be prepared by using synthetic methods described above.

| Example | Structure/Name | Synthetic Method | NMR | LCMS |
|---|---|---|---|---|
| | 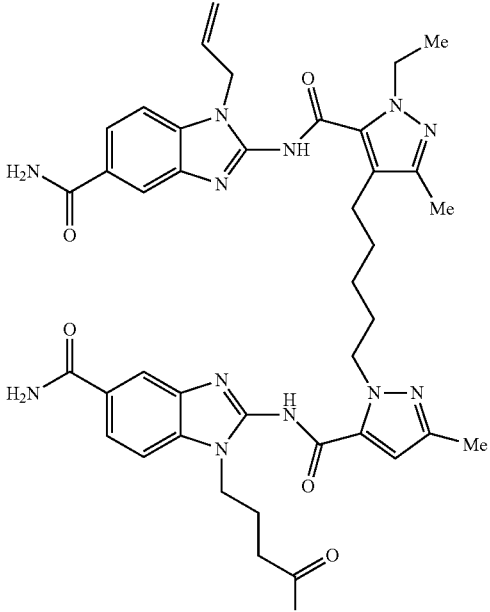 | | Hz, 1H), 7.78 (d, J = 8.28 Hz, 1H), 7.37 (d, J = 8.53 Hz, 1H), 7.24 (d, J = 8.53 Hz, 1H), 6.68 (s, 1H), 5.83-5.95 (m, 1 H), 5.20 (d, J = 10.29 Hz, 1 H), 5.07 (d, J = 17.32 Hz, 1 H), 4.77 (d, J = 4.27 Hz, 2H), 4.59-4.65 (m, 2 H), 4.54 (q, J = 6.94 Hz, 2H), 4.23 (t, J = 6.65 Hz, 2H), 4.03 (q, J = 7.19 Hz, 2H), 2.79 (t, J = 7.40 Hz, 2H), 2.38 (t, J = 6.90 Hz, 2H), 2.23 (s, 3H), 2.15 (s, 3H), 2.08-2.14 (m, 2 H), 1.80-1.92 (m, 2H), 1.51-1.63 (m, 2H), 1.36 (t, J = 7.03 Hz, 5H), 1.15 (t, J = 7.03 Hz, 3H) | |
| Example 192 | ethyl 4-(5-carbamoyl-2-(1-(5-(5-((5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazol-1-yl)butanoate 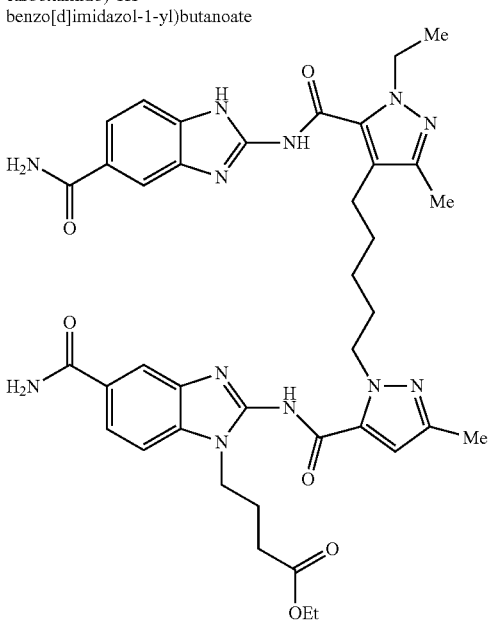 | Method 23 | $^1$H NMR (400 MHz, DMSO-$d_6$) δ ppm 7.11 (s, 1 H), 7.07 (s, 1H), 6.99 (dd, J = 8.44, 1.34 Hz, 1H), 6.91 (dd, J = 8.31, 1.47 Hz, 1H), 6.58 (d, J = 8.56 Hz, 1H), 6.54 (d, J = 8.56 Hz, 1H), 5.78 (s, 1H), 4.04 (br. s., 5H), 3.75 (t, J = 6.85 Hz, 2H), 3.54 (q, J = 6.85 Hz, 2H), 3.37 (t, J = 6.72 Hz, 2H), 3.14 (q, J = 7.09 Hz, 2H), 1.84 (t, J = 7.09 Hz, 2H), 1.50-1.57 (m, 2H), 1.33 (s, 3H), 1.32 (s, 3H), 1.19-1.28 (m, 2 H), 0.92-1.02 (m, 2H), 0.64-0.73 (m, 2H), 0.52 (t, J = 7.09 Hz, 3H), 0.40-0.49 (m, 2H), 0.28 (t, J = 7.21 Hz, 3H) | LCMS Method D: Rt = 0.88 min, [M + H]$^+$ = 779.6 |
| Example 193 | 3-(2-(1-(5-(5-((1-(2-(((benzyloxy)carbonyl)amino)ethyl)-5-carbamoyl-1H-benzo[d]imidazol-2-yl)carbamoyl)-1-ethyl-3-methyl- | Method 23 | $^1$H NMR (400 MHz, METHANOL-$d_4$) δ ppm 7.91 (s, 1 H), 7.77-7.82 | LCMS Method E: Rt = 0.81 min, [M + H]$^+$ = |

Table 1 provides Example 89 to Example 197. The compounds can be prepared by using synthetic methods described above.

| Example | Structure/Name | Synthetic Method | NMR | LCMS |
|---|---|---|---|---|
| | 1H-pyrazol-4-yl)pentyl)-3-methyl-1H-pyrazole-5-carboxamido)-5-carbamoyl-1H-benzo[d]imidazol-1-yl)propanoic acid 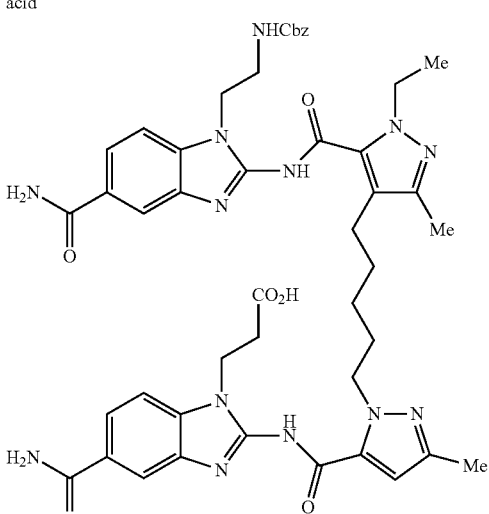 | | (m, 2H), 7.70 (dd, J = 8.56, 1.47 Hz, 1H), 7.44 (d, J = 8.31 Hz, 1H), 7.33 (d, J = 8.56 Hz, 1H), 7.12-7.30 (m, 5H), 6.69 (s, 1H), 4.93 (s, 2H), 4.49-4.65 (m, 4 H), 4.41 (t, J = 6.85 Hz, 2H), 4.30 (t, J = 5.75 Hz, 2H), 3.55 (t, J = 5.75 Hz, 2H), 2.88 (t, J = 6.72 Hz, 2H), 2.75-2.82 (m, 2H), 2.21 (s, 3H), 2.16 (s, 3H), 1.81-1.91 (m, 2 H), 1.53-1.63 (m, 2H), 1.36 (t, J = 7.09 Hz, 5H) | 914.5 |
| Example 194 | methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate 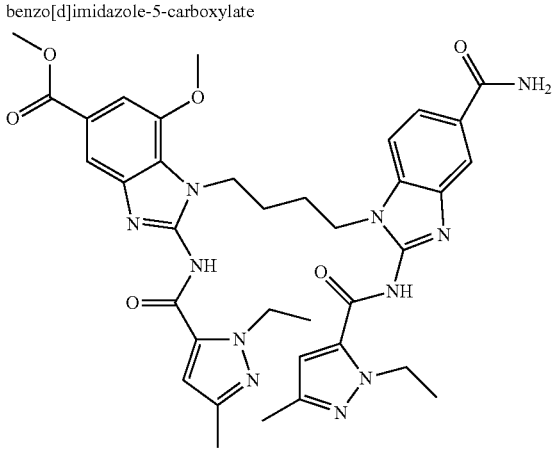 | Method 11 | $^1$H NMR (400 MHz, DMSO-d$_6$) δ ppm 12.66-13.03 (m, 2H) 7.97 (s, 2H) 7.78 (s, 2H) 7.50-7.57 (m, 1 H) 7.37 (d, J = 1.01 Hz, 2H) 6.59 (s, 2H) 4.57 (br. s., 4H) 4.34-4.44 (m, 2 H) 4.20-4.31 (m, 2H) 3.88 (d, J = 3.79 Hz, 6H) 2.11 (s, 6H) 1.86 (br. s., 4H) 1.27-1.37 (m, 6 H) | LCMS Method C: Rt = 0.93 min, [M + H]$^+$ = 724.6 |
| Example 195 | 2-(1-ethyl-3-methyl-1H-pyrazole-5-carboxamido)-1-(4-(2-(1-ethyl-3-methyl-1H-pyrazole-5-carboxamido)-1H-benzo[d]imidazol-1-yl)butyl)-1H-benzo[d]imidazole-5-carboxamide | Method 11 | $^1$H NMR (400 MHz, DMSO-d$_6$) δ ppm 1.25 (t, J = 6.95 Hz, 6H) 1.76 (br. s., 4H) 2.10 (s, 6H) 4.11 (br. s., 4H) | LCMS Method C: Rt = 0.88 min, [M + H]$^+$ = 636.5 |

-continued

Table 1 provides Example 89 to Example 197. The compounds can be prepared by using synthetic methods described above.

| Example | Structure/Name | Synthetic Method | NMR | LCMS |
|---|---|---|---|---|
| | | | 4.50-4.68 (m, 4 H) 6.35 (s, 2H) 6.84-7.03 (m, 4 H) 7.12 (d, J = 7.07 Hz, 2H) 7.36-7.52 (m, 2 H) 7.68 (br. s., 1 H) 8.00 (s, 1H) | |
| Example 196 | tert-butyl bis(2-(5-carbamoyl-2-(1-ethyl-3-methyl-1H-pyrazole-5-carboxamido)-1H-benzo[d]imidazol-1-yl)ethyl)carbamate | Method 15 | $^1$H NMR (400 MHz, METHANOL-d4) δ ppm 0.96-1.17 (m, 9H) 1.25-1.49 (m, 6H) 2.08-2.37 (m, 6 H) 3.58 (br. s., 4 H) 4.05-4.39 (m, 4H) 4.62 (br. s., 4H) 6.38 - 6.63 (m, 2H) 7.06-7.30 (m, 2 H) 7.63 (br. s., 2 H) 7.96 (br. s., 2 H) | LCMS Method C: Rt = 0.83 min, [M + H]$^+$ = 794.7 |
| Example 197 | 7,7'-(propane-1,3-diylbis(oxy))bis(1-allyl-2-(1-ethyl-3-methyl-1H-pyrazole-5-carboxamido)-1H-benzo[d]imidazole-5-carboxamide), 2Trifluoroacetic acid salt | Method 21 | $^1$H NMR (400 MHz, DMSO-d$_6$) δ ppm 1.34 (t, J = 7.07 Hz, 6H) 2.18 (s, 6H) 2.33-2.46 (m, 2 H) 4.41 (t, | LCMS Method C: Rt = 0.94 min, [M + H]$^+$ = 777.7 |

Table 1 provides Example 89 to Example 197. The compounds can be prepared by using synthetic methods described above.

| Example | Structure/Name | Synthetic Method | NMR | LCMS |
|---|---|---|---|---|
| | 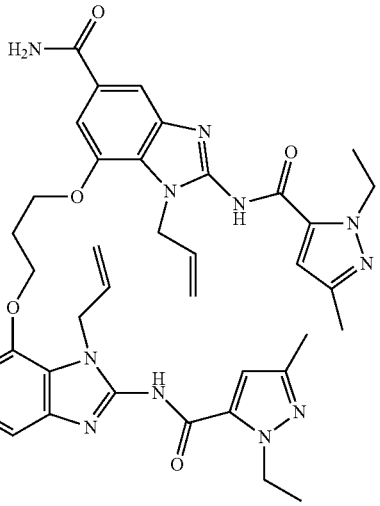 | | 35.81 Hz, 4H) 4.60 (q, J = 7.07 Hz, 4H) 4.85-5.11 (m, 8H) 5.97-6.11 (m, 2H) 6.64 (s, 2H) 7.39 (br. s., 2H) 7.45 (s, 2H) 7.69 (s, 2H) 8.02 (br. s., 2H) | |

AlexaFluor-488 FRET Assay Ligand

3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic Acid

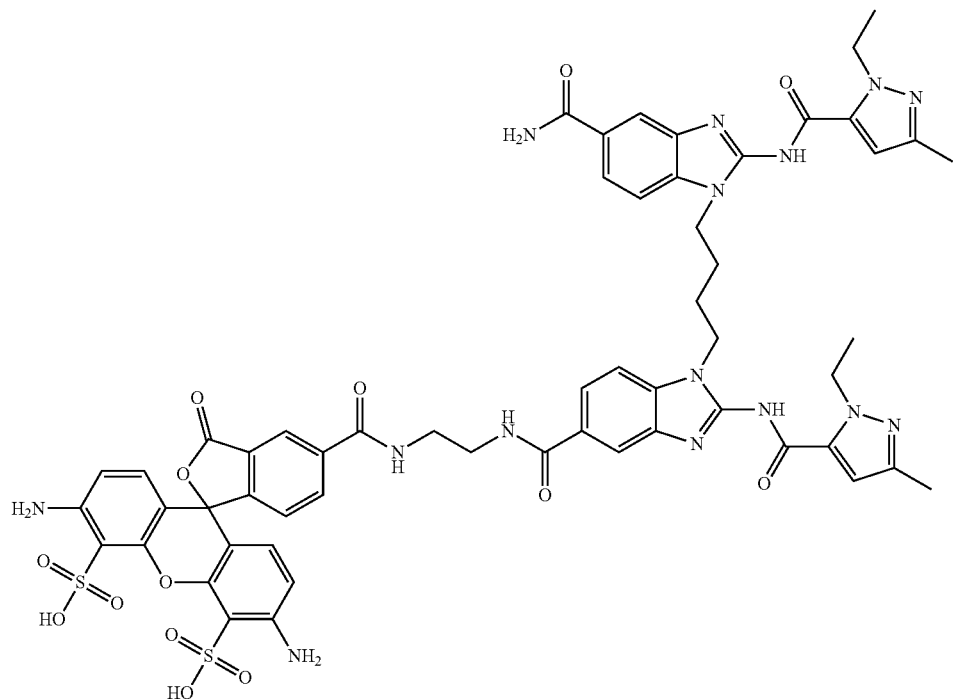

-continued
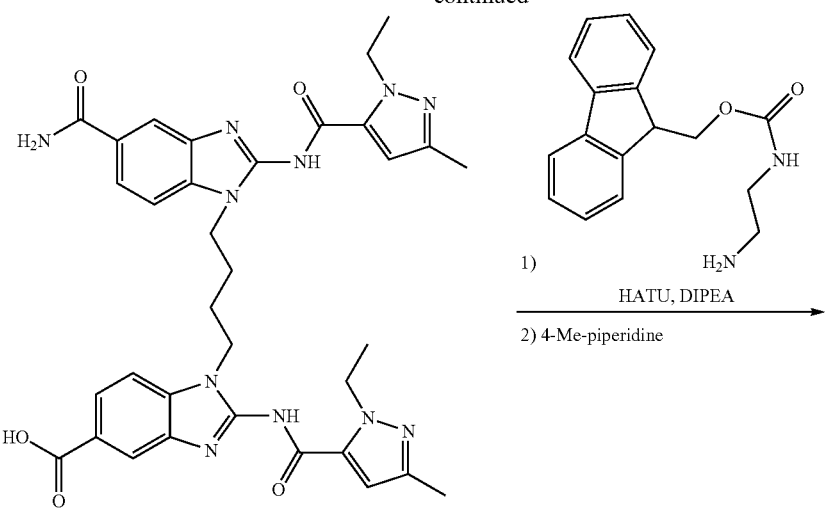
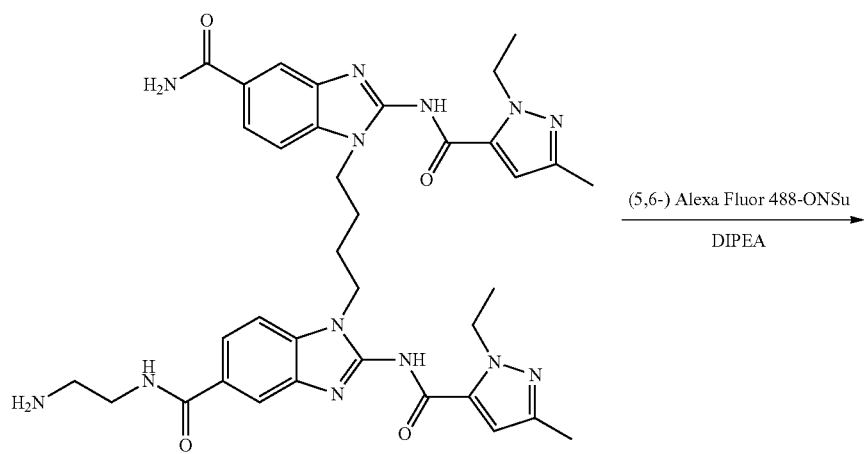
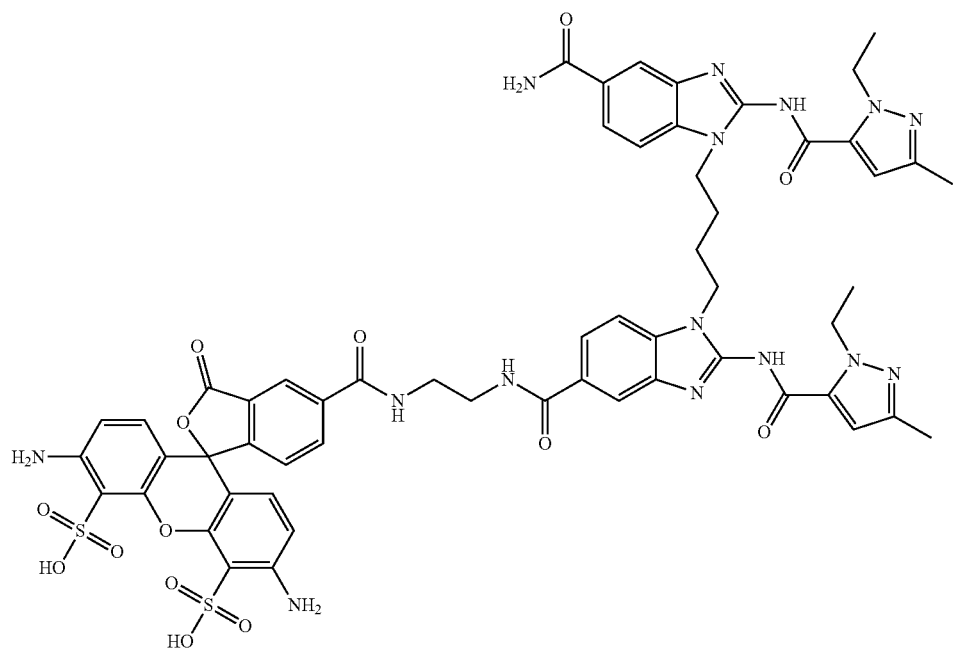

509

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic Acid Dihydrochloride

510

Step 1: N-(2-Aminoethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide Trifluoroacetic Acid Salt

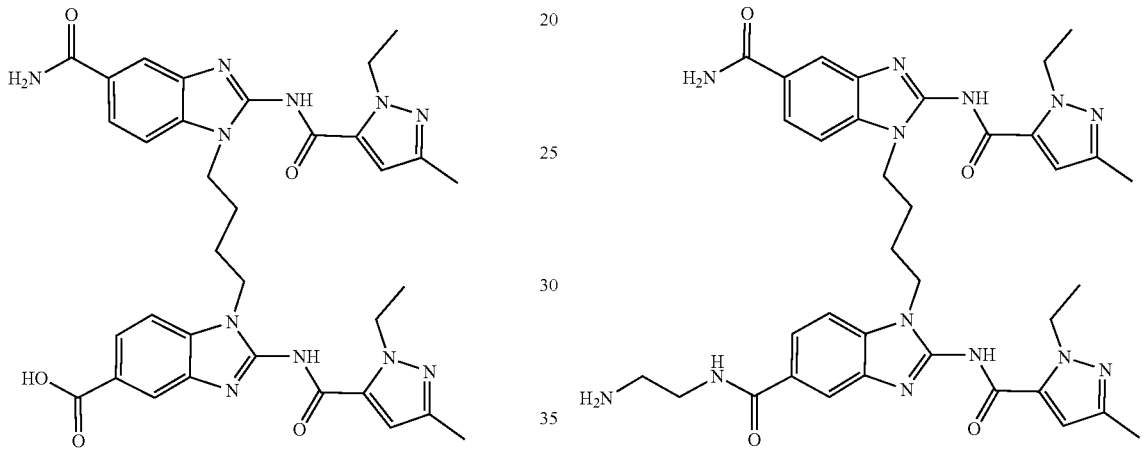

To methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate bis trifluoroacetic acid salt (400 mg, 0.434 mmol, Example 23) in THF (3.47 mL), MeOH (3.47 mL) and water (1.74 mL) at RT was added 8 M potassium hydroxide (1.09 mL, 8.68 mmol). After stirring overnight, the reaction was concentrated, and water was added. The mixture was acidified to pH 4-5 with 7 N aq HCl, and the resulting grey solid was collected by filtration to yield the title compound (335 mg, 0.423 mmol, 97% yield). $^1$H NMR (400 MHz, DMSO-$d_6$) δ ppm 12.82-12.95 (m, 3H), 8.08 (s, 1H), 7.99 (br. s., 2H), 7.83 (d, J=8.34 Hz, 1H), 7.78 (d, J=8.34 Hz, 1H), 7.58 (t, J=7.33 Hz, 2H), 7.36 (br. s., 1H), 6.60 (d, J=4.80 Hz, 2H), 4.58 (d, J=6.57 Hz, 4H), 4.29 (br. s., 4H) 2.10 (s, 6H), 1.88 (br. s., 4H), 1.31 (t, J=6.95 Hz, 6H); LCMS (LCMS Method C): Rt=0.83 min, [M+H]$^+$=680.5

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic acid (10 mg, 0.015 mmol) was dissolved (with sonication) in DMSO (300 μL) at 37° C. To this was added a solution of (9H-fluoren-9-yl)methyl (2-aminoethyl) carbamate hydrochloride (6.9 mg, 0.022 mmol) and HATU (7.6 mg, 0.020 mmol) in DMSO (100 μL) followed by DIEA (10 μL, 0.057 mmol). After stirring overnight, the reaction was diluted with DMF (600 μL), 4-methylpiperidine (400 μL) was added and the reaction was stirred at RT 1 hr. The mixture was concentrated, and the resulting residue diluted with 1:1 DMSO: MeOH (<1 mL) and purified by reverse-phase chromatography (Jupiter C18 preparative column, 10 mL/min), eluting with 30-100% (9:1 ACN: water) in water (0.1% TFA additive) to yield the title compound (8.45 mg, 10.1 μmol, 69% yield). LCMS (LCMS Method G): Rt=0.62 min, [M+H]$^+$=722.4

Step 2: 3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic Acid MeOH (<1 mL) and purified by reverse-phase chromatography (Jupiter C18 preparative column, 10 mL/min), eluting with 15-100% (9:1 ACN: water) in water (0.1% TFA additive). The early eluting positional isomer was obtained in high purity. In contrast, the fractions of the late eluting isomer also contained unreacted starting material. These fractions containing the impure late eluting isomer were pooled and concentrated. This residue was dissolved in 1:1

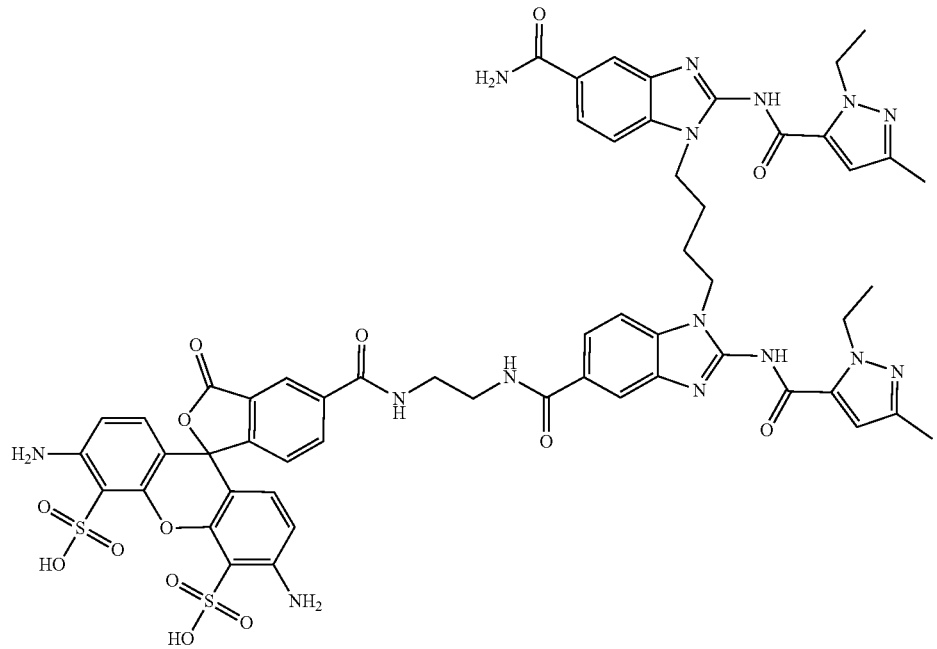 [SMILES: CCn1nc(C)cc1C(=O)Nc1nc2cc(C(N)=O)ccc2n1CCCCn1c(NC(=O)c2cc(C)nn2CC)nc2cc(C(=O)NCCNC(=O)c3ccc4c(c3)C(=O)OC43c4ccc(N)c(S(=O)(=O)O)c4Oc4c3ccc(N)c4S(=O)(=O)O)ccc21]

N-(2-Aminoethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide trifluoroacetic acid salt (8.45 mg, 10.1 μmol) was dissolved in DMF (200 μl) and added to solid (5,6-) Alexa Fluor 488-ONSu (5.00 mg, 7.92 μmol). The commercial Alexa Fluor 488-ONSu reagent was a mixture of the 5- and 6-positional isomers.

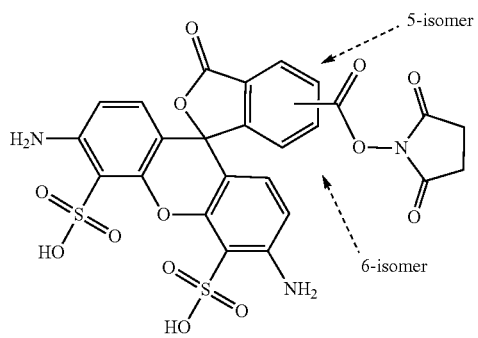

When solution was effected, DIPEA (2 μL, 0.01 mmol) was added, and the mixture was agitated (by vortex action) overnight in the absence of light. LCMS revealed formation of early and late eluting product peaks with the anticipated molecular weight ([M+H] 1238.6). The reaction was concentrated, and the residue was dissolved in 1:1 DMSO:

DMSO: MeOH (<1 mL) and purified by reverse-phase chromatography (Waters SymmetryPrep preparative column, 10 mL/min), eluting with 15-100% (9:1 ACN: water) in water (0.1% TFA additive) to yield the title compound (late eluting isomer, 1.94 mg, 1.49 μmol, 19% yield). LCMS (LCMS Method H): Rt=0.69 min, [M+H]$^+$=1238.6. Note that the putative structure of the title compound (5-isomer) is not based on rigorous structural determination but instead is based on previous observations that the 5-positional isomer is typically the later eluting isomer by reverse phase HPLC methods.

Biological Assays and Data

As stated above, the compounds of present invention are modulators of STING, and are useful in the treatment of diseases mediated by STING. The biological activities of the compounds of present invention can be determined using any suitable assay for determining the activity of a compound as a modulator of STING, as well as tissue and in vivo models.

The pIC$_{50}$ value for each compound was either reported in at least one experiment or the average of multiple experiments. It is understood that the data described herein may have reasonable variations depending on the specific conditions and procedures used by the person conducting the experiments.

Binding Assays (1) SPA

A radioligand binding assay was developed to measure quantitate interactions of compounds of Formula (I-N), (I-P) or (I) and the carboxy terminal domain (CTD) of STING by competition with 3H-cGAMP (tritium-labeled cyclic guanine (2',5') monophosphate-adenine (3',5') monophosphate). See also Li et al. (*Nature Chemical Biology*, 10, 1043-1048, (2014)). A protein encoding the sequence of human STING spanning residues 149 to 379 (Gene ID 340061) was expressed in bacteria with a carboxy terminal Flag® peptide fused to AviTag™ for biotinylation and hexahistidine tag for affinity purification. The purified STING-Flag-AviTag-6× his protein was biotinylated to completion using the enzyme BirA (Beckett D. et al, *Protein Science*, 1999, 8:921-929). The relative potency of compounds of Formula (I-N), (I-P) or (I) were determined by competition in equilibrium binding reactions containing 50 nM biotinylated-STING, 50 nM 3H-cGAMP, and 1.25 mg/mL streptavidin-coated scintilation proximity assay beads (Perkin Elmer) in phosphate-buffered saline buffer. Binding reactions were incubated at room temperature for 30 minutes and read using a luminescence plate reader. Dose response curves were normalized to a control that reflect complete inhibition of 3H-cGAMP binding by 10 M unlabeled cGAMP and no compound control. The apparent $pIC_{50}$ was determined using a conventional two-state binding model. Under these conditions, the apparent inhibition constant for positive control compound cGAMP is 40-50 nM which is approximately ten-fold greater than its actual affinity of 4-5 nM (Zhang X et al, *Molecular Cell*, 2013, 51:1-10).

(2) FRET Assay

The binding potency of molecules to the C-terminal Domain (CTD) of human STING was determined using a competition binding assay. In this assay, STING (149-379) recombinant protein with a C-terminal biotinylated Avi-tag was employed. When bound to STING, an Alexa488-labeled active site probe (see pages 226-229 for the synthesis for the FRET assay ligand) accepts the 490 nm emission from Tb-Streptavidin-Avi-STING and an increase in fluorescence is measured at 520 nm. Molecules that compete for the probe binding site will result in a low 520 nm signal. The assay was run in Greiner black 384-well plates (Catalog #784076) containing 100 nL compounds in neat DMSO. A solution of 500 pM STING, 500 pM Streptavidin-Lumi4-Tb, and 100 nM Alexa488 probe in phosphate buffered saline containing 0.02% (w/v) pluronic F127 and 0.02% (w/v) bovine serum albumin was added to the plate using a Combi liquid handler (ThermoFisher). Plates were centrifuged for 1 min at 500 rpm, incubated for 15 min at room temperature, and then fluorescence emission at 520 nm following 337 nm laser excitation on an Envision plate reader (Perkin-Elmer) was measured. The $pIC_{50}$ values were determined using a standard four parameter curve fit in ABASE XE.

Using the SPA assay described above, the compounds of Examples 1-9, 11, 13, 15, 16, 23, 25-30, 33-35, 47, 49, 50, 54, 55, 57-61, 63-66, 68-74, 76-79, 81-83, 85-88, 90, 92, 102, 104, 105, 107-110, 112-114, 117, 118, 120, 122-144, 146-149, 151-160, 163-167, 169, 170, 172-183, and 186-197 exhibited $pIC_{50}$ values in the range of 3.6 to 7.7. For example, the compounds of Example 1 and Example 5, above, inhibited binding of 3H-cGAMP to STING in the above method with mean $pIC_{50}$ of 7.5 (#1, n=4; #5, n=2).

Using the FRET assay described above, Examples 1-106, 110, 112-125, 129, 131, 133, 134, 138, 142-144, 146-153, 155-186, 188-193, and 196 exhibited $pIC_{50}$ values in the range of 4.1 to beyond the upper limit of the assay at 9.9. For example, $pIC_{50}$ of FRET assay for following examples are:

| Example No | FRET assay (pIC50) |
|---|---|
| 10 | 9.5 |
| 11 | 9.8 |
| 13 | 9.7 |
| 14 | 9.6 |
| 16 | 9.3 |
| 18 | 9.6 |
| 19 | 9.1 |
| 21 | 9.4 |
| 27 | 9.9 |
| 31 | 9.5 |

Cellular Functional Assays

The function of compounds of Formula (I) may be determined in cellular assays that detect STING specific activation and/or inhibition of IFNβ protein secretion.

(1) Functional Assay I (PBMC antagonist assay): Inhibition of STING by compounds of Formula (I-N), (I-P) or (I) may be determined by measuring loss of interferon β secreted from PBMCs stimulated with Bacmam virus, a double stranded DNA virus, following treatment with different doses of compounds of Formula (I-N), (I-P) or (I). Frozen PBMC cells were thawed and diluted in media (RPMI-1640 with 1.5 g/L $NaHCO_3$, 4.5 g/L glucose, 10 mM Hepes and 1 mM NaPyruvate, 10% FBS) to a final concentration of $5 \times 10^5$ cells/mL followed by infection with Bacmam virus at a final MOI of 43. The PBMC-Bacmam virus suspension was dispensed into a 384-well tissue culture plate (Griener 781073) at a density of 25,000 cells per well containing 250 nL of compound diluted in DMSO. The level IFNβ protein secreted into the growth media was measured after 24 hours of incubation at 37° C. using a human IFNβ electrochemiluminescence kit (Meso Scale Diagnostics) following the manufacturer's instructions. Percent inhibition was determined relative to controls that lack compound treatment or Bacmam virus infection and plotted as a function of compound concentration to determine $pIC_{50}$ using a standard two-state model of receptor-ligand inhibition.

(2) Functional Assay II (PBMC agonist assay): Activation of STING by compounds of Formula I was determined by measuring levels of IFNβ secreted from human peripheral blood mononuclear cells (PBMC) treated with different doses of compounds of Formula I. Frozen PBMC cells were thawed, resuspended in media (RPMI-1640 with 1.5 g/L $NaHCO_3$, 4.5 g/L glucose, 10 mM Hepes and 1 mM NaPyruvate, 10% FBS, 10 ng/mL lipopolysaccharide) to a final concentration of $5 \times 10^5$ cells/mL and dispensed into a 384-well tissue culture plate (Griener 781073) at a density of 15,000 cells per well containing 250 nL of compound diluted in DMSO. The level of IFNβ protein secreted into the growth media was measured after three hours of incubation at 37° C. using a human IFNβ electrochemiluminescence kit (Meso Scale Diagnostics) following the manufacturer's instructions. Percent activation was determined relative to control DMSO treatment and plot as a function of compound concentration to determine pEC50 using a standard model of receptor activation.

(3) Functional Assay III (HEK WT agonist assay): Activation of STING in cells may be determined using a luciferase reporter assay in human embryonic kidney cells (HEK293T) co-transfected with plasmids expressing STING and the enzyme firefly luciferase driven by the interferon stimulated response element promoter (pISRE-Luc) (Agilent Technologies). Full-length human STING (Gene ID 340061) and full-length human cyclic guanine adenine synthase (cGAS) (reference sequence NM_138441.2) was cloned into mammalian cell expression vectors containing a cytomegalovirus promoter. Transfections were prepared using a cell suspension with Fugene® 6 following the manufacturer's instructions (3:1 Fugene®:DNA). Fifty microliters of the transfection suspension was dispensed into wells of a 384-well plate containing 250 nL of a compound of Formula (I-N), (I-P) or (I). The final well composition contained 20,000 cells/well, 1 ng STING, 20 ng pISRE-Luc, and empty vector pcDNA3.1(Invitrogen) to bring the total DNA concentration to 125 ng. Control wells expected to generate maximal activation of STING were cotransfected with a cGAS expression plasmid. Plates were sealed and incubated for 24 hours at 37° C. The expression of firefly luciferase was processed using Steady-Glo® luciferase assay system (Promega) and was analyzed using a standard laboratory luminescence plate reader. Data was normalized to luminescence response in the presence of cGAS, was plotted as a function of compound concentration, and fit using a standard model of receptor activation to derive the $pEC_{50}$.

Using the functional assay III (HEK WT agonist assay) described above, Examples 1-23, 25-42, 44, 47-55, 57-61, 63-94, and 97-197 exhibited $pEC_{50}$ values in the range of 4.4 to beyond the upper limit of the assay at 9.1. Examples 1, 3, 8, 100, 116, and 194 exhibited $pEC_{50}$ lower than 4.3. For example, $pEC_{50}$ of for following examples are:

| Example No | HEK WT agonist assay (pEC50) |
|---|---|
| 10 | 7.5 |
| 11 | 7.8 |
| 13 | 7.4 |
| 14 | 7.5 |
| 16 | 7.6 |
| 18 | 7.5 |
| 19 | 7.5 |
| 21 | 7.3 |
| 27 | 7.6 |
| 31 | 7.8 |

What is claimed is:

1. A compound which is (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide
having the structure of

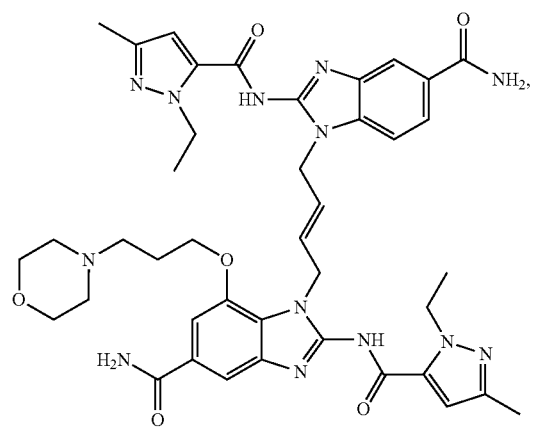 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCN3CCOCC3)c21]

or a tautomer thereof, or a pharmaceutically acceptable salt thereof, or a hydrate thereof.

2. The compound according to claim 1, which is a pharmaceutically acceptable salt of (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide, or a tautomer thereof.

3. The compound according to claim 1, which is (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide, or a tautomer thereof.

4. The compound according to claim 1, which is (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide having the structure of

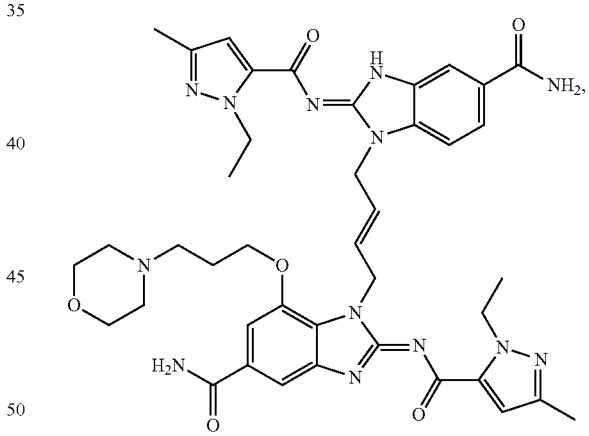

or a pharmaceutically acceptable salt thereof.

5. A pharmaceutical composition comprising a compound which is (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide having the structure of

517

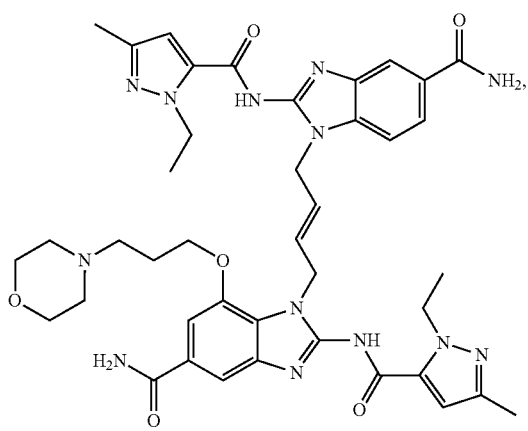

or a tautomer thereof,
or a pharmaceutically acceptable salt thereof,
or a hydrate thereof, and
a pharmaceutically acceptable excipient.

6. The pharmaceutical composition according to claim 5, wherein the compound is
(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide having the structure of

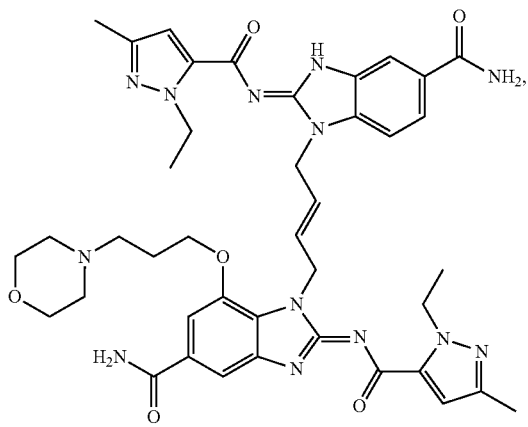

or a pharmaceutically acceptable salt thereof.

7. A method of treating a STING-mediated disease or disorder comprising administering a therapeutically effective amount of a compound which is (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide

518 having the structure of

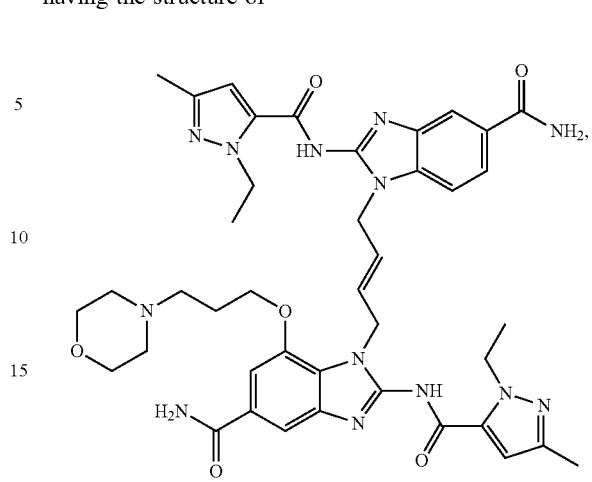

or a tautomer thereof,
or a pharmaceutically acceptable salt thereof,
or a hydrate thereof,
to a human in need thereof.

8. The method according to claim 7, wherein the compound is (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide having the structure of

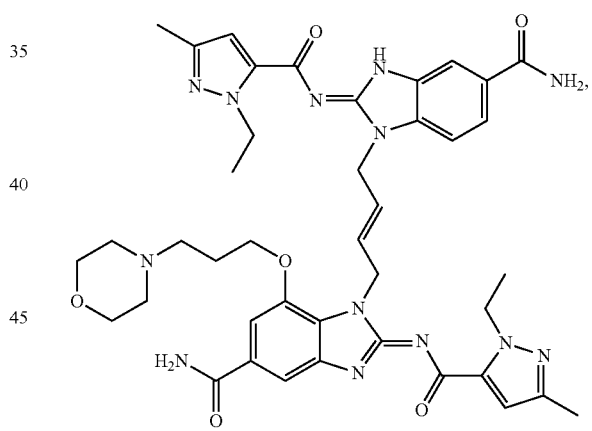

or a pharmaceutically acceptable salt thereof.

9. The method according to claim 7, wherein the STING-mediated disease or disorder is an infectious disease.

10. The method according to claim 9, wherein the infectious disease is HIV.

* * * * *